United States Patent
Corbin et al.

(10) Patent No.: US 9,725,510 B2
(45) Date of Patent: *Aug. 8, 2017

(54) MODULATORS

(71) Applicant: XOMA (US) LLC, Berkeley, CA (US)

(72) Inventors: John Corbin, Oakland, CA (US);
Mark Leslie White, Antioch, CA (US);
Susan R. Watson, El Cerrito, CA (US);
Vinay Bhaskar, San Francisco, CA (US)

(73) Assignee: XOMA (US) LLC, Berkeley, CA (US)

( * ) Notice: Subject to any disclaimer, the term of this patent is extended or adjusted under 35 U.S.C. 154(b) by 333 days.

This patent is subject to a terminal disclaimer.

(21) Appl. No.: 14/555,243

(22) Filed: Nov. 26, 2014

(65) Prior Publication Data

US 2015/0322157 A1   Nov. 12, 2015

Related U.S. Application Data

(63) Continuation of application No. 12/890,598, filed on Sep. 24, 2010, now Pat. No. 8,926,976.

(60) Provisional application No. 61/358,749, filed on Jun. 25, 2010, provisional application No. 61/306,321, filed on Feb. 19, 2010, provisional application No. 61/246,067, filed on Sep. 25, 2009.

(51) Int. Cl.
*A61K 39/395* (2006.01)
*C07K 16/28* (2006.01)
*C07K 16/26* (2006.01)
*A61K 39/00* (2006.01)

(52) U.S. Cl.
CPC .............. *C07K 16/28* (2013.01); *C07K 16/26* (2013.01); *C07K 16/2869* (2013.01); *A61K 2039/505* (2013.01); *C07K 2316/95* (2013.01); *C07K 2316/96* (2013.01); *C07K 2317/21* (2013.01); *C07K 2317/32* (2013.01); *C07K 2317/55* (2013.01); *C07K 2317/56* (2013.01); *C07K 2317/565* (2013.01); *C07K 2317/622* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,708,871 A | 11/1987 | Geysen |
| 4,761,371 A | 8/1988 | Bell et al. |
| 4,816,567 A | 3/1989 | Cabilly et al. |
| 4,833,092 A | 5/1989 | Geysen |
| 5,164,295 A | 11/1992 | Kisilevsky et al. |
| 5,223,409 A | 6/1993 | Ladner et al. |
| 5,348,867 A | 9/1994 | Georgiou et al. |
| 5,403,484 A | 4/1995 | Ladner et al. |
| 5,427,908 A | 6/1995 | Dower et al. |
| 5,432,018 A | 7/1995 | Dower et al. |
| 5,498,530 A | 3/1996 | Schatz et al. |
| 5,556,762 A | 9/1996 | Pinilla et al. |
| 5,565,332 A | 10/1996 | Hoogenboom et al. |
| 5,571,689 A | 11/1996 | Heuckeroth et al. |
| 5,573,905 A | 11/1996 | Lerner et al. |
| 5,580,717 A | 12/1996 | Dower et al. |
| 5,610,031 A | 3/1997 | Burgeson et al. |
| 5,643,768 A | 7/1997 | Kawasaki |
| 5,658,754 A | 8/1997 | Kawasaki |
| 5,663,143 A | 9/1997 | Ley et al. |
| 5,698,426 A | 12/1997 | Huse |
| 5,723,286 A | 3/1998 | Dower et al. |
| 5,723,287 A | 3/1998 | Russell et al. |
| 5,723,323 A | 3/1998 | Kauffman et al. |
| 5,734,018 A | 3/1998 | Rutter et al. |
| 5,750,373 A | 5/1998 | Garrard et al. |
| 5,763,192 A | 6/1998 | Kauffman et al. |
| 5,766,886 A | 6/1998 | Studnicka et al. |
| 5,766,905 A | 6/1998 | Studier et al. |
| 5,770,434 A | 6/1998 | Huse |
| 5,859,205 A | 1/1999 | Adair et al. |
| 5,877,293 A | 3/1999 | Adair et al. |
| 5,969,108 A | 10/1999 | McCafferty et al. |
| 6,028,169 A | 2/2000 | Kreider et al. |
| 6,054,287 A | 4/2000 | Gao et al. |
| 6,342,358 B1 | 1/2002 | Collins et al. |
| 6,699,658 B1 | 3/2004 | Wittrup et al. |
| 7,732,154 B2 | 6/2010 | Ebina et al. |
| 7,888,042 B2 | 2/2011 | Chen |
| 2002/0004215 A1 | 1/2002 | Osbourn et al. |
| 2003/0044772 A1 | 3/2003 | Watkins et al. |
| 2003/0190317 A1 | 10/2003 | Baca et al. |
| 2003/0236190 A1 | 12/2003 | Pillutla et al. |
| 2004/0101904 A1 | 5/2004 | Pardridge et al. |
| 2011/0008452 A1 | 1/2011 | Epshtein et al. |

FOREIGN PATENT DOCUMENTS

| | | |
|---|---|---|
| WO | WO-99/58572 A1 | 11/1999 |
| WO | WO-02/072778 A2 | 9/2002 |
| WO | WO-02/094194 A2 | 11/2002 |

(Continued)

OTHER PUBLICATIONS

Amstutz et al., In vitro display technologies: novel developments and applications, *Curr. Opin. Biotechnol.*, 12:400-5 (2001).

Arioglu et al., Clinical course of the syndrome of autoantibodies to the insulin receptor (type B insulin resistance), *Medicine*, 81:87-100 (2002).

Arulmozhi et al., Metabolic effects of various antidiabetic and hypolipidaemic agents on a high-fat diet and multiple low-dose streptozocin (MLDS) mouse model of diabetes, *J. Pharm. Pharmacol.*, 60:1167-73 (2008).

Barbas et al., Assembly of combinatorial antibody libraries on phage surfaces: the gene III site, *Proc. Natl. Acad. Sci. USA*, 88:7978-82 (1991).

(Continued)

*Primary Examiner* — Zachary Skelding
(74) *Attorney, Agent, or Firm* — Marshall, Gerstein & Borun LLP

(57) ABSTRACT

Antibodies that modulate insulin receptor signaling are provided.

20 Claims, 60 Drawing Sheets

(56) References Cited

FOREIGN PATENT DOCUMENTS

| | | |
|---|---|---|
| WO | WO-03/008930 A2 | 1/2003 |
| WO | WO-03/099199 A2 | 12/2003 |
| WO | WO-2004/050016 A2 | 6/2004 |
| WO | WO-2004/085618 A2 | 10/2004 |
| WO | WO-2007/147213 A1 | 12/2007 |
| WO | WO-2007/149010 A1 | 12/2007 |
| WO | WO-2009/087173 A2 | 7/2009 |
| WO | WO-2010/142296 A1 | 12/2010 |
| WO | WO-2011/038301 A2 | 3/2011 |

OTHER PUBLICATIONS

Baron et al., The insulin receptor activation process involves localized conformational changes, *J. Biol. Chem.*, 267(32):23290-4 (1992).

Bayer et al., The biotin transport system in yeast, *Methods Enzymol.*, 62:371-8 (1979).

Beals et al., CD18 activation epitopes induced by leukocyte activation, *J. Immunol.*, 167:6113-22 (2001).

Beattie et al., Effects of complexation with in vivo enhancing monoclonal antibodies on activity of growth hormone in two responsive cell culture systems, *J. Mol. Endocrinol.*, 23:307-13 (1999).

Blackard et al., Effect of Anti-Insulin Receptor Antibody on Insulin Dissociation from IM-9 lymphocytes, *Horm. Metab. Res.*, 13:480-3 (1981).

Boado et al., Humanization of anti-human insulin receptor antibody for drug targeting across the human blood-brain barrier, *Biotechnol. Bioeng.*, 96:381-91 (2007).

Brindle et al., Anti-(insulin receptor) monoclonal antibody-stimulated tyrosine phosphorylation in cells transfected with human insulin receptor cDNA, *Biochem. J.*, 268:615-20 (1990).

Brunetti et al., Monoclonal antibodies to the human insulin receptor mimic a spectrum of biological effects in transfected 3T3/HIR fibroblasts without activating receptor kinase, *Biochem. Biophys. Res. Commun.*, 165:212-8 (1989).

Burton et al., Human antibodies from combinatorial libraries, *Adv. Immunol.*, 57:191-280 (1994).

Cama et al., Immunological abnormalities in insulin receptors on cultured EBV-transformed lymphocytes from insulin-resistant patient with leprechaunism, *Diabetes*, 37(7): 982-8 (1988).

Clackson et al., In vitro selection from protein and peptide libraries, *Trends Biotechnol.*, 12:173-84 (1994).

Clackson et al., Making antibody fragments using phage display libraries, *Nature*, 352:624-8 (1991).

Coligan et al. (eds), Current Protocols in Immunology, John Wiley & Sons, Inc. (1999).

Cosgrove, The Type I IGF receptor and the insulin receptor, Technical Bulletin No. 7, 2 pages (Sep. 2004).

Cwirla et al., Peptides on phage: a vast library of peptides for identifying ligands, *Proc. Natl. Acad. Sci. USA*, 87:6378-82 (1990).

Damschroder et al., Analysis of human and primate CD2 molecules by protein sequence and epitope mapping with anti-human CD2 antibodies, *Mol. Immunol.*, 41(10):985-1000 (2004).

Dayer et al., Lack of TNFR2 expression by CD4(+) T cells exacerbates experimental colitis, *Eur. J. Immunol.*, 39:1743-53 (2009).

De Luca et al., Inflammation and insulin resistance, *FEBS Lett.*, 582:97-105 (2008).

De Meyts et al., Structural biology of insulin and IGF1 receptors: implications for drug design, *Nat. Rev. Drug Discov.*, 1:769-83 (2002).

De Meyts et al., Timing-dependent modulation of insulin mitogenic versus metabolic signaling, *Novartis Found. Symp.*, 227:46-57 (2000).

De Meyts, Insulin and its receptor: structure, function and evolution, *Bioessays*, 26:1351-62 (2004).

De Meyts, The insulin receptor: a prototype for dimeric, allosteric membrane receptors?, *Trends Biochem. Sci.*, 33(8): 376-84 (2008).

De Pirro et al., Characterization of the serum from a patient with insulin resistance and hypoglycemia, *Diabetes*, 33: 301-304 (1984).

Dinarello, The many worlds of reducing interleukin-1, *Arthritis Rheum.*, 52:1960-7 (2005).

Dove et al., Cell signaling branches out, *Nat. Methods*, 3:223-9 (2006).

Forsayeth et al., Effect of monoclonal antibodies on human insulin receptor autophosphorylation, negative cooperativity, and down-regulation, *J. Biol. Chem.*, 262:4134-40 (1987).

Forsayeth et al., Monoclonal antibodies to the human insulin receptor that activate glucose transport but not insulin receptor kinase activity, *Proc. Natl. Acad. Sci. USA*, 84:3448-51 (1987).

Fuchs et al., Targeting recombinant antibodies to the surface of *Escherichia coli*: fusin to a peptidoglycan associated lipoprotein, *Bio/Technology*, 9:1370-2 (1991).

Ganderton et al., A monoclonal anti-peptide antibody reacting with the insulin receptor beta-subunit. Characterization of the antibody and its epitope and use in immunoaffinity purification of intact receptors, *Biochem. J.*, 288:195-205 (1992).

Garrard et al., Fab assembly and enrichment in a monovalent phage display system, *Biotechnology*, 9:1373-7 (1991).

Gasparini et al., Allosteric modulators for mGlu receptors, *Curr. Neuropharmacol.*, 5:187-94 (2007).

Geysen et al., Small peptides induce antibodies with a sequence and structural requirement for binding antigen comparable to antibodies raised against the native protein, *Proc. Natl. Acad. Sci. USA*, 82:178-82 (1985).

Geysen et al., Strategies for epitope analysis using peptide synthesis, *J. Immunol. Methods*, 102:259-74 (1987).

Geysen et al., The delineation of peptides able to mimic assembled epitopes, *Ciba Found Symp.*, 130-49 (1986).

Geysen et al., Use of peptide synthesis to probe viral antigens for epitopes to a resolution of a single amino acid, *Proc. Natl. Acad. Sci. USA*, 81:3998-4002 (1984).

Gherzi et al., Reevaluation of the evidence that an antibody to the insulin receptor is insulinmimetic without activating the protein tyrosine kinase activity of the receptor, *J. Biol. Chem.*, 262(35):16900-5 (1987).

Goldfine, The insulin receptor: molecular biology and transmembrane signaling, *Endocr. Rev.*, 8:235-55 (1987).

Goodman et al., Antibody binding to the juxtamembrane region of the insulin receptor alters receptor affinity, *J. Recept. Res.*, 14:381-98 (1994).

Gram et al., In vitro selection and affinity maturation of antibodies from a naive combinatorial immunoglobulin library, *Proc. Natl. Acad. Sci. USA*, 89:3576-80 (1992).

Gregory et al., Allosteric modulation of muscarinic acetylcholine receptors, *Curr. Neuropharmacol.*, 5:157-67 (2007).

Grell et al., The transmembrane form of tumor necrosis factor is the prime activating ligand of the 80 kDa tumor necrosis factor receptor, *Cell*, 83(5):793-802 (1995).

Griffiths et al., Human anti-self antibodies with high specificity from phage display libraries, *EMBO J.*, 12:725-34 (1993).

Gu et al., Reversal of insulin-induced negative cooperativity by monoclonal antibodies that stabilize the slowly dissociating ("Ksuper") state of the insulin receptor, *Biochem. Biophys. Res. Commun.*, 150:694-701 (1988).

Hanes et al., In vitro selection and evolution of functional proteins by using ribosome display, *Proc. Natl. Acad. Sci. USA*, 94:4937-42 (1997).

Hansen et al., Sustained signalling from the insulin receptor after stimulation with insulin analogues exhibiting increased mitogenic potency, *Biochem. J.*, 315:271-9 (1996).

Harlow et al., Antibodies, Cold Spring Harbor Laboratory, 285-7 (1998).

Harlow, Using Antibodies: A Laboratory Manual, Cold Spring Harbor Laboratory Press, 4 (1999).

Hawkins et al., Selection of phage antibodies by binding affinity. Mimicking affinity maturation, *J. Mol. Biol.*, 226:889-96 (1992).

(56) References Cited

OTHER PUBLICATIONS

Hawley et al., Insulin receptor monoclonal antibodies that mimic insulin action without activating tyrosine kinase, *J. Biol. Chem.*, 264:2438-44 (1989).
Hay et al., Bacteriophage cloning and *Escherichia coli* expression of a human IgM Fab, *Hum Antibodies Hybridomas*, 3:81-5 (1992).
Heffetz et al., Receptor aggregation is necessary for activation of the soluble insulin receptor kinase, *J. Biol. Chem.*, 261:889-94 (1986).
Herrera et al., Antibodies to deduced sequences of the insulin receptor distinguish conserved and nonconserved regions in the IGF-I receptor, *J. Biol. Chem.*, 261:2489-91 (1986).
Hoogenboom et al., Multi-subunit proteins on the surface of filamentous phage: methodologies for displaying antibody (Fab) heavy and light chains, *Nucleic Acids Res.*, 19:4133-7 (1991).
Huse et al., Generation of a large combinatorial library of the immunoglobulin repertoire in phage lambda, *Science*, 246:1275-81 (1989).
International Search Report and Written Opinion for International application No. PCT/US2010/050312, dated May 26, 2011.
International Search Report and Written Opinion from International application No. PCT/US2010/050313, dated Jun. 27, 2011.
Jacobs et al., Antibodies to purified insulin receptor have insulin-like activity, *Science*, 200:1283-4 (1978).
Jacobs et al., Insulin receptors and insulin receptor antibodies: structure-function relationships, *Ciba Found. Symp.*, 90:82-90 (1982).
Jahns et al., Modulation of beta1-adrenoceptor activity by domain-specific antibodies and heart failure-associated autoantibodies, *J. Am. Coll. Cardiol.*, 36:1280-7 (2000).
Janas et al., Rituxan (anti-CD20 antibody)-induced translocation of CD20 into lipid rafts is crucial for calcium influx and apoptosis, *Clin. Exp. Immunol.*, 139:439-46 (2005).
Jensen et al., Activation of the insulin receptor by insulin and a synthetic peptide leads to divergent metabolic and mitogenic signaling and responses, *J. Biol. Chem.*, 282(48):35179-86 (2007).
Jensen et al., Allosteric modulation of the calcium-sensing receptor, *Curr. Neuropharmacol.*, 5:180-6 (2007).
Jensen et al., Molecular mechanisms of differential intracellular signaling from the insulin receptor, *Vitam. Horm.*, 80:51-75 (2009).
Jespers et al., Guiding the selection of human antibodies from phage display repertoires to a single epitope of an antigen, *Biotechnology*, 12:899-903 (1994).
Jiang et al., Display of a PorA peptide from Neisseria meningitidis on the bacteriophage T4 capsid surface, *Chemical Abstracts*, 128(5):44380q (1997).
Kahn et al., Direct demonstration that receptor crosslinking or aggregation is important in insulin action, *Proc. Natl. Acad. Sci. USA*, 75:4209-13 (1978).
Kang et al., Linkage of recognition and replication functions by assembling combinatorial antibody Fab libraries along phage surfaces, *Proc. Natl. Acad. Sci. USA*, 88:4363-6 (1991).
Kenakin, Allosteric agonist modulators, *J. Recept. Signal Transduct. Res.*, 27:247-59 (2007).
Kenakin, Allosteric theory: Taking therapeutic advantage of the malleable nature of GPCRs, *Curr. Neuropharmacol.*, 5:149-56 (2007).
Klimka et al., Human anti-CD30 recombinant antibodies by guided phage antibody selection using cell planning, *Br. J. Cancer*, 83(2):252-60 (2000).
Kull et al., A monoclonal antibody to human insulin receptor, *Biochem. Biophys. Res. Commun.*, 106(3):1019-26 (1982).
Kull et al., Monoclonal antibodies to receptors for insulin and somatomedin-C, *J. Biol. Chem.*, 258:6561-6 (1983).
Kurtzhals et al., Correlations of receptor binding and metabolic and mitogenic potencies of insulin analogs designed for clinical use, *Diabetes*, 49:999-1005 (2000).
Le Marchand-Brustel et al., Anti-insulin receptor antibodies inhibit insulin binding and stimulate glucose metabolism in skeletal muscle, *Diabetologic*, 14:311-7 (1978).
Le Marchand-Brustel et al., Anti-insulin receptor antibodies inhibit insulin binding and stimulate glucose metabolism in skeletal muscle, *Diabetologia*, 14: 311-317 (1978).
LeBrun et al., Antibodies to the extracellular receptor domain restore the hormone-insensitive kinase and conformation of the mutant insulin receptor valine 382, *J. Biol. Chem.*, 268:11272-7 (1993).
Lee et al., Microbial cell-surface display, *Trends Biotechnol.*, 21:45-52 (2003).
Li et al., Small molecule insulin receptor activators potentiate insulin action in insulin-resistant cells, *Diabetes*, 50:2323-8 (2001).
Liu et al., Development of a novel GLUT4 translocation assay for identifying potential novel therapeutic targets for insulin sensitization, *Biochem. J.*, 418:413-20 (2009).
Lou et al., The first three domains of the insulin receptor differ structurally from the insulin-like growth factor 1 receptor in the regions governing ligand specificity, *Proc. Natl. Acad. Sci. USA*, 103:12429-34 (2006).
Lowman et al., Selecting high-affinity binding proteins by monovalent phage display, *Biochem.*, 30:10832-8 (1991).
Lupsa et al. Autoimmune forms of hypoglycemia, *Medicine*, 88:141-153 (2009).
Malmqvist et al., Kinetic analysis of engineered antibody-antigen interactions, *J. Mol. Recognit.*, 7:1-7 (1994).
Manchem et al., A novel small molecule that directly sensitizes the insulin receptor in vitro and in vivo, *Diabetes*, 50:824-30 (2001).
Marks et al., By-passing immunization. Human antibodies from V-gene libraries displayed on phage, *J. Mol. Biol.*, 222:581-97 (1991).
Marks et al., By-passing immunization: building high affinity human antibodies by chain shuffling, *Biotechnology*, 10:799-83 (1992).
Massart et al., Monoclonal antibodies to bovine growth hormone potentiate hormonal activity in vivo by enhancing growth hormone binding to hepatic somatogenic receptors, *J. Endocrinol.*, 139:383-93 (1993).
May et al., Allosteric modulation of G protein-coupled receptors, *Annu. Rev. Pharmacol. Toxicol.*, 47:1-51 (2007).
Mc Kern et al., Structure of the insulin receptor ectodomain reveals a folded-over conformation, *Nature*, 443:218-21 (2006).
McCafferty et al., Phage antibodies: filamentous phage displaying antibody variable domains, *Nature*, 348:552-4 (1990).
McPherson et al., The nuclear transcription factor CREB: involvement in addiction, deletion models and looking forward, *Curr. Neuropharmacol.*, 5:202-12 (2007).
Moller, New drug targets for type 2 diabetes and the metabolic syndrome, *Nature*, 414:821-7 (2001).
Morgan et al., Insulin action is blocked by a monoclonal antibody that inhibits the insulin receptor kinase, *Proc. Natl. Acad. Sci. USA*, 83:328-32 (1986).
Morgan et al., Mapping surface structures of the human insulin receptor with monoclonal antibodies: localization of main immunogenic regions to the receptor kinase domain, *Biochemistry*, 25(6):1364-71 (1986).
Mukai et al., Fast binding kinetics and conserved 3D structure underlie the antagonistic activity of mutant TNF: useful information for designing artificial proteo-antagonists, *J. Biochem.*, 146:167-72 (2009).
Mutel et al., Editorial: The pros of not being competitive, *Curr. Neuropharmacol.*, 5: 148 (2007).
O'Brien et al., Monoclonal antibodies for the human insulin receptor stimulate intrinsic receptor-kinase activity, *Biochemical Society Transactions*, 14:1021-3 (1986).
Orgad et al., Single chain antibody against the common epitope of mutant p53 restores wild-type activity to mutant p53 protein, *FEBS Lett.*, 579:5609-15 (2005).
Ortlepp et al., Antibodies that activate b2 integrins can generate different ligand binding states, *Eur. J. Immunol.*, 25:637-43 (1995).
Padlan, Anatomy of the antibody molecule, *Mol. Immunol.*, 31:169-217 (1994).

(56) References Cited

OTHER PUBLICATIONS

Pandini et al., Insulin/insulin-like growth factor I hybrid receptors have different biological characteristics depending on the insulin receptor isoform involved, *J. Biol. Chem.*, 277(42):39684-85 (2002).
Pender et al., Regulation of insulin receptor function by a small molecule insulin receptor activator, *J. Biol. Chem.*, 277:43565-71 (2002).
Petruzzelli et al., Activation of lymphocyte function-associated molecule-1 (CD11a/CD18) and Mac-1 (CD11b/CD18) mimicked by an antibody directed against CD18, *J. Immunol.*, 155:854-66 (1995).
Pin et al., Allosteric modulators of GABAB receptors: mechanism of action and therapeutic perspective, *Curr. Neuropharmacol.*, 5:195-201 (2007).
Ponzio et al., Insulin and rabbit anti-insulin receptor antibodies stimulate additively the intrinsic receptor kinase activity, *EMBO J.*, 6:333-40 (1987).
Ponzio et al., Use of an anti-insulin receptor antibody to discriminate between metabolic and mitogenic effects of insulin: correlation with receptor autophosphorylation, *EMBO J.*, 7:4111-7 (1988).
Portolano et al., Lack of Promiscuity in autoantigen-specific H and L chain combinations as revealed by human H and L chain "roulette"., *J. Immunol.*, 150(3):880-7 (1993).
Pradillo et al., TNFR1 upregulation mediates tolerance after brain ischemic preconditioning, *J. Cereb. Blood Flow Metab.*, 25:193-203 (2005).
Prigent et al., Identification of epitopes on the human insulin receptor reacting with rabbit polyclonal antisera and mouse monoclonal antibodies, *J. Biol. Chem.*, 265:9970-7 (1990).
Qureshi et al., Activation of insulin signal transduction pathway and anti-diabetic activity of small molecule insulin receptor activators, *J. Biol. Chem.*, 275:36590-5 (2000).
Rakatzi et al., A novel insulin analog with unique properties: LysB3,GluB29 insulin induces prominent activation of insulin receptor substrate 2, but marginal phosphorylation of insulin receptor substrate 1, *Diabetes*, 52:2227-38 (2003).
Roth et al., Monoclonal antibodies to the human insulin receptor block insulin binding and inhibit insulin action, *Proc. Natl. Acad. Sci. USA*, 79:7312-6 (1982).
Roth et al., Monoclonal antibodies to the insulin receptor, *Pharmacol. Ther.*, 28:1-16 (1985).
Roth et al., Regulation of the insulin receptor by a monoclonal anti-receptor antibody. Evidence that receptor down regulation can be independent of insulin action., *J. Biol. Chem.*, 258:12094-7 (1983).
Saxena et al., Allosteric control of acetylcholinesterase activity by monoclonal antibodies, *Biochem.*, 37:145-54 (1998).
Schaffer et al., A novel high-affinity peptide antagonist to the insulin receptor, *Biochem. Biophys. Res. Commun.*, 376:380-3 (2008).
Schaffer et al., Assembly of high-affinity insulin receptor agonists and antagonists from peptide building blocks, *Proc. Natl. Acad. Sci. USA*, 100:4435-9 (2003).
Schoofs et al., Epitopes of an influenza viral peptide recognized by antibody at single amino acid resolution, *J. Immunol.*, 140:611-6 (1988).
Sergeeva et al., Display technologies: application for the discovery of drug and gene delivery agents, *Adv. Drug Deliv. Rev.*, 58:1622-54 (2006).
Shechter et al., Modulation of binding and bioactivity of insulin by anti-insulin antibody: relation to possible role of receptor self-aggregation in hormone action, *Proc. Natl. Acad. Sci. USA*, 76(6):2720-4 (1979).
Siddle et al., Monoclonal antibodies as probes of the structure and function of insulin receptors, *Biochem. Soc. Trans.*, 15:47-51 (1987).
Silverstein et al., Care of children and adolescents with type 1 diabetes: a statement of the Diabetes Association, *Diabetes Care*, 28:186-212 (2005).

Smith et al., Structural resolution of a tandem hormone-binding element in the insulin receptor and its implications for design of peptide agonists. *Proc. Natl. Acad. Sci. USA*, 107:6771-76 (2010).
Smith, Surface presentation of protein epitopes using bacteriophage expression systems, *Curr. Opin. Botechnol.*, 2:668-73 (1991).
Sojar et al., A chemical method for the deglycosylation of proteins, *Arch. Biochem. Biophys.*, 259:52-7 (1987).
Soos et al., Monoclonal antibodies reacting with multiple epitopes on the human insulin receptor, *Biochem. J.*, 235:199-208 (1986).
Soos et al., Monoclonal antibodies to the insulin receptor mimic metabolic effects of insulin but do not stimulate receptor autophosphorylation in transfected NIH 3T3 fibroblasts, *Proc. Natl. Acad. Sci. USA*, 86(14):5217-21 (1989).
Spasov et al., Study of antidiabetic activity of a new ultralow-dose antibody preparation on the model of streptozotocin diabetes in rats, *Bull. Exp. Biol. Med.*, 144:46-8 (2007).
Steele-Perkins et al., Insulin-mimetic anti-insulin receptor monoclonal antibodies stimulate receptor kinase activity in intact cells, *J. Biol. Chem.*, 265:9458-63 (1990).
Strowski et al., Small-molecule insulin mimetic reduces hyperglycemia and obesity in a nongenetic mouse model of type 2 diabetes, *Endocrinology*, 145:5259-68 (2004).
Surinya et al., Role of insulin receptor dimerization domains in ligand binding, cooperativity, and modulation by anti-receptor antibodies, *J. Biol. Chem.*, 277(19):16718-25 (2002).
Taylor et al., Hypoglycemia associated with antibodies to the insulin receptor, *N. Engl. J. Med.*, 307:1422-6 (1982).
Taylor et al., Insulin-like and insulin-inhibitory effects of monoclonal antibodies for different epitopes on the human insulin receptor, *Biochem. J.*, 242:123-9 (1987).
Towbin et al., Neoepitope immunoassay: an assay for human interleukin 1 beta based on an antibody induced conformational change, *J. Immunoassay*, 17:353-69 (1996).
Tulloch et al., Single-molecule imaging of human insulin receptor ectodomain and its Fab complexes, *J. Struct. Biol.*, 125:11-8 (1999).
Vajdos et al., Comprehensive functional maps of the antigen-binding site of an anti-ErbB2 antibody obtained with shotgun scanning mutagenesis, *J. Mol. Biol.*, 320(2):415-28 (2002).
Walshe et al., Induction of cytosolic calcium flux by CD20 is dependent upon B Cell antigen receptor signaling, *J. Biol. Chem.*, 283:16971-84 (2008).
Wang et al., Negative and positive site-site interactions, and their modulation by pH, insulin analogs, and monoclonal antibodies, are preserved in the purified insulin receptor, *Proc. Natl. Acad. Sci. USA*, 85(22):8400-4 (1988).
Ward et al., Ligand-induced activation of the insulin receptor: a multi-step process involving structural changes in both the ligand and the receptor, *Bioessays*, 31:422-34 (2009).
Ward et al., Structural insights into ligand-induced activation of the insulin receptor, *Acta Physiol. (Oxf.)*, 192:3-9 (2008).
Watkins, Screening of phage-expressed antibody libraries by capture lift, *Methods Mol. Biol.*, 178:187-93 (2002).
Wickstrom, Effects of nicotine during pregnancy: human and experimental evidence, *Curr. Neuropharmacol.*, 5:213-22 (2007).
Winter et al., Making antibodies by phage display technology, *Annu. Rev. Immunol.*, 12:433-55 (1994).
Wittrup, Protein engineering by cell-surface display, *Curr. Opin. Biotechnol.*, 12:395-9 (2001).
Yip et al., Localization of the insulin-binding site to the cysteine-rich region of the insulin receptor alpha-subunit, *Biochem. Biophys. Res. Commun.*, 157(1):321-9 (1988).
Zhang et al., A region of the insulin receptor important for ligand binding (residues 450-601) is recognized by patients' autoimmune antibodies and inhibitory monoclonal antibodies, *Proc. Natl. Acad. Sci. USA*, 88:9858-62 (1991).
Zhang et al., Discovery of a small molecule insulin mimetic with antidiabetic activity in mice, *Science*, 284:974-7 (1999).
Zick et al., The role of antireceptor antibodies in stimulating phosphorylation of the insulin receptor, *J. Biol. Chem.*, 259:4396-400 (1984).

Figure 1.
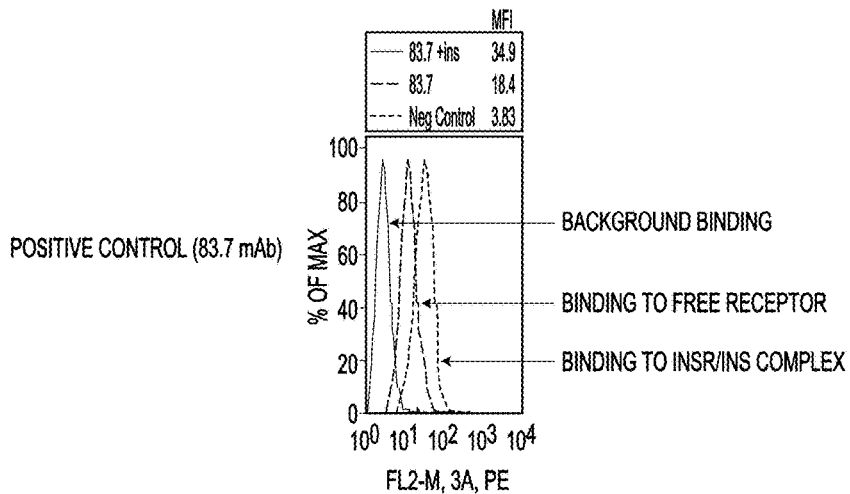
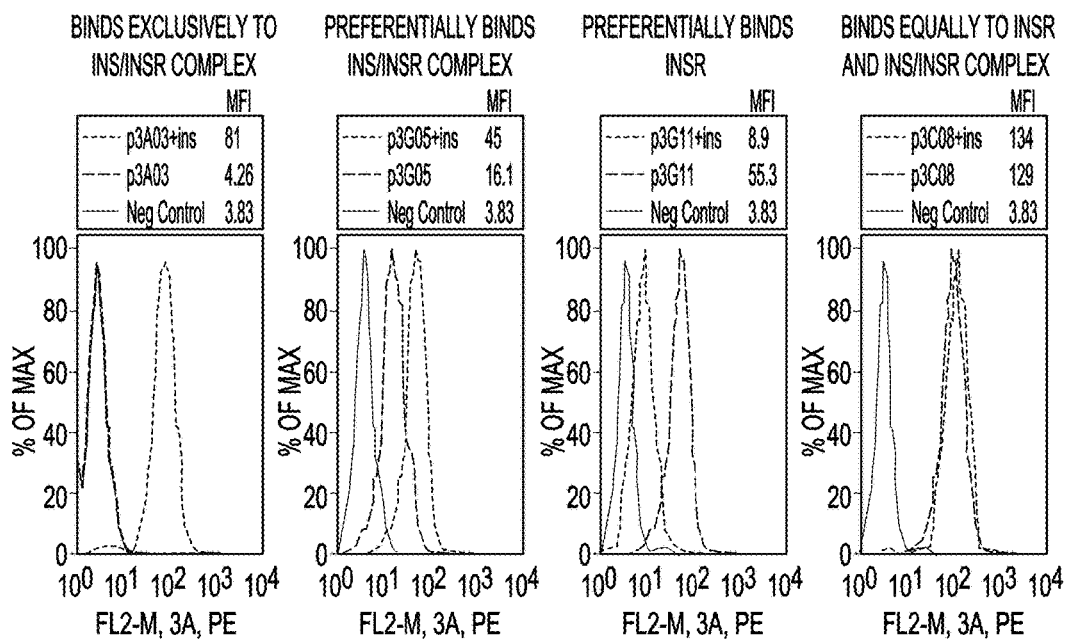

Figure 2
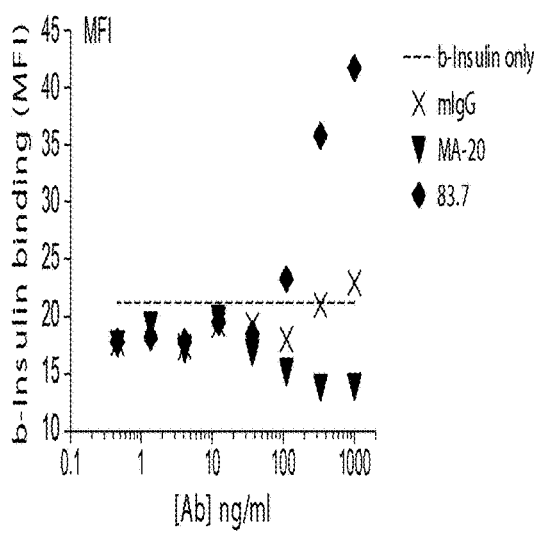
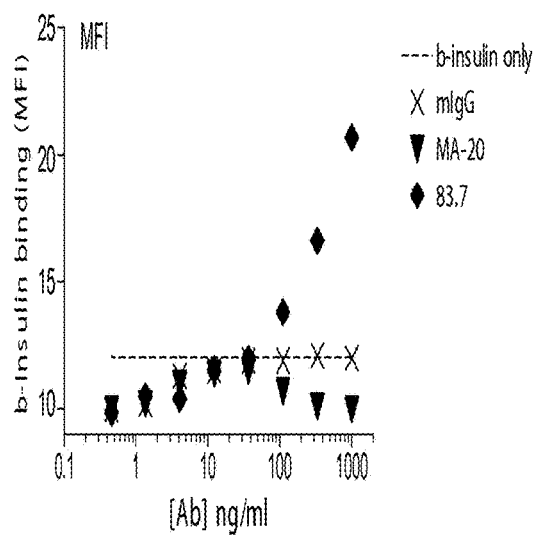
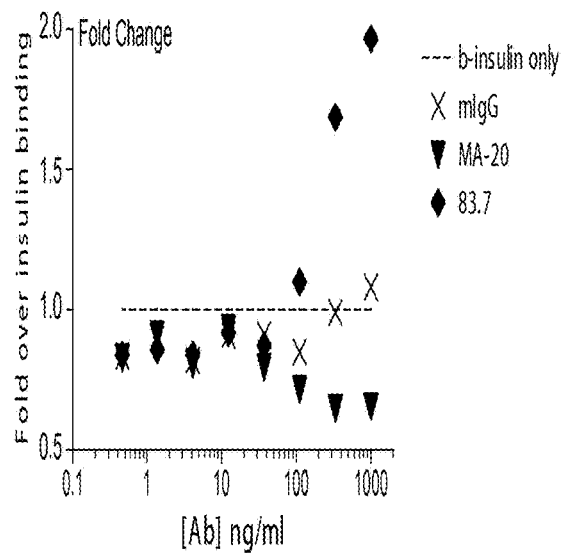
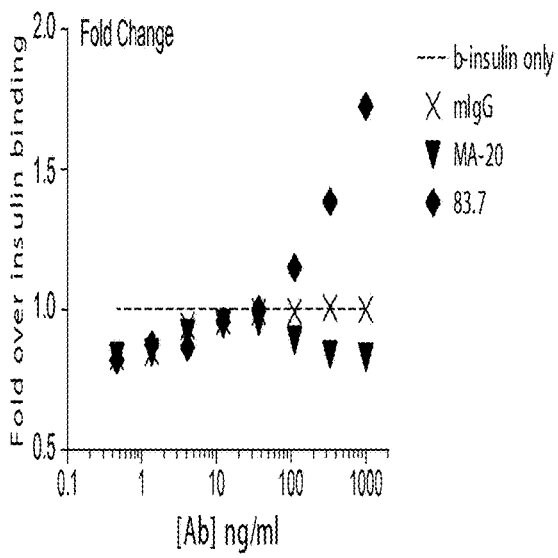

Figure 4
Figure 4A. Positive modulator
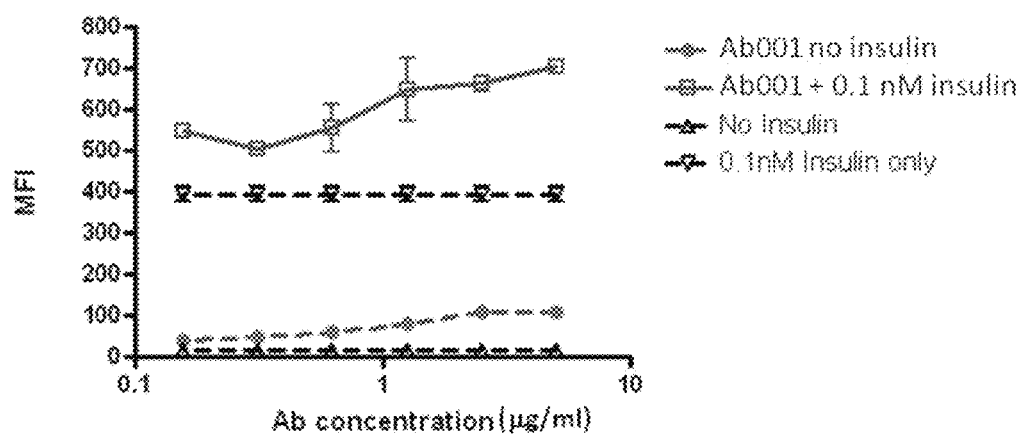
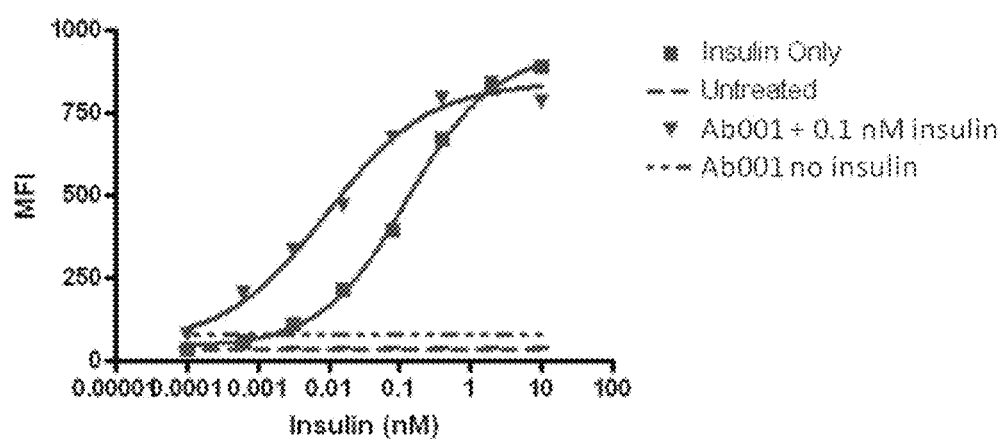

Figure 4B. Positive modulator with significant agonism
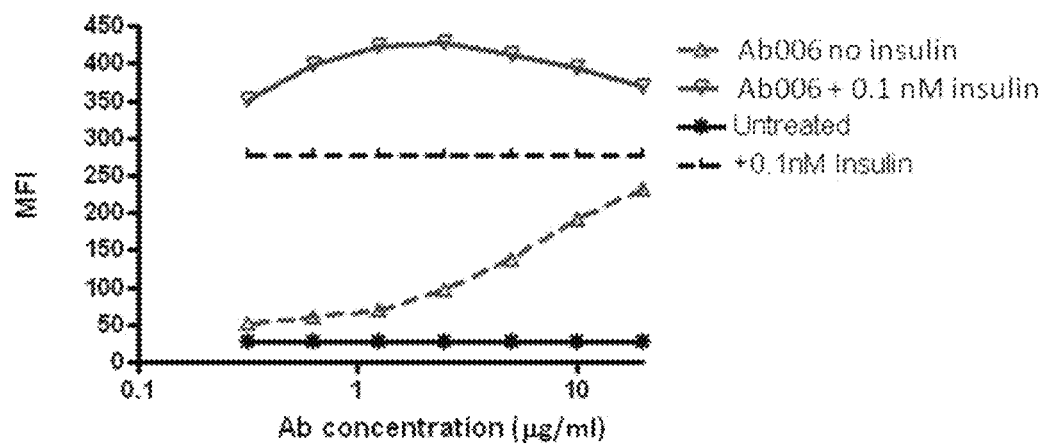
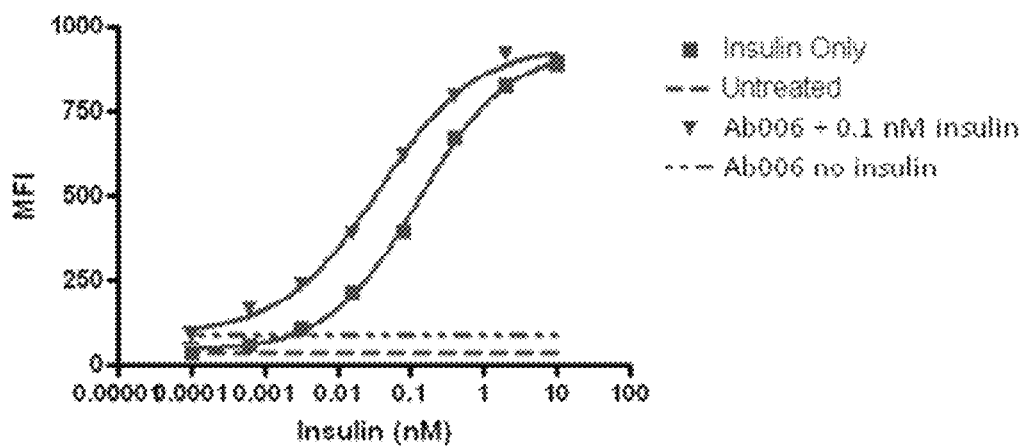

Figure 4C. Non-modulator
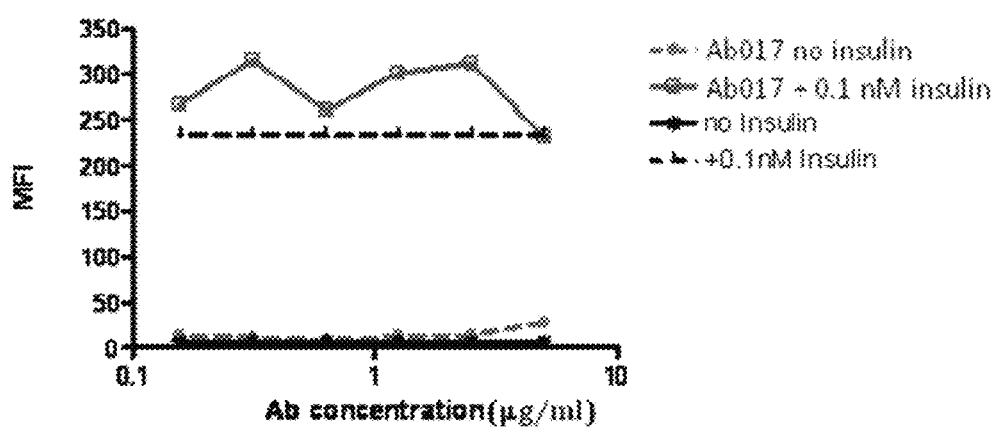
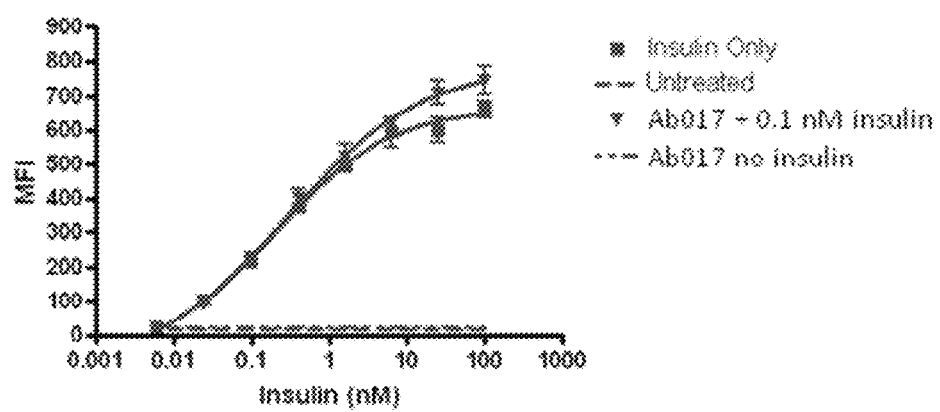

Figure 4D. Agonist Abs
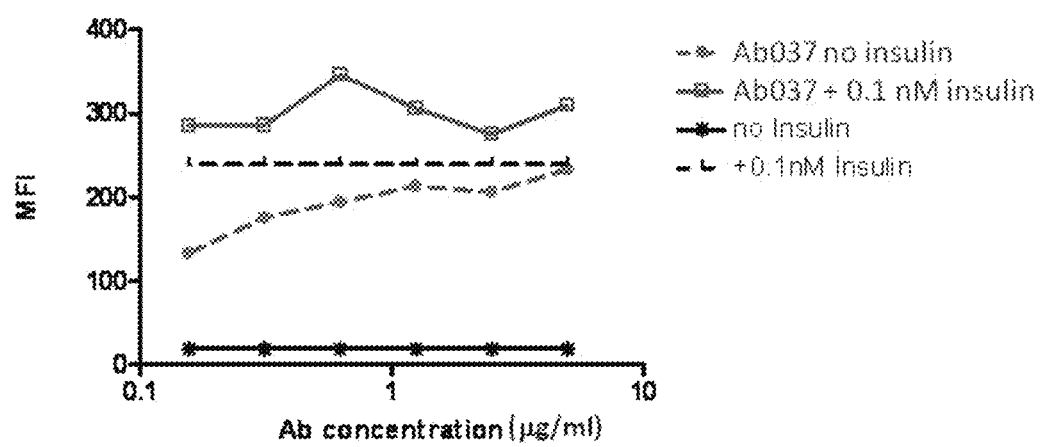
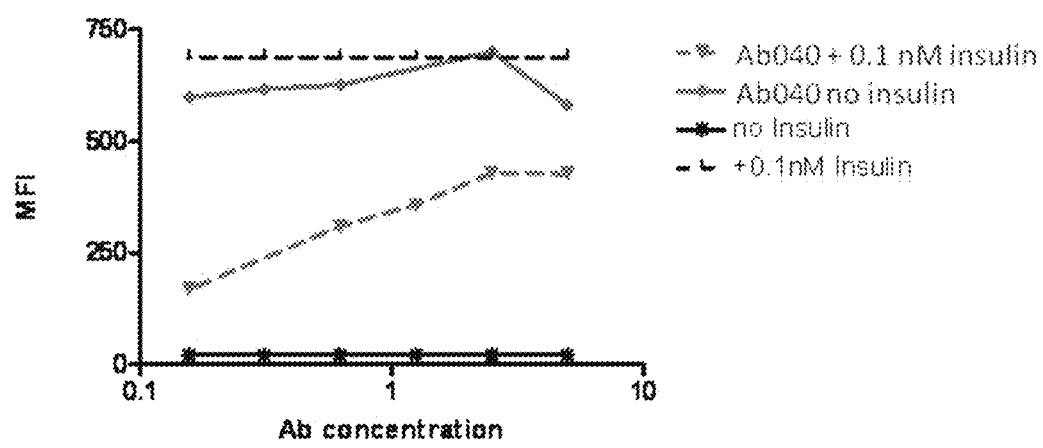

Figure 4E. Negative modulator
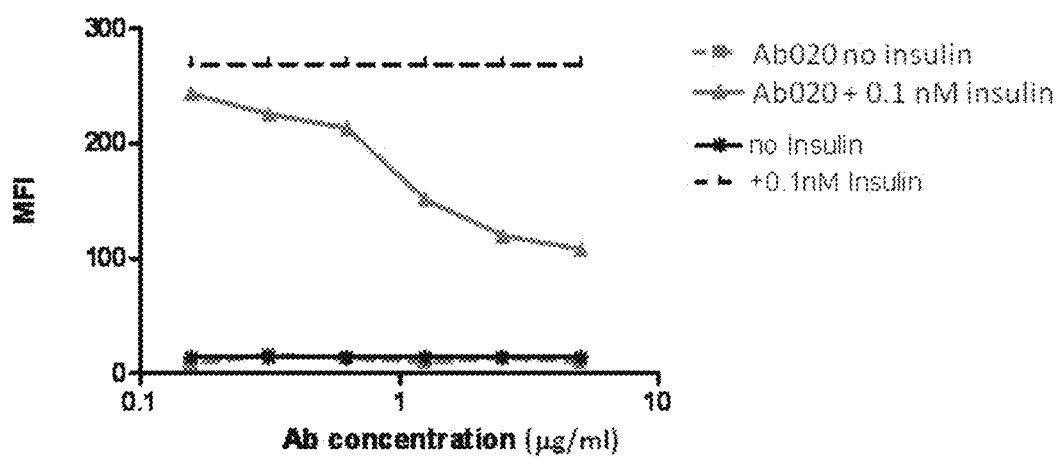
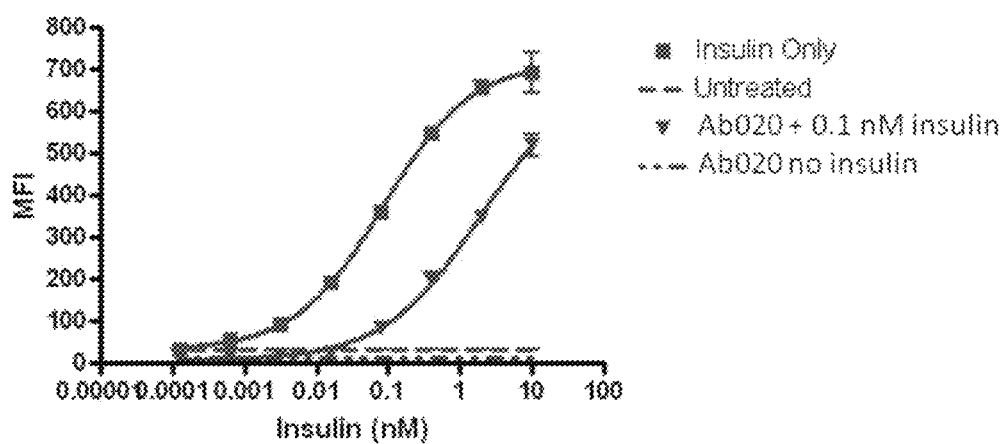

Figure 5

| Ab | Ab type | [Ab] (ug/ml) | Insulin EC50 (nM) | | Fold change in insulin EC50 | | | Ab property |
|---|---|---|---|---|---|---|---|---|
| | | | insulin alone | Insulin + antibody | -Ab EC50/+Ab EC50 | +Ab EC50/-Ab EC50 | absolute change | |
| Ab001 | IgG2 | 5.00 | 0.11 | 0.0048 | 23.32 | 0.04 | 23.32 | Abs with significant positive modulation |
| Ab002 | IgG2 | 2.50 | 0.12 | 0.0166 | 7.32 | 0.14 | 7.32 | |
| Ab003 | IgG2 | 2.25 | 0.12 | 0.0171 | 7.11 | 0.14 | 7.11 | |
| Ab004 | IgG2 | 5.00 | 0.13 | 0.0239 | 5.34 | 0.19 | 5.34 | |
| Ab005 | Fab | 2.50 | 0.08 | 0.0188 | 4.48 | 0.22 | 4.48 | |
| Ab006 | IgG2 | 1.25 | 0.13 | 0.0367 | 3.47 | 0.29 | 3.47 | |
| Ab007 | IgG2 | 5.00 | 0.11 | 0.0346 | 3.22 | 0.31 | 3.22 | |
| Ab008 | Fab | 0.63 | 0.08 | 0.0270 | 3.11 | 0.32 | 3.11 | |
| Ab009 | IgG2 | 5.00 | 0.13 | 0.0461 | 2.77 | 0.36 | 2.77 | |
| Ab010 | IgG2 | 2.50 | 0.12 | 0.0463 | 2.62 | 0.38 | 2.62 | |
| Ab011 | IgG2 | 2.50 | 0.13 | 0.0719 | 1.78 | 0.56 | 1.78 | Abs without significant modulation |
| Ab012 | IgG2 | 2.50 | 0.08 | 0.0504 | 1.67 | 0.60 | 1.67 | |
| Ab013 | IgG2 | 1.25 | 0.08 | 0.0540 | 1.56 | 0.64 | 1.56 | |
| Ab014 | IgG2 | 5.00 | 0.11 | 0.0984 | 1.13 | 0.88 | 1.13 | |
| Ab015 | IgG2 | 1.25 | 0.20 | 0.2450 | 0.82 | 1.23 | 1.23 | |
| Ab016 | IgG2 | 1.25 | 0.20 | 0.2714 | 0.74 | 1.36 | 1.36 | |
| Ab017 | IgG2 | 2.50 | 0.20 | 0.2747 | 0.73 | 1.37 | 1.37 | |
| Ab018 | IgG2 | 5.00 | 0.09 | 0.2969 | 0.29 | 3.48 | 3.48 | Abs with significant negative modulation |
| Ab019 | Fab | 5.00 | 0.09 | 0.4527 | 0.19 | 5.31 | 5.31 | |
| Ab020 | IgG2 | 5.00 | 0.09 | 1.8570 | 0.05 | 21.79 | 21.79 | |

Figure 6
Figure 6A. Positive modulator with very low agonism
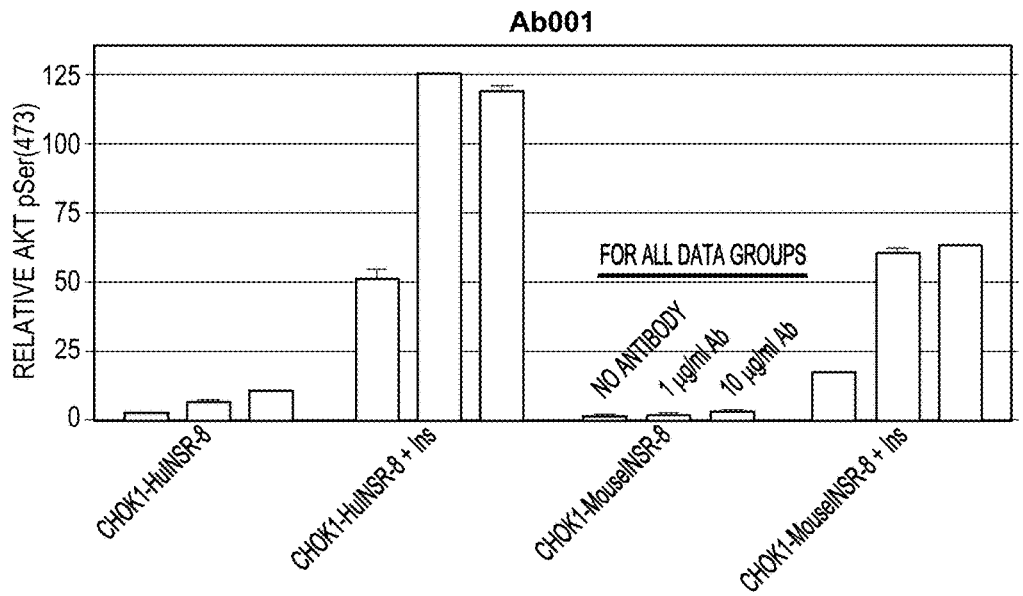
Figure 6B. Positive modulator with agonism
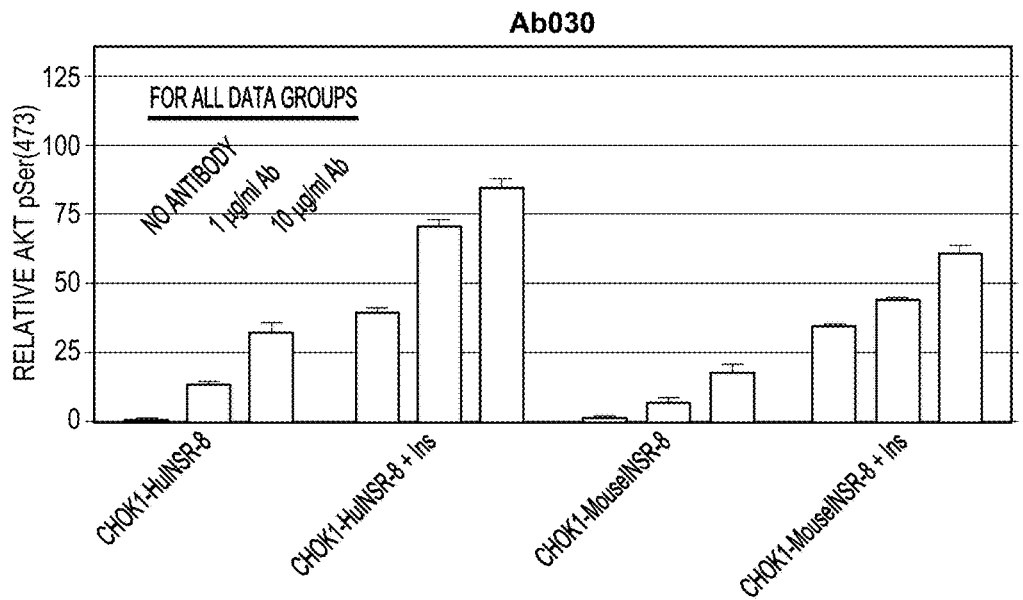

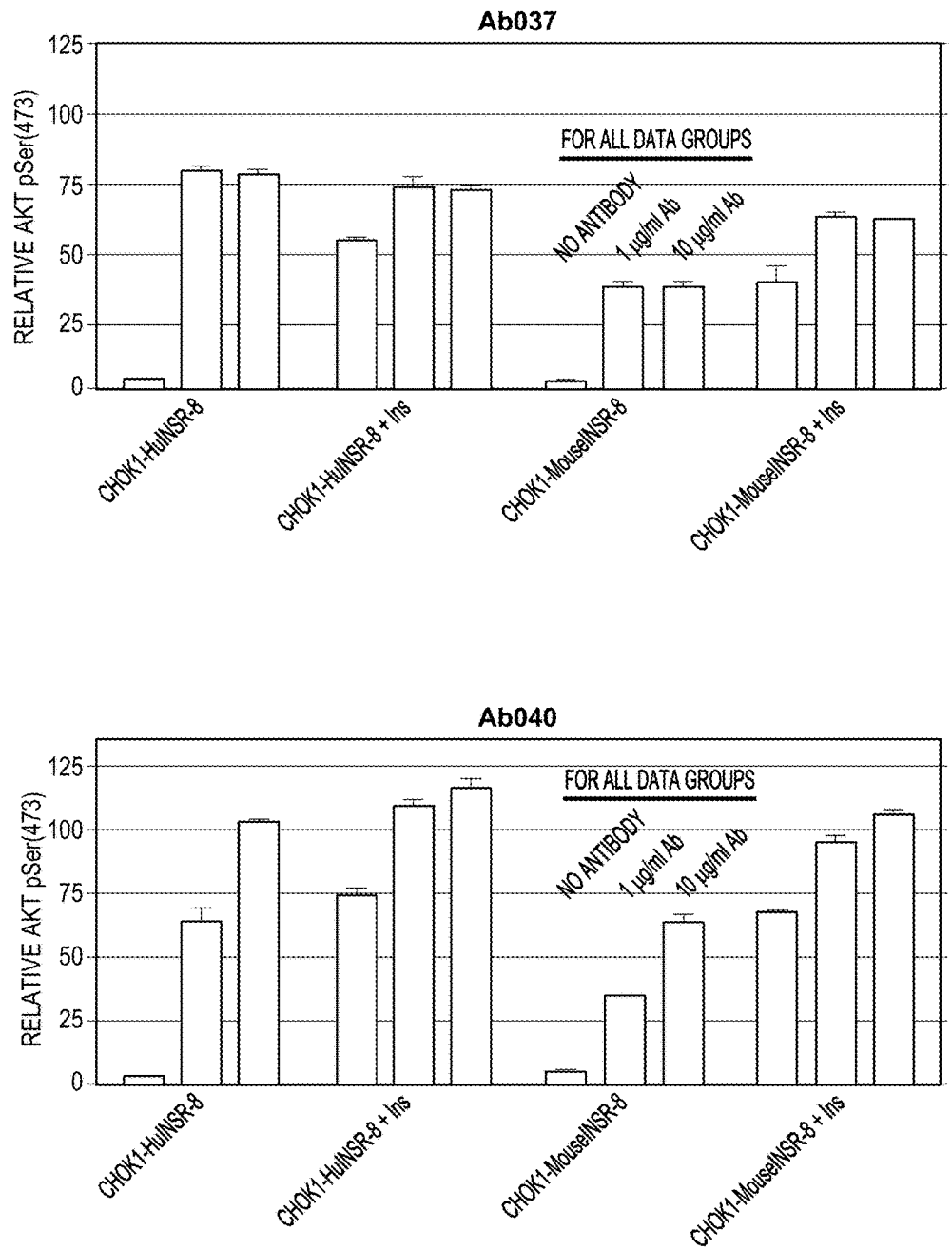
Figure 6C. Agonist Abs

Figure 6D. 83-7
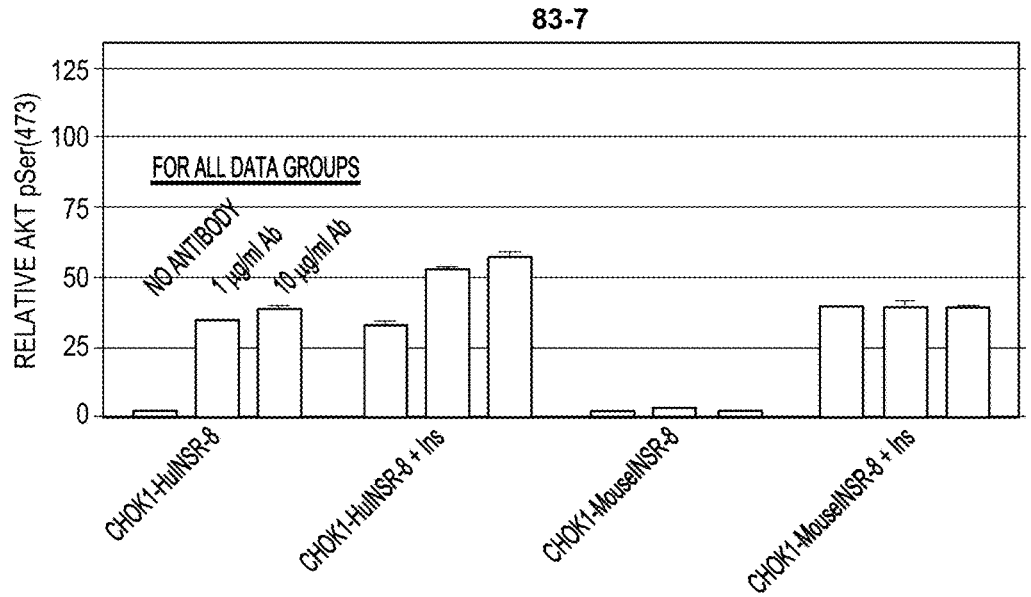
Figure 6E. Insulin and background response in the absence of antibody
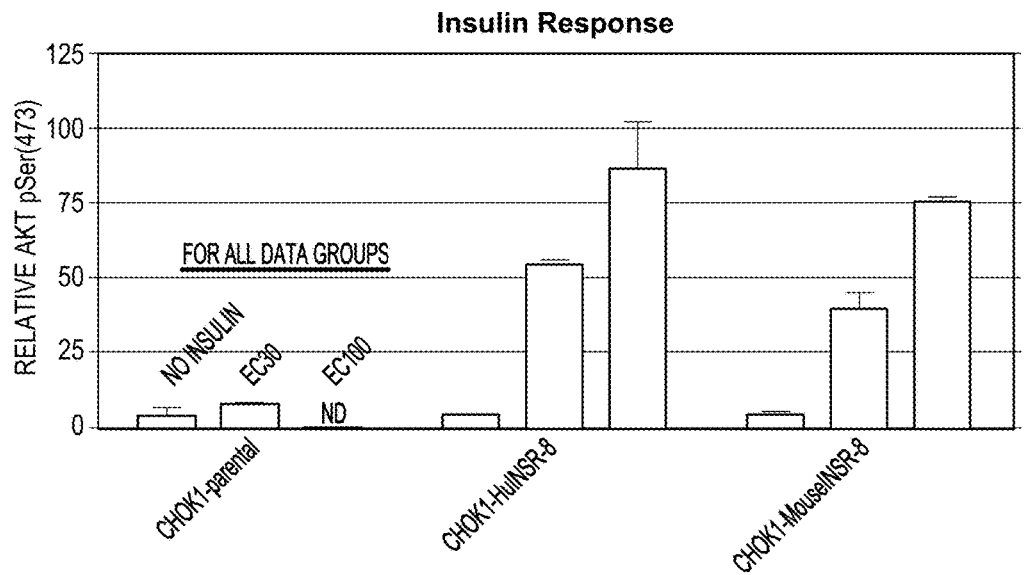

Figure 7

| Agonism class | Antibody | agonist of human INSR by pIRS-1 | agonist of human INSR by pAkt | agonist of mouse INSR by pAkt | cross reactive to mouse INSR by FACS | cross reactive to mouse INSR by pAkt |
|---|---|---|---|---|---|---|
| Abs with weak or very weak agonism | Ab021 | yes | nd | nd | nd | nd |
| | Ab022 | yes | nd | nd | nd | nd |
| | Ab023 | yes | nd | nd | nd | nd |
| | Ab024 | yes | nd | nd | no | nd |
| | Ab025 | yes | nd | nd | no | nd |
| | Ab026 | yes | nd | nd | no | nd |
| | Ab027 | yes | nd | nd | no | nd |
| | Ab028 | yes | nd | nd | no | nd |
| | Ab013 | yes | nd | nd | no | nd |
| | Ab011 | yes | nd | nd | yes | nd |
| | Ab001 | yes | yes | no | yes | yes |
| | Ab015 | yes | yes | no | no | no |
| | Ab002 | yes | yes | no | no | no |
| Abs with moderate agonism | Ab029 | yes | nd | nd | nd | nd |
| | Ab017 | yes | yes | no | yes | no |
| | Ab030 | yes | yes | yes | yes | yes |
| | Ab031 | yes | nd | nd | no | nd |
| | Ab009 | yes | yes | yes | yes | yes |
| | Ab032 | yes | yes | yes | yes | yes |
| | Ab018 | yes | nd | nd | yes | nd |
| | Ab033 | yes | nd | nd | yes | nd |
| | Ab012 | yes | yes | no | no | yes |
| | Ab014 | yes | yes | yes | yes | yes |
| | Ab034 | yes | nd | nd | nd | nd |
| | Ab010 G1 | yes | yes | no | no | no |
| | Ab010 G2 | yes | yes | no | yes | yes |
| | Ab003 | yes | nd | nd | nd | nd |
| Abs with strong agonism | Ab006 | yes | yes | yes | yes | yes |
| | Ab035 | yes | nd | nd | no | nd |
| | Ab036 | yes | yes | yes | yes | yes |
| | Ab037 | yes | yes | yes | yes | yes |
| | Ab038 | yes | yes | no | yes | no |
| | Ab039 | yes | yes | yes | yes | yes |
| | Ab040 | yes | yes | yes | yes | yes |
| | Ab041 | yes | nd | nd | nd | nd |
| | Ab042 | yes | nd | nd | no | nd |
| | Ab043 | yes | yes | yes | yes | yes |

| Agonism class | Antibody | agonist of human INSR by pIRS-1 | agonist of human INSR by pAkt | agonist of mouse INSR by pAkt | cross reactive to mouse INSR by FACS | cross reactive to mouse INSR by pAkt |
|---|---|---|---|---|---|---|
| | Ab044 | yes | nd | nd | yes | nd |
| | Ab045 | yes | nd | nd | yes | nd |
| | Ab046 | yes | yes | yes | yes | yes |
| | Ab047 | yes | nd | nd | no | nd |
| | Ab048 | yes | yes | no | yes | no |
| | Ab049 | yes | yes | no | no | no | nd = not determined

Figure 7 (cont'd)

| Ab Concentration (ug/mL) | HILLSLOPE | EC50 (pM) | Fold-change in EC50 |
|---|---|---|---|
| 1.25 Ab001 | 1.49 | 51 | 5.9 |
| 0.62 Ab001 | 1.44 | 53 | 5.7 |
| 0.31 Ab001 | 1.32 | 57 | 5.3 |
| 0.15 Ab001 | 1.33 | 68 | 4.4 |
| 1.25 anti-KLH | 0.76 | 301 | |

Figure 10
Blood Glucose Levels in DIO Mice Treated with Partial Agonist Anti-INSR Antibodies
Figure 10A.
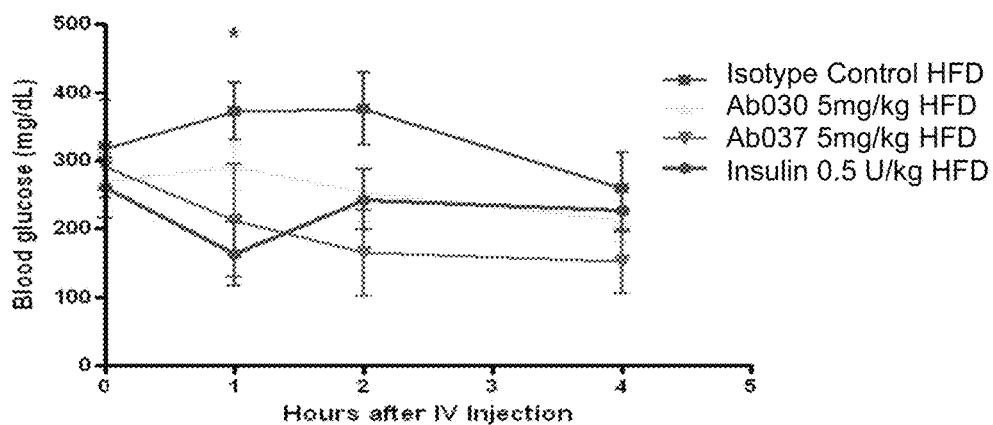
* $p < 0.01$ (one-tailed) ND/isotype compared to HFD/isotype
Figure 10B.
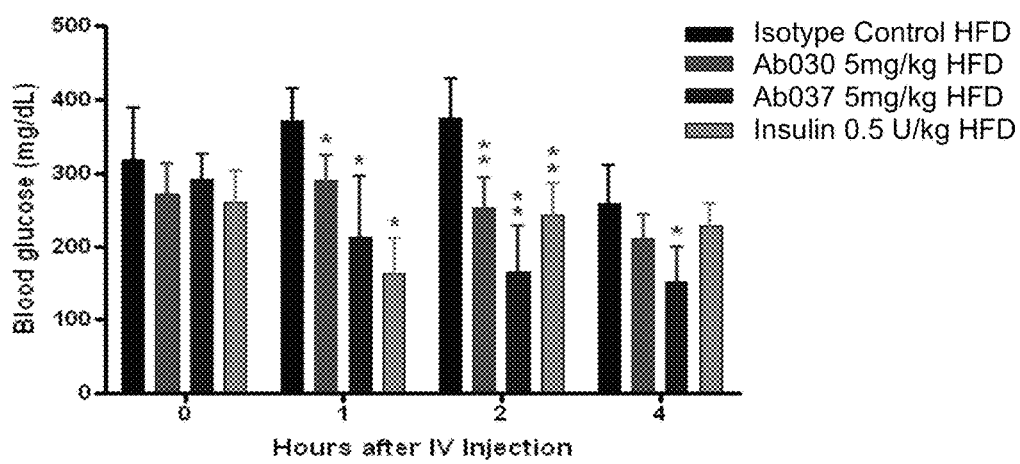
* $p \leq 0.01$ (two-tailed) compared to HFD/isotype
⁑ $p < 0.001$ (two tailed) compared to HFD/isotype

Figure 11
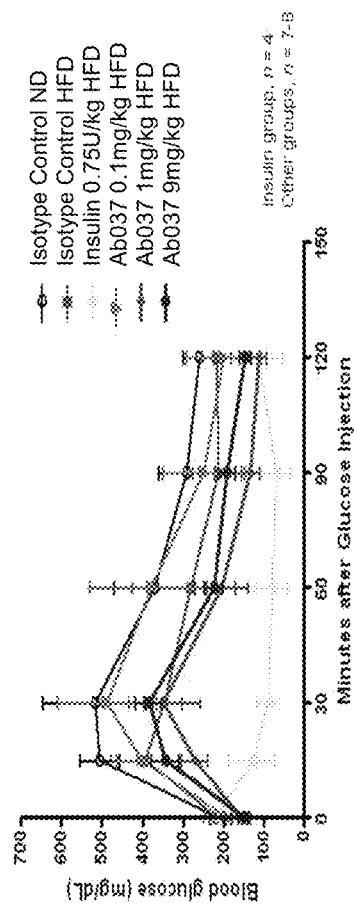
Figure 11A.
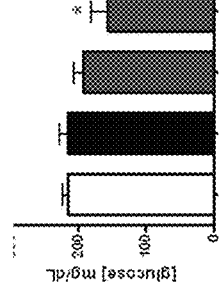
Figure 11B.
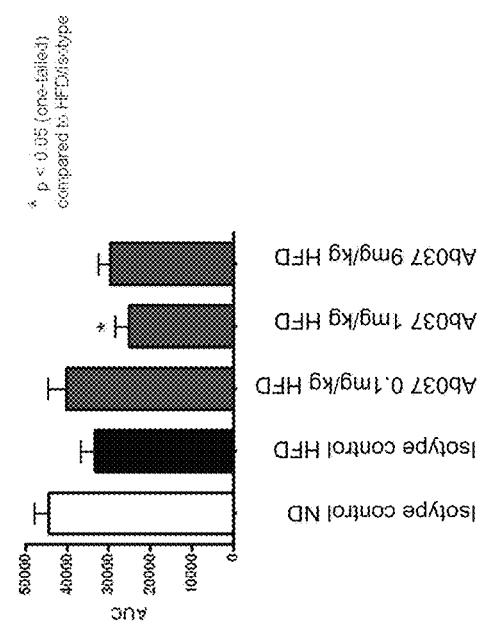
Figure 11C.

Figure 12
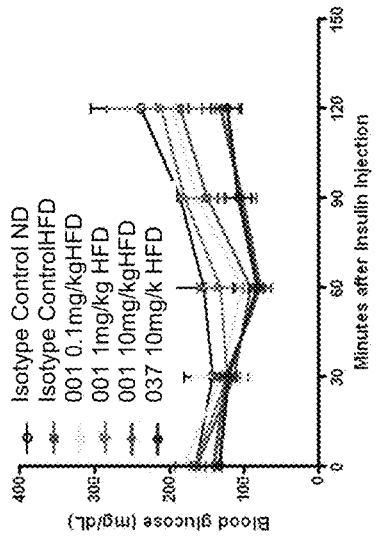
Figure 12A.
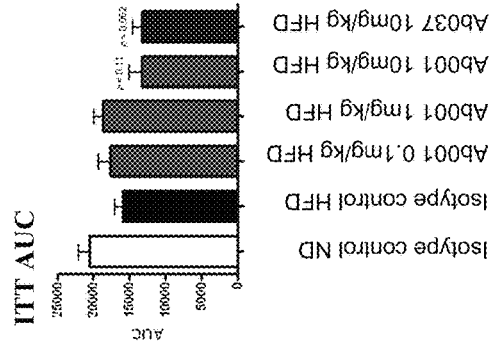
Figure 12C.
Figure 12B.

Figure 13
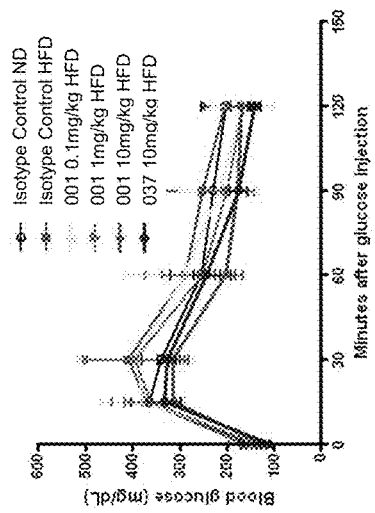
Figure 13A.
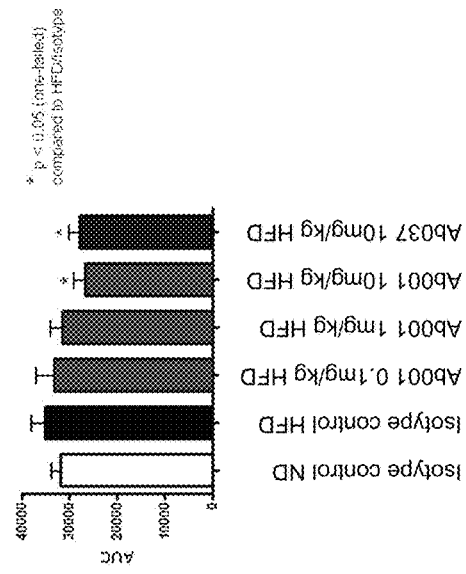
Figure 13C.
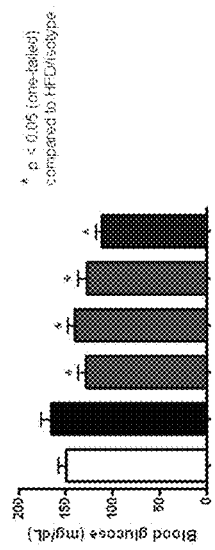
Figure 13B.

Figure 15
Figure 15A.
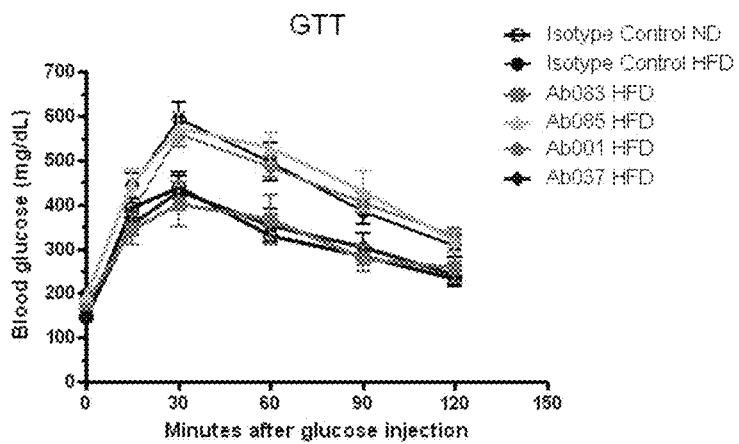
Figure 15B.
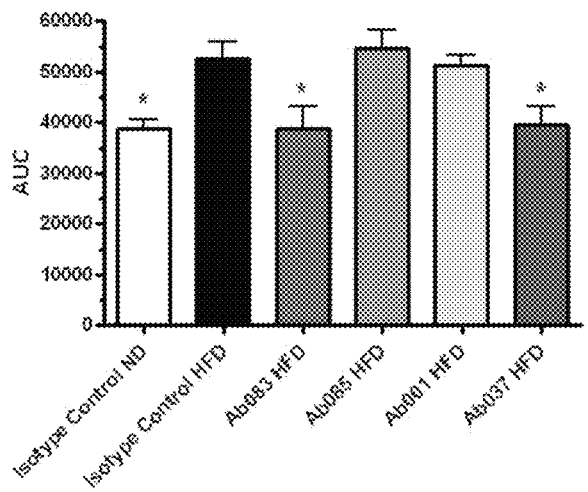
Figure 15C.
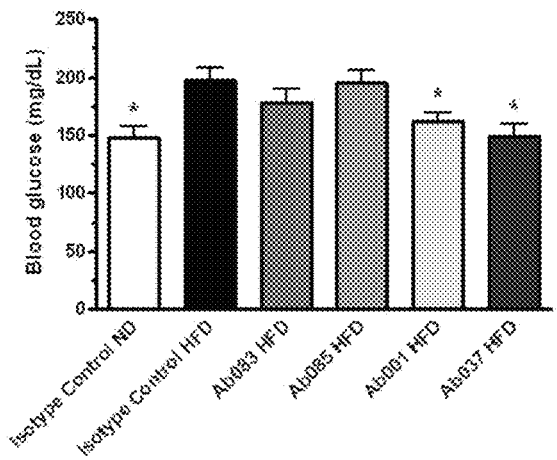

Figure 16
Figure 16A.
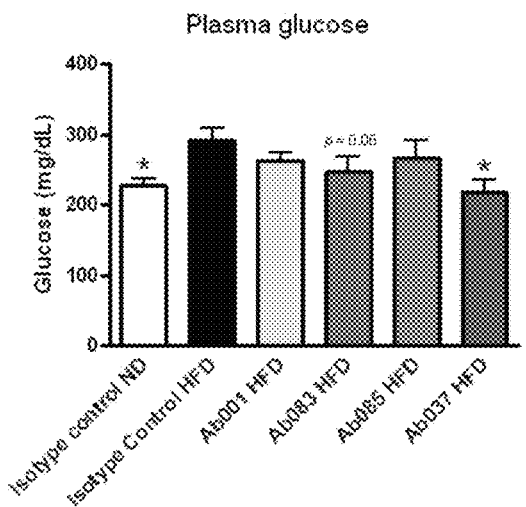
Figure 16B.
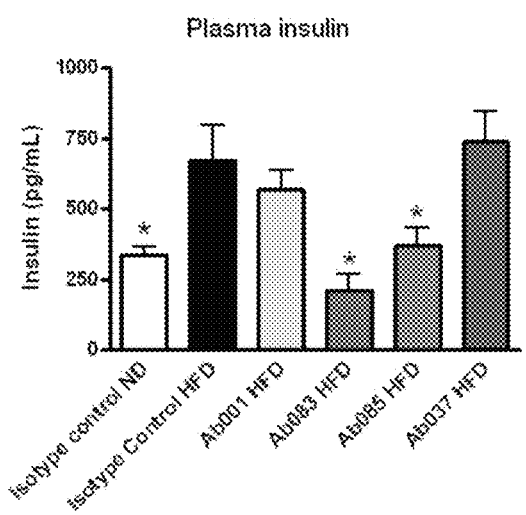
Figure 16C.
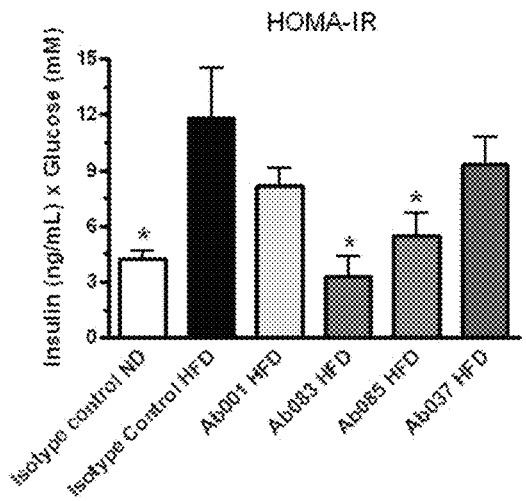

Figure 16 (Cont'd)
Figure 16D.
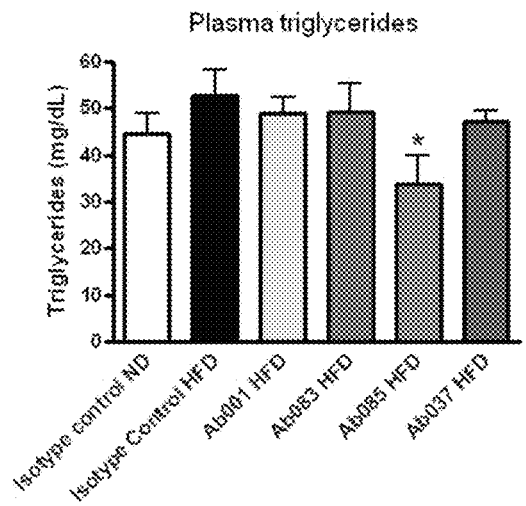
Figure 16E.
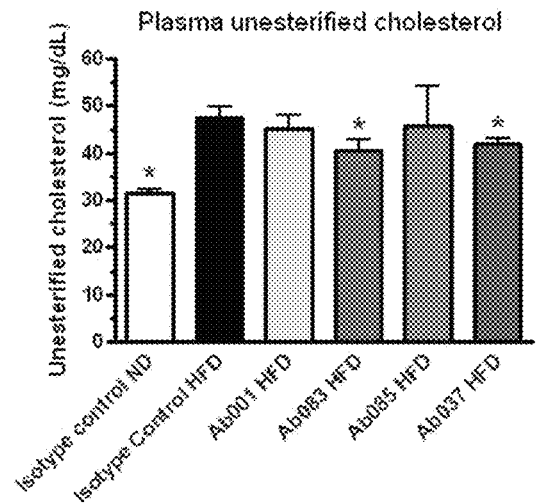
Figure 16F.
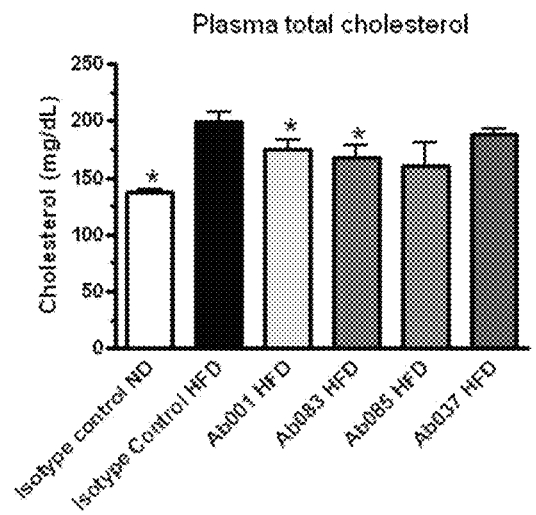

Figure 16 (Cont'd)
Figure 16G.
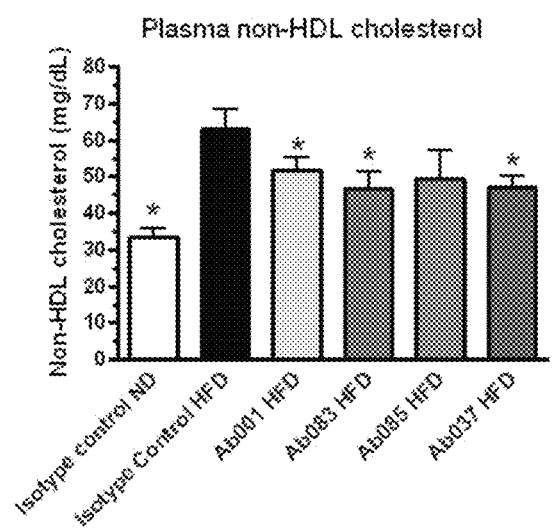
Figure 16H.
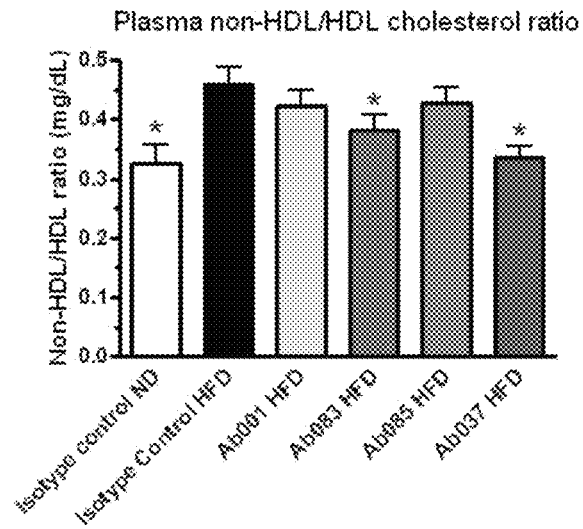

Figure 17
Figure 17A.
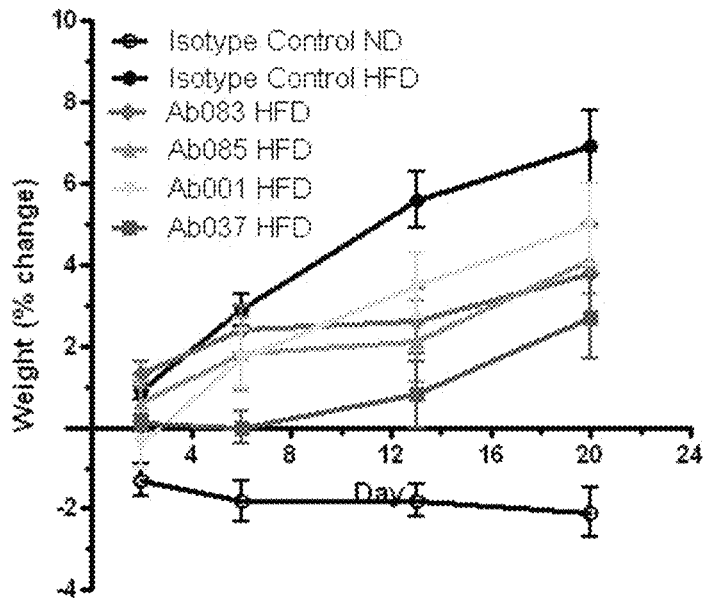
Figure 17B.
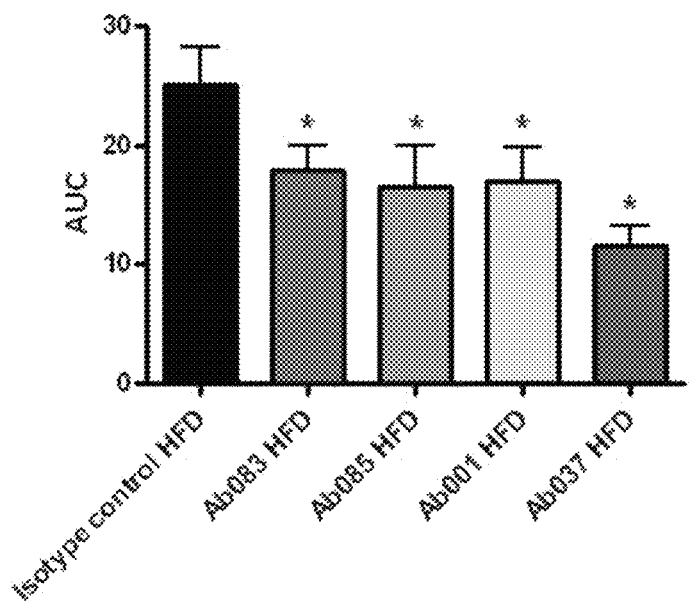

Figure 18
Figure 18A.
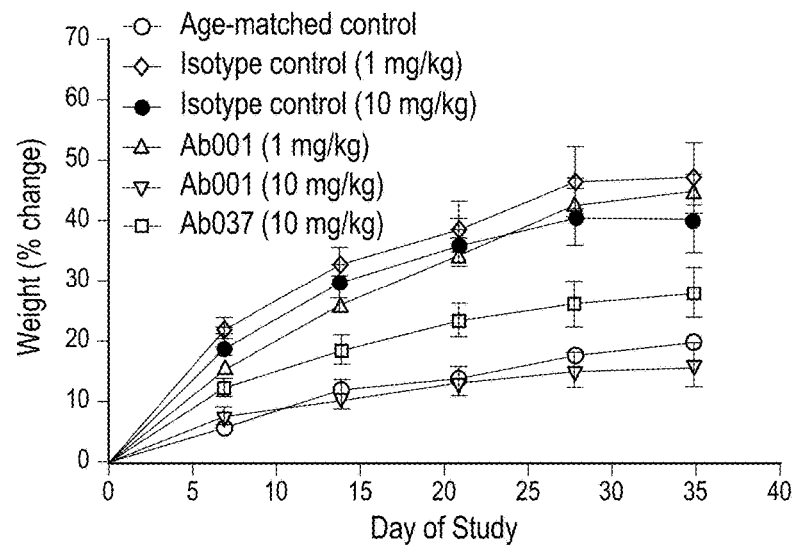
Change in Body Weight
Figure 18B.
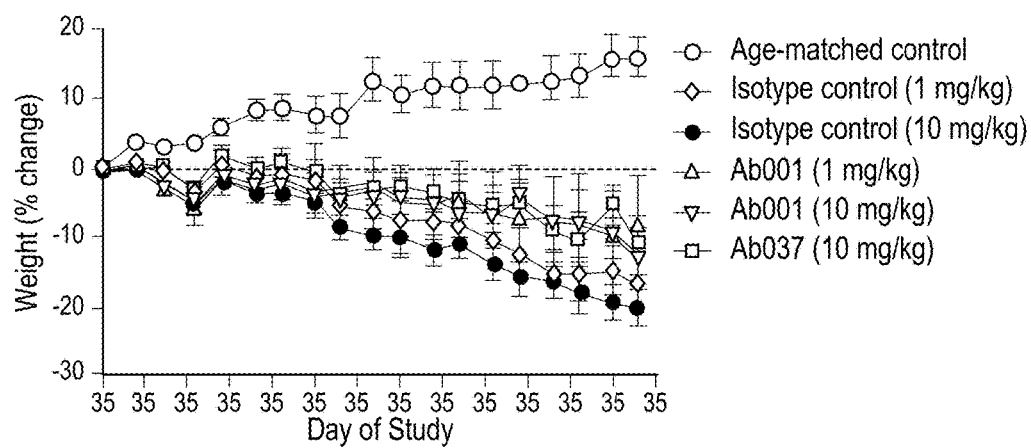
Change in Body Weight

Figure 18 (cont'd)
Figure 18C.
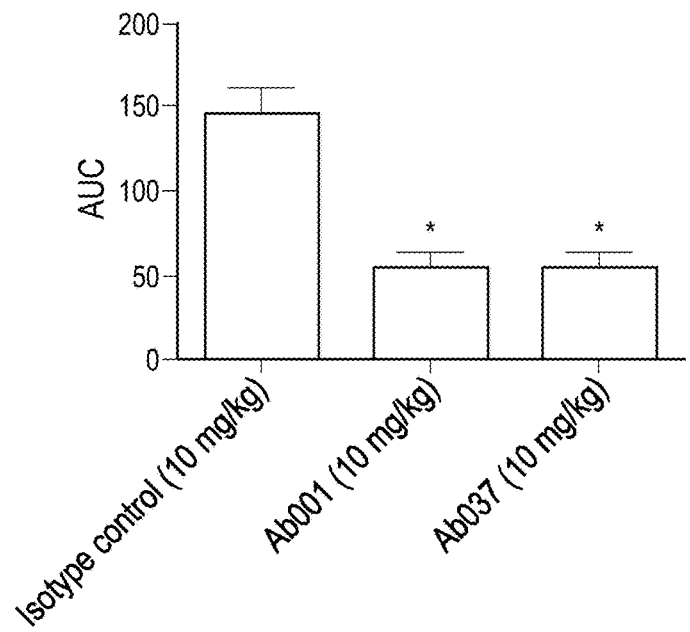
Figure 18D.
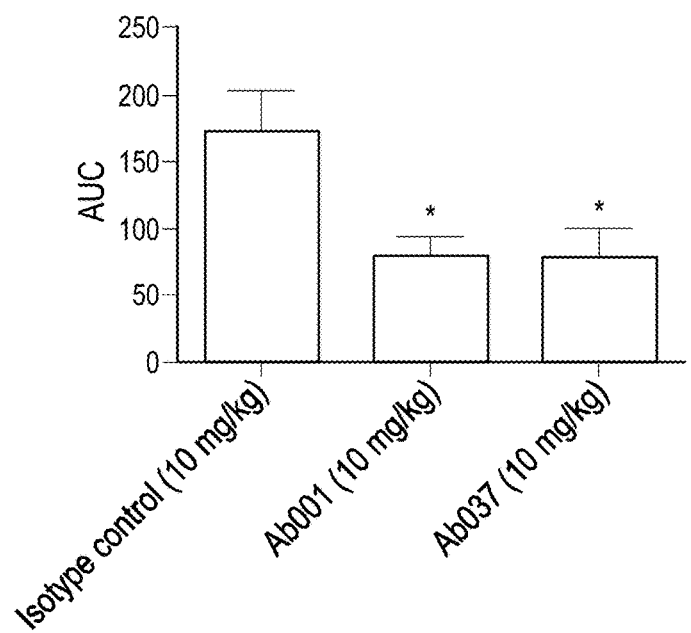

Figure 19
Figure 19A.
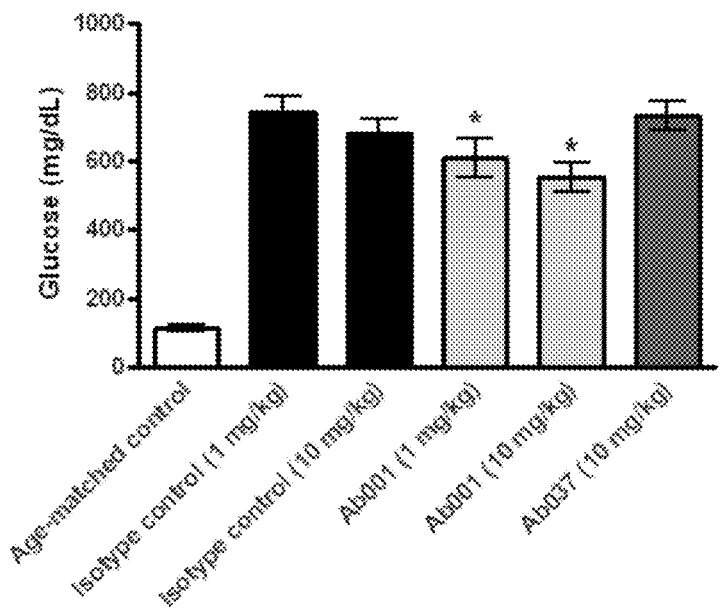
Figure 19B.
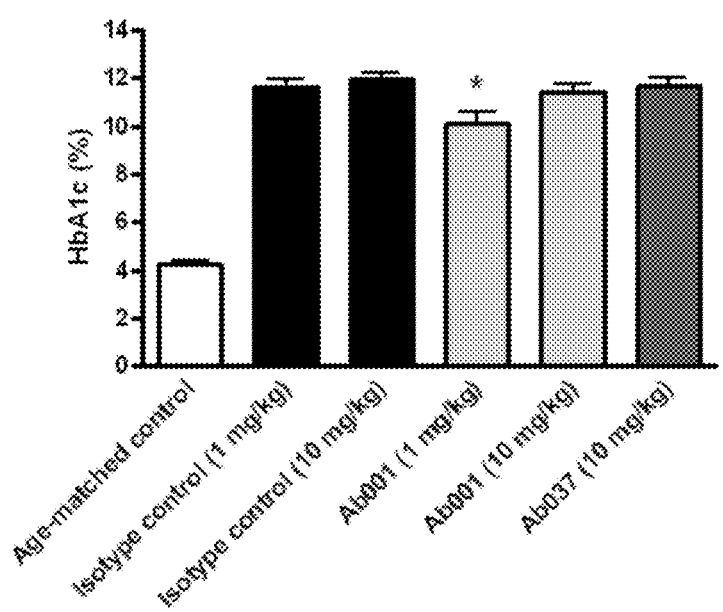

Figure 20
Figure 20A.
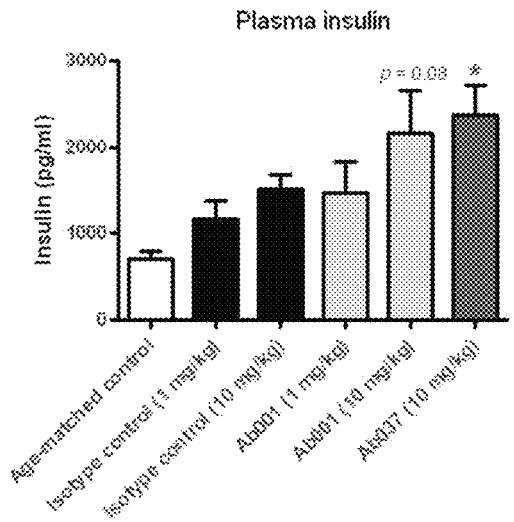
Figure 20B.
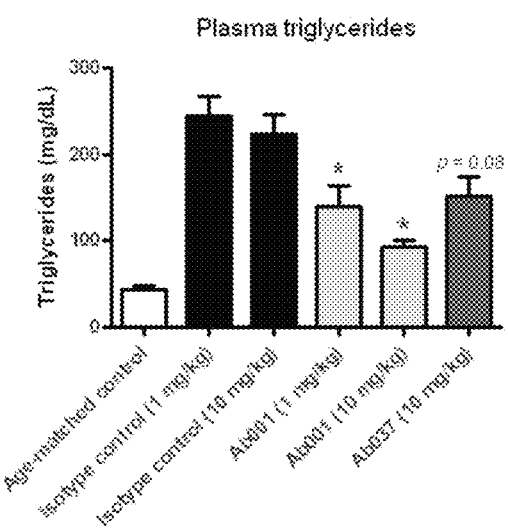
Figure 20C.
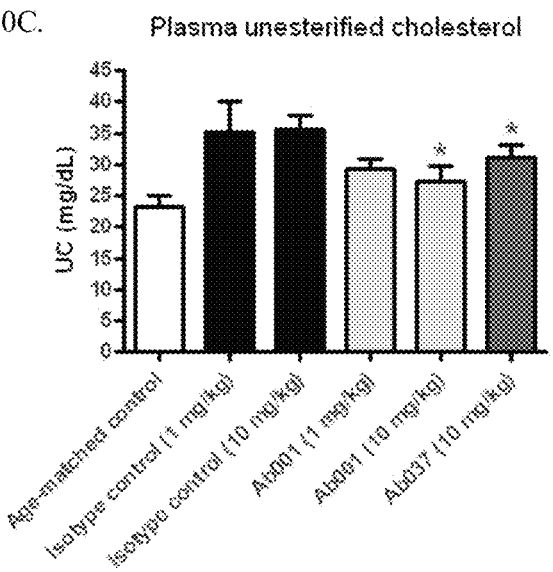

Figure 20 (Cont'd)
Figure 20D.
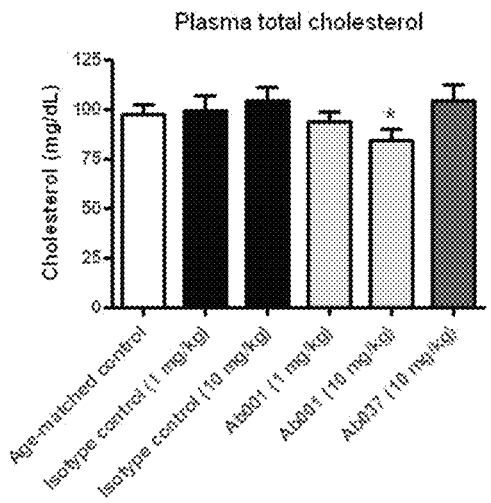
Figure 20E.
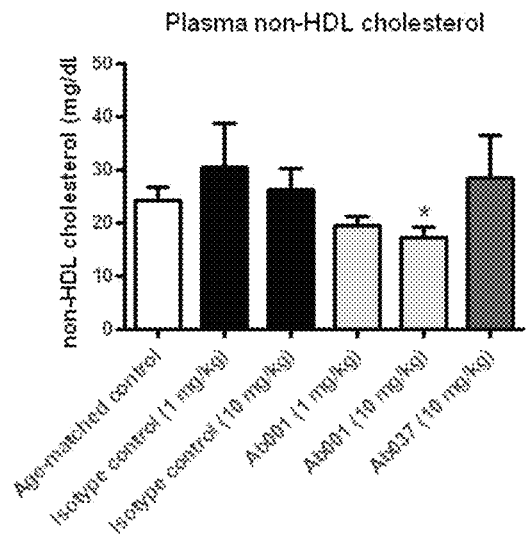
Figure 20F.
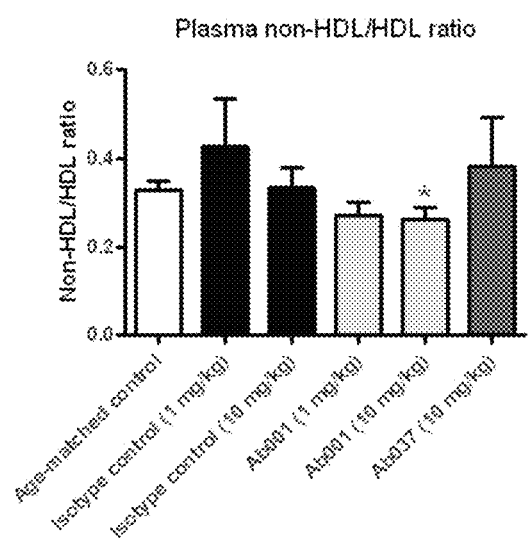

Figure 23
Figure 23A.
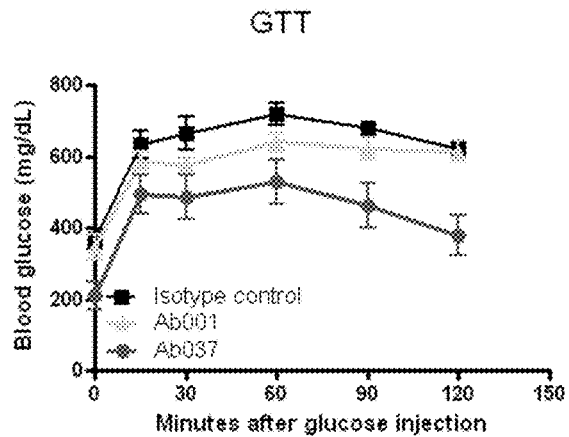
Figure 23B.
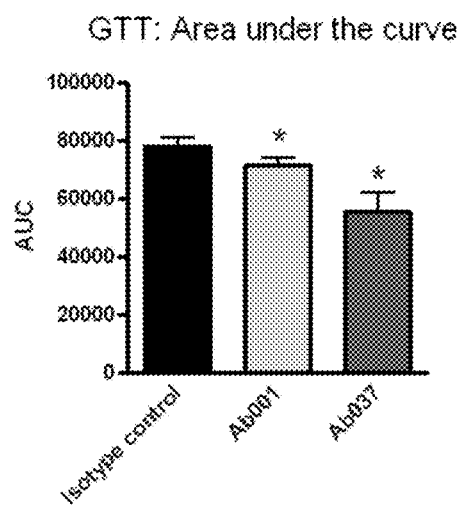
Figure 23C.
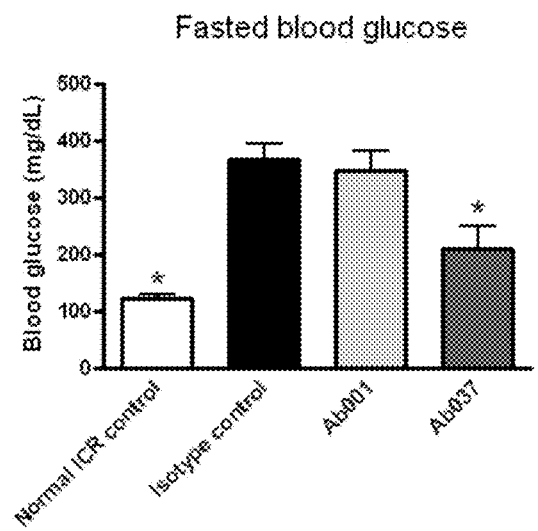

Figure 24
Figure 24A.
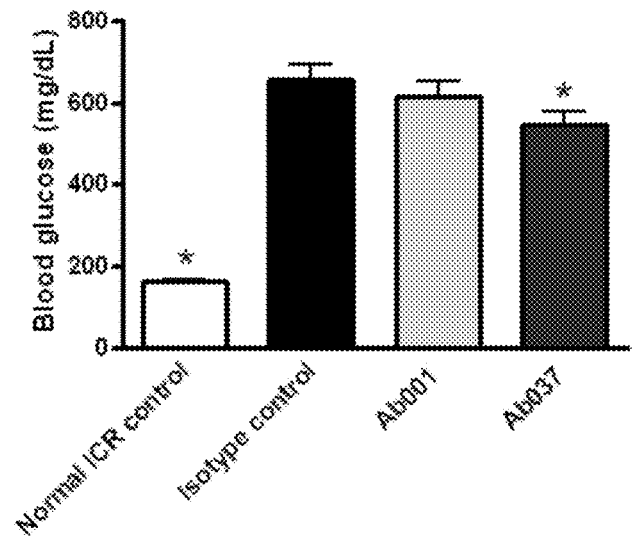
Figure 24B.
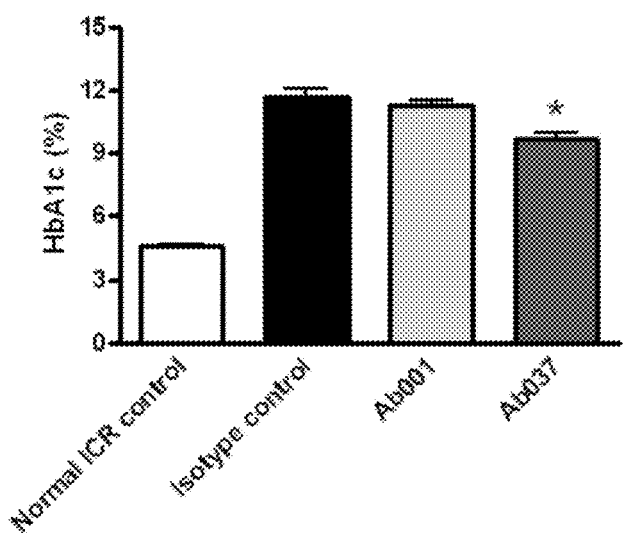

Figure 25
Figure 25A.
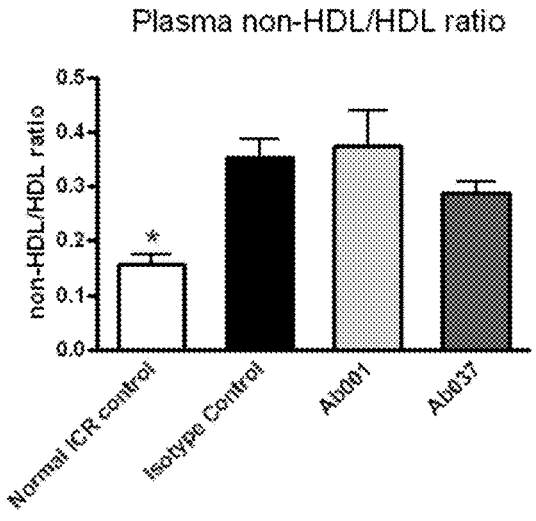
Figure 25B.
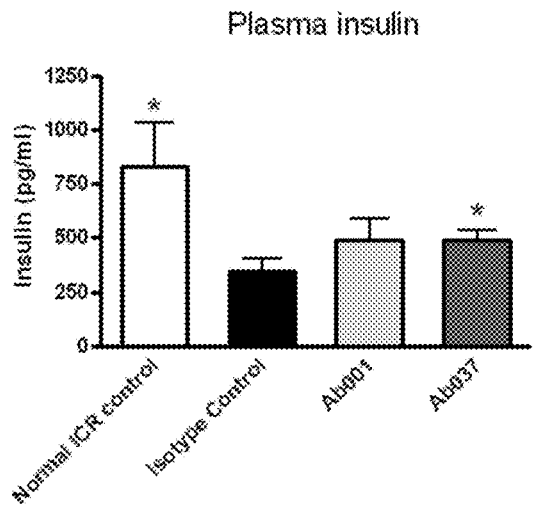
Figure 25C.
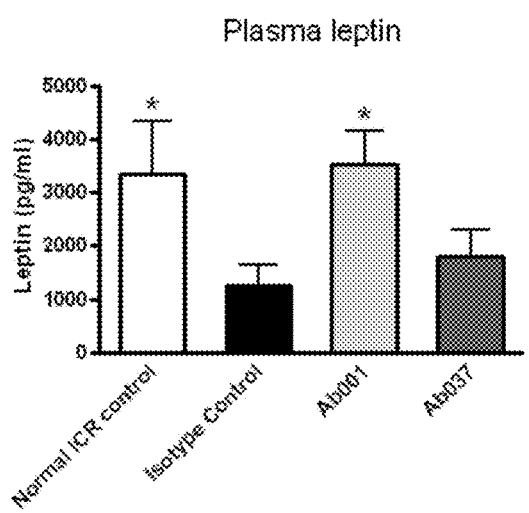

Figure 27
Figure 27A.
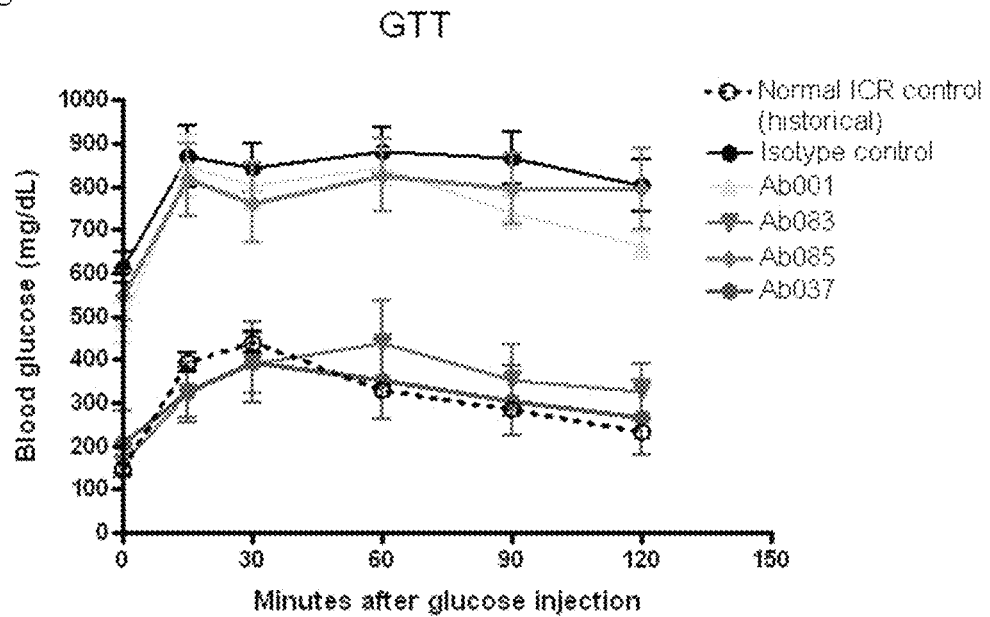
Figure 27B.
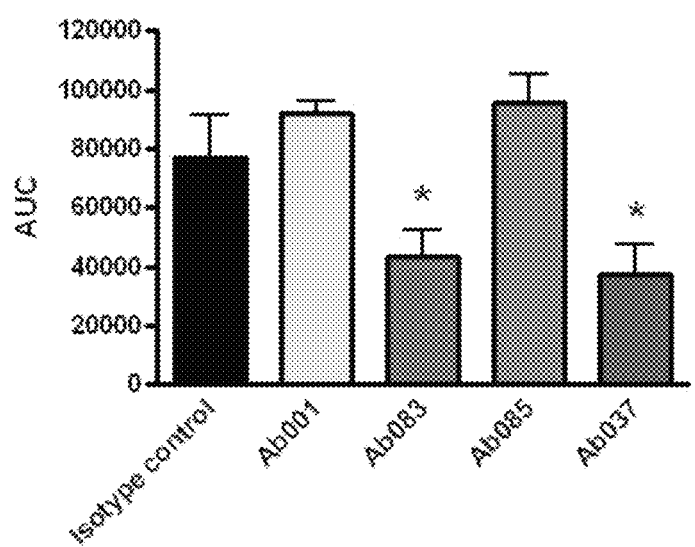

Figure 29
Figure 29A.
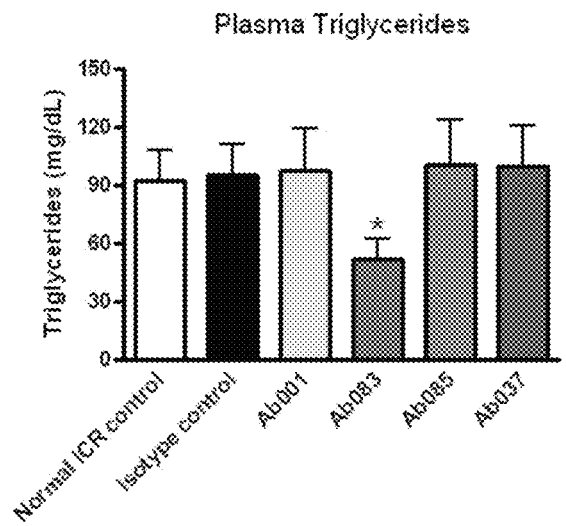
Figure 29B.
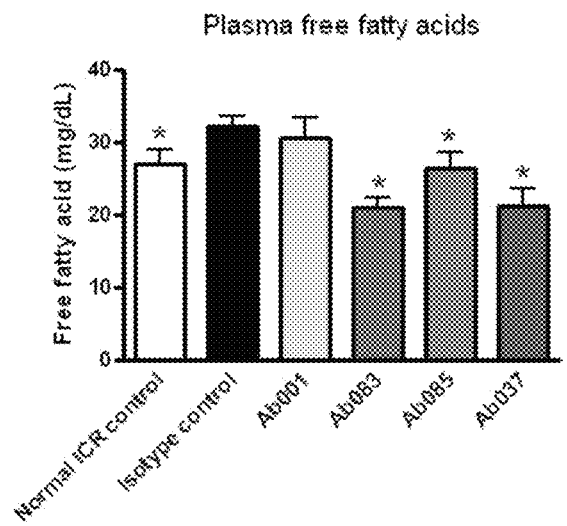
Figure 29C.
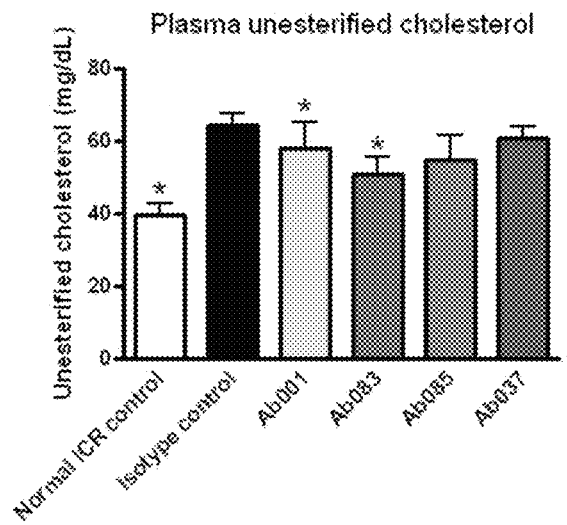

Figure 29 cont'd
Figure 29D.
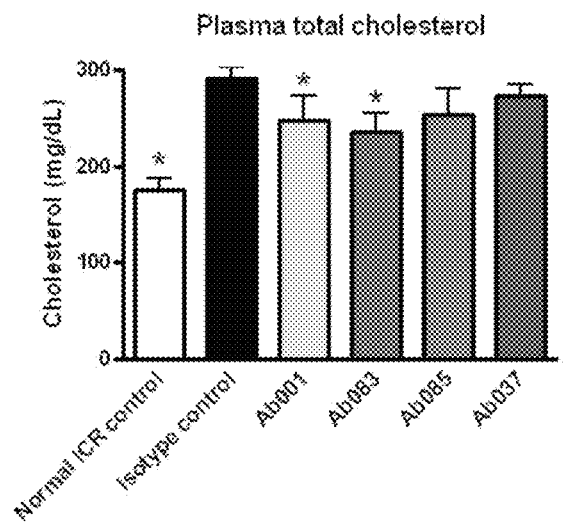
Figure 29E.
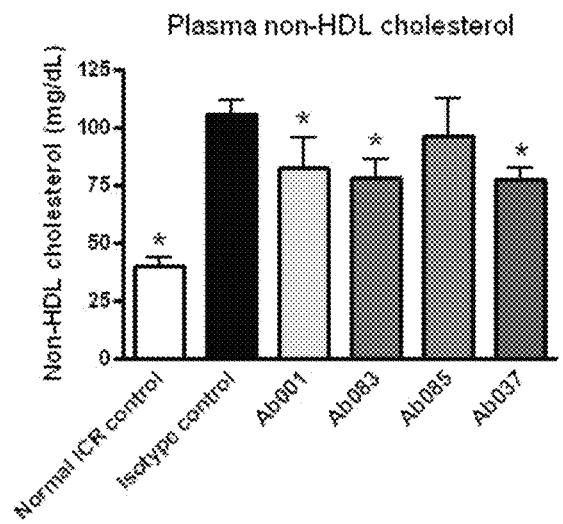
Figure 29F.
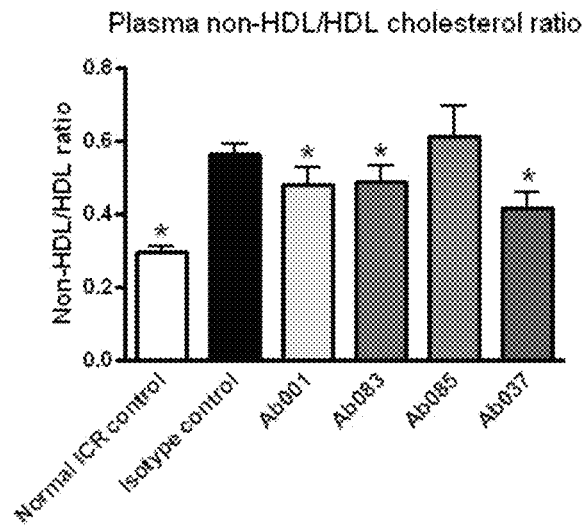

Figure 32
Figure 32A.
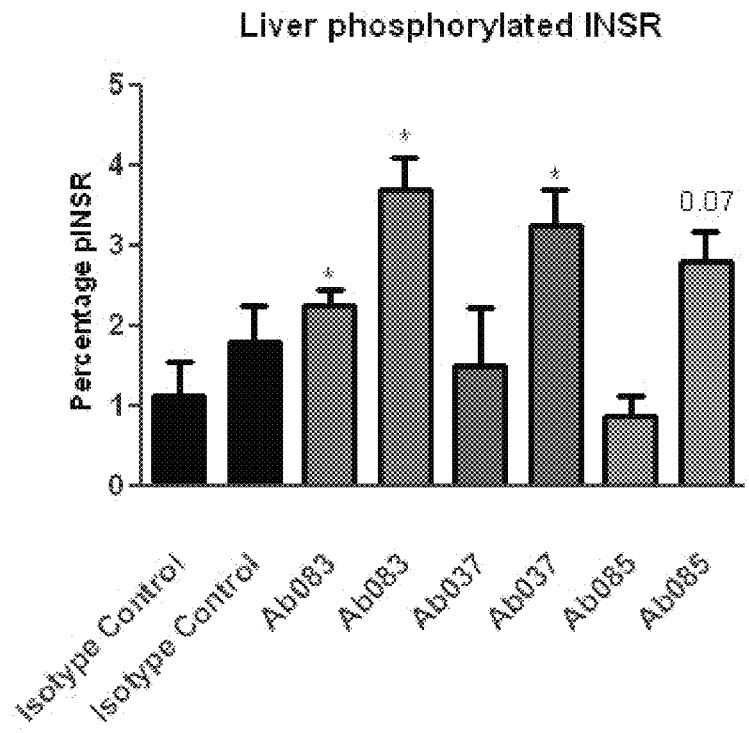
Figure 32B.
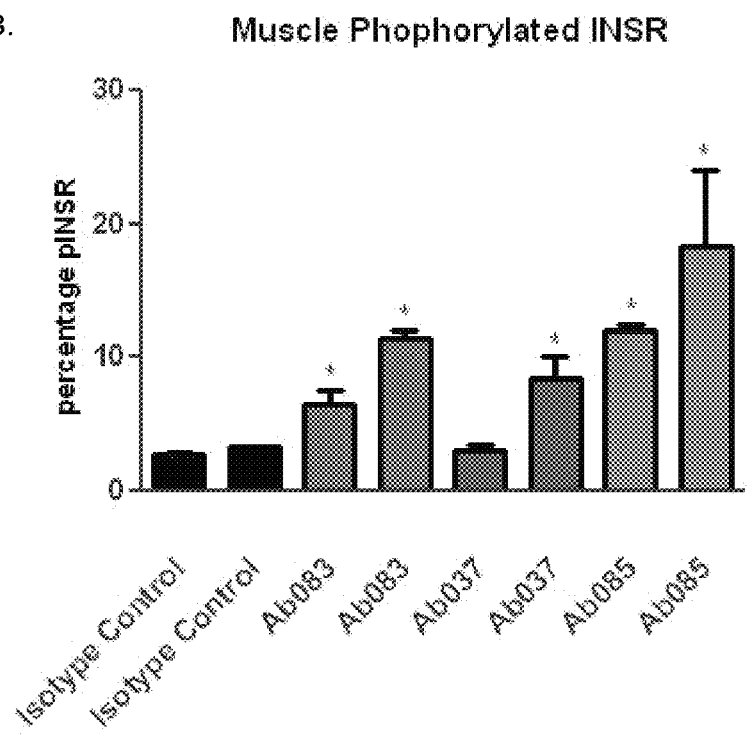

Figure 33

| Antibody tested | FACS area under log transformed data MFI of clones binding to INSR CHO-K1 cells following serum starvation | | | | FACS area under log transformed data MFI ratio of clones binding to human INSR CHO-K1 with insulin and without insulin (+insulin/-insulin) | |
|---|---|---|---|---|---|---|
| | human INSR, no insulin | mouse INSR, no insulin | human INSR, with insulin | mouse INSR, with insulin | human INSR | mouse INSR |
| Ab050 | 252 | 424 | 81 | 170 | 0.32 | 0.40 |
| Ab051 | 554 | 663 | 378 | 470 | 0.68 | 0.71 |
| Ab052 | 445 | 892 | 134 | 397 | 0.30 | 0.45 |
| Ab053 | 1331 | 1131 | 451 | 574 | 0.34 | 0.51 |
| Ab054 | 1128 | 1027 | 356 | 519 | 0.32 | 0.51 |
| Ab055 | 1192 | 1300 | 759 | 1050 | 0.64 | 0.81 |
| Ab056 | 1110 | 21 | 927 | 41 | 0.84 | 1.98 |
| Ab057 | 155 | 409 | 87 | 250 | 0.56 | 0.61 |
| Ab058 | 1407 | 812 | 370 | 388 | 0.26 | 0.48 |
| Ab059 | 22 | 14 | 764 | 13 | 34.25 | ND |
| Ab060 | 460 | 210 | 308 | 388 | 0.67 | 1.85 |
| Ab061 | 204 | 462 | 59 | 170 | 0.29 | 0.37 |
| Ab062 | 1398 | 1448 | 790.3 | 1009 | 0.57 | 0.70 |
| Ab063 | 943 | 1025 | 674 | 733 | 0.71 | 0.72 |
| Ab064 | 1710 | 1019 | 1271 | 813 | 0.74 | 0.80 |
| Ab065 | 205 | 483 | 57 | 177 | 0.28 | 0.37 |
| Ab066 | 1564 | 1516 | 1157 | 1145 | 0.74 | 0.76 |
| Ab067 | 1537 | 1281 | 1063 | 786 | 0.69 | 0.61 |
| Ab068 | 1422 | 803 | 1028 | 445 | 0.72 | 0.55 |
| Ab069 | 357 | 642 | 146 | 383 | 0.41 | 0.60 |

| Antibody tested | FACS area under log transformed data MFI of clones binding to INSR CHO-K1 cells following serum starvation | | | | FACS area under log transformed data MFI ratio of clones binding to human INSR CHO-K1 with insulin and without insulin (+insulin/-insulin) | |
|---|---|---|---|---|---|---|
| | human INSR, no insulin | mouse INSR, no insulin | human INSR, with insulin | mouse INSR, with insulin | human INSR | mouse INSR |
| Ab070 | 283 | 587 | 150 | 389 | 0.53 | 0.66 |
| Ab071 | 490 | 818 | 194 | 518 | 0.40 | 0.63 |
| Ab072 | 226 | 508 | 84 | 267 | 0.37 | 0.53 |
| Ab073 | 729 | 307 | 341 | 321 | 0.47 | 1.05 |
| Ab074 | 596 | 932 | 260 | 503 | 0.44 | 0.54 |
| Ab075 | 692 | 425 | 353 | 446 | 0.51 | 1.05 |
| Ab076 | 552 | 268 | 543 | 391 | 0.98 | 1.46 |
| Ab077 | 127 | 45 | 268 | 103 | 2.12 | 2.28 |
| Ab078 | 11 | 12 | 704 | 217 | 66 | 17.6 |
| Ab079 | 296 | 154 | 385 | 215 | 1.30 | 1.39 |
| Ab080 | 282 | 157 | 386 | 191 | 1.37 | 1.22 |
| Ab081 | 176 | 189 | 75 | 125 | 0.42 | 0.66 |
| Ab082 | 399 | 257 | 236 | 267 | 0.59 | 1.04 |
| Ab083 | 97 | 81 | 294 | 179 | 3.03 | 2.21 |
| Ab084 | 532 | 196 | 508 | 344 | 0.95 | 1.75 |
| Ab001+anti-human IgG APC p1 | 294 | 34 | 565 | 127 | 1.92 | 3.68 |
| Ab001+anti-human IgG APC p2 | 687 | 443 | 1017 | 1062 | 1.48 | 2.40 |
| Ab001+anti-human IgG APC p3 | | | | | | |
| Ab001+anti-human IgG APC p5 | 534 | 176 | 1006 | 485 | 1.89 | 2.76 |
| Ab001+anti-human IgG APC p6 cropped | 693 | 232 | 1030 | 518 | 1.49 | 2.24 |

ND = not determine

Figure 33 (cont'd)

Figure 34 Figure 34A. Figure 34B.
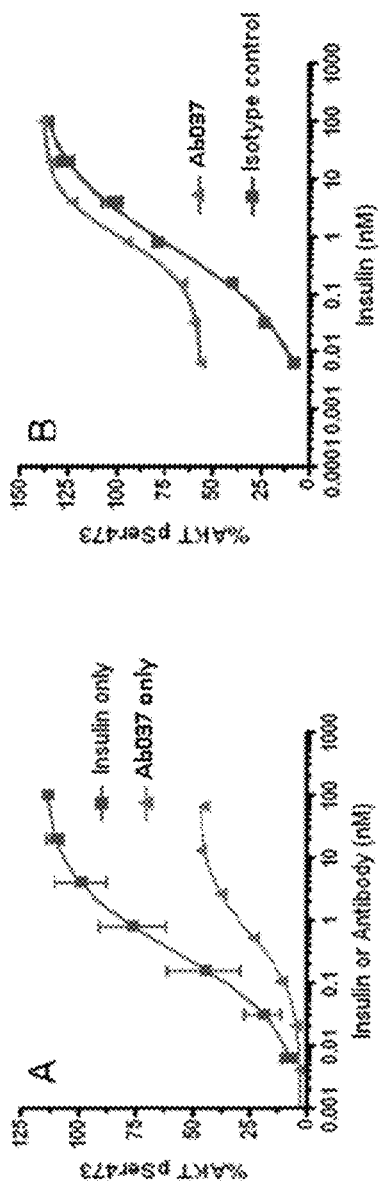
Figure 35 Figure 35A. Figure 35B.
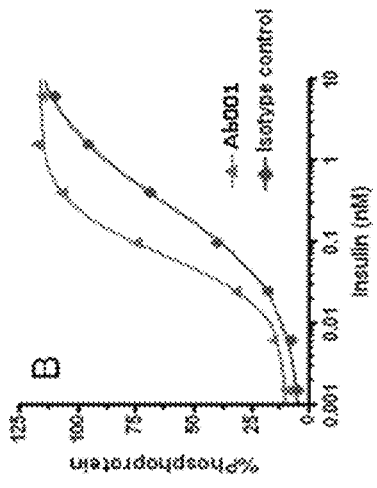
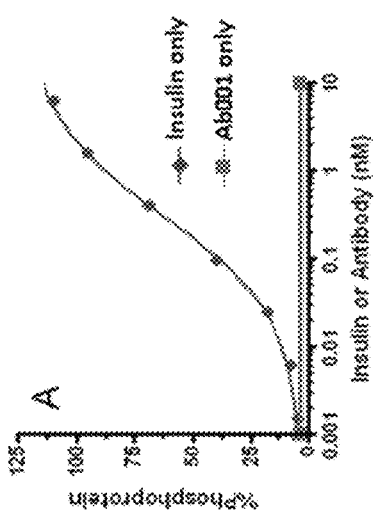

Figure 36

| Engineered insulin receptor cell line used in the assay | Assay parameter determined from sigmoidal dose-response curve fit | Human Insulin | Ab037 | Ab030 | Ab040 | Ab018 |
|---|---|---|---|---|---|---|
| Human INSR CHO-K1 | Relative maximum activation of pAkt by insulin or antibody alone | 100% | 44% | 47% | 19% | 36% |
| | $EC_{50}$ (nM) of insulin or antibody alone | 0.6 | 0.8 | 12 | 4 | 1 |
| | Hill coefficient of insulin or antibody alone | 0.8 | 0.9 | 1.8 | 1.4 | 1.4 |
| Mouse INSR CHO-K1 | Relative maximum activation of pAkt by insulin or antibody alone | 100% | 29% | 37% | 25% | 26% |
| | $EC_{50}$ (nM) of insulin or antibody alone | 3.4 | 1.4 | 11 | 4 | 3 |
| | Hill coefficient of insulin or antibody alone | 0.7 | 1 | 1.7 | 1.3 | 1 |

Figure 37

| Engineered insulin receptor cell line used in the assay | Assay parameter determined from sigmoidal dose-response curve fit | Assay 1 | | Assay 2 | |
|---|---|---|---|---|---|
| | | Hu Insulin with 10 ug/ml control antibody | Hu Insulin with 10 ug/ml Ab037 | Hu Insulin with 10 ug/ml control antibody | Hu Insulin with 10 ug/ml Ab040 |
| Human INSR CHO-K1 | Relative maximum activation of pAkt in the presence of 10 ug/ml antibody | 100 ± 5% | 93 ± 2% | 100 ± 3% | 85 ± 1% |
| | EC50 of insulin in the presence of 10 ug/ml antibody (nM) | 0.7 ± 0.3 | 1 ± 0.3 | 0.8 ± 0.2 | 0.3 ± 0.1 |
| Mouse INSR CHO-K1 | Relative maximum activation of pAkt in the presence of 10 ug/ml antibody | 100 ± 2% | 99 ± 1% | 100 ± 3% | 98 ± 1% |
| | EC50 of insulin in the presence of 10 ug/ml antibody (nM) | 3.3 ± 0.6 | 2.1 ± 0.4 | 3 ± 1 | 0.6 ± 0.2 |

Figure 38
Figure 38A.
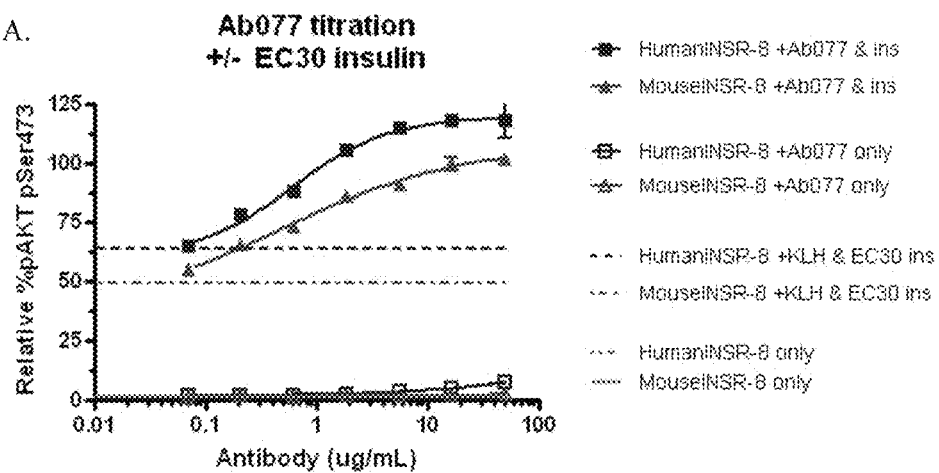
Figure 38B.
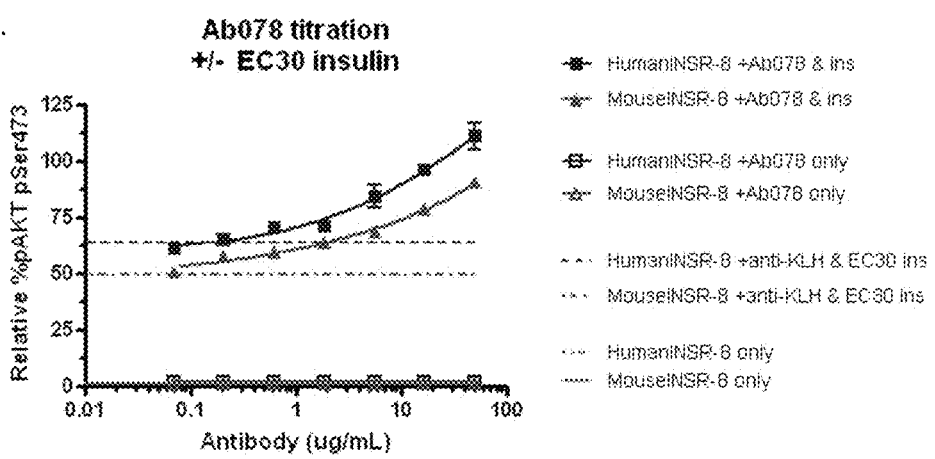
Figure 38C.
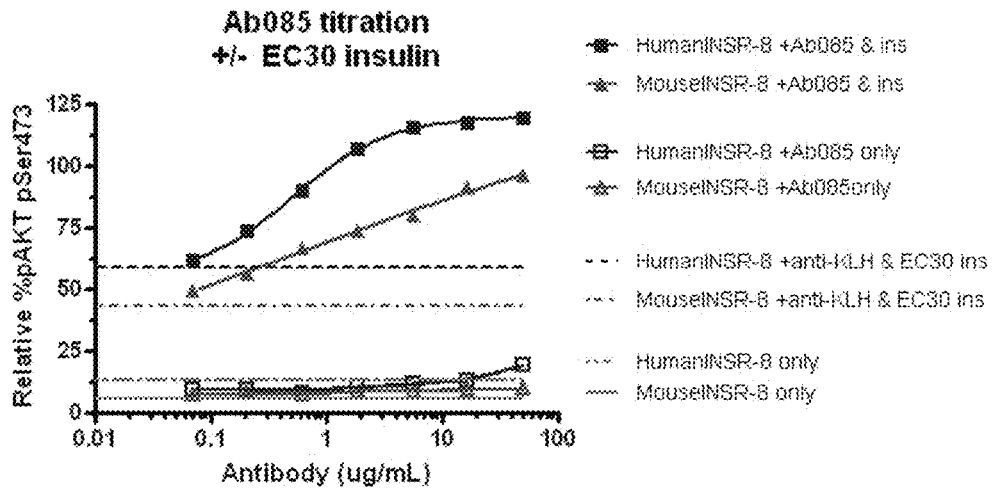

Figure 39
Figure 39A.
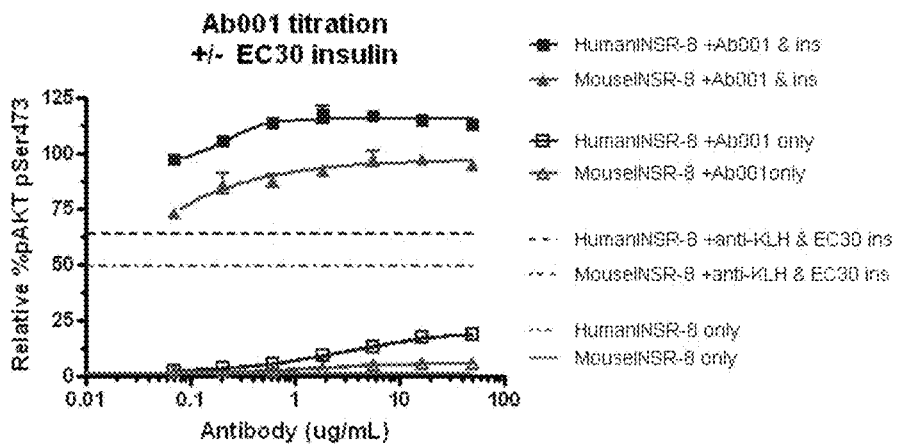
Figure 39B.
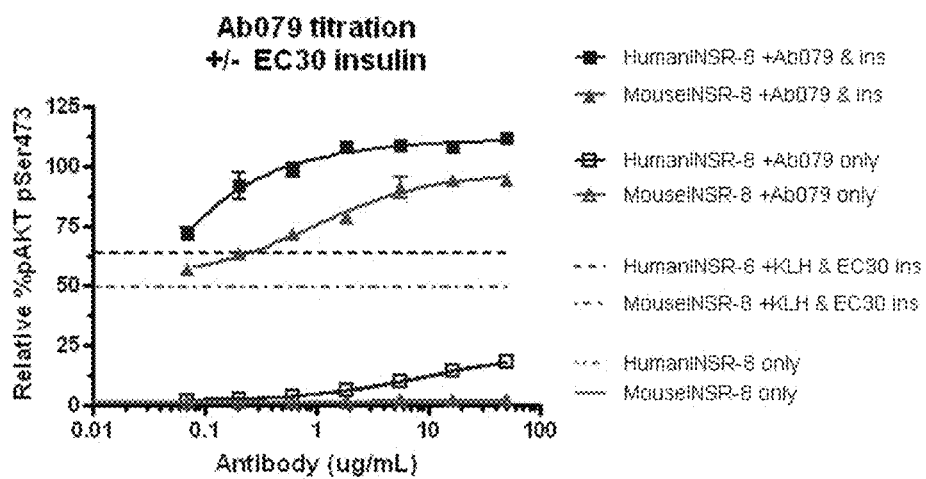
Figure 39C.
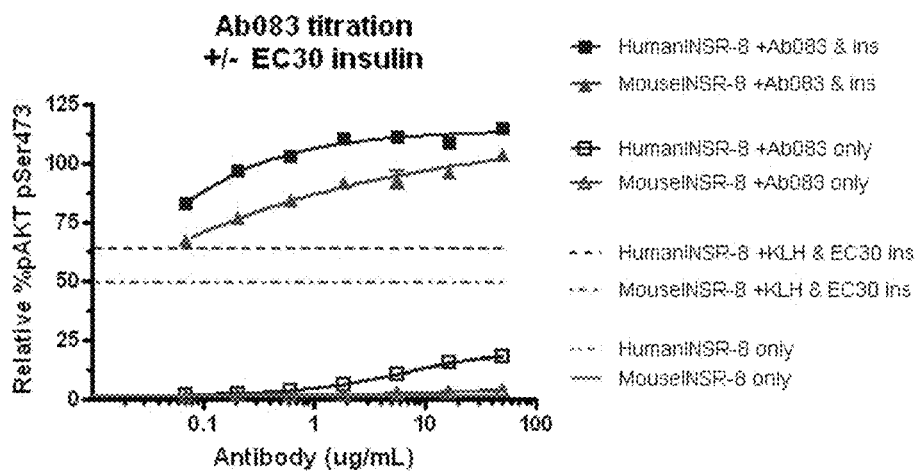

Figure 41
Figure 41A.
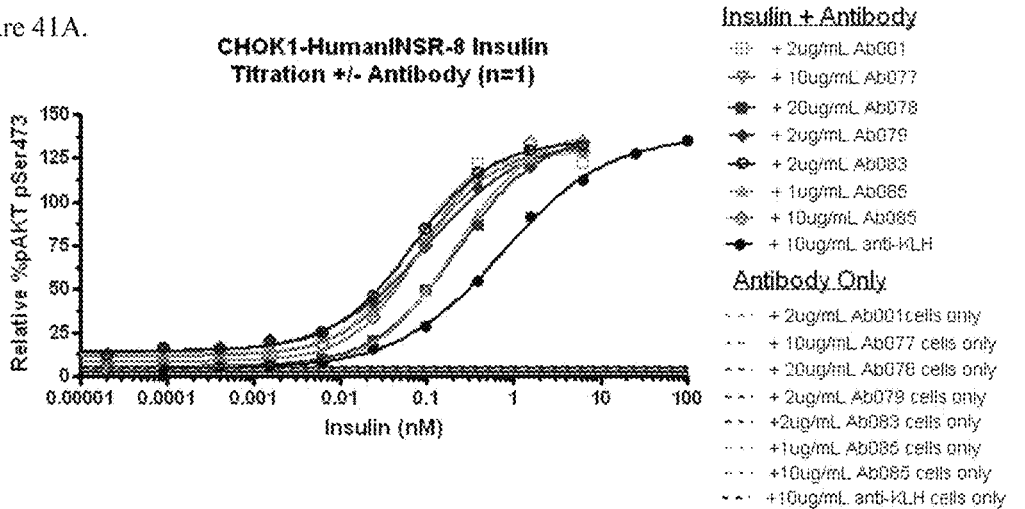
Figure 41B.
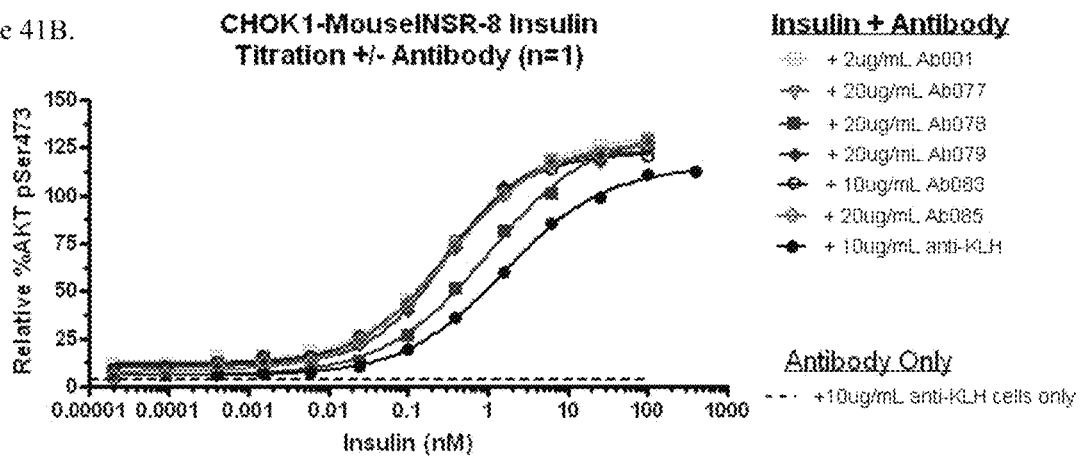
Figure 41C.
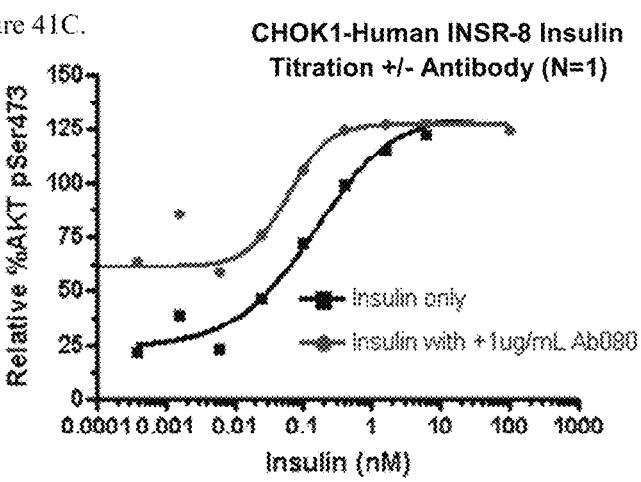

Figure 42
Figure 42A.
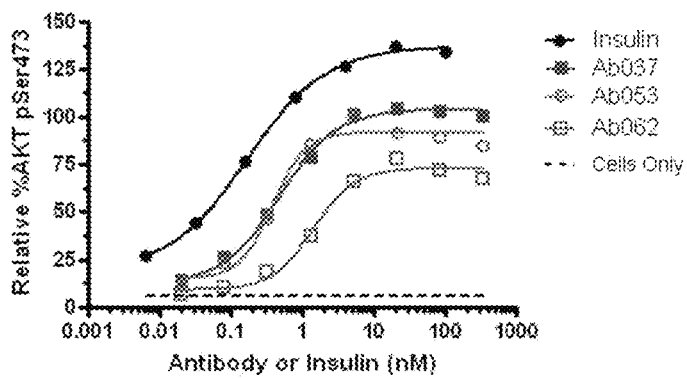
Figure 42B.
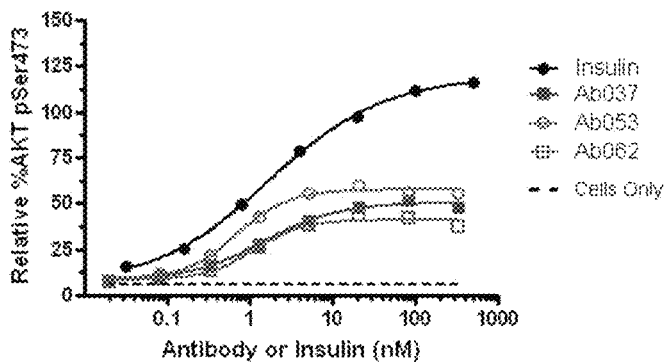
Figure 43
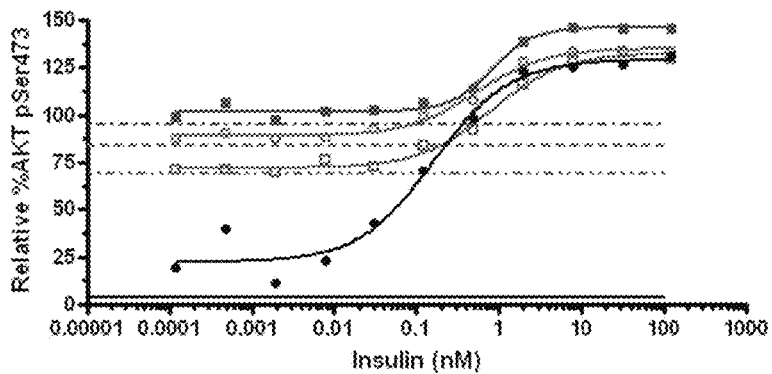

Figure 44
Figure 44A.
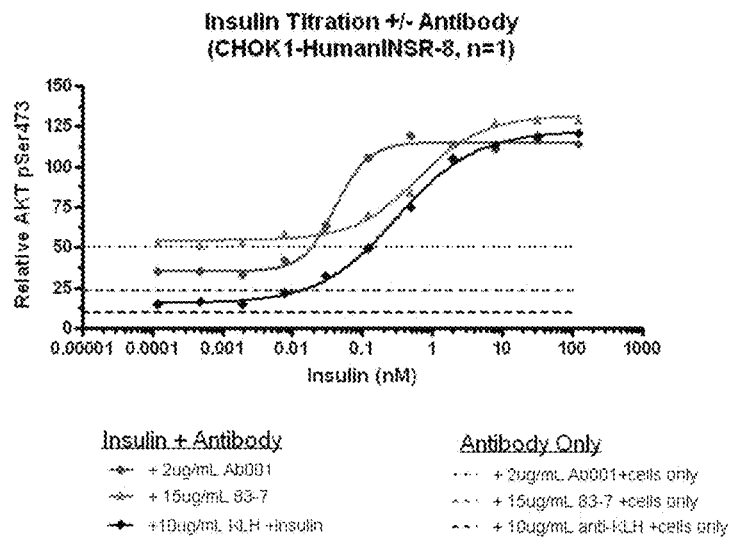
| | +2ug/mL Ab001 | +15ug/mL 83-7 | +2ug/mL anti-KLH |
|---|---|---|---|
| EC50 | 0.04093 | 0.6235 | 0.3129 |
| EC50 (95% Confidence Interval) | 0.03330 to 0.05030 | 0.4215 to 0.9225 | 0.2483 to 0.3942 |
Figure 44B.
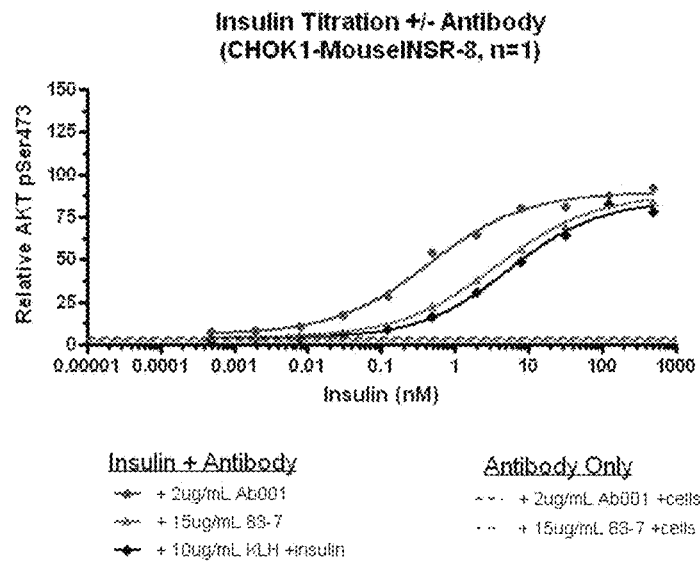
| | +2ug/mL Ab001 | +15ug/mL 83-7 | +10ug/mL anti-KLH |
|---|---|---|---|
| EC50 | 0.4418 | 3.622 | 5.293 |
| EC50 (95% Confidence Interval) | 0.2741 to 0.7121 | 2.681 to 4.893 | 3.294 to 8.505 |

Figure 54

| Clone | Human PBMC | | CHO Hu InsR | | Cyno PBMC | | CHO Cyno InsR | | Rabbit PBMC | | CHO Rabbit InsR | |
|---|---|---|---|---|---|---|---|---|---|---|---|---|
| | (-) insulin | (+) insulin | (-) insulin | (+) insulin | (-) insulin | (+) insulin | (-) insulin | (+) insulin | (-) insulin | (+) insulin | (-) insulin | (+) insulin |
| Ab001 | + | ‡ | + | ‡ | + | ‡ | + | ‡ | + | ‡ | ‡ | + |
| Ab010 | + | ‡ | | | | | | | | | | |
| Ab018 | | | | | · | ‡ | | | | | | |
| Ab030 | + | ‡ | | | + | + | | | | | | |
| Ab037 | + | + | + | ‡ | + | ‡ | | ‡ | + | + | ‡ | + |
| Ab040 | + | | | | + | ‡ | | | | | | |
| Ab050 | | | ‡ | | | + | + | + | + | + | + | + |
| Ab052 | | | + | | | | ‡ | + | | | ‡ | + |
| Ab053 | | | ‡ | | | + | + | + | | | ‡ | + |
| Ab054 | | | + | | + | | + | + | | | ‡ | + |
| Ab058 | | | + | | | | + | + | + | + | ‡ | + |
| Ab062 | | | ‡ | | + | ‡ | + | ‡ | | | | |
| Ab077 | | | | ‡ | + | ‡ | ‡ | | + | | ‡ | |
| Ab078 | | | + | ‡ | + | ‡ | | ‡ | · | ‡ | · | ‡ |
| Ab079 | | | | ‡ | + | ‡ | + | ‡ | · | ‡ | + | ‡ |
| Ab080 | | | + | ‡ | + | + | + | ‡ | + | + | + | ‡ |
| Ab083 | | | | ‡ | + | ‡ | + | ‡ | + | ‡ | + | · |
| Ab085 | | | · | ‡ | + | ‡ | + | ‡ | + | ‡ | · | ‡ |

FIG. 55

| Epitope Bins | | | | | | |
|---|---|---|---|---|---|---|
| 1 | 2 | 3 | 4 | 5 | 6 | 7 |
| Ab030 | 83-14 | Ab079 | Ab020 | Ab078 | Ab061 | Ab004 |
| Ab037 | | Ab080 | Ab019 | Ab085 | Ab074 | |
| Ab053 | | Ab083 | Ab088 | | Ab077 | |
| Ab001 | | | Ab089 | | | |
| Ab018 | | | Ab087 | | | |
| Ab086 | | | 83-7 | | | |
| Ab062 | | | | | | |
| Ab064 | | | Human Specific | | | |
| Ab040 | | | | | | |
| | | | Agonist | | | |
| | | | Positive modulator (complex-specific binding) | | | |
| | | | Positive modulator (binds complexed and free INSR) | | | |
| | | | Negative Modulator | | | |

MODULATORS

CROSS-REFERENCE TO RELATED APPLICATION

The present application is a continuation of U.S. patent application Ser. No. 12/890,598, filed Sep. 24, 2010, now U.S. Pat. No. 8,926,976, issued Jan. 6, 2015, which claims the priority benefit of U.S. Provisional Patent Application No. 61/246,067, filed Sep. 25, 2009, U.S. Provisional Patent Application No. 61/306,321, filed Feb. 19, 2010, and U.S. Provisional Patent Application No. 61/358,749, filed Jun. 25, 2010, each of which is incorporated by reference in its entirety.

FIELD OF THE INVENTION

The present disclosure relates to novel modulators and/or agonists of the insulin-insulin receptor signaling complex and to methods of screening for such modulators and/or agonists. Such modulators and/or agonists may, for example, be used to treat a mammalian subject suffering from Type 2 diabetes, obesity, hyperglycemia, hyperinsulinemia, insulin overdose, chronic kidney disease, Type 1 diabetes, insulin resistance and disease states and conditions characterized by insulin resistance or to prevent occurrence of the same in an at risk subject.

BACKGROUND OF THE INVENTION

The present disclosure relates to novel modulators and/or agonists of the insulin-insulin receptor signaling complex, to methods of screening for such modulators and/or agonists and to the use of such modulators and/or agonists in the treatment or prevention of disease states and conditions characterized by abnormal production and/or utilization of insulin.

The peptide hormone insulin is a major regulator of glucose homeostasis and cell growth. The first step in insulin action is the binding of the hormone to the insulin receptor (INSR), an integral membrane glycoprotein, also designated as CD220 or HHF5. The INSR belongs to the tyrosine kinase growth factor receptor superfamily and is composed of two extracellular a subunits that bind insulin, and two transmembrane β subunits with intrinsic tyrosine kinase activity. The amino acid sequence of the INSR is described in U.S. Pat. No. 4,761,371 and as NCBI Reference Sequence NP_000199.2. The INSR is expressed in two isoforms, INSR-A and INSR-B. The three-dimensional structure of the intact homodimeric ectodomain fragment of human INSR has been elucidated using X-ray crystallography (WO07/147213). INSR isoforms also form heterodimers, INSR-A/INSR-B, and hybrid INSR/IGF-1R receptors, whose role in physiology and disease is not yet fully understood (Belfiore et al, Endocrine Rev., 30(6):586-623, 2009).

When insulin binds to the INSR, the receptor is activated by tyrosine autophosphorylation and the INSR tyrosine kinase phosphorylates various effector molecules, including the insulin receptor substrate-1 (IRS-1), leading to hormone action (Ullrich et al, Nature 313: 756-761, 1985; Goldfine et al, Endocrine Reviews 8: 235-255, 1987; White and Kahn, Journal Biol. Chem. 269: 1-4, 1994). IRS-1 binding and phosphorylation eventually leads to an increase in the high affinity glucose transporter (Glut4) molecules on the outer membrane of insulin-responsive tissues, including muscle cells and adipose tissue, and therefore to an increase in the uptake of glucose from blood into these tissues. Glut4 is transported from cellular vesicles to the cell surface, where it then can mediate the transport of glucose into the cell. A decrease in INSR signaling, leads to a reduction in the uptake of glucose by cells, hyperglycemia (an increase in circulating glucose), and all the sequelae which result.

Reduction in glucose uptake can result in insulin resistance, which describes a condition in which physiological amounts of insulin are inadequate to produce a normal insulin response from cells or tissues. Severe insulin resistance is associated with diabetes, while less severe insulin resistance is also associated with a number of disease states and conditions present in approximately 30-40% of non-diabetic individuals (reviewed in Woods et al, End, Metab & Immune Disorders—Drug Targets 9: 187-198, 2009).

Current treatments for diabetes and insulin resistance are directed toward improving insulin secretion, reducing glucose production, and enhancing insulin action.

Currently, there are various pharmacological approaches for the treatment of Type 2 diabetes (Scheen et al, Diabetes Care, 22(9):1568-1577, 1999; Zangeneh et al, Mayo Clin. Proc. 78: 471-479, 2003; Mohler et al, Med Res Rev 29(1): 125-195, 2009). They act via different modes of action: 1) sulfonylureas (e.g., glimepiride, glisentide, sulfonylurea, AY31637) essentially stimulate insulin secretion; 2) biguanides (e.g., metformin) act by promoting glucose utilization, reducing hepatic glucose production and diminishing intestinal glucose output; 3) alpha-glucosidase inhibitors (e.g., acarbose, miglitol) slow down carbohydrate digestion and consequently absorption from the gut and reduce post-prandial hyperglycemia; 4) thiazol-idinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054) enhance insulin action, thus promoting glucose utilization in peripheral tissues; 5) glucagon-like-peptides and agonists (e.g. exendin) or stabilizers thereof (e.g. DPP4 inhibitors, such as sitagliptin) potentiate glucose-stimulated insulin secretion; and 6) insulin or analogues thereof (e.g. LANTUS®) stimulate tissue glucose utilization and inhibits hepatic glucose output. The above mentioned pharmacological approaches may be utilized individually or in combination therapy. However, each approach has its limitations and adverse effects. Over time, a large percentage of Type 2 diabetic subjects lose their response to these agents. 63% of Type 2 diabetes patients fail to reach global $HbA_{1c}$ levels of <7% as advised by the American Diabetes Association, and are thus at high risk of developing complications. Moreover, almost invariably patients progress through the stages of declining pancreatic function. Insulin treatment is typically instituted after diet, exercise, and oral medications have failed to adequately control blood glucose. The drawbacks of insulin treatment are the need for drug injection, the potential for hypoglycemia, and weight gain. Consequently there is still an urgent need for novel anti-diabetic agents.

Antibodies binding to human INSR have been reported in Soos et al, Biochem. J. 235: 199-208, 1986; Taylor et al, Biochem. J. 242: 123-129, 1987; Prigent et al, J. Biol. Chem. 265(17):9970-9977, 1990; Brindle et al, Biochem. J. 268: 615-620, 1990; Steele-Perkins and Roth, J. Biol. Chem. 265(16): 9458-9463, 1990; McKern et al, Nature 443(14): 218-221; Boado et al, Biotech and BioEng. 96(2): 381-391; WO04/050016; Roth et al, Proc. Natl. Acad. Sci. USA 79: 7312-7316, 1982; Morgan et al, Proc. Natl. Acad. Sci. USA 83: 328-332, 1986; Lebrun et al, J. Bl. Chem. 268(15): 11272-11277, 1993; Forsayeth et al, Proc. Natl. Acad. Sci.

USA 84: 3448-3451, 1987; Forsayeth et al, J. Biol. Chem. 262(9): 4134-4140, Goodman et al, J. Receptor Res. 14(6-8), 381-398, 1994; Ganderton et al, Biochem J. 288: 195-205, 1992; Spasov et al, Bull. of Exp. Biol. and Med. 144(1): 46-48, 2007; EP 2 036 574 A1.

SUMMARY OF THE INVENTION

The present disclosure is directed to polypeptide binding agents, e.g., antibodies or fragments thereof, that modulate and/or agonize the insulin-INSR signaling complex by binding to extracellular regions of the INSR uncomplexed to insulin, to the INSR complexed with insulin, or to both. INSR is a membrane-bound cell surface receptor.

In one aspect, the invention provides an antibody that binds to insulin receptor and/or a complex comprising insulin and insulin receptor with an equilibrium dissociation constant $K_D$ of $10^{-5}$M or less that is capable of strengthening binding affinity or binding rate parameter between insulin and insulin receptor (INSR) by about 5-fold to 200-fold. In one embodiment, the antibody is capable of strengthening the binding affinity or binding rate parameter between insulin and insulin receptor by about 1.5-fold to about 100-fold, or about 2-fold to 25-fold. It is further contemplated that the modulation is about 2-fold to about 50-fold, or about 1.5-fold to about 25-fold, or about 1.5-fold to about 50-fold, e.g., at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 100-fold, or up to 90-fold, or up to 80-fold, or up to 70-fold, or up to 60-fold, or up to 50-fold, or up to 40-fold, or up to 30-fold, or up to 20-fold, or up to 10-fold. In a further embodiment, the antibody strengthens binding affinity or binding rate parameter by 1.5, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95 or 100 fold or more, or any range between any of these values. In some embodiments, the binding affinity is any one of $K_A$, $K_D$, the ratio of on rate divided by off rate, or the ratio of off rate divided by on rate. In specific exemplary embodiments, the antibody increases $K_A$ by the desired fold, or decreases $K_D$ by the desired fold, or increases the ratio of on rate to off rate by the desired fold, or decreases the ratio of off rate to on rate by the desired fold. In some embodiments, the binding rate parameter is the on rate or off rate. In specific exemplary embodiments, the antibody increases the on rate or decreases the off rate. Alternatively, in some embodiments where the binding affinity does not change detectably or significantly, increasing the on rate and increasing the off rate may shift the signaling pathway away from mitogenic signaling towards metabolic signaling (glucose uptake).

In one embodiment, an antibody that strengthens the binding affinity between insulin and INSR is a positive modulator.

In another aspect, the antibody is an agonist.

In a related aspect, an antibody that activates the INSR without dependence on insulin is an allosteric agonist. In certain embodiments, the invention provides an allosteric agonist antibody that binds to insulin receptor with an affinity of at least $10^{-5}$, $10^{-6}$, $10^{-7}$, $10^{-8}$, $10^{-9}$ M and (a) exhibits maximal agonist activity that is 20%-80% that of insulin's maximal agonist activity when measured in a pAKT assay, (b) when present does not alter the EC50 of insulin for INSR by more than 2-fold, and (c) when present does not alter the $K_D$ of insulin for INSR by more than 2-fold.

In a related embodiment, the allosteric agonist exhibits a maximal agonist response that is 80% or less of the maximal agonist response of insulin, for example 15%-80%, 20-60%, 20%-40% or 15%-30%. In certain embodiments, the antibodies constitutively activate INSR with a maximal agonist response that is at least about 15%, 20%, 25%, 30%, 35%, 40%; and up to 45%, 50%, 55%, 60%, 65%, 70%, 75% or 80% of the maximal agonist response of insulin. It is understood that any combination of any of these range endpoints is contemplated without having to recite each possible combination.

In another aspect, the invention provides an antibody that binds to insulin receptor and/or a complex comprising insulin and insulin receptor with an equilibrium dissociation constant $K_D$ of $10^{-5}$M or less that is capable of weakening the binding affinity or binding rate parameter between insulin and insulin receptor by about 1.5-fold to 100-fold. In one embodiment, the antibody is capable of weakening the binding affinity or binding rate parameter between insulin and insulin receptor by about 2-fold to 25-fold, or 1.5-fold to 25 fold, or 2-fold to 50-fold. It is further contemplated that the modulation is about 2-fold to about 50-fold, or about 1.5-fold to about 25-fold, or about 1.5-fold to about 50-fold, e.g. at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 100-fold, or up to 90-fold, or up to 80-fold, or up to 70-fold, or up to 60-fold, or up to 50-fold, or up to 40-fold, or up to 30-fold, or up to 20-fold, or up to 10-fold. In a further embodiment, the antibody weakens binding affinity or binding rate parameter by 1.5, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95 or 100 fold or more, or any range between any of these values. In some embodiment, the binding affinity is any one of $K_A$, $K_D$, the ratio of on rate divided by off rate, or the ratio of off rate divided by on rate. In specific exemplary embodiments, the antibody decreases $K_A$ by the desired fold, or increases $K_D$ by the desired fold, or decreases the ratio of on rate to off rate by the desired fold, or increases the ratio of off rate to on rate by the desired fold. In some embodiments, the binding rate parameter is the on rate or off rate. In specific exemplary embodiments, the antibody decreases the on rate or increases the off rate.

In one embodiment, an antibody that weakens the binding affinity between insulin and INSR is a negative modulator. In some specific embodiments, an antibody that weakens the binding affinity between insulin and INSR is an antagonist.

In still another embodiment, an antibody that strengthens or weakens binding affinity or binding rate parameter between insulin and insulin receptor comprises at least one heavy chain CDR (HCDR1, HCDR2 and HCDR3) set out in SEQ ID NOS: 151-303. In a related embodiment, the antibody comprises a mature heavy chain variable region of SEQ ID NO: 151-303. It is contemplated that any of the above antibodies further comprises a suitable human or human consensus or human-derived constant region, e.g. IgG1, IgG2, IgG3, or IgG4 or a hybrid thereof.

In a further embodiment, the antibody that strengthens or weakens binding affinity or binding rate parameter between insulin and insulin receptor comprises at least one light chain CDR (LCDR1, LCDR2, or LCDR3) set out in SEQ ID NOS: 1-150. In still another embodiment, the antibody comprises a mature light chain variable region of SEQ ID NO: 1-150. It is contemplated that any of the above antibodies further comprises a human kappa or lambda light chain constant region.

In one embodiment, the antibody binds insulin receptor. In a related embodiment, the antibody binds the a subunit of INSR. In a further embodiment, the antibody binds the β subunit of INSR. In yet another embodiment, the antibody binds the α and β subunit of the receptor. In a related embodiment, the antibody binds an insulin/insulin receptor complex. In another embodiment, the antibody that binds the insulin/INSR complex does not detectably bind insulin receptor alone, e.g., in the absence of insulin, or insulin alone.

In another aspect, the invention provides an antibody that specifically binds insulin receptor and/or a complex comprising insulin and insulin receptor with an equilibrium dissociation constant $K_D$ of $10^{-5}$M or less, comprising at least one heavy chain CDR (HCDR1, HCDR2 and HCDR3) of SEQ ID NOS: 151-303. In a related embodiment, the antibody comprises a heavy chain variable region of SEQ ID NO: 151-303. It is contemplated that any of the above antibodies further comprises a suitable human or human consensus or human-derived constant region, e.g. IgG1, IgG2, IgG3, or IgG4 or a hybrid thereof.

In a further embodiment, the antibody that specifically binds insulin receptor and/or a complex comprising insulin and insulin receptor with an equilibrium dissociation constant $K_D$ of $10^{-5}$M or less, comprises at least one light chain CDR (LCDR1, LCDR2, or LCDR3) set out in SEQ ID NOS: 1-150. In still another embodiment, the antibody comprises a light chain variable region of SEQ ID NO: 1-150. It is contemplated that any of the above antibodies further comprises a human kappa or lambda light chain constant region.

It is further contemplated that any of the antibodies described above comprises one, two, three, four, five or six CDRs. In one embodiment, the antibody comprises one, two or three heavy chain CDRs set out in SEQ ID NO: 151-303. In another embodiment, the antibody comprises one, two or three light chain CDRs set out in SEQ ID NO: 1-150.

In one embodiment, the antibody binds insulin receptor. In a related embodiment, the antibody binds an insulin/INSR complex. In another embodiment, the antibody that binds the insulin/INSR complex does not detectably bind insulin receptor alone or insulin alone.

It is further contemplated that an antibody that strengthens binding affinity or binding rate parameter of insulin and insulin receptor activates insulin receptor by at least 10% of the maximal signal of insulin, optionally in a phosphorylated AKT assay. In a related embodiment, the INSR is activated by at least 11%, 12%, 13%, 14%, 15%, 16%, 17%, 18%, 19%, 20%, 25%, 30%, 40%, 50%, 60%, 70%, or 80% of the maximal signal of insulin. In another embodiment, the antibody that strengthens binding affinity or binding rate parameter of insulin/INSR activates less than 10% of the maximal signal of insulin, optionally in a phosphorylated AKT assay. In a related embodiment, the INSR is activated by less than 9%, 8%, 7%, 6%, 5%, 4%, 3%, 2%, or 1% of the maximal signal of insulin. In some embodiments, the INSR is not detectably activated by the antibody.

It is further contemplated that the antibody reduces fasting blood glucose levels, in a subject having elevated blood glucose, hyperglycemia or disorder associated with insulin resistance, toward the normal range of glucose levels. In one embodiment, the positive modulating antibody or agonist reduces fasting blood glucose levels in the subject by approximately 15%, 20%, 25%, 30%, 35%, 40%, 45%, 50% or more.

In one embodiment, antibody refers to an antibody or fragment thereof, or a polypeptide comprising an antigen binding domain of an antibody. Exemplary antibodies or antibody fragments include polyclonal antibodies, monoclonal antibodies, chimeric antibodies, humanized antibodies, human antibodies, multispecific antibodies, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences. In one embodiment, the antibody is a monoclonal antibody. In a related embodiment, the antibody is a human antibody.

In some specific embodiments, the invention excludes rodent antibodies, i.e. antibodies produced by a hybridoma of rodent (e.g. murine, rat) cells. Such antibodies, whether produced by the hybridoma or recombinantly, would have rodent framework amino acid sequence and be immunogenic if administered to humans. In some specific embodiments, the invention excludes the rodent antibodies disclosed in any one of the following references, hereby incorporated by reference in their entirety: Soos et al, Biochem. J. 235: 199-208, 1986; Taylor et al, Biochem. J. 242: 123-129, 1987; Prigent et al, J. Biol. Chem. 265(17): 9970-9977, 1990; Brindle et al, Biochem. J. 268: 615-620, 1990; Steele-Perkins and Roth, J. Biol. Chem. 265(16): 9458-9463, 1990; McKern et al, Nature 443(14): 218-221; Boado et al, Biotech and BioEng. 96(2): 381-391; WO04/050016; Roth et al, Proc. Natl. Acad. Sci. USA 79: 7312-7316, 1982; Morgan et al, Proc. Natl. Acad. Sci. USA 83: 328-332, 1986; Lebrun et al, J. Bl. Chem. 268(15): 11272-11277, 1993; Forsayeth et al, Proc. Natl. Acad. Sci. USA 84: 3448-3451, 1987; Forsayeth et al, J. Biol. Chem. 262(9): 4134-4140, Goodman et al, J. Receptor Res. 14(6-8), 381-398, 1994; Ganderton et al, Biochem J. 288: 195-205, 1992; Spasov et al, Bull. of Exp. Biol. and Med. 144(1): 46-48, 2007; EP 2 036 574 A1. However, the invention may include humanized versions of such rodent antibodies, treatment methods using such humanized antibodies, and sterile pharmaceutical compositions comprising such humanized antibodies. In some specific embodiments, the invention excludes the humanized antibody 83-14 reported in Boado et al, Biotech and BioEng. 96(2): 381-391 or WO04/050016.

In exemplary embodiments, the invention contemplates:

a monoclonal antibody that retains any one, two, three, four, five, or six of HCDR1, HCDR2, HCDR3, LCDR1, LCDR2, or LCDR3 of any one of SEQ ID NOs: 151-303 and SEQ ID NOs: 1-150, respectively, optionally including one or two mutations in such CDR(s), e.g., a conservative or non-conservative substitution, and optionally paired as set forth in Table 3;

a monoclonal antibody that retains all of HCDR1, HCDR2, HCDR3, or the heavy chain variable region of any one of SEQ ID NOs: 151-303, optionally including one or two mutations in any of such CDR(s), optionally further comprising any suitable heavy chain constant region, e.g., IgG1, IgG2, IgG3, IgG4, IgM, IgA1, IgA2, or IgE or hybrid thereof;

a monoclonal antibody that retains all of LCDR1, LCDR2, LCDR3, or the light chain variable region of any one SEQ ID NOs: 1-150, optionally including one or two mutations in any of such CDR(s), optionally further comprising to any suitable light chain constant region, e.g. a kappa or lambda light chain constant region;

a purified preparation of a monoclonal antibody, comprising the light chain variable region and heavy chain variable regions as set forth in SEQ ID NOs: 1-303 and paired as set forth in Table 3;

a monoclonal antibody that binds to the same linear or three-dimensional epitope of INSR as an antibody comprising a variable region set out in SEQ ID NO: 1-303 a, e.g., as determined through X-ray crystallography or other biophysical or biochemical techniques such as deuterium exchange mass spectrometry, alanine scanning and peptide fragment ELISA;

a monoclonal antibody that competes with an antibody comprising a variable region set out in SEQ ID NO: 1-303, optionally paired as in Table 3, for binding to human INSR by more than about 75%, more than about 80%, or more than about 81%, 82%, 83%, 84%, 85%, 86%, 87%, 88%, 89%, 90%, 91%, 92%, 93%, 94% or 95%.

In some embodiments, the antibody comprises all three light chain CDRs, all three heavy chain CDRs, or all six CDRs of an antibody comprising a variable region set out in SEQ ID NO: 1-303. In some exemplary embodiments, two light chain CDRs from an antibody may be combined with a third light chain CDR from a different antibody. Alternatively, a LCDR1 from one antibody can be combined with a LCDR2 from a different antibody and a LCDR3 from yet another antibody, particularly where the CDRs are highly homologous. Similarly, two heavy chain CDRs from an antibody may be combined with a third heavy chain CDR from a different antibody; or a HCDR1 from one antibody can be combined with a HCDR2 from a different antibody and a HCDR3 from yet another antibody, particularly where the CDRs are highly homologous.

Consensus CDRs may also be used. Any one of the consensus CDRs derived herein may be combined with two other CDRs from the same chain (e.g., heavy or light) of any of the antibodies described herein, e.g. to form a suitable heavy or light chain variable region.

In another aspect, the invention provides variants or derivatives of the antibodies described herein. For example, in one embodiment the antibody is labeled with a detectable moiety as described herein. In a further embodiment, the antibody is conjugated to a hydrophobic moiety described herein.

Variants of the antibodies include antibodies having a mutation or alteration in an amino acid sequence provided herein, including an amino acid insertion, deletion or substitution, e.g., a conservative or non-conservative substitution.

In some embodiments, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the heavy chain variable region set out in SEQ ID NO: 151-303 and/or an amino acid sequence an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the light chain variable region set out in SEQ ID NO: 1-150, the antibody further comprising at least one, two, three, four, five or all of CDRH1, CDRH2, CDRH3, CDRL1, CDRL2 or CDRL3. In some embodiments, the amino acid sequence with percentage identity to the light chain variable region may comprise one, two or three of the light chain CDRs. In other embodiments, the amino acid sequence with percentage identity to the heavy chain variable region may comprise one, two, or three of the heavy chain CDRs.

It is contemplated that the antibodies of the invention may have one, or two or more amino acid substitutions in the CDR regions of the antibody, e.g. conservative substitutions.

In a related embodiment, the residues of the framework are altered. The heavy chain framework regions which can be altered lie within regions designated H-FR1, H-FR2, H-FR3 and H-FR4, which surround the heavy chain CDR residues, and the residues of the light chain framework regions which can be altered lie within the regions designated L-FR1, L-FR2, L-FR3 and L-FR4, which surround the light chain CDR residues. An amino acid within the framework region may be replaced, for example, with any suitable amino acid identified in a human framework or human consensus framework.

It is further contemplated that the invention provides a purified polypeptide comprising any one of the amino acid sequences of SEQ ID NO: 1-150 fused to any one of the amino acid sequences of SEQ ID NO: 151-303, optionally paired as the heavy/light chain variable regions set forth in Table 3, or fragments thereof that include at least a portion of SEQ ID NO: 1-150 and SEQ ID NO: 151-303, optionally paired as set forth in Table 3, wherein the polypeptide binds insulin receptor, insulin or the insulin/insulin receptor complex.

It is contemplated that antibodies of the invention, including polypeptides comprising all or a portion of an antigen binding fragment in any one of SEQ ID NOs: 1-303, retain binding affinity, e.g. as measured by $K_D$, to insulin receptor, insulin or a complex of insulin/INSR of $10^{-5}$, $10^{-6}$, $10^{-7}$, $10^{-8}$, $10^{-9}$ M or less (wherein a lower value indicates a higher binding affinity), optionally as measured by surface plasmon resonance.

In some of the preceding embodiments, the invention contemplates an antibody that binds to insulin receptor and/or a complex comprising insulin and insulin receptor, with an equilibrium dissociation constant $K_D$ of $10^{-5}$M or less, that is capable of strengthening the binding affinity between insulin and insulin receptor by about 5-fold to 500-fold. In one embodiment, the antibody is characterized by the following equilibrium dissociation constant $K_D$ binding properties: (i) said antibody binds with an equilibrium dissociation constant $K_D$ of about $10^{-5}$M, $10^{-6}$, $10^{-7}$, $10^{-8}$, $10^{-9}$ $10^{-10}$, $10^{-11}$ M or less, to a complex comprising insulin (C1) or and insulin receptor (C2); and (ii) any of $K_{[C1C2]A}$, $K_{[AC2]C1}$, or $K_{[AC1]C2}$ is at least about 5-fold lower than any of $K_{AC2}$ or $K_{AC1}$. In a related embodiment, any of $K_{[C1C2]A}$, $K_{[AC2]C1}$, or $K_{[AC1]C2}$ is about 5-fold to 200-fold lower than any of $K_{AC2}$ or $K_{AC1}$.

In some embodiments, the antibody binds an insulin/insulin receptor complex. In further embodiments, the antibody binds insulin receptor alone, in an uncomplexed form. In a related embodiment, the antibody does not detectably bind insulin receptor alone, e.g., in the absence of insulin. In certain embodiments, the antibody is capable of strengthening the binding affinity between insulin and insulin receptor by at least about 5-fold, optionally to about 200-fold, optionally to about 100-fold. It is further provided that in some embodiments, the binding affinity is any one of $K_A$, $K_D$, the ratio of on rate to off rate, or the ratio of off rate to on rate.

In some embodiments, for any of the antibodies described herein, the difference in binding affinity or binding rate parameter ranges from about 1.5-fold to about 1000-fold, or about 1.5-fold to about 500-fold, about 1.5-fold to about 100-fold, or about 2-fold to 25-fold, or about 2-fold to about 50-fold, or about 1.5-fold to about 25-fold, or about 1.5-fold to about 50-fold, about 5-fold to about 500-fold, or about 5-fold to about 200-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, up to 30-fold, up to 20-fold, or up to 10-fold, or up to 5-fold or up to 3-fold.

In some embodiments, the invention provides an agonist antibody that binds to insulin receptor with an affinity, e.g. $K_D$, of $10^{-5}$, $10^{-6}$, $10^{-7}$, $10^{-8}$, $10^{-9}$ $10^{-10}$, $10^{-11}$ M or less, optionally that exhibits maximal agonist activity that is 20%-100% that of insulin's maximal agonist activity when measured in pAKT assay. In a related aspect, the invention contemplates an allosteric agonist antibody that binds to insulin receptor with an affinity, e.g., $K_D$ of $10^{-5}$, $10^{-6}$, $10^{-7}$, $10^{-8}$, $10^{-9}$ $10^{-10}$, $10^{-11}$ M or less and (a) exhibits maximal agonist activity that is 20%-80% that of insulin's maximal agonist activity when measured in pAKT assay, (b) when present does not alter the EC50 of insulin for INSR by more than 2-fold or 3-fold, and (c) when present does not alter the $K_D$ of insulin for INSR by more than 2-fold or 3-fold. It is further provided that in some embodiments, the binding affinity is any one of $K_A$, $K_D$, the ratio of on rate to off rate, or the ratio of off rate to on rate.

It is contemplated, in certain embodiments, that any of the above antibodies may also exhibit weak agonist activity, e.g., activates insulin receptor by at least 10% of the maximal signal of insulin, optionally in a phosphorylated AKT assay. In a further embodiment, the antibody activates insulin receptor by less than 10% of the maximal signal of insulin, optionally in a phosphorylated AKT assay.

In some embodiments, the antibody comprises a heavy chain variable region selected from the group consisting of the mature heavy chain variable region sequences set forth in SEQ ID NOs: 281, 278, 277, 209, 275, 223, 284, 276, and 236 and a light chain variable region selected from the group consisting of the mature light chain variable sequences set forth in SEQ ID NOs: 141, 138, 137, 35, 135, 57, 144, 136, and 98, optionally paired as set forth in Table 3.

In another embodiment, the antibody comprises (a) the heavy chain variable region of any of Ab006, Ab030, Ab004, Ab013, Ab009, Ab007, Ab011, Ab001, Ab012, Ab010, Ab003, Ab008, Ab002, Ab005, Ab076, Ab077, Ab079, Ab080, Ab083, Ab059, Ab078, Ab085 or set out in SEQ ID NO: 291, 196, 239, 267 and 271 and the light chain variable region of any of Ab006, Ab030, Ab004, Ab013, Ab009, Ab007, Ab011, Ab001, Ab012, Ab010, Ab003, Ab008, Ab002, Ab005, Ab076, Ab077, Ab079, Ab080, Ab083, Ab059, Ab078, Ab085 or set out in SEQ ID NO: 76, 80, 101, 128, and 132, optionally paired as set forth in Table 3 and preferably the mature portions thereof, or (b) one, two or three heavy chain CDRs of any of Ab006, Ab030, Ab004, Ab013, Ab009, Ab007, Ab011, Ab001, Ab012, Ab010, Ab003, Ab008, Ab002, Ab005, Ab076, Ab077, Ab079, Ab080, Ab083, Ab059, Ab078, Ab085 or set out in SEQ ID NO: 291, 196, 239, 267 and 271 and/or one, two or three light chain CDRs of any of Ab006, Ab030, Ab004, Ab013, Ab009, Ab007, Ab011, Ab001, Ab012, Ab010, Ab003, Ab008, Ab002, Ab005, Ab076, Ab077, Ab079, Ab080, Ab083, Ab059, Ab078, Ab085 or set out in SEQ ID NO: 76, 80, 101, 128, and 132, optionally including one or two mutations in any one, two or three of such heavy or light chain CDRs, e.g., a conservative or non-conservative substitution, optionally paired as set forth in Table 3; or (c) all six CDRs of any of Ab006, Ab030, Ab004, Ab013, Ab009, Ab007, Ab011, Ab001, Ab012, Ab010, Ab003, Ab008, Ab002, Ab005, Ab076, Ab077, Ab079, Ab080, Ab083, Ab059, Ab078, Ab085 or antibodies having the variable regions set out in SEQ ID NO: 76, 80, 101, 128, 132, 291, 196, 239, 267, and 271, optionally paired as set forth in Table 3.

In other embodiments, the invention provides an antibody that competes with any of the antibodies described herein, e.g. by at least 70%, 75%, or 80%. In certain embodiments, the antibody exhibits greater than or equal to 70% competition, e.g. at least 75% or at least 80% competition, with any one, two, three or all antibodies selected from the group consisting of Ab079, Ab076, Ab083, Ab080, Ab062, Ab020, Ab019, Ab088, and Ab089, and optionally exhibits greater than or equal to 30% competition with any one, two, three or all antibodies selected from the group consisting of Ab086, Ab064, Ab001, and Ab018. Optionally, the antibody does not compete with one or more of Ab062 and Ab086, and optionally may bind both human and murine insulin receptor or complex.

In a related embodiment, the antibody exhibits greater than or equal to 70% competition, e.g., at least 75% or at least 80% competition, with any one, two, three or all antibodies selected from the group consisting of Ab040, Ab062, Ab030, Ab001, and Ab018, and optionally exhibits greater than or equal to 30% competition with any one, two, three or all antibodies selected from the group consisting of Ab037, Ab078, Ab083, Ab080, and Ab085. In a related embodiment, the antibody does not compete with any one, two, three or more of antibodies selected from the group consisting of Ab053, Ab064, 83-7, Ab019, Ab088, and Ab089. Optionally, the antibody binds both human and murine insulin receptor or complex. In another embodiment, the antibody exhibits greater than or equal to 70% competition, e.g. at least 75% or at least 80% competition, with any one, two, three or all antibodies selected from the group consisting of Ab064, Ab062, Ab085, and Ab078. Optionally, the antibody exhibits no competition with any one, two, three or more of antibodies selected from the group consisting of Ab077, Ab001, Ab018, Ab030, Ab037, Ab079, Ab076, Ab083, Ab019, Ab088, Ab089, and Ab040. Optionally, the antibody binds both human and murine insulin receptor or complex.

In a further aspect, the invention provides an antibody that binds to insulin receptor and/or a complex comprising insulin and insulin receptor with an equilibrium dissociation constant $K_D$ of $10^{-5}$M or less that is capable of weakening the binding affinity between insulin and insulin receptor by at least about 3-fold, optionally up to 1000-fold. In certain embodiments, the antibody weakens the affinity between said insulin and insulin receptor by about 3-fold to 500-fold. In some embodiments, the binding affinity is any one of $K_A$, $K_D$, the ratio of on rate to off rate, or the ratio of off rate to on rate.

In some embodiments, for any of the antibodies described herein, the difference in binding affinity or binding rate parameter ranges from about 1.5-fold to about 1000-fold, or about 1.5-fold to about 500-fold, about 1.5-fold to about 100-fold, or about 2-fold to 25-fold, or about 2-fold to about 50-fold, or about 1.5-fold to about 25-fold, or about 1.5-fold to about 50-fold, about 5-fold to about 500-fold, or about 5-fold to about 200-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, up to 30-fold, up to 20-fold, or up to 10-fold, or up to 5-fold or up to 3-fold.

In a related embodiment, the antibody increases the EC50 of insulin signaling activity by about 2-fold to 1000-fold, optionally in a pAKT assay. In certain embodiments, the antibody increases the EC50 by at least about 5, 10, 15, 20, 25, 30, 35, 40, 45, 50, 60, 70, 80, 90, 100, 150, 200, 250, 300, 350, 400, 450, 500, 550, 600, 650, 700, 750, 800, 850, 900, 950 or 1000-fold.

In certain embodiments, the antibody comprises a heavy chain variable region selected from the group consisting of the mature heavy chain variable region sequences set forth in SEQ ID NOs: 241, 279, 258, 155, and 228 and a light chain variable region selected from the group consisting of the mature light chain variable region sequences set forth in SEQ ID NOs: 103, 139, 119, 8, and 89, optionally paired as set forth in Table 3.

In a further embodiment, the antibody comprises (a) the heavy chain variable region of any of Ab087, Ab019, Ab088, Ab089, Ab020, Ab050, Ab052, Ab055, Ab057, Ab061, Ab063, Ab065, Ab070, Ab072, Ab074, Ab081 and the light chain variable region of any of Ab087, Ab019, Ab088, Ab089, Ab020, Ab050, Ab052, Ab055, Ab057, Ab061, Ab063, Ab065, Ab070, Ab072, Ab074, Ab081, preferably the mature portions thereof, or (b) one, two or three heavy chain CDRs of any of Ab087, Ab019, Ab088, Ab089, Ab020, Ab050, Ab052, Ab055, Ab057, Ab061, Ab063, Ab065, Ab070, Ab072, Ab074, Ab081 and/or one, two or three light chain CDRs of any of Ab087, Ab019, Ab088, Ab089, Ab020, Ab050, Ab052, Ab055, Ab057, Ab061, Ab063, Ab065, Ab070, Ab072, Ab074, Ab081, optionally including one or two mutations in any one, two or three of such heavy or light chain CDRs, e.g., a conservative or non-conservative substitution; or (c) all six CDRs of any of Ab087, Ab019, Ab088, Ab089, Ab020, Ab050, Ab052, Ab055, Ab057, Ab061, Ab063, Ab065, Ab070, Ab072, Ab074, Ab081.

In a further embodiment, the invention provides an antibody that competes with the above antibodies, wherein the antibody exhibits greater than or equal to 70% competition, e.g., at least 75% or at least 80% competition, with any one, two, three or all antibodies selected from the group consisting of Ab079, Ab076, Ab083, Ab080, Ab062, and Ab020, Ab019, Ab088, Ab089. Optionally, the antibody does not exhibit competition with any one, two, three or more of the antibodies selected from the group consisting of Ab062, Ab086, Ab001, Ab018, Ab030, Ab037, Ab064; and optionally, the antibody is human reactive only, and does not bind murine insulin receptor or complex.

In one embodiment, the invention provides an antibody that is an agonist, wherein the antibody comprises a heavy chain variable region selected from the group consisting of the mature heavy chain variable region sequences set forth in SEQ ID NOs: 195, 220, 303, 197, 208, 243, 245 and 251 and a light chain variable region selected from the group consisting of the mature light chain variable region sequences set forth in SEQ ID NOs: 77, 50, 90, 84, 34, 104, 106 and 112, optionally paired as set forth in Table 3.

In a related embodiment, the antibody comprises (a) the heavy chain variable region of any of Ab021, Ab029, Ab022, Ab017, Ab023, Ab024, Ab025, Ab026, Ab031, Ab035, Ab027, Ab036, Ab037, Ab028, Ab038, Ab039, Ab040, Ab041, Ab042, Ab032, Ab043, Ab044, Ab045, Ab046, Ab047, Ab018, Ab033, Ab048, Ab014, Ab015, Ab049, Ab034, Ab051, Ab053, Ab054, Ab056, Ab058, Ab062, Ab064, Ab066, Ab067, Ab068, Ab086, Ab069, Ab071, Ab073, Ab075, Ab082, Ab084 set out in SEQ ID NOs: 252, 253, 263, 265 and 269 and the light chain variable region of any of Ab021, Ab029, Ab022, Ab017, Ab023, Ab024, Ab025, Ab026, Ab031, Ab035, Ab027, Ab036, Ab037, Ab028, Ab038, Ab039, Ab040, Ab041, Ab042, Ab032, Ab043, Ab044, Ab045, Ab046, Ab047, Ab018, Ab033, Ab048, Ab014, Ab015, Ab049, Ab034, Ab051, Ab053, Ab054, Ab056, Ab058, Ab062, Ab064, Ab066, Ab067, Ab068, Ab086, Ab069, Ab071, Ab073, Ab075, Ab082, Ab084 or set out in SEQ ID NOs: 7, 113, 114, 124, 126 and 130, optionally paired as set forth in Table 3 and preferably the mature portions thereof, or (b) one, two or three heavy chain CDRs of any of Ab021, Ab029, Ab022, Ab017, Ab023, Ab024, Ab025, Ab026, Ab031, Ab035, Ab027, Ab036, Ab037, Ab028, Ab038, Ab039, Ab040, Ab041, Ab042, Ab032, Ab043, Ab044, Ab045, Ab046, Ab047, Ab018, Ab033, Ab048, Ab014, Ab015, Ab049, Ab034, Ab051, Ab053, Ab054, Ab056, Ab058, Ab062, Ab064, Ab066, Ab067, Ab068, Ab086, Ab069, Ab071, Ab073, Ab075, Ab082, Ab084 or set out in SEQ ID NOs: 252, 253, 263, 265 and 269 and/or one, two or three light chain CDRs of any of Ab021, Ab029, Ab022, Ab017, Ab023, Ab024, Ab025, Ab026, Ab031, Ab035, Ab027, Ab036, Ab037, Ab028, Ab038, Ab039, Ab040, Ab041, Ab042, Ab032, Ab043, Ab044, Ab045, Ab046, Ab047, Ab018, Ab033, Ab048, Ab014, Ab015, Ab049, Ab034, Ab051, Ab053, Ab054, Ab056, Ab058, Ab062, Ab064, Ab066, Ab067, Ab068, Ab086, Ab069, Ab071, Ab073, Ab075, Ab082, Ab084 or set out in SEQ ID NOs: 7, 113, 114, 124, 126 and 130, optionally including one or two mutations in any one, two or three of such heavy or light chain CDRs, e.g., a conservative or non-conservative substitution, optionally paired as set forth in Table 3; (c) all six CDRs of any of Ab021, Ab029, Ab022, Ab017, Ab023, Ab024, Ab025, Ab026, Ab031, Ab035, Ab027, Ab036, Ab037, Ab028, Ab038, Ab039, Ab040, Ab041, Ab042, Ab032, Ab043, Ab044, Ab045, Ab046, Ab047, Ab018, Ab033, Ab048, Ab014, Ab015, Ab049, Ab034, Ab051, Ab053, Ab054, Ab056, Ab058, Ab062, Ab064, Ab066, Ab067, Ab068, Ab086, Ab069, Ab071, Ab073, Ab075, Ab082, Ab084 or set out in SEQ ID NOs: 7, 113, 114, 124, 126, 130, 252, 253, 263, 265 and 269, optionally paired as set forth in Table 3.

In a related embodiment, the invention provides an antibody that competes with the above antibodies for binding to target, wherein the antibody exhibits greater than or equal to 70% competition, e.g., at least 75% or at least 80% competition, with any one, two, three or all antibodies selected from the group consisting of Ab030, Ab037, Ab053, Ab001, Ab018, Ab064, Ab040 and optionally exhibits greater than or equal to 30% competition with any one, two, three or all antibodies selected from the group consisting of Ab085 and Ab086. Optionally, the antibody exhibits no competition with any one, two, three or more of the antibodies selected from the group consisting of Ab079, Ab076 and Ab088; and optionally binds to both human and murine insulin receptor or complex.

In a another aspect, the invention provides polynucleotides encoding antibodies and polypeptides of the invention, vectors comprising such polynucleotides, host cells comprising such polynucleotides or vectors, and methods of producing antibodies and polypeptides of the invention comprising growing such host cells in culture medium under suitable conditions and optionally isolating the encoded antibody or polypeptide from the host cells or culture medium, optionally followed by further purification of the antibody or polypeptide, e.g., as described herein.

Antibodies having the properties described herein may be isolated using a screening method to determine binding to the INSR and modulation of the insulin/INSR complex.

In one embodiment, the invention provides a positive modulating antibody that strengthens the binding of a first component (C1) to a second component (C2) of a signaling complex, said antibody characterized by the following equilibrium dissociation constant $K_D$ binding properties: (i) said antibody binds with an equilibrium dissociation constant $K_D$ of about $10^{-5}$M or less, e.g., $10^{-6}$M or less, or $10^{-7}$M or less, or $10^{-8}$M or less, to any one of C1, C2, or a complex comprising C1 and C2 (C1C2); and (ii) any of $K_{[C1C2]A}$, $K_{[AC2]C1}$, or $K_{[AC1]C2}$ is at least about 50% (1.5-fold) lower than any of $K_{AC2}$ or $K_{AC1}$. In some embodiments any of $K_{[C1C2]A}$, $K_{[AC2]C1}$, or $K_{[AC1]C2}$ is about 1.5-fold to about 100-fold lower than any of $K_{AC2}$ or $K_{AC1}$; or about 2-fold to 25-fold, or about 2-fold to about 50-fold, or about 1.5-fold to about 25-fold, or about 1.5-fold to about 50-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to about 100-fold, or up to about 90-fold, or up to about 80-fold, or up to about 70-fold, or up to about 60-fold, or up to about 50-fold, or up to about 40-fold, or up to about 30-fold, or up to about 20-fold, or up to about 10-fold lower. In some embodiments, any of $K_{[C1C2]A}$; $K_{[AC2]C1}$, or $K_{[AC1]C2}$ is at least about 1.5-fold lower than both of $K_{AC2}$ or $K_{AC1}$; or 1.5-fold to about 100-fold lower, or about 2-fold to 25-fold, or about 2-fold to about 50-fold, or about 1.5-fold to about 25-fold, or about 1.5-fold to about 50-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to about 100-fold, or up to about 90-fold, or up to about 80-fold, or up to about 70-fold, or up to about 60-fold, or up to about 50-fold, or up to about 40-fold, or up to about 30-fold, or up to about 20-fold, or up to about 10-fold lower.

In some embodiments, the invention provides a negative modulating antibody that weakens the binding of a first component (C1) to a second component (C2) of a signaling complex, said antibody characterized by the following equilibrium dissociation constant $K_D$ binding properties: (i) said antibody binds with an equilibrium dissociation constant $K_D$ of about $10^{-5}$M or less, e.g., $10^{-6}$M or less, or $10^{-7}$M or less, or $10^{-8}$M or less, to any one of C1, C2, or a complex comprising C1 and C2 (C1C2), and (ii) any of $K_{AC2}$ or $K_{AC1}$ is at least about 50% (1.5-fold) lower than any of $K_{[C1C2]A}$; $K_{[AC2]C1}$; or $K_{[AC1]C2}$. In some embodiments, any of $K_{AC2}$ or $K_{AC1}$ is at least about 1.5-fold to 100-fold lower than any of $K_{[C1C2]A}$, $K_{[AC2]C1}$; or $K_{[AC1]C2}$; or about 2-fold to 25-fold, or about 2-fold to about 50-fold, or about 1.5-fold to about 25-fold, or about 1.5-fold to about 50-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to about 100-fold, or up to about 90-fold, or up to about 80-fold, or up to about 70-fold, or up to about 60-fold, or up to about 50-fold, or up to about 40-fold, or up to about 30-fold, or up to about 20-fold, or up to about 10-fold lower. In some embodiments, any of $K_{AC2}$ or $K_{AC1}$ is at least about 1.5-fold lower than all of $K_{[C1C2]A}$; $K_{[AC2]C1}$; or $K_{[AC1]C2}$; or 1.5-fold to about 100-fold lower, or about 2-fold to 25-fold, or about 2-fold to about 50-fold, or about 1.5-fold to about 25-fold, or about 1.5-fold to about 50-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to about 100-fold, or up to about 90-fold, or up to about 80-fold, or up to about 70-fold, or up to about 60-fold, or up to about 50-fold, or up to about 40-fold, or up to about 30-fold lower, or up to about 20-fold, or up to about 10-fold.

In specific embodiments, C1 and C2 are selected from the group consisting of insulin and insulin receptor.

In another aspect, the invention contemplates a method of preparing a sterile pharmaceutical composition, comprising adding a sterile pharmaceutically acceptable diluent to an antibody of the invention. Optionally small amounts of a preservative such as a bactericidal or bacteriostatic agent are also included in the composition.

Also contemplated is a sterile composition comprising an antibody of the invention and a sterile pharmaceutically acceptable diluent.

The invention further contemplates that the antibodies of the invention modulate binding between the INSR and insulin or insulin analogs or insulin mimetics. The antibodies of the invention preferably also exhibit desirable biological properties, including but not limited to enhancing glucose uptake in vitro or in vivo in animal models, and preferably the glucose uptake induced by exogenous insulin. In some embodiments, the antibodies are capable of increasing the rate or total amount of glucose uptake, or both.

In a further aspect, the invention contemplates a method of treating a disorder associated with insulin resistance, comprising administering to a subject in need thereof a positive modulating antibody or agonist antibody of the invention in an amount effective to treat insulin resistance. In a related embodiment, the treatment enhances glucose uptake. In a further embodiment, the enhanced glucose uptake is selected from the group consisting of an increase in the rate of glucose uptake, an increase in the total amount of glucose uptake, or both. It is further contemplated that the treatment reduces fasting blood glucose levels, in a subject having elevated levels of blood glucose, hyperglycemia or a disorder associated with insulin resistance, back toward the normal range of fasting blood glucose levels. In a related embodiment, the fasting blood glucose is reduced by approximately 15%, 20%, 25%, 30%, 35%, 40%, 45%, 50% or more compared to an untreated subject.

In related aspects, the treatment reduces elevated HbA1c levels, which are a marker of elevated glucose levels over the preceding several-month period, and are indicative of diabetes. In further embodiments, treatment improves impaired glucose tolerance. In one embodiment glucose tolerance is measured by glucose tolerance test (GTT).

In other embodiments, the treatment slows, reduces, or normalizes weight gain of a subject. In one embodiment, the treatment reduces or slows weight gain by at least 5%, 10%, 15%, 20%, 25%, 30%, 35%, 40%, 45% or 50% compared to an untreated subject. In some embodiments, the treatment slows, reduces, or normalizes weight loss of a subject. In one embodiment, the treatment reduces or slows weight loss by at least 5%, 10%, 15%, 20%, 25%, 30%, 35%, 40%, 45% or 50% compared to an untreated subject.

In a related aspect, it is contemplated that the antibodies or polypeptides described herein promote or induce weight loss in a subject. In one embodiment, the invention provides a method to promote or induce weight loss by administration of a modulating antibody, fragment thereof or polypeptide as described herein. In one embodiment, the modulating antibody is a positive modulator or partial agonist. In a related embodiment, the modulating antibody is a negative modulator.

It certain embodiments, the treatment further results in improvement of one, two, three or more symptoms of diabetes or insulin resistance selected from the group consisting of dyslipidemia, elevated plasma triglycerides, elevated HOMA-IR, elevated plasma unesterified cholesterol, plasma total cholesterol elevated plasma insulin (indicative of insulin resistance), low non-HDL/HDL cholesterol ratio (or low total cholesterol/HDL cholesterol ratio), and elevated plasma leptin levels (indicative of leptin resistance).

It is further provided that the effects of treatment are also measured using in vitro and in vivo analysis using factors as described in the Detailed Description.

In one embodiment, the disorder associated with insulin resistance is selected from the group consisting of hyperglycemia, pre-diabetes, metabolic syndrome (also referred to as insulin resistance syndrome), Type 2 diabetes mellitus, polycystic ovary disease (PCOS), non-alcoholic fatty liver disease (NAFLD), non-alcoholic steatohepatitis (NASH), steatosis, obesity, dyslipidemia, Rabson-Mendenhall syndrome, Donohue syndrome or Leprechaunism.

In another aspect, the invention provides a method of treating a condition or disorder associated with hyperinsulinemia, abnormal production and/or sensitivity to insulin that manifests as excess insulin signaling, comprising administering to a subject in need thereof a negative modulating antibody or an antagonist antibody of the invention in an amount effective to treat insulin overproduction and/or sensitivity. In one embodiment, the disorder associated with insulin sensitivity is selected from the group consisting of cancer, Kaposi's sarcoma, insulinoma, diabetic renal disease, hypoglycemia, nesidioblastosis (KATP-Hl Diffuse Disease, KATP-Hl Focal Disease, or "PHHI"), GDH-Hl (Hyperinsulinism/Hyperammonaemia Syndrome (HI/HA), leucine-sensitive hypoglycemia, or diazoxide-sensitive hypoglycemia), islet cell dysregulation syndrome, idiopathic hypoglycemia of infancy, Persistent Hyperinsulinemic Hypoglycemia of Infancy (PHHI), and Congenital Hyperinsulinism, insulin overdose, hypoglycemia due to renal failure (acute or chronic), and chronic kidney disease, e.g., type III, IV or V.

Use of any of the foregoing antibodies or polypeptides of the invention that modulate the insulin-INSR signaling interaction in preparation of a medicament for treatment of any of the disorders described herein is also contemplated. Syringes, e.g., single use or pre-filled syringes, sterile sealed containers, e.g. vials, bottle, vessel, and/or kits or packages comprising any of the foregoing antibodies or polypeptides, optionally with suitable instructions for use, are also contemplated.

Any of the foregoing antibodies or polypeptides of the invention may be concurrently administered with any antidiabetic agents known in the art or described herein, as adjunct therapy. Compositions comprising any of the foregoing antibodies or polypeptides of the invention together with other anti-diabetic agents are also contemplated.

A number of anti-diabetic agents are known in the art, including but not limited to: 1) sulfonylureas (e.g., glimepiride, glisentide, sulfonylurea, AY31637); 2) biguanides (e.g., metformin); 3) alpha-glucosidase inhibitors (e.g., acarbose, miglitol); 4) thiazol-idinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054); 5) glucagon-like-peptides (GLP) and GLP analogs or agonists of GLP-1 receptor (e.g. exendin) or stabilizers thereof (e.g. DPP4 inhibitors, such as sitagliptin); and 6) insulin or analogues or mimetics thereof (e.g. LANTUS®).

In a related aspect, the invention provides a method of diagnosing insulin resistance or insulin sensitivity using antibodies as described herein. In one embodiment, the method comprises measuring levels of insulin or insulin receptor in a sample from a subject using an insulin receptor antibody described herein, wherein an increased level of insulin or free insulin receptor, or a decreased level of membrane-bound insulin receptor indicates the subject has or is at risk for diabetes or insulin resistance, and optionally administering a diabetes therapeutic to said subject who has or is at risk of diabetes or insulin resistance. In another embodiment, the method comprises measuring levels of insulin receptor in a sample from a subject using an insulin receptor antibody described herein, wherein an increased level of free insulin receptor or a decreased level of membrane-bound insulin receptor indicates the subject has or is at risk for cancer, and optionally administering a cancer therapeutic to said subject.

In another aspect, the invention provides methods for identifying antibodies that modulate the binding of insulin to the insulin receptor as described herein.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment", "some embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the invention. Similarly, where a method describes identifying polypeptide binding agents, such as antibodies, characterized by certain features, polypeptide binding agents characterized by those features are also contemplated by the invention. Where examples of values falling within ranges are disclosed, any of these examples are contemplated as possible endpoints of a range, any and all numeric values between such endpoints are contemplated, and any and all combinations of upper and lower endpoints are envisioned.

BRIEF DESCRIPTION OF THE FIGURES

FIG. 1 depicts representative results from an INSR receptor occupancy screen showing test antibodies binding to IM-9 cells expressing the INSR in the presence and absence of insulin.

FIG. 2 shows representative results from a biotinylated ligand screen showing the effects of test antibodies on insulin binding to insulin receptor.

FIG. 4 depicts results from a pIRS-1 activity assay showing binding of representative antibodies to INSR from different functional classes. FIG. 4A: Positive Modulators; FIG. 4B: Positive modulators with significant agonism; FIG. 4C: Non-modulators; FIG. 4D: Agonist Antibodies; FIG. 4E: Negative modulators.

FIG. 5 is a table showing insulin EC50 values for representative antibodies from the pIRS-1 assay ranked according to EC50 ratio +Ab/−Ab.

FIG. 6 shows results of a pAKT assay for representative antibodies: FIG. 6A: Positive modulator with very low agonism; FIG. 6B: Positive modulator with agonism; FIG. 6C: Agonist antibodies; FIG. 6D: 83-7; Figure E: Insulin and background response in the absence of antibody.

FIG. 7 is a table showing agonism and mouse cross reactivity properties of representative test antibodies. (nd=not determined).

FIG. 8 shows pAKT assay results showing changes in sensitivity (EC50, fold-change in EC50) and cooperativity (Hillslope) of the insulin dose response effected by a positive modulator INSR antibody at four different concentrations. FIG. 8A shows the results graphically while FIG. 8B shows the results in tabular form.

FIG. 10 shows blood glucose levels in 20 week old DIO mice fed a high fat diet and treated with partial agonist anti-INSR antibodies: FIG. 10A: Line graph of glucose levels. FIG. 10B: Bar chart of glucose levels showing statistically significant reduction in blood glucose after injection of partial agonist anti-INSR antibody.

FIG. 11 illustrates that administration of a partial agonist anti-INSR antibody improves glycemic control in DIO mice: FIG. 11A: Glucose tolerance test timecourse; FIG. 11B: Fasting blood glucose levels; FIG. 11C: Glucose tolerance test; area under curve (AUC).

FIG. 12 shows that a positive modulator anti-INSR antibody improves insulin sensitivity in DIO mice: FIG. 12A: Insulin tolerance test timecourse; FIG. 12B: Fasting blood glucose levels; FIG. 12C: Insulin tolerance test; area under curve (AUC).

FIG. 13 shows that a positive modulator anti-INSR antibody improves glycemic control in DIO mice: FIG. 13A: Glucose tolerance test timecourse; FIG. 13B: Fasting blood glucose levels; FIG. 13C: Glucose tolerance test; area under curve (AUC).

FIG. 14 demonstrates that positive modulator and partial agonist anti-INSR antibodies improve triglyceride and cholesterol levels in DIO Mice. Plasma triglyceride and cholesterol levels were measured in 30-week old DIO mice injected intraperitoneally (IP) with Ab001, Ab037 or isotype control (10 mg/kg; * p<0.05 relative to isotype control/HFD)

FIG. 15 illustrates improvement of glycemic control in DIO mice after administration of positive modulator and partial agonist anti-INSR antibodies. Glycemic control measurements were observed in DIO mice injected intraperitoneally (IP) with Ab001, Ab037, Ab083, Ab085 or isotype control (10 mg/kg; * p<0.05 relative to isotype control/HFD): FIG. 15A: Glucose tolerance test timecourse; FIG. 15B: Glucose tolerance test; area under curve (AUC); FIG. 15C: Fasting blood glucose levels.

FIG. 16 shows positive modulator and partial agonist anti-INSR antibodies improve glycemic parameters, insulin resistance and and/or dyslipidemia in 18-week old DIO mice treated with mAb for 4 weeks. Analysis of plasma from DIO mice injected intraperitoneally (IP) with Ab001, Ab037, Ab083, Ab085 or isotype control for 4 weeks (10 mg/kg; * p<0.05 relative to isotype control/HFD) was performed. FIG. 16A: Plasma glucose levels FIG. 16B: Plasma insulin levels; FIG. 16C: HOMA-IR; FIG. 16D: Plasma triglyceride levels; FIG. 16E: Plasma unesterified cholesterol levels; FIG. 16F: Plasma total cholesterol levels; FIG. 16G: Plasma non-HDL cholesterol levels; FIG. 16H: Plasma non-HDL/HDL cholesterol ratio.

FIG. 17 demonstrates that positive modulator and partial agonist anti-INSR antibodies reduce weight gain in DIO mice as assessed by body weight measurements in 18-week old DIO mice injected intraperitoneally (IP) with Ab001, Ab037, Ab083, Ab085 or isotype control for 3 weeks (10 mg/kg; * p<0.05 relative to isotype control/HFD): FIG. 17A: Percent change in body weight relative to pre-dose weight; FIG. 17B: Percent change in body weight relative to pre-dose weight: Area under the curve.

FIG. 18 depicts positive modulator and partial agonist anti-INSR antibody-induced normalization of weight gain in db/db mice analyzed by body weight measurements in 5 week old db/db mice injected intraperitoneally (IP) with Ab001 (1 mg/kg or 10 mg/kg), Ab037 (10 mg/kg) or isotype control (1 mg/kg or 10 mg/kg) for 14 weeks (* p<0.05 relative to isotype control): FIG. 18A: Percent change in body weight relative to pre-dose weight until day 35 of study; FIG. 18B: Percent change in body weight relative to weight at day 35 of study; FIG. 18C: Percent change in body weight relative to pre-dose weight until day 35 of study: Area under the curve; FIG. 18D: Percent change in body weight relative to weight at day 35 of study: Area under the curve.

FIG. 19 shows that positive modulator antibody reduces fasting blood glucose and HbA1c in db/db mice as assessed using glycemic control measurements in 5 week old db/db mice injected intraperitoneally (IP) with Ab001 (1 mg/kg or 10 mg/kg), Ab037 (10 mg/kg) or isotype control (1 mg/kg or 10 mg/kg) for 14 weeks (* p<0.05 relative to isotype control at same dose): FIG. 19A: Fasting blood glucose levels; FIG. 19B: % HbA1c levels.

FIG. 20 illustrates that administration of positive modulator antibody improves dyslipidemia in db/db mice. Analysis of plasma from 5-week old db/db mice injected intraperitoneally (IP) with Ab001 (1 mg/kg or 10 mg/kg), Ab037 (10 mg/kg) or isotype control (1 mg/kg or 10 mg/kg) for 14 weeks (* p<0.05 relative to isotype control at same dose) was carried out. FIG. 20A: Plasma insulin levels; FIG. 20B: Plasma triglyceride levels; FIG. 20C: Plasma unesterified cholesterol levels; FIG. 20D: Plasma total cholesterol levels; FIG. 20E: Plasma non-HDL cholesterol levels; FIG. 20F: Plasma non-HDL/HDL cholesterol ratio.

FIG. 23 illustrates that positive modulator and partial agonist anti-INSR antibodies improve glycemic control in MLDS/HFD mice. Glycemic control measurements were taken from 10-week old MLDS/HFD mice injected intraperitoneally (IP) with Ab001, Ab037 or isotype control (10 mg/kg; * p<0.05 relative to isotype control): FIG. 23A: Glucose tolerance test timecourse; FIG. 23B: Glucose tolerance test; area under curve (AUC); FIG. 23C: Fasting blood glucose levels.

FIG. 24 shows administration of a partial agonist antibody reduces fed blood glucose and HbA1c in MLDS/HFD mice. Glycemic control measurements were taken in 10-week old MLDS/HFD mice injected intraperitoneally (IP) with Ab001, Ab037 or isotype control for 6 weeks (10 mg/kg; * p<0.05 relative to isotype control): FIG. 24A: Fed blood glucose levels; FIG. 24B: % HbA1c levels.

FIG. 25 shows positive modulator and/or partial agonist anti-INSR antibodies partially correct insulin, leptin and non-HDL/HDL cholesterol levels in MLDS/HFD mice. Plasma cholesterol, insulin and leptin levels were measured in 10-week old MLDS/HFD mice injected intraperitoneally (IP) with Ab001, Ab037 or isotype control for 6 weeks (10 mg/kg; * p<0.05 relative to isotype control): FIG. 25A: Plasma non-HDL/HDL cholesterol ratio; FIG. 25B: Plasma insulin levels; FIG. 25C: Plasma leptin levels.

FIG. 27 illustrates that positive modulator and partial agonist anti-INSR antibodies improve glycemic control in MLDS/HFD mice. A glucose tolerance test (GTT) was carried out in 10-week old MLDS/HFD mice injected intraperitoneally (IP) with Ab001, Ab083, Ab085, Ab037 or isotype control for 3 weeks (10 mg/kg; * p<0.05 relative to isotype control). FIG. 27A: Glucose tolerance test timecourse; FIG. 27B: Glucose tolerance test; area under curve (AUC).

FIG. 29 illustrates that positive modulator and partial agonist anti-INSR antibodies improve dyslipidemia in MLDS/HFD mice. Analysis of plasma from of 10-week old MLDS/HFD mice injected intraperitoneally (IP) with Ab001, Ab083, Ab085, Ab037 or isotype control for 6 weeks (10 mg/kg; * p<0.05 relative to isotype control) was carried out. FIG. 29A: Plasma triglyceride levels; FIG. 29B: Plasma free fatty acid levels; FIG. 29C: Plasma unesterified cholesterol levels; FIG. 29D: Plasma total cholesterol levels; FIG. 29E: Plasma non-HDL cholesterol levels; FIG. 29F: Plasma non-HDL/HDL cholesterol ratio.

FIG. 32 shows that positive modulator and partial agonist anti-INSR antibodies augment insulin signaling in vivo. Ten week-old C56BL/6 male mice were injected with Ab083, Ab085, Ab037 or isotype control (10 mg/kg) for 24 hours, and effects on liver (FIG. 32A) and muscle (FIG. 32B) INSR tyrosine phosphorylation were determined by ELISA after an insulin bolus.

FIG. 33 is a table showing the binding characteristics of INSR-specific antibodies reformatted with an IgG2 constant region.

FIG. 34A illustrates the dose response from a partial allosteric agonist anti-INSR antibody in comparison to the dose response to the endogenous ligand and FIG. 34B illustrates activation by ligand in the presence or absence of the allosteric agonist antibody.

FIG. 35A shows the dose response from a positive modulator antibody in comparison to the dose response to the endogenous ligand and FIG. 35B shows the dose response of an endogenous ligand in the presence and absence of a positive modulator antibody.

FIG. 36 illustrates the activation parameters for a set of partial allosteric agonists alone relative to the endogenous ligand insulin. Data obtained from measurements of percent Akt phosphorylation at Ser473.

FIG. 37 illustrates the activation properties of insulin in the presence of 10 ug/ml partial allosteric agonist antibodies relative to the maximal response to the endogenous ligand in the presence of a negative control antibody. Data obtained from measurements of percent Akt phosphorylation at Ser473.

FIGS. 38-40 depict pAkt activation by antibodies in the absence of insulin or in the presence of a sub-maximal concentration of insulin for parental CHO-K1 cells, CHO-K1 cells expressing human insulin receptor and CHO-K1 cells expressing mouse insulin receptor. FIGS. 38A-C show the effects of sensitizer Abs (Ab077, Ab078, Ab085) with little or no agonism of pAkt activity (<10% pAkt activation in the absence of insulin with 50 ug/ml antibody). FIGS. 39A-C show the effects of sensitizer Abs (Ab001, Ab079, Ab083) with weak to moderate agonism of pAkt activity (10-20% pAkt activation in the absence of insulin with 50 ug/ml antibody). FIG. 40 illustrates the effects of a sensitizer Ab (Ab080) with moderate agonism of pAkt activity (>20% pAkt activation in the absence of insulin with 50 ug/ml antibody).

FIG. 41A and FIG. 41C shows insulin dependent pAkt activation in CHO cells expressing the human and FIG. 41B shows mouse INSR in the presence of fixed concentrations of sensitizing anti-INSR antibodies.

FIG. 42A demonstrates pAkt activation in CHO cells expressing the human and FIG. 42B demonstrates mouse INSR by partial allosteric agonist antibodies in the absence of insulin compared to insulin-alone.

FIG. 43 depicts the results of insulin dependent pAkt activation in CHO cells expressing the human INSR in the presence of fixed concentrations of partial allosteric agonist antibodies.

FIG. 44 shows pAKT assay results for antibody 83-7 and Ab001 on CHOK1 cells expressing: FIG. 44A: human INSR, or; FIG. 44B: mouse INSR.

FIG. 54 is a table showing cross-reactivity of insulin receptor antibodies, and illustrates that certain antibodies that bind to the human insulin receptor also bind to the rabbit and the cynomolgous insulin receptor and that this binding was modulated by the presence of insulin.

FIG. 55 shows the result of competition assays by binning assays and grouping of the various antibody clones.

DETAILED DESCRIPTION

Figure 3:
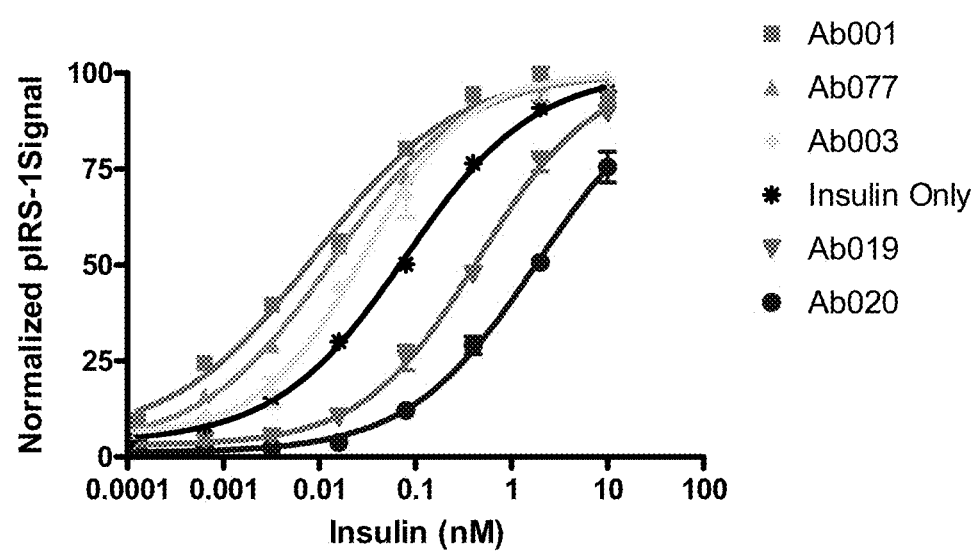
FIG. 3 shows results from an assay measuring the ability of test antibodies to modulate insulin dependent pIRS-1 phosphorylation.

The invention provides antibodies specific for the insulin receptor (INSR) or the insulin receptor-insulin complex and uses thereof in the treatment of disorders related to aberrant glucose levels, e.g. hyperglycemia or hypoglycemia, aberrant insulin levels or aberrant insulin sensitivity, e.g. disorders of insulin resistance or disorders of insulin sensitivity. These antibodies can induce either a positive or negative effect on the cellular response in the INSR by altering the kinetic rate constants for assembly and dissociation of INSR-INS signaling complex components or by other mechanisms including altering the structural state of the signaling complex, e.g., by binding to a transition state and accelerating the activation of signaling.

Modulation of a signaling complex can result in an increase or decrease in sensitivity to signal input and concomitant increases or decreases in signal transduction. Administration of modulator antibodies increases or decreases the sensitivity of the cellular pathway and/or absolute levels of the cellular response. The modulators of the invention, depending on their properties, can function as a modulator, potentiator, regulator, effector or sensitizer.

Many antibody drugs act to block signaling pathways by binding to either a cell-surface receptor or its cognate ligand and eliminating the ability of the ligand to bind to and activate the receptor. Such blocking drugs mediate their effect stoichiometrically by preventing the formation of receptor-ligand complex.

Successful treatment of some diseases may require attenuation rather than complete inhibition of signaling pathways to restore a normal physiological state with acceptable side-effect profiles. The antibodies provided by the invention are expected to provide such advantages.

Other therapeutic drugs affect cellular signaling pathways by binding to a cell-surface receptor and altering the activity of the receptor. Such direct agonist drugs may mediate their effects by mimicking the natural activity of the ligand and thus have inherent activity, i.e., they do not require the presence of ligand to mediate their effects. Further therapeutic drugs affect cellular signaling pathways by binding to a ligand. Such indirect agonist drugs may mediate their effects by altering ligand stability or valency.

Biological processes are generally regulated in a continuous rather than binary manner, and thus in many cases modulation of pathway activity may be a more appropriate therapeutic strategy than complete pathway blockade or stimulation. Performing functional, cell-based screens for modulation of pathway activity, rather than for complete pathway blockade or stimulation, is laborious and may not readily be performed in a high throughput manner, since such screens generally require a known concentration of test compound and may be sensitive to any impurities in the test compound preparation. In particular, the ability to perform high throughput functional, cell-based screens for modulation of pathway activity is restricted for cell-impermeable molecules which are unable to enter the intracellular environment, and especially for recombinant biological molecules which may have different expression levels, degrees of purity and stability in the production system used. In addition, some binding interactions may have no signaling output to measure in a functional screen (e.g. in the case of decoy receptors, decoy substrates, or inactive forms of a target) making it difficult to identify agents that perturb these interactions.

The present invention overcomes these disadvantages and provides a means for identifying positive and negative modulators of the INSR activity and desired potency of drug in a high throughput manner. The present invention also provides positive and negative modulators of the INSR activity with a desired range of modulation of activity, and provides data showing that these modulators exhibit the desired biological effect of altering glucose uptake.

Definitions

The term "compound" refers to any chemical compound, organic or inorganic, endogenous or exogenous, including, without limitation, polypeptides, proteins, peptides, small molecules, nucleic acids (e.g. DNA and RNA), carbohydrates, lipids, fatty acids, steroids, purines, pyrimidines, peptidomimetics, polyketides and derivatives, structural analogs or combinations thereof. "Endogenous" means naturally occurring in a mammal, while "exogenous" means not naturally occurring in the mammal, e.g. an administered foreign compound.

The term "polypeptide binding agent" refers to a polypeptide that is capable of specifically binding an antigen, e.g. a target or its signaling partner, or that is capable of binding an antigen with a measurable binding affinity. Examples of polypeptide binding agents include antibodies, peptibodies, polypeptides and peptides, optionally conjugated to other peptide moieties or non-peptidic moieties. Antigens to which a polypeptide binding agent may bind include any proteinaceous or non-proteinaceous molecule that is capable of eliciting an antibody response, or that is capable of binding to a polypeptide binding agent with detectable binding affinity greater than non-specific binding. The antigen to which a modulating polypeptide binding agent binds may include a target, a signaling partner of a target, and/or a complex comprising the target and its signaling partner.

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences, as long as the antibody retains the desired biological activity.

"Monoclonal antibody" refers to an antibody obtained from a population of substantially homogeneous antibodies, i.e., the individual antibodies comprising the population are identical except for possible naturally occurring mutations that may be present in minor amounts.

"Antibody variant" as used herein refers to an antibody polypeptide sequence that contains at least one amino acid substitution, deletion, or insertion in the variable region of the natural antibody variable region domains. Variants may be substantially homologous or substantially identical to the unmodified antibody.

A "chimeric antibody," as used herein, refers to an antibody containing sequence derived from two different antibodies (see, e.g., U.S. Pat. No. 4,816,567) which typically originate from different species. Most typically, chimeric antibodies comprise human and rodent antibody fragments, generally human constant and mouse variable regions.

A "neutralizing antibody" is an antibody molecule which is able to eliminate or significantly reduce a biological function of an antigen to which it binds. Accordingly, a "neutralizing" antibody is capable of eliminating or significantly reducing a biological function, such as enzyme activity, ligand binding, or intracellular signaling.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Heavy chain variable region" as used herein refers to the region of the antibody molecule comprising at least one complementarity determining region (CDR) of said antibody heavy chain variable domain. The heavy chain variable region may contain one, two, or three CDR of said antibody heavy chain.

"Light chain variable region" as used herein refers to the region of an antibody molecule, comprising at least one complementarity determining region (CDR) of said antibody light chain variable domain. The light chain variable region may contain one, two, or three CDR of said antibody light chain, which may be either a kappa or lambda light chain depending on the antibody.

As used herein, an antibody that "specifically binds" is "antigen specific", is "specific for" antigen target or is "immunoreactive" with an antigen refers to an antibody or polypeptide binding agent of the invention that binds an antigen with greater affinity than other antigens of similar sequence. In one aspect, the polypeptide binding agents of the invention, or fragments, variants, or derivatives thereof, will bind with a greater affinity to human antigen as compared to its binding affinity to similar antigens of other, i.e., non-human, species, but polypeptide binding agents that recognize and bind orthologs of the target are within the scope of the invention.

For example, a polypeptide binding agent that is an antibody or fragment thereof "specific for" its cognate antigen indicates that the variable regions of the antibodies recognize and bind the desired antigen with a detectable preference (e.g., where the desired antigen is a polypeptide, the variable regions of the antibodies are able to distinguish the antigen polypeptide from other known polypeptides of the same family, by virtue of measurable differences in binding affinity, despite the possible existence of localized sequence identity, homology, or similarity between family members). It will be understood that specific antibodies may also interact with other proteins (for example, S. aureus protein A or other antibodies in ELISA techniques) through interactions with sequences outside the variable region of the antibodies, and in particular, in the constant region of the molecule. Screening assays to determine binding specificity of a polypeptide binding agent, e.g. antibody, for use in the methods of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies for use in the invention can be produced using any method known in the art.

The term "epitope" refers to that portion of any molecule capable of being recognized by and bound by a selective binding agent at one or more of the antigen binding regions. Epitopes usually consist of chemically active surface groupings of molecules, such as, amino acids or carbohydrate side chains, and have specific three-dimensional structural characteristics as well as specific charge characteristics. Epitopes as used herein may be contiguous or non-contiguous.

The term "derivative" when used in connection with polypeptide binding agents and polypeptides of the invention refers to polypeptides chemically modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins. Derivatives retain the binding properties of underivatized molecules of the invention.

"Detectable moiety" or a "label" refers to a composition detectable by spectroscopic, photochemical, biochemical, immunochemical, or chemical means. For example, useful labels include 32P, 35S, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to another labeled nucleic acid molecule. The detectable moiety often generates a measurable signal, such as a radioactive, chromogenic, or fluorescent signal, that can be used to quantitate the amount of bound detectable moiety in a sample.

"Peptides" or "oligopeptides" are short amino acid sequences, typically between 3 and 100 amino acid residues in length and encompass naturally occurring amino acid residues and non-naturally occurring analogs of residues which may be used singly or in combination with naturally occurring amino acid residues in order to give the peptide a particular conformational specificity or a particular biological activity, such as resistance to proteolysis. Peptides include repeats of peptide sequences and may include 2, 3, 4, 5, 6, 7, 8, 9, 10 or more copies of an amino acid sequence arranged head-to-tail or head-to-head. Peptides may be conjugated to non-peptidic moieties, e.g. [expand]. Peptides include dimers, trimers or higher order multimers, e.g. formed through conjugation to other polymeric or non-polymeric moieties, such as PEG.

"Polypeptides" are longer amino acid sequences, typically 100 or more amino acid residues in length, and encompass naturally occurring amino acid residues and non-naturally occurring analogs of residues which may be used singly or in combination with naturally occurring amino acid residues in order to give the polypeptide a particular conformational specificity or a particular biological activity, such as resistance to proteolysis.

As used herein, a "peptibody" is a fusion polypeptide comprising one or more peptides fused to all or a portion of an immunoglobulin (Ig) constant region. See, e.g., U.S. Pat. No. 6,660,843. The peptide may be any naturally occurring or recombinantly prepared or chemically synthesized peptide that binds to the antigen. The peptide may be repeated and may include 2, 3, 4, 5, 6, 7, 8, 9, 10 or more copies of an amino acid sequence arranged head-to-tail or head-to-head. The portion of the Ig constant region may include at least one constant region domain (e.g., CH1, CH2, CH3, and/or CH4), multiple domains (e.g., CH2 with CH3), multiple copies of domains (e.g., CH2-CH2), any fragment of a constant domain that retains the desired activity, e.g. the salvage receptor epitope responsible for the prolonged half-life of immunoglobulins in circulation, or any combinations thereof.

A "small" molecule or "small" organic molecule is defined herein as a non-polymeric organic chemical compound having a molecular weight of about 1000 Daltons or less.

As used herein, a "signaling complex" is an assembly of proteins and/or endogenous or exogenous compounds that mediate the transduction of a cellular signal. Examples of a signaling complex include, but are not limited to, a ligand bound to a membrane bound receptor, an enzyme bound to a substrate or any cellular molecules that associate to propagate biochemical reactions that are involved in a signal cascade. Signaling complexes can also include coreceptors, cofactors, scaffold proteins, allosteric modulators and numerous other types of proteins and molecules that are involved in cellular signal transduction. Signaling complexes can be formed transiently or can be long lived. The molecular constituents or components of a signaling complex can vary over time and can be dependent on activation state of each component and the cellular environment. Signaling complexes can undergo chemical modification and regulation that can induce a spectrum of effects on the complex including subtle changes in transduction activity, complete inactivation and constitutive activation or both positive and negative modulation.

The term "therapeutically effective amount" is used herein to indicate the amount of target-specific composition of the invention that is effective to ameliorate or lessen symptoms or signs of disease associated with abnormal (e.g. abnormally high or abnormally low) signaling of the signaling complex.

As used herein "binding" is the physical association between two or more distinct molecular entities that results from a specific network of non-covalent interactions consisting of one or more of the weak forces including hydrogen bonds, Van der Waals, ion-dipole and hydrophobic interactions and the strong force ionic bonds. The level or degree of binding may be measured in terms of affinity. Affinity is a measure of the strength of the binding interaction between two or more distinct molecular entities that can be defined by equilibrium binding constants or kinetic binding rate parameters. Examples of suitable constants or parameters and their measurement units are well known in the art and include but are not limited to equilibrium association constant ($K_A$), e.g. about $10^5 M^{-1}$ or higher, about $10^6 M^{-1}$ or higher, about $10^7 M^{-1}$ or higher, about $10^8 M^{-1}$ or higher, about $10^9 M^{-1}$ or higher, about $10^{10} M^{-1}$ or higher, about $10^{11} M^{-1}$ or higher or about $10^{12} M^{-1}$ or higher; equilibrium dissociation constant ($K_D$), e.g., about $10^{-5} M$ or less, or about $10^{-6} M$ or less, or about $10^{-7} M$ or less, or about $10^{-8} M$ or less, or about $10^{-9} M$ or less, or about $10^{-10} M$ or less, or about $10^{-11} M$ or less, or about $10^{-12} M$ or less; on-rate (e.g., $sec^{-1}$, $mol^{-1}$) and off-rate (e.g., $sec^{-1}$)). In the case of $K_A$, higher values mean "stronger" or "strengthened" binding affinity while in the case of $K_D$, lower values mean "stronger" or "strengthened" binding affinity. As used herein, a "strengthened" binding rate parameter means increased residency time, stronger association or weaker dissociation. As used herein, a "weakened" binding rate parameter means decreased residency time, weaker association or stronger dissociation. In the case of on-rate, higher values mean faster or more frequent association and thus generally result in strengthened binding affinity. In the case of off-rate, lower values generally mean slower dissociation and thus generally result in stronger binding affinity. However, it is the ratio of the on-rate and off-rate that indicates binding affinity, as explained in further detail later.

Affinity between two compounds, e.g., between an antibody and an antigen, or between first and second components of a signaling complex, may be measured directly or indirectly. Indirect measurement of affinity may be performed using surrogate properties that are indicative of, and/or proportional to, affinity. Such surrogate properties include: the quantity or level of binding of a first component to a second component of a signaling complex, or a biophysical characteristic of the first component or the second component that is predictive of or correlated to the apparent binding affinity of the first component for the second component. Specific examples include measuring the quantity or level of binding of first component to a second component at a subsaturating concentration of either the first or the second component. Other biophysical characteristics that can be measured include, but are not limited to, the net molecular charge, rotational activity, diffusion rate, melting temperature, electrostatic steering, or conformation of one or both of the first and second components. Yet other biophysical characteristics that can be measured include determining stability of a binding interaction to the impact of varying temperature, pH, or ionic strength.

Measured affinity is dependent on the exact conditions used to make the measurement including, among many other factors, concentration of binding components, assay setup, valence of binding components, buffer composition, pH, ionic strength and temperature as well as additional components added to the binding reaction such as allosteric modulators and regulators. Quantitative and qualitative methods may be used to measure both the absolute and relative strength of binding interactions.

Apparent affinity is a measure of the strength of the binding interaction between two or more distinct molecular entities under conditions where the affinity is altered by conditions or components in the binding reaction such as allosteric modulators, inhibitors, binding component valence etc.

As used herein a "subsaturating concentration" is a concentration of one or more components in a binding reaction that is significantly below the binding affinity $K_D$ and/or a concentration of one component in a binding reaction that is less than is required to occupy all of the binding sites of the other component(s). Under subsaturating conditions a significant percentage of one of the binding components in the binding reaction has available binding sites.

As used herein a "biophysical assay" is any method that measures, in an absolute or relative fashion, the binding, association, dissociation, binding affinity, binding level, or binding rate parameters between at least two compounds. Biophysical assays are generally performed in vitro and may be conducted with purified binding components, unpurified components, cell associated components as well as a combination of purified and cell associated components.

An "agonist" is a term used to describe a type of ligand or drug that binds and activates signaling of a receptor. The ability to alter the activity of a receptor, also known as the agonist's efficacy, is a property that distinguishes it from antagonists, a type of receptor ligand which also binds a receptor but which does not activate signaling of the receptor. The efficacy of an agonist may be positive, causing an increase in the receptor's activity, or negative causing a decrease in the receptor's activity. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. A co-agonist works with other co-agonists to produce the desired effect together.

Competitive, or orthosteric, agonists reversibly bind to receptors at the same binding site (active site) as the ligand, thereby competing with ligand for the same binding site on the receptor.

In a different aspect, antibodies disclosed herein act as allosteric agonists. They bind to a portion of INSR that is distinct from the active insulin-binding site, and do not appreciably change the binding affinity of insulin and INSR by more than 2-fold. They also do not appreciably affect the EC50 of insulin activation of INSR, e.g. alter EC50 by less than 2-fold. Such antibodies constitutively activate INSR with a maximal agonist response that is 80% or less of the maximal agonist response of insulin, for example 15%-80%, 20-60%, 20%-40% or 15%-30%. In certain embodiments, the antibodies constitutively activate INSR with a maximal agonist response that is at least about 15%, 20%, 25%, 30%, 35%, 40%; and up to 45%, 50%, 55%, 60%, 65%, 70%, 75% or 80% of the maximal agonist response of insulin. It is understood that any combination of any of these range endpoints is contemplated without having to recite each possible combination. In some embodiments, maximal agonist response is measured by Akt assay. In further embodiments, the invention provides an allosteric agonist antibody that binds to insulin receptor with an affinity of $10^{-5}$, $10^{-6}$, $10^{-7}$, $10^{-8}$, $10^{-9}$, $10^{-10}$, $10^{-11}$ M or less M. Without being bound by a theory of the invention, the weak agonist activity of allosteric agonists serves to mimic the effect of natural basal insulin secretion levels, while permitting exogenously administered insulin to have its normal glucose-lowering effect. In certain embodiments, an allosteric agonist is a partial allosteric agonist. An antagonist blocks a receptor from activation by agonists. A selective agonist is selective for one certain type of receptor. It can additionally be of any of the aforementioned types.

The potency of an agonist is usually defined by the inverse of its EC50 value. This can be calculated for a given agonist by determining the concentration of agonist needed to elicit half of the maximum biological response of the agonist. The lower the EC50, the greater the potency of the agonist.

A receptor "antagonist" is a type of receptor ligand or drug that does not provoke a biological response itself upon binding to a receptor, but blocks or dampens agonist-mediated responses. Antagonists may have affinity but no efficacy for their cognate receptors, and binding will disrupt the interaction and inhibit the function of an agonist or inverse agonist at receptors. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist—receptor complex, which, in turn, depends on the nature of antagonist receptor binding. The majority of antagonists achieve their potency by competing with endogenous ligands or substrates at structurally-defined binding sites on receptors.

Antagonists display no efficacy to activate the receptors they bind. Once bound, however, antagonists may inhibit the function of agonists, inverse agonists and partial agonists. In functional antagonist assays, a dose-response curve measures the effect of the ability of a range of concentrations of antagonists to reverse the activity of an agonist. The potency of an antagonist is usually defined by its IC50 value. This can be calculated for a given antagonist by determining the concentration of antagonist needed to elicit half inhibition of the maximum biological response of an agonist. The lower the IC50, the greater the potency of the antagonist.

Competitive, or orthosteric, antagonists reversibly bind to receptors at the same binding site (active site) as the ligand or agonist, but without activating the receptor, thereby competing with agonist for the same binding site on the receptor. Non-competitive, or allosteric, antagonists bind to a separate binding site from the agonist, exerting their action to that receptor via that separate binding site. Thus, they do not compete with agonists for binding. Uncompetitive antagonists differ from non-competitive antagonists in that they require receptor activation by an agonist before they can bind to a separate allosteric binding site.

"Insulin resistance" describes a condition in which physiological amounts of insulin are inadequate to produce a normal insulin response from cells or tissues.

"Insulin sensitizer" is a compound or drug that increases cell- or tissue-sensitivity to insulin resulting in greater levels of glucose uptake for a given subsaturating concentration of insulin.

Advantages

The present invention relates to the discovery that it is possible to develop therapeutic agents that modulate the insulin-INSR signaling complex by binding to extracellular regions of the INSR. Novel selection and screening methods are employed to identify, for example, insulin-sensitizers that target extracellular regions of the INSR and potentiate insulin action. In particular, some of the antibodies identified herein are non-agonistic antibodies which bind to extracellular regions of the INSR and positively or negatively modulate the insulin-INSR signaling complex.

The present invention encompasses insulin-INSR signaling complex modulators that offer unique advantages over existing therapies. They act at the level of the INSR, which should allow induction of the entire range of actions of insulin while minimizing unwanted side effects. Avoiding INSR agonism should reduce the risk of functional hypoglycemia. Additionally, more precise control of glucose levels might be achieved. Thus, when blood glucose levels increase, leading to elevation of insulin levels, such a modulator would have a greater effect. Targeting the extracellular region of the INSR allows for the use of biological molecules as insulin-INSR signaling complex modulators that modulate the effect of endogenous or exogenous insulin, insulin analogs or insulin mimetics; these may have advantages such as improved half-life, reduced dosage or frequency of dosage, reduced toxicity and greater ease of manufacture. The present invention encompasses insulin-INSR signaling complex modulators that are expected to reduce peripheral insulin resistance and improve glycemic control. The sensitizing effect of the modulators should allow for improved levels of glucose uptake by peripheral tissues in patients whose insulin levels are not high enough to stimulate adequate glucose uptake in the absence of exogenous insulin therapy. Thus, administration of the antibodies of the invention may be used in the early stages of insulin resistance in place of other drugs, or as adjunct therapy to other anti-diabetic agents. When administered as an adjunct therapy to other anti-diabetic agents, the antibodies of the invention may reduce the total daily amount of anti-diabetic agent required to maintain blood glucose levels closer to normal range, or may reduce the frequency of dosing of the anti-diabetic agent, or may achieve improved glycemic control with the same dose and/or frequency, e.g. with fewer episodes of hyperglycemia or a reduced level of maximal hyperglycemia (reduction in the highest aberrant glucose level observed).

The Insulin Receptor (INSR)

The INSR is a tyrosine kinase receptor found in organisms as primitive as cnidarians and insects. In higher organisms it is essential for glucose homeostasis. Mouse knockout studies have also shown the INSR to be important in adipogenesis, neovascularization, the regulation of hepatic glucose synthesis and glucose-induced pancreatic insulin secretion (Kitamura et al, Ann. Rev. Physiol., 65: 313-332 2003). INSR signaling is also important in the brain, where it is involved in the regulation of food intake, peripheral fat deposition and the reproductive endocrine axis as well as in learning and memory (Wada et al, J. Pharmacol. Sci. 99: 128-143, 2005). Dysfunctional INSR signaling has been implicated in diseases including type I and type II diabetes, dementia and cancer.

The domains of the closely related insulin-like growth factor receptor (IGFR-1) exhibit high (47-67%) amino acid identity with the INSR. While similar in structure, IGF-IR and INSR serve different physiological functions. IGF-IR is expressed in almost all normal adult tissue except for liver, which is itself the major site of IGF-I production. INSR is primarily involved in metabolic functions whereas IGF-IR mediates growth and differentiation (Adams et al, Cell. Mol. Life Sci. 57: 1050-1093, 2000).

INSR exists as two splice variant isoforms, INSR-A and INSR-B, which respectively lack or contain the 12 amino acids coded by exon 11. The longer variant, INSR-B, is the isoform responsible for signaling metabolic responses. In contrast, INSR-A signals predominantly mitogenic responses, is the preferentially expressed isoform in several cancers (Denley et al., Horm. Metab. Res. 35: 778-785, 2003) and is capable of binding insulin-like growth factor 2 (IGF-II) with high affinity (Denley et al, Mol. Endocrinol. 18: 2502-2512, 2004).

The mature human INSR is a homodimer comprising two $\alpha$ subunits and two $\beta$ subunits (chains). The $\alpha$ and $\beta$ chains are encoded by a single gene and arise from the post-translational cleavage of a 1370 amino acid precursor at a furin cleavage site located at residues 720-723. The $\alpha$-chain and 194 residues of the $\beta$-chain comprise the extracellular portion of the INSR. There is a single transmembrane sequence and a 403 residue cytoplasmic domain containing a tyrosine kinase. The N-terminal half of each ectodomain monomer consists of two homologous leucine-rich repeat domains (L1 and L2) of approximately 150 amino acids, separated by a cysteine-rich region (CR), also approximately 150 amino acids in size. The C-terminal half of each ectodomain monomer (approximately 460 residues) consists of three fibronectin type III domains (FnIII-1, FnIII-2 and FnIII-3). The FnIII-2 domain contains an insert domain (ID) of approximately 120 residues, within which lies the furin cleavage site that generates the $\alpha$ and $\beta$ chains of the mature receptor. Intracellularly, each monomer contains a tyrosine kinase catalytic domain flanked by two regulatory regions (the juxtamembrane region and the C-tail) that contain the phosphotyrosine binding sites for signaling molecules (Ward et al, Acta Physiol. 192: 3-9, 2008).

Current models for insulin binding proposes that, in the basal state, the INSR homodimer contains two identical pairs of binding sites (referred to as Site 1 and Site 2) on each monomer (De Meyts, Bioessays, 26: 1351-1362, 2004). Binding of insulin to a low affinity site (Site 1) on one $\alpha$-subunit is followed by a second binding event between the bound insulin and a different region of the second INSR $\alpha$-subunit (Site 2). This ligand-mediated bridging between the two a subunits generates the high affinity state that results in signal transduction. In contrast, soluble INSR ectodomain, which is not tethered at its C-terminus, cannot generate the high affinity receptor-ligand complex. It can bind two molecules of insulin simultaneously at its two Site 1's, but only with low affinity (Adams et al, Cell. Mol. Life Sci. 57: 1050-1093, 2000). Site 1 is thought to be comprised of elements from the central $\beta$-sheet of the L1 domain and the last 16 residues of the $\alpha$-chain (referred to as the CT peptide). Site 2 most likely includes the loops at the junction of FnIII-1 and FnIII-2. Insulin binding is thought to involve structural changes in both insulin and its receptor (Ward and Lawrence, BioEssays 31: 422-434, 2009).

Once an insulin molecule has docked onto the receptor and effected its action, it may be released back into the extracellular environment or it may be degraded by the cell. Degradation normally involves endocytosis of the insulin-INSR complex followed by the action of insulin degrading enzyme. Most insulin molecules are degraded by liver cells. It has been estimated that a typical insulin molecule is finally degraded about 71 minutes after its initial release into circulation (Duckworth et al, Endocr. Rev. 19(5): 608-24, 1998).

Insulin Signaling

Insulin induces a signaling network of molecules, carrying the information from the INSR to the effector proteins involved in metabolism and growth. Insulin binding to INSR induces a conformational change that promotes activation of an intrinsic tyrosine kinase activity, leading to autophosphorylation of the INSR β-subunit. Insulin receptor substrate (IRS) proteins are recruited to the plasma membrane through an interaction with the phosphorylated INSR, and these also become phosphorylated on tyrosine residues, promoting recruitment of additional signaling proteins to the complex resulting in signaling through two major pathways (1) the PI3 kinase/PDK1/PKB pathway which primarily regulates metabolism, with some influence on growth ad (2) the Ras/ERK mitogenic pathway which primarily regulates cell growth.

Certain marketed insulin analogues have been reported to display IGF-1-like mitogenic and anti-apoptotic activities in cultured cancer cells, raising questions over their long-term safety in humans (Weinstein et al, Diabetes Metab Res Rev 25: 41-49, 2009). Therefore, it would be desirable to obtain an INSR agonist that did not alter the balance in metabolic vs. mitogenic INSR signaling, or promoted metabolic signaling preferentially over mitogenic INSR signaling.

Methods of Identifying Antibodies that are Modulators

The invention provides methods of identifying a candidate polypeptide binding agent, e.g., an antibody, that modulates binding between first and second components of a signaling complex, e.g., a receptor such as the insulin receptor and its ligand insulin.

Without being bound by a theory of the invention, the present disclosure provides that kinetic perturbation of an interaction between two components (first component, C1 and second component, C2) of a signaling complex with a modulator (M) can be described mathematically as:

$$K'_{C1C2} = K_{C1C2} \frac{(1 + M/K_{MC1})(1 + M/K_{MC2})}{(1 + M/K_{[C1C2]M})}$$

where the change in binding equilibrium constant between the components ($K'_{C1C2}$) is a function of equilibrium constant between the components ($K_{C1C2}$), modulator concentration (M), modulator affinity for the complex ($K_{[C1C2]M}$) and modulator affinity for either the first component ($K_{MC1}$) or the second component ($K_{MC2}$).

In cases where the signaling complex is a receptor-ligand complex, and the modulator is an antibody, the kinetic perturbation of the receptor-ligand interaction with an antibody can be described mathematically as:

$$K'_{RL} = K_{RL} \frac{\left(1 + \frac{A}{K_{AR}}\right)\left(1 + \frac{A}{K_{AL}}\right)}{\left(1 + \frac{A}{K_{RLA}}\right)}$$

where the change in receptor-ligand binding equilibrium constant ($K'_{RL}$) is a function of receptor-ligand equilibrium constant ($K_{RL}$), antibody concentration (A), antibody affinity for the complex ($K_{[RL]A}$) and antibody affinity for either the receptor ($K_{AR}$) or ligand ($K_{AL}$).

A modulator binds the target, or its signaling partner, or a complex of the target and signaling partner, in such a manner that the binding affinity or binding rate parameter of the target for its signaling partner is weakened or strengthened. For example, where the target is either a receptor or ligand, the binding affinity or binding rate parameter of the ligand for its receptor is weakened or strengthened in the presence of the modulator. A modulator with complete blocking activity represents a boundary condition in this analysis, since when $K_{[C1C2]M}$ is sufficiently high, $K'_{C1C2}$ approaches infinity. One implication of this model is that the degree of signaling modulation is independent of modulator concentration when the concentration of modulator ([M]) is sufficiently above the equilibrium dissociation constant ($K_D$) for the modulator/antigen interaction to be saturating for binding ligand. Hence, modulation of the interaction is related to the ratio of affinities for the complex versus the components where [M]>$K_D$ for the modulator and its antigen.

The present disclosure provides that the biophysical properties of a modulator's interactions with a target and/or its signaling partner can be used to predict the functional effect of the modulator on the target signaling pathway. Modulators which alter the signaling pathway can therefore be identified based on their relative affinity for target (and/or its signaling partner) in complexed versus uncomplexed form. The invention contemplates that kinetic perturbation of an interaction between two components (first component, C1 and second component, C2) of a signaling complex with a modulator (M) can be predicted in the following manner:

$K_{[C1C2]M}$ or $K_{[MC2]C1}$ or $K_{[MC1]C2}$<$K_{MC2}$ or $K_{MC1}$ leads to positive modulation $K_{[C1C2]M}$ or $K_{[MC2]C1}$ or $K_{[MC1]C2}$=$K_{MC2}$ or $K_{MC1}$ leads to no modulation $K_{[C1C2]M}$ or $K_{[MC2]C1}$ or $K_{[MC1]C2}$>$K_{MC2}$ or $K_{MC1}$ leads to negative modulation In cases where the signaling complex is a receptor (R)-ligand(L) complex, and the kinetic modulator is an antibody (A), the kinetic perturbation can be predicted in the following manner:

$K_{[RL]A}$ or $K_{[AL]R}$ or $K_{[AR]L}$<$K_{AL}$ or $K_{AR}$ leads to positive kinetic modulation $K_{[RL]A}$ or $K_{[AL]R}$ or $K_{[AR]L}$=$K_{AL}$ or $K_{AR}$ leads to no kinetic modulation $K_{[RL]A}$ or $K_{[AL]R}$ or $K_{[AR]L}$>$K_{AL}$ or $K_{AR}$ leads to negative kinetic modulation In some embodiments, a modulator, such as an antibody (A) can be identified by its ability to alter a binding interaction, such as a receptor(R)-ligand(L) interaction at any given sub-saturating concentration of the first or second component (e.g. ligand (L) concentration). A modulator antibody or polypeptide could effectively shift the affinity and the corresponding dose response of the receptor ligand interaction from the 500 pM interaction to either the 10 pM (positive modulator) or 10 nM (negative modulator) as depicted. In some embodiments the modulator will produce a higher level of R-L binding at a given ligand concentration, shifting the assay curve to the left (positive modulation). In other embodiments the modulator will produce a lower level of R-L binding at a given ligand concentration, shifting the assay curve to the right (negative modulation). In some embodiments the shift is uniform. In other embodiments the shift is non-uniform, reflecting the involvement of other factors e.g. accessory proteins in the complex, receptor internalization, etc.

The binding properties of the interaction(s) between the modulator and the target, its signaling partner and/or a complex comprising the target and its signaling partner, are generally predictive of the functional effect of the kinetic modulator on the target signaling pathway. Depending on the target being studied, certain other factors may need to be considered. These include: (1) the concentration of the kinetic modulator, the concentration of the target, and/or the concentration of its signaling partner (e.g., the prediction is optimized if the modulator concentration ([M]) is significantly greater than the $K_D$ of the binding between modulator and its antigen), (2) the structural form of the modulator used e.g. monovalent vs. divalent or bivalent, (3) inter/intra target crosslinking, which may restrict the conformation of target and/or cause target activation, (4) the modulator's ability to alter assembly or docking, or to alter additional components of the signaling complex by steric or allosteric mechanisms, (5) signaling pathway specific properties such as alterations in the signal pathway due to disease that introduce a "bottleneck," (6) negative/positive feedback regulation of the signaling pathway, (7) alteration of clearance/internalization rates of the components of the signaling complex, (8) alterations in the target that uncouple or differentially alter ligand binding and activation e.g. a modulator enhances ligand binding but traps its receptor in a desensitized state, or a modulator attenuates ligand binding but induces a conformational change in its receptor that is activating.

In some aspects the invention provides methods for measuring the differential binding of a first component of a signaling complex for a second component of the signaling complex in the presence or absence of a test polypeptide agent. In these aspects, differential binding is preferably observed when there are sub-saturating concentrations of the first or second component. In some preferred embodiments the concentration of the first or second component may be reduced to provide sub-saturating conditions.

In some aspects the invention provides methods for measuring the differential binding of a test polypeptide binding agent, e.g. antibody, to target and/or its signaling partner, in complexed and uncomplexed form. In these aspects, differential binding is preferably observed when there are sub-saturating concentrations of test polypeptide binding agent. In some preferred embodiments the concentration of test polypeptide binding agent may be reduced to provide sub-saturating conditions.

In some embodiments, testing in the absence of a test polypeptide agent is performed using a control compound which is preferably a compound belonging to a similar structural class as the test polypeptide agent, but which binds to a different antigen that has no effect on the signaling complex being tested. For example, a control for a test antibody may be an isotype-matched antibody binding to an unrelated antigen, e.g. keyhole limpet hemocyanin (KLH).

For positive modulators, at a given sub-saturating concentration of C1, higher C1 affinity will be reflected in a higher signal for C1 binding to C2 in the presence of the positive modulator. Preferential binding of the modulator will be reflected in a higher signal for the complex comprising C1 and C2, compared to the signal for either C1 alone or C2 alone. In some aspects, there may be binding of the modulator to the complex of C1 and C2, but no measurable binding to either C1 alone or C2 alone.

For negative modulators, at a given sub-saturating concentration of C1, lower C1 affinity will be reflected in a lower signal for C1 binding to C2 in the presence of the modulator. Preferential binding of the modulator will be reflected in a higher signal for binding of the modulator to C1 alone, or to C2 alone, compared to the signal for binding of the modulator to the complex of C1 and C2.

The invention provides methods of identifying a candidate polypeptide binding agent, e.g., an antibody, that modulates binding between first and second components of a signaling complex. In some embodiments, the first and second components are polypeptides. In exemplary specific embodiments, the first and second components are endogenous.

In one aspect, the methods of identifying a candidate modulating antibody include (a) measuring a binding affinity or binding rate parameter of said first component for said second component, in the presence of a test polypeptide binding agent, e.g. antibody, (b) measuring a binding affinity or binding rate parameter of said first component for said second component in the absence of said test polypeptide binding agent; and (c) identifying said test polypeptide binding agent as a candidate modulating drug when said test polypeptide binding agent exhibits at least a 1.5-fold difference in the binding affinity or binding rate parameter measured in steps (a) and (b). In some embodiments, the difference in binding affinity or binding rate parameter ranges from about 1.5-fold (i.e., 50%) to about 1000-fold, or about 1.5-fold to about 100-fold, or about 2-fold to 25-fold, or about 2-fold to about 50-fold, or about 1.5-fold to about 25-fold, or about 1.5-fold to about 50-fold.

In some embodiments, the test polypeptide binding agent is identified as a candidate positive modulator if the test polypeptide agent strengthens the binding affinity or binding rate parameter between said first component and said second component. In other embodiments, the test polypeptide agent is identified as a candidate negative modulator if the test polypeptide agent weakens the binding affinity or binding rate parameter between said first component and said second component.

Whether a change (increase or decrease) in a particular binding affinity value or binding rate parameter value represents "strengthened" (or stronger) or "weakened" (or weaker) binding affinity or binding rate parameter depends on the value of the parameter and its units, and is well known in the art. For example, in the case of the parameter $K_A$, higher values mean "strengthened" binding affinity, such that a $K_A$ of about $10^6 M^{-1}$ is stronger than a $K_A$ of about $10^5 M^{-1}$. As another example, in the case of the parameter $K_D$, lower values mean "strengthened" binding affinity, such that a $K_D$ of about $10^{-6}$M is stronger than a $K_D$ of about $10^{-5}$M. Conversely, in the case of $K_A$, lower values mean "weakened" binding affinity, such that a $K_A$ of about $10^5 M^{-1}$ is a weakened binding affinity compared to a $K_A$ of about $10^6 M^{-1}$. As another example, in the case of $K_D$, higher values mean "weakened" binding affinity, such that a $K_D$ of about $10^{-5}$M is weakened binding affinity compared to a $K_D$ of about $10^{-6}$M.

As used herein, a "strengthened" binding rate parameter means increased residency time, stronger association or weaker dissociation. As used herein, a "weakened" binding rate parameter means decreased residency time, weaker association or stronger dissociation.

Binding affinity can also be determined through the ratio of the on-rate and off-rate binding rate parameters. Generally, in the case of on-rate, higher values mean faster or stronger association or increased residence time, and typically result in stronger binding affinity. Conversely, lower values for on-rate mean slower or weaker association or decreased residence time, and typically result in weaker binding affinity. Generally, in the case of off-rate, higher values mean faster dissociation or decreased residence time, and typically result in weaker binding affinity. Conversely, lower values for off-rate mean slower dissociation or increased residence time, and typically result in stronger binding affinity. This is because the ratio of off-rate to on-rate, or on-rate to off-rate, indicates binding affinity as displayed in the equations below.

| Target Binding Characteristics | | | | Functional effect |
|---|---|---|---|---|
| R | L | R-L | KD ratios | (pAKT assay shift) |
| − | − | + | $K_{[RL]A} < K_R, K_L$ | Positive modulation |
| − | + | + | $K_{[AL]R} < K_L$ | Positive modulation |
| + | − | + | $K_{[AR]L} < K_R$ | Positive modulation |
| − | + | + | $K_{[AL]R} > K_L$ | Negative modulation |
| + | − | + | $K_{[AR]L} > K_R$ | Negative modulation |

Illustrative examples of data showing that the functional effects of anti-INSR antibodies correlate with their binding characteristics are shown in the following table.

| | Target Binding Characteristics | | | | Functional effect (pAKT assay, fold-decrease in insulin $EC_{50}$ relative to |
|---|---|---|---|---|---|
| Ab | R | L | R-L | KD ratios | isotype control Ab) # |
| Predicted | − | − | + | $K_{[RL]A} < K_R, K_L$ | Positive modulation |
| Ab078 | Out of Range* | | 3.4e−10 | | 3.3 |
| Ab085 | No Binding | | 2e−10 | | 8.9 |
| Predicted | + | − | + | $K_{[AR]L} < K_R$ | Positive modulation |
| Ab001 | 1.2e−8 | | 1.16e−10 | 103.4 | 9.7 |
| Ab079 | 9.6e−9 | | 4.96e−10 | 19.4 | 6.7 |
| Ab080 | 1.2e−8 | | 6.8e−10 | 17.6 | 8.4 |
| Ab083 | 7.6e−9 | | 3.76e−10 | 20.2 | 8.5 |
| Predicted | + | − | + | $K_{[AR]L} = K_R$ | Non-Modulators |
| Ab037 | 1.08e−10 | | 8e−11 | 1.4 | No change |
| Ab053 | 1.48e−10 | | 9.6e−11 | 1.5 | No change |
| Ab062 | 1.24e−10 | | 1.08e−10 | 1.1 | No change |

$$\text{Affinity} \begin{cases} K_D = \dfrac{[A][L]}{[AL]} = \dfrac{\textit{off-rate}}{\textit{on-rate}} \\ K_A = \dfrac{[AL]}{[A][L]} = \dfrac{\textit{off-rate}}{\textit{on-rate}} \end{cases}$$

where $$A + L \underset{K_{off}}{\overset{K_{on}}{\rightleftharpoons}} AL$$

Even when binding affinity is not detectably or significantly altered, however, the change in residence time, i.e. an increased residence time via increased on-rate or decreased off-rate, or a decreased residence time via a decreased on-rate or increased off-rate, may still result in differential activation of signaling pathways. For example, in some instances where a receptor may activate two different pathways, the pathways differ in the degree of receptor activation required for a full effect. One signaling pathway can be fully activated at low levels of receptor activation or residence time, while full activation of the second pathway requires higher levels of receptor activation or residence time.

The predicted correlation of binding characteristics to functional effect is depicted in the table below.

Thus, the binding properties of the interaction(s) between the modulator and the target, its signaling partner and/or a complex comprising the target and its signaling partner, are generally predictive of the functional effect of the modulator polypeptide on the target signaling pathway.

In another aspect, the methods of identifying a candidate modulating antibody include (a) (i) measuring a binding affinity or binding rate parameter of a test polypeptide binding agent, e.g. antibody, for said first component in the presence of said second component, or (ii) measuring a binding affinity or binding rate parameter of a test polypeptide binding agent for said second component in the presence of said first component; and (b) (i) measuring a binding affinity or binding rate parameter of said test polypeptide binding agent for said first component in the absence of said second component, or (ii) measuring a binding affinity or binding rate parameter of said test polypeptide binding agent for said second component in the absence of said first component; and (c) identifying said test polypeptide binding agent as a candidate kinetic modulating drug when said test polypeptide binding agent exhibits at least a 1.5-fold (i.e., 50%) difference in the binding affinity or binding rate parameters measured in steps (a) and (b).

In some embodiments, the test polypeptide binding agent is identified as a candidate positive modulator if the binding affinity or binding rate parameter measured in step (a) is at least 1.5-fold (i.e., 50%) stronger than the binding affinity or binding rate parameter measured in step (b). In specific embodiments, the binding affinity or binding rate parameter measured in step (a) compared to that measured in step (b) is about 1.5-fold (i.e., 50%) to about 1000-fold stronger for step (a) vs. step (b), or about 1.5-fold to about 100-fold, or about 2-fold to 25-fold, or about 2-fold to about 50-fold, or about 1.5-fold to about 25-fold, or about 1.5-fold to about 50-fold, e.g., at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, up to 30-fold, up to 20-fold, or up to 10-fold.

In other embodiments, the test polypeptide binding agent is identified as a candidate negative modulator if the binding affinity or binding rate parameter measured in step (b) is at least 1.5-fold (i.e., 50%) stronger than the binding affinity or binding rate parameter measured in step (a). In specific embodiments, the binding affinity or binding rate parameter measured in step (b) compared to that measured in step (a) is about 1.5-fold (i.e., 50%) to about 1000-fold stronger for step (b) vs. step (a), or about 1.5-fold to about 100-fold, or about 2-fold to 25-fold, or about 2-fold to about 50-fold, or about 1.5-fold to about 25-fold, or about 1.5-fold to about 50-fold, e.g. at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, up to 30-fold, up to 20-fold, or up to 10-fold.

In some embodiments, the binding affinity or binding rate parameter of the test polypeptide binding agent for the first component alone is measured. In some embodiments, the binding affinity or binding rate parameter of the test polypeptide binding agent for the second component alone is measured.

In some embodiments, the test polypeptide binding agent is identified as a candidate positive modulator if one or more binding affinity or binding rate parameters selected from the group consisting of (A) the binding affinity or binding rate parameter of the test polypeptide binding agent for a complex comprising the first and second components, optionally $K_{[C1C2]M}$, (B) the binding affinity or binding rate parameter of the first component for a complex comprising the polypeptide binding agent and the second component, optionally $K_{[MC2]C1}$, or (C) the binding affinity or binding rate parameter of the second component for a complex comprising the polypeptide binding agent and the first component, optionally $K_{[MC1]C2}$, is at least about 1.5-fold stronger than one or more binding affinity or binding rate parameter selected from the group consisting of (1) the binding affinity or binding rate parameter of the test polypeptide binding agent for the second component alone, optionally $K_{MC2}$ or (2) the binding affinity or binding rate parameter of the test polypeptide binding agent for the first component alone, optionally $K_{MC1}$. In some embodiments, the specific binding affinity or binding rate parameter of any one or more of (A), (B) or (C) is about 1.5-fold (i.e., 50%) to about 1000-fold stronger than the binding affinity or binding rate parameter of any one or more of (1) or (2); or alternatively, about 1.5-fold to about 100-fold stronger, or about 2-fold to 25-fold, or about 2-fold to about 50-fold, or about 1.5-fold to about 25-fold, or about 1.5-fold to about 50-fold, e.g. at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, up to 30-fold, up to 20-fold, or up to 10-fold. For example, in some embodiments, the binding affinity or binding rate parameter of any one or more of (A), (B) or (C) is stronger than the binding affinity or binding rate parameter of both (1) and (2). In some embodiments, the binding affinity or binding rate parameter of (1) is stronger than the binding affinity or binding rate parameter of (2). In other embodiments, the binding affinity or binding rate parameter of (2) is stronger than the binding affinity or binding rate parameter of (1). In some embodiments, two or more binding affinity or binding rate parameters are measured and compared, e.g. off-rate and on-rate, or $K_A$ and $K_D$, or any combination thereof.

In specific embodiments, wherein the binding affinity measured is the equilibrium dissociation constant $K_D$, any of $K_{[C1C2]M}$, $K_{[MC2]C1}$, or $K_{[MC1]C2}$ is lower, e.g., about 1.5-fold to 1000-fold lower, than any of $K_{MC2}$ or $K_{MC1}$. Similarly, wherein the binding affinity measured is the off-rate, any of the off-rates between (A) [C1C2] and M, or (B) [MC2] and C1, or (C) [MC1] and C2 are lower, e.g. about 1.5-fold to 1000-fold lower, than any of the off-rates between (1) M and C2 or (2) M and C1. In one exemplary embodiment, $K_{[C1C2]M}$ is about 1.5-fold to 1000-fold lower than $K_{MC2}$. In another exemplary embodiment, $K_{[MC2]C1}$ is about 1.5-fold to 1000-fold lower than $K_{MC2}$. In another exemplary embodiment, $K_{[MC1]C2}$ is about 1.5-fold to 1000-fold lower than $K_{MC2}$. In another exemplary embodiment, $K_{[C1C2]M}$ is about 1.5-fold to 1000-fold lower than $K_{MC1}$. In another exemplary embodiment, $K_{[MC2]C1}$ is about 1.5-fold to 1000-fold lower than $K_{MC1}$. In yet another exemplary embodiment, $K_{[MC1]C2}$ is about 1.5-fold to 1000-fold lower than $K_{MC1}$. Similar examples can be envisioned for each of the off-rates between (A) [C1C2] and M, or (B) [MC2] and C1, or (C) [MC1] and C2, compared to each of the off-rates between (1) M and C2 or (2) M and C1.

Conversely, where the binding affinity measured is the equilibrium association constant $K_A$, any of $K_{[C1C2]M}$, $K_{[MC2]C1}$, or $K_{[MC1]C2}$ is higher, e.g., about 1.5-fold to 1000-fold higher, than any of $K_{MC2}$ or $K_{MC1}$. Similarly, wherein the binding affinity measured is the on-rate, any of the on-rates between (A) [C1C2] and M, or (B) [MC2] and C1, or (C) [MC1] and C2 are higher, e.g. about 1.5-fold to 1000-fold higher, than any of the on-rates between (1) M and C2 or (2) M and C1. In one exemplary embodiment, $K_{[C1C2]M}$ is about 1.5-fold to 1000-fold higher than $K_{MC2}$. In another exemplary embodiment, $K_{[MC2]C1}$ is about 1.5-fold to 1000-fold higher than $K_{MC2}$. In another exemplary embodiment, $K_{[MC1]C2}$ is about 1.5-fold to 1000-fold higher than $K_{MC2}$. In another exemplary embodiment, $K_{[C1C2]M}$ is about 1.5-fold to 1000-fold higher than $K_{MC1}$. In another exemplary embodiment, $K_{[MC2]C1}$ is about 1.5-fold to 1000-fold higher than $K_{MC1}$. In yet another exemplary embodiment, $K_{[MC1]C2}$ is about 1.5-fold to 1000-fold higher than $K_{MC1}$. Similar examples can be envisioned for each of the on-rates between (A) [C1C2] and M, or (B) [MC2] and C1, or (C) [MC1] and C2, compared to each of the on-rates between (1) M and C2 or (2) M and C1.

In some embodiments, the test polypeptide binding agent is identified as a candidate negative modulator if one or more binding affinity or binding rate parameters selected from the group consisting of (1) the binding affinity or binding rate parameter of the test polypeptide binding agent for the second component alone, optionally $K_{MC2}$, or (2) the binding affinity or binding rate parameter of the test polypeptide binding agent for the first component alone, optionally $K_{MC1}$, is at least about 1.5-fold stronger than one or more binding affinity or binding rate parameter selected from the group consisting of (A) the binding affinity or binding rate parameter of the test polypeptide binding agent for a complex comprising the first and second components, optionally $K_{[C1C2]M}$, (B) the binding affinity or binding rate parameter of the first component for a complex comprising the polypeptide binding agent and the second component, optionally $K_{[MC2]C1}$, or (C) the binding affinity or binding rate parameter of the second component for a complex comprising the polypeptide binding agent and the first component, optionally $K_{[MC1]C2}$. In some embodiments, the specific binding affinity or binding rate parameter of any one or more of (1) or (2) is about 1.5-fold (i.e., 50%) to about 1000-fold stronger than the binding affinity or binding rate parameter of any one or more of (A), (B) or (C); or alternatively, about 1.5-fold to about 100-fold stronger, or about 2-fold to 25-fold, or about 2-fold to about 50-fold, or about 1.5-fold to about 25-fold, or about 1.5-fold to about 50-fold, e.g., at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, up to 30-fold, up to 20-fold, or up to 10-fold. In some embodiments, the binding affinity or binding rate parameter of any of (1) or (2) is stronger than the binding affinity or binding rate parameter of all of (A), (B) and (C). In some embodiments, the binding affinity or binding rate parameter of (1) is stronger than the binding affinity or binding rate parameter of (2). In other embodiments, the binding affinity or binding rate parameter of (2) is stronger than the binding affinity or binding rate parameter of (1). In some embodiments, two or more binding affinity or binding rate parameters are measured and compared, e.g. off-rate and on-rate, or $K_A$ and $K_D$, or any combination thereof.

In specific embodiments, where the binding affinity measured is the equilibrium dissociation constant $K_D$, any of $K_{MC2}$ or $K_{MC1}$ is lower, e.g., about 1.5-fold to 1000-fold lower, than any of $K_{[C1C2]M}$, $K_{[MC2]C1}$, or $K_{[MC1]C2}$. Similarly, wherein the binding affinity measured is the off-rate, any of the off-rates between (1) M and C2 or (2) M and C1 are lower, e.g. about 1.5-fold to 1000-fold lower, than any of the off-rates between (A) [C1C2] and M, or (B) [MC2] and C1, or (C) [MC1] and C2. In one exemplary embodiment $K_{MC2}$ is about 1.5-fold to 1000-fold lower than $K_{[C1C2]M}$. In another exemplary embodiment, $K_{MC2}$ is about 1.5-fold to 1000-fold lower than $K_{[MC2]C1}$. In another exemplary embodiment, $K_{MC2}$ is about 1.5-fold to 1000-fold lower than $K_{[MC1]C2}$. In another exemplary embodiment, $K_{MC1}$ is about 1.5-fold to 1000-fold lower than $K_{[C1C2]M}$. In another exemplary embodiment, $K_{MC1}$ is about 1.5-fold to 1000-fold lower than $K_{[MC2]C1}$. In yet another exemplary embodiment, $K_{MC1}$ is about 1.5-fold to 1000-fold lower than $K_{[MC1]C2}$. Similar examples can be envisioned for each of the off-rates between (1) M and C2 or (2) M and C1, compared to each of the off-rates between (A) [C1C2] and M, or (B) [MC2] and C1, or (C) [MC1] and C2.

Conversely, wherein the binding affinity is the equilibrium association constant $K_A$, any of $K_{MC2}$ or $K_{MC1}$ is higher, e.g., about 1.5-fold to 1000-fold higher, than any of $K_{[C1C2]M}$, $K_{[MC2]C1}$, or $K_{[MC1]C2}$. Similarly, wherein the binding affinity measured is the on-rate, any of the on-rates between (1) M and C2 or (2) M and C1 are higher, e.g. about 1.5-fold to 1000-fold higher, than any of the on-rates between (A) [C1C2] and M, or (B) [MC2] and C1, or (C) [MC1] and C2. In one exemplary embodiment $K_{MC2}$ is about 1.5-fold to 1000-fold higher than $K_{[C1C2]M}$. In another exemplary embodiment, $K_{MC2}$ is about 1.5-fold to 1000-fold higher than $K_{[MC2]C1}$. In another exemplary embodiment, $K_{MC2}$ is about 1.5-fold to 1000-fold higher than $K_{[MC1]C2}$. In another exemplary embodiment, $K_{MC1}$ is about 1.5-fold to 1000-fold higher than $K_{[C1C2]M}$. In another exemplary embodiment, $K_{MC1}$ is about 1.5-fold to 1000-fold higher than $K_{[MC2]C1}$. In yet another exemplary embodiment, $K_{MC1}$ is about 1.5-fold to 1000-fold higher than $K_{[MC1]C2}$. Similar examples can be envisioned for each of the on-rates between (1) M and C2 or (2) M and C1, compared to each of the on-rates between (A) [C1C2] and M, or (B) [MC2] and C1, or (C) [MC1] and C2.

In certain embodiments, the modulator is an antibody and C1 and C2 are selected from the group consisting of insulin and insulin receptor.

In any of these embodiments, the test polypeptide binding agent and second component can be contacted with multiple different concentrations of said first component. In any of these embodiments, the test polypeptide binding agent and first component can be contacted with multiple different concentrations of said second component. In any of these embodiments, multiple different concentrations of the test polypeptide binding agent can be contacted with said first component and said second component.

When the effect of test polypeptide binding agent on the binding interaction between the first component and second component is determined, in some specific embodiments, when the antigen for the test polypeptide binding agent is the first component, e.g., ligand, the test polypeptide binding agent is at a saturating concentration compared to the concentration of the first component. Alternatively, when the antigen for the test polypeptide binding agent is the second component, e.g., receptor, the test polypeptide binding agent is at a saturating concentration compared to the concentration of the second component. In some embodiments, the concentration of the test polypeptide binding agent is greater than or equal to the $K_D$ of the test polypeptide binding agent for a complex comprising the first component and the second component. In further embodiments, the concentration of the second component is less than the $K_D$ of the test polypeptide binding agent for the first component, e.g., ligand. In yet further embodiments, the concentration of the first component, e.g., ligand, is at a subsaturating concentration for the binding of first component to second component, e.g., receptor. In some embodiments, the concentration of the first component, e.g., ligand is within the range of about $EC_{20}$ to $EC_{80}$ for the interaction of the first component with the second component. In some embodiments, one or more concentrations of the test polypeptide binding agent is contacted with multiple different concentrations of the first component, e.g., ligand, in the presence of one or more concentrations of the second component, e.g., receptor. In some embodiments, one or more concentrations of the test polypeptide binding agent is contacted with multiple different concentrations of the second component, e.g., receptor, in the presence of one or more concentrations of the first component, e.g., ligand.

When differential binding of test polypeptide binding agent to complexed vs. uncomplexed target and/or signaling partner is determined in order to identify a positive modulator, in some embodiments, the test polypeptide binding agent is at a saturating concentration for a complex comprising the first component and the second component. In some embodiments, the concentration of test polypeptide binding agent is greater than or equal to the $K_D$ of the test polypeptide binding agent for a complex comprising the first component, e.g., ligand, and the second component, e.g., receptor. In further embodiments, the concentration of the second component, e.g., receptor is greater than the $K_D$ of the second component, e.g., receptor, for the first component, e.g., ligand. In further embodiments, the concentration of the first component, e.g., ligand, is a saturating concentration for the second component, e.g., receptor. In yet further embodiments, the test polypeptide binding agent is at a subsaturating concentration for a complex comprising the first component and the second component. In some embodiments, the concentration of the polypeptide binding agent is within the range of about $EC_{20}$ to $EC_{80}$ for the interaction of the first component with the second component. In some embodiments, the concentration of the second component, e.g., receptor, is greater than the $K_D$ of the second component, e.g., receptor, for the first component, e.g., ligand. In some embodiments, the concentration of the first component, e.g., ligand, is a saturating concentration for the second component, e.g., receptor.

When differential binding of test polypeptide binding agent to complexed vs. uncomplexed target and/or signaling partner is determined in order to identify a negative modulator, in some embodiments, when the antigen to which the test polypeptide binding agent binds is the first component, e.g., ligand, the test polypeptide binding agent is at a subsaturating concentration for the first component. When the antigen to which the test polypeptide binding agent binds is the second component, e.g., receptor, the test polypeptide binding agent is at a subsaturating concentration for the second component. In further embodiments, the concentration of the polypeptide binding agent is within the range of about $EC_{20}$ to $EC_{80}$ for the interaction of the first component with the second component. In further embodiments, the concentration of the second component, e.g., receptor, is greater than the $K_D$ of the second component, e.g., receptor, for the first component, e.g., ligand. In further embodiments, the concentration of the first component, e.g., ligand, is a saturating concentration for the second component, e.g., receptor.

In some embodiments, the methods further involve assaying a plurality of test polypeptide binding agents, e.g. antibodies, for binding affinity to any one of (a) the first component, (b) the second component, or (c) a complex comprising the first component and second component. In some specific embodiments, the polypeptide binding agents have a binding affinity characterized, e.g., by an equilibrium dissociation constant $K_D$ of about $10^{-5}$M or less, or about $10^{-6}$M or less, or about $10^{-7}$M or less, or about $10^{-8}$M or less, where a lower $K_D$ means stronger binding affinity. In some embodiments, the plurality of test polypeptide binding agents screened are variants of a parent polypeptide binding agent made by introducing one or more different mutations into a parent polypeptide binding agent.

In further embodiments, the polypeptide binding agents may be screened for selectivity of effect for the first or second component, compared to a different binding partner such as a decoy receptor, clearance receptor, or alternate signal pathway component. Such methods may involve identifying a polypeptide binding agent that does not significantly change the binding affinity or binding rate parameter of the first or second component for a different binding partner, such binding partner being neither the first nor second component. In some embodiments, the presence of the polypeptide binding agent changes the binding affinity or binding rate parameter of the first or second component for a different binding partner no more than 5-fold, or no more than 10-fold, or no more than 20-fold, or no more than 30-fold, or no more than 40-fold, or no more than 50-fold.

Any of the preceding methods may further include measuring the level of signaling mediated by the signaling complex in the presence and absence of the test polypeptide binding agent, and determining whether the test polypeptide binding agent is additionally an agonist, partial agonist, antagonist or partial antagonist. Antagonism or agonism can be measured in any in vitro or in vivo assay known in the art, including but not limited to signaling in a phosphorylation assay, ion flux assay, molecular transport assay, or gene expression assay.

In some embodiments, the test polypeptide binding agent shifts (positively or negatively) the dose-response curve of the interaction of the first component, e.g. ligand, with the second component, e.g. receptor. The shift may manifest as an increased or decreased $EC_{50}$ by at least about 1.5-fold, e.g. about 1.5-fold to about 100-fold. In some embodiments, the test polypeptide binding agent does not significantly change the maximal agonist response of the signal produced by interaction of the first and second components of the signaling complex. In other embodiments, the test polypeptide binding agent itself acts as an antagonist (e.g., reduces the maximal agonist response of the signaling produced by said signaling complex) or agonist (e.g. increases the maximal agonist response of the signaling produced by said signaling complex).

Where the test polypeptide binding agent acts as an antagonist or partial antagonist, the maximal agonist response may be decreased, e.g., by about 1.5-fold to about 100-fold, or about 2-fold to about 25-fold, or about 1.5-fold to about 50-fold; or, decreased by about 10%, 25%, 50% (1.5-fold), 75%, 2-fold, 3-fold, or 4-, 5-, 6-, 7-, 8-, 9- or 10-fold. Alternatively, where the test polypeptide binding agent acts as an agonist or partial agonist, the maximal agonist response may be increased, e.g. by at least about 10%, 25%, 50% (1.5-fold), 75%, 2-fold, 3-fold, or 4-, 5-, 6-, 7-, 8-, 9- or 10-fold. Moreover, when the test polypeptide binding agent acts as an antagonist or partial antagonist, the IC50 may be $1 \times 10^{-5}$ or less. The test polypeptide binding agent may exhibit further desirable characteristics, e.g. the test polypeptide binding agent does not significantly decrease clearance of said first component, or said second component, or said signaling complex comprising said first and second components.

Methods of identifying modulating agents, e.g., kinetic modulating agents, are described further in co-pending, co-owned U.S. Patent Application No. 61/246,079, filed Sep. 25, 2009, U.S. Patent Application No. 61/306,324, filed Feb. 19, 2010, and International Patent Application No. PCT/US10/50312, filed Sep. 24, 2010.

The test polypeptide binding agent may exhibit further desirable characteristics, e.g. the test polypeptide binding agent does not significantly decrease clearance of said first component, or said second component, or said signaling complex comprising said first and second components.

In a related aspect, the invention provides methods of identifying modulators of the insulin/insulin receptor signaling complex and an antibody or other modulator identified by any of the methods described above or anywhere in the present application.

Types and Sources of Antibodies

The present invention encompasses target specific antibodies that bind to insulin, insulin receptor or the insulin/insulin receptor complex. In exemplary embodiments, a target specific antibody of the invention can comprise a human kappa (κ) or a human lambda (λ) light chain or an amino acid sequence derived therefrom, or a human heavy chain or a sequence derived therefrom, or both heavy and light chains together in a single chain, dimeric, tetrameric or other form. In some embodiments, a heavy chain and a light chain of a target specific immunoglobulin are different amino acid molecules. In other embodiments, the same amino acid molecule contains a heavy chain variable region and a light chain variable region of a target specific antibody.

The term "antibody" is used in the broadest sense and includes fully assembled antibodies, tetrameric antibodies, monoclonal antibodies, polyclonal antibodies, multispecific antibodies (e.g., bispecific antibodies), human and humanized antibodies, antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, as long as the antibody retains the desired biological activity.

In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa (κ) and lambda (λ) light chains. Heavy chains are classified as mu (μ), delta (Δ), gamma (γ), alpha (α), and epsilon (ε), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., *J. Mol. Biol.* 196:901-917, 1987).

Immunoglobulin variable domains exhibit the same general structure of relatively conserved framework regions (FR) joined by three hypervariable regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk, (*J. Mol. Biol.* 196:901-917, 1987); Chothia et al., (*Nature* 342:878-883, 1989).

The hypervariable region of an antibody refers to the CDR amino acid residues of an antibody which are responsible for antigen-binding. The hypervariable region comprises amino acid residues from a CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5$^{th}$ Ed. Public Health Service, National Institutes of Health, Bethesda, Md. (1991)] and/or those residues from a hypervariable loop (i.e., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., *J. Mol. Biol.* 196: 901-917 (1987)]. However, one of skill in the art understands that the actual location of the CDR residues may vary from the projected residues described above when the sequence of the particular antibody is identified.

Framework or FR residues are those variable domain residues other than the hypervariable region residues.

Depending on the amino acid sequence of the constant domain of their heavy chains, immunoglobulins can be assigned to different classes, IgA, IgD, IgE, IgG and IgM, which may be further divided into subclasses or isotypes, e.g. IgG1, IgG2, IgG3, IgG4, IgA1 and IgA2. The subunit structures and three-dimensional configurations of different classes of immunoglobulins are well known. Different isotypes have different effector functions; for example, IgG1 and IgG3 isotypes have ADCC activity. An antibody of the invention, if it comprises a constant domain, may be of any of these subclasses or isotypes.

In exemplary embodiments, an antibody of the invention can comprise a human kappa (κ) or a human lambda (λ) light chain or an amino acid sequence derived therefrom, or a human heavy chain or a sequence derived therefrom, or both heavy and light chains together in a single chain, dimeric, tetrameric or other form.

Monoclonal antibody refers to an antibody obtained from a population of substantially homogeneous antibodies. Monoclonal antibodies are generally highly specific, and may be directed against a single antigenic site, in contrast to conventional (polyclonal) antibody preparations that typically include different antibodies directed against different determinants (epitopes). In addition to their specificity, monoclonal antibodies are advantageous in that they are synthesized by the homogeneous culture, uncontaminated by other immunoglobulins with different specificities and characteristics.

Monoclonal antibodies to be used in accordance with the present invention may be made by the hybridoma method first described by Kohler et al., (*Nature,* 256:495-7, 1975), or may be made by recombinant DNA methods (see, e.g., U.S. Pat. No. 4,816,567). The monoclonal antibodies may also be isolated from phage antibody libraries using the techniques described in, for example, Clackson et al., (*Nature* 352:624-628, 1991) and Marks et al., (*J. Mol. Biol.* 222:581-597, 1991).

In the hybridoma method, a mouse or other appropriate host animal, such as a hamster or macaque monkey, is immunized to elicit lymphocytes that produce or are capable of producing antibodies that will specifically bind to the protein used for immunization (Harlow & Lane; Antibodies: A Laboratory Manual, Cold Spring Harbor Laboratory Press: Cold Spring Harbor, N.Y. (1988).

Recombinant Production of Antibodies

The present invention also encompasses nucleic acid molecules encoding antibodies of the invention. In some embodiments, different nucleic acid molecules encode a heavy chain variable region and a light chain variable region of an antigen-specific antibody. In other embodiments, the same nucleic acid molecule encodes a heavy chain and a light chain variable regions of an antigen-specific antibody.

DNA encoding a monoclonal antibody of the invention may be isolated and sequenced from a hybridoma cell secreting the antibody using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or, preferably, mRNA (i.e., cDNA) encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. Nucleotide probe reactions and other nucleotide hybridization reactions are carried out at conditions enabling the identification of polynucleotides which hybridize to each other under specified conditions. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51

In a preferred embodiment, the polymerase chain reaction (PCR) is used to amplify cDNAs (or portions of full-length cDNAs) encoding an immunoglobulin gene segment of interest (e.g., a light chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest. As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described further herein and is also well-known in the art. See e.g., Dower et al., WO 91/17271, McCafferty et al., WO 92/01047, and Caton and Koprowski, (Proc. Natl. Acad. Sci. USA, 87:6450-54 (1990)), each of which is incorporated herein by reference. In one embodiment, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard phage display techniques such as panning.

The sequence of the amplified or cloned nucleic acid is then determined. Typically the sequence encoding an entire variable region of the immunoglobulin polypeptide is determined, however, it will sometimes by adequate to sequence only a portion of a variable region, for example, the CDR-encoding portion. Typically the portion sequenced will be at least 30 bases in length, more often based coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be placed into expression vectors, which are then transfected into host cells such as E. coli cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

In an alternative embodiment, the amino acid sequence of an immunoglobulin of interest may be determined by direct protein sequencing. Suitable encoding nucleotide sequences can be designed according to a universal codon table.

Amino acid sequence variants of the desired antibody may be prepared by introducing appropriate nucleotide changes into the encoding DNA, or by peptide synthesis. Such variants include, for example, deletions from, and/or insertions into and/or substitutions of, residues within the amino acid sequences of the antibodies. Any combination of deletion, insertion, and substitution is made to arrive at the final construct, provided that the final construct possesses the desired characteristics. The amino acid changes also may alter post-translational processes of the antibody, such as changing the number or position of glycosylation sites.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

The invention also provides isolated nucleic acid encoding antibodies of the invention, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium Various systems and methods for antibody production are reviewed by Birch & Racher (Adv. Drug Deliv. Rev. 671-685 (2006)).

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence.

Suitable host cells for cloning or expressing the DNA in the vectors herein are prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastors* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, *petunia*, tomato, tobacco, *lemna*, and other plant cells can also be utilized as hosts.

Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., *Proc. Natl. Acad. Sci. USA* 77: 4216 (1980)); monkey kidney CV1 line transformed by SV40 (COS-7, ATCC CRL 1651); human embryonic kidney line (293 or 293 cells subcloned for growth in suspension culture, (Graham et al., *J. Gen Virol.* 36: 59, 1977); baby hamster kidney cells (BHK, ATCC CCL 10); mouse sertoli cells (TM4, Mather, (*Biol. Reprod.* 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y Acad. Sci.* 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that bind the desired antigen.

Host cells containing desired antibody nucleic acid sequences may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., (*Meth. Enz.* 58: 44, 1979), Barnes et al., *Anal. Biochem.* 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. (*Science* 240:1041-43, 1988; ICSU Short Reports 10:105 (1990); and *Proc. Natl. Acad. Sci. USA* 90:457-461 (1993) describe a procedure for isolating antibodies which are secreted to the periplasmic space of *E. coli*. [See also, (Carter et al., *Bio/Technology* 10:163-167 (1992)].

The antibody composition prepared from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62: 1-13, 1983). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Antibodies of the Invention

The present invention encompasses target specific antibodies that bind insulin, insulin receptor and/or the insulin/insulin receptor complex, and preferably alter (e.g. increase or decrease) signaling of the insulin receptor and/or its effect on glucose levels and glucose uptake. In exemplary embodiments, a target specific antibody of the invention can comprise a human kappa (κ) or a human lambda (λ) light chain or an amino acid sequence derived therefrom, or a human heavy chain or a sequence derived therefrom, or both heavy and light chains together in a single chain, dimeric, tetrameric or other form. In some embodiments, a heavy chain and a light chain of a target specific immunoglobulin are different amino acid molecules. In other embodiments, the same amino acid molecule contains a heavy chain variable region and a light chain variable region of a target specific antibody.

In some embodiments, the amino acid sequence of the anti-target antibody comprises one or more CDRs of the amino acid sequence of the mature (i.e., missing signal sequence) light chain variable region ($V_L$) of antibodies in SEQ ID NO: 1-150 or variants thereof. In some embodiments, the $V_L$ comprises the amino acid sequence from the beginning of the CDR1 to the end of the CDR3 of the light chain of any one of the foregoing antibodies.

In one embodiment, the target specific antibody comprises a light chain CDR1, CDR2 or CDR3 (LCDR1, LCDR2, LCDR3), each of which are independently selected from the CDR1, CDR2 and CDR3 regions of an antibody having a light chain variable region comprising the amino acid sequence of the $V_L$ region set out in SEQ ID NOs: 1-150. In one aspect the light chain CDR1 is within residues 24-36, CDR2 is within residues 50-56 and CDR3 is within residues 89-101, according to Chothia numbering. A polypeptide of the target specific antibody may comprise the CDR1, CDR2 and CDR3 regions of an antibody having the amino acid sequence of the $V_L$ region selected from the group consisting of SEQ ID NOs: 1-150.

In some embodiments, the target specific antibody comprises one or more CDRs of the amino acid sequence of the mature (i.e., missing signal sequence) heavy chain variable region ($V_H$) of antibodies set out in SEQ ID NOs: 151-303 or variants thereof. In some embodiments, the $V_H$ comprises the amino acid sequence from the beginning of the CDR1 to the end of the CDR3 of any one of the heavy chain of the foregoing antibodies.

In one embodiment, the target specific antibody comprises a heavy chain CDR1, CDR2 or CDR3 (HCDR1, HCDR2, HCDR3), each of which are independently selected from the CDR1, CDR2 and CDR3 regions of an antibody having a heavy chain variable region comprising the amino acid sequence of the $V_H$ region set out in SEQ ID NOs: 151-303. It is further contemplated that a target specific antibody comprises a heavy chain CDR1, CDR2 or CDR3, each of which are independently selected from the CDR1, CDR2 and CDR3 regions of an antibody having a heavy chain variable region having the amino acid sequence of the $V_H$ region set out in SEQ ID NOs: 151-303. In one aspect the heavy chain CDRs are located according to Chothia numbering: CDR1 is within residues 26-35, CDR2 is within residues 50-58 and CDR3 is within residues 95-111 or 97-118. A polypeptide of the target specific antibody may comprise the CDR1, CDR2 and CDR3 regions of an antibody having the amino acid sequence of the $V_H$ region selected from the group consisting of SEQ ID NOs: 151-303.

CDRs in Tables 1 and 2 and SEQ ID NO: 1-303 were determined according to the IMGT system, LeFranc et al IMGT, the INTERNATIONAL IMMUNOGENETICS INFORMATION SYSTEM®, Nucl. Ac. Res. 33 D593-597 (2005).

In another embodiment, the antibody comprises a mature light chain variable region as disclosed above and a mature heavy chain variable region as disclosed above, paired as set forth in Table 3. In another embodiment, the invention contemplates a purified preparation of a monoclonal antibody, comprising the light chain variable region and heavy chain variable regions of any of antibodies as set forth in SEQ ID NOs: 1-303 and paired as set forth in Table 3.

In exemplary embodiments, the invention contemplates: a monoclonal antibody that retains any one, two, three, four, five, or six of HCDR1, HCDR2, HCDR3, LCDR1, LCDR2, or LCDR3 of any one of SEQ ID NOs: 151-303 and SEQ ID NOs: 1-150, respectively, optionally including one or two mutations in any of such CDR(s), e.g., a conservative or non-conservative substitution, and optionally paired as set forth in Table 3;

a monoclonal antibody that retains all of HCDR1, HCDR2, HCDR3, or the heavy chain variable region of any one of SEQ ID NOs: 151-303, optionally including one or two mutations in any of such CDR(s), optionally further comprising any suitable heavy chain constant region, e.g., IgG1, IgG2, IgG3, IgG4, IgM, IgA1, IgA2, or IgE, a human sequence thereof, or a hybrid thereof or a human consensus thereof;

a monoclonal antibody that retains all of LCDR1, LCDR2, LCDR3, or the light chain variable region of any one SEQ ID NOs: 1-150, optionally including one or two mutations in any of such CDR(s), optionally further comprising to any suitable light chain constant region, e.g. a kappa or lambda light chain constant region, a human sequence thereof, or a hybrid thereof or a human consensus thereof;

a monoclonal antibody that binds to the same linear or three-dimensional epitope of INSR as an antibody comprising variable regions set out in SEQ ID NO: 1-303, e.g., as determined through X-ray crystallography or other biophysical or biochemical techniques such as deuterium exchange mass spectrometry, alanine scanning and peptide fragment ELISA;

a monoclonal antibody that competes with an antibody comprising variable regions set out in SEQ ID NO: 1-303 for binding to human INSR by more than about 75%, more than about 80%, or more than about 81%, 82%, 83%, 84%, 85%, 86%, 87%, 88%, 89%, 90%, 91%, 92%, 93%, 94% or 95%.

In some embodiments, the antibody comprises all three light chain CDRs, all three heavy chain CDRs, or all six CDRs of the light and heavy chain, paired as set forth in Table 3. In some exemplary embodiments, two light chain CDRs from an antibody may be combined with a third light chain CDR from a different antibody. Alternatively, a LCDR1 from one antibody can be combined with a LCDR2 from a different antibody and a LCDR3 from yet another antibody, particularly where the CDRs are highly homologous. Similarly, two heavy chain CDRs from an antibody may be combined with a third heavy chain CDR from a different antibody; or a HCDR1 from one antibody can be combined with a HCDR2 from a different antibody and a HCDR3 from yet another antibody, particularly where the CDRs are highly homologous.

Consensus CDRs may also be used. Any one of the consensus CDRs derived herein may be combined with two other CDRs from the same chain (e.g. heavy or light) of any of antibodies, e.g. to form a suitable heavy or light chain variable region.

In some embodiments, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the heavy chain variable region set out in SEQ ID NO: 148-284 and/or an amino acid sequence an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the light chain variable region set out in SEQ ID NO: 1-150, the antibody further comprising at least one, two, three, four, five or all of CDRH1, CDRH2, CDRH3, CDRL1, CDRL2 or CDRL3. In some embodiments, the amino acid sequence with percentage identity to the light chain variable region may comprise one, two or three of the light chain CDRs. In other embodiments, the amino acid sequence with percentage identity to the heavy chain variable region may comprise one, two, or three of the heavy chain CDRs.

It is contemplated that the antibodies of the invention may have one, or two or more amino acid substitutions in the CDR regions of the antibody, e.g., non-conservative or conservative substitutions.

In a related embodiment, the residues of the framework are altered. The heavy chain framework regions which can be altered lie within regions designated H-FR1, H-FR2, H-FR3 and H-FR4, which surround the heavy chain CDR residues, and the residues of the light chain framework regions which can be altered lie within the regions designated L-FR1, L-FR2, L-FR3 and L-FR4, which surround the light chain CDR residues. An amino acid within the framework region may be replaced, for example, with any suitable amino acid identified in a human framework or human consensus framework.

It is further contemplated that the invention provides a purified polypeptide comprising any one of the amino acid sequences of SEQ ID NO: 1-150 fused to any one of the amino acid sequences of SEQ ID NO: 151-303, optionally paired as the heavy/light chain variable regions set forth in Table 3, or fragments thereof that include at least a portion of SEQ ID NO: 1-150 and SEQ ID NO: 151-303, optionally paired as set forth in Table 3, wherein the polypeptide binds insulin receptor, insulin or the insulin/insulin receptor complex.

In another aspect, the invention provides a purified polypeptide comprising at least one CDR of a light chain variable region described herein, wherein the light chain variable region comprises an amino acid sequence at least 90% identical to the LCDR sequences set out in SEQ ID NO: 1-150. In one embodiment, the polypeptide may be 90%, 95%, 96%, 97%, 98%, or 99% identical to any one of the LCDRs set out in SEQ ID NO: 1-150. In a further aspect, the invention provides a purified polypeptide comprising at least one CDR of a heavy chain variable region described herein, wherein the heavy chain variable region comprises an amino acid sequence at least 90% identical to the HCDR sequences set out in SEQ ID NO: 151-303. In one embodiment, the polypeptide may be 90%, 95%, 96%, 97%, 98%, or 99% identical to any one of the HCDRs set out in SEQ ID NO: 151-303.

It is further contemplated that the CDR of the antibody heavy and light chains comprise variant amino acid sequences which may improve antibody binding affinity and are derived through, for example, affinity maturation. In one aspect it is contemplated that an antibody of the invention comprises a heavy chain HCDR2 sequence having about 35% identity to a HCDR2 of a parent antibody sequence set out in SEQ ID NOs: 151-303. In a related aspect it is contemplated that an antibody of the invention comprises a heavy chain HCDR3 sequence having about 50% identity to a HCDR3 of a parent antibody sequence set out in SEQ ID NOs: 151-303.

In one embodiment the invention provides antigen-binding compounds, including functional fragments, having a variable region amino acid sequence set forth in any one of SEQ ID NOs: 1-150 and 151-303. In a related embodiment, an aforementioned antigen binding compound is selected from the group consisting of a fully assembled tetrameric antibody, a polyclonal antibody, a monoclonal antibody including a HUMAN ENGINEERED™ antibody; a humanized antibody; a human antibody; a chimeric antibody; a multispecific antibody, an antibody fragment, Fab, F(ab')$_2$; Fv; scFv or single-chain antibody fragment; a diabody;

triabody, tetrabody, minibody, linear antibody; chelating recombinant antibody, a tribody or bibody, an intrabody, a nanobody, a small modular immunopharmaceutical (SMIP), a binding-domain immunoglobulin fusion protein, a camelized antibody, a $V_{HH}$ containing antibody, or a variant or derivative of any one of these antibodies, that comprise one or more CDR sequences of the invention and exhibit the desired biological activity. The antigen binding compounds of the invention preferably retain binding affinity of $10^{-5}$, $10^{-6}$, $10^{-7}$, $10^{-8}$, $10^{-9}$, $10^{-10}$, $10^{-11}$ M or less as measured by surface plasmon resonance.

In one aspect, the antibodies of the invention comprise a heavy chain variable region or light chain variable region as set out in amino acid sequences SEQ ID NO: 151-303 and SEQ ID NO: 1-150, respectively, as paired in Table 3. It is further contemplated that the antibodies may comprise all or part of the antibodies set out in the above amino acid sequences. In one embodiment, the antibodies comprise at least one of CDR1, CDR2, or CDR3 of the heavy chain of SEQ ID NOs: 151-303, or at least one of CDR1, CDR2 or CDR3 of the light chain of SEQ ID NOs: 1-150, as paired in Table 3.

In one embodiment, the heavy chain comprises an amino acid sequence identified as a heavy chain CDR3 sequence. Such a "heavy chain CDR3 sequence" (HCDR3) includes an amino acid sequence identified as a heavy chain CDR3 sequence set out in Table 2 and SEQ ID NOs: 151-303. Alternatively, the HCDR3 sequence comprises an amino acid sequence that contains one or more amino acid changes compared to any HCDR3 amino acid sequence identified in Table 2, i.e., a substitution, insertion or deletion. Preferable substitutions include a substitution to an amino acid at the corresponding position within another HCDR3 of Table 2. Alternatively, the HCDR3 sequence may comprise a consensus amino acid sequence of the HCDR3 described herein.

Alternatively, the heavy chain comprising a HCDR3 sequence of the invention described above may further comprise a "heavy chain CDR2 sequence" (HCDR2) of the invention, which includes any of the amino acid sequences identified as an HCDR2 in SEQ ID NO: 151-303 and Table 2, amino acid sequences that contain one or more amino acid changes compared to any HCDR2 identified in SEQ ID NO: 151-303 and Table 2, preferably a substitution to an amino acid at the corresponding position within another HCDR2 of Table 2, or a consensus sequence of the HCDR2 described herein.

The heavy chain comprising a heavy chain CDR3 sequence of the invention described above may also comprise both (a) a heavy chain CDR1 sequence of the invention described above and (b) a heavy chain CDR2 sequence of the invention described above.

One aspect of the invention provides an antibody that binds target antigen comprising a heavy chain that comprises any one, two, and/or three of the heavy chain CDR sequences of the invention described below.

Any of the heavy chain CDR sequences described above may also include amino acids added to either end of the CDRs. Preparation of variants and derivatives of antibodies and antigen-binding compounds of the invention, including affinity maturation or preparation of variants or derivatives containing amino acid analogs, is described in further detail herein. Exemplary variants include those containing a conservative or non-conservative substitution of a corresponding amino acid within the amino acid sequence, or a replacement of an amino acid with a corresponding amino acid of a human antibody sequence.

Antibodies comprising any one of the heavy chains described above may further comprise a light chain, preferably a light chain that binds to target antigen, and most preferably a light chain comprising light chain CDR sequences of the invention described below.

Another aspect of the invention provides an antibody that binds target antigen comprising a light chain that comprises any one, two, and/or three of the light chain CDR sequences of the invention described below.

Preferably the light chain comprises an amino acid sequence identified as a light chain CDR3 sequence. Such a "light chain CDR3 sequence" (LCDR3) includes an amino acid sequence identified as a light chain CDR3 sequence in Table 1 and within SEQ ID NOs: 1-150. Alternatively, the light chain CDR3 sequence comprises an amino acid sequence that contains one or more amino acid changes compared to any light chain CDR3 amino acid sequence identified in Table 1, i.e. a substitution, insertion or deletion. Preferable substitutions include a substitution to an amino acid at the corresponding position within another light chain CDR3 of Table 1. Alternatively, the light chain CDR3 sequence may comprise a consensus amino acid sequence of light chain CDR3 shown in Table 1.

The light chain comprising a light chain CDR3 sequence of the invention described above may further comprise a "light chain CDR1 sequence" of the invention, which includes any of the amino acid sequences identified as a light chain CDR1 in SEQ ID NO: 1-150 or Table 1, amino acid sequences that contain one or more amino acid changes compared to any light chain CDR1 identified in SEQ ID NO: 1-150 or Table 1, preferably a substitution to an amino acid at the corresponding position within another light chain CDR1 of Table 1, or a consensus sequence of light chain CDR1 described herein.

Alternatively, the light chain comprising a light chain CDR3 sequence of the invention described above may further comprise a "light chain CDR2 sequence" of the invention, which includes any of the amino acid sequences identified as a light chain CDR2 in SEQ ID NO: 1-150 or Table 1, amino acid sequences that contain one or more amino acid changes compared to any light chain CDR2 identified in Table 1, preferably a substitution to an amino acid at the corresponding position within another light chain CDR2 of SEQ ID NO: 1-150 or Table 1, or a consensus sequence of light chain CDR2 shown in Table 1.

In a related aspect, the invention contemplates a purified polypeptide comprising at least one HCDR of SEQ ID NO: 151-303 or LCDR of SEQ ID NO: 1-150, wherein the framework regions of the heavy chain variable region and the framework regions of the light chain variable region comprise framework regions from a human antibody. In another embodiment, the framework regions of the heavy chain variable region and the framework regions of the light chain variable region are chemically altered by amino acid substitution to be more homologous to a human antibody sequence. For example, within each heavy chain framework region (H-FR1-4) it is contemplated that at least one, at least two, at least three, at least four, at least five, or at least six native framework region residues of the murine heavy chain variable region have been altered by amino acid substitution, and wherein within each light chain framework region (L-FR1-4), at least one, at least two, at least three, at least four, at least five or at least six native framework residues of the murine light chain variable region have been altered by amino acid substitution.

The light chain comprising a light chain CDR3 sequence of the invention described above may also comprise both (a)

a light chain CDR1 sequence of the invention described above and (b) a light chain CDR2 sequence of the invention described above.

Antibodies comprising any one of the light chain variable regions described above may further comprise a heavy chain variable region, optionally paired as described in Table 3, preferably a heavy chain variable region that binds to target antigen, and most preferably a heavy chain variable region comprising heavy chain CDR sequences of the invention described above.

In one aspect, the antibody binds to insulin receptor or a complex comprising insulin and insulin receptor with an equilibrium dissociation constant $K_D$ of $10^{-5}$M or less that is capable of strengthening the binding affinity between insulin and insulin receptor by about 5-fold to 200-fold. In one embodiment, the antibody is a positive modulator antibody, e.g., that strengthens the binding affinity between insulin and insulin receptor. In some embodiments, the positive modulator antibody includes, but is not limited to Ab006, Ab030, Ab004, Ab013, Ab009, Ab007, Ab011, Ab001, Ab012, Ab010, Ab003, Ab008, Ab002, Ab005, Ab076, Ab077, Ab079, Ab080, Ab083, Ab059, Ab078, Ab085 or any polypeptide comprising one or more of the CDRs corresponding to any one of the above antibodies as set out in Tables 1 and 2, or in an antibody variable region set out in SEQ ID NOs: 76, 80, 101, 128, 132 and SEQ ID NOs: 291, 196, 239, 267, 271.

In further embodiments, the positive modulator antibody binds to insulin receptor, the insulin/insulin receptor complex, or binds both insulin receptor and the insulin/insulin receptor complex. In a related embodiment, the positive modulator antibody that binds to insulin receptor or insulin/insulin receptor complex, or both, includes, but is not limited to Ab006, Ab030, Ab004, Ab013, Ab009, Ab007, Ab011, Ab001, Ab012, Ab010, Ab003, Ab008, Ab002, Ab005, Ab076, Ab077, Ab079, Ab080, Ab083 or any polypeptide comprising one or more of the CDRs corresponding to any one of the above antibodies as set out in Tables 1 and 2, or in an antibody variable region set out in SEQ ID NOs: 76, 80, 101 and SEQ ID NOs: 291, 196 and 239.

In a further embodiment, the positive modulator antibody binds to the insulin/insulin receptor complex but not detectably to uncomplexed insulin receptor. In a related embodiment, the positive modulator antibody that binds to the insulin/insulin receptor complex includes, but is not limited to, Ab059, Ab078, Ab085 or any polypeptide comprising one or more of the CDRs corresponding to any one of the above antibodies as set out in Tables 1 and 2, or in an antibody variable region set out in SEQ ID NOs: 128, 132 and SEQ ID NOs: 267 and 271.

In a related aspect, the antibody is an agonist antibody. In one embodiment, the antibody is an agonist antibody that binds to insulin receptor with an affinity of $10^{-5}$, $10^{-6}$, $10^{-7}$, $10^{-8}$, $10^{-9}$ $10^{-10}$, $10^{-11}$ M or less, optionally that exhibits maximal agonist activity that is 20%-100% that of insulin's maximal agonist activity when measured in pAKT assay. In a further embodiment, the antibody is an allosteric agonist antibody that binds to insulin receptor with an affinity of $10^{-5}$, $10^{-6}$, $10^{-7}$, $10^{-8}$, $10^{-9}$ $10^{-10}$, $10^{-11}$ M or less and (a) exhibits maximal agonist activity that is 20%-80% that of insulin's maximal agonist activity when measured in pAKT assay, (b) when present does not alter the EC50 of insulin for INSR by more than 2-fold, and (c) when present does not alter the $K_D$ of insulin for INSR by more than 2-fold.

In certain embodiments, the agonist antibody includes, but is not limited to, Ab021, Ab029, Ab022, Ab017, Ab023, Ab024, Ab025, Ab026, Ab031, Ab035, Ab027, Ab036, Ab037, Ab028, Ab038, Ab039, Ab040, Ab041, Ab042, Ab032, Ab043, Ab044, Ab045, Ab046, Ab047, Ab018, Ab033, Ab048, Ab014, Ab015, Ab049, Ab034, Ab051, Ab053, Ab054, Ab056, Ab058, Ab062, Ab064, Ab066, Ab067, Ab068, Ab086, Ab069, Ab071, Ab073, Ab075, Ab082, Ab084 or any polypeptide comprising one or more of the CDR corresponding to any one of the above antibodies as set out in Tables 1 and 2, or in an antibody variable region set out in SEQ ID NOs: 7, 113, 114, 124, 126, 130 and SEQ ID NOs: 164, 252, 253, 263, 265 and 269.

In a further aspect, the antibody binds to insulin receptor or a complex comprising insulin and insulin receptor with an equilibrium dissociation constant $K_D$ of $10^{-5}$M or less that is capable of weakening the binding affinity between insulin and insulin receptor by at least about 3-fold, optionally up to 1000-fold. In one embodiment, the antibody is a negative modulator antibody that weakens the binding affinity between insulin and the insulin receptor. In a related embodiment, the negative modulator antibody includes, but is not limited to the following antibodies: Ab087, Ab019, Ab088, Ab089, Ab020, Ab050, Ab052, Ab055, Ab057, Ab061, Ab063, Ab065, Ab070, Ab072, Ab074 and Ab081.

In a further aspect, the antibody is an antibody that competes with any of the antibodies described herein for binding to the insulin receptor or insulin/insulin receptor complex. In certain embodiments, the antibody exhibits partial competition. In a related embodiment, partial competition is competition of about 30% to 70%, about 30% to 80%, or about 30%, 35%, 40%, 45%, 50%, 55%, 60%, 65%, 70%, 75%, or 80%. In some embodiments, the antibody exhibits complete competition. In one embodiment, complete competition is competition of greater than 70%, 75%, 80%, 85%, 90%, 95% or 100%. Exemplary assays for measuring antibody competition include, but are not limited to, receptor loading assays and epitope binning assays as described herein and in the art.

In one embodiment, the antibody exhibits greater than or equal to 70% competition with any one, two, three or all antibodies selected from the group consisting of Ab079, Ab076, Ab083, Ab080, Ab062, Ab020, Ab019, Ab088, and Ab089, and optionally, exhibit greater than or equal to 30% competition with any one, two, three or all antibodies selected from the group consisting of Ab086, Ab064, Ab001, and Ab018. In a further embodiment, the antibody optionally does not compete with one or more of Ab062 and Ab086. In certain embodiments, the antibody binds to both human and murine insulin receptor or complex.

In a further embodiment, the antibody that competes with an antibody described herein exhibits greater than or equal to 70% competition with any one, two, three or all antibodies selected from the group consisting of Ab040, Ab062, Ab030, Ab001, and Ab018, and optionally exhibit greater than or equal to 30% competition with any one, two, three or all antibodies selected from the group consisting of AB037, Ab078, AB083, AB080, and AB085. In a related embodiment, the antibody does not compete with Ab053, Ab064, 83-7, Ab019, Ab088, and Ab089. Optionally, the antibody binds to human and murine insulin receptor or complex.

In a further embodiment, the antibody that competes with an antibody described herein exhibits greater than or equal to 70% competition with any one, two, three or all antibodies selected from the group consisting of Ab030, Ab037, Ab053, Ab001, Ab018, Ab064, Ab040, and optionally exhibit greater than or equal to 30% competition with any one, two, three or all antibodies selected from the group consisting of Ab085 and Ab086. Optionally, the antibody exhibits no competition with Ab079, Ab076 and Ab088, and optionally binds to both human and murine insulin receptor or complex.

In a further embodiment, the antibody that competes with an antibody described herein that exhibits greater than or equal to 70% competition with any one, two, three or all antibodies selected from the group consisting of Ab064, Ab062, Ab085, and Ab078, and optionally exhibits no competition with Ab077, Ab001, Ab018, Ab030, Ab037, Ab079, Ab076, Ab083, Ab019, Ab088, Ab089, and Ab040. Optionally, the antibody binds both human and murine insulin receptor or complex.

In a further embodiment, the antibody that competes with an antibody described herein exhibits greater than or equal to 70% competition with any one, two, three or all antibodies selected from the group consisting of Ab079, Ab076, Ab083, Ab080, Ab062, Ab020, Ab019, Ab088, Ab089. Optionally, the antibody does not exhibit competition with Ab062, Ab086, Ab001, Ab018, Ab030, Ab037, Ab064; and optionally, the antibody is human reactive only, and does not bind murine insulin receptor or complex.

In a further embodiment, the antibody shows greater than or equal to 30% competition with any antibody. Optionally, the antibody shows greater than or equal to 30% competition with Ab061, and optionally has less than 30% competition with Ab019 and Ab074, optionally shows no competition with Ab088. Optionally, the antibody binds with both human and murine receptor or complex.

In yet another embodiment, the antibody comprises a heavy chain variable region selected from the group consisting of SEQ ID NOs: 281, 278, 277, 209, 275, 223, 284, 276, and 236 and a light chain variable region selected from the group consisting of SEQ ID NOs: 141, 138, 137, 35, 135, 57, 144, 136, and 98.

In yet another embodiment, the antibody comprises a heavy chain variable region selected from the group consisting of SEQ ID NOs: 195, 220, 303, 197, 208, 243, 245 and 251 and a light chain variable region selected from the group consisting of SEQ ID NOs: 77, 50, 90, 84, 34, 104, 106 and 112.

In yet another embodiment, the antibody comprises a heavy chain variable region selected from the group consisting of SEQ ID NOs: 241, 279, 258, 155, and 228 and a light chain variable region selected from the group consisting of SEQ ID NOs: 103, 139, 119, 8, and 89.

Antibody Nucleic Acids of the Invention

The present invention also encompasses nucleic acid molecules encoding target specific antibodies as described above. In some embodiments, different nucleic acid molecules encode a heavy chain variable region and a light chain variable region of a target specific antibody. In other embodiments, the same nucleic acid molecule encodes a heavy chain and a light chain variable regions of a target specific antibody. In one embodiment, the nucleic acid encodes a target specific antibody of the invention.

In one aspect, a nucleic acid molecule of the invention comprises a nucleotide sequence that encodes the $V_L$ amino acid sequence set out in any one of SEQ ID NOs: 1-150 or a portion thereof. In a related aspect, the $V_L$ amino acid sequence is a consensus sequence. In some embodiments, the nucleic acid encodes the amino acid sequence of the light chain CDRs of said antibody. In some embodiments, said portion is a contiguous portion comprising CDR1-CDR3. In one embodiment, said portion comprises at least one, two or three of a light chain CDR1, CDR2, or CDR3 region.

In some embodiments, the nucleic acid molecule encodes a $V_L$ amino acid sequence that is at least 60, 65, 70, 75, 80, 85, 90, 91, 92, 93, 94, 95, 96 97, 98 or 99% identical to a $V_L$ amino acid sequence set out in SEQ ID NOs: 1-150. Nucleic acid molecules of the invention include nucleic acids that hybridize under highly stringent conditions.

It is further contemplated that a nucleic acid molecule of the invention comprises a nucleotide sequence that encodes the $V_H$ amino acid sequence of any one of SEQ ID NO: 151-303, or a portion thereof. In a related aspect, the $V_H$ amino acid sequence is a consensus sequence. In some embodiments, the nucleic acid encodes the amino acid sequence of the heavy chain CDRs of said antibody. In some embodiments, said portion is a contiguous portion comprising heavy chain CDR1-CDR3. In one embodiment, said portion comprises at least one, two or three of a heavy chain CDR1, CDR2, or CDR3 region.

In some embodiments, the nucleic acid molecule encodes a $V_H$ amino acid sequence that is at least 70%, 75%, 80%, 85%, 90%, 95%, 96%, 97%, 98% or 99% identical to a $V_H$ amino acid sequence set out in SEQ ID NOs: 151-303. Nucleic acid molecules of the invention include nucleic acids that hybridize under highly stringent conditions.

It is further contemplated that the nucleic acids of the invention encode a full-length light chain or heavy chain of an antibody comprising a heavy chain or light chain variable region set out in SEQ ID NOs: 1-303 and optionally paired as described in Table 3, wherein a full-length light chain or full-length heavy chain comprises a light chain constant region or a heavy chain constant region, respectively.

The invention further contemplates nucleic acids encoding antibody variants and polypeptides comprising antigen binding regions of the invention as described above.

Methods of preparing and isolating polynucleotide encoding antibodies of the invention are well-known to those of skill in the art. A polynucleotide according to the invention can be joined to any of a variety of other nucleotide sequences by well-established recombinant DNA techniques (see Sambrook et al., (2d Ed.; 1989) Molecular Cloning: A Laboratory Manual, Cold Spring Harbor Laboratory, Cold Spring Harbor, N.Y.). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, sequencing vectors, and retroviral vectors. A host cell according to the invention can be a prokaryotic or eukaryotic cell and can be a unicellular organism or part of a multicellular organism. Large numbers of suitable vectors and promoters are known to those of skill in the art and are commercially available for generating the recombinant constructs of the present invention.

A variety of expression vector/host systems may be utilized to contain and express the coding sequence. These include, but are not limited to, microorganisms such as bacteria transformed with recombinant bacteriophage, plasmid, phagemid, or cosmid DNA expression vectors; yeast transformed with yeast expression vectors; insect cell systems infected with viral expression vectors (e.g., baculovirus); plant cell systems transfected with virus expression vectors (e.g., Cauliflower Mosaic Virus, CaMV; Tobacco Mosaic Virus, TMV) or transformed with bacterial expression vectors (e.g., Ti or pBR322 plasmid); or even animal cell systems. Mammalian cells that are useful in recombinant protein productions include, but are not limited to, VERO cells, HeLa cells, Chinese hamster ovary (CHO) cells, COS cells (such as COS-7), WI38, BHK, HepG2, 3T3, RIN, MDCK, A549, PC12, K562 and HEK 293 cells.

Polynucleotide variants and antibody fragments may be readily generated by a worker of skill to encode biologically active fragments, variants, or mutants of the naturally occurring antibody molecule that possess the same or similar biological activity to the naturally occurring antibody. This may be done by PCR techniques, cutting and digestion of DNA encoding the antibody heavy and light chain regions, and the like. For example, point mutagenesis, using PCR and other techniques well-known in the art, may be employed to identify with particularity which amino acid residues are important in particular activities associated with antibody activity. Thus, one of skill in the art will be able to generate single base changes in the DNA strand to result in an altered codon and a missense mutation.

Antibody Fragments

Antibody fragments comprise a portion of an intact full length antibody, preferably an antigen binding or variable region of the intact antibody. Examples of antibody fragments include Fab, Fab', F(ab')$_2$, and Fv fragments; diabodies; linear antibodies; single-chain antibody molecules (e.g., scFv); multispecific antibody fragments such as bispecific, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; $V_{HH}$ containing antibodies; and other polypeptides formed from antibody fragments. See for example Holliger & Hudson (Nat. Biotech. 23(9) 1126-36 (2005))

Papain digestion of antibodies produces two identical antigen-binding fragments, called "Fab" fragments, monovalent fragments consisting of the $V_L$, $V_H$, $C_L$ and $C_H$ domains each with a single antigen-binding site, and a residual "Fc" fragment, whose name reflects its ability to crystallize readily. Pepsin treatment yields a F(ab')$_2$ fragment, a bivalent fragment comprising two Fab fragments linked by a disulfide bridge at the hinge region, that has two "Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains that enables the Fv to form the desired structure for antigen binding, resulting in a single-chain antibody (scFv), in which a $V_L$ and $V_H$ region are paired to form a monovalent molecule via a synthetic linker that enables them to be made as a single protein chain (Bird et al., *Science* 242:423-426, 1988, and Huston et al., *Proc. Natl. Acad. Sci. USA* 85:5879-5883, 1988). For a review of scFv see Pluckthun, in The Pharmacology of Monoclonal Antibodies, vol. 1 13, Rosenburg and Moore eds., Springer-Verlag, New York, pp. 269-315 (1994). An Fd fragment consists of the $V_H$ and $C_H$1 domains.

Additional antibody fragments include a domain antibody (dAb) fragment (Ward et al., *Nature* 341:544-546, 1989) which consists of a $V_H$ domain. Diabodies are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., *Proc. Natl. Acad. Sci. USA* 90:6444-6448, 1993, and Poljak et al., *Structure* 2:1121-1123, 1994). Diabodies can be bispecific or monospecific.

Functional heavy-chain antibodies devoid of light chains are naturally occurring in nurse sharks (Greenberg et al., *Nature* 374:168-73, 1995), wobbegong sharks (Nuttall et al., *Mol Immunol.* 38:313-26, 2001) and Camelidae (Hamers-Casterman et al., *Nature* 363: 446-8, 1993; Nguyen et al., *J. Mol. Biol.* 275: 413, 1998), such as camels, dromedaries, alpacas and llamas. The antigen-binding site is reduced to a single domain, the VHH domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelid $V_{HH}$ reportedly recombines with IgG2 and IgG3 constant regions that contain hinge, CH2, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains. Camelid $V_{HH}$ domains have been found to bind to antigen with high affinity (Desmyter et al., *J. Biol. Chem.* 276:26285-90, 2001) and possess high stability in solution (Ewert et al., *Biochemistry* 41:3628-36, 2002). Classical $V_H$-only fragments are difficult to produce in soluble form, but improvements in solubility and specific binding can be obtained when framework residues are altered to be more $VH_H$-like. (See, e.g., Reichman, et al., J Immunol Methods 1999, 231:25-38.) Methods for generating antibodies having camelid heavy chains are described in, for example, in U.S. Patent Publication Nos. 20050136049 and 20050037421.

The variable domain of an antibody heavy-chain is has a molecular mass of 15 kDa, and is referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001) or using recombinant methods as described in Revets et al, Expert Opin. Biol. Ther. 5(1): 111-24 (2005).

Production of bispecific Fab-scFv ("bibody") and trispecific Fab-(scFv)(2) ("tribody") are described in Schoonjans et al. (*J Immunol.* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab.

A "minibody" consisting of scFv fused to CH3 via a peptide linker (hingeless) or via an IgG hinge has been described in Olafsen, et al., Protein Eng Des Sel. 2004 April; 17(4):315-23.

Intrabodies are single chain antibodies which demonstrate intracellular expression and can manipulate intracellular protein function (Biocca, et al., *EMBO J.* 9:101-108, 1990; Colby et al., *Proc Natl Acad Sci USA.* 101:17616-21, 2004). Intrabodies, which comprise cell signal sequences which retain the antibody construct in intracellular regions, may be produced as described in Mhashilkar et al (*EMBO J* 14:1542-51, 1995) and Wheeler et al. (*FASEB J.* 17:1733-5. 2003). Transbodies are cell-permeable antibodies in which a protein transduction domain (PTD) is fused with single chain variable fragment (scFv) antibodies Heng et al., (*Med Hypotheses.* 64:1105-8, 2005).

Further contemplated are antibodies that are SMIPs or binding domain immunoglobulin fusion proteins specific for an antigen. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

In yet another embodiment, the antibody or antigen-binding compound comprises a constant region and one or more heavy and light chain variable framework regions of a human antibody sequence. In a related embodiment, the antibody comprises a modified or unmodified constant region of a human IgG1, IgG2, IgG3 or IgG4.

Alternatively, antibody fragments may be fused to a protein scaffold. Libraries of protein scaffolds include, but are not limited to, Adnectins, Affibodies, Anticalins, DARPins, engineered Kunitz-type inhibitors, tetranectins, A-domain proteins, lipocalins, repeat proteins such as ankyrin repeat proteins, immunity proteins, α2p8 peptide, insect defensin A, PDZ domains, charybdotoxins, PHD fingers, TEM-1 β-lactamase, fibronectin type III domains, CTLA-4, T-cell resptors, knottins, neocarzinostatin, carbohydrate binding module 4-2, green fluorescent protein, thioredoxin (Gebauer & Skerra, Curr. Opin. Chem. Biol. 13:245-55 (2009); Gill & Damle, Curr. Opin. Biotech 17: 653-58 (2006); Hosse et al, Protein Sci. 15:14-27 (2006); Skerra, Curr. Opin. Biotech 18: 295-3-4 (2007)).

Thus, a variety of compositions comprising one, two, and/or three CDRs of a heavy chain variable region or a light chain variable region of an antibody may be generated by techniques known in the art.

Multispecific Antibodies

In some embodiments, it may be desirable to generate multispecific (e.g. bispecific) antibodies of the invention having binding specificities for at least two different epitopes of the same or different molecules. Exemplary bispecific antibodies may bind to two different epitopes of the antigen. Alternatively, an antigen-specific antibody arm may be combined with an arm which binds to a cell surface molecule, such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the desired antigen. Bispecific antibodies may also be used to localize cytotoxic agents to cells which express or take up the desired antigen. These antibodies possess an antigen-binding arm and an arm which binds the cytotoxic agent (e.g., saporin, anti-interferon-60, vinca alkaloid, ricin A chain, methotrexate or radioactive isotope hapten). Bispecific antibodies can be prepared as full length antibodies or antibody fragments (e.g., F(ab')2 bispecific antibodies).

According to another approach for making bispecific antibodies, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., (Science 229:81-83, 1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from *E. coli* can be chemically coupled in vitro to form bispecific antibodies. (Shalaby et al., *J. Exp. Med.* 175:217-225 (1992))

Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor antigens.

Various techniques for making and isolating bispecific antibody fragments directly from recombinant cell culture have also been described. For example, bispecific antibodies have been produced using leucine zippers. (Kostelny et al., *J. Immunol.* 148:1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Holliger et al. (*Proc. Natl. Acad. Sci. USA* 90:6444-48, 1993) has provided an alternative mechanism for making bispecific antibody fragments.

The fragments comprise a heavy chain variable region ($V_H$) connected to a light-chain variable region ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (scFv) dimers has also been reported. See Gruber et al., *J. Immunol.* 152: 5368 (1994).

Alternatively, the bispecific antibody may be a "linear antibody" produced as described in Zapata et al. Protein Eng. 8:1057-62 (1995) Linear antibodies comprise a pair of tandem Fd segments ($V_H$-$C_H$1-$V_H$-$C_H$1) which form a pair of antigen binding regions. Linear antibodies can be bispecific or monospecific.

In a further embodiment, the bispecific antibody may be a chelating recombinant antibody (CRAb). A chelating recombinant antibody recognizes adjacent and non-overlapping epitopes of the antigen, and is flexible enough to bind to both epitopes simultaneously (Neri et al., *J Mol Biol.* 246:367-73, 1995).

Antibodies with more than two valencies are also contemplated. For example, trispecific antibodies can be prepared. (Tutt et al., *J. Immunol.* 147:60, 1991).

Chimeric and Humanized Antibodies

Because chimeric or humanized antibodies are less immunogenic in humans than the parental mouse monoclonal antibodies, they can be used for the treatment of humans with far less risk of anaphylaxis.

Chimeric monoclonal antibodies, in which the variable Ig domains of a mouse monoclonal antibody are fused to human constant Ig domains, can be generated using standard procedures known in the art (See Morrison et al., *Proc. Natl. Acad. Sci. USA* 81, 6841-6855 (1984); and, Boulianne et al, *Nature* 312, 643-646, (1984)). Although some chimeric monoclonal antibodies have proved less immunogenic in humans, the mouse variable Ig domains can still lead to a significant human anti-mouse response.

Humanized antibodies may be achieved by a variety of methods including, for example: (1) grafting the non-human complementarity determining regions (CDRs) onto a human framework and constant region (a process referred to in the art as humanizing through "CDR grafting") (2) transplanting the entire non-human variable domains, but "cloaking" them with a human-like surface by replacement of surface residues (a process referred to in the art as "veneering"), or, alternatively, (3) substituting human amino acids at positions determined to be unlikely to adversely effect either antigen binding or protein folding, but likely to reduce immunogenicity in a human environment (a process referred to in the art as HUMAN ENGINEERING™). In the present invention, humanized antibodies will include both "humanized", "veneered" and "HUMAN ENGINEERED™" antibodies. These methods are disclosed in, e.g., Jones et al., *Nature* 321:522 525 (1986); Morrison et al., *Proc. Natl. Acad. Sci., U.S.A.,* 81:6851-6855 (1984); Morrison and Oi, *Adv. Immunol.,* 44:65-92 (1988); Verhoeyer et al., *Science* 239:1534-1536 (1988); Padlan, *Molec. Immun.* 28:489-498 (1991); Padlan, *Molec. Immunol.* 31:169-217 (1994); Kettleborough et al., *Protein Eng.* 4:773-783 (1991); Studnicka et al. U.S. Pat. No. 5,766,886; Studnicka et al., (*Protein Eng* 7: 805-814, 1994) each of which is incorporated herein by reference.

Human Antibodies from Transgenic Animals

Human antibodies to antigen can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598, 6,657,103 and 6,833,268.

Using a transgenic animal described above, an immune response can be produced to a selected antigen, and antibody producing cells can be removed from the animal and used to produce hybridomas that secrete human monoclonal antibodies Immunization protocols, adjuvants, and the like are known in the art, and are used in immunization of, for example, a transgenic mouse as described in WO 96/33735. This publication discloses monoclonal antibodies against a variety of antigens including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (*Nat. Biotechnol.* 14:845-851 (1996)), which contains gene sequences from unrearranged human antibody genes that code for the heavy and light chains of human antibodies Immunization of a HuMAb-MOUSE® enables the production of fully human monoclonal antibodies to the antigen.

Also, Ishida et al. (*Cloning Stem Cells.* 4:91-102 (2002)) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4) Immunization of the TCMOUSE™ with various human antigens produces antibody responses comprising human antibodies.

See also Jakobovits et al., *Proc. Natl. Acad. Sci. USA,* 90:2551 (1993); Jakobovits et al., *Nature,* 362:255-258 (1993); Bruggermann et al., *Year in Immunol.,* 7:33 (1993); and U.S. Pat. No. 5,591,669, U.S. Pat. No. 5,589,369, U.S. Pat. No. 5,545,807; and U.S. Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human Antibodies from Display Technology

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments-usually Fv or Fab fragments-in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

The invention contemplates a method for producing antigen-specific antibody or antigen-binding portion thereof comprising the steps of synthesizing a library of human antibodies on phage, screening the library with antigen or a portion thereof, isolating phage that bind antigen, and obtaining the antibody from the phage. By way of example, one method for preparing the library of antibodies for use in phage display techniques comprises the steps of immunizing a non-human animal comprising human immunoglobulin loci with antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant antigen-specific antibodies of the invention may be obtained in this way. In another example, antibody producing cells can be extracted from non-immunized animals, RNA isolated from the extracted cells and reverse transcribed to produce cDNA, which is amplified using a primer, and inserted into a phage display vector such that antibodies are expressed on the phage. Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies of the invention can be isolated by screening of a recombinant combinatorial antibody library, preferably a scFv phage display library, prepared using human $V_L$ and $V_H$ cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum. Antibod. Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc Acid Res* 19:4133-4137; and Barbas et al. (1991) *Proc. Natl. Acad. Sci. USA* 88:7978-7982.

In one embodiment, to isolate human antibodies specific for an antigen, with the desired binding characteristics, a human $V_H$ and $V_L$ library are screened to select for antibody fragments having the desired specificity. The antibody libraries used in this method are preferably scFv libraries prepared and screened as described herein and in the art (McCafferty et al., PCT Publication No. WO 92/01047, McCafferty et al., (*Nature* 348:552-554 (1990)); and Griffiths et al., (*EMBO J* 12:725-734 (1993)). The scFv antibody libraries preferably are screened using the antigen.

Alternatively, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., *Bio/Technology* 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.*, 227:381 (1991); Marks et al., *J. Mol. Biol*, 222:581-597 (1991); U.S. Pat. Nos. 5,565,332 and 5,573,905; Clackson, T., and Wells, J. A., *TIBTECH* 12, 173-184 (1994)). In particular, in vitro selection and evolution of antibodies derived from phage display libraries has become a powerful tool (See Burton, D. R., and Barbas III, C. F., *Adv. Immunol.* 57, 191-280 (1994); Winter, G., et al., *Annu. Rev. Immunol.* 12, 433-455 (1994); U.S. patent publication no. 20020004215 and WO 92/01047; U.S. patent publication no. 20030190317; and U.S. Pat. Nos. 6,054,287 and 5,877,293.

Watkins, "Screening of Phage-Expressed Antibody Libraries by Capture Lift," Methods in Molecular Biology, Antibody Phage Display: Methods and Protocols 178:187-193 (2002), and U.S. patent publication no. 20030044772, published Mar. 6, 2003, describe methods for screening phage-expressed antibody libraries or other binding molecules by capture lift, a method involving immobilization of the candidate binding molecules on a solid support.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, fl, Ifl, Ike, ZJ/Z, Ff and one of the class II phages Xf, Pfl and Pf3. The phage may be M13, or fd or a derivative thereof.

Once initial human $V_L$ and $V_H$ segments are selected, "mix and match" experiments, in which different pairs of the initially selected $V_L$ and $V_H$ segments are screened for antigen binding, may be performed to select preferred $V_L/V_H$ pair combinations. Additionally, to further improve the quality of the antibody, the $V_L$ and $V_H$ segments of the preferred $V_L/V_H$ pair(s) can be randomly mutated, preferably within the any of the CDR1, CDR2 or CDR3 region of $V_H$ and/or $V_L$, in a process analogous to the in vivo somatic mutation process responsible for affinity maturation of antibodies during a natural immune response. This in vitro affinity maturation can be accomplished by amplifying $V_L$ and $V_H$ regions using PCR primers complimentary to the $V_H$ CDR1, CDR2, and CDR3, or $V_L$ CDR1, CDR2, and CDR3, respectively, which primers have been "spiked" with a random mixture of the four nucleotide bases at certain positions such that the resultant PCR products encode $V_L$ and $V_H$ segments into which random mutations have been introduced into the $V_H$ and/or $V_L$ CDR3 regions. These randomly mutated $V_L$ and $V_H$ segments can be rescreened for binding to antigen.

Following screening and isolation of an antigen-specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3, hyperphage; and phage displaying or encoding a binding molecule fused to a capsid protein.

Antibodies may also be generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al, (*Bio/Technology*, 10:779-783 (1992)).

Methods for display of polypeptides on the surface of viruses, yeast, microbial and mammalian cells have also been used to identify antigen specific antibodies. See, for example, U.S. Pat. Nos. 5,348,867; 5,723,287; 6,699,658; Wittrup, Curr Op. Biotech. 12:395-99 (2001); Lee et al, Trends in Biotech. 21(1) 45-52 (2003); Surgeeva et al, Adv. Drug Deliv. Rev. 58: 1622-54 (2006). Antibody libraries may be attached to yeast proteins, such as agglutinin, effectively mimicking the cell surface display of antibodies by B cells in the immune system.

In addition to phage display methods, antibodies may be isolated using in vitro display methods including ribosome display and mRNA display (Amstutz et al, Curr. Op. Biotech. 12: 400-05 (2001)). Selection of polypeptide using ribosome display is described in Hanes et al., (*Proc. Natl Acad Sci USA*, 94:4937-4942 (1997)) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

Altered Glycosylation

Antibody variants can also be produced that have a modified glycosylation pattern relative to the parent antibody, for example, deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody.

Fc glycans influence the binding of IgG to Fc receptors and C1q, and are therefore important for IgG effector functions. Antibody variants with modified Fc glycans and altered effector function may be produced. For example, antibodies with modified terminal sugars such as sialic acids, core fucose, bisecting N-acetylglucosamine, and mannose residues may have altered binding to the FcγRIIIa receptor and altered ADCC activity. In a further example, antibodies with modified terminal galactose residues may have altered binding to C1q and altered CDC activity (Raju, Curr. Opin. Immunol. 20: 471-78 (2008).

Also contemplated are antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., *Biotechnol Bioeng*. 87:614-22 (2004)). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., *Mol Immunol*. 26:1113-23 (1989)). Some host cell strains, e.g. Lec13 or rat hybridoma YB2/0 cell line naturally produce antibodies with lower fucosylation levels. (Shields et al., *J Biol Chem*. 277:26733-40 (2002); Shinkawa et al., *J Biol Chem*. 278: 3466-73 (2003)). An increase in the level of bisected carbohydrate, e.g. through recombinantly producing antibody in cells that overexpress GnTIII enzyme, has also been determined to increase ADCC activity (Umana et al., *Nat*

Biotechnol. 17:176-80 (1999)). It has been predicted that the absence of only one of the two fucose residues may be sufficient to increase ADCC activity (Ferrara et al., *Biotechnol Bioeng.* 93:851-61 (2006)).

Variants with Altered Effector Function

Other modifications of the antibody are contemplated. In one aspect, it may be desirable to modify the antibody of the invention with respect to effector function, for example, to enhance the effectiveness of the antibody in treating cancer (Natsume et al, Drug Design Dev't & Ther. 3: 7-16 (2009). Exemplary effector functions include C1q binding; CDC; Fc receptor binding; ADCC; phagocytosis; down regulation of cell surface receptors (e.g. B cell receptor; BCR), etc. One method for modifying effector function teaches that cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., (*J. Exp Med.* 176: 1191-1195 (1992)) and Shopes, B. (*J. Immunol.* 148: 2918-2922 (1992)). Homodimeric antibodies with enhanced anti-tumor activity may also be prepared using heterobifunctional cross-linkers as described in Wolff et al., (*Cancer Research* 53: 2560-2565 (1993)). Alternatively, an antibody can be engineered which has dual Fc regions and may thereby have enhanced complement lysis and ADCC capabilities. See Stevenson et al., (*Anti-Cancer Drug Design* 3: 219-230 (1989)). In addition, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Also see Steplewski et al., (*Proc Natl Acad Sci USA.* 85:4852-56 (1998)), which described chimeric antibodies wherein a murine variable region was joined with human gamma 1, gamma 2, gamma 3, and gamma 4 constant regions.

In certain embodiments of the invention, it may be desirable to use an antibody fragment, rather than an intact antibody, to increase tumor penetration, for example. In this case, it may be desirable to modify the antibody fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., WO96/32478).

The salvage receptor binding epitope preferably constitutes a region wherein any one or more amino acid residues from one or two loops of an Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the $C_L$ region or $V_L$ region, or both, of the antibody fragment. See also International applications WO 97/34631 and WO 96/32478 which describe Fc variants and their interaction with the salvage receptor.

Thus, antibodies of the invention may comprise a human Fc portion, a human consensus Fc portion, or a variant thereof that retains the ability to interact with the Fc salvage receptor, including variants in which cysteines involved in disulfide bonding are modified or removed, and/or in which the a met is added at the N-terminus and/or one or more of the N-terminal 20 amino acids are removed, and/or regions that interact with complement, such as the C1q binding site, are removed, and/or the ADCC site is removed [see, e.g., Sarmay et al., *Molec. Immunol.* 29:633-9 (1992)].

Previous studies mapped the binding site on human and murine IgG for FcR primarily to the lower hinge region composed of IgG residues 233-239. Other studies proposed additional broad segments, e.g. Gly316-Lys338 for human Fc receptor I, Lys274-Arg301 and Tyr407-Arg416 for human Fc receptor III, or found a few specific residues outside the lower hinge, e.g., Asn297 and Glu318 for murine IgG2b interacting with murine Fc receptor II. The report of the 3.2-Å crystal structure of the human IgG1 Fc fragment with human Fc receptor IIIA delineated IgG1 residues Leu234-Ser239, Asp265-Glu269, Asn297-Thr299, and Ala327-Ile332 as involved in binding to Fc receptor IIIA. It has been suggested based on crystal structure that in addition to the lower hinge (Leu234-Gly237), residues in IgG CH2 domain loops FG (residues 326-330) and BC (residues 265-271) might play a role in binding to Fc receptor IIA. See Shields et al., (*J. Biol. Chem.,* 276:6591-604 (2001)), incorporated by reference herein in its entirety. Mutation of residues within Fc receptor binding sites can result in altered effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position).

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. In addition to the residues identified above for all FcR, additional IgG1 residues that reduced binding to Fc receptor IIIA by 40% or more are as follows: Ser239, Ser267 (Gly only), His268, Glu293, Gln295, Tyr296, Arg301, Val303, Lys338, and Asp376. Variants that improved binding to FcRIIIA include T256A, K290A, S298A, E333A, K334A, and A339T. Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA See also Presta et al., (Biochem. Soc. Trans. 30:487-490, 2001), incorporated herein by reference in its entirety, which described several positions in the Fc region of IgG1 were found which improved binding only to specific Fc gamma receptors (R) or simultaneously improved binding to one type of Fc gamma R and reduced binding to another type.

Selected IgG1 variants with improved binding to Fc gamma RIIIa were then tested in an in vitro antibody-dependent cellular cytotoxicity (ADCC) assay and showed an enhancement in ADCC when either peripheral blood mononuclear cells or natural killer cells were used.

For example, U.S. Pat. No. 6,194,551, incorporated herein by reference in its entirety, describes variants with altered effector function containing mutations in the human IgG Fc region, at amino acid position 329, 331 or 322 (using Kabat numbering), some of which display reduced C1q binding or CDC activity. As another example, U.S. Pat. No. 6,737,056, incorporated herein by reference in its entirety, describes variants with altered effector or Fc-gamma-receptor binding containing mutations in the human IgG Fc region, at amino acid position 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 (using Kabat numbering), some of which display receptor binding profiles associated with reduced ADCC or CDC activity. Of these, a mutation at amino acid position 238, 265, 269, 270, 327 or 329 are stated to reduce binding to FcRI, a mutation at amino acid position 238, 265, 269, 270, 292, 294, 295, 298, 303, 324, 327, 329, 333, 335, 338, 373, 376, 414, 416, 419, 435, 438 or 439 are stated to reduce binding to FcRII, and a mutation at amino acid position 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 is stated to reduce binding to FcRIII.

U.S. Pat. No. 5,624,821, incorporated herein in its entirety, reports that C1q binding activity of an murine antibody can be altered by mutating amino acid residue 318, 320 or 322 of the heavy chain and that replacing residue 297 (Asn) results in removal of lytic activity.

U.S. Patent Publication No. 20040132101, incorporated by reference herein in its entirety, describes variants with mutations at amino acid positions 240, 244, 245, 247, 262, 263, 266, 299, 313, 325, 328, or 332 (using Kabat numbering) or positions 234, 235, 239, 240, 241, 243, 244, 245, 247, 262, 263, 264, 265, 266, 267, 269, 296, 297, 298, 299, 313, 325, 327, 328, 329, 330, or 332 (using Kabat numbering), of which mutations at positions 234, 235, 239, 240, 241, 243, 244, 245, 247, 262, 263, 264, 265, 266, 267, 269, 296, 297, 298, 299, 313, 325, 327, 328, 329, 330, or 332 may reduce ADCC activity or reduce binding to an Fc gamma receptor.

Chappel et al. (*Proc Natl Acad Sci USA.* 88:9036-40 (1991)), incorporated herein by reference in its entirety, report that cytophilic activity of IgG1 is an intrinsic property of its heavy chain CH2 domain. Single point mutations at any of amino acid residues 234-237 of IgG1 significantly lowered or abolished its activity. Substitution of all of IgG1 residues 234-237 (LLGG) into IgG2 and IgG4 were required to restore full binding activity. An IgG2 antibody containing the entire ELLGGP sequence (residues 233-238) was observed to be more active than wild-type IgG1.

Isaacs et al. (*J Immunol.* 161:3862-9 (1998)), incorporated herein by reference in its entirety, report that mutations within a motif critical for Fc gammaR binding (glutamate 233 to proline, leucine/phenylalanine 234 to valine, and leucine 235 to alanine) completely prevented depletion of target cells. The mutation glutamate 318 to alanine eliminated effector function of mouse IgG2b and also reduced the potency of human IgG4.

Armour et al. (*Mol Immunol.* 40:585-93 (2003)), incorporated by reference herein in its entirety, identified IgG1 variants which react with the activating receptor, FcgammaRIIa, at least 10-fold less efficiently than wildtype IgG1 but whose binding to the inhibitory receptor, FcgammaRIIb, is only four-fold reduced. Mutations were made in the region of amino acids 233-236 and/or at amino acid positions 327, 330 and 331. See also WO 99/58572, incorporated by reference herein in its entirety.

Xu et al. (*J Biol Chem.* 269:3469-74 (1994)), incorporated by reference herein in its entirety, report that mutating IgG1 Pro331 to Ser markedly decreased C1q binding and virtually eliminated lytic activity. In contrast, the substitution of Pro for Ser331 in IgG4 bestowed partial lytic activity (40%) to the IgG4 Pro331 variant.

Schuurman et al. (*Mol Immunol.* 38:1-8 (2001)), incorporated by reference herein in its entirety, report that mutating one of the hinge cysteines involved in the inter-heavy chain bond formation, Cys226, to serine resulted in a more stable inter-heavy chain linkage. Mutating the IgG4 hinge sequence Cys-Pro-Ser-Cys to the IgG1 hinge sequence Cys-Pro-Pro-Cys also markedly stabilizes the covalent interaction between the heavy chains.

Angal et al. (*Mol Immunol.* 30:105-8 (1993)), incorporated by reference herein in its entirety, report that mutating the serine at amino acid position 241 in IgG4 to proline (found at that position in IgG1 and IgG2) led to the production of a homogeneous antibody, as well as extending serum half-life and improving tissue distribution compared to the original chimeric IgG4.

Covalent Modifications

Covalent modifications of the polypeptide binding agents of the invention, e.g., antibodies, are also included within the scope of this invention. They may be made by chemical synthesis or by enzymatic or chemical cleavage of the polypeptide binding agent, if applicable. Other types of covalent modifications of the polypeptide binding agent are introduced into the molecule by reacting targeted amino acid residues of the polypeptide binding agent with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK$_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the polypeptide binding agent. These procedures are advantageous in that they do not require production of the polypeptide binding agent in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 and in Aplin and Wriston, (CRC Crit. Rev. Biochem., pp. 259-306 (1981)).

Removal of any carbohydrate moieties present on the polypeptide binding agent may be accomplished chemically or enzymatically. Chemical deglycosylation requires exposure of the polypeptide binding agent to the compound trifluoromethanesulfonic acid, or an equivalent compound. This treatment results in the cleavage of most or all sugars except the linking sugar (N-acetylglucosamine or N-acetylgalactosamine), while leaving the polypeptide binding agent intact. Chemical deglycosylation is described by Hakimuddin, et al., (Arch. Biochem. Biophys. 259: 52 (1987)) and by Edge et al., (Anal. Biochem. 118: 131 (1981)). Enzymatic cleavage of carbohydrate moieties on polypeptide binding agents can be achieved by the use of a variety of endo- and exo-glycosidases as described by Thotakura et al., (Meth. Enzymol. 138: 350 (1987)).

Another type of covalent modification of the polypeptide binding agent comprises linking the polypeptide binding agent to one of a variety of hydrophobic moieties or non-proteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Derivatives

Derivative refers to polypeptide binding agents, including antibodies, chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine. Derivatives of the polypeptide binding agents of the invention, such as an antibody, are also useful as therapeutic agents and may be produced by the method of the invention The conjugated moiety can be incorporated in or attached to a polypeptide binding agent either covalently, or through ionic, van der Waals or hydrogen bonds, e.g., incorporation of radioactive nucleotides, or biotinylated nucleotides that are recognized by streptavidin.

Polyethylene glycol (PEG) may be attached to the polypeptide binding agents to provide a longer half-life in vivo. The PEG group may be of any convenient molecular weight and may be linear or branched. The average molecular weight of the PEG will preferably range from about 2 kiloDalton ("kD") to about 100 kDa, more preferably from about 5 kDa to about 50 kDa, most preferably from about 5 kDa to about 10 kDa. The PEG groups will generally be attached to the polypeptide binding agents of the invention via acylation or reductive alkylation through a natural or engineered reactive group on the PEG moiety (e.g., an aldehyde, amino, thiol, or ester group) to a reactive group on the polypeptide binding agent (e.g., an aldehyde, amino, or ester group). Addition of PEG moieties to polypeptide binding agents can be carried out using techniques well-known in the art. See, e.g., International Publication No. WO 96/11953 and U.S. Pat. No. 4,179,337.

Ligation of the polypeptide binding agent with PEG usually takes place in aqueous phase and can be easily monitored by reverse phase analytical HPLC. The PEGylated substances are purified by preparative HPLC and characterized by analytical HPLC, amino acid analysis and laser desorption mass spectrometry.

Antibody Conjugates

A polypeptide binding agent may be administered in its "naked" or unconjugated form, or may be conjugated directly to other therapeutic or diagnostic agents, or may be conjugated indirectly to carrier polymers comprising such other therapeutic or diagnostic agents. In some embodiments the polypeptide binding agent is conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). Suitable chemotherapeutic agents include: daunomycin, doxorubicin, methotrexate, and vindesine (Rowland et al., (1986) supra). Suitable toxins include: bacterial toxins such as diphtheria toxin; plant toxins such as ricin; small molecule toxins such as geldanamycin (Mandler et al J. Natl. Cancer Inst. 92(19):1573-81 (2000); Mandler et al., Bioorg. Med. Chem. Letters 10:1025-1028 (2000); Mandler et al., Bioconjugate Chem. 13.786-91 (2002)), maytansinoids (EP 1391213; Liu et al., Proc. Natl. Acad. Sci. USA 93:8618-23 (1996)), auristatins (Doronina et al., Nat. Biotech. 21: 778-

84 (2003) and calicheamicin (Lode et al., Cancer Res. 58:2928 (1998); Hinman et al., Cancer Res. 53:3336-3342 (1993)).

Polypeptide binding agents can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

Conjugation of polypeptide binding agent moieties is described in U.S. Pat. No. 6,306,393. General techniques are also described in Shih et al., Int. J. Cancer 41:832-839 (1988); Shih et al., Int. J. Cancer 46:1101-1106 (1990); and Shih et al., U.S. Pat. No. 5,057,313. This general method involves reacting a polypeptide binding agent component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate.

Alternatively, conjugated polypeptide binding agents can be prepared by directly conjugating a polypeptide binding agent component with a therapeutic agent. The general procedure is analogous to the indirect method of conjugation except that a therapeutic agent is directly attached to an oxidized polypeptide binding agent component. For example, a carbohydrate moiety of a polypeptide binding agent can be attached to polyethyleneglycol to extend half-life.

Alternatively, a therapeutic agent can be attached at the hinge region of a reduced antibody component via disulfide bond formation, or using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Antibody Fusion Proteins

Methods of making antibody fusion proteins are well known in the art. See, e.g., U.S. Pat. No. 6,306,393. Antibody fusion proteins comprising an interleukin-2 moiety are described by Boleti et al., Ann. Oncol. 6:945 (1995), Nicolet et al., Cancer Gene Ther. 2:161 (1995), Becker et al., Proc. Nat'l Acad. Sci. USA 93:7826 (1996), Hank et al., Clin. Cancer Res. 2:1951 (1996), and Hu et al., Cancer Res. 56:4998 (1996). In addition, Yang et al., (Hum. Antibodies Hybridomas 6:129 (1995)), describe a fusion protein that includes an F(ab')$_2$ fragment and a tumor necrosis factor alpha moiety. Further examples of antibody fusion proteins are described by Pastan et al, Nat. Reviews Cancer 6: 559-65 (2006).

Methods of making antibody-toxin fusion proteins in which a recombinant molecule comprises one or more antibody components and a toxin or chemotherapeutic agent also are known to those of skill in the art. For example, antibody-Pseudomonas exotoxin A fusion proteins have been described by Chaudhary et al., Nature 339:394 (1989), Brinkmann et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol. Chem. 271:10560 (1996), Kuan et al., Biochemistry 35:2872 (1996), and Schmidt et al., Int. J. Can. 65:538 (1996). Antibody-toxin fusion proteins containing a diphtheria toxin moiety have been described by Kreitman et al., Leukemia 7:553 (1993), Nicholls et al., J. Biol. Chem. 268:5302 (1993), Thompson et al., J. Biol. Chem. 270: 28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOT005. As a further example, Dohlsten et al., Proc. Nat'l Acad. Sci. USA 91:8945 (1994), reported an antibody-toxin fusion protein comprising Staphylococcal enterotoxin-A.

Illustrative of toxins which are suitably employed in the preparation of such fusion proteins are ricin, abrin, ribonuclease, DNase I, Staphylococcal enterotoxin-A, pokeweed antiviral protein, gelonin, diphtherin toxin, Pseudomonas exotoxin, and Pseudomonas endotoxin. See, for example, Pastan et al., Cell 47:641 (1986), and Goldenberg, Calif.—A Cancer Journal for Clinicians 44:43 (1994). Other suitable toxins are known to those of skill in the art.

Antibodies of the present invention may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the this invention include, but are not limited to: alkaline phosphatase; arylsulfatase; cytosine deaminase, 5-fluorouracil; proteases, such as *serratia* protease, thermolysin, subtilisin, carboxypeptidases and cathepsins (such as cathepsins B and L); D-alanylcarboxy-peptidases; carbohydrate-cleaving enzymes such as β-galactosidase and neuraminidase; β-lactamase; and penicillin amidases, such as penicillin V amidase or penicillin G amidase. Alternatively, antibodies with enzymatic activity, also known in the art as abzymes, can be used to convert the prodrugs of the invention into free active drugs (See, e.g., Massey, *Nature* 328: 457-458 (1987). Antibody-abzyme conjugates can be prepared as described herein for delivery of the abzyme to a tumor cell population.

The enzymes above can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (See, e.g., Neuberger et al., *Nature* 312: 604-608 (1984))

Preparing Amino Acid Sequence Variants

It is contemplated that modified polypeptide compositions comprising one, two, three, four, five, and/or six CDRs of an antibody or polypeptide binding agent are generated, wherein a CDR or non-CDR region is altered to provide increased specificity or affinity to the antigen, or to provide increased modulation of binding affinity between the target and its signaling partner. For example, sites within antibody CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the targeted site. It is contemplated that conservative substitutions within the CDR allow the variable region to retain biological activity. For example, using the conserved framework sequences surrounding the CDRs, PCR primers complementary to these consensus sequences are generated to amplify the antigen-specific CDR sequence located between the primer regions. Techniques for cloning and expressing nucleotide and polypeptide sequences are well-established in the art [see e.g. Sambrook et al., Molecular Cloning: A Laboratory Manual, 2nd Edition, Cold Spring Harbor, N.Y. (1989)]. The amplified CDR sequences are ligated into an appropriate plasmid. The plasmid comprising one, two, three, four, five and/or six cloned CDRs optionally contains additional polypeptide encoding regions linked to the CDR.

Polypeptide binding agents comprising the modified CDRs are screened for binding affinity for the original antigen. Additionally, the antibody or polypeptide is further tested for its ability to neutralize the activity of its antigen. For example, antibodies of the invention may be analyzed as set out in the Examples to determine their ability to interfere with the biological activity of the target.

Modifications may be made by conservative or non-conservative amino acid substitutions described in greater detail below. "Insertions" or "deletions" are preferably in the range of about 1 to 20 amino acids, more preferably 1 to 10 amino acids. The variation may be introduced by systematically making substitutions of amino acids in an antibody polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for altering antibody sequences and expressing antibody polypeptide compositions useful in the invention are described in greater detail below.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue or the antibody (including antibody fragment) fused to an epitope tag or a salvage receptor epitope. Other insertional variants of the antibody molecule include the fusion to a polypeptide which increases the serum half-life of the antibody, e.g. at the N-terminus or C-terminus.

The term "epitope tagged" refers to the antibody fused to an epitope tag. The epitope tag polypeptide has enough residues to provide an epitope against which an antibody there against can be made, yet is short enough such that it does not interfere with activity of the antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu hemagglutinin (HA) tag polypeptide and its antibody 12CA5 (Field et al., *Mol. Cell. Biol.* 8: 2159-2165 (1988)); the c-myc tag and the 8F9, 3C7, 6E10, G4, B7 and 9E10 antibodies thereto (Evan et al., *Mol. Cell. Biol.* 5:3610-16 (1985)); and the Herpes Simplex virus glycoprotein D (gD) tag and its antibody (Paborsky et al., *Protein Engineering* 3:547-53 (1990)). Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Another type of variant is an amino acid substitution variant. These variants have at least one amino acid residue in the antibody molecule removed and a different residue inserted in its place. Substitutional mutagenesis within any of the hypervariable or CDR regions or framework regions is contemplated. Conservative substitutions involve replacing an amino acid with another member of its class. Non-conservative substitutions involve replacing a member of one of these classes with a member of another class.

Conservative amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E).

Any cysteine residue not involved in maintaining the proper conformation of the antibody also may be substituted, generally with serine, to improve the oxidative stability of the molecule and prevent aberrant crosslinking Conversely, cysteine bond(s) may be added to the antibody to improve its stability (particularly where the antibody is an antibody fragment such as an Fv fragment).

Affinity Maturation

Affinity maturation generally involves preparing and screening antibody variants that have substitutions within the CDRs of a parent antibody and selecting variants that have improved biological properties such as stronger binding affinity relative to the parent antibody. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., *J. Mol. Biol.* 260, 359-68 (1996)), and saturation mutagenesis (Nishimiya et al., *J. Biol. Chem.* 275:12813-20 (2000); Chowdhury, P. S. *Methods Mol. Biol.* 178, 269-85 (2002)) are typical examples of stochastic mutagenesis methods (Rajpal et al., *Proc Natl Acad Sci USA*. 102:8466-71 (2005)). Nonstochastic techniques often use alanine-scanning or site-directed mutagenesis to generate limited collections of specific variants. Some methods are described in further detail below.

Affinity Maturation Via Panning Methods—

Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (*Cancer Immunol Immunother.* 50:163-71 (2001)). Methods of affinity maturation using phage display technologies are described elsewhere herein and known in the art (see e.g., Daugherty et al., *Proc Natl Acad Sci USA*. 97:2029-34 (2000)).

Look-Through Mutagenesis—

Look-through mutagenesis (LTM) (Rajpal et al., *Proc Natl Acad Sci USA*. 102:8466-71 (2005)) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all variants. After positive selection, clones with stronger binding affinity are sequenced, and beneficial mutations are mapped.

Error-Prone PCR—

Error-prone PCR involves the randomization of nucleic acids between different selection rounds. The randomization occurs at a low rate by the intrinsic error rate of the polymerase used but can be enhanced by error-prone PCR (Zaccolo et al., *J. Mol. Biol.* 285:775-783 (1999)) using a polymerase having a high intrinsic error rate during transcription (Hawkins et al., *J Mol Biol.* 226:889-96 (1992)). After the mutation cycles, clones with stronger binding affinity for the antigen are selected using routine methods in the art.

DNA Shuffling—

Nucleic acid shuffling is a method for in vitro or in vivo homologous recombination of pools of shorter or smaller polynucleotides to produce variant polynucleotides. DNA shuffling has been described in U.S. Pat. No. 6,605,449, U.S. Pat. No. 6,489,145, WO 02/092780 and Stemmer, *Proc. Natl. Acad. Sci. USA*, 91:10747-51 (1994). Generally, DNA shuffling is comprised of 3 steps: fragmentation of the genes to be shuffled with DNase I, random hybridization of fragments and reassembly or filling in of the fragmented gene by PCR in the presence of DNA polymerase (sexual PCR), and amplification of reassembled product by conventional PCR.

DNA shuffling differs from error-prone PCR in that it is an inverse chain reaction. In error-prone PCR, the number of polymerase start sites and the number of molecules grows exponentially. In contrast, in nucleic acid reassembly or shuffling of random polynucleotides the number of start sites and the number (but not size) of the random polynucleotides decreases over time.

In the case of an antibody, DNA shuffling allows the free combinatorial association of all of the CDR1s with all of the CDR2s with all of the CDR3s, for example. It is contemplated that multiple families of sequences can be shuffled in the same reaction. Further, shuffling generally conserves the relative order, such that, for example, CDR1 will not be found in the position of CDR2. Rare shufflants will contain a large number of the best (e.g. highest affinity) CDRs and these rare shufflants may be selected based on their superior affinity.

The template polynucleotide which may be used in DNA shuffling may be DNA or RNA. It may be of various lengths depending on the size of the gene or shorter or smaller polynucleotide to be recombined or reassembled. Preferably, the template polynucleotide is from 50 by to 50 kb. The template polynucleotide often should be double-stranded.

It is contemplated that single-stranded or double-stranded nucleic acid polynucleotides having regions of identity to the template polynucleotide and regions of heterology to the template polynucleotide may be added to the template polynucleotide, during the initial step of gene selection. It is also contemplated that two different but related polynucleotide templates can be mixed during the initial step.

Alanine Scanning—

Alanine scanning mutagenesis can be performed to identify hypervariable region residues that contribute significantly to antigen binding. Cunningham and Wells, (*Science* 244:1081-1085 (1989)). A residue or group of targeted residues are identified (e.g., charged residues such as arg, asp, his, lys, and glu) and replaced by a neutral or negatively charged amino acid (most preferably alanine or polyalanine)

to affect the interaction of the amino acids with antigen. Those amino acid locations demonstrating functional sensitivity to the substitutions then are refined by introducing further or other variants at, or for, the sites of substitution.

Computer-Aided Design—

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Formulation of Pharmaceutical Compositions

To administer polypeptide binding agents of the invention to human or test mammals, it is preferable to formulate the polypeptide binding agent in a sterile composition comprising one or more sterile pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

The polypeptide binding agent is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site.

Pharmaceutical compositions of the present invention containing a polypeptide binding agent of the invention as an active ingredient may contain sterile pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. A variety of aqueous carriers are suitable, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations of the polypeptide binding agent are prepared for storage by mixing the polypeptide binding agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, succinate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum *acacia*; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

The antibodies of the invention can be lyophilized for storage and reconstituted in a suitable carrier prior to use.

This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of polypeptide binding agent in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 ml sterile buffered water, and 50 mg of polypeptide binding agent. A typical composition for intravenous infusion could be made up to contain 250 ml of sterile Ringer's solution, and 150 mg of polypeptide binding agent. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of polypeptide binding agent is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancers include for example, salicylate, glycocholate/linoleate, glycholate, aprotinin, bacitracin, SDS, caprate and the like. See, e.g., Fix (*J. Pharm. Sci.*, 85:1282-1285 (1996)) and Oliyai and Stella (*Ann. Rev. Pharmacol. Toxicol.*, 32:521-544 (1993)).

Biophysical Assays

Complex biological events can be studied via molecular biophysical approaches which consider them as systems of interacting units which can be understood in terms of statistical mechanics, thermodynamics and chemical kinetics In certain embodiments, the assays of the present invention may employ a detectable moiety. The detectable moiety can be any one which is capable of producing, either directly or indirectly, a measurable signal, such as a radioactive, chromogenic, luminescence, or fluorescent signal, which can be used to quantitate the amount of bound detectable moiety or label in a sample. Detectable labels known in the art include radioisotopes, such as $^3$H, $^{14}$C, $^{32}$P, $^{35}$S, or $^{125}$I, electrochemiluminescent labels (such as Ruthenium (Ru)-based catalyst in conjunction with substrates, etc.), luminescent or bioluminescent labels (e.g., Europium, Vanadium), fluorescent or chemiluminescent compounds, such as fluorescein isothiocyanate, rhodamine, or luciferin, enzymes (e.g., enzyme, such as alkaline phosphatase, β-galactosidase, or horseradish peroxidase), colorimetric labels such as colloidal gold, colored glass or plastic beads (e.g., polystyrene, polypropylene, latex, etc.), paramagnetic atoms or magnetic agents, electron-dense reagents, a nano- or microbead containing a fluorescent dye, nanocrystals, a quantum dot, a quantum bead, a nanotag, dendrimers with a fluorescent label, a micro-transponder, an electron donor molecule or molecular structure, or a light reflecting particle. the microparticles may be nanocrystals or quantum dots. Nanocrystals are substances that absorb photons of light, then re-emit photons at a different wavelength (fluorophores). In addition, additional florescent labels, or secondary antibodies may be conjugated to the nanocrystals. Nanocrystals are commercially available from sources such as Invitrogen and Evident Technologies (Troy, N.Y.). Other labels include E)-5-[2-(methoxycarbonyl)ethenyl]cytidine, which is a non-fluorescent molecule that when subjected to ultraviolet (UV) irradiation yields a product, 3-.beta.-D-ribofuranosyl-2,7-dioxopyrido[2,3-d]pyrimidine, which displays a strong fluorescence signal. Bar code labels are described in U.S. Patent Publication No. US 20070037195.

A variety of assay methods known in the art may be employed in the present invention, such as competitive binding assays, direct and indirect sandwich assays, immunoprecipitation assays, fluorescent resonance energy transfer (FRET), electroimmunoassays surface plasmon resonance (SPR), and nanoparticle-derived techniques Competitive binding assays rely on the ability of a labeled standard (e.g., an antigen or a fragment thereof to which a polypeptide binding agent binds) to compete with antigen in the test sample for binding to the polypeptide binding agent. The amount of antigen in the test sample is inversely proportional to the amount of standard that becomes bound to the antibodies. To facilitate determining the amount of standard that becomes bound, the antibodies typically are insolubilized before or after the competition, so that the bound antigen may conveniently be separated from the unbound antigen. In alternative embodiments, competitive binding assays measure the ability of a labeled polypeptide binding agent to compete with unlabeled polypeptide binding agent for binding to antigen or a fragment thereof.

Sandwich assays typically involve the use of two antibodies, each capable of binding to a different immunogenic portion, or epitope, of the protein to be detected and/or quantitated. In a sandwich assay, the analyte in the test sample is typically bound by a first polypeptide binding agent which is immobilized on a solid phase, and thereafter a second polypeptide binding agent binds to the analyte, thus forming an insoluble three-part complex. See, e.g., U.S. Pat. No. 4,376,110. The second polypeptide binding agent may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme. See, for example, chapter 18, Current Protocols in Molecular Biology, Ausubel et al., eds., John Wiley & Sons, New York, N.Y. (1995).

Yet another example of an assay method involves fluorescent resonance energy transfer (FRET) emissions. For example, one compound is labeled with a FRET donor molecule and its binding partner is labeled with a FRET acceptor molecule, or vice versa. When binding occurs between the binding partners, the FRET donor and FRET acceptor molecules are brought into proximity and emit fluorescence at a certain wavelength. A narrow band pass filter can be used to block all wavelengths except that of the label. FRET molecule pairs are commercially available in the art (e.g., from Invitrogen), and may be used according to the manufacturer's protocol. FRET emissions are detected using optical imaging techniques, such as a CCD camera.

Yet another example of an assay method is bioluminescence resonance energy transfer (BRET), for example using biosensors as described in WO/06/086883.

Another type of assay involves labeling with an electron donor. One molecule is labeled with an electron donor and the interacting molecule is bound to an electrical contact, or vice versa. When binding occurs between the binding partners, the label donates electrons to the electrical contact. See, for example, Ghindilis, Biochem Soc Trans. 28:84-9, (2000) and Dai et al., Cancer Detect Prev. 29:233-40 (2005), which describe methods for electro immunoassays. The electron contact would then be read by an A to D (analog to digital) converter and quantified. The higher the electron count the more interactions took place.

One embodiment of a label capable of single molecule detection is the use of plasmon-resonant particles (PRPs) as optical reporters, as described in Schultz et al., Proc. Natl. Acad. Sci. USA 97:996-1001 (2000), incorporated herein by reference. PRPs are metallic nanoparticles, e.g. 40-100 nm in diameter, which scatter light because of a collective resonance of the conduction electrons in the metal (i.e., the surface plasmon resonance). The magnitude, peak wavelength, and spectral bandwidth of the plasmon resonance associated with a nanoparticle are dependent on the particle's size, shape, and material composition, as well as the local environment. By influencing these parameters during preparation, PRPs can be formed that have scattering peak anywhere in the visible range of the spectrum. For spherical PRPs, both the peak scattering wavelength and scattering efficiency increase with larger radius, providing a means for producing differently colored labels. Populations of silver spheres, for example, can be reproducibly prepared for which the peak scattering wavelength is within a few nanometers of the targeted wavelength, by adjusting the final radius of the spheres during preparation. Because PRPs are bright, yet nano sized, they are used as indicators for single-molecule detection; that is, the presence of a bound PRP in a field of view can indicate a single binding event. An example of a surface plasmon resonance detector system is the BIAcore assay system. See, e.g., Malmquist, J Molec Recognition, 7:1-7 (1994).

Molecular interactions may also be detected using nanoparticle-derived techniques. See, for example, Ao et al., Anal Chem. 78:1104-6 (2006), which describes gold nanoparticle quenching, Tang et al., Biosens Bioelectron. 2005 Nov. 30, which describes $SiO(2)/Au$ nanoparticle surfaces in antibody detection, and Lieu et al., J Immunol Methods. 307: 34-40 (2005), which describes silicon dioxide nanoparticles containing dibromofluorescein for use in solid substrate-room temperature phosphorescence immunoassay (SS-RTP-IA).

A KinExA assay is also useful to measure the affinity of a modulating antibody for its antigen. An exemplary KinExA assay is described in Example 20. For example, a KinExA assay measures very low levels of ligand in cell culture media. This assay allows the binding of ligand to cells expressing the cognate receptor to be measured by determining the level of ligand depletion from the cell culture media. As the ligand becomes bound to the cells, the concentration of ligand in the cell culture media drops. By using a titration of cells expressing the receptor and measuring the percent free ligand, the affinity of the ligand-receptor interaction is estimated using KinExA software (Sapidyne, Boise Id.). This assay is used to measure the degree of modulation of ligand binding activity shown by various anti-receptor antibodies.

Any of the preceding measurements of binding affinity or binding rate parameters may be carried out in assays where one or more of the first component, second component and polypeptide binding agent are in solution, or in assays where one or more of the first component, second component and polypeptide binding agent are linked to a solid phase (covalently or noncovalently), or in assays where one or more of the first component, second component and polypeptide binding agent are expressed on a cell surface. The first and/or second components may each themselves be complexes of multiple compounds.

Administration and Dosing

In one aspect, methods of the invention include a step of administering a pharmaceutical composition.

Methods of the invention are performed using any medically-accepted means for introducing a therapeutic directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intramammary, intraperitoneal, intrathecal, retrobulbar, intrapulmonary injection and or surgical implantation at a particular site is contemplated as well. Suitable delivery devices may include those developed for the delivery of insulin (see e.g. Owens et al Diabetic Med. 20(11):886-898, 2003).

In one embodiment, administration is performed at the site of a cancer or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the invention implanted at the site.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, weekly, every 2 weeks, every 3 weeks, or monthly.

Also contemplated in the present invention is the administration of multiple agents, such as an antibody composition in conjunction with a second agent as described herein.

The amounts of antibody composition in a given dosage will vary according to the size of the individual to whom the therapy is being administered as well as the characteristics of the disorder being treated. In exemplary treatments, it may be necessary to administer about 1 mg/day, 5 mg/day, 10 mg/day, 20 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses. Standard dose-response studies, first in animal models and then in clinical testing, reveal optimal dosages for particular disease states and patient populations.

Combination Therapy

It one embodiment, an antibody of the invention is administered with a second agent useful to treat a disease or disorder as described herein. It is contemplated that two or more antibodies to different epitopes of the target antigen may be mixed such that the combination of antibodies together to provide still improved efficacy against a condition or disorder to be treated associated with the target polypeptide. Compositions comprising one or more antibody of the invention may be administered to persons or mammals suffering from, or predisposed to suffer from, a condition or disorder to be treated associated with the target polypeptide.

Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

A second agent may be other therapeutic agents, such as anti-diabetic agents, cytokines, growth factors, other anti-inflammatory agents, anti-coagulant agents, agents that will lower or reduce blood pressure, agents that will reduce cholesterol, triglycerides, LDL, VLDL, or lipoprotein(a) or increase HDL, agents that will increase or decrease levels of cholesterol-regulating proteins, anti-neoplastic drugs or molecules. For patients with a hyperproliferative disorder, such as cancer or a tumor, combination with second therapeutic modalities such as radiotherapy, chemotherapy, photodynamic therapy, or surgery is also contemplated.

Exemplary anti-diabetic agents include, but are not limited to, 1) sulfonylureas (e.g., glimepiride, glisentide, sulfonylurea, AY31637); 2) biguanides (e.g., metformin); 3) alpha-glucosidase inhibitors (e.g., acarbose, miglitol); 4) thiazol-idinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054); 5) glucagon-like-peptides (GLP) and GLP analogs or agonists of GLP-1 receptor (e.g. exendin) or stabilizers thereof (e.g. DPP4 inhibitors, such as sitagliptin); and 6) insulin or analogues or mimetics thereof (e.g. LANTUS®).

It is contemplated the antibody of the invention and the second agent may be given simultaneously, in the same formulation. It is further contemplated that the agents are administered in a separate formulation and administered concurrently, with concurrently referring to agents given within 30 minutes of each other.

In another aspect, the second agent is administered prior to administration of the antibody composition. Prior administration refers to administration of the second agent within the range of one week prior to treatment with the antibody, up to 30 minutes before administration of the antibody. It is further contemplated that the second agent is administered subsequent to administration of the antibody composition. Subsequent administration is meant to describe administration from 30 minutes after antibody treatment up to one week after antibody administration.

It is further contemplated that other adjunct therapies may be administered, where appropriate. For example, the patient may also be administered a diabetic diet or food plan, surgical therapy, or radiation therapy where appropriate.

It will also be apparent that dosing may be modified if traditional therapeutics are administered in combination with therapeutics of the invention.

Methods of Use

Therapeutic Indications for INSR Agonists/Positive Modulators

In another embodiment, the invention provides a method for inhibiting target activity by administering a target-specific antibody to a patient in need thereof. Any of the types of antibodies described herein may be used therapeutically. In exemplary embodiments, the target specific antibody is a human, chimeric or humanized antibody. In another exemplary embodiment, the target is human and the patient is a human patient. Alternatively, the patient may be a mammal that expresses a target protein that the target specific antibody cross-reacts with. The antibody may be administered to a non-human mammal expressing a target protein with which the antibody cross-reacts (i.e. a primate) for veterinary purposes or as an animal model of human disease. Such animal models may be useful for evaluating the therapeutic efficacy of target specific antibodies of the invention.

Insulin resistance describes a condition in which physiological amounts of insulin are inadequate to produce a normal insulin response from cells or tissues. Insulin resistance is associated with a number of disease states and conditions and is present in approximately 30-40% of non-diabetic individuals. These disease states and conditions include, but are not limited to, pre-diabetes, metabolic syndrome (also referred to as insulin resistance syndrome), Type 2 diabetes mellitus, polycystic ovary disease (PCOS) and non-alcoholic fatty liver disease (NAFLD) (reviewed in Woods et al, End, Metab & Immune Disorders—Drug Targets 9: 187-198, 2009).

Pre-diabetes is a state of abnormal glucose tolerance characterized by either impaired glucose tolerance (IGT) or impaired fasting glucose (IFG). Patients with pre-diabetes are insulin resistant and are at high risk for future progression to overt Type 2 diabetes. Metabolic syndrome is an associated cluster of traits that include, but is not limited to, hyperinsulinemia, abnormal glucose tolerance, obesity, redistribution of fat to the abdominal or upper body compartment, hypertension, dysfibrinolysis, and a dyslipidemia characterized by high triglycerides, low HDL-cholesterol, and small dense LDL particles. Insulin resistance has been linked to each of the traits, suggesting metabolic syndrome and insulin resistance are intimately related to one another. The diagnosis of metabolic syndrome is a powerful risk factor for future development of Type 2 diabetes, as well as accelerated atherosclerosis resulting in heart attacks, strokes, and peripheral vascular disease.

Diabetes mellitus is a metabolic disorder in humans with a prevalence of approximately one percent in the general population (Foster, D. W., Harrison's Principles of Internal Medicine, Chap. 114, pp. 661-678, 10th Ed., McGraw-Hill, New York). The disease manifests itself as a series of hormone-induced metabolic abnormalities that eventually lead to serious, long-term and debilitating complications involving several organ systems including the eyes, kidneys, nerves, and blood vessels. Pathologically, the disease is characterized by lesions of the basement membranes, demonstrable under electron microscopy. Diabetes mellitus can be divided into two clinical syndromes, Type 1 and Type 2 diabetes mellitus.

Type 1, or insulin-dependent diabetes mellitus (IDDM), also referred to as the juvenile onset form, is a chronic autoimmune disease characterized by the extensive loss of beta cells in the pancreatic Islets of Langerhans, which produce insulin. As these cells are progressively destroyed, the amount of secreted insulin decreases, eventually leading to hyperglycemia (abnormally high level of glucose in the blood) when the amount of secreted insulin drops below the normally required blood glucose levels. Although the exact trigger for this immune response is not known, patients with IDDM have high levels of antibodies against proteins expressed in pancreatic beta cells. However, not all patients with high levels of these antibodies develop IDDM. Type 1 diabetics characteristically show very low or immeasurable plasma insulin with elevated glucagon. Regardless of what the exact etiology is, most Type 1 patients have circulating antibodies directed against their own pancreatic cells including antibodies to insulin, to Islet of Langerhans cell cytoplasm and to the enzyme glutamic acid decarboxylase. An immune response specifically directed against beta cells (insulin producing cells) leads to Type 1 diabetes. The current treatment for Type 1 diabetic patients is the injection of insulin, and may also include modifications to the diet in order to minimize hyperglycemia resulting from the lack of natural insulin, which in turn, is the result of damaged beta cells. Diet is also modified with regard to insulin administration to counter the hypoglycemic effects of the hormone.

Type 2 diabetes (also referred to as non-insulin dependent diabetes mellitus (NIDDM), maturity onset form, adult onset form) develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing insulin output. Over time, these cells become unable to produce enough insulin to maintain normal glucose levels, indicating progression to Type 2 diabetes. Type 2 diabetes is brought on by a combination of genetic and acquired risk factors, including a high-fat diet, lack of exercise, and aging. Greater than 90% of the diabetic population suffers from Type 2 diabetes and the incidence continues to rise, becoming a leading cause of mortality, morbidity and healthcare expenditure throughout the world (Amos et al., Diabetic Med. 14:S1-85, 1997).

Type 2 diabetes is a complex disease characterized by defects in glucose and lipid metabolism. Typically there are perturbations in many metabolic parameters including increases in fasting plasma glucose levels, free fatty acid levels and triglyceride levels, as well as a decrease in the ratio of HDL/LDL. As discussed above, one of the principal underlying causes of diabetes is thought to be an increase in insulin resistance in peripheral tissues, principally muscle and fat. The causes of Type 2 diabetes are not well understood. It is thought that both resistance of target tissues to the action of insulin and decreased insulin secretion ("β-cell failure") occur. Major insulin-responsive tissues for glucose homeostasis are liver, in which insulin stimulates glycogen synthesis and inhibits gluconeogenesis; muscle, in which insulin stimulates glucose uptake and glycogen stimulates glucose uptake and inhibits lipolysis. Thus, as a consequence of the diabetic condition, there are elevated levels of glucose in the blood, which can lead to glucose-mediated cellular toxicity and subsequent morbidity (nephropathy, neuropathy, retinopathy, etc.). Insulin resistance is strongly correlated with the development of Type 2 diabetes.

Currently, there are various pharmacological approaches for the treatment of Type 2 diabetes (Scheen et al, Diabetes Care, 22(9):1568-1577, 1999; Zangeneh et al, Mayo Clin. Proc. 78: 471-479, 2003; Mohler et al, Med Res Rev 29(1): 125-195, 2009). They act via different modes of action: 1) sulfonylureas (e.g., glimepiride, glisentide, sulfonylurea, AY31637) essentially stimulate insulin secretion; 2) biguanides (e.g., metformin) act by promoting glucose utilization, reducing hepatic glucose production and diminishing intestinal glucose output; 3) alpha-glucosidase inhibitors (e.g., acarbose, miglitol) slow down carbohydrate digestion and consequently absorption from the gut and reduce postprandial hyperglycemia; 4) thiazol-idinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054) enhance insulin action, thus promoting glucose utilization in peripheral tissues; 5) glucagon-like-peptides and agonists (e.g. exendin) or stabilizers thereof (e.g. DPP4 inhibitors, such as sitagliptin) potentiate glucose-stimulated insulin secretion; and 6) insulin or analogues thereof (e.g. LANTUS®) stimulate tissue glucose utilization and inhibits hepatic glucose output. The above mentioned pharmacological approaches may be utilized individually or in combination therapy. However, each approach has its limitations and adverse effects. Over time, a large percentage of Type 2 diabetic subjects lose their response to these agents. 63% of Type 2 diabetes patients fail to reach global $HbA_{1c}$ levels of <7% as advised by the American Diabetes Association, and are thus at high risk of developing complications. Moreover, almost invariably patients progress through the stages of declining pancreatic function. Insulin treatment is typically instituted after diet, exercise, and oral medications have failed to adequately control blood glucose. The drawbacks of insulin treatment are the need for drug injection, the potential for hypoglycemia, and weight gain. Consequently there is still an urgent need for novel anti-diabetic agents.

Schaffer et al. used phage display to identify a series of peptides binding to two discrete hotspots on the INSR, which showed agonistic or antagonistic activity when covalently linked to form homodimers or heterodimers (Schaffer et al, Proc. Natl. Acad. Sci. USA, 100(8):4435-4439, 2003).

A further pharmacological approach for the treatment of Type 2 diabetes is the use of non-peptide small molecules that can activate the INSR, or potentiate INSR activation by insulin (Moller, Nature 414: 821-827). Such molecules have proved elusive to identify, but two groups have reported examples. L783281 (DMAQ-B1, L7) and its derivative, compound 2, are insulin mimetics identified from a screen for small molecules that activate the INSR tyrosine kinase (Zhang et al, Science 284: 974-977, 1999; Qureshi et al, J. Biol. Chem. 275(47): 36590-36595, 2000). TLK16998 and TLK19780 are insulin sensitizers identified by their ability to increase autophosphorylation of isolated, naturally expressed human INSR (Manchem et al, Diabetes 50: 824-830, 2001; Pender et al, J. Biol. Chem. 277(46): 43565-43571, 2002). Both L783281 and TLK16998 potentiate insulin action in insulin-resistant cells by acting on the intracellular portion of the INSR β-subunit, enhancing β-subunit autophosphorylation and subsequent downstream signaling (Li et al, Diabetes 50: 2323-2328, 2001). Compound 2 and TLK16998 have been shown to reduce blood glucose levels in mouse models of diabetes when given continuously at high doses (Strowski et al, Endocrinology 145(11):5259-5268, 2004; Manchem et al, Diabetes 50: 824-830, 2001). However, none of these compounds appears to have entered clinical testing. Agents that target the INSR tyrosine kinase domain are expected to have side effects due to non-specific activation homologous tyrosine kinase domains in other molecules. The intracellular portion of the INSR β-subunit is not a suitable target for larger molecules, such as antibodies, which are unable to diffuse into the cell.

Polyclonal autoantibodies from the sera patients with insulin-resistant diabetes have been identified and used as probes to study insulin action. These autoantibodies inhibited insulin binding to INSR and bivalent (but not monovalent) forms produced insulin-like biological effects when exposed to tissues in vitro (Kahn et al, Proc. Natl. Acad. Sci. USA 75(9): 4209-4213, 1978; Heffetz and Zick, J. Biol. Chem. 261(2): 889-894, 1986).

Jacobs and Cuatrecasas described two rabbit polyclonal antibodies and reported that these antibodies, as well as a number of polyclonal antibodies produced by other investigators, were able to mediate various insulin-like effects (Jacobs and Cuatrecasas, CIBA Found. Symp. 90: 82-90, 1982).

Kull et al described three mouse monoclonal antibodies, αIR-1, αIR-2 and αIR-3 and a polyclonal, A410, and their use to investigate the immunochemical cross-reactivity of, and identify the subunits of, the insulin and somatomedin-C(IGF-1) receptors (Kull et al, J. Biol. Chem. 258(10): 6561-6566, 1983). Herrera et al also made antibodies (rabbit polyclonal anti-INSR peptide antibodies P4 and P5) to study the relationship between the human INSR and IGF-1 receptors (Herrera et al, J. Biol. Chem. 261(6): 2489-2491, 1986).

A positive modulator antibody that increases the on-rate or decreases the off-rate of insulin (insulin analog or INSR agonist) for the INSR could result in an increased residency time of receptor bound insulin (insulin analog or INSR agonist), a change in the rate of INSR internalization and/or a change in the degree of phosphorylation of signaling proteins activated or deactivated by the INSR. These changes could significantly alter both the metabolic and mitogenic activity of insulin (insulin analog or INSR agonist) and the level and frequency of dosing of exogenous insulin (insulin analog or INSR agonist).

A negative modulating antibody that increases the on-rate or decreases the off-rate of insulin (insulin analog or INSR agonist) for the receptor could result in an decreased residency time of receptor bound insulin (insulin analog or INSR agonist), a change in the rate of INSR internalization and/or a change in the degree of phosphorylation of signaling proteins activated or deactivated by the INSR. These changes could significantly alter both the metabolic and mitogenic activity of insulin (insulin analog or INSR agonist) and the level and frequency of dosing of exogenous insulin (insulin analog or INSR agonist).

It is contemplated that diabetic patients receiving a positive modulating antibody of the invention would have improvement in blood glucose levels, glucose tolerance test, and other measures of insulin sensitivity compared to patients not receiving treatment. For example, administration of a positive modulator antibody of the invention is expected to reduce elevated blood glucose levels toward normal glucose levels, which are between approximately 70 mg/dL to 125 mg/dL for fasting blood glucose levels according to the American Diabetes Association. In one embodiment, administration of an antibody of the invention reduces blood glucose levels by approximately 15%, 20%, 25%, 30%, 35%, 40% or greater compared to a patient not receiving antibody treatment.

According to the criteria of the World Health Organization and the American Diabetes Association, normal glucose tolerance is defined as glucose levels of below 140 mg per dL measured two hours after ingesting 75 g of oral glucose Impaired glucose tolerance is defined as two-hour glucose levels of 140 to 199 mg per dL (7.8 to 11.0 mmol) after ingesting 75-g oral glucose. A patient is said to have impaired glucose tolerance when the glucose level is elevated (compared to a normal healthy patient) after 2 hours, but less elevated than would qualify for a diagnosis type 2 diabetes mellitus. A patient with impaired glucose tolerance may still have a fasting glucose that is either normal or only mildly elevated. In one embodiment, administration of an antibody of the invention reduces two-hour glucose levels (after the 75-g oral glucose dose) by approximately 15%, 20%, 25%, 30%, 35%, 40%, 45%, 50% or greater compared to a patient not receiving antibody treatment.

The ADA also recommends a hemoglobin A1c target level of less than 7% in adults. For children, the ADA recommends higher target levels of A1c. In children younger than 6 years old, the recommended level is from 7.5% to 8.5%. In children 6 to 12 years old, the recommended level is less than 8%. the recommended level for teens 13 to 19 years old, is less than 7.5%. A1c is a measure of how well blood sugar levels have remained within a target range over the previous 2 to 3 months. (American Diabetes Association, Diabetes Care, 28(1): 186-212, 2005.) It is contemplated that administration of an antibody of the invention to treat diabetes reduces A1c levels towards that observed in a non-diabetic individual. In one embodiment, administration of an antibody of the invention reduces A1c levels in a patient by an absolute HbA1c percentage measurement of at least 0.5%, 0.7%, 1.0% or 1.5%.

Beta cells in the pancreatic islets of Langerhans make and release insulin, a hormone that controls the level of glucose in the blood. There is a baseline level of insulin maintained by the pancreas, but it can respond quickly to spikes in blood glucose by releasing stored insulin while simultaneously producing more. The response time is fairly rapid. In Type 1 diabetes, progressive and extensive loss of beta cells results in decreased levels of secreted insulin, eventually leading to hyperglycemia (abnormally high level of glucose in the blood). In Type 2 diabetes, beta cells initially compensate for insulin resistance in a subject by increasing insulin output, but, over time, the cells become unable to produce enough insulin to maintain normal glucose levels. It is thought that both resistance of target tissues to the action of insulin and decreased insulin secretion, in part due to beta cell failure, occur. Administration of antibodies or polypeptides described herein which improve glucose uptake and other diabetic symptoms are also useful to improve beta cell function in a subject in need thereof. Such improvement includes, but is not limited to, preservation of beta cell viability or reduction of beta cell turnover, increased beta cell proliferation, or enhanced insulin secretion. Additional methods for and results of improvement of beta cell function are disclosed in co-owned international application no. WO 2010/028273.

In certain embodiments, treatment with a positive modulating antibody or partial agonist antibody results in an improvement of one, two, three or more symptoms of diabetes or insulin resistance selected from the group consisting of elevated plasma triglycerides, elevated plasma unesterified cholesterol, elevated plasma total cholesterol elevated plasma insulin (indicative of insulin resistance), elevated HOMA-IR, high non-HDL/HDL cholesterol ratio (or high total cholesterol/HDL cholesterol ratio), improved beta cell function, and elevated plasma leptin levels (indicative of leptin resistance). Where elevated levels are indicative of diabetes, insulin resistance or increased risk for cardiovascular complications, an "improvement" manifests as a reduced level, and vice versa. "Improvement" as used herein refers to a normalization of a level toward the level seen in healthy subjects.

Although the "normal" levels determined upon testing vary on a laboratory-by-laboratory basis, and each laboratory has its own normal range, in general, normal triglyceride levels are less than 150 mg/dl in diabetes (borderline high 150-199 mg/dL); normal cholesterol levels are less than 200 mg/dL, a normal or target non-HDL/HDL cholesterol ratio is approximately <3.25 (based on <130 mg/dL non-HDL target and >41 ng/dL target HDL), a normal or target range for fasting insulin is approximately 5-20 microU/m, and a normal or target range for leptin (usually also associated with body mass index (BMI) or hyperinsulinemia) is between 3-25 ng/ml, e.g., 3 ng/mL appears to be required for normal metabolic function and 20-25 ng/mL appears to be associated with disease. In some embodiments, treatment normalizes any one or more of the above symptoms by at least 5%, 10%, 15%, 20%, 25%, 30%, 35%, 40%, 45%, 50% or more.

Polycystic ovary syndrome (PCOS) is the most common gynecological endocrine disorder and is present in approximately 5-10% of women of childbearing age. Clinical presentations include menstrual disorders, obesity, infertility and hirsutism. Insulin resistance in PCOS results from a post-insulin binding defect in signaling. INSR and insulin receptor substrate (IRS)-1 serine hyperphosphorylation by an unidentified kinase(s) contributes to this defect. Mitogenic signaling was observed to be enhanced in skeletal muscle from women with PCOS (Corbould et al, Diabetes 55: 751-59, 2006). Agonists and/or positive modulators of insulin binding to INSR may therefore be useful for treating and/or reducing the likelihood of the onset of disorders and symptoms related to PCOS. Agonists and/or positive modulators of insulin binding to INSR that do not increase the ratio of mitogenic to metabolic signaling may be particularly useful for treating PCOS.

Non-alcoholic steatohepatitis (NASH) is part of a spectrum of pathology (known as NAFLD) ranging from simple steatosis (fatty infiltration) to NASH, through to cirrhosis and hepatocellular carcinoma (Farrell and Larter, Hepatol. 43, S99-112, 2006). Insulin resistance is associated with fat accumulation in the liver and this organ is now recognized as a major target of injury in patients with insulin resistance. It is estimated that about 20% of all adults have NAFLD, and 2-3% of adults have NASH. Up to one third of patients with NASH will develop cirrhosis over longer follow up. Liver disease is a significant complication of Type 2 diabetes.

Individuals with obesity and dyslipidemia exhibit poorer insulin sensitivity than that found in the average population. Obesity is a chronic disease that is highly prevalent and is associated not only with a social stigma, but also with decreased life span and numerous medical problems including adverse psychological development, dermatological disorders such as infections, varicose veins, exercise intolerance, diabetes mellitus, insulin resistance, hypertension, hypercholesterolemia, and coronary heart disease (Rissanen et al., British Medical Journal, 301: 835-837, 1990). Obesity is highly correlated with insulin resistance and diabetes in experimental animals and humans. Indeed, obesity and insulin resistance, the latter of which is generally accompanied by hyperinsulinemia or hyperglycemia, or both, are hallmarks of Type 2 diabetes. In addition, Type 2 diabetes is associated with a two- to four-fold risk of coronary artery disease. Despite decades of research on these serious health problems, the etiology of obesity and insulin resistance is unknown. It is disclosed herein that positive modulator antibodies and partial agonist antibodies can reduce or slow the weight gain, i.e., normalize weight gain, observed in diabetic animals. It is contemplated that the antibodies have the same effect on weight gain in obese patients. It has also been demonstrated that administration of positive modulator antibodies can slow or reduce weight loss, i.e., normalize weight loss, in diabetic animals whose beta cell population is depleted, which often results in significant weight loss and wasting.

In some embodiments it is contemplated that administration of positive modulator antibodies or partial agonist antibodies described herein can reduce or slow weight gain in a subject by at least 5%, 10%, 15%, 20%, 25%, 30%, 35%, 40%, 45% or 50% compared to an untreated subject.

In an alternate embodiment, it is contemplated that administration of positive modulator antibodies or partial agonist antibodies described herein can reduce or slow weight loss in an individual, such as a diabetic patient or an individual having at least partial beta cell depletion, by at least 5%, 10%, 15%, 20%, 25%, 30%, 35%, 40%, 45% or 50% compared to an untreated subject.

In some embodiments, it is contemplated that administration of positive modular antibodies or partial agonist antibodies described herein can promote or induce weight loss relative to untreated subjects, e.g. by at least 5%, 10%, 15%, 20%, 25%, 30%, 35%, 40%, 45% or 50% compared to an untreated subject.

Protease inhibitors used for the treatment of HIV patients are associated with development of a group of metabolic disorders, including insulin resistance (Graham, JAIDS 25: S4-S11, 2000). HIV protease inhibitor-induced insulin resistance may lead to hyperglycemia that can progress to diabetes and ultimately life threatening ketoacidosis. (Carr et al, Lancet 351:1881-1883, 1998). For some patients, these metabolic side-effects greatly limit the use of these life sustaining drugs. Murata et al (J. Biol. Chem. 275(27): 20251-54, 2000) reported that at least three of the commercialized HIV protease inhibitor drugs also inhibit the glucose transporter from localizing to the cell membrane of in 3T3 L1 adipocytes, with the subsequent inhibition of glucose uptake by these cells. This inhibition of cellular glucose transport into cells by these HIV protease inhibitors is consistent with the elevation of glucose and lipids observed in the clinic for some patients being treated with these protease inhibitor drugs. Thus agonists and/or positive modulators of insulin binding to INSR may be useful for treating the metabolic side-effects of HIV protease inhibitors.

Insulin resistance is also one of the pathological features in patients with hepatitis C virus (HCV) infection and plays a crucial role in the development of various complications and events associated with HCV infection (Kawaguchi and Sata, World J. Gastroenterol. 16: 1943-52, 2010). Thus agonists and/or positive modulators of insulin binding to INSR may be useful for treating complications and events associated with HCV infection.

INSR signaling may also play a role in other diseases. For example, it has been speculated that INSR/IGF-1R signaling may play a role in amyloid-beta metabolism (Freude et al, Curr. Alzheimer Res. 6(3): 213-23, 2009). Activation of IR has been postulated to be an essential element of photoreceptor neuroprotection (Raj ala et al, J. Biol. Chem. 283 (28):19781-92, 2008). Insulin signaling has also been suggested to promote bone formation (Rosen and Motyl, Cell 142: 198-200). Treatment with insulin sensitizers has been reported to improve pulmonary function in patients with both chronic obstructive pulmonary disease and diabetes mellitus (Kim et al, Int. J. Tuberc. Lung Dis. 14(3): 362-67, 2010).

A few patients with homozygous mutations in the INSR gene have been described, which causes Donohue syndrome or Leprechaunism. This autosomal recessive disorder results in a totally non-functional insulin receptor. These patients have low set, often protuberant, ears, flared nostrils, thickened lips, and severe growth retardation. In most cases, the outlook for these patients is extremely poor with death occurring within the first year of life. Other mutations of the INSR gene cause the less severe Rabson-Mendenhall syndrome, in which patients have characteristically abnormal teeth, hypertrophic gingiva (gums) and enlargement of the pineal gland. Both diseases present with fluctuations of the glucose level: after a meal the glucose is initially very high, and then falls rapidly to abnormally low levels (Longo et al, Hum Mol. Genet. 11(12): 1465-75, 2002).

Therapeutic Indications for INSR Antagonists/Negative Modulators

The INSR has also been implicated in cancer. Several epidemiological studies have shown that insulin resistance states, characterized by hyperinsulinemia, are associated with an increased risk for a number of malignancies, including carcinomas of the breast, prostate, colon and kidney. INSR, particularly the INSR-A form, is overexpressed in several human malignancies. INSR forms hybrid receptors with IGF-IR, which is also commonly overexpressed in cancer. Hybrid receptors containing INSR-A hemidimers have broad binding specificity as they bind IGF-I and also IGF-II and insulin. By binding to hybrid receptors, insulin may stimulate specific IGF-IR signaling pathways. Antagonists and/or negative modulators of insulin binding to INSR and/or to hybrid INSR/IGF-1R receptors may therefore be useful as novel anti-cancer therapies (Belfiore Current Pharm. Design 13 (7): 671-686, 2007). INSR has been reported to be essential for virus-induced tumorigenesis of Kaposi's sarcoma (Rose et al, Onogene 26: 1995-2005, 2007).

Hyperinsulinemia is a condition defined by abnormally high levels of insulin in the blood. Causes of hyperinsulinemia include insulinoma and insulin resistance, which may be caused by congenital hyperinsulinemia or other conditions, such as a lack of activity, obesity, polycystic ovary syndrome or insulin overdose. An insulinoma is a tumor of the pancreas that produces excessive amounts of insulin. High insulin levels cause hypoglycemia, or low blood glucose (sugar). Hyperinsulinemia is the most common cause of neonatal hypoglycemia following the first few hours of life. Treatment of such a condition may often be necessary to prevent onset of seizures and neurologic sequelae.

Insulin overdose may be caused, for example by: administration of too much insulin; by administration of the right amount of insulin but the wrong type, such as of short acting insulin instead of long-acting insulin; by administration of insulin followed by a failure to eat; or by intentional insulin over-administration.

In general, hypoglycemia may be mild and lead to symptoms such as anxiety and hunger, but patients are also at risk for severe hypoglycemia, which can cause seizures, coma, and even death. Typical symptoms associated with hypoglycemia that patients complain about include tiredness, weakness, tremulous and hunger. Many patients have to eat frequently to prevent symptoms from the low blood sugar. Some patients may develop psychiatric symptoms because of the low blood sugar.

Currently, patients with insulinomas or other severe forms of hyperinsulinemia are treated by surgery such as partial pancreatectomy or by administration of drugs such as diazoxide or somatostatin which in some cases reduces insulin production. In some cases glucose must be infused continuously. Although peptide INSR antagonists have been described (Schaffer et al, BBRC 376: 380-383, 2008), there is no existing treatment which reduces the effects of circulating insulin. Antagonists and/or negative modulators of insulin binding to INSR may be useful for stabilizing patients with insulinomas before surgery or as part of the therapeutic armamentarium Antagonists and/or negative modulators are also useful to treat Kaposi's sarcoma.

Additionally, a significant number of patients (25,000-100,000) in the US who undergo dialysis present with hypoglycemia due to renal failure (chronic kidney disease, chronic renal disease, chronic kidney failure, chronic renal failure, established chronic kidney disease) and may benefit from treatment with an antagonist or negative modulator of INSR described herein.

Antagonists and/or negative modulators of insulin binding to INSR may be useful for treating and/or reducing the likelihood of the onset of disorders and symptoms related to hyperinsulinemia in a subject, such as reducing anxiety, abnormal hunger, abnormal fatigue, overeating, psychiatric symptoms associated with low blood sugar, and/or hypoglycemia (including hypoglycemia-related seizure, coma, and death). Antagonists and/or negative modulators of insulin binding to INSR may therefore be used to treat various types of persistent hyperinsulinemia conditions, such as nesidioblastosis (KATP-Hl Diffuse Disease, KATP-Hl Focal Disease, or "PHHI"), GDH-Hl (Hyperinsulinism/Hyperammonaemia Syndrome (HI/HA), leucine-sensitive hypoglycemia, or diazoxide-sensitive hypoglycemia), islet cell dysregulation syndrome, idiopathic hypoglycemia of infancy, Persistent Hyperinsulinemic Hypoglycemia of Infancy (PHHI), Congenital Hyperinsulinism, insulinoma, insulin overdose, hypoglycemia due to renal failure (acute or chronic), and chronic kidney disease, e.g., type III, IV or V.

Diagnostic Indications for INSR Agonists/Positive Modulators

Antibodies specific for insulin receptor have been used as tools to diagnose diabetes. U.S. Pat. No. 7,732,154 describes polyclonal antibodies to insulin receptor subunit A (IR-A) as a diagnostic for diabetes, and reports that elevated levels of free IR-A were detected in sera of diabetes and cancer patients. The INSR antibodies disclosed herein are useful to measure insulin receptor, e.g. soluble insulin receptor-A, or insulin levels in a sample from a patient to determine if the levels of INSR or insulin are indicative of diabetes or insulin resistance in the patient. A subject with altered levels of insulin or insulin receptor compared to normal acceptable levels of these factors in an otherwise healthy individual may have or be at risk of diabetes or insulin resistance. The INSR antibodies disclosed herein are also useful to measure insulin receptor, e.g. soluble insulin receptor A, or insulin levels in a sample from a patient to determine if the levels of INSR or insulin are indicative of cancer in the patient. A subject with altered levels of insulin or insulin receptor compared to normal acceptable levels of these factors in an otherwise healthy individual may have or be at risk of cancer.

In one embodiment, the invention provides a method of diagnosing insulin resistance or insulin sensitivity using any of the antibodies as described herein. In one embodiment, the method comprises measuring levels of insulin or insulin receptor, e.g. soluble insulin-receptor-A, in a sample from a subject using an antibody described herein, wherein an altered level of insulin or insulin receptor indicates the subject has or is at risk for diabetes, insulin resistance, insulin sensitivity or cancer, and optionally, administering a therapeutic to said subject who has or is at risk of diabetes, insulin resistance, insulin sensitivity or cancer. In certain embodiments, the sample is a biological sample. In some embodiments, the biological sample is selected from the group consisting of blood, serum, plasma, urine, papillary secretions, cerebrospinal fluid and tumor biopsy. Methods of measuring insulin receptor in a sample include, but are not limited to, immunoassays, competitive inhibition assays, immunoprecipitation assays, and other assays as described herein.

Assays Useful to Measure the Effects of Modulator Administration

Effects of administration of positive or negative modulator antibodies to subjects are measured in vivo and in vitro. In one embodiment, it is contemplated that antibodies that positively modulate insulin/insulin receptor activity decrease in vivo levels of HbA1c, cholesterol, LDL, triglycerides, or non-esterified fatty acids, and HDL in a subject. These factors are measured using techniques common to those of skill in the art.

Subjects receiving a positive modulator antibody also may show reduced weight or reduced weight gain, a decreased frequency and/or number of hypoglycemic or hyperglycemic events, and improved: HDL/LDL ratio, insulin secretion, glycemic control (as measured by glucose tolerance test GTT)), insulin sensitivity as measured by insulin tolerance test (ITT)), beta-cell function (as measured by, e.g., cell mass, insulin secretion, C-peptide levels), beta-cell dormancy, dyslipidemia.

Improved insulin resistance is measured by normalized gene expression of any of the following in liver, adipose tissue and/or muscle: Pck1 (PEPCK), G6pc (G6Pase), Srebf1 (SREBP-1), Gck (GK), Ppargc1a (PGC-1), Abca1 (ABC-1), Acaca (acetyl-CoA carboxylase), IL1b (IL-1beta), IL6 (IL-6), Tnf (TNF-alpha), Ccl2 (MCP-1), Slc2a4 (GLUT4), Il-1rn (IL-1ra), CD68, SAA1, SAA2, FAS (fatty acid synthase), Emr1 (F4/80), Irs1, Irs2. The above are measured by well-known techniques in the art.

In vitro assays are also useful to measure the effects of administration of a modulator of insulin/insulin receptor activity. Positive modulator antibodies are expected to result in increased translocation of GLUT4 to the cell surface. Methods for measuring the translocation of GLUT4 from an intracellular location to the plasma membrane are provided for example in U.S. Pat. No. 6,632,924, US 2007/0141635, US 2003/0104490 and Liu et al, Biochem. J. 418(2), 413-20 (2009). Effects of positive modulators may also be assessed by analyzing enhanced glucose uptake by liver, adipose and/or muscle cells, enhanced depletion of glucose from liver, adipose and/or muscle cell culture medium, and measuring the ratio of metabolic to mitogenic INSR signaling increased or unchanged, pAKT activation, and pIRS-1 activation. The relative Hill slope of insulin-INSR interaction is also measurable. Some dose response curves, however, are steeper or shallower than the standard curve. The steepness is quantified by the Hill slope, also called a slope factor. A dose response curve with a standard slope has a Hill slope of 1.0. A steeper curve has a higher slope factor and a shallower curve has a lower slope factor. Exemplary assays to analyze these factors are described in the Examples.

Use of INSR Antibodies as Drug Delivery Agents

An antibody to INSR, 83-14, has been humanized for the purpose of creating a "molecular Trojan horse" to deliver protein and non-viral gene therapies across the blood-brain-barrier. 83-14 binding drives rapid internalization of the INSR. Hence, further antibodies with this property, or improved properties, may be useful for drug delivery to the brain and central nervous system (Boado et al, Biotech and BioEng. 96(2): 381-391; WO04/050016).

Kits

As an additional aspect, the invention includes kits which comprise one or more compounds or compositions packaged in a manner which facilitates their use to practice methods of the invention. In one embodiment, such a kit includes a compound or composition described herein (e.g., a composition comprising a insulin receptor or insulin/insulin receptor complex-specific antibody alone or in combination with a second agent), packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration or for practicing a screening assay. Preferably, the kit contains a label that describes use of the antibody composition.

Additional aspects and details of the invention will be apparent from the following examples, which are intended to be illustrative rather than limiting.

EXAMPLES

Example 1

Isolation of Anti-INSR Antibodies from Antibody Phage Display Libraries (1) Phage Panning and Rescue A. Naïve Antibody Phage Display Libraries Human insulin receptor (hINSR) (R&D Systems, MN) was biotinylated with Sulfo-NHS-LC-Biotin (Pierce, Rockford, Ill.) using the manufacturer's protocol and 16-fold molar excess of biotin reagent. The biotinylation of hINSR was confirmed by surface plasmon resonance (SPR).

For the first round of phage panning, $1.6 \times 10^{11}$ cfu of phage particles from an scFv phage display library (BioInvent, Lund, Sweden) were blocked for 1 h at room temperature (RT) in 1 ml of 5% milk/PBS (Teknova, Hollister, Calif.) with gentle rotation. Blocked phage were twice deselected for 30 minutes against streptavidin-coated magnetic Dynabeads® M-280 (Invitrogen Dynal AS, Oslo, Norway). To form the biotin-hINSR-hINS complex, 100 pmoles of biotinylated hINSR was preincubated with excess (2,100 pmoles) human insulin (hINS) (Sigma, Mo.) dissolved in 5% milk/PBS, for 1 h at RT with gentle rotation. For the second round of panning, 50 pmoles of biotin-hINSR was used with 1050 pmoles hINS. For the final round of panning, 25 pmoles of biotin-hINSR was incubated with 525 pmoles hINS.

The biotin-hINSR/hINS solution was incubated with blocked streptavidin-coated magnetic Dynabeads® M-280 (Invitrogen Dynal AS, Oslo, Norway) for 30 minutes with gentle rotation in order to immobilize the biotin-hINSR-hINS complex. The deselected phage were incubated with the biotin-hINSR-hINS streptavidin beads for 2 h at RT. In order to saturate the hINSR with hINS, additional hINS (2,100 pmoles) was added to the solution. The beads were washed. For the first round of panning, beads were quickly washed (i.e. beads were pulled out of solution using a magnet and resuspended in 1 ml wash buffer) three times with PBS-0.1% TWEEN, followed by three times with PBS. For the second round of panning, beads were quickly washed five times with PBS-0.1% TWEEN followed by a one 5 minute wash (in 1 ml wash buffer at room temperature with gentle rotation) with PBS-0.1% TWEEN and then five times with PBS followed by one 5 minute wash with PBS. For the third round of panning, beads were quickly washed four times with PBS-0.1% TWEEN, followed by two washes for five minutes with PBS-0.1% TWEEN and then four quick washes with PBS, followed by two 5 minute washes with PBS.

The hINSR-hINS-bound phage were eluted with 100 mM triethylamine (TEA) (30 min incubation at RT) which was then neutralized with 1M Tris-HCl (pH 7.4). The eluted phage were used to infect TG1 bacterial cells (Stratagene, Calif.) when they reached an $OD_{600}$ of ~0.5. Following infection for 30 min at 37° C. without shaking, and for 30 min at 37° C. with shaking at 90 rpm, cells were pelleted and resuspended in 2YT media supplemented with 100 ug/ml ampicillin and 2% glucose. The resuspended cells were plated on 2YT agar plates with 100 ug/ml carbenicillin and 2% glucose and incubated overnight at 30° C.

Phage was then rescued with helper phage VCSM13 (New England Biolabs, MA) at a multiplicity of infection (MOI) ~10. Following helper phage infection at an $OD_{600}$ of 0.6 at 37° C. for 30 min without rotation and 30 min incubation at 37° C. at 150 rpm, cell pellets were resuspended in 2YT media supplemented with 100 ug/ml ampicillin and 50 ug/ml kanamycin and allowed to grow overnight at 30° C. Phage in the supernatant were recovered after rigorous centrifugation and used for the next round of panning. In order to monitor the enrichment resulting from the phage selections, the amount of input and output phage was titered for the three rounds of panning Gene III Excision and Generation of Bacterial Periplasmic Extracts Before screening the phage panning output scFv clones for binding to the hINSR-hINS complex, the gene III gene was first excised from the phagemid vectors to enable production of secreted scFv. In order to do this, a plasmid midi prep (Qiagen, Valencia, Calif.) of the third panning round output pool of clones was digested with the restriction enzyme EagI (New England Biolabs, MA). The digestion product without the gene III was then allowed to self-ligate with T4 DNA ligase (New England Biolabs, MA) and used to transform chemically-competent TOP10 E. coli cells (Invitrogen, Carlsbad, Calif.). Individual transformed colonies in 96-well plates were then used to generate bacterial periplasmic extracts according to standard methods, with a 1:3 volume ratio of ice-cold PPB solution (Teknova, Hollister, Calif.) and double distilled water (ddH2O) and two protease inhibitor cocktail tablets (Roche, Ind.). The lysate supernatants were assayed by ELISA, as described below.

B. Immunized Antibody Phage Display Libraries

An Omniclonal™ phage display library was generated from mice hyperimmunized with hINSR-hINS complex according to the methods described in U.S. Pat. No. 6,057,098. The immunization material consisted of approximately equal molar amounts of recombinant human insulin (cat # I9278, Sigma-Aldrich, Inc. St. Louis, Mo.) and recombinant human INSR (28-956) (cat #1544-IR/CF, R&D Systems, MN). The protein concentration of the complex was around 0.24 mg/ml. Single colonies, obtained from the Omniclonal' library according to the protocol in U.S. Pat. No. 6,057,098, were screened for binding activity in an ELISA assay as described below.

(2) ELISA Screening of Antibody Clones on hINSR/hINS Complex

ELISA Maxisorp® plates (Thermo Fisher Scientific, Rochester, N.Y.) were coated overnight at 4° C. with 3 ug/ml hINSR in PBS. Plates were then blocked for 1 h at RT with 400 ul/well 5% milk/PBS. To generate wells containing the hINSR-hINS complex, 50 ul/well of hINS (2.1 uM) was allowed to bind to the hINSR for 30 min at RT. Bacterial periplasmic extracts were also blocked with 5% milk/PBS for 1 h and then added to the coated ELISA plate (50 ul/well) and allowed to bind to either hINSR or hINSR-hINS complex on the ELISA plate for 2 h at RT. The murine 83-7 anti-hINSR mAb was used as a positive ELISA screening control (Soos et al, Biochem. J. 235: 199-208, 1986). Bound scFv fragments were detected with murine anti-c-myc mAb (Roche, Ind.) for 1 h at RT followed by goat anti-mouse HRP-conjugated antisera (Thermo Scientific, Rockford, Ill.). Three washes with PBS-0.1% TWEEN-20 (Teknova, Hollister, Calif.) were performed following every stage of the ELISA screens. The positive control 83-7 mAb was detected by goat-anti-mouse HRP (Thermo Scientific, Rockford, Ill.) following incubation for 1 h at RT. Color was developed at 450 nm absorbance with 50 ul/well soluble 3.3',5.5'-tetramethylbenzidine (TMB) substrate (EMD chemicals, Calbiochem, N.J.) and stopped with 1M $H_2SO_4$ (50 ul/well).

Results

ELISA screening of the bacterial periplasmic extracts identified multiple hINSR or hINSR-hINS complex binders that originated from the phage panning selection. Fifty-eight percent (868 out of 1,488) of the clones selected from the naïve library were able to bind the hINSR or hINSR-hINS complex. Forty-three percent (200 out of 465) of the clones selected from the immunized library were able to bind the hINSR or hINSR-hINS complex. Periplasmic extracts from the selected clones were also assayed by FACS (see Example 2). Selected clones were reformatted as IgG1 or IgG2 antibodies. The variable heavy (VH) and light (VL) chains of the selected scFv fragments were PCR-amplified, cloned into plasmid vectors containing antibody constant genes, and transfected into 293E EBNA human cells using standard methods.

Example 2

Receptor Occupancy Screen to Determine Antibody Binding to INSR in the Presence or Absence of Human Insulin This example describes the use of flow cytometric (FACS) based assays to measure differential antibody binding to cells in the presence or absence of human insulin (hINS). Anti-insulin receptor (INSR) antibodies from phage display libraries were screened in the assays to identify modulators of INS-INSR binding.

IM-9 cells were obtained from the American Type Culture Collection (ATCC) and maintained in RPMI 1640+10% FBS. Prior to use in assays cells were washed in serum-free RPMI 1640, counted and the concentration adjusted to $2\times10^6$ cells/ml in RPMI 1640+0.5% BSA (Sigma-Aldrich). The cells were cultured overnight in this media and as such were designated as "serum-starved." These cells were washed once and resuspended at $2\times10^6$ cells/ml in PBS containing 0.5% BSA and 0.01% sodium azide (FACS buffer).

Cells exposed to insulin were resuspended in FACS buffer supplemented with 70 nM human insulin (Sigma-Aldrich, St. Louis, Mo.). Both cell populations (+hINS) or (−hINS) were incubated at 4° C. for 30 minutes, washed once with FACS buffer and resuspended at $2\times10^6$ cells/ml in FACS buffer. Twenty five microliter aliquots of cells were plated into 96 well plates, mixed with 25 ul of antibody or PPE and incubated on ice for 1 h.

The cells were then washed once with FACS buffer and the binding of the antibody was detected by the addition of 25 ul of an appropriate fluorochrome-conjugated secondary antibody. If the initial incubation had been with PPE containing a myc-tagged antibody, 25 ul of a 1/1000 dilution of an anti-c-myc antibody (Roche) was added to the wells and the cells incubated on ice for 30 mins. The cells were then washed once with FACS buffer and the binding of the anti-c-myc revealed by the addition of a phycoerythrin-conjugated anti-mouse IgG. After a final 15 min incubation on ice the cells were washed and the pellets resuspended in FACS buffer. The cells were analyzed on a FACSCAN™ (Becton-Dickinson, Milipitas, Calif.) and the data analyzed in both FLOWJO™ (Treestar, Ashland, Oreg.) and Microsoft Excel™.

This assay allowed the detection of four types of antibody, examples of which are shown in FIG. 1:
1. Antibodies that only bind to IM-9 cells if they have been exposed to human insulin (bind exclusively to INS/INSR complex)
2. Antibodies that bind better to IM-9 cells if they have been exposed to human insulin (bind preferentially to INS/INSR complex)
3. Antibodies that bind less well to IM-9 cells if they have been exposed to human insulin (bind preferentially to uncomplexed INSR).

Antibodies were scored as predicted positive modulators if the ratio of antibody binding to INS/INSR complex: antibody binding to uncomplexed INSR was greater than 1.3. Antibodies were scored as predicted negative modulators if the ratio of antibody binding to INS/INSR complex: antibody binding to uncomplexed INSR was less than 0.6. Antibodies were scored as predicted non-modulators if the ratio of antibody binding to INS/INSR complex: antibody binding to uncomplexed INSR was greater than 0.9 but less than 1.1.

Example 3

Biotinylated Ligand Screen to Determine the Effects of Anti-INSR Antibodies on Insulin Binding to INSR This example describes the use of FACS based assays to measure differential ligand (human insulin) binding to cells in the presence or absence of anti-INSR antibodies. Anti-INSR antibodies from phage display libraries were screened in the assays to identify modulators of the INS-INSR complex.

IM 9 cells were obtained from the American Type Culture Collection (ATCC) and maintained in RPMI 1640+10% FBS. Prior to use in assays cells were washed in serum-free RPMI 1640, counted and the concentration adjusted to $2\times10^6$ cells/ml in RPMI 1640+0.5% BSA (Sigma-Aldrich). The cells were cultured overnight in this media and as such were designated as "serum-starved." These cells were washed once and resuspended at $2\times10^6$ cells/ml in PBS containing 0.5% BSA (binding buffer).

Serum-starved cells were pre-exposed to INSR antibodies at room temperature for 15 minutes and then incubated with various concentrations of biotinylated human insulin purchased from R&D Systems for a further 30 minutes at room temperature. The binding of the biotinylated insulin was revealed by the addition of a 1/100 dilution of streptavidin-phycoerythrin to this mixture for a further 15 minutes at room temperature. The cells were then washed once with binding buffer and resuspended in equal volumes of PBS containing 0.5% BSA, 0.1% sodium azide and 2% paraformaldehyde. The cells were analyzed on a FACSCAN™ (Becton-Dickinson, Milipitas, Calif.) and the data analyzed in both FLOWJO™ (Treestar, Ashland, Oreg.) and Microsoft Excel™.

FIG. 2 shows the binding of biotinylated insulin to IM9 cells in the presence or absence of anti-INSR antibodies at different insulin concentrations. Antibody 83-7 enhanced binding of biotinylated insulin; antibody MA-20 diminished binding of biotinylated insulin; control mouse IgG had no effect on binding of biotinylated insulin.

Example 4

Assay to Determine the Ability of Anti-INSR Antibodies to Stimulate pIRS-1 Phosphorylation The substrate proteins which are phosphorylated by the INSR include a protein called insulin receptor substrate 1 (IRS-1). IRS-1 phosphorylation to form pIRS-1 eventually leads to an increase in the high affinity glucose transporter (Glut4) molecules on the outer membrane of insulin-responsive tissues, and therefore to an increase in the uptake of glucose from blood into these tissues. A pIRS-1 assay was developed using the Luminex® technology platform (Luminex Corp., Austin, Tex.). Two modes of assay were developed: (a) titration of test antibody at a fixed concentration of insulin, and (b) titration of insulin at a fixed concentration of antibody. Anti-INSR antibodies selected on the basis of their differential binding to complexed and uncomplexed INSR were tested in the assays to identify modulators of the INS-INSR complex signaling.

Cell Treatment and Lysis

IM-9 cells were serum starved for 16-20 hours by counting, centrifuging, washing once with PBS and re-suspending at about $2\times10^6$ cells/ml in RPMI+0.5% Sigma Cohn V BSA (10% stock in RPMI, filter sterilized, stored 4° C.).

2× concentrated solutions of insulin (Sigma 1-9278 (10 mg/ml) 1.77 mM liquid stock stored at 4'C) dilutions were prepared in RPMI+0.5% BSA. A standard insulin titration may include 4-fold serial dilutions of for example: 6.25 nM, 1.56 nM, 0.39 nM, 0.097 nM, 0.024 nM, 0.006 nM, 0.0015 nM, 0 nM.

Milliplex MAP Cell Signaling Buffer and Detection Kit (Millipore catalog #48-602) and Phospho-IRS-1 MAP Mates (Millipore catalog #46-627) were employed for the detection of pIRS-1 levels, according to the manufacturer's instructions. Briefly, V-bottomed plates containing 50 ul/well of 2× treatment media (RPMI containing 0.5% BSA+/−test antibody) were prepared and $1\times10^6$ cells serum-starved IM-9 cells resuspended in 50 ul RPMI+0.5% BSA were added per well. Antibody pretreatment was performed for 15 minutes prior to insulin treatment, either (a) as a bulk antibody/cell mixture at a single antibody concentration that was then applied to wells containing serial dilutions of insulin, or (b) by adding cells directly to wells containing serial dilutions of antibody and spiking in insulin at 0.1 nM. Plates were placed in a 37° C. incubator and centrifuged at 1500 rpm at RT for the last 3 minutes of treatment time (total of 15 minutes). Supernatant was removed by inversion and gentle blotting and treated cell pellets were lysed by triturating 3 times using a multi channel pipette with 100 ul Lysis Buffer prepared according to Table 4 below (labile components, i.e. protease inhibitors and benzonase, were added just prior to use). Plates were placed on a shaker at RT for 30 minutes and centrifuged at 3000 rpm for 10 minutes to clarify the lysate and remove any air bubbles that may have occurred during trituration. 50 ul of cleared lysate was removed and diluted 1:1 in 50 uL Assay Buffer-1 (AB-1) from the Detection Kit, triturated 2-3 times to mix and 50 ul was loaded onto a filter plate membrane on top of the 25 ul/well of diluted beads (see below).

TABLE 4

| Lysis Buffer | 10 wells 1 ml | 20 wells 2 mls | 25 wells 2.5 mls | 30 wells 3 mls | 40 wells 4 mls | 50 wells 5 mls | 60 wells 6 mls | 100 wells 10 mls |
|---|---|---|---|---|---|---|---|---|
| Lysis Buffer components | | | | | | | | |
| Lysis Buffer (Millipore cat. # 43-040) | 1 | 2 | 2.5 | 3 | 4 | 5 | 6 | 10 |
| SDS 20% stock | 0.045 | 0.09 | 0.1125 | 0.135 | 0.18 | 0.225 | 0.27 | 0.45 |
| MgCl 50 mM (Invitrogen cat. # Y02016) | 0.02 | 0.04 | 0.05 | 0.06 | 0.08 | 0.1 | 0.12 | 0.2 |
| Protease inhibitors (50X) (Millipore cat. # 20-201) | 0.02 | 0.04 | 0.05 | 0.06 | 0.08 | 0.1 | 0.12 | 0.2 |
| Benzonase EMD 1.01697.0002 @ 250 ug/ml | 0.004 | 0.008 | 0.01 | 0.012 | 0.016 | 0.02 | 0.024 | 0.04 |

Filter plate membranes (Millipore Catalog# MABVN1250) were pre-wet with 25 ul AB-1/well. Pre-wetting buffer was aspirated from the filter plate using a Millipore vacuum manifold, being careful not to dry the membranes, and any remaining liquid was blotted from the bottom of the filter plate. 25 ul of 1× bead suspension was added per well (pIRS-1 beads (Millipore catalog #46-627) were pre-prepared by diluting from 20× concentrate into AB-1 buffer and alternately vortexing and sonicating for 5 seconds 3 times each).

Filter plate wells were covered with a plate sealer, covered in aluminum foil to prevent light exposure, and incubated on a plate shaker (setting 7-8 on a Labline, Bellco plate shaker or similar model) at either RT for 2 hours or alternatively at 4° C. overnight.

Luminex Detection

The filter plates were aspirated and their bottoms blotted. The beads remained in the well and were washed with 100 ul of AB-1 and placed on shaker for 1-2 minutes. Plates were aspirated, and the wash step was repeated.

25 ul per well 1× biotinylated detection antibody, diluted from a 20× stock into AB-1 buffer, was added and plates were incubated on a shaker at RT for 1 hour. Plates were aspirated and their bottoms blotted. 25 ul per well 1× streptavidin phycoerythrin diluted from a 25× stock into AB-1 buffer, was added and plates were incubated on a shaker at RT for 15 minutes. 25 ul of Amplification Buffer (Millipore catalog #48-602) was added to each well, and plates were incubated on a shaker at RT for further 15 minutes. The plates were aspirated and the beads were resuspended in 150 uL AB-1 and read on the Luminex® instrument.

Results

FIG. 3 shows pIRS-1 assay results from titrations of insulin in the presence of fixed concentrations of representative test antibodies. MFIs were normalized such that the curve fit maximum was adjusted to 100%. Some antibodies (positive modulators) shifted the insulin titration curve to the left. Other antibodies (negative modulators) shifted the insulin titration curve to the right. Varying magnitudes of modulation were observed. The data in FIG. 3 shows antibodies producing up to a 9-fold increase, or up to a 24-fold decrease, in insulin sensitivity.

FIG. 4 shows representative examples of the various functional classes of antibody based on pIRS-1 assay data. In each case results from the two modes of assay are shown: (i) titration of insulin at a fixed concentration of antibody, and (ii) titration of test antibody at a fixed concentration of insulin.

FIG. 5 is a table showing insulin EC50 values from the pIRS-1 assay in the presence or absence of fixed concentrations of various test antibodies. The results are ranked according to EC50 ratio +Ab/−Ab.

Example 5

Measurement of Effects of Anti-INSR Antibodies on INSR-Induced Phosphorylation of AKT and MAPK The INSR is a tyrosine kinase that undergoes autophosphorylation after insulin binding and subsequently catalyzes the phosphorylation of intracellular proteins such as insulin receptor substrate (IRS) family members, Shc, and Gab1. Each of these proteins serves as a docking site for the recruitment of downstream signaling molecules resulting in the activation of various signaling pathways including the PI(3)K/AKT and MAP kinase (MAPK) pathways. These pathways ultimately coordinate to regulate cell growth and differentiation, gene expression, glycogen, protein and lipid synthesis, and glucose metabolism.

The effects of a test antibody on signaling via the INS/INSR complex can be measured by assessing the ability of the antibody to augment insulin-induced serine or tyrosine phosphorylation of specific intracellular proteins, such as AKT and MAPK (ERK1/2), which are specific to the INSR signaling pathway. The phosphorylation of these proteins can be measured and quantified by electrochemiluminescence, Western blotting, ELISA, and other techniques known in the art.

In this example assay, CHOK1 cells, engineered to express either the human or mouse INSR, were used. These cells were maintained in Growth Medium containing EX-CELL 302 Serum-Free Medium for CHO Cells (Sigma-Aldrich, St. Louis, Mo.), 2 mM L-glutamine, and 0.4 mg/mL GENETICIN® (Invitrogen, Carlsbad, Calif.). The parental CHOK1 cells were used as a control and were maintained in Growth Medium without GENETICIN®.

On the day before the assay, the cells were washed with PBS, resuspended at $1 \times 10^6$ cells/mL in Starvation Medium containing RPMI 1640 (Invitrogen), 2 mM L-Glutamine, 0.4 mg/mL GENETICIN®, and 0.5% BSA, and incubated for 16-20 hours in a 37° C., 5% $CO_2$ incubator. The parental CHOK1 cells were incubated in Starvation Medium without GENETICIN®. The next day, cells were resuspended in PBS with 0.5% BSA and $1 \times 10^5$ cells were added to wells of a 96-well plate. The test antibody was added at 0, 1, or 10 ug/ml, approximately 10 minutes prior to the addition of insulin. After incubation for 5-60 minutes in a 37° C., 5% $CO_2$ incubator, the treated cells were centrifuged and lysed in a buffer containing 20 mM Tris-HCl (pH 7.5), 150 mM NaCl, 1 mM EDTA, 1 mM EGTA, 1% Triton X-100, 10 mM NaF, Phosphatase Inhibitor Cocktails 1 and 2 (Sigma-Aldrich), and Complete Mini Protease Inhibitor (Roche Diagnostics Corporation, Indianapolis, Ind.) for 1 hour with shaking at 4° C. The lysates were clarified by centrifugation at 485×g for 3 minutes. Electrochemiluminescence using the MesoScale Discovery Multi-spot Assay System (Meso Scale Discovery, Gaithersburg, Md.) was used to quantify the amount of phosphorylated AKT or MAPK present within the lysates. Data were analyzed using GraphPad Prism® (GraphPad Software Inc., La Jolla, Calif.) software to calculate EC50 values from a 4-parameter logistic equation.

For analysis of agonist activity, the assay was performed as follows. On the day before the assay, cells are washed with PBS, resuspended at $1 \times 10^6$ cells/mL in Starvation Medium containing RPMI 1640 (Invitrogen), 2 mM L-Glutamine, 0.4 mg/mL GENETICIN®, and 0.5% BSA, and incubated for 16-20 hours in a 37° C., 5% $CO_2$ incubator. The parental CHOK1 cells were incubated in Starvation Medium without GENETICIN®. The next day, cells were resuspended in PBS with 0.5% BSA and $1 \times 10^5$ cells are added to wells of a 96-well plate. After incubation with test antibody for 5-60 minutes in a 37° C., 5% $CO_2$ incubator, the treated cells were centrifuged and lysed in a buffer containing 20 mM Tris-HCl (pH 7.5), 150 mM NaCl, 1 mM EDTA, 1 mM EGTA, 1% Triton X-100, 10 mM NaF, Phosphatase Inhibitor Cocktails 1 and 2 (Sigma-Aldrich), and Complete Mini Protease Inhibitor (Roche Diagnostics Corporation, Indianapolis, Ind.) for 1 hour with shaking at 4° C. The lysates were clarified by centrifugation at 485×g for 3 minutes. Electrochemiluminescence using the MesoScale Discovery Multi-spot Assay System (Meso Scale Discovery, Gaithersburg, Md.) was used to quantify the amount of phosphorylated AKT or MAPK is present within the lysates. Data were analyzed using GraphPad Prism® (GraphPad Software Inc., La Jolla, Calif.) software to calculate EC50 values from a 4-parameter logistic equation.

FIG. 6 shows pAKT assay results for antibodies representative of: (A) positive modulators (increase insulin-induced signal transduction); (B) positive modulators with agonism (increase insulin-induced signal transduction and increase insulin-independent signal transduction) (C) non-modulators (no significant effect on insulin-induced signal transduction); (D) agonists (increase signal transduction independently of insulin; may or may not have modulatory activity) (E) negative modulators (decrease insulin-induced signal transduction). The assay results also indicate whether the antibodies show functional cross-reactivity i.e. have effects on both human and mouse INSR-mediated signaling.

Example 6

Anti-INSR Antibodies Exhibit a Spectrum of Agonism

The pIRS-1 assay of Example 4 and the pAKT assay of Example 5 were used to measure the degree of agonism of the selected anti-INSR antibodies. Rather than using titrations of antibodies or insulin, 5 ug/ml anti-INSR antibody was added to the assay in the absence of insulin. The assay measured the level of antibody-induced activation of signaling through INSR in the absence of insulin (agonism).

FIG. 7 shows tabulated results to illustrate that the selected antibodies exhibit a spectrum of agonism.

Example 7

Figures 8, 8A, 8B:
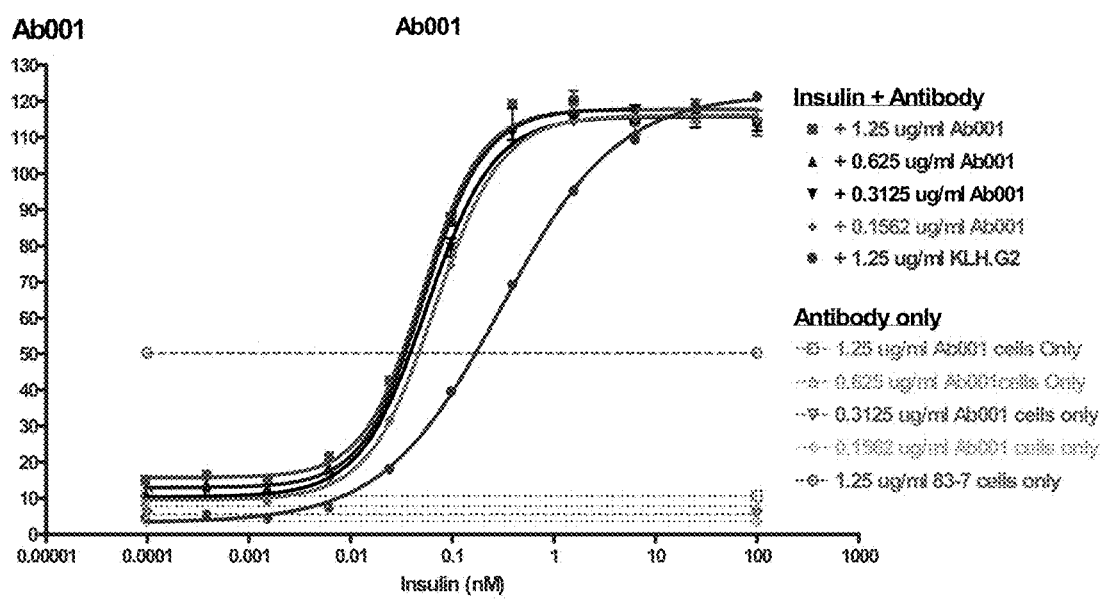

Change in Cooperativity of Insulin Binding to INSR Effected by a Positive Modulator INSR Antibody The pAKT assay of Example 5 was performed on one of the positive modulator antibodies, using various antibody concentrations and adding a serial dilution of insulin. The results are shown in FIG. 8. FIG. 8A shows there is a dose response of INSR binding in the presence of differing concentrations of antibody and insulin. FIG. 8B shows the relative Hill slope of insulin-INSR interaction in the presence of varying concentrations of antibody.

Example 8

Enhancement of Glucose Uptake by a Positive Modulator INSR Antibody

The effects of a positive modulator INSR antibody on glucose uptake in 3T3-L1 adipocytes were measured. Upon insulin treatment, INSR is phosphorylated, activating a signal transduction pathway which leads to increased glucose uptake by glucose transporter 4 (GLUT4) in adipocytes (fat) or myocytes (muscle). Measuring glucose uptake provides a relevant end point assay for insulin sensitivity.

An assay using $^3$H-2-deoxyglucose as a substrate for GLUT4 was employed (Zen-Bio, Inc., Research Triangle Park, N.C.). Briefly, 3T3-L1 preadipocytes were differentiated in 96-well isoplates. After maturation, the cells were washed 2 times with assay buffer and the cells were allowed to rest in Assay buffer for 4 hours. The cells were treated with anti-INSR antibody, or control antibody (10 ug/ml) and serial concentrations of insulin, or insulin at 0.8 nM for 15 minutes. After 15 minutes glucose uptake was initiated by adding $^3$H-2-deoxyglucose cocktail and the cells were incubated at 37° C., 5% $CO_2$ for 10 minutes. After 10 minutes, the cells were washed with PBS, lysed, and mixed with scintillation fluid. The CPM of each well measured. Cytochalasin B (10 µM) was used as a negative control.

Figure 9:
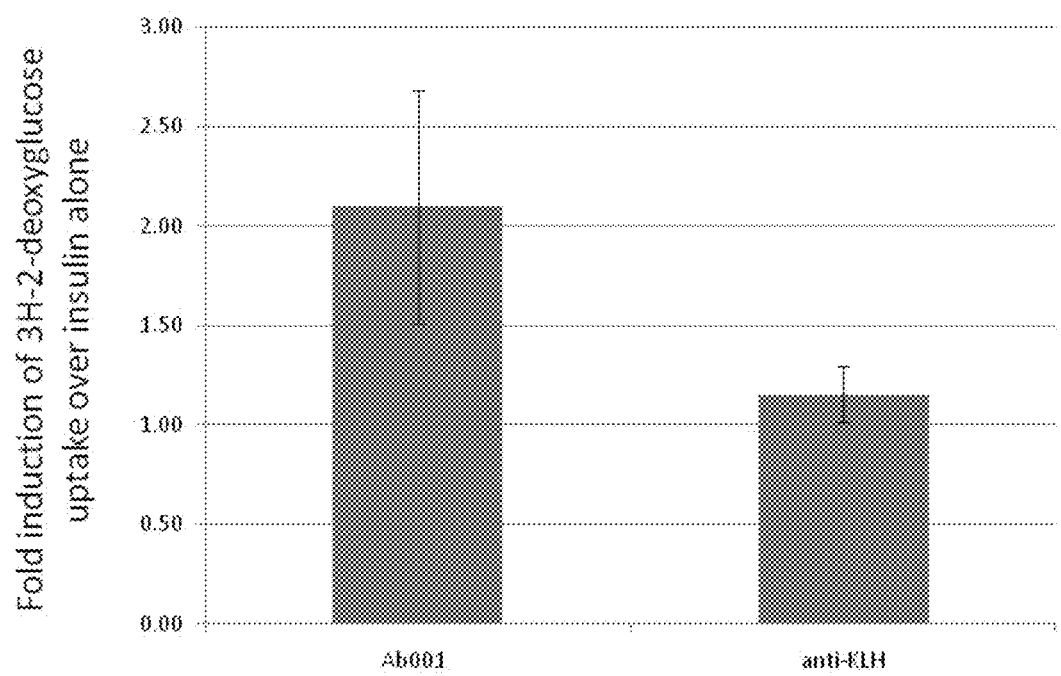
FIG. 9 illustrates the enhancement of insulin dependent glucose uptake by a positive modulator antibody. $^3$H-2-deoxyglucose uptake in 3T3-L1 cells was induced by 0.8 nM insulin in the presence of 10 ug/ml test antibody Ab001 or anti-KLH isotype control.

Results are shown in FIG. 9. FIG. 9 shows the enhancement of insulin dependent glucose uptake by a positive modulator antibody. The positive modulator antibody results in approximately a 2-fold increase in $^3$H-2-deoxyglucose uptake by 3T3-L1 cells in the presence of 10 ug/ml test antibody Ab001 compared to insulin alone.

These results suggest that positive modulator antibodies are useful to induce glucose uptake in vivo and treat patients exhibiting insulin resistance.

Example 9

Measurement of the Effects of Anti-INSR Antibodies on Depletion of Glucose in Cell Culture Media Depletion of glucose from cell culture media can be used a surrogate measurement of glucose uptake. The effects of anti-INSR antibodies on media depletion of glucose is measured as follows.

To measure glucose depletion, a Wako autokit glucose (Cat#439-90901, Autokit C) is used according to the manufactures directions. Briefly, CHOK1 cell lines adapted to adherent with DMEM+10% FBS in 24 or 96 well plates are plated at an appropriate concentration. The cells are glucose and serum starved overnight in 0.5% BSA DMEM (no glucose) before use. The starvation media is aspirated and media consisting of the following is added in the presence and absence of test antibody or isotype control antibody: group 1, 4 parts DMEM no glucose:1 part DMEM high glucose (0.9 mg/mL); group 2, 4 parts DMEM no glucose:1 part DMEM high glucose (0.9 mg/mL)+insulin. At each desired time point, 2 uL samples of media from each well are removed and added to 118 uL of Wako working solution. In some embodiments, sample as are taken at 0, 1, 2-5, 5, 10, and 24 hours. Glucose uptake is evaluated with the FLEXSTATION at absorbance 505 nm and 600 nM. The amount of glucose is determined as follows: [Average reading for similar samples]/[average reading for standards]. Cell count is obtained before and at the end of the experiment to normalize for cell growth.

Example 10

Measurement of the Effects of Anti-INSR Antibodies on the Balance Between Mitogenic and Metabolic INSR Signaling INSR signals through two major pathways (1) the PI3 kinase/PDK1/PKB pathway which primarily regulates metabolism, with some influence on growth and (2) the Ras/ERK mitogenic pathway which primarily regulates cell growth. The effects of anti-INSR antibodies on the balance between mitogenic and metabolic INSR signaling is measured as described in the art. See, e.g., Jensen et al. (Vitam Horm. 80:51-75, 2009), De Meyts and Shymko, (Novartis Found. Symp. 227:46-57, 2000); and Rakatzi et al. (Diabetes 52:2227-2238, 2003).

Example 11

Measurement of the In Vivo Effects of Anti-INSR Antibodies

Anti-INSR antibodies found to be cross-reactive with mouse INSR are measured in a number of in vivo models. In the DIO model, C57BL/6J (B6) male mice (The Jackson Laboratory, Maine) are fed a high fat diet (HFD) for twelve weeks, becoming obese, mildly to moderately hyperglycemic and impaired for glucose tolerance. This model is used to evaluate the ability of INSR antibodies to affect insulin sensitivity in a tightly controlled setting. This system also allows a direct comparison of INSR action and modulation under normal versus diseased conditions. In this experiment, DIO or age-matched B6 mice are dosed with INSR antibody 24 hours prior to administration of a pre-defined submaximal dose of insulin in an insulin tolerance test (ITT). Control IgG or maximal insulin serve as negative and positive controls, respectively. Responsiveness to insulin is assessed by measuring plasma glucose; a greater decrease in glucose over 60 minutes is suggestive of an increased INSR response. In a separate study, DIO or B6 mice are dosed with antibody 24 hours prior to a glucose tolerance test (GTT). By this measure, lowered fasting glucose and area under the curve (AUC) indicates improved insulin sensitivity.

Two murine models are used to assess the impact of INSR antibodies on type-2 diabetes progression. ob/ob mice (The Jackson Laboratory, ME) are leptin deficient, becoming obese and only mildly hyperglycemic due to compensatory hyperinsulemia. hr this model, animals receive INSR antibodies beginning at 6 weeks of age or rosiglitazone (PPAR-gamma agonist), an agent previously shown to improve glycemic control in these animals. As in the DIO study, glycemic control is assessed by ITT and GTT, every 2 weeks for 6 weeks. In addition, hemoglobin A1c (HbA1c), a key indicator of prolonged elevated plasma glucose, and a lipid panel, is evaluated at the end of the study. In the second model, the streptozotocin (STZ)/HFD model, pancreatic beta cells in Swiss Albino mice (The Jackson Laboratory, Maine) are ablated via multiple low-dose of streptozotocin, while insulin resistance is induced through HFD feeding. In this model, animals are severely hyperglycemic due to impairment of pancreatic insulin output, a situation analogous to late stage T2D (Dakshinamoorty et al, J. Pharm. and Pharmacology 60: 1167-73 (2008)). STZ/HFD animals are treated and evaluated in a manner similar to the ob/ob model to measure the effect of INSR antibodies on disease progression.

Example 12

Effects of Partial Agonist Anti-INSR Antibodies on Glycemic Control in DIO Mice

In the diet-induced obesity (DIO) model, C57BL/6 mice can become insulin resistant after approximately 12-14 weeks on a high-fat diet (HFD). Anti-INSR antibodies demonstrated to behave as partial agonists or positive modulators in vitro were evaluated in this model to determine if these antibodies improved insulin sensitivity and/or glycemic control in vivo.

To determine whether partial agonist anti-INSR antibodies reduce fasted blood glucose, 20 week-old DIO mice (14 weeks on HFD; n=8/group) were fasted for 5 hours and challenged intravenously with partial agonist antibodies Ab030 and Ab037, or an isotype control (5 mg/kg). In additional control studies, DIO mice were treated with insulin (0.5 U/kg), or age-matched mice fed a normal diet (ND) were dosed with isotype control (5 mg/kg). Blood glucose was sampled prior to injection (time=0) and 1, 2 and 4 hours post-administration. Compared to age-matched controls, increased blood glucose was observed in DIO mice (HFD-fed/isotype control) at the 1-hour time point, consistent with insulin resistance in animals fed HFD (FIG. 10A). Administration of insulin or either of the partial agonist antibodies resulted in a statistically significant reduction ($p<0.05$; one-tailed t-test) in blood glucose (FIG. 10B). Neither antibody induced hypoglycemia at any time point (defined as blood glucose <36 mg/dL). These results suggest that anti-INSR partial agonist antibodies safely and effectively reduce fasting blood glucose.

To further evaluate the effect of a partial agonist anti-INSR antibody on glycemic control, 18-week old DIO mice (12 weeks on HFD; n=8/group) were injected intraperitoneally (IP) with Ab037 (0.1, 1.0 or 9 mg/kg) or isotype control (1.0 mg/kg). As additional controls, age-matched control mice were dosed with isotype control (1.0 mg/kg) or DIO animals were given insulin (0.75 U/kg; IP). A glucose tolerance test (GTT) was performed 24 hours after antibody administration (30 min after insulin) by fasting the animals for 16 hours (beginning approximately 8 hours after antibody administration), injecting glucose (1.0 U/kg) and following blood glucose over 2 hours. In this experiment, HFD did not have a significant impact on fasting glucose (FIG. 11B) or post-bolus peak glucose (FIG. 11A). Nevertheless, in DIO mice, partial agonist antibody significantly reduced fasting blood glucose relative to isotype control when dosed at or above 1.0 mg/kg (FIG. 11B) and reduced GTT area under the curve (AUC) at 9.0 mg/kg (FIG. 11C).

This outcome demonstrates that an anti-INSR partial agonist antibody can reduce fasting glucose and improve glycemic control in vivo.

Example 13

Effects of Positive Modulator Anti-INSR Antibodies on Glycemic Control in DIO Mice To determine if a positive modulator anti-INSR antibody improves insulin sensitivity in vivo, 18-week old DIO mice (n=8/group) were given IP injections of Ab001 (positive modulator)(0.1, 1.0 or 10 mg/kg), partial agonist antibody (Ab037) (10 mg/kg) or isotype control (1.0 mg/kg). Age-matched mice fed ND dosed with isotype control (1.0 mg/kg) served as an additional control (FIG. 12A). Twenty-four hours later, an insulin tolerance test (ITT) was carried out by administering insulin (0.5 U/kg) after a 5 hour fast and monitoring blood glucose levels over 2 hours. A HFD did not have a significant impact on fasting glucose (FIG. 12B) or ITT AUC (FIG. 12C) relative to regular diet, and neither partial agonist antibody (Ab037) nor positive modulator antibody (Ab001) administration resulted in a statistically significant lower AUC ITT, relative to isotype control treated DIO animals (FIG. 12C). Partial agonist antibody Ab037 significantly reduced fasting glucose, while positive modulator antibody Ab001 induced a non-statistically significant, dose-dependent trend towards reduced fasting glucose.

The following week, a GTT was carried out on the same animals after an additional dose of antibody (FIG. 13A). In this study, HFD resulted in a non-statistical increase in fasting glucose (FIG. 13B) and GTT AUC (FIG. 13C) compared to control fed animals. Compared to isotype control-treated DIO mice, partial agonist antibody and positive modulator antibody significantly reduced fasting glucose at all doses tested. In addition, both partial agonist antibody and positive modulator antibody significantly reduced GTT AUC at 10 mg/kg relative to isotype control.

Figure 14A:
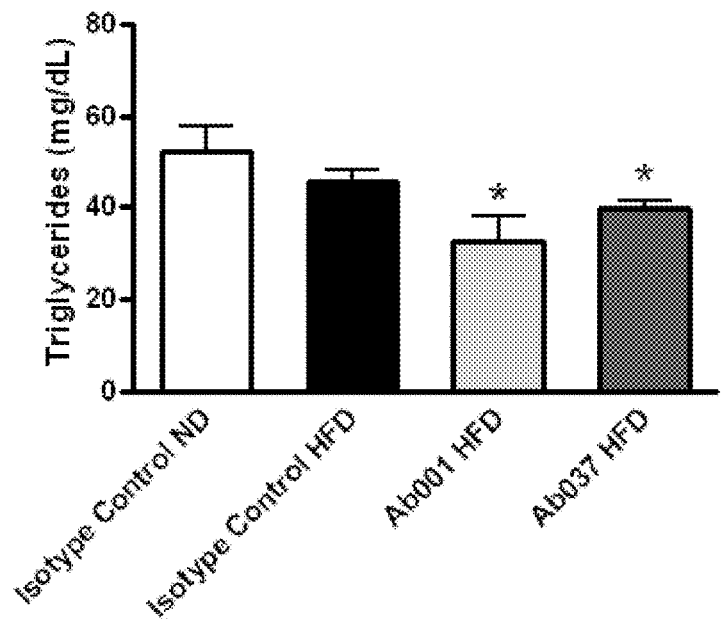
FIG. 14A: Plasma triglyceride levels.
Figure 14B:
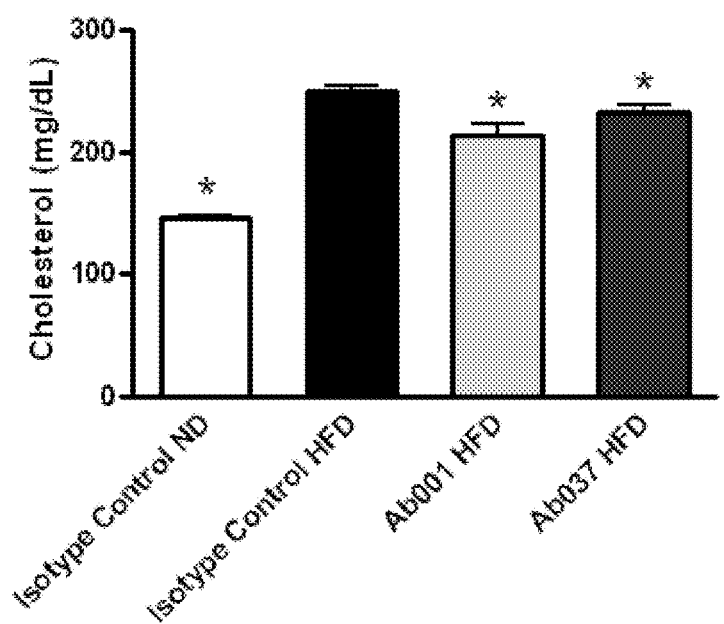
FIG. 14B: Plasma cholesterol levels.

The effect of Ab001 and Ab037 on lipid parameters was investigated by treating 18-week old DIO mice IP twice weekly (BIW) with antibody (10 mg/kg; n=5/group) for twelve weeks. In this experiment, similar efficacy to the two-week study (as described above) was observed with respect to fasting glucose, GTT and ITT. At the end of the study, plasma was collected to measure lipids using standard ELISA-based techniques. Relative to isotype control, both Ab001 and Ab037 reduced fasting triglyceride and total cholesterol levels in DIO mice ($p<0.05$; FIGS. 14A and 14B), suggesting that these antibodies are able to improve lipid dysregulation associated with insulin resistance.

Two additional positive modulator anti-INSR antibodies were evaluated for improvement of glycemic parameters in vivo using 18-week old DIO mice (n=10/group). In this study, positive modulator antibodies Ab083 and Ab085 were compared against Ab001 and Ab037 and an isotype control antibody. A ND fed, age-matched group treated with isotype control antibody served as an additional control. All antibodies were dosed IP at 10 mg/kg BIW. A day after the third dose of antibody, fasting blood glucose was measured and a GTT was performed. Glycemic control was significantly impaired in isotype control-treated DIO mice relative to similarly treated age-matched ND fed animals, as reflected by a GTT time course assessment and the corresponding AUC determination (FIGS. 15A and 15B). In this experiment, Ab037 and Ab083 improved AUC to levels indistinguishable from normal ($p<0.05$ relative to HFD/isotype control), whereas Ab001 did not produce significant improvements. Similarly, with respect to fasting glucose, a significant difference was observed between isotype control treated DIO and age-matched ND-fed mice and both Ab037 and Ab001 exerted statistically significant normalizing effects ($p<0.05$; FIG. 15C). Ab083 yielded a small, non-statistically significant improvement in fasting blood glucose, whereas Ab085 did not elicit any change in this parameter.

Another measure of the effects of anti-INSR antibodies on in vivo function is by Homeostasis model assessment-insulin resistance (HOMA-IR). HOMA-IR is an empirical mathematical formula based on fasting plasma glucose and fasting plasma insulin levels that was developed as a surrogate measurement of in vivo insulin sensitivity: HOMA-IR=fasting plasma insulin (µIU/mL)×fasting plasma glucose (mmol/L)/22.5, or alternatively using the formula: Insulin (ng/mL)×Glucose (mM), which incorporates the 22.5 conversion factor. Examples of HOMA-IR are described in Owyang et al., Endocrinology 151:2515-27, 2010 and Matthews et al., Diabetologia. 28:412-9, 1985.

After 4 weeks of dosing, plasma glucose, insulin and lipids were evaluated. Ab083 and Ab037 reduced plasma glucose at this time point, whereas Ab083 and Ab085 reduced insulin ($p<0.05$; FIGS. 16A and 16B). These effects translated into improved insulin sensitivity in this model of insulin resistance for Ab083 and Ab085, as determined by HOMA-IR (p<0.05; FIG. 16C). With respect to lipids, Ab085 significantly improved only triglycerides (p<0.05; FIG. 16D), while Ab083 and Ab037 significantly reduced unesterified, total and non-HDL cholesterol (p<0.05; FIG. 16E-G). The latter two antibodies also improved the non-HDL/HDL cholesterol ratio (FIG. 16H). Ab001 significantly reduced both total and non-HDL cholesterol.

Surprisingly, all four antibodies reduced weight gain in DIO mice relative to isotype control over 3 weeks of treatment, without reducing body weight to below baseline (FIGS. 17A and 17B). These results demonstrate that the positive modulator antibody Ab083 and agonist antibody Ab037 correct impaired glucose tolerance in DIO mice, that modulator antibodies Ab083 and Ab085 improve insulin sensitivity and suggest that all four antibodies have the capacity to decrease weight gain resulting from HFD.

These results suggest that partial agonist and positive modulator antibodies specific for the INSR improve glycemic control in diabetic subjects.

Example 14

Effects of Partial Agonist and Positive Modulator Anti-INSR Antibodies on Glycemic Control and Disease in Db/Db Mice Mice homozygous for the spontaneous $Lepr^{db}$ allele lack leptin receptor function and become progressively insulin resistant and obese beginning at three to four weeks of age. In these mice, insulin levels rise, until about 8-10 weeks of age, at which time the animals are severely insulin resistant and hyperinsulinemic. This genetic background nevertheless results in uncontrolled hyperglycemia, leading to pancreatic beta cell dysfunction after approximately 10 weeks of age and ultimately to beta cell failure. Anti-INSR antibodies demonstrated to behave as partial agonists or positive modulators in vitro were evaluated in this model to determine if these antibodies improved insulin sensitivity, glycemic control and/or disease progression in vivo.

The db/db mouse was utilized to assess the activity of Ab001 and Ab037 in a setting of progressive insulin resistance and beta cell dysfunction, combined with severe obesity. In this experiment, Ab001 (1 mg/kg or 10 mg/kg), Ab037 (10 mg/kg) or isotype control antibody (1 mg/kg or 10 mg/kg) were dosed IP, BIW to 5 week-old db/db mice (n=10/group). As an additional control, a group of age-matched heterozygous littermates, which are generally phenotypically normal, were dosed similarly with 10 mg/kg isotype control antibody. As in the DIO model, weight gain was significantly reduced in animals treated with 10 mg/kg of either Ab001 or Ab037 relative to isotype control-treated mice over the first five weeks of treatment (p<0.05; FIGS. 18A and 18C) Importantly, after 5 weeks of treatment, which corresponds to 10 weeks of age, when db/db mice generally begin losing weight as a result of pancreatic beta-cell depletion, both antibodies reduce weight loss (p<0.05; FIGS. 18B and 18D). After 10 weeks of treatment, treatment with either Ab001 or Ab037 at 10 mg/kg significant improvements were observed in fasting blood glucose relative to corresponding isotype control-treated groups (p<0.05; FIG. 19A). In addition, at this time point, HbA1c was significantly reduced in the 1 mg/kg Ab001 group, and also reduced to a lesser degree in the 10 mg/kg Ab001 group (p<0.05; FIG. 19B).

Plasma insulin and lipids were evaluated after 14 weeks of dosing. At this time, both Ab001 (10 mg/kg) and Ab037 increased circulating insulin at an age (approximately 20 weeks old) at which these animals would be expected to have pancreatic beta-cell failure (p<0.05; FIG. 20A), suggesting that both mAbs are capable of restoring insulin output in insulinopenic animals. In addition, Ab001 (10 mg/kg) significantly reduced plasma triglycerides, total cholesterol, non-HDL cholesterol, unesterified cholesterol and the non-HDL/HDL cholesterol ratio (p<0.05; FIG. 20B-F) A significant reduction in unesterified cholesterol and a trend towards lowered triglycerides was observed in plasma from Ab037-treated animals (p<0.05 and p=0.08, respectively; FIGS. 20B and 20C).

Interestingly, the reduction in weight gain occurred early, while the animals were insulin resistant, but not expected to have severe beta cell depletion, as is the case in the DIO model. However, in this experiment, Ab001-induced changes in glycemic control and glycated hemoglobin occurred only during the late phase, when the animals would be expected to have beta cell dysfunction. Moreover, during this time period, both antibodies reduced pathological weight loss. Not to be bound by theory, this outcome suggests that the anti-INSR antibody effects on weight and glycemic control can occur in tandem, but are separable. These data suggest that Ab001 is capable of normalizing weight, improving glycemic control and partially correcting dyslipidemia under conditions of combined insulin resistance and beta cell depletion.

Figure 21:
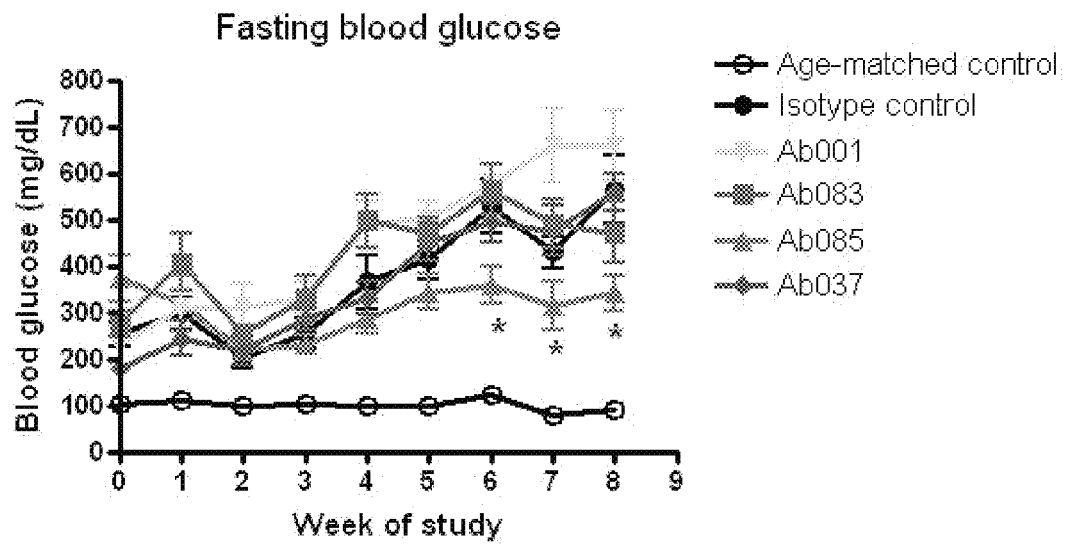
FIG. 21 shows that administration of positive modulator antibody reduces fasting blood glucose in db/db Mice. Weekly fasting blood glucose assessment of 5-week old db/db mice injected intraperitoneally (IP) with Ab001 (1 mg/kg or 10 mg/kg), Ab037 (10 mg/kg) or isotype control (1 mg/kg or 10 mg/kg) for 14 weeks (* p<0.05 for Ab085 relative to isotype control at same dose).

To evaluate the activity of antibodies under severely insulin resistant and insulinopenic conditions, 10-week old db/db mice, which would be expected to manifest with progressive pancreatic beta cell dysfunction, were treated with Ab001, Ab037, Ab083, Ab085 or isotype control antibody, at 10 mg/kg IP, BIW for eight weeks. Fasting blood glucose was measured weekly for the duration of the study. In this study, Ab085 significantly reduced fasting blood glucose relative to isotype control (p<0.05; FIG. 21). This demonstrates that Ab085 improves disease under insulin resistant, hypoinsulinemic conditions.

Figure 22:
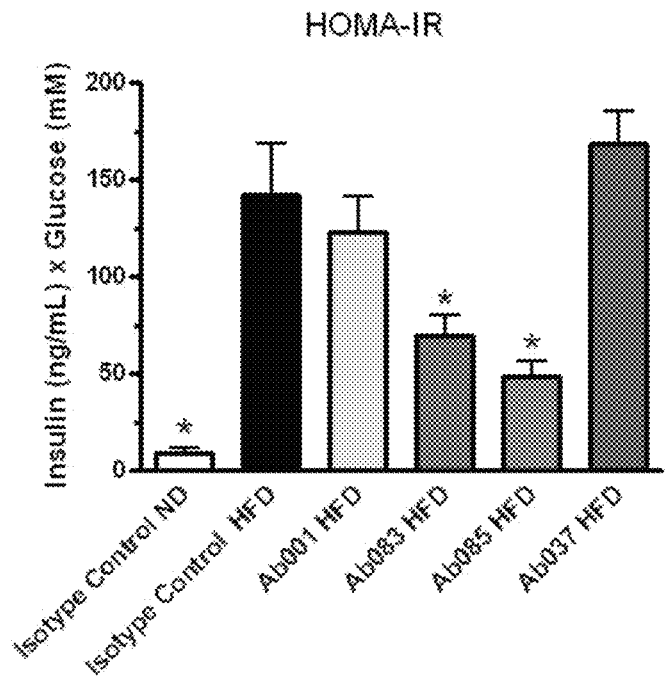
FIG. 22 illustrates that positive modulator antibodies improve insulin resistance in db/db mice as assessed by analysis of plasma from 5-week old db/db mice injected intraperitoneally (IP) with Ab001, Ab037, Ab083, Ab085 or isotype control for 4 weeks (10 mg/kg; * p<0.05 relative to isotype control at same dose) and shows Homeostatic model assessment for Insulin Resistance (HOMA-IR) after 4 weeks of dosing.

Two additional positive modulator anti-INSR antibodies were evaluated for improvement of insulin resistance in 5-week old db/db mice, which would be expected to manifest with severe insulin resistance. Mice were treated with Ab001, Ab037, Ab083, Ab085 or isotype control antibody, at 10 mg/kg IP, BIW for four weeks to evaluate the effect of antibodies on insulin resistance before the onset of beta cell dysfunction. Fasting plasma glucose and fasting plasma insulin were measured at the end of the study and HOMA-IR was calculated. In this study, Ab083 and Ab085 significantly improved insulin resistance compared to isotype control (p<0.05; FIG. 22), demonstrating that these antibodies improves insulin sensitivity in this model of diabetes.

Example 15

Effects of Partial Agonist and Positive Modulator Anti-INSR Antibodies on Glycemic Control and Disease in MLDS/HFD Mice In the multi-low dose streptozotocin (MLDS)/HFD model, insulin resistance is achieved by feeding 6-week old ICR mice a HFD (40 kcal % fat) for four weeks, during which time 5 daily doses of streptozotocin (40 mg/kg, during the third week) are administered IP to partially ablate beta cell function. Anti-INSR antibodies demonstrated to behave as partial agonists or positive modulators in vitro were evaluated in this model to determine if these antibodies improved insulin sensitivity, glycemic control and/or disease progression in vivo.

Figure 26:
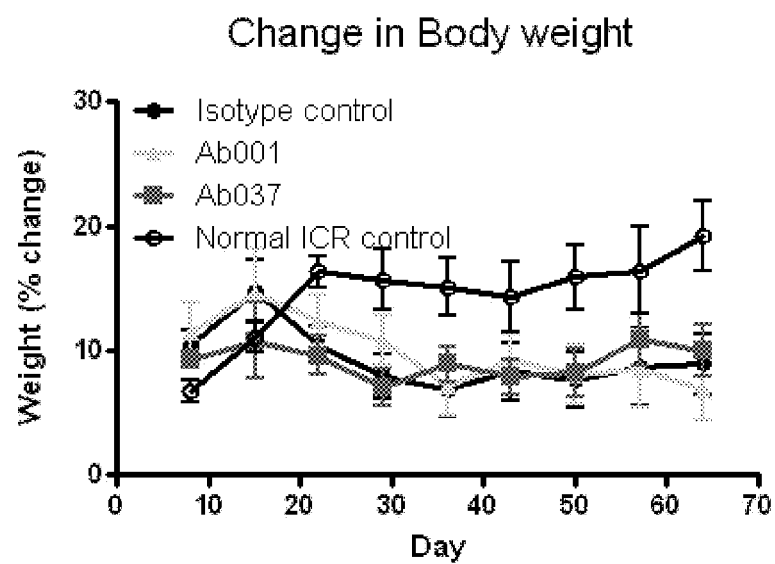
FIG. 26 illustrates that positive modulator and partial agonist anti-INSR antibodies do not affect body weight in MLDS/HFD mice. Body weight measurements were taken in 10-week old MLDS/HFD mice injected intraperitoneally (IP) with Ab001, Ab037 or isotype control for 6 weeks (10 mg/kg;) and results expressed as percent change in body weight relative to pre-dose weight.

To evaluate the effect of Ab001 and Ab037 on disease in a model of combined insulin resistance and beta cell dysfunction, MLDS/HFD mice (n=10/group) were dosed with Ab001, Ab037 or isotype control antibody, at 10 mg/kg IP, BIW for six weeks. One week after the first dose, a threefold increase in fasting blood glucose was observed in isotype control treated diseased mice, relative to age-matched normal animals, confirming that a diabetic phenotype was achieved. At this time, a GTT was carried out, revealing significant improvements in glycemic control for both Ab001 and Ab037 (p<0.05; FIGS. 23A and 23B). Fasting blood glucose was also significantly reduced in the group of mice treated with Ab037 (p<0.05), whereas no significant change was elicited by Ab001 (FIG. 23C). One week later, fed glucose was evaluated Similar to fasting glucose, disease in MLDS/HFD mice was manifested by significantly elevated fed glucose levels, which was ameliorated by Ab037 (p<0.05; FIG. 24A). Consistent with these improvements in GTT and fed/fasting glucose, Ab037 reduced HbA1c by approximately 1.5% after six weeks of dosing (p<0.05; FIG. 24B). End of study plasma analysis revealed that Ab037 treatment led to a statistically significant normalization in plasma insulin and a smaller reduction in non-HDL/HDL cholesterol ratio, whereas Ab001 significantly improved plasma leptin levels, with a similar, but smaller corrective impact on plasma insulin (p<0.05; FIG. 25A-C). This model does not present with consistent, disease-related weight change as observed in the db/db model, and neither Ab001 nor Ab037 impacted body weight in this model (FIG. 26), suggesting that the reduced weight gain observed with these antibodies in the other in vivo models was not a non-specific effect. This data demonstrates Ab037 improves multiple manifestations of disease in MLDS/HFD mice, while Ab001 also corrects some parameters of impaired glycemic control in this model.

Figure 28:
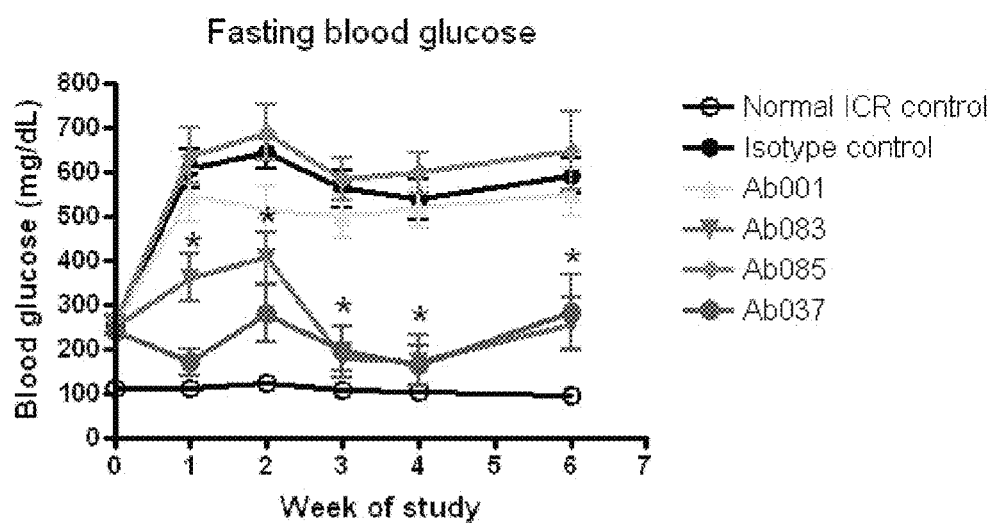
FIG. 28 shows that positive modulator and partial agonist anti-INSR antibodies improve glycemic control in MLDS/HFD mice as determined by a weekly fasting blood glucose assessment of 10-week old MLDS/HFD mice injected intraperitoneally (IP) with Ab001, Ab083, Ab085, Ab037 or isotype control for 6 weeks (10 mg/kg; * p<0.05 for Ab083 and Ab037 relative to isotype control).
Figure 30:
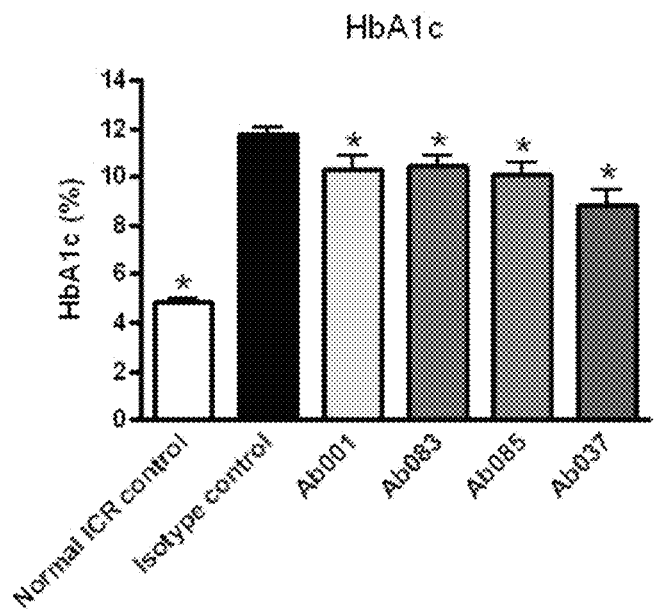
FIG. 30 shows that positive modulator and partial agonist anti-INSR antibodies improve glycemic control (HbA1c) in MLDS/HFD mice as determined by a blood HbA1c evaluation in 10-week old MLDS/HFD mice injected intraperitoneally (IP) with Ab001, Ab083, Ab085, Ab037 or isotype control for 6 weeks (10 mg/kg; * p<0.05 for Ab083 and Ab037 relative to isotype control).
Figure 31:
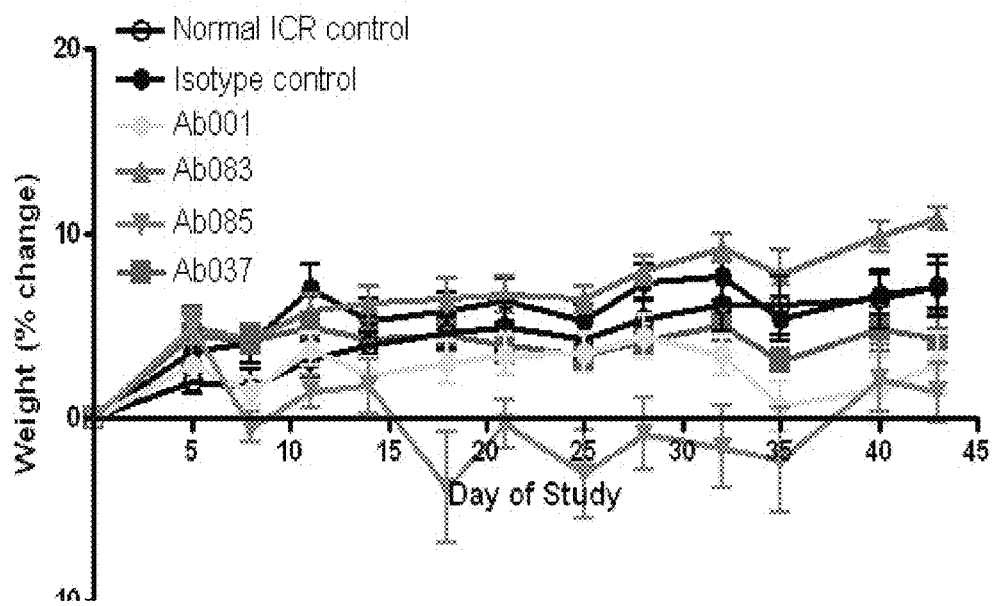
FIG. 31 shows that positive modulator and partial agonist anti-INSR antibodies generally do not affect body weight in MLDS/HFD mice as determined using body weight measurements in 10-week old MLDS/HFD mice injected intraperitoneally (IP) with Ab001, Ab083, Ab085, Ab037 or isotype control for 6 weeks (10 mg/kg).

Two additional positive modulator anti-INSR antibodies were evaluated for improvement of glycemic parameters in vivo. MLDS/HFD mice (n=10/group) were dosed with Ab001, Ab037, Ab083, Ab085 or isotype control antibody, at 10 mg/kg IP, BIW for six weeks. After 3 weeks of treatment, a GTT was performed, revealing that Ab037 and Ab083 a completely normalize glycemic control, relative to isotype control (p<0.05; FIGS. 27A and 27B). Fasting blood glucose was also significantly reduced in mice treated with Ab037 or Ab083 over the duration of the 6-week study (p<0.05), whereas no significant change was elicited by Ab001 or Ab085 (FIG. 28). At the end of the study, plasma lipids were evaluated. Ab083 significantly improved plasma triglycerides, unesterified cholesterol, total cholesterol, non-HDL cholesterol, non-HDL/HDL cholesterol ratio and free fatty acids (p<0.05; FIG. 29A-F). In addition, Ab001 significantly reduced total, non-HDL and unesterified cholesterol, as well as non-HDL/HDL cholesterol ratio. Ab037 improved non-HDL cholesterol, unesterified cholesterol, non-HDL/HDL cholesterol ratio and free fatty acids. In this experiment, Ab085 significantly reduced only free fatty acids. Consistent with the observed improvements in GTT and fasting glucose, Ab037 and Ab083 significantly reduced HbA1c after six weeks of dosing (p<0.05; FIG. 30). In addition, Ab001 and Ab085, which exerted less of an effect on fasting glucose and glucose tolerance, but did improve certain lipid parameters, also reduced HbA1c. As in the previous experiment, none of the mAbs meaningfully impacted body weight in this model, except Ab085, with reduced weight gain over the first 3 weeks of dosing (FIG. 31). This data demonstrates that all four antibodies tested improve multiple manifestations of disease in MLDS/HFD mice, without impacting body mass in this weight neutral model.

Example 16

Effects of 24 Hour Administration of Partial Agonist and Positive Modulator Anti-INSR Antibodies on INSR Phosphorylation In Vivo The increase in INSR tyrosine phosphorylation in insulin-sensitive tissues such as liver and muscle by short-term administration of anti-INSR antibodies confirms that the antibodies are bioavailable and capable of acting similarly on INSR in vivo as observed in vitro. In this experiment, anti-INSR antibodies identified as partial agonists or positive modulators in vitro were dosed for 24 hours in C56BL/6 male mice and evaluated for their effects on basal and insulin-induced liver and muscle INSR phosphorylation.

To determine if INSR partial agonist and positive modulators increase INSR phosphorylation in liver and muscle, 10 week-old C56BL/6 male mice (n=3) were given anti-INSR or isotype control antibodies (10 mg/kg) for 24 hours, and effects on liver and muscle INSR tyrosine phosphorylation were determined by ELISA in mice given an insulin bolus (1 U/kg) or PBS for 10 minutes. Phosphorylated INSR concentrations were normalized to total insulin receptor concentrations and expressed as a percentage.

Exogenous insulin (1 U/kg) did not significantly increase INSR phosphorylation in control animals (although there was a positive trend) in either liver or muscle (FIGS. 32A, B). However, in liver, significant increases in insulin-stimulated INSR phosphorylation were observed in Ab083- and Ab037-treated mice (p<0.05) as well as a nearly significant increase in Ab085-treated mice (p=0.07; FIG. 32A). This outcome suggests that partial agonist and positive modulator antibodies are capable of increasing responsiveness to insulin in vivo. Interestingly, in liver, Ab083 significantly increased INSR phosphorylation even in the basal state (no exogenous insulin), suggesting that Ab083 is able to sensitize the response to insulin even in presence of low, fasting levels of endogenous insulin.

The most pronounced effects from anti-INSR partial agonist and positive modulator antibodies were seen in the muscle. While all three anti-INSR antibodies positively-modulated insulin signaling in mice receiving an insulin bolus, Ab083, and to a greater extent, Ab085, also sensitized muscle INSR signaling to endogenous, fasting levels of insulin when compared to control animals (FIG. 32B).

These results suggest that both partial agonist and positive modulator anti-INSR antibodies improve responsiveness to insulin-mediated signaling in liver and muscle in vivo. Relative to the effects of Ab037, antibodies Ab083 and Ab085 sensitize INSR at relatively low insulin concentrations.

Example 17

Isolation of Anti-INSR Antibodies from Additional Antibody Phage Display Libraries Additional naïve antibody libraries were screened for antibodies specific for INSR.
(I) Phage Panning and Rescue
Human insulin receptor (hINSR) (R&D Systems, Minneapolis, Minn.) was biotinylated as described in Example 1 and used for panning of additional naïve antibody phage display libraries.
A. scFv Library
scFv Naïve Library: For the first round of phage panning, $4.5 \times 10^{12}$ cfu of phage particles from an scFv lambda phage display library or $4.12 \times 10^{12}$ cfu of phage particles from an scFv kappa phage display library (XOMA LLC, Berkeley, Calif.) were blocked for 1 h at room temperature (RT) in 1 ml of 5% milk/PBS (Teknova, Hollister, Calif.) with gentle rotation. This represents two separate pannings, scFv-kappa and scFv-lambda. Blocked phage were deselected twice for 30 minutes against streptavidin-coated magnetic Dynabeads® M-280 (Invitrogen Dynal AS, Oslo, Norway). To form the biotin-hINSR-hINS complex 103 pmoles of biotinylated hINSR was preincubated with excess (2,100 pmoles) human insulin (hINS) (Sigma, St Louis, Mo.) dissolved in 5% milk/PBS, for 1 h at RT with gentle rotation. For the second round of panning, 50 pmoles of biotin-hINSR was used with 1050 pmoles hINS. For the final round of panning, 25 pmoles of biotin-hINSR was incubated with 525 pmoles hINS.

B. Fab Library

Fab Naïve Library: For the first round of phage panning, $1.2 \times 10^{13}$ cfu of phage particles or $1.8 \times 10^{13}$ cfu of phage particles from two different rescues of an Fab lambda library (XOMA LLC, Berkeley, Calif.), or $7.2 \times 10^{12}$ cfu of phage particles or $1.8 \times 10^{13}$ cfu of phage particles from two different rescues of an Fab kappa library (XOMA LLC, Berkeley, Calif.) were blocked for 1 h at room temperature (RT) in 1 ml of 5% milk/PBS (Teknova, Hollister, Calif.) with gentle rotation. This represents four separate pannings Blocked phage were twice deselected for 30 minutes against streptavidin-coated magnetic Dynabeads® M-280 (Invitrogen Dynal AS, Oslo, Norway). To form the biotin-hINSR-hINS complex, 103 pmoles of biotinylated hINSR was preincubated with excess (2,100 pmoles) human insulin (hINS) (Sigma, St. Louis, Mo.) dissolved in 5% milk/PBS, for 1 h at RT with gentle rotation. For the second round of panning, 50 pmoles of biotin-hINSR was used with 1050 pmoles hINS. For the final round of panning, 25 pmoles of biotin-hINSR was incubated with 525 pmoles hINS.

The biotin-hINSR/hINS solution was incubated with blocked streptavidin-coated magnetic Dynabeads® M-280 (Invitrogen Dynal AS, Oslo, Norway) for 30 minutes with gentle rotation in order to immobilize the biotin-hINSR-hINS complex. The deselected phage were incubated with the biotin-hINSR-hINS streptavidin beads for 2 h at RT. In order to saturate the hINSR with hINS, additional hINS (2,100 pmoles) was added to the solution. The beads were washed. For the first round of panning, beads were quickly washed (i.e. beads were pulled out of solution using a magnet and resuspended in 1 ml wash buffer) three times with 0.5% milk-PBS-0.1% TWEEN, followed by three washes with 0.5% milk-PBS followed by one quick wash with PBS. For the second round of panning, beads were quickly washed five times with 0.5% milk-PBS-0.1% TWEEN followed by one 5 minute wash (in 1 ml wash buffer at room temperature with gentle rotation) with 0.5% milk-PBS-0.1% TWEEN and then five washes with 0.5% milk-PBS followed by one 5 minute wash with 0.5% milk-PBS and then one quick wash with PBS. For the third round of panning, beads were quickly washed four times with 0.5% milk-PBS-0.1% TWEEN, followed by two washes for five minutes with 0.5% milk-PBS-0.1% TWEEN and then four quick washes with 0.5% milk-PBS, followed by two 5 minute washes with 0.5% milk-PBS and then one quick wash with PBS.

C. Elution and Rescue

The hINSR-hINS-Streptavidin bead-bound phage were eluted with 0.5 ml 100 mM triethylamine (TEA) for 30 minutes at RT with gentle rotation. The beads were separated from the eluate. The eluate was removed and neutralized with 0.5 ml 1M Tris-HCl (pH 7.4). The beads were neutralized with 1 ml 1M Tris-HCl (pH 7.4). The eluted phage from beads or eluate, were used separately to infect TG1 bacterial cells (Stratagene, La Jolla, Calif.) when they reached an $OD_{600}$ of ~0.5. Following infection for 30 min at 37° C. without shaking, and for 30 min at 37° C. with shaking at 90 rpm, cells were pelleted and resuspended in 2YT media supplemented with 100 ug/ml carbenicillin and 2% glucose. The resuspended cells were plated on 2YT agar plates with 100 ug/ml carbenicillin and 2% glucose and incubated overnight at 30° C.

Phage was then rescued with helper phage M13KO7 (New England Biolabs, MA) at a multiplicity of infection (MOI) ~20. Following helper phage infection of TG1 cells at an $OD_{600}$ of 0.5 at 37° C. for 30 min without shaking and 30 min incubation at 37° C. at 100 rpm, cell pellets were resuspended in 2YT media supplemented with 100 ug/ml carbenicillin and 50 ug/ml kanamycin and allowed to grow overnight at 25° C. and 250 rpm. Phage in the supernatant were recovered after rigorous centrifugation and used for the next round of panning. In order to monitor the enrichment resulting from the phage selections, the amount of input and output phage was titered for the three rounds of panning.

(2) FACS Screening of Antibody Clones on Human INSR/hINS or Murine INSR/hINS Complex Individual colonies were picked and grown in 96-well plates and were then used to generate bacterial periplasmic extracts according to standard methods, with a 1:3 volume ratio of ice-cold PPB solution (Teknova, Hollister, Calif.) and ddH2O and protease inhibitor (Roche, Indianapolis, Ind.). The lysate supernatants were assayed by FACS on hINSR/hINS or murine INSR/hINS complex, using the protocol described in Example 2, except that suspension adapted CHO-K1 transfected with either hINSR or muINSR were used instead of IM-9 cells, and cells exposed to insulin were resuspended in FACS buffer supplemented with 150 nM rather than 70 nM human insulin. This assay allowed the detection of at least 6 types of antibody:

1. Antibodies that only bind to hINSR-CHO cells if they have been exposed to human insulin (bind exclusively to INS/INSR complex in a species specific manner)
2. Antibodies that only bind to muINSR-CHO cells if they have been exposed to human insulin (bind exclusively to INS/INSR complex in a species specific manner)
3. Antibodies that bind to both hINSR-CHO and muINSR-CHO cells if they have been exposed to human insulin (bind exclusively to INS/INSR complex in a species cross-reactive manner)
4. Antibodies that only bind to hINSR-CHO cells (bind exclusively to INSR in a species specific manner)
5. Antibodies that only bind to muINSR-CHO cells (bind exclusively to INSR in a species specific manner)
6. Antibodies that bind to both hINSR-CHO and muINSR-CHO cells (bind exclusively to INSR in a species cross-reactive manner)

Antibodies were scored as described in Example 2. Light chain and heavy chain sequences of the isolated antibodies were sequenced and are set out in SEQ ID NOs: 87-147 (light chain) and SEQ ID NOs: 223-284 (heavy chain).

Results

FACS screening of the bacterial periplasmic extracts identified multiple antibodies that bound human receptor or receptor/ligand complex, hINSR or hINSR-hINS, or murine receptor or receptor/ligand complex, muINSR or muINSR/hINS. Thirty-three percent (484 out of 1,488) of the clones selected from these naïve libraries were able to bind the hINSR or hINSR-hINS complex. Twenty-five percent (370 out of 1,488) of the clones selected from these naïve libraries were able to bind the muINSR or muINSR-hINS complex.

Sixteen percent (234 out of 1,488) of the clones bound to both hINSR or hINSR-hINS and muINSR or muINSR/hINS complexes by FACS.

Selected clones were reformatted as IgG2 antibodies. The variable heavy (VH) and light (VL) chains of the selected scFv fragments were PCR-amplified, cloned into plasmid vectors containing antibody constant genes, and transfected into 293E EBNA human cells using standard methods. Binding of the reformatted antibodies to hINSR or hINSR-hINS or muINSR or muINSR/hINS were assessed by FACS as described above. Results are set out in FIG. 33.

Results show that certain reformatted antibodies bind to both mouse and human INSR. FIG. 33 also shows that certain reformatted antibodies bind differentially to INSR in the presence and absence of insulin and are therefore predicted to modulate insulin binding to INSR.

Example 18

Panning for Allosteric Agonist Antibodies Against INSR

Selection of agonist antibodies that exhibit greater binding to the complex of receptor/ligand than to the free receptor enhances the probability of identifying antibodies that are noncompetitive with the ligand and do not block or diminish binding of the ligand to the orthosteric site of the receptor. An antibody of this type, that binds to a site on the target receptor distinct from the endogenous binding site, is known as an allosteric agonist (Kenakin et al., Journal of Receptors and Signal Transduction, 27:247-259, 2007; Jahns et al., J Am Coll Cardiol. 36:1280-87, 2000; May et al., Ann Rev Toxicol. 47: 1-51, 2007).

Methods described above to screen for agonist antibodies are also useful to screen for allosteric agonists. Preferential binding of the test antibody to the receptor ligand complex is consistent with allosteric activity whereas preferential binding of the test antibody to the free receptor is consistent with an antibody that competes with insulin for the orthosteric site. The screen is useful to enrich the pool of candidate clones for allosteric agonists by eliminating the some if not all competitive agonists.

Allosteric antibodies are less likely to interfere with the binding affinity and efficacy of the ligand and therefore, are less likely to interfere with the maximum ligand signaling or maximum sensitivity to ligand. Allosteric antibodies can exhibit a range of agonism from weak partial agonists to agonism levels similar to the endogenous ligand. A partial allosteric agonist will elicit a maximum signaling response that is of significantly lower in magnitude than the maximum response of the endogenous ligand. In some applications, where sustained sub maximal signal activation is preferred over maximum signal activation, a partial agonist antibody is preferable to a full agonist antibody. The distinguishing characteristics between a partial allosteric agonist and a positive modulator (sensitizer) are evident from a comparison of the dose response curves shown in FIGS. 34 and 17, which show the different binding curves for a partial allosteric agonist (FIG. 34) and a positive modulator (sensitizer) antibody (FIG. 35).

FIG. 34A illustrates an example of the dose response from a partial allosteric agonist in comparison to the dose response to the endogenous ligand and FIG. 34B demonstrates activation by ligand in the presence or absence of the allosteric agonist. FIG. 35A shows the dose response from a positive allosteric modulator antibody in comparison to the dose response to the endogenous ligand while FIG. 35B shows a dose response curve of an endogenous ligand in the presence and absence of a positive modulator antibody. FIG. 36 provides the activation parameters for a set of partial allosteric agonists relative to the endogenous ligand. The nature of signal activation by the partial allosteric agonists is distinct from that of a positive modulator obtained from the same primary screening approach.

A non-competitive partial allosteric agonist antibody may offer a therapeutic advantage over a competitive agonist where it is beneficial to have independent signal activation by both the partial agonist and an endogenous ligand simultaneously. For example, and not to be bound by theory, a partial allosteric agonist can be used to elevate the basal activation of a signaling pathway while still allowing response from transient fluctuations in endogenous ligand levels. In certain instances, under conditions where a partial allosteric agonist of this sort is present, the endogenous ligand dose response will exhibit an increase in the baseline (constitutive or basal) signaling level and will achieve the same or greater maximal response to the endogenous ligand with little or no significant change in the ligand EC50. For example, FIG. 34B shows the dose response of an endogenous ligand in the presence and absence of a partial allosteric agonist and FIG. 37 shows the maximal activation of insulin in the presence partial allosteric agonist antibodies relative to the maximal response to the endogenous ligand in the presence of a negative control antibody. FIG. 37 demonstrates that the partial allosteric agonist antibodies Ab037 and Ab040 have little or no significant impact on the EC50 of the dose response and maximum phosphorylation of Akt at Ser473 by insulin when compared to a negative control antibody within the same assay.

Example 19

Examples of Functional Classes of Anti-INSR Antibodies: Differential Effects on Insulin-Induced Phosphorylation of Akt The effects of test antibodies on signaling via the insulin/ insulin receptor complex were measured by assessing the ability of the antibodies to sensitize and agonize insulin-induced phosphorylation of Akt. Assays were performed using the method described in Example 5. In all data shown, the percent pAtk pSer473 values are relative and do not necessarily represent absolute cellular pAkt pSer473 levels.

Figure 40:
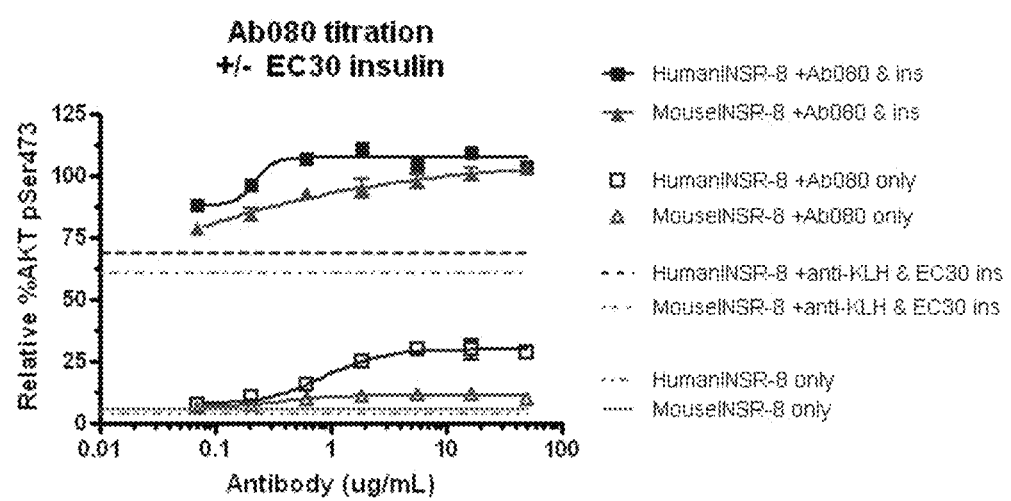

FIGS. 38-40 show pAkt antibody dose response curves in the absence of insulin or in the presence of a sub-maximal concentration of insulin for parental CHO-K1 cells, CHO-K1 cells expressing human insulin receptor and CHO-K1 cells expressing mouse insulin receptor. The titrations of antibodies in the absence of insulin (open symbols) provide an indication of antibody agonism activity. Parallel titration of antibodies in the presence of a sub-maximal level of insulin (closed symbols) provides an indication of sensitizing activity relative to the agonism activity. The sensitizing activity can be seen as an increase in the pAkt levels above that caused by an EC30 concentration of insulin (dashed line) which is greater in magnitude than the agonism activity at the same antibody concentration. Antibodies Ab077, Ab078 and Ab085 (FIG. 38A-C) do not exhibit significant agonism in the absence of insulin. Antibodies Ab001, Ab079 and Ab083 are weak agonists (FIG. 39A-C) and antibody Ab080 shows a moderate level of agonism (FIG. 40). The assay results also indicate whether the antibodies show functional cross-reactivity, i.e., have effects on both human and mouse INSR-mediated signaling. Note that antibodies Ab078 and Ab085 only bind the insulin receptor in the presence of insulin, i.e., they do not detectably bind unoccupied insulin receptor as assessed by binding to insulin receptor expressed in CHO-K1 cells in a FACS based assay.

FIG. 41A-C shows insulin induced pAkt activation in the presence of fixed concentrations of sensitizing antibodies in comparison to insulin in the presence of IgG2 isotype control antibody anti-KLH (solid lines). pAkt activation levels for antibodies in the absence of insulin at the concentrations used in the insulin dose response titrations are shown as dashed lines. EC50 values for insulin induced pAkt activation in the presence of the sensitizing antibodies and fold change in EC50 values relative to isotype control are listed in Table 5.

TABLE 5

EC50 values for insulin induced activation of pAkt in the presence of sensitizer antibodies.

| Experiment | Antibody | Antibody Concentration (ug/ml) | EC50 (pM) | Fold-change in EC50 relative to isotype control |
|---|---|---|---|---|
| Human INSR CHO-K1 cells | Ab001 | 2 | 59 | 12 |
|  | Ab077 | 10 | 81 | 9 |
|  | Ab078 | 20 | 221 | 3 |
|  | Ab079 | 10 | 100 | 7 |
|  | Ab083 | 2 | 68 | 11 |
|  | Ab085 | 1 | 207 | 3 |
|  | Ab085 | 10 | 81 | 9 |
|  | anti-KLH.G2 | 10 | 724 |  |
| Mouse INSR CHO-K1 cells | Ab001 | 2 | 354 | 7 |
|  | Ab077 | 20 | 301 | 8 |
|  | Ab078 | 20 | 990 | 2 |
|  | Ab079 | 20 | 300 | 8 |
|  | Ab083 | 10 | 276 | 9 |

TABLE 5-continued

EC50 values for insulin induced activation of pAkt in the presence of sensitizer antibodies.

| Experiment | Antibody | Antibody Concentration (ug/ml) | EC50 (pM) | Fold-change in EC50 relative to isotype control |
|---|---|---|---|---|
|  | Ab085 | 20 | 312 | 8 |
|  | anti-KLH.G2 | 10 | 2414 |  |

FIGS. 42A-B show pAkt activation activity of partial allosteric agonist antibodies in the absence of insulin in comparison to insulin alone. Antibodies Ab037, Ab053 and Ab062 all act as agonists of pAkt activity having maximal activation plateaus that are significantly less than insulin in CHO-K1 cells expressing either human or mouse insulin receptor. The assay results also indicate whether the antibodies show functional cross-reactivity i.e. have effects on both human and mouse insulin receptor-mediated signaling. Antibody EC50 values and maximum activation levels are given in Table 6.

TABLE 6

Maximum activation levels and EC50 values for partial allosteric agonists

|  |  | Hu Insulin | Ab037 | Ab053 | Ab062 |
|---|---|---|---|---|---|
| Human INSR CHO-K1 | Relative maximum activation | 100% | 79% | 64% | 52% |
|  | $EC_{50}$ (nM) | 0.15 | 0.65 | 0.42 | 2.43 |
| Mouse INSR CHO-K1 | Relative maximum activation | 100% | 42% | 48% | 34% |
|  | $EC_{50}$ (nM) | 1.70 | 1.42 | 0.69 | 1.10 |

FIG. 43 shows insulin dependent pAkt activation in the presence of fixed concentrations of partial allosteric agonist antibodies in comparison to insulin alone. Agonist activity of antibodies is seen as an increase in the baseline of the insulin dose response. The agonist antibodies Ab037 and Ab053 have little effect on insulin sensitivity which is reflected in the lack of significant change in the insulin EC50 and Hill coefficient in the presence of these antibodies (see Table 7). Antibody Ab062 appears to reduce insulin sensitivity as the EC50 for insulin in the presence of Ab062 is 6.6-fold higher (see Table 7).

TABLE 7

Insulin activation parameters in the presence and absence of agonist antibodies

| Engineered insulin receptor cell line used in the assay | Assay parameter determined from sigmoidal dose-response curve fit | Hu Insulin with 2 ug/ml control antibody (95% confidence interval) | Hu Insulin with 2 ug/ml Ab037 (95% confidence interval) | Hu Insulin with 2 ug/ml Ab053 (95% confidence interval) | Hu Insulin with 2 ug/ml Ab062 (95% confidence interval) |
|---|---|---|---|---|---|
| Human INSR CHO-K1 | Relative maximum activation of pAkt in the presence of 2 ug/ml antibody | 100% (93% to 108%) | 109% (106% to 112%) | 99% (97% to 102%) | 106% (100% to 112%) |
|  | $EC_{50}$ of insulin in the presence of 2 ug/ml antibody (nM) | 0.58 (0.35 to 0.96) | 1.11 (0.84 to 1.5) | 0.92 (0.68 to 1.3) | 3.91 (2.7 to 5.7) |
|  | Hill coeff. of insulin in the presence of 2 ug/ml antibody | 0.74 (0.48 to 1.0) | 0.79 (0.63 to 0.95) | 0.93 (0.69 to 1.2) | 0.71 (0.54 to 0.89) |

Example 20

Anti-INSR Antibody 83-7 is not a Positive Modulator of Insulin Binding to hINSR Anti-INSR antibody 83-7 has been identified previously as specific for human insulin receptor, however, the 83-7 antibody has not been demonstrated to have any modulating abilities on insulin-insulin receptor binding. In order to assess the ability of the 83-7 antibody to kinetically modulate insulin-insulin receptor interactions, insulin-induced serine phosphorylation of AKT was measured in the presence of 83-7.

The VH and VL sequences encoding antibody 83-7 (McKern et al., Nature 443: 218-221, 2006) were synthesized and the antibody (IgG1, lambda light chain) was transiently expressed in HEK293 EBNA cells. The antibody was purified using protein A capture and size exclusion chromatography. The ability of 83-7 to augment insulin-induced serine phosphorylation of AKT was measured using the method described in Example 5. FIG. 44 shows pAKT assay results for 83-7 and Ab001 on CHOK1 cells expressing: (A) human INSR, or; (B) mouse INSR. Antibody 83-7 did not positively modulate insulin-dependent INSR signaling, showing only agonist activity on human INSR and did not exhibit agonism on mouse INSR. In contrast, Ab001 positively modulated insulin-dependent INSR signaling by about 10-fold on both human INSR and mouse INSR.

Example 21

Assay to Measure Modulation of Insulin Binding Affinity for INSR by Anti-INSR Antibodies To determine the ability of the modulating antibodies to affect the binding of insulin to the insulin receptor, the affinity of unmodified insulin binding to human INSR expressed on the surface of serum starved CHOK1 cells (hINSR8-CHOK1) was measured in the presence and absence of monoclonal antibodies to INSR. A KinExA assay was developed to measure very low levels of insulin in cell culture media. This assay allowed the binding of insulin to cells expressing INSR to be measured by determining the level of insulin depletion from the cell culture media. As insulin became bound to the cells, the concentration of insulin in the cell culture media dropped. By using a titration of cells expressing INSR and measuring the percent free insulin, the affinity of the INS-INSR interaction could be estimated using KinExA software. This assay was used to measure the degree of modulation of insulin binding activity shown by various anti-INSR antibodies.

hINSR8-CHOK1 cells were serum starved overnight and then prepared for assay by pelleting cells and resuspending at a concentration of 2× the final assay concentration for the highest dilutions (between 3.5×10$^7$ and 2.0×10$^7$ cells/mL in assay dilution buffer of PBS (Teknova, Hollister Calif.) with 500 μg/mL BSA and 0.1% sodium azide (Sigma Aldrich, St. Louis, Mo.)). A two-fold serial dilution of cells was prepared creating a ten-point dilutions series and a no-cells control was also used. Cell suspensions were aliquoted into polypropylene assay tubes in 2 mL volume each. To these cell suspensions 1 mL of 40 ug/mL test antibody (or 100 ug/mL for Ab078) was added to each tube, gently mixed and incubated for 30-45 minutes on ice. The antibodies used were tested in comparison to the negative control human IgG2 anti-KLH antibody. 1 mL of 200 pM insulin was added to each tube to establish a final insulin concentration of 50 pM (300 pg/mL) (Sigma-Aldrich, St. Louis, Mo.). Samples were incubated overnight at 4° C. for 18 hours then centrifuged to pellet cells and supernatants were removed for testing.

KinExA 3000 analysis was performed using beads coated with an anti-insulin monoclonal antibody. 2 grams of poly (methyl methacrylate) (PMMA) beads (Sapidyne, Boise, Id.) was suspended in 9 mL of assay buffer PBS containing 65 ug/mL of clone D6C4 mouse anti-insulin monoclonal antibody (Fitzgerald Industries, Acton Mass.). Beads were rotated at room temperature for 6 hours then allowed to settle. Supernatant was replaced with PBS with 50 mg/mL BSA Fraction V (Sigma-Aldrich, St. Louis, Mo.) and rotated overnight at 4° C. Detection solution used was biotinylated mouse anti-insulin clone D3E7 (Fitzgerald Industries, Acton Mass.) at 0.15 μg/mL in assay dilution buffer with Streptavidin-PE at 1 ug/mL (Invitrogen, Carlsbad, Calif.). On the KinExA 3000 the sample was injected at 0.25 mL/minute for 240 seconds, then rinsed for 60 seconds in running buffer (PBS with 0.05% sodium azide), then 240 seconds of the detection solution was injected, followed by a final 90 second wash at 1 mL/minute. The difference in voltage from an early initial time-point and a time point near the end of the run was measured and used to calculate affinities. The INSR concentration on the cells was estimated at 2.5×10$^5$ receptors/cell. Affinity was determined using the KinExA software (Sapidyne, Boise Id.) and EC50's were calculated by non-linear fit in Prism (GraphPad Software, La Jolla Calif.).

Figure 45:
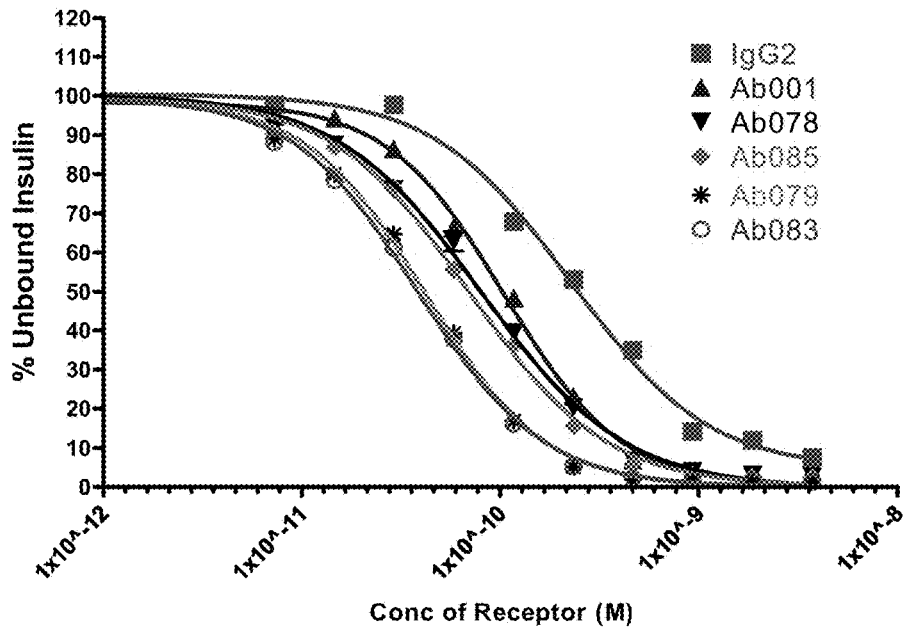
FIG. 45 shows free insulin percentage plotted against estimated insulin receptor concentration. The insulin level was fixed at 50 pM and the antibody concentration was 10 ug/mL (67 nM) for all clones except Ab078 which was tested at 25 ug/mL (167 nM). Curves shown are the non-linear regression Prism fit used to calculate EC50.

A number of anti-INSR antibodies enhanced the affinity of insulin for the cells. Other antibodies had no effect on insulin affinity for the cells (Table 8). One of the tested antibodies decreased the affinity of insulin for the cells by approximately three-fold. FIG. 45 shows free insulin percentage plotted against estimated insulin receptor concentration. The insulin level was fixed at 50 pM and the antibody concentration was 10 ug/mL (67 nM) for all clones except Ab078 which was tested at 25 ug/mL (167 nM). Curves shown are the non-linear regression Prism fit used to calculate EC50.

Figure 46:
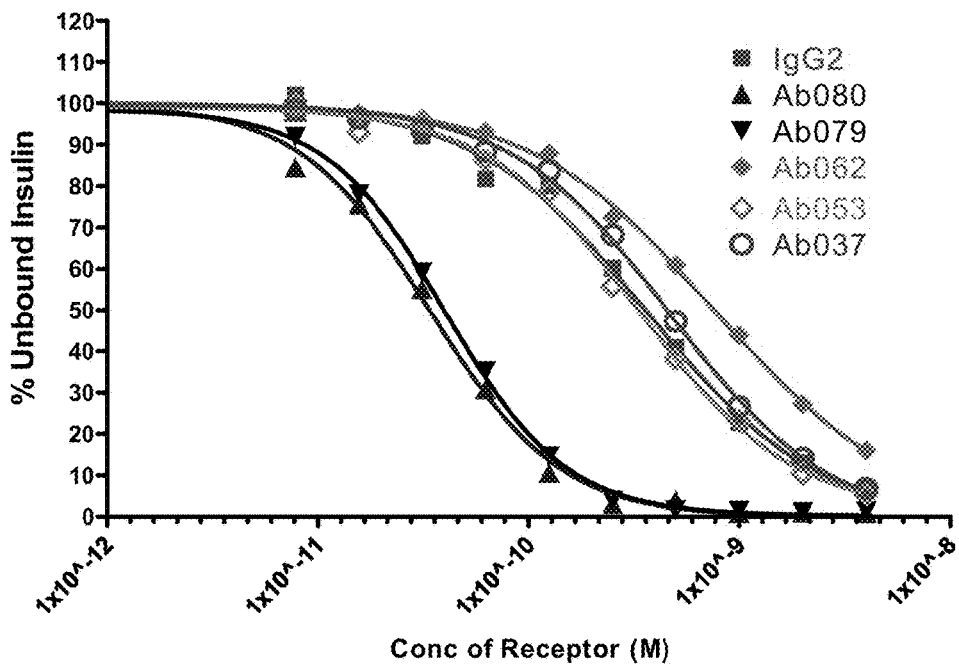
FIG. 46 shows free insulin percentage plotted against estimated insulin receptor concentration. The insulin level was fixed at 50 pM and the antibody concentration was 10 ug/mL (67 nM) for all clones. Curves shown are the non-linear regression Prism fit used to calculate EC50.

FIG. 46 shows free insulin percentage plotted against estimated insulin receptor concentration. The insulin level was fixed at 50 pM and the antibody concentration was 10 ug/mL (67 nM) for all clones. Curves shown are the non-linear regression Prism fit used to calculate EC50.

TABLE 8

Insulin Affinity and IC50 Table

| Antibody | $K_D$ (pM) | EC50 (pM) | Fold Shift in Affinity |
| --- | --- | --- | --- |
| IgG2-KLH | 272 | 365 | 1.0 |
| Ab037 | 271 | 471 | 1.0 |
| Ab001 | 49 | 104 | +5.6 |
| Ab053 | 228 | 33 | +1. |
| Ab062 | 762 | 760 | 2.8 |
| Ab078 | 41 | 80 | +6.6 |
| Ab079 | 12.1 | 40 | +22.5 |
| Ab080 | 11.2 | 34 | +24.3 |
| Ab083 | 13.7 | 39 | +19.9 |
| Ab085 | 34 | 70 | +8.0 |

Example 22

Assay to Measure Insulin, IGF-1, and IGF-2 Mediated Proliferation of MCF-7 Cells in the Presence or Absence of Anti-INSR Antibodies Insulin, IGF-1, and IGF-2 promote mitogenesis in MCF-7 human mammary adenocarcinoma cells. Previous studies have shown that insulin analogs promote mitogenic signaling in addition to metabolic signaling following binding to INSR. The positive modulator and agonist anti-INSR antibodies described herein were expected to promote INSR-mediated mitogenic signaling in parallel to their activation of INSR-mediated metabolic signaling. The effects of the modulating antibodies on insulin-mediated mitogenic stimuli were measured using MCF-7 cells expressing the receptors.

MCF-7 cells were cultured in Dulbecco's Modified Eagles Medium (DMEM) containing glucose at 4.5 g/L supplemented with 10% FBS and 2 mM glutamine (Invitrogen) for normal maintenance. For the proliferation assay, cells were seeded in 96 well white opaque microtiter plates at a density of $1 \times 10^4$ cells/well (Costar 3917) and allowed to re-attach for 24 hrs. After 24 hrs, the cells were washed 2× with pre-warmed PBS and incubated in DMEM containing glucose at 1 g/L and no phenol red supplemented with 0.1% FBS and 2 mM glutamine (Invitrogen), which will be referred to as "starvation media," for another 24 hrs. Insulin (Sigma), IGF-1 (R&D Systems), and IGF-2 (R&D Systems) were prepared as 10× stocks in starvation media and serially diluted 5-fold starting from 1 uM down to 64 nM (6 dilutions), and added to the cells after the 24 hr starvation period. For the co-incubation experiments that include the anti-INSR antibodies along with the growth factor, a 50 ug/ml stock of each antibody was prepared in starvation media and added to the cells prior to addition of growth factor to a final concentration of 5 ug/ml. The cells were incubated at 37° C. for 48 hrs and cell proliferation was measured using the CellTiter-Glo Luminescent Cell Viability Assay (Promega). The results are shown in Table 9.

TABLE 9

MCF-7 proliferation results $EC_{50}$ and 95% confidence interval values

| | Insulin (nM) | | IGF-1 (nM) | | IGF-2 (nM) | |
|---|---|---|---|---|---|---|
| | $EC_{50}$ | 95% CI | $EC_{50}$ | 95% CI | $EC_{50}$ | 95% CI |
| No antibody | 0.80 | 0.48-1.33 | 1.73 | 1.07-2.80 | 1.30 | 0.80-2.11 |
| KLH* | 1.54 | 1.03-2.29 | 2.10 | 1.33-3.30 | 2.66 | 1.75-4.06 |
| Ab001* | 3.46 | 2.22-5.40 | 4.71 | 3.28-6.75 | 2.54 | 1.87-3.43 |
| Ab037* | 1.54 | 1.00-2.37 | 2.33 | 1.51-3.58 | 2.09 | 1.44-3.05 |
| Ab083* | 1.08 | 0.49-2.38 | 0.91 | 0.58-1.43 | 1.47 | 0.77-2.81 |
| Ab085* | 0.48 | 0.28-0.81 | 2.11 | 1.38-3.21 | 1.84 | 1.30-2.60 |

*antibody concentration @ 5 ug/ml

These results show that, surprisingly, in the presence anti-INSR antibodies, no significant changes in the mitogenic responses to any of the aforementioned growth factors were observed within a 95% confidence interval. It is possible that these antibodies may cross-react and weakly bind IGF-1 and IGF-2, but the above assay demonstrates that any possible crossreactive binding does not elicit a functional effect, i.e., does not promote signaling through the receptor. This suggests the antibodies are able to increase the ratio of metabolic to mitogenic INSR-mediated signaling.

Example 23

The Effects of Anti-INSR Antibodies to Reverse Insulin Resistant Fatty Acid Uptake in Differentiated 3T3-L1 Adipocytes TNFα can inhibit insulin dependent fatty acid uptake. Since TNFα is known to cause insulin resistance by deactivation of insulin signaling pathway intermediates such as IRS-1 (Nguyen et al, J. Biol. Chem. 280(42): 35361-71, 2005; Luca and Olefsky, FEBS Let. 582: 97-105, 2008) that are also part of the insulin dependent glucose uptake pathway, reversal of TNFα inhibition of insulin dependent fatty acid uptake by anti-INSR antibodies is indicative of the ability of these antibodies to reverse TNFα mediated inhibition of insulin dependent glucose uptake.

3T3-L1 mouse embryonic fibroblasts can be induced to differentiate into adipocytes, after which they become highly responsive to insulin-mediated fatty acid uptake. High fat feeding has been established as a cause of adipose tissue insulin resistance. To examine this condition in vitro, 3T3-L1 adipocytes have been treated with free fatty acids (FFA) which result in impaired insulin receptor-mediated signal transduction and ultimately decreased insulin-stimulated glucose uptake. One of the downstream effector molecules induced by FFA treatment that contributes to insulin resistance is TNFα. TNFα has also been shown to inhibit insulin-mediated fatty acid uptake and provides a well defined in vitro system to assess whether anti-INSR antibodies can reverse insulin-resistant fatty acid transport.

3T3-L1 cells were cultured in Dulbecco's Modified Eagles Medium (DMEM) containing glucose at 4.5 g/L supplemented with 10% newborn calf serum (NCS; Invitrogen) and 2 mM glutamine (Invitrogen) for normal maintenance. To differentiate cells into adipocytes in 96-well microtiter plates, the following protocol was used: (1) at day −5, $2 \times 10^3$ cells per well were seeded in a black/clear bottom 96-well plate (BD Falcon 353948), (2) at day −2, cells reach confluency and are left for 2 additional days, (3) at day 0 differentiation media is added, (4) at day 3, media is changed to normal growth media containing 0.425 uM insulin, (5) at day 7 media is changed to normal growth media. To induce insulin resistance, 10× stocks of TNFα (R&D Systems) were prepared in normal growth media and added to cells on day 9 of the differentiation process. Working concentrations of TNFα used were between 1-10 ng/ml. Fatty acid uptake was run on cells at day 10. The fatty acid uptake protocol used was as follows. Cells were washed in 2× in Hank's Balanced Salt Solution (HBSS; Invitrogen) containing 0.2% fatty acid-free BSA (FAF-BSA; Sigma) and 20 mM HEPES (Invitrogen), and then serum starved in HBSS for 1-2 hrs at 37° C. Anti-INSR antibodies or other relevant controls were added from a 10× stock or HBSS alone and incubate at 37° C. for 30 minutes, and insulin added at dilutions from a 10× stock and incubated at 37° C. for 30 minutes. An equal volume of reconstituted QBT Fatty Acid Uptake Assay (Molecular Devices) loading buffer was then added and incubated at 37° C. for up to 3 hours, and the plates read on a fluorescent plate reader to measure internalized fluorescent fatty acid analogs.

Figure 47:
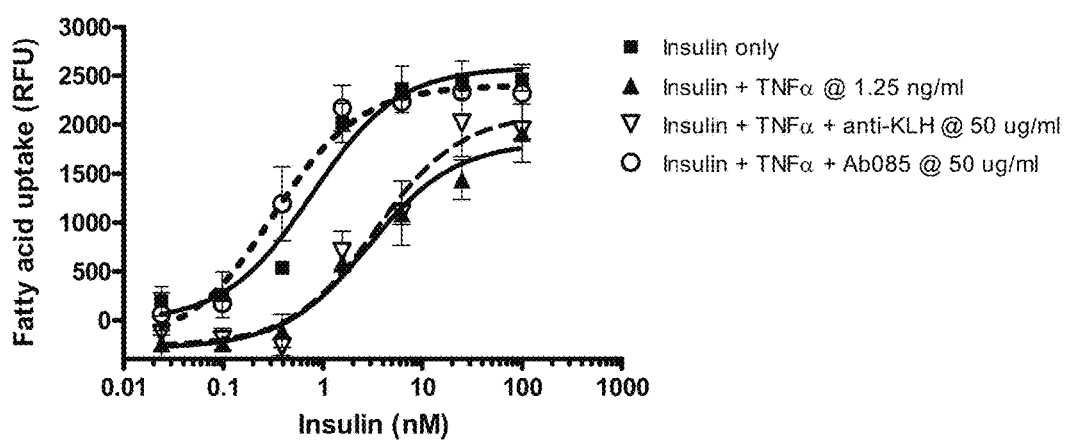
FIG. 47 shows that TNFα-induces desensitization of insulin-mediated fatty acid uptake in 3T3-L1 adipocytes in the presence of anti-INSR antibody Ab085.

FIG. 47 shows that TNFα-induces desensitization of insulin-mediated fatty acid uptake in 3T3-L1 adipocytes in the presence of anti-INSR antibody Ab085. Table 10 shows relative EC50 for the antibodies for fatty acid uptake, demonstrating that Ab085 decreases the EC50 for fatty acid uptake. In the presence of anti-INSR antibody Ab085, the TNFα-induced desensitization of insulin-mediated fatty acid uptake was completely reversed back to the untreated control values. Similar results were observed for Ab083.

TABLE 10

| $EC_{50}$ and 95% confidence interval values | | |
|---|---|---|
| | Insulin (nM) | |
| | $EC_{50}$ | 95% CI |
| Insulin only | 0.77 | 0.37-1.60 |
| +TNFα | 2.89 | 1.37-6.08 |
| +TNFα, +anti-KLH | 3.39 | 1.42-8.11 |
| +TNFα, +Ab085 | 0.32 | 0.14-0.75 |

TNFα concentration @ 1.25 ng/ml
Ab085 concentration @ 50 ug/ml

These results demonstrate that the positive-modulator antibody can increase fatty acid uptake in adipocytes, which suggests the antibody is useful to treat a disorder or condition that would benefit from increasing fatty acid uptake.

Example 24

Characterization of Highly Purified Anti-INSR Antibodies by Insulin Dependent pAkt Activation A certain amount of assay-to-assay variation was noted in the functional pIRS-1 and pAKT assays. It was determined that this variation could be reduced when the test antibodies were purified using a further step in addition to protein-A purification, e.g., size-exclusion chromatography, resulting in antibodies that were approximately >95% pure. This purification step reduced or eliminated aggregates and contaminating growth factors thought to interfere with the functional assay.

A number of highly purified anti-INSR antibodies were tested in the pAKT assay described in Example 5, using CHOK1 cells expressing either the human INSR or mouse INSR. In addition, certain anti-INSR antibodies were tested for activity on a CHOK1 cell line transfected with cynomolgous monkey INSR (CHOK1-cynoINSR-4).

Figure 48:
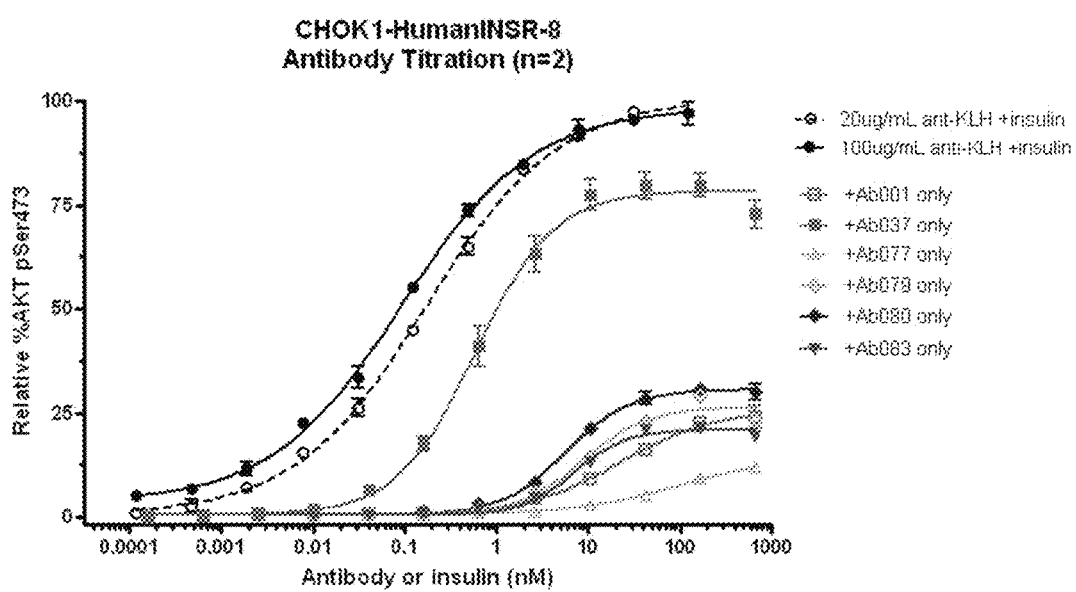
FIG. 48 and FIG. 49 illustrate the effects of purified positive modulator anti-INSR antibodies Ab001, Ab037, Ab077, Ab079, AB080, Ab083 on human INSR (FIG. 48) and mouse INSR (FIG. 49). as measured in the pAKT assay.
Figure 49:
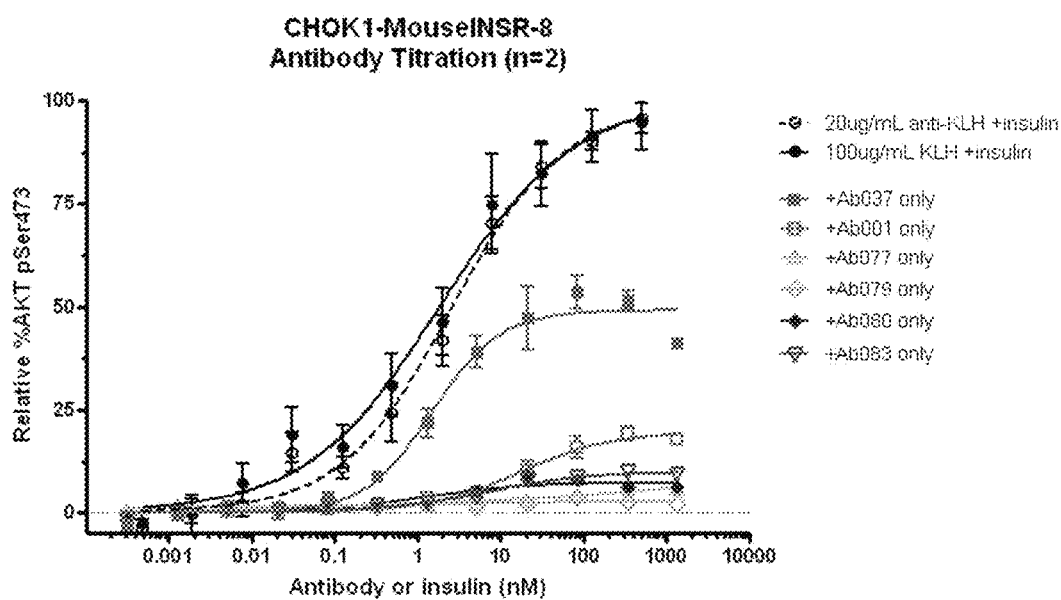

The effects of positive modulator anti-INSR antibodies Ab001, Ab037, Ab077, Ab079, AB080, Ab083 were measured in the pAKT assay and results are shown in FIG. 48 (human INSR) and FIG. 49 (mouse INSR).

Figure 50:
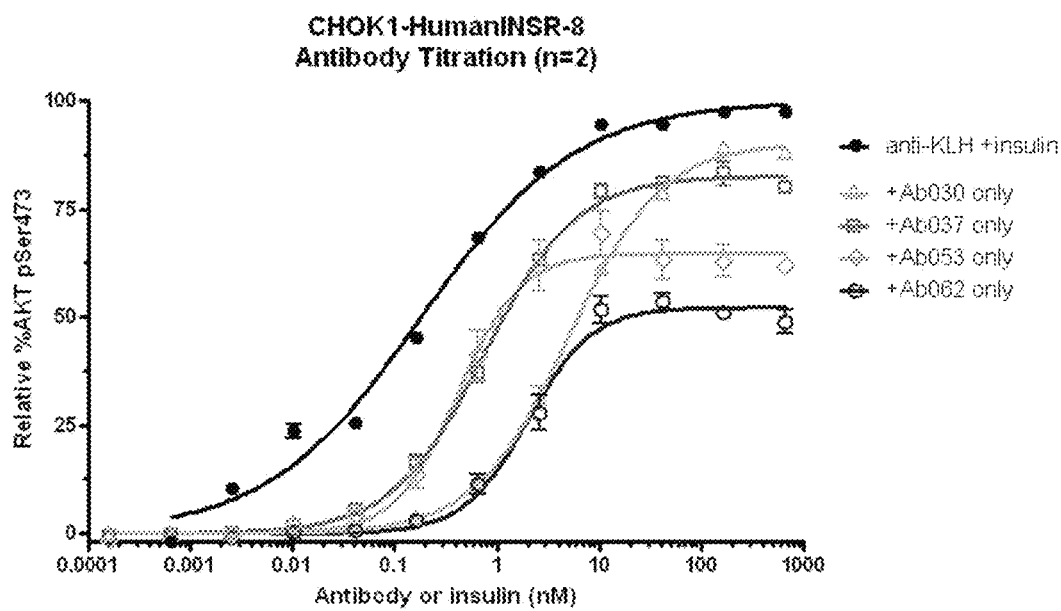
FIGS. 50 and 51 demonstrates the relative % pAKT of purified agonist antibodies Ab037, Ab030, Ab053 and Ab062 on human INSR (FIG. 50) and mouse INSR (FIG. 51).
Figure 51:
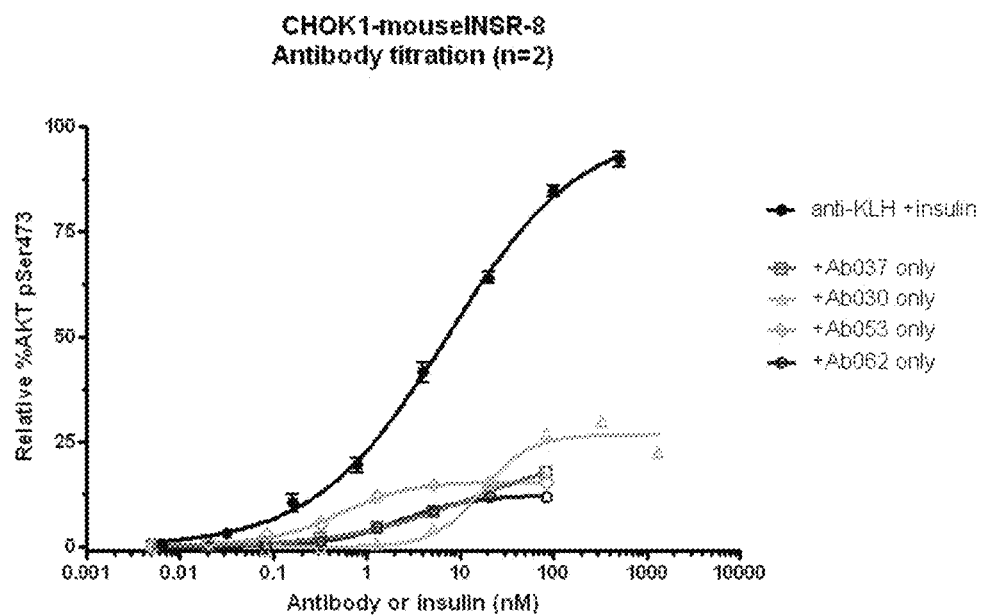

The relative % pAKT of agonist antibodies Ab037, Ab030, Ab053 and Ab062 on human INSR and mouse INSR are shown in FIGS. 50 and 51, respectively.

Figure 52:
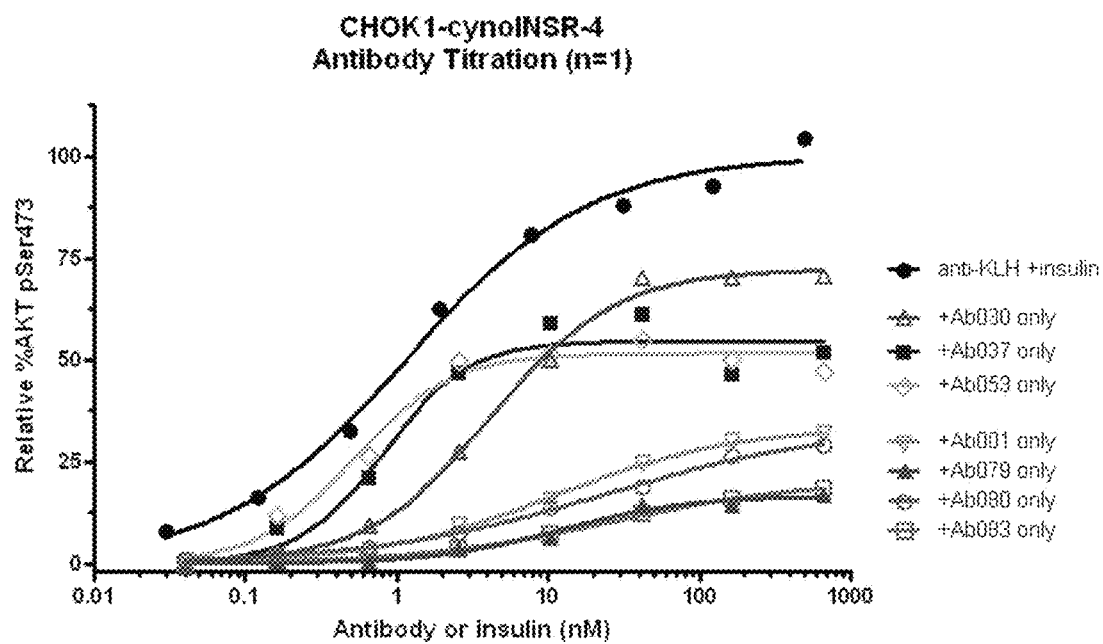
FIG. 52 demonstrates that the purified anti-INSR antibodies Ab030, Ab037, Ab053, Ab001, Ab079, AB080 and Ab083 are capable of inducing AKT phosphorylation (relative % pAKT) after activation of monkey INSR.

The relative % pAKT of positive modulator antibodies and agonist antibodies were also measured in CHOK1 cells expressing cynomolgous monkey INSR4. FIG. 52 demonstrates that the anti-INSR antibodies Ab030, Ab037, Ab053, Ab001, Ab079, AB080 and Ab083 are capable of inducing AKT phosphorylation after activation of monkey INSR.

Figure 53:
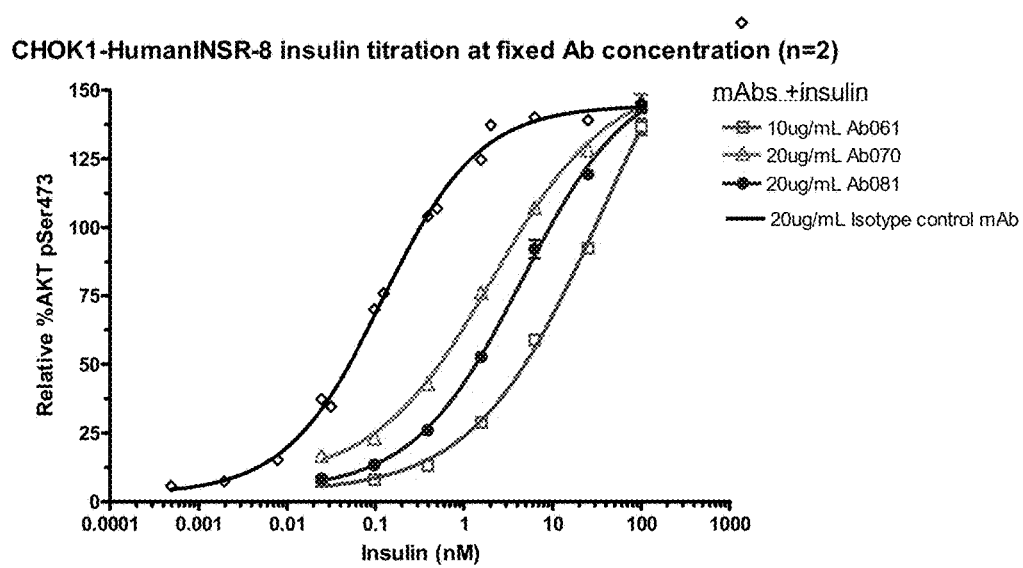
FIG. 53 shows the relative % pAKT of negative modulator antibodies Ab061, Ab070 and Ab081 measured in CHOK1 cells expressing human INSR.

Additionally, the relative % pAKT of negative modulator antibodies Ab061, Ab070 and Ab081 were also measured in CHOK1 cells expressing human INSR. The results are shown in Table 11 and FIG. 53.

TABLE 11

| | 10 ug/mL Ab061 | 20 ug/mL Ab070 | 20 ug/mL Ab081 | 20 ug/mL Isotype control mAb |
|---|---|---|---|---|
| Insulin EC50 | 32.43 | 2.09 | 4.53 | 0.12 |
| Fold change in EC50 relative to Isotype control mAb | 269 | 17 | 38 | |
| EC50 95% Confidence Intervals | 14.36 to 73.25 | 1.686 to 2.598 | 3.503 to 5.843 | 0.09691 to 0.1496 |

These results demonstrate that negative modulator antibodies increase the EC50 of insulin, in some cases by several hundred-fold.

Example 25

Assessment of Species Cross Reactivity of Anti-INSR Antibodies

This example describes the use of a FACS based assay to assess the binding of insulin receptor antibodies to cells of species such as rabbit and cynomolgous monkey that are often used in toxicological studies. Anti-INSR antibodies from phage display libraries were screened for both binding to peripheral blood monocytes of human, rabbit and cynomolgous monkeys and for differential binding in the presence or absence of the ligand (insulin) to the monocytes of the above named species.

Cynomolgous monkey whole blood was obtained from California National Primate Research Center (Davis, Calif.) and rabbit whole blood was obtained from LifeSource Biomedical, LLC (Moffett Field, Calif.). Human PBMC were purified using Ficoll Hypaque from buffy coats obtained from the American Red Cross. Cynomolgous and Rabbit PBMC were than purified using Ficoll Hypaque gradients (Pharmacia). Purified PBMC were frozen and stored in liquid nitrogen prior to use in the assay. Human, cynomolgous and rabbit PBMC were thawed and washed with FACS Buffer (0.5% BSA and 0.1% NaN3 in PBS). Once the cells were prepared, they were used in the FACS staining assay at a final concentration of $2 \times 10^6$ cells/ml.

To look at differential binding, cells were incubated in the presence or absence of the insulin with decreasing concentrations of anti-INSR antibody at 4° C. for 1 hour and washed once with FACS Buffer. The binding of anti-INSR antibody was revealed by the addition of goat anti-human IgG Alexa647 (Jackson ImmunoResearch) for 30 minutes at 4° C. After washing twice with FACS buffer, cells were stained with various markers to capture monocytes population. Human and cynomolgous cells were stained with CD45 and CD14. Rabbit cells were stained with CD11b and CD14. Antibodies were than incubated for 20 minutes and washed twice with FACS Buffer. Cells were than fixed with 2% paraformaldehyde and equal volume of FACS Buffer was added prior to cell analysis. The cells were analyzed on a FACScan™ (Becton-Dickinson, Franklin Lakes, N.J.) and the data was analyzed using both FloJo™ (Tristar, Paso Robles, Calif.) and GraphPad Prism 5 (GraphPad Software, La Jolla, Calif.).

The binding seen on human, rabbit or cynomolgous monkey PBMC was confirmed by generating CHO cell-lines that expressed the appropriate species insulin receptor and repeating the binding assay described above. Data shown in FIG. 54 shows that many of the antibodies that bound to the human insulin receptor also bound to the rabbit and the cynomolgous insulin receptor and that this binding was modulated by the presence of insulin.

Example 26

Measurement of the Affinity of Anti-INSR Antibodies in the Presence and Absence of Human Insulin The affinity of various anti-INSR antibodies for recombinant human INSR expressed on the surface of serum starved CHOK1 cells (hINSR8-CHOK1) was measured in the presence and absence of insulin. A KinExA assay was developed to measure very low levels of antibody in an incubation buffer. This assay allowed the binding of antibodies to cells expressing INSR to be measured by determining the level of antibody depletion from the incubation buffer. As antibody became bound to the cells, the concentration of antibody in the buffer solution dropped. By using a titration of cells expressing INSR and measuring the percent free antibody, the affinity of the antibody to INSR interaction could be estimated using KinExA software. This assay was used to determine the relative affinities of the tested antibody clones in the presence or absence of insulin and demonstrated insulin-dependent modulation of antibody binding to the cells.

hINSR8-CHOK1 cells were serum starved overnight and then prepared for assay as described in Example 20. One mL of 4 ug/mL insulin or buffer was added to each tube of cells to establish a final insulin concentration of 0 or 175 nM (1 ug/mL). Then 1 mL of 40 ng/mL antibody was added to each tube to yield a final antibody concentration of 10 ng/mL or 66.6 pM. Samples were incubated overnight at 4° C. for 18 hours then centrifuged to pellet cells and supernatants were removed for testing on the KinExA. The KinExA 3000 analysis was performed as described in Example 20 using beads coated with an (Fab')2 fragment goat anti-human IgG (H+L) (Jackson Immuno Research, West Grove Pa.). Detection solution used was R-PE-(Fab')2 fragment goat anti-Human IgG(H+L) (Jackson Immuno Research, West Grove Pa.). For the 83-7 murine antibody the beads were conjugated as above with a rabbit anti-mouse F(ab')2 antibody (Jackson Immuno Research, West Grove Pa.) and the detection solution used was an R-PE-(Fab')2 fragment Goat anti-Mouse IgG(H+L) (Jackson Immuno Research). The INSR concentration on the cells was estimated at $2.5 \times 10^5$ receptors/cell and bivalent antibody binding to INSR was assumed.

The affinities of a number of anti-INSR antibodies in the presence and absence of insulin are shown in Table 12. The agonist antibodies Ab037, Ab053, and Ab062 have binding that is independent of insulin and showed less than a two-fold affinity shift in the presence or absence of insulin. The 83-7 mouse antibody had a modest three-fold affinity shift in the presence of insulin, where as the positive modulator antibodies Ab001, Ab079, Ab080, and Ab083 all showed positive binding modulation in the presence of insulin ranging from seventeen-fold for Ab080 to over 100-fold for Ab001. The positive modulators Ab077 and Ab078 have a weaker affinity in the absence of insulin than the other clones and, as a result, their "without insulin" affinity was beyond the range of the assay, which is limited in maximum receptor concentration given the use of the cells as a receptor source. Although binding can be seen with these clones in the absence of insulin, it is substantially weaker than in the presence of insulin and modulated to a much greater extent than 83-7, but the degree of modulation cannot be accurately estimated with these assay conditions. Ab085 showed little to no evidence of binding in the absence of insulin and its binding is considered insulin dependent.

TABLE 12

Affinity of Antibodies to hINSRS-CHOK1 Cells

| mAb | With Insulin | Without Insulin | Fold Improvement with Insulin |
| --- | --- | --- | --- |
| Ab001 | 1.16E−10 | 1.20E−08 | 103 |
| Ab037 | 8.00E−11 | 1.08E−10 | 1.4 |
| Ab053 | 9.60E−11 | 1.48E−10 | 1.5 |
| Ab062 | 1.08E−10 | 1.24E−10 | 1.1 |
| Ab077 | 6.40E−09 | Out of Range* | |
| Ab078 | 3.40E−10 | Out of Range* | |
| Ab079 | 4.96E−10 | 9.60E−09 | 19.4 |
| Ab080 | 6.80E−10 | 1.20E−08 | 17.6 |
| Ab083 | 3.76E−10 | 7.60E−09 | 20.2 |
| Ab085 | 2.00E−10 | No Binding | |
| 83-7 | 1.60E−10 | 4.80E−10 | 3.0 |

Example 27

Epitope Binning of Anti-INSR Antibodies

A multifactoral approach was taken to epitope binning to determine if various anti-INSR antibodies bind to potentially similar epitopes or if they have demonstrated differential binding properties and different epitope recognition. Competitive binding or "binning" experiments were performed as well as analysis of the antibodies' ability to bind to different human and murine species of the insulin receptor and their ability to bind in the presence and absence of insulin. All of these are factors in determining the potential similarity or difference of antibody binding epitopes. Flow cytometry assays were performed by analyzing the binding of biotinylated IgG's to serum starved hINSR8-CHOK1 cells and mINSR-CHOK1 cells in the presence and absence of insulin For the competitive binding assay, hINSR8-CHOK1 cells and mINSR-CHOK1 cells were serum starved overnight and then prepared for assay as described in Example 20. In some embodiments, it is useful to calculate the number of receptors on the cell surface to carry out the competition binding assays. For example, hINSR8-CHOK1 receptor expression levels were determined initially by standard cell staining and flow cytometry techniques. Briefly this was carried out by staining the cells with a saturating concentration of MA-20 monoclonal Ab (ThermoFisher Scientific, Waltham Mass.) and detecting with R-Phycoerythrin conjugated goat anti-mouse IgG antibody (Jackson Immuno Research, West Grove Pa.) and then comparing relative fluorescence with BD Quantibrite™ PE Beads (BD Biosciences, Franklin Lakes N.J.) to provide an estimation of number of Phyco-erythrin molecules bound and extrapolate the number of insulin receptors based on the number of phycoerythrin molecules bound. This number was then further tested and refined using KinExA as described in Rathanaswami et al, (Analytical Biochemistry 373:52-60, 2008). Briefly, KinExA experiments were performed looking at both antibody and insulin binding where the ligand concentration used was much higher than that described herein for the determination of affinities which creates a more stoichiometrically limited dose response. This was then analyzed in the KinExA software (Sapidyne, Boise Id.) using an unknown ligand model and determination of a ligand multiplier parameter that was used to confirm binding receptor concentration. In the present assay, for example, it is estimated that the hINSR8-CHOK1 cells when serum starved express roughly 250,000 tetrameric INSR receptors per cell. For the antibody affinity, this means the stoichiometry of 2 antibodies per receptor tetramer and for the high affinity insulin binding site, a 1:1 tetramer to insulin ratio.

The antibodies to be tested were biotinylated using standard amine chemistry and the activated PEG4-biotin (Thermo-Fisher, Waltham Mass.). Mouse antibodies 83-7 and 83-14 were also tested. These antibodies have been reported to bind to amino acids 233-281 of the CR domain and to the FnIII-I domain of INSR, respectively (McKern et al, 2006; Nature 443: 218-21). After serum starving the transfected cells overnight, the cells were stained with a titration of the biotinylated antibodies in the presence of 1 ug/mL insulin. Antibodies were incubated on cells at 4° C. for approximately 30 minutes. Samples were then washed 2× in FACS buffer and Streptavidin-phycoerythrin (Jackson ImmunoResearch Labs, West Grove, Pa., USA) was used to detect biotinylated antibody. The concentrations of biotinylated antibodies used in the binning experiment were selected based on them having a subsaturating, but still strong, signal to the human cell line in the presence of insulin. Once the concentrations of the biotinylated antibodies to be used were experimentally determined, the competition assay was performed as below.

The cells were serum starved overnight and then resuspended in cold FACS buffer with or without 1 ug/mL human insulin. The cells were then mixed 1:1 with 60 ug/mL cold or unlabelled competitor antibody and incubated at 4° C. for approximately 30 minutes establishing a cold Ab concentration of 30 ug/mL. The biotinylated antibodies were then added in a 1:2 dilution as a 3× concentration and incubated at 4° C. for approximately 30 minutes. The cells were then washed 2× in FACS buffer and detected with Streptavidin-phycoerythrin and assayed on a FACS analyzer (Becton Dickinson, San Jose, Calif.).

MFI was compared between the biotinylated antibodies when mixed with a non-binding control antibody or with a competitor antibody. The extent of binding was measured on the human and the murine cell lines and in the presence or absence of insulin. A matrix approach was used where each biotinylated antibody was tested against each cold competitor. Antibodies with the same competition profiles are considered to be in the same bin. Exemplary bin groupings as presented in Table 13 are derived from the hINSR8-CHOK1 cells in the presence of insulin as virtually all clones had the strongest binding under those conditions. Clones shown in Table 13 are labeled to reflect other binding properties such as insulin dependence and murine reactivity.

Results of the experiment resulted in approximately seven different competition bins among the anti-INSR antibodies. An antibody with no competition is defined as one exhibiting less than 30% competition, partial competition is competition greater than 30% and less than 80%, and complete competition is greater than 80% competition using the method described above with hINSR8-CHOK1.

The antibodies that map to Bin 1, which are human and murine reactive, exhibited no competition with AB079, AB076, AB083, partial to complete competition with AB085 and AB086 and complete competition with AB030, AB037, AB053, AB001, AB018, and AB064, AB040.

The antibodies of Bin 2, which are human and murine reactive, exhibited the same profile as those antibodies in Bin 1, but demonstrated no competition with AB086 and partial competition with AB078.

The antibodies in Bin 3, which bind to both human and murine INSR, showed no competition with Ab062 and Ab086, partial Competition with Ab086, Ab064, Ab001, Ab018 and complete competition with Ab079, Ab076, Ab083, Ab080, Ab062, and Ab020, Ab019, Ab088, Ab089.

Bin 4 antibodies, which bind to human receptor only, exhibited no competition with Ab062, Ab086, Ab001, Ab018, Ab030, Ab037, Ab064 and complete competition with Ab079, Ab076, Ab083, Ab080, Ab062, and Ab020, Ab019, Ab088, Ab089

Bin 5 antibodies exhibit no competition with AB077, AB001, AB018, AB030, AB037, AB079, AB076, AB083, AB019, AB088, AB089, and AB040 and show complete competition with AB064, AB062, AB085, and AB078. These antibodies react with both human and murine receptor.

Bin 6 antibodies showed complete to partial competition with almost all clones tested. Clone Ab061 had less than 30% competition with Ab019 and clone Ab074 showed no competition with Ab088. These antibodies react with both human and murine receptor.

The antibodies grouped in Bin 7 showed no competition with Ab053, Ab064, 83-7, Ab019, Ab088, and Ab089, showed partial competition with Ab037, Ab078, Ab083, Ab080, and Ab085, and showed complete competition with Ab040, Ab062, Ab030, Ab001, and Ab018. These antibodies react with both human and murine receptor.

Competition Bin 4 which contains the murine 83-7 clone contained all of the clones that lacked murine reactivity. The antibody groupings correlated with their functional properties. All of the human agonist antibodies grouped into Bin 1. Positive modulator antibodies grouped into Bins 3 and 5 with the exception of Ab004. The Bin 3 antibodies bind both INSR-insulin complex and INSR alone, whereas the Bin 5 antibodies bind INSR-insulin complex but do not bind INSR alone.

| Epitope Bins | | | | | | |
|---|---|---|---|---|---|---|
| 1 | 2 | 3 | 4 | 5 | 6 | 7 |
| Ab030 | 63-14 | Ab079 | Ab020 | Ab078 | Ab061 | Ab004 |
| Ab037 | | Ab080 | Ab019 | Ab085 | Ab074 | |
| Ab053 | | Ab083 | Ab088 | | Ab077 | |
| Ab001 | | | Ab089 | | | |
| Ab018 | | | Ab087 | | | |
| Ab086 | | | 83-7 | | | |
| Ab062 | | | | | | |
| Ab064 | | | Human | | | |
| Ab040 | | | Specific | | | |
| | | | Aganist | | | |
| | | | Positive modulator (complex-specific binding) | | | |
| | | | Positive modulator (binds complexed and free INSR) | | | |
| | | | Negative Modulator | | | |

Numerous modifications and variations in the invention as set forth in the above illustrative examples are expected to occur to those skilled in the art. Consequently only such limitations as appear in the appended claims should be placed on the invention.

TABLE 1

Light Chain Sequences

| Name | Ab # | L-FR1 | L-CDR1 | L-FR2 | L-CDR2 | L-FR3 | L-CDR3 | L-FR4 | SEQ ID NO: |
|---|---|---|---|---|---|---|---|---|---|
| XPA-15-093_VL | Ab023 | QSVLT--QPP-SASGTPGQRVTISCSGS | ISNIGSNY- | VSWYQQLPGTAPKLLIY | GNS | NRPSGVPDRFSGSKSGTSASLAISGLRSEDEADYYC | AAWDDS-LSPHV | VFGGGTKLTVLG | 21 |
| XPA-15-096_VL | | QSVLT--QPP-SASGTPGQRVTISCSGS | FSNIGSNY- | VTWYQQLPGTARKLLIY | ADT | FRPSGVPDRFSGSKSGTSASLAISGLRSEDEADYYC | AAWDDS-LNGV- | VFGGGTKLTVLG | 22 |
| XPA-15-094_VL | Ab043 | QSVLT--QPP-SASGTPGQRVTISCSGS | ISNIGSNY- | VSWYQQLPGTAPKLLIY | GNS | NRPSGVPDRFSGSKSGTSASLAISGLRSEDEADYYC | AAWDDS-LSPHV | VFGGGTKLTVLG | 23 |
| XPA-15-106_VL | | QSVLT--QPP-SASGTPGQRVTISCSGS | SSNIGSNT- | VTWYQQLPGTAPKLLIY | SNN | QRPSGVPDRFSGSKSGTSASLAISGLRSEDEADYYC | ATWDDS-LSGW- | VFGGGTKLTVLG | 24 |
| XPA-15-105_VL | | QSVLT--QPP-SASGTPGQRVTISCSGG | PSNIGSNI- | VNWYQQLPGTAPKLLIY | SNN | QRPSGVPDRFSGSKSGTSASLAISGLRSEDEADYYC | ETWDSN--TQ-- | VFGGGTKLTVLG | 25 |
| XPA-15-100_VL | | QSVLT--QPP-SASGTPGQRVTISCSGS | ASNLGMHF- | VSWYQQLPGTAPKLLIY | DND | QRPSGVPDRFSGSKSGTSASLAISGLRSEDEADYYC | QSYDSS-LSGPV | LFGGGTKLTVLG | 26 |
| XPA-15-124_VL | | QSVLT--QPP-SASGTPGQRVTISCSGG | SSNIGAGYD | VHWYQQLPGTAPKLLIY | GNN | NRPSGVPDRFSGSKSGTSASLAISGLRSEDEADYYC | AAWDDS-LSGP- | VFGGGTKLTVLG | 27 |
| XPA-15-121_VL | Ab047 | QSVLT--QPP-SASGTPGQRVTISCSGS | SSNIGSNT- | VNWYQQLPGTAPKLLIY | DNN | KRPSGVPDRFSGSKSGTSASLAISGLRSEDEADYYC | QSYDSS-LSGWE | VFGGGTKLTVLG | 28 |
| XPA-15-122_VL | | QSVLT--QPP-SASGTPGQRVTISCSGS | SSNIGRNP- | VNWYQQLPGTAPKLLIY | GNS | NRPSGVPDRFSGSKSGTSASLAISGLRSEDEADYYC | AAWDDS-LNGQ- | VFGGGTKLTVLG | 29 |
| XPA-15-127_VL | | QSVLT--QPP-SASGTPGQRVTISCSGS | SSNIGNNY- | VAWYQQLPGTAPKLLIY | SDH | QRPSGVPDRFSGSKSGTSASLAISGLRSEDEADYYC | AAWDDS-LSGHV | IFGGGTKLTVLG | 30 |
| XPA-15-125_VL | | QSVLT--QPP-SASGTPGQRVTISCSGN | NSNIGSRT- | VNWYQQLPGTAPKLLIY | ENN | KRPSGVPDRFSGSKSGTSASLAISGLRSEDEADYYC | SSYAGS--NNLG | VFGGGTKLTVLG | 31 |
| XPA-15-133_VL | | QSVLT--QPP-SASGTPGQRVTISCSGS | FSNIGGNT- | VNWYQQLPGTAPKLLIY | SYD | QRPSGVPDRFSGSKSGTSASLAISGLRSEDEADYYC | ASWDVS-LSGV- | VFGGGTKLTVLG | 32 |
| XPA-15-135_VL | | QSVLT--QPP-SASGTPGQRVTISCSGS | SSNIGNNA- | VNWYQQLPGTAPKLLIY | TDS | RRPSGVPDRFSGSKSGTSASLAISGLRSEDEADYYC | VSRDDS-LNGW- | VFGGGTKLTVLG | 33 |
| XPA-15-139_VL | Ab018 | QSVLT--QPP-SASGTPGQRVTISCSGS | SSNIGSNT- | VNWYQQLPGTAPKLLIY | DNN | KRPSGVPDRFSGSKSGTSASLAISGLRSEDEADYYC | ATWDDS-LNGP- | IFGGGTKLTVLG | 34 |
| XPA-15-138_VL | Ab001 | QSVLT--QPP-SASGTPGQRVTISCSGS | TSNIGSNT- | VNWYQQLPGTAPKLLIY | RNN | QRPSGVPDRFSGSKSGTSASLAISGLRSEDEADYYC | AAWDDS-LNGFV | VFGGGTKLTVLG | 35 |

TABLE 1-continued

Light Chain Sequences

| Name | Ab # | L-FR1 | L-CDR1 | L-FR2 | L-CDR2 | L-FR3 | L-CDR3 | L-FR4 | SEQ ID NO: |
|---|---|---|---|---|---|---|---|---|---|
| XPA-15-143_VL_ | | QSVLT--QPP-SASGTPGQRVTISCSGS | SSNIGSNT- | VNWYQQLPGTAPKLLIY | GNT | NRPSGVPDRFSGSKSGTSASLAISGLRSEDEADYYC | AAWDDS-LSGV- | VFGGGTKLTVLG | 36 |
| XPA-15-141_VL_ | | QSVLT--QPP-SASGTPGQRVTISCSGS | SSNIGNNY- | VFWYQQLPGTAPKLLIY | RNY | QRPSGVPDRFSGSKSGTSASLAISGLRSEDEADYYC | ATWDDS-LTGW- | VFGGGTKLTVLG | 37 |
| XPA-15-145_VL_ | Ab012 | QSVLT--QPP-SASGTPGQRVTISCSGS | RSNIGANT- | VNWYQQLPGTAPKLLIY | GVN | HRPSGVPDRFSGSKSGTSASLAISGLRSEDEADYYC | AAWDDS-LNGW- | VFGGGTKLTVLG | 38 |
| XPA-15-140_VL_ | Ab015 | QSVLT--QPP-SASGTPGQRVTISCSGS | SSNIGSNT- | VSWYQQLPGTAPKLLIY | GAT | NRPSGVPDRFSGSKSGTSASLAISGLRSEDEADYYC | SSWDDS-LSGP- | VFGGGTKLTVLG | 39 |
| XPA-15-159_VL_ | | QSVLT--QPP-SASGTPGQRVTISCSGS | TSNIGNNY- | VSWYQQLPGTAPKLLIY | GNS | NRPSGVPDRFSGSKSGTSASLAISGLRSEDEADYYC | SAWDDT-LNGP- | VFGGGTKLTVLG | 40 |
| XPA-15-167_VL_ | | QSVLT--QPP-SASGTPGQRVTISCSGS | SSNIGNNY- | VSWYQQLPGTAPKLLIY | GDI | NRPSGVPDRFSGSKSGTSASLAISGLRSEDEADYYC | AAWDDR-LNGP- | VFGGGTKLTVLG | 41 |
| XPA-15-169_VL_ | Ab034 | QSVLT--QPP-SASGTPGQRVTISCSGG | SSNIGSNT- | VTWYQQLPGTAPKLLIY | DNN | KRPAGVPDRFSGSKSGTSASLAISGLRSEDEADYYC | AAWDDS-LSPHV | VFGGGTKLTVLG | 42 |
| XPA-15-013_VL_ | Ab006 | QSVLT--QPP-SASGTPGQRVTISCSGS | ISNIGSNY- | VSWYQQLPGTAPKLLIY | GNS | NRPSGVPDRFSGSKSGTSASLAISGLRSEDEADYYC | AAWDDS-LNGP- | VFGGGTKLTVLG | 43 |
| XPA-15-020_VL_ | | QSVLT--QPP-SASGTPGQRVTISCSGS | SSNIGNNY- | VSWYQQLPGTAPKLLIY | SNN | QRPSGVPDRFSGSKSGTSASLAISGLRSEDEADYYC | AAWDDS-LSPHV | VFGGGTKLTVLG | 44 |
| XPA-15-017_VL_ | Ab017 | QSVLT--QPP-SASGTPGQRVTISCTGS | SSNIGAGYD | VHWYQQLPGTAPKLLIY | GNS | NRPSGVPDRFSGSKSGTSASLAISGLRSEDEADYYC | AAWDDS-LNGL- | VFGGGTKLTVLG | 45 |
| XPA-15-009_VL_ | Ab022 | QSVLT--QPP-SASGTPGQRVTISCTGS | SSNIGAGYD | VHWYQQLPGTAPKLLIY | RND | QRPSGVPDRFSGSKSGTSASLAISGLRSEDEADYYC | AAWDDS-LSGW- | VFGGGTKLTVLG | 46 |
| XPA-15-033_VL_ | | QSVLT--QPP-SASGTPGQRVTISCSGT | SSNFGRRT- | VNWYQQLPGTAPKLLIY | SNN | LRPSGVPDRFSGSKSGTSASLAISGLRSEDEADYYC | AAWDHS-LSAHV | VFGGGTKLTVLG | 47 |
| XPA-15-037_VL_ | Ab031 | QSVLT--QPP-SASGTPGQRVTISCSGR | SSNIGINY- | VSWYQQLPGTAPKLLIY | GNS | NRPSGVPDRFSGSKSGTSASLAISGLRSEDEADYYC | AAWDDS-LNGW- | VFGGGTKLTVLG | 48 |
| XPA-15-042_VL_ | Ab027 | QSVLT--QPP-SASGTPGQRVTISCSGR | SSNIENNY- | VSWYQQLPGTAPKLLIY | GNS | NRPSGVPDRFSGSKSGTSASLAISGLRSEDEADYYC | AAWDDS-LSGP- | VFGGGTKLTVLG | 49 |
| XPA-15-036_VL_ | Ab030 | QSVLT--QPP-SASGTPGQRVTISCTGS | SSNIGAGYD | VHWYQQLPGTAPKLLIY | DNN | KRPSGVPDRFSGSKSGTSASLAISGLRSEDEADYYC | AAWDDS-LNGV- | VFGGGTKLTVLG | 50 |
| XPA-15-047_VL_ | Ab036 | QSVLT--QPP-SASGTPGQRVTISCSGS | SSNIGGNS- | VHWYQQLPGTAPKLLIY | GNS | NRPSGVPDRFSGSKSGTSASLAISGLRSEDEADYYC | ASWDDS HLHV-- | LFGGGTKLTVLG | 51 |
| | | | | | | | AAWDDS-LSPHV | VFGGGTKLTVLG | |

TABLE 1-continued

Light Chain Sequences

| Name | Ab # | L-FR1 | L-CDR1 | L-FR2 | L-CDR2 | L-FR3 | L-FR4 | L-CDR3 | L-FR4 | SEQ ID NO: |
|---|---|---|---|---|---|---|---|---|---|---|
| XPA-15-007_VL_ | Ab029 | QSVLT--QPP-SASGTPGQRVTISCSGN | SSNIGNSY- | VSWYQQLPGTAPKLLIY | SND | IRPSGVPDRFSGSKSGTSASLAISGLRSEDEADYYC | AAWDDS-LSGP- | VFGGGTKLTVLG | 52 |
| XPA-15-074_VL_ | Ab039 | QSVLT--QPP-SASGTPGQRVTISCSGS | SSNIGSNT- | VNWYQQLPGTAPKLLIY | RNN | QRPSGVPDRFSGSKSGTSASLAISGLRSEDEADYYC | AAWDDS-LSGP- | VFGGGTKLTVLG | 53 |
| XPA-15-085_VL_ | Ab011 | QSVLT--QPP-SASGTPGQRVTISCSGS | ISNIGSNY- | VSWYQQLPGTAPKLLIY | GNS | NRPSGVPDRFSGSKSGTSASLAISGLRSEDEADYYC | AAWDDS-LSPHV | VFGGGTKLTVLG | 54 |
| XPA-15-075_VL_ | Ab009 | QSVLT--QPP-SASGTPGQRVTISCSGS | ISNIGSNY- | VSWYQQLPGTAPKLLIY | GNS | NRPSGVPDRFSGSKSGTSASLAISGLRSEDEADYYC | AAWDDS-LSPHV | VFGGGTKLTVLG | 55 |
| XPA-15-082_VL_ | Ab041 | QSVLT--QPP-SASGTPGQRVTISCSGS | SSNIGSNT- | VTWYQQLPGTAPKLLIY | SNN | QRPSGVPDRFSGSKSGTSASLAISGLRSEDEADYYC | ATWDDS-LSGW- | VFGGGTKLTVLG | 56 |
| XPA-15-066_VL_ | Ab004 | QSVLT--QPP-SASGTPGQRVTISCSGG | NSNIGSNY- | VSWYQQLPGTAPKLLIY | RNN | QRPSGVPDRFSGSKSGTSASLAISGLRSEDEADYYC | AAWDDS-LSGR- | VFGGGTKLTVLG | 57 |
| XPA-15-080_VL_ | | QSVLT--QPP-SASGTPGQRVTISCTGS | SSNIGAGYV | VHWYQQLPGTAPKLLIY | TND | QRPSGVPDRFSGSKSGTSASLAISGLRSEDEADYYC | QSYDRS-LSGS- | VFGGGTKLTVLG | 58 |
| XPA-15-099_VL_ | | QSVLT--QPP-SASGTPGQRVTISCSGS | ISNIGSNY- | VSWYQQLPGTAPKLLIY | GNS | NRPSGVPDRFSGSKSGTSASLAISGLRSEDEADYYC | AAWDDS-LSPHV | VFGGGTKLTVLG | 59 |
| XPA-15-102_VL_ | Ab044 | QSVLT--QPP-SASGTPGQRVTISCSGS | TSNIGNNY- | VSWYQQLPGTAPKLLIY | GNS | NRPSGVPDRFSGSKSGTSASLAISGLRSEDEADYYC | SAWDDT-LNGP- | VFGGGTKLTVLG | 60 |
| XPA-15-115_VL_ | Ab046 | QSVLT--QPP-SASGTPGQRVTISCSGS | ISNIGSNY- | VSWYQXLPGTAPKLLIY | GNS | NRPSGVPDRFSGSKSGTSASLAISGLRSEDEADYYC | AAWDDS-LSPHV | VFGGGTKLTVLG | 61 |
| XPA-15-111_VL_ | Ab045 | QSVLT--QPP-SASGTPGQRVTISCSGS | SSNIGSNT- | VNWYQQLPGTAPKLLIY | GNS | NRSSGVPDRFSGSKSGTSASLAISGLRSEDEADYYC | AAWDDR-LNGP- | VFGGGTKLTVLG | 62 |
| XPA-15-142_VL_ | | QSVLT--QPP-SASGTPGQRVTISCSGR | NSNIGSNY- | VSWYQQLPGTAPKLLIY | RNN | QRPSGVPDRFSGSKSGTSASLAISGLRSEDVADYYC | SSYAGS--NNFV | VFGGGTKLTVLG | 63 |
| XPA-15-146_VL_ | | QSVLT--QPP-SASGTPGQRVTISCSGT | DSNFGSNS- | VNWYQQLPGTAPKLLIY | GNS | NRPSGVPDRFSGSKSGTSASLAISGLRSEDEADYYC | AAWDDS-LNGW- | VFGGGTKLTVLG | 64 |
| XPA-15-144_VL_ | | QSVLT--QPP-SASGTPGQRVTISCTGS | SSNIGAGYD | VHWYQQLPGTAPKLLIY | GNS | NRPSGVPDRFSGSKSGTSASLAISGLRSEDEADYYC | TSYTGN--NQFV | IFGGGTKLTVLG | 65 |
| XPA-15-154_VL_ | Ab033 | QSVLT--QPP-SASGTPGQRVTISCSGI | SSNIGNNF- | VSWYQQLPGTAPKLLIY | GNS | NRPSGVPDRFSGSKSGTSASLAISGLRSEDEADYYC | AAWDDS-PRGP- | VFGGGTKLTVLG | 66 |
| XPA-15-158_VL_ | Ab014 | QSVLT--QPP-SASGTPGQRVTISCSGC | SSNIGNNA- | VNWYQQLPGTAPKLLIY | RSD | QRLAGVPDRFSGSKSGTSASLAISGLRSEDEADYYC | QSYDSS-LIGHW | VFGGGTKLTVLG | 67 |

TABLE 1-continued

Light Chain Sequences

| Name | Ab # | L-FR1 | L-CDR1 | L-FR2 | L-CDR2 | L-FR3 | L-CDR3 | L-FR4 | SEQ ID NO: |
|---|---|---|---|---|---|---|---|---|---|
| XPA-15-155_VL_ | Ab048 | QSVLT--QPP-SASGTPGQRVTISCSGI | SSNIGNNF- | VSWYQQLPGTAPKLLIY | GNS | NRPSGVPDRFSGSKSGTSASLAISGLRSEDEADYYC | AAWDDS-PRGP- | VFGGGTKLTVLG | 68 |
| XPA-15-165_VL_ | Ab049 | QSVLT--QPP-SASGTPGQRVTISCSGR | SSNIGYNY- | VSWYQQLPGTAPKLLIY | GNS | NRPSGVPDRFSGSKSGTSASLAISGLRSEDEADYYC | AAWDDS-LSGP- | VFGGGTKLTVLG | 69 |
| XPA-15-023_VL_ | Ab025 | QSVLT--QPP-SASGTPGQRVTISCSGS | TSNIGNNY- | VSWYQQLPGTAPKLLIY | GNS | NRPSGVPDRFSGSKSGTSASLAISGLRSEDEADYYC | SAWDDT-LNGP- | VFGGGTKLTVLG | 70 |
| XPA-15-022_VL_ | Ab024 | QSVLT--QPP-SASGTPGQRVTISCSGT | SSNLGSHT- | VSWYQQLPGTAPKLLIY | DNN | ERPSGVPDRFSGSKSGTSASLAISGLRSEDEADYYC | AAWDDS-LSAW- | VFGGGTKLTVLG | 71 |
| XPA-15-019_VL_ | | QSVLT--QPP-SASGTPGQRVTISCSGS | SSNIGNNA- | VNWYQQLPGTAPKLLIY | SNN | QRPSGVPDRFSGSKSGTSASLAISGLRSEDEADYYC | GTWDDS-LSVW- | VFGGGTKLTVLG | 72 |
| XPA-15-021_VL_ | Ab023 | QSVLT--QPP-SASGTPGQRVTISCSGS | SSNIGSNP- | VNWYQQLPGTAPKLLIY | DNS | KRPSGVPDRFSGSKSGTSASLAISGLRSEDEADYYC | GTWDDS-LSVW- | VFGGGTKLTVLG | 73 |
| XPA-15-006_VL_ | Ab021 | QSVLT--QPP-SASGTPGQRVTISCTGT | SSNIGAGFD | VHWYQQLPGTAPKLLIY | SNN | QRPSGVPDRFSGSKSGTSASLAISGLRSEDEADYYC | AAWDDS-LNGL- | VFGGGTKLTVLG | 74 |
| XPA-15-026_VL_ | Ab026 | QSVLT--QPP-SASGTPGQRVTISCSGS | SSNIGNNY- | VSWYQQLPGTAPKLLIY | GNS | NRPSGVPDRFSGSKSGTSASLAISGLRSEDEADYYC | AAWDDS-LNGP- | VFGGGTKLTVLG | 75 |
| XPA-15-043_VL_ | | QSVLT--QPP-SASGTPGQRVTISCTGS | SSNIGAGYD | VHWYQQLPGTAPKLLIY | KNN | QRPSGVPDRFSGSKSGTSASLAISGLRSEDEADYYC | AAWDDS-LGG-- | VFGGGTKLTVLG | 76 |
| XPA-15-048_VL_ | Ab037 | QSVLT--QPP-SASGTPGQRVTISCSGS | SSNIGNSA- | VNWYQQLPGTAPKLLIY | DNN | NRPSGVPDRFSGSKSGTSASLAISGLRSEDEADYYC | QVWDSG--TA-- | VFGGGTKLTVLG | 77 |
| XPA-15-062_VL_ | | QSVLT--QPP-SASGTPGQRVTISCSGS | SSNIGNNY- | VSWYQQLPGTAPKLLIY | GNS | KRPSGVPDRFSGSKSGTSASLAISGLRSEDEADYYC | AAWDDS-LNGP- | VFGGGTKLTVLG | 78 |
| XPA-15-059_VL_ | Ab028 | QSVLT--QPP-SASGTPGQRVTISCSGS | SSNIGNNY- | VSWYQQLPGTAPKLLIY | SNN | NRPSGVPDRFSGSKSGTSASLAISGLRSEDEADYYC | AAWDDS-LNGL- | VFGGGTKLTVLG | 79 |
| XPA-15-064_VL_ | | QSVLT--QPP-SASGTPGQRVTISCSGS | SSNIGRRT- | VNWYQQLPGTAPKLLIY | DNN | QRPSGVPDRFSGSKSGTSASLAISGLRSEDEADYYC | ATWDDS-LNGW- | VFGGGTKLTVLG | 80 |
| XPA-15-068_VL_ | Ab013 | QSVLT--QPP-SASGTPGQRVTISCSGS | TSNIGNNY- | VSWYQQLPGTAPKLLIY | GNS | KRPSGVPDRFSGSKSGTSASLAISGLRSEDEADYYC | SAWDDT-LNGP- | VFGGGTKLTVLG | 81 |
| XPA-15-081_VL_ | Ab007 | QSVLT--QPP-SASGTPGQRVTISCSGS | TSNIGNNY- | VSWYQQLPGTAPKLLIY | GNS | NRPSGVPDRFSGSKSGTSASLAISGLRSEDEADYYC | SAMDDT-LNGP- | VFGGGTKLTVLG | 82 |
| XPA-15-065_VL_ | Ab038 | QSVLT--QPP-SASGTPGQRVTISCSGS | SSNIGSNT- | VTWYQQLPGTAPKLLIY | SNN | QRPSGVPDRFSGSKSGTSASLAISGLRSEDEADYYC | ATWDDS-LSGW- | VFGGGTKLTVLG | 83 |

TABLE 1-continued

Light Chain Sequences

| Name | Ab # | L-FR1 | L-CDR1 | L-FR2 | L-CDR2 | L-FR3 | L-CDR3 | L-FR4 | SEQ ID NO: |
|---|---|---|---|---|---|---|---|---|---|
| XPA.15-077_VL_ | Ab040 | QSVLT---QPP-SASGTPGQRVTISCSGS | SSNIGSNS-NS | VNWYQQLPGTAPKLLIY | DNN | KRPSGVPDRFSGSKSGTSASLAISGLRSEDEADYYC | AAWDDS-LSGP- | VFGGGTKLTVLG | 84 |
| XPA.15-086_VL_ | Ab042 | QSVLT---QPP-SASGTPGQRVTISCSGS | SSNIGSNT-NT | VTWYQQLPGTAPKPLIY | SNN | QRPSGVPDRFSGSKSGTSASLAISGLRSEDEADYYC | ATWDDS-LSGW- | VFGGGTKLTVLG | 85 |
| XPA.15-088_VL_ |  | QSVLT---QPP-SASGTPGQRVTISCSGS | ASNLGMHF- | VSWYQQLPGTAPKLLIY | DND | QRPSGVPDRFSGSKSGTSASLAISGLRSEDEADYYC | QSYDSS-LSGPV | LFGGGTKLTVLG | 86 |
| XPA.015.175_VL_ | Ab019 | DLVLTQSPASLAVSLGQR ATISCRAS | KSVSTSGYSY | IHWYQQKPGQPPKLLIY | LAS | NLESGVPARFSGSGSGTDFTLNIHPVEEEDAATYYC | -QHNREP | RTFGGGTNLEIKR | 1 |
| XPA.015.176_VL_ | Ab088 | DLVLTQSPASLAVSLGQR ATISCRAS | KSVTTSGYSY | IHWYQQKPGQPPKLLIY | LAS | NLESGAPARFSGSGSGTDFTLNIHPVEEEDAGNYYC | -QHNREP | RTFGGGTKLEIKR | 2 |
| XPA.015.177_VL_ |  | DIVMTQSPASLAVSLGQR ATISCRAS | KSVSTSGYSY | IHWYQQKPGQPPKLLIY | LAS | NLESGVPARFSGSGSGTDFTLNIHPVEEEDAATYYC | -QHNREL | RTFGGGTNLEIKR | 3 |
| XPA.015.178_VL_ | Ab089 | DLVLTQSPASLAVSLGQR ATISCRAS | KSVSTSGYSY | IHWYQQKPGQPPKLLIY | LAS | NLESGVPARFSGSGSGTDFTLNIHPVEEEDAATYYC | -QHNREL | RTFGGGTKLEIKR | 4 |
| XPA.015.179_VL_ |  | DLVLTQSPASVAVSLGQR ATISCRAS | KSVSTSGYSY | MHWYQQKPGQPPKLLIY | LAS | NLESGVPARFSGSGSGTDFTLNIHPVEEEDVATYYC | -QHNRDP | RTFGGGTKLEIKR | 5 |
| XPA.015.181_VL_ | Ab010* | DVQIIQSPSYLAASPGET KSIS---ITINCRAS | KY | LAWYQEKPGKTNKLLIY | SGS | TLQSGIPSRFSGSGSGTDFTLTISSLEPEDFAMYYC | QQHNEYP | LTFGAGTKLELKR | 6 |
| XPA.015.182_VL_ | Ab020 | DVQITQSPSYLAASPGET KSIS---ITINCRAS | KY | LAWYQEKPGKTNKLLIY | SGS | TLQSGIPSRFSGSGSGTDFTLTISSLEPEDFAMYYC | QQHNEYP | RTFGGGTKLEIKR | 7 |
| XPA.015.183_VL_ |  | DLVLTQSPASLAVSLGQR ATISCRAS | KSVSTSGYSY | IHWYQQKPGQPPKLLIY | LAS | NLESGVPARFSGSGSGTDFTLNIHPVEEEDAATYYC | -QHNREL | RTFGGGTKLEIKR | 8 |
| XPA.015.184_VL_ |  | DIVMTQSPTSLAVSLGQR ATISCRAS | RSVSISGYSY | IHWYQQRPGQPPKLLIY | LAS | NLESGVPARFSGSGSGTDFTLNIHPVEEEDAATYYC | -QHNRDP | RTFGGGTKLEIKR | 9 |
| XPA.015.185_VL_ | Ab003 | DIQMTQSPSYLAASPGET KSIS---ITINCRAS | KY | LAWYQEKPGKTNKLLIY | SGS | TLQSGIPSRFSGSGSGTDFTLTISSLEPEDFAMYYC | QQHNEYP | LTFGAGTKLELKR | 10 |
| XPA.015.186_VL_ |  | DIQMTQSPSSLSASLGDT ITITCHAS | QNIN---VW | LTWYQQKPGNIPKLLIS | KAS | NLHTGVPSRFSGSGSGTGFTLTISSLQPEDIATYYC | QQGQSYP | WTFGGGTKLEIKR | 11 |
| XPA.015.187_VL_ |  | DLVLTQSPASLAVSLGQR ATISCRAS | KSVSTSGYSY | IHWYQQKPGQPPKLLIY | LAS | NLESGVPARFSGSGSGTDFTLNIHPVEEEDAGNYYC | -QHNREP | RTFGGGTKLEIKR | 12 |
| XPA.015.188_VL_ | Ab008 | DVQITQSPSYLTASPGET ITINCRAS | KSIS---NY | LAWYQEKPGKTNKLLIY | SGS | TLQSGIPSRFSGSGSGTDFTFTISSLEPEDFAMYYC | QQHNEYP | LTFGAGTKLELKR | 13 |

TABLE 1-continued

Light Chain Sequences

| Name | Ab # | L-FR1 | L-CDR1 | L-FR2 | L-CDR2 | L-FR3 | L-CDR3 | L-FR4 | SEQ ID NO: |
|---|---|---|---|---|---|---|---|---|---|
| XPA.015.189_VL_ | | DIVMTQSPASLAVSLGQR ATISCRAS | KSVSISGYSY | IHWYQQKPGQPPKLLIY | LAS | NLESGVPARFSGSGSGTDFTLNIHPVEEEDAGNYYC | -QHNREP | RTFGGGTKLEIKR | 14 |
| XPA.015.190_VL_ | Ab002 | DIQMTQTTSSLSASLGDR VTISCRAS | QDIS----NY | LNWYQQKPDGTVKLLIY | YTS | RLHSGVPSRFSGSGSGTDYSLTISNLEPEDIATFYC | QQYSDLP | YTFGGGTKLEIKR | 15 |
| XPA.015.191_VL_ | | DVQITQSPSSLSASLGER VSLTCRAS | QDIG----SS | LNWLQQEPDGTIKRLIS | ATS | TLDSGVPKRFSGSRSGDYSLTISSLEPEDFVDYYC | LQYASYP | FTFGSGTKVEIKR | 16 |
| XPA.015.192_VL_ | Ab005 | DIQMTQSPSYLAASPGET ITINCRAS | KSIS----KY | LAWYQEKPGKTNKLLIY | SGS | TLQSGIPSRFSGSGSGTDFTLTISSLEPEDFAMYYC | QQHNEYP | LTFGAGTKLELKR | 17 |
| XPA.015.173_VL_ | Ab087 | DIQMTQSPSSLSASLGGK VTITCKAS | QHIN----KY | IAWYQHKPGKGPRLLIH | YTS | TLQPGIPSRFSGSGSGRDYSFSISNLEPEDIATYYC | LQYDNL- | YTFGGGTKLEIKR | 18 |
| XPA.015.174_VL_ | | DIQMTQSPSSLFASLGER VSLTCRAS | QDIG----DR | LYWLQQEPDGAIKRLIF | ATS | SLDSGVPKRFSGSRSGSEYSLTISSLESEDFVDYYC | LQYASSP | WTFGGGTKLEIKR | 19 |
| XPA.015.172_VL_ | | DIVMTQSPTSLAVSLGQR ATISCRAS | KSVSTSGYSY | IHWYQQKPGQPPKLLIY | LAS | NLESGVPARFSGSGSGTDFILNIHPVEEEDAATYYC | -QHNRDP | RTFGGGTKLELKR | 20 |
| XPA.15.193 | Ab050 | NFMLTQPHSVSESPGKTV SISCTGS | SGSIGSNY | VQWYQQRPGSAPTVIY | EDN | QRPSGVPDRFSGSIDSSNSALTISGLKTEDEADYYC | QSYYNSNV | VFGGGTKLTVL | 87 |
| XPA.15.194 | Ab051 | SSELTQDPAVSVALGQTV RITCQGN | SLRSFY | ATWYQQKPGQAPVLVIY | GKN | IRPSGIPDRFSGNSGDTASLTITGQAEDEADYYC | NSRDNNRNHL | LFAGGTKVTVL | 88 |
| XPA.15.195 | Ab052 | QAMLTQPASLSAPGASA SLTCTLR | SGINVVAYN | IYWYRQKSGSPPQSVLR | YKSDSDS | ERDSGVPSRFSGSKDVSANAGILLISGLQSEDEADYYC | LIWHNSAW | VFGGGTKVTVL | 89 |
| XPA.15.196 | Ab053 | QSALTQPRSVSESPGKTV TISCTGS | SGSIGSNY | VQWYQQRPGSAPTVIF | EDN | RRPSGVPDRFSGSIHSSSNSASLTISGLKTEDEADYYC | QSYVGTIV | VFGGGTKVTVL | 90 |
| XPA.15.197 | Ab054 | QSALTQPRSVSESPGKTV TISCTGS | SGSIGSNY | VQWYQQRPGSAPTVIF | EDN | RRPSGVPDRFSGSIHSSSNSASLTISGLKTEDEADYYC | QSYVGTIV | VFGGGTKVTVL | 91 |
| XPA.15.198 | Ab055 | SYELTQLPSVSVSPGQTA RITCSGD | ALPNKY | ATWYQQKSGQAPVLVIY | EDT | RRPSEIPERFSASSSGTMATLTISGAQVEDEAEYYC | YSTDSSGNER | VFGGGTKLTVL | 92 |
| XPA.15.199 | Ab056 | QSALTQPASVSESPGQSI TISCTGT | GSDIGTYNL | VSWYQHHPGKAPKLMIY | EVT | KRPSGVSNRFSGSKSGNTASLTISGLQAEDEADYYC | SSYTSSSTLY | VFGTGTKLTVL | 93 |
| XPA.15.200 | Ab057 | QTVVTQEPSFSVSPGGTV TLTCGLT | SGSVSTSYY | PSWYQQTPGQAPRMLVH | STS | TRYSGVPDRFSGSILGNKAALTITGAQADDESDYYC | ALYMGGGIY | VFGGGTQLTVL | 94 |
| XPA.15.201 | | QAVLTQPSSSSAPGESA RLTCTLP | SDINVRYHN | IYWYQEKPGSPPRYLLY | YYSDSSK | GQGSGVPSRFSGSKDVSTNTGILVISLQSEDEAEYYC | MTWSSNGSG | VFGGGTQLTVL | 95 |

TABLE 1-continued

Light Chain Sequences

| Name | Ab # | L-FR1 | L-CDR1 | L-FR2 | L-CDR2 | L-FR3 | L-CDR3 | L-FR4 | SEQ ID NO: |
|---|---|---|---|---|---|---|---|---|---|
| XPA.15.202 | Ab058 | QSVLTQPPSVSGAPGQRV TISCTGS | RSNIGADHD | VHWYQQIPGRAPKLLIY | GNS | NRPSGVPDRFSGSRSGTSASLAITGLQAEDEADYYC | QSYDNS LSGS | VFGGGTKLTVL | 96 |
| XPA.15.203 |  | QTVVTQEPSFSVSPGGTV TLTCGLN | SASVSTYSY | PSWYQQTPGQAPRMLIY | STN | TRSSGVPDRFSGSILGNKAALTITGAQADDESDYYC | ALYMGS GIW | VFGGGTKLTVL | 97 |
| XPA.15.204 | Ab059 | QAVLTQPASLSASPGASA SLICTLR | SDISVGYR | ISWYQQKPGSPPQYLLS | YNSD SNN | HQGSGVPDRFSGSKDASANAGLLLISGLQSEDEADYYC | MIWHIN AW | VFGGGTKVTVL | 98 |
| XPA.15.205 |  | QSVLTQPPSVSGAPGQRV TISCIGS | RSDIGYYA | VHWYRQLPGTAPKLVIY | AND | NRPSGVPDRFSGSKSGTSAFLAISGLQADDEADYYC | QSYDTV TGKG | VFGGGTKVTVL | 99 |
| XPA.15.206 |  | QSVLTQPPSVSGAPGQRV TISCGS | SSNIGAGYY | AHWYQQLPGTAPRLLIY | GNS | NRPSGVPDRFSGSKSGTSASLAITGLQAEDEADYYC | QSYDSS LSGPNY | VFGTGTKVTVL | 100 |
| XPA.15.207 | Ab060 | QAVLTQPASLSASPGESA RLTCTLP | SDINVRYN | IYWYQQKPGSPPRYLLY | YYSD SNK | DQGSGVPSRFSGSKDVSTNTGILVISGLQSEDEAEYYC | MTWSSN GSG | VFGGGTQLTVL | 101 |
| XPA.15.208 |  | QAVLTQPASLSASPGESA RLTCTLP | SDINVRYHN | IYWYQEKPGSPPRYLLY | YYSD SSK | GQGSGVPSRFSGSKDVSTNTGILVISGLQSEDEAEYYC | MTWSSN GSG | VFGGGTKLTVL | 102 |
| XPA.15.209 | Ab061 | QTVVTQEPSFSVSPGGTV TLTCGLS | SGSVSTGYS | PGWYQQTPGQAPRTLVY | NTN | TRSSGVPDRFSGSILGNKAALTITGAQADDESDYYC | ALYMGS GTY | VFGGGTKVTVL | 103 |
| XPA.15.211 |  | QSVLTQPPSVSGAPGQRV TISCTGS | SSNIGAGYD | VHWYQQLPGTAPKLLIY | GNS | NRPSGVPDRFSGSKSGTSASLAITGLQAEDEADYYC | QSYDSS LSGSG | VFGGGTKVTVL | 104 |
| XPA.15.212 | Ab063 | SSELTQPPSVSVAPGKTA TITCGGD | NIASKS | VHWYQQKPGQAPVLVLY | DDS | VRPSDIPERFSGSNSANTATLTLTRVEAGDEGEYYC | QVWDVR SDHP | FFGPGTKVTVL | 105 |
| XPA.15.213 | Ab064 | QAVVTQEPSLTVSPGGTV TLTCASS | TGAVTSGYY | PNWFQQKPGQAPRALIY | STS | NKHSWTPARFSGSLLGGKAALTLSGVQPEDEAEYYC | LLYYGG AQPW | VFGGGTQLTVL | 106 |
| XPA.15.214 | Ab065 | QAGLTQPPSVSKLRQTAN TLTCTGD | NIVGDQG | AAWLQHQGHPPKLLSF | RNN | SRPSGISERFSASRSRNTASLTITRLQPEDAADYYC | SAWDSF LSAW | VFGGGTKLTVL | 107 |
| XPA.15.215 | Ab066 | SSELTQDPAVSVAVGQSV RITCQGD | SLKNFY | ATWYQQRPGQAPLLVIF | GKN | NRPSGIPDRFSGSSSGNTASLTVTGAQADDEADYYC | NSPDSS NKLV | VFGGGTKLTVL | 108 |
| XPA.15.216 | Ab067 | EIVLTQSPGTLSLSPGER ATLSCRAS | QSVSSSY | LAWYQQKPGQAPRLLIY | GAS | SRATGIPDRFSGSGSGTDFTLTISRLEPEDFAVYYC | QQYGSSL | GTFGQGTKLEIK | 109 |
| XPA.15.217 | Ab068 | DVVMTQTPLSLSVTPGQP ASISCKAS | QSLLYTNGD TY | VSWYVQKPGQAPQLLFS | DVS | SRFFGVPDRFSASGSGTDFTLKISRVEAEDVGVYYC | VQAMYLP | LVFGQGTKVEIK | 110 |
| XPA.15.218 |  | SSELTQDPAVSVALGQTV RITCQGD | SLRSYY | ASWYQKPGQAPVLVIY | GKN | NRPSGIPDRFSGSSSGNTASLTITGAQAEDEADYYC | NSRDSS GNHL | MEGGGTQLTVL | 111 |

TABLE 1-continued

Light Chain Sequences

| Name | Ab # | L-FR1 | L-CDR1 | L-FR2 | L-CDR2 | L-FR3 | L-CDR3 | L-FR4 | SEQ ID NO: |
|---|---|---|---|---|---|---|---|---|---|
| XPA.15.219 | Ab086 | QSALTQPASVSGSLGQSITISCTGT | SSDIGLYKF | VSWYQQHPGKAPKLMIY | DVS | YRPSGVSNRFSGSSSGNTASLTISGLQAEDEADYYC | NSYTSSSTLV | VFGGGTKLTVL | 112 |
| XPA.15.220 | | SSELTQDDPAVSVSPAVSVALGQTVRITCQGD | SLRNYY | ASWYQQKPGQAPLLVMY | DRN | SRPSGIPDRFSGSRSGNTASLTITGAQAEDEADYYC | NSRDSSGNHA | VFGGGTQLTVL | 113 |
| XPA.15.221 | | SYELMQPPSVSVAPGQTANIGTKSTITCGGN | SLRSYY | VHWYQQKTGQAPVLVVY | DDS | DRPSGIPERFSGSNSGNTATLTISRLEAGDEADYYC | QVWDRSSEHH | VFGGGTQLTVL | 114 |
| XPA.15.222 | Ab069 | SSELTQDDPAVSVALGQTVRITCQGD | SLRSYY | ASWYQQKPGQAPVLVIY | GKN | NRPSGIPDRFSGSSSGNTASLTITGAQAEDEADYYC | NSRDSSGNHV | VFGGGTKVTVL | 115 |
| XPA.15.223 | | SSELTQDDPAVSVALGQTVRITCQGD | SLRSYS | VAWYQQKPGQAPLLVIY | GNT | NRPSGIPDRFSGSSSGNTASLTITGAQAEDEADYYC | NSRASSGFSW | VFGGGTKVTVL | 116 |
| XPA.15.224 | | SSELTQDDPAVSVALGQTVRITCQGD | SLRSYY | ASWYQQKPGQAPVLVIY | GKN | NRPSGIPDRFSGSSSGNTASLTITGAQAEDEADYYC | NSRDSSGNHA | VFGGGTQLTVLG | 117 |
| XPA.15.225 | | SYELMQPPSVSVAPGQTANIGTKSTITCGGN | SLRSYY | VHWYQQKTGQAPVLVVY | DDS | DRPSGIPERFSGSNSGNTATLTISRLEAGDEADYYC | QVWDRSSEHH | VFGGGTQLTVL | 118 |
| XPA.15.226 | Ab070 | SSELTQDDPAVSVALGQTVRITCQGD | SLRSYY | TSWYQQKPGQAPVLVIF | GKN | NRPSGIPDRFSGSSSGNTASLTITGAQAEDEADYYC | NSRDSSGNYA | VFGGGTQLTVL | 119 |
| XPA.15.227 | Ab071 | SSELTQDDPAVSVSPAVSVALGQTVRITCQGD | SLRSYY | ASWYQQKPGQAPVLVFY | GKN | NRPSGIPDRFSGSKSGNTASLTITGAQAEDEADYYC | NSRDSSGNHW | VFGGGTKLTVL | 120 |
| XPA.15.228 | Ab072 | STVLTQPPSASGTPGQRVTISCSGS | NSNIGSNF | VTWYQQLPGAAPKLLIY | TNS | QRPSGVPDRFSGSRSGTSASLAISGLQSEDEADYFC | AAWDDSLNGP | VFGGGTQLTVL | 121 |
| XPA.15.229 | Ab073 | QSVLTQPPSVSAAAGQKVTISCSGS | SSNIGNNY | VTWYQHVPGTAPKLLIF | DND | KRPSGIPDRFSGSKSGTSATLAITGLQTGDEADYYC | GTWDSSLNP | LFGGGTQLTVL | 122 |
| XPA.15.230 | Ab074 | SSELTQDDPAVSVALGQTVRITCQGD | SLRSYY | ASWYQQKPGQAPVLVIY | GKN | NRPSGIPDRFSGSSSGNTASLTITGAQAEDEADYYC | SSRDSSGDQW | VFGGGTKLTVL | 123 |
| XPA.15.231 | | SSELTQNPAVSVALGQTVRITCQGD | SLRNYY | ASWYQQKPGQAPLLVMY | DRN | SRPSGIPDRFSGSRSGNTASLTITGAQAEDEADYYC | NSRDSSGNHA | VFGGGTQLTVL | 124 |
| XPA.15.232 | Ab075 | QSVLTQPPSVSAAPGQKVTISCSGS | SSNIGNNY | VTWYQHVPGTAPKLLIF | DND | KRPSGIPDRFSGSKSGTSATLAITGLQTGDEADYYC | GTWDSSLNP | LFGGGTQLTVL | 125 |
| XPA.15.233 | | QSVLTQPPSVSAAAGQKVTISCSGS | SSNIGNNY | VTWYQHVPGTAPKLLIF | DND | KRPSGIPDRFSGSKSGTSATLAITGLQTGDEADYYC | GTWDSSLNP | LFGGGTQLTVL | 126 |

TABLE 1-continued

Light Chain Sequences

| Name | Ab # | L-FR1 | L-CDR1 | L-FR2 | L-CDR2 | L-FR3 | L-CDR3 | L-FR4 | SEQ ID NO: |
|---|---|---|---|---|---|---|---|---|---|
| XPA.15.234 | | QSVLTQPPSVSAAAGQKV TISCSGS | SSNIGNNY | VTWYQHVPGTAPKLLIF | DND | KRPSGIPDRFSGSKSGTSATLAITGLQTGDEADYYC | GTWDSS LNP | LFGGGTQLTVL | 127 |
| XPA.15.235 | | DVVMTQSPLSLPVTLGQP ASISCRSS | QSLVYSDGN TY | LNWFQQRPGQSPRRLIY | KVS | NRDSGVPDRFSGSGSGTDFTLKISRVEAEDVGVYYC | MQGTH | WSFGQGTRLEIK | 128 |
| XPA.15.236 | | EIVLTQSPDFQSVTPKEK VTITCRAS | QSIGSS | LHWYQQKPDQSPKLLIK | YAS | QSISGVPSRFSGSGSGTDFTLTTNSLEAEDAATYYC | HQSSSLP | WTFGQGTKVEIK | 129 |
| XPA.15.237 | | DIQLTQSPSSLSASVGDR VTITCRAS | QGISNS | LAWYQQKPGKAPKLLIY | AAS | RLESGVPSRFSGSGSGTDYTLTISSLQPEDFATYYC | QQYYSTL | LTFGGGTKVDIK | 130 |
| XPA.15.238 | | EIVLTQSPGTLSLSPGER ATLSCRAS | QSVSSSY | LAWYQRKPGRAPRLLIY | GAS | SRATGIPNRFSGSGSGTDFTLTISRLEPEDFAVYYC | QQYGSSP | PTFGQGTKLEIK | 131 |
| XPA.15.239 | | DIVMTQSPLSLPVTPGEP ASISCRSS | QSLLHSNGY NY | LDWYLQKPGQSPQLLIY | LGS | NRASGVPDRFSGSGSGTDFTLKISRVEAEDVGVYYC | MQALQTP | HTFGQGTKLEIK | 132 |
| XPA.15.241 | Ab076 | EIVMTQSPATLSVSPGER ATLSCRAS | QSISTN | LAWYQQKPGQTPRLLIY | GAS | TRATGIPARFSGSGSGTEFTLTISSLQSEDFAVYYC | QQYNSE | ISFGQGTRLEIK | 133 |
| XPA.15.242 | Ab077 | DIQMTQSPSSLSASVGDR VTITCRAS | QGISNS | LAWYQQKPGKAPKLLIY | ATS | RLETGVPSRFSGSGSGTDFTLTISSLQPEDFASYYC | QQFYSN | PSFGQGTKVEIK | 134 |
| XPA.15.243 | Ab078 | DIQLTQSPSSLSASVGDR VTITCRAS | QGISSW | LAWYQQKPGKAPKLLIY | AAS | SLQSGVPSRFSGSGSGTDFTLTISSLQPEDFATYYC | QQANSFP | ITFGQGTKLEIK | 135 |
| XPA.15.244 | Ab079 | AIRMTQSPSTLSASVGDR VTITCRAS | QGISSA | LAWYQQKPGKAPKVLIY | DAS | SLERGVPSRFSGSGSGTDFTLTISSLQPEDFASYYC | HQFNSYP | DTFGQGTRLEIK | 136 |
| XPA.15.245 | Ab080 | EIVLTQSPGTLSLSPGER ATLSCRAS | QSISTW | LAWYQQKPGKAPKLLIY | TTS | TLESGVPSRFSGSRSGTEFTLTISSLQPDDFATYYC | QQYNSYP | LTFGGGTKVEIK | 137 |
| XPA.15.246 | Ab081 | DVVMTQSPLSLSVTLGQP ASISCRSS | QSLSSSF | LAWYQQKPGQAPRLLIY | GAG | SRATGVPDRFSGSGYGTDFTLTISRLELEDFAVYYC | QQYDRSQ | ITFGQGTRLEIK | 138 |
| XPA.15.247 | Ab082 | DVVMTQSPLSLSVTLGQP ASISCRSS | LSLVYGDEN TY | LNWFQQRPGQSPRRLLY | KVS | DRDSGVPDRFSGSGSGTDFTLKISRVEAADVGVYYC | MQGTHWP | YTFGQGTRLEIK | 139 |
| XPA.15.248 | | EIVLTQSPDFQSVTPKET VTITCRAS | QNIGVS | LHWYQQKPDQSPKVLIK | YAS | QSLSGVPSRFSGTGSSTDFTLTIKSLEAEDAATYYC | LQTSSLP | WTFGQGTKVEIK | 140 |
| XPA.15.249 | Ab083 | AIQLTQSPSSLSASVGDR VTISCRAS | QSITSY | LNWYQQKPGKAPNLLIY | AAS | SLQSGVPSRFSGSGSGTDFTLTIAGLQPEDFATYYC | QQFDSYP | FTFGGGTKLEIK | 141 |

TABLE 1-continued

Light Chain Sequences

| Name | Ab # | L-FR1 | L-CDR1 | L-FR2 | L-CDR2 | L-FR3 | L-CDR3 | L-FR4 | SEQ ID NO: |
|---|---|---|---|---|---|---|---|---|---|
| XPA.15.250 | Ab084 | AIRMTQSPSTLSASVGDR VTITCRAS | QSISSW | LAWYQQTPGKAPKLLIY | AAS | NLQSGVPSRFSGSGSGTDFTLTISSLQPEDFATYYC | QQSYNTP | LTFGGGTKVEIK | 142 |
| XPA.15.272 | | QSALTQPASVSGSPGQSI TISCLGT | INDVGLYNL | VSWYQQHPGKAPKLMIY | EVS | KRPSGVSNRFSGSKSGNTASLTISGLQAEDEAVYYC | NSYTSS SNFW | VFGGGTQLTVLG | 143 |
| XPA.15.275 | Ab085 | QTVVTQEPSFSVSPGGTV TLTCGLT | SGSVSTRNF | PGWYQQTPGQTLRTLIY | NTN | TRSSGVPDRFSGSILGNKAALTITGAQADDESDYYC | VLYMTG DIW | VFGGGTKVTVLG | 144 |
| XPA.15.282 | | QSVLTQPPSVSAAAGQKV TISCSGS | SSNIGNNY | VTWYQHVPGTAPKLLIF | DND | KRPSGIPDRFSGSKSGTSATLAITGLQTGDEADYYC | GTWDSS LNP | LFGGGTQLTVLG | 145 |
| XPA.15.284 | | QSVLTQPPSVSAAAGQKV TISCSGS | SSNIGNNY | VTWYQHVPGTAPKLLIF | DND | KRPSGIPDRFSGSKSGTSATLAITGLQTGDEADYYC | GTWDSS LNP | LFGGGTQLTVLG | 146 |
| XPA.15.293 | | DIVMTQTPLSLPVTPGEP QSLLDSDDG ASISCRSS NTY | | LDWYVQKPGQSPQLLMY | SLS | YRASGVPDRFSGSGSGTDFTLKISRVEAEDVGVYYC | MQRIEFP | YTFGQGTKLEIKR | 147 |
| XPA.15.110 | | QSVLTQPPSASGTPGQRV TISCSGS | SSNIGRNP | ISWYQQLPGTAPKLLIY | NND | QRPSGVPDRFSGSKSGTSASLAISGLRSEDEADYYC | AAWDDS LNGPVW | VFGGGTKLTVLG | 148 |
| XPA.15.120 | | QSVLTQPPSASGTPGQRV TISCSGS | SSNIGNNY | VSWYQQLPGTAPKLLIY | GNS | NRPSGVPDRFSGSKSGTSASLAISGLRSEDEADYYC | AAWDDS LSAV | VFGGGTKLTVLG | 149 |
| XPA.15.163 | | QSVLTQPPSASGTPGLRV SSNIGAGYD IISCAGS | | VHWYHQLPGTAPKLLIY | GNS | NQPSGVPDRFSGSKSGTSASLAISGLRSEDEADYYC | TSYTGN NQFV | IFGGGTKLTVLG | 150 |

TABLE 2

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA.015.172_VH | | QVQLQQSEAELVK PGASVKISCKAS | GYTFSSYW | MSWVKQRPGKGLEWIGQ | IYPGDGD T-- | NYNGKFKGKATLTADKSSGTAYMQLSSLTSEDSAVYFC | ARGVS-GYGAMDY | WGQGTSVTVSS | 151 |
| XPA.015.173_VH | Ab087 | EVQLVESGGGLVK PGGSLKLSCAAS | GFTFSNYA | MSWVRQTPEKRLEWVAT | IS--DGGHYI | DYPDNVKGRFTISRDNAKNNLYLQMSHLRSEDSAMYYC | ARA----TNFAY | WGQGTLVTVSA | 169 |
| XPA.015.174_VH | | QVQLQQSGPELVK PGASVKLSCKAS | GYTFTSYD | INWVKQRPGQGLEWIGW | IYPRDGS T-- | KSNEKFKGKATLTVDTSSSTAYMELHSLTSEDSAVYFC | AR-----EFDY | WGQGTLVTVSA | 170 |
| XPA.015.175_VH | Ab019 | QVQLQQSEAELVK PGASVKISCKAS | GYTFSNYW | MNWVKQRPGKGLEWIGQ | IYPGDGD T-- | NYNGKFKGKATLIADKSSSTAYMQLSSLTSEDSAVYFC | ARGVS-GYGAMDY | WGQGTSVTVSS | 160 |
| XPA.015.176_VH | Ab088 | QVQLQQSEAELVK PGASVKISCKAS | GYTFSSYW | MSWVKQRPGKGLEWIGQ | IYPGDGD T-- | NYNGKFKGKATLTADKSSGTAYMQLSSLTSEDSAVYFC | ARGVS-GYGAMDY | WGQGTSVTVSS | 153 |
| XPA.015.177_VH | | QVQLQQSEAELVK PGASVKISCKAS | GYTFSNYW | MNWVKQRPGKGLEWIGQ | IYPGDGD T-- | NYNGKFKGEATLIADKSSSTAYMQLSSLTSEDSAVYFC | ARGVS-GYGAMDY | WGQGTSVTVSS | 159 |
| XPA.015.178_VH | Ab089 | QVQLQQSEAELVK PGASVKISCKAS | GYTFSSYW | MNWVKQRPGKGLEWIGQ | IYPGDGD T-- | NYNVKFKGKATLTADKSSGTAYMQLSSLTSEDSAVYFC | ARGVS-GYGAMDY | WGQGTSVTVSS | 154 |
| XPA.015.179_VH | | QVQLQQSEAELVK PGASVKISCKAS | GYTFSNYW | MNWVKQRPGKGLEWIGQ | IYPGDGD T-- | NYNGRFKGKATLTADKSSGTAYMQLSSLTSEDSAVYFC | ARGVS-GYGAMDY | WGQGTSVTVSS | 161 |
| XPA.015.181_VH | Ab010* | EVQLQQSGPVLVK PGASVKMSCKAA | GYTFTDSY | MNWVKQSHGKSLEWIGD | INPYNGG T-- | SYNQHFKGKATLTVDKSSSTAYMELNSLTSEDSAVYYC | AR-----RRGAMDY | WGQGTSVTVSS | 163 |
| XPA.015.182_VH | | EIQLQQSGPVLVK PGASVKMSCKAA | GYTFTDSY | MNWVKQSHGKSLEWIGD | INPYNGG T-- | SYNQHFKGKATLTVDKSSSTAYMELNSLTSEDSAVYYC | AR-----RRGAMDY | WGQGTSVTVSS | 164 |
| XPA.015.183_VH | Ab020 | QVQLQQSEAELVK PGASVKISCKAS | GYTFSSYW | MNWVKQRPGKGLEWIGQ | IYPGDGD T-- | NYNVKFKGKATLTADKSSGTAYMQLSSLTSEDSAVYFC | ARGVS-GYGAMDY | WGQGTSVTVSS | 155 |
| XPA.015.184_VH | | EVQLQQSGPVLVK PGASVKMSCKAA | GYTFTDSY | MNWVKQSHGKSLEWIGD | INPNNGG T-- | NYNQKFKGKATLTADKSSGTAYMQLSSLTSEDSAVYFC | ARGVS-GYGAMDY | WGQGTSVTVSS | 162 |
| XPA.015.185_VH | Ab003 | EVQLQQSGPVLVK PGASVKISCKAS | GYTFTDSY | MNWVKQSHGKSLKWIGD | IHPNSGG S-- | NYNEKFRSKATLTGDKSSTAYMQLNSLTSDDSAVYYC | AR-----RRGAMDY | WGQGTLIVSS | 157 |
| XPA.015.186_VH | | QVQLQQSGAELVK PGASVKLSCKAS | GYTFTRYW | MHWVKQRPGQGLEWIGM | IYPGDGD T-- | NYNGKFKGKATLTVDKSSSTAYMQLSSLTSEDSADYFC | ARWDYGSASYFDF | WGQGTLVTVSS | 165 |
| XPA.015.187_VH | | EVQLQQSGPELVK PGASVKISCKAS | GYTFSNYW | MNWVKQRPGKGLEWIGQ | IYPGDGD T-- | NYNGKFKGKATLTVDKSSSSAFMELRSLTSEDSAVYFC | ARGVS-GYGAVDH | WGQGTSVTVSS | 166 |
| XPA.015.188_VH | Ab008 | EVQLQQSGPELVK PGASVKISCKAS | GYTFTDSY | MNWVKQSHGKSLEWIGD | INPNNGG T-- | NYNQKFKDKATLTVDKSSSAFMELRSLTSEDSAVYYC | AR-----RRGAMDY | WGQGTSVTVSS | 156 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA.015.189_VH | | EVQLQQSVAELVK PGASVKISCKAS | GYAFSSYW | MNWVKQRPGKGLEWIGQ | IYPGDGD T-- | NYNGKFKGKATLTADKSSGTAVMQLSSLTSEDSAVYFC | ARGVS-GYGAMDY | WGQGTSVTVSS | 152 |
| XPA.015.190_VH | Ab002 | EVKLVESEEGLVK PGGSLKLSCAAS | GFTFSNYA | MSWVRQTPEKRLEWVAT | IS-- DGGHYT | YYSDTIKGRFTISRDNAKNNLFLQLSHLKSEDTAIYYC | ARG----- TVFDY | WGQGTLVTVSS | 167 |
| XPA.015.191_VH | | QVQLQQPGAELVK PGASVKLSCKAS | GYIFTNYW | MHGVKQRPGQGLEWIGM | IHPNSGS T-- | SYNEKFKTKATLTVDKSSSTAYMQLSSLTSEDSAVYYC | ARGYGSTYW YFDV | WGTGTTVTVSS | 168 |
| XPA.015.192_VH | | EVQLQQSGPELVK PGASVKISCKAS | GYTFTDSY | MNWVKQSHGKSLEWIGD | INPNNGD T-- | NYNQKFKDKATLTVDKSSSSAFMELRSLTSEDSAVYYC | AR----- RRGAMDY | WGQGTSVTVSS | 158 |
| XPA.15.006 | Ab021 | EVQLLESGGGLVQ PGGSLRLSCAAS | GFTFSSYE | MNWVRQAPGKGLEWVSA | ISGSGGST | YYADSVKGRFTISRDNSKNTLYLQMNSLRAEDTAVYYC | ARATGIGGY HEDY | WGQGTLVTVSQ | 288 |
| XPA.15.009 | Ab022 | EVQLLESGGGLVQ PGGSLRLSCAAS | GFTFSSYW | MHWVRQAPGKGLEWVSG | INNSGGTT | FYADAVKGRFTISRDNSKNTLYLQMNSLRAEDTAVYYC | ARDRRFLEW TFDY | WGQGTLVTVSQ | 289 |
| XPA.15.019 | | EVQLLESGGGLVQ PGGSLRLSCAAS | GFTFSNAM | MSWVRQAPGKGLEWVSA | IGTGGGT | YYADSVKGRFTISRDNSKNTLYLQMNSLRAEDTAVYYC | AKSRWLPYF DY | WGQGTLVTVSQ | 290 |
| XPA.15.043 | | EVQLLESGGGLVQ PGGSLRLSCAAS | GFTFSDHY | MDWVRQAPGKGLEWVSA | ISGSGGST | YYADSVKGRFTISRDNSKNTLYLQMNSLRAEDTAVYYC | AKEIPGRWL QLGGFDY | WGQGTLVTVRL | 291 |
| XPA.15.062 | | EVQLLESGGGLVQ PGGSLRLSCAAS | GFTFSNVV | ISWVRQAPGKGLEWVSA | ISGSGGST | FYPDSVKGRFTISRDNSKNTLYLQMNSLRAEDTAMYYC | ARVGLSGWY YFDY | WGQGTLVTVSS | 292 |
| XPA.15.085 | Ab011 | EVQLLESGGGLVQ PGGSLRLSCAAS | GFTFSNYA | MGWVRQAPGKGLEWVSS | ISGSGGTT | YYADSVKGRFTISRDNSKNTLYLQMNSLRAEDTAVYYC | ARHKGLQPL DY | WGQGTLVTVSF | 293 |
| XPA.15.099 | | EVQLLESGGGLVQ PGGSLRLSCAAS | GFTFSNYA | MGWVRQAPGKGLEWVSS | ISGSGGTT | YYADSVKGRFTISRDNSKNTLYLQMNSLRAEDTAVYYC | ARHKGLQPL DY | WGQGTLVTVSQ | 294 |
| XPA.15.141 | | EVQLLESGGGLVQ PGGSLRLSCAAS | GFTFDDYG | MNWVRQAPGKGLEWVSG | VSWNGSRT HYAYS | VKGRFTISRDNSKNTLYLQMNSLRAEDTAVYYC | ARRSPLKDG FDI | WGLGTLVTVTQ | 295 |
| XPA.15.142 | | EVQLLESGGGLVQ PGGSLRLSCAAS | GFTFNKFA | VHWVRQAPGKGLEWVSA | ISGSGGST | YYADSVKGRFTISRDNSKNTLYLQMNSLRAEDTAVYYC | ASDVEGGYF HNSGPDY | WGQGTLVTVSS | 296 |
| XPA.15.144 | Ab033 | EVQLLESGGGLVQ PGGSLRLSCAAS | GFTFTNVN | MIWVRQAPGKGLEWVSA | VSWNGSRT HYADS | VKGRFTISRDNSKNTLYLQMNSLRAEDTAVYYC | ARERGSWDT TGYYNYYYY GMDV | WGQGTLVTVSS | 297 |
| XPA.15.146 | | EVQLLESGGGLVQ PGGSLRLSCAAS | GFTFSNVW | MSWVRQAPGKGLEWVST | VSATGPHT | YYADSAKGRFTISRDNSKNTLYLQMNSLRAEDTAVYYC | ARQVGGGPF DI | WGQGTLVTVSS | 298 |
| XPA.15.154 | | EVQLLESGGGLVQ PGGSLRLSCAAS | GFTFSSNY | MSWVRQAPGKGLEWVSA | ISGSGGST | YYADSVKGRFTISRDNSKNTLYLQMNSLRAEDTAVYYC | ARVGSSGWY YFDY | WGQGTLVTVSS | 299 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA.15.155 | Ab014 | EVQLLESGGGLVQPGGSLRLSCAAS | GFTFSSNY | MSWVRQAPGKGLEWVSA | ISGSGGST | YYADSVKGRFTISRDNSKNTLYLQMNSLRAEDTAVYYC | ARVGSSGWYYFDY | WGQGTLVTVSS | 300 |
| XPA.15.158 | Ab049 | EVQLLESGGGLVQPGGSLRLSCAAS | GFTFSNAW | MSWVRQAPGKGLEWVSA | ISGSGGST | YYADSVKGRFTISRDNSKNTLYLQMNSLRAEDTAVYYC | AAPTVPYYYGMDV | WGQGTLVTVSS | 301 |
| XPA.15.165 | Ab050 | EVQLLESGGGLVQPGGSLRLSCAAS | GFTFSSNY | MSWVRQAPGKGLEWVSS | ISGGGST | YYADSRKGRFTISRDNSKNTLYLQMNSLRAEDTAVYYC | ARLDWSSGAFDI | WGQGTLVTVSS | 302 |
| XPA.15.193 | Ab051 | QVQLVQSGAELKKGYTFGDYHPGATVKISCKVS | MHWVKQAPGKGLEWMGL | VDPENGET | EYGEKFQDRIMAADTSDTAYMELSSLRSEDTAVYYC | ARSPSSSGYFRVDGFDI | WGQGTMVTVSS | 226 |
| XPA.15.194 | Ab052 | QVQLVQSGAEVKKPGSSVKVSCKAS | GGTFSSYA | ISWVRQAPGQGLEWMGG | IIPIFGTA | NYAQKFQGRVTITADESTSTAYMELSSLRSEDTAVYYC | AGKLYSRDYWYFDL | WGRGTLVTVSS | 227 |
| XPA.15.195 | Ab053 | EVQLVQSGAEVKKPGESLKISCKGS | GYRFTSYW | IGWVRQMPGRGLEWMGI | IYPGDSDT | RYSPSFQGQVTISVDKSISTAYLQWSSLKASDTAMYYC | ATHHASGRGLDP | WGQGTLVTVSS | 228 |
| XPA.15.196 | Ab054 | QVQVVQSGAEVKKPGASVKVSCKAS | GYTFTGHY | MHWVRQAPGQGLEWMGW | INPNSGGT | NYAQKFQGRVTMTRDTSISTAYMELSRLRSDDTAVYYC | ARGSSSSWPVYFYYMDV | WGKGSTVTVSS | 229 |
| XPA.15.197 | Ab055 | QVQLVQSGAEVKKPGASVKVSCKAS | GYTFTGHY | MHWVRQAPGQGLEWMGW | INPNSGGT | NYAQKFQGRVTMTRDTSISTAYMELSRLRSDDTAVYYC | ARGSSSSWPVYFYYMDV | WGKGTTVTVSS | 230 |
| XPA.15.198 | Ab056 | QVQLVQSGAEVKKGGTFSSYAPGSSVKVSCKAS | ISWVRQAPGQGLEWMGG | IIPIFGTA | NYAQKFQGRVTITADESTSTAYMELSSLRSEDTAVYYC | ARGQGWLRFYGMDV | WGQGTTVTVSS | 231 |
| XPA.15.199 | Ab057 | QVQLVQSGSEVKKGYTFTNSYPGASVKVSCKVS | MHWVRQAPGQGLEWMGI | INPSAGT | SYAQKFQGRVTMTRDTSTSTVMELSSLKSEDTAVYYC | ARDVGWLPGDY | WGQGTLVTVSS | 232 |
| XPA.15.200 | Ab058 | QMQLVQSGAEVKKGYRFSDNWPGESLKISCKGY | IGWVRQMPGRGLEWMGI | IYPGDSET | RYSPSFQGQVTISADKSISTAYLQWSSLKASDTAMYYC | ARHAPLAVAGMALGD | WGQGTLVTVSS | 233 |
| XPA.15.202 | Ab058 | QLQLQQWGAGLLKSGSFSGYYPSETLSLTCAVY | YSWIRQSPGRGLEWIGD | ISHTGST | DYNPSLKTRVTISVDTSKNQFSLNLNSVTAADTAVYYC | ARDAPKGGSGLYLFDY | WGQGTLVTVSS | 234 |
| XPA.15.203 | Ab058 | QVQLVQSGAEVKKGGTFSSYAPGSSVKVSCKAS | ISWVRQAPGQGLEWMGR | IIPILGIA | NYAQKFQGRVTITADKSTSTAYMELSSLRSEDTAVYYC | ARDSYSSGWYSHGPEYFQH | WGQGTLVTVSS | 235 |
| XPA.15.204 | Ab059 | EVQLVQSGAEVKKGGTFSSYAPGSSVKVSCKAS | ISWVRQAPGQGLEWMGR | IIPIFGIA | NYAQKFQGRVTITADKSTSTAYMELSSLRSEDTAVYYC | AREPDYDFWNDAFDI | WGQGTMVTVSS | 236 |
| XPA.15.205 | | QVQLVQSGAEVKKGYTFSSYAPGSSVKVSCKAS | ISWVRQAPGQGLEWMGG | IIPIFGTA | NYAQKFQGRVTITADESTSTAYMELSSLRSEDTAVYYC | ASHYDFWSGYQYYYGMDV | WGQGTTVTVSS | 237 |
| XPA.15.206 | | QMQLVQSGAEVKKGYTFTSYAPGASVKVSCKAS | MHWVRQAPGQRLEWMGW | INAGNGNT | RYSQKFQGRVTITRDTSASTAYMELSSLRSEDTAVYYC | ARYTSGSFDY | WGQGTLVTVSS | 238 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA.15.207 | Ab060 | QMQLVQSGAEVKK PGSSVKVSCKAS | GGTFSSYA | ISWVRQAPGQGLEWMGI | INPSGGST | SYAQKFQGRVTMTRDRSTSTVYMELSSLITSEDTAVYYC | VRDNHGWSF DY | WGQGTLVTVSS | 239 |
| XPA.15.208 | | QMQLVQSGAEVKK PGSSVKVSCKAS | GGTFSSYA | ISWVRQAPGQGLEWMGG | IIPIFGTA | NYAQKFQGRVTIADESTSTAYMELSSLRSEDTAVYYC | ATKGSDFWS GYYYYYYM DV | WGKGTTVTVSS | 240 |
| XPA.15.209 | Ab061 | QMQLVQSGAEVKK TGESLKISCQGY | GYRFTDNW | IGWVRQMPGRGLEWMGI | IYPGDSET | RYSPSFQQVTISADKSISTAYLEWSSLKASDTAMYYC | ARHAPLAVA GMALGD | WGQGTLVTVSS | 241 |
| XPA.15.210 | | QVQLVQSGAEVKK PGSSVKVSCKAS | GGTFSSYA | ISWVRQAPGQGLEWMGG | IIPIFGTA | NYAQKFQGRVTIADESTSTAYMELSSLRSEDTAVYYC | ARGLPPKPY YDFWSGYWG YYYYGMDV | WGQGTLVTVSS | 242 |
| XPA.15.211 | Ab062 | QVQLQQWGAGLLK PSETLSLTCAVY | GGSFSGYY | WSWIRQPPKGLEWIGE | INHSGST | NYNPSLKSRVTISVDTSKNQFSLKLSSVTAADTAVYYC | ARGPSGWYI REFDY | WGQGTLVTVSS | 243 |
| XPA.15.212 | Ab063 | QVQLQQSGPGLVK PSQTLSLTCAIS | GDSVSSNS AA | WNWIRQSPSRGLEWLGR | TYYRSKW YT | DYALSVKSRITINPDTSKNQFSLHLNSVTPEDTAVYYC | AREGWLGYF DF | WGQGTLVTVSS | 244 |
| XPA.15.213 | Ab064 | QVQLVQSGAEVKK PGESLKISCKGS | GFSFPSYW | IGWVRQMPGKGLELVGI | IYPGDSDI | RYSPSFQQVTISADTSISTVYLQWSSLQTTDTATYYC | ARGGFMWFDP | WGQGTLVTVSS | 245 |
| XPA.15.214 | Ab065 | QVQLVQSGAEVKK PGESLKISCKGS | GYSFTSYW | IGWVRQMPGKGLEWMGI | IYPGDSDT | RYSPSFQQVTISADKSISTAYLQWSSLKASDTAMYYC | ARHELGIDY | WGQGTLVTVSS | 246 |
| XPA.15.215 | Ab066 | EVQLVQSGAEVKK PGSSVKVSCKAS | GGTFSSYA | ISWVRQAPGQGLEWMGG | IIPIFGTA | NYAQKFQGRVTITADKSTSTAYMELSRLRSDDTAVYYC | ARDASYGGN SEGFDY | WGQGTLVTVSS | 247 |
| XPA.15.216 | Ab067 | EVQLVQSGAEVKK PGSSVKVSCKAS | GGTFSSYA | ISWVRQAPGQGLEWMGG | IIPIFGTA | NYAQKFQGRVTIADESTSTAYMELSSLRSEDTAVYYC | ARASGDYDF WSGYYGAEY FQH | WGQGTLVTVSS | 248 |
| XPA.15.217 | Ab068 | EVQLVQSGAEVKQ PGSSVKVSCKAS | GGSFNSYT | FSWVRQAPGQGLEWMGW | ISAYNGG TNYFA | NYALKFQGRVTMTDTSTGTAYMELRSLRSDDTAVYYC | ARVRDSWSH EDYSYYYM DV | WGKGTTVTVSS | 249 |
| XPA.15.218 | | QVQLVESGGLVQ PGGSLRLSCAAS | GFTFSSYA | MSWVRQAPGKGLEWVSA | ISGSGGST | YYADSVKGRFTISRDNSKNSLYLQMNSLRAEDTAVYYC | ARERVFPDY YDSIASNYP LDDI | WGQGTMVTVSS | 250 |
| XPA.15. | 2l9Ab086 | EVQLVETGGGVVR PGGSLRLSCAAS | GFTFGDYG | MSWVRQAPGKGLEWVSG | INWNGGST | GYADSVKGRFTISRDNAKNSLYLQMNSLRAEDTALYYC | ARDILGVEF DY | WGQGTLVTVSS | 251 |
| XPA.15.220 | | EVQLVQSGAEVKK PGESLKISCKGS | GYSFTSYW | IGWVRQMPGKGLEWMGI | IYPGDSDT | RYSPSFQQVTISADKSISTAYLQWSSLKASDTAMYYC | ARLGSGSYS FDY | WGQGTLVTVSS | 252 |
| XPA.15.221 | | EVQLVESGGGVVQ PGMSLRLSCAAS | GFTFDDYA | MHWVRQAPGKGLEWVSS | ISWNSANI | VYADSVRGRFTISRDNAKNSLYLQMNSLRADDMALYYC | VKGDTTMIY YAMAV | WGQGTTVTVSS | 253 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA.15.222 | Ab069 | EVQLVQSGAEVKK PGESLKISCKGS | GYSFTSYW | IGWVRQMPGKGLEWMGI | IYPGDSDT | RYSPSFQQVTISADKSISIAYLQWSSLKASDTAMYYC | ARLGRGYYG MDV | WGQTTVTVSS | 254 |
| XPA.15.223 | | QMQLVQSGAEVKK PGESLKISCKGS | GYSFTSYW | IGWVRQMPGKGLEWMGI | IYPGDSDT | RYSPSFQQVTISADKSISTAYLQWSSLKASDTAMYYC | ARWGPDAFDI | WGQGTMVTVSS | 255 |
| XPA.15.224 | | EVQLVESGGSVVQ PGGSLRLSCAAS | GFTFSDYY | MSWIRQAPGKGLEWVSA | ISGSGGST | YYADSVKGRFTISRDNSENTLYLQMNSLRAEDTAVYYC | AKDDYDFWS GYYDPYYYG MDV | WGQGTMVTVSS | 256 |
| XPA.15.225 | | EVQLLESGGGLVQ PGMSLRLSCAAS | GFTFDDYA | MHWVRQAPGKGLEWVSS | ISWNSANI | VYADSVRGRFTISRDNAKNSLYLQMNSIRADDMALYYC | VKGDTTMIY YAMAV | WGQGTLVTVSS | 257 |
| XPA.15.226 | Ab070 | EVQLVQSGAEVKK PGESLKISCKGS | GYSFTSYW | IGWVRQMPGKGLEWMGI | IYPGDSDT | RYSPSFQQVTISADKSISTSYLQWSSLRASDTAMYYC | ARLGSGWYG NDY | WGQGTLVTVSS | 258 |
| XPA.15.227 | Ab071 | EVQLVESGGSVVQ PGGSLRLSCAAS | GFTFSDYY | MSWIRQAPGKGLEWVSA | ISGSGGST | YYADSVKGRFTISRDNSENTLYLQMNSLRAEDTAVYYC | | | |
| XPA.15.227 | Ab071 | EVQLVQSGAEVKK PGESLKISCKGS | GYSFTSYW | IGWVRQMPGKGLEWMGI | IYPGDSDT | RYSPSFQQVTISADKSISTAYLQWSSLKASDTAMYYC | ARWDAGYSP | WGQGTLVTVSS | 259 |
| XPA.15.228 | Ab072 | QMQLVQSGAEVKK PGESLKISCKGS | GYSFTGYW | IGWVRQMPGKGLEWMGI | IYPGDSDT | RYSPSFQQVTISADKSISTAYLQWSSLKVSDTAMYYC | GRISTPYAF DI | WGQGTMVTVSS | 260 |
| XPA.15.229 | Ab073 | QVQLQESGPGLVK PSGTLSLTCAVS | GGSISSNW | WSWVRQPPGKGLEWIGE | IYHSGST | NYNPSLKSRVTISVDKSKNQFSLKLSSVTAADTAVYYC | ARVGAAAAW FDP | WGQGTLVTVSS | 261 |
| XPA.15.230 | Ab074 | EVQLVQSGAEVKK PGESLKISCKGS | GYSFTSYW | IGWVRQMPGKGLEWMGI | IYPGDSDT | RYSPSFQQVTISADKSISTAYLQWSSLKASDTAMYYC | ARWDAGYSP | WGQGTMVTVSS | 262 |
| XPA.15.231 | | QMQLVQSGAEVKK PGESLKISCKGS | GYSFSSSW | IGWVRQMPGKGLEWMGI | IYPGDSDT | RYSPSFQQVTISADRSISTAYLQWSSLKASDTAMYYC | ARVGASGWT FDY | WGQGTLVTVSS | 263 |
| XPA.15.232 | Ab075 | EVQLVETGGGVVQ PGRSLRLSCAAS | GFSFSSVD | MYWVRQAPGKGLEWVAV | ISYDGNDK | QYADSVKGRFTISRDNSKRTLYLQMDSLRTEDTATYYC | TREGNGREI DY | WGPGTLVTVSS | 264 |
| XPA.15.233 | | QVQLVQSGAEVRR PGASVKVSCEAS | GYTFHSYD | INWVRQATGQGLEWVGW | MNPNSGNT | DFAQKFQGRVTMTRNTSINTAYMELSSLRSDDTAVYYC | ARVNWNYGG TSDS | WGQGTLVTVSS | 265 |
| XPA.15.234 | | QVQLQESGPGLVK PSGTLSLTCAVS | GGSISSSNW | WSWVRQPPGKGLEWIGE | IYHSGST | NYNPSLKSRVTISVDKSKNQFSLKLSSVTAADTAVYYC | ARVGVAAFDY | WGQGTMVTVSS | 266 |
| XPA.15.235 | | EVQLVESGGGVVQ PGRSLRLSCAAS | GFTFSSYA | MHWVRQAPGKGLEWVAV | ISYDGSNK | YYADSVKGRFTISRDNSKNTLCLQMNSLRAEDTAVYYC | AREEAYGDA FDI | WGQGTMVTVSS | 267 |
| XPA.15.236 | | QMQLVQSGAEVKK PGESLKISCKGS | GYSFTSYW | IGWVRQMPGKGLEWMGI | IYPGDSDT | RYSPSFQQVTISADKSISTAYLQWSSLKASDTAMYYC | ARWGPDAFDI | WGQGTMVTVSS | 268 |
| XPA.15.237 | | EVQLVETGGGVVR PGRSLRLSCAAS | GFTFEDYA | MHWVRQGPGKGLEWVSS | ISWNGGFI | GYADSVKGRFTISRDNAKNSLYLQMNSLSAEDTALYYC | AKGASYDSY AAMDV | WGQGTTVTVSS | 269 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA.15.238 | | EVQLVESGGGVVQPGGSLRLSCAAS | GFTFSSYA | MSWVRQAPGKGLEWVSA | ISGSGGST | YYADSVKGRFTISRDNSKNTLYLQMNSLRAEDTAVYYC | AKDPRVVHRFDI | WGQGTMVTVSS | 270 |
| XPA.15.239 | | QLQLQESGPGLVKPSETLSLTCTVS | GGSFSTYY | WSWVRQAPGKGLEWIGN | IYYSGKT | NYNPSLESRVTISVDTSKNQFSLKLSSVTTADTAVYYC | ARDSFYFESSRSWNDLFDI | WGQGTMVTVSS | 271 |
| XPA.15.240 | | QLQLQESGPGLVKPSETLSLTCTVS | GGSFSTYY | WSWVRQAPGKGLEWIGN | IYYSGKT | NYNPSLGSRVTISVDTSKNQFSLKLSSVTAADTAVYYC | ARDSFYFESSRSWNDLFDI | WGQGTMVTVSS | 272 |
| XPA.15.241 | Ab076 | EVQLVESGGGVVQPGGSLRLSCAAS | GFTFDDYA | MHWVRQAPGKGLEWVSL | ISWDGGST | YYADSVKGRFTISRDNSKNSLYLQMNSLRAEDTALYYC | AKARGVVIIDY | WGQGTLVTVSS | 273 |
| XPA.15.242 | Ab077 | QLQLQESGPGLVKPSETLSLTCTVS | GGSFSTYY | WSWIRQAPGKGLEWIGN | IYYSGKT | NYNPSLESRVTISVDTSKNQFSLKLSSVTAADTAVYYC | ARDSFYFESSRSWNDLFDI | WGQGTMVTVSS | 274 |
| XPA.15.243 | Ab078 | EVQLVESGGGVVQPGGSLRLSCAAS | GFTFSSYW | MTWVRQAPGKGLEWVAN | INQDGSEK | HYVDSVKGRFTISRDNAKNSLYLQMNSLRGEDTAVYYC | ARGRGAWAFDY | WGQGTLVTVSS | 275 |
| XPA.15.244 | Ab079 | QVQLVQSGGGLVQPGGSLRLSCAAS | GFTFSSYS | MNWVRQAPGKGLEWVSS | ISSSSSYI | YYADSVKGRFTISRDNAKNSLYLQMNSLRAEDTAVYYC | ARDQGGELLGFTGYFDY | WGQGTLVTVSS | 276 |
| XPA.15.245 | Ab080 | QMQLVQSGAEMKKPGASVKVSCKAS | GYSFSDYG | ITWVRQAPGQGPEWMGW | ISGYNGNT | NYAQKFQDRVIMTTDTSTAYMELRSLKSDDTAVYFC | ARARGVVMFDN | WGQGTMVTVSS | 277 |
| XPA.15.246 | Ab081 | EVQLVESGGGVVQPGGSLRLSCAAS | GFTFDDYA | MHWVRQAPGKGLEWVSL | ISWDGGST | YYADSVKGRFTISRDNSKNSLYLQMNSLRAEDTALYYC | AKARGVVIIDY | WGQGTLVTVSS | 278 |
| XPA.15.247 | | EVQLVETGGGVVQPGRSLRLSCAAS | GFTFSSYA | MHWVRQAPGKGLEWVAV | ISYDGSNK | YYADSVKGRFTISRDNSKNTLYLQMNSLRAEDTAVYYC | ARHEWGFGMDV | WGQGTTVTVSS | 279 |
| XPA.15.248 | | QMQLVQSGAEVKKPGESLKISCKGS | GYSFTSYW | IGWVRQMPGKGLEWMGI | IYPGDSDT | RYSPSFQGQVTISADKSISTAYLQWSSLKASDTAMYYC | ARWGPDAPDI | WGQGTMVTVSS | 280 |
| XPA.15.249 | | QVQLVESGGGLVQPGGSLRLSCAAS | GFTFSSYA | MSWVRQAPGKGLEWVSA | ISGSGGST | YYADSVKGRFTISRDNSKNTLYLQMNSLRAEDTAVYYC | AKDRVGAANGWFDP | WGQGTMVTVSS | 281 |
| XPA.15.250 | | QVQLVESGGGLVQPGGSLRLSCAAS | GFTFKNYW | MTWVRQAPGKGLEWVAD | IKGDGSRQ | HYADSVKGRFTISRDNARNSLFLQMNSLRVEDTALYYC | ATDPPWDRDAFDL | WGQGTMVTVSS | 282 |
| XPA.15.272 | | QVQLVESGGGLVQPGGSLRLSCAAS | GFTFGGYW | MSWVRQAPGKGLEWVSN | IKQDGSEQ | YYVDSVKGRFTISRDNAKNSLYLQMNSLRAEDTAIYYC | ARDRMDYIFDI | WGRGTLVTVSS | 283 |
| XPA.15.275 | | EVQLVESGGGVVQPGRSLRLSCAAS | GFIFSSYG | MHWVRQVPDKGLEWVAG | ISLRGSDN | YYADSVKGRFTISRDNSKNTLYLQMNNLRPDDTAVYYC | ARGFRWPVTPFDH | WGQGTLVTVSS | 284 |
| XPA.15.282 | | QVQLQESGPGLVKPSGTLSLTCAVS | GGSISSSNW | WSWVRQPPGKGLEWIGE | IYHSGST | NYNPSLKSRVTISVDKSKNQFSLKLSSVTAADTAVYYC | ARPDYSNYGGAFDY | WGQGTLVTVSS | 285 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA.15.284 | | QVQLQESGPGLVK GGSISSSNW PSGTLSLTCAVS | WSWVRQPPGKGLEWIGE | IYHSGST | NYNPSLKSRVTISVDKSKNQFSLKLSSVTAADTAVYYC | ARVGAAAAW FDP | WGQGTLVTVSS | 286 |
| XPA.15.293 | | QLQLQESGPGLVK GGSFSTYY PSETLSLTCTVS | WSWVRQAPGKGLEWIGN | IYYSGKT | NYNPSLESRVTISVDTSKNQFSLKLSSVTAADTAVYYC | ARDSFYFES SRSWNDLFDI | WGQGTMVTVSS | 287 |
| XPA-15-007_VH | Ab029 | EVQLLESGGGLVQ GFTFSS- PGGSLRLSCAAS YG | MHWVRQAPGKGLEWVSA | ISGSGGST | YYADSVKGRFTISRDNSKNTLYLQMNSLRAEDTAVYYC | ARDRYSSGW YW----- SDY------ | WGQGTLVTVSS | 221 |
| XPA-15-013_VH | Ab006 | EVQLLESGGGLVQ GFTFSN- PGGSLRLSCAAS YA | MGWVRQAPGKGLEWVSS | ISGSGGTT | YYADSVKGRFTISRDNSKNTLYLQMNSLRAEDTAVYYC | ----AR--- -HKGLQ--- -PLDY---- -- | WGQGTLVTVSS | 179 |
| XPA-15-017_VH | | EVQLLESGGGLVQ GFTFSS- PGGSLRLSCAAS YS | MNWVRQAPGKGLEWVSV | IY- SGDST | YYADSVKGRFTISRDNSKNTLYLQMNSLRAEDTAVYYC | ----ARQV- -RDGDY--- GDWFDP--- -- | WGQGTLVTVSS | 216 |
| XPA-15-020_VH | | EVQLLESGGGLVQ GFTFSS- PGGSLRLSCAAS YS | MNWVRQAPGKGLEWVSL | IYRDGST | -TYADSVRGRFTISRDNSKNTLYLQMNSLRAEDTAVYYC | ----ARES- -TR------ LRGSYYYGM DV | WGQGTLVTVSS | 215 |
| XPA-15-021_VH | Ab023 | EVQLLESGGGLVQ GFTFSN- PGGSLRLSCAAS AW | MSWVRQAPGKGLEWVSA | IGTGGGT | -YYADSVKGRFTISRDNSKNTLYLQMNSLRAEDTAVYYC | ----AK--- -SRWLP--- -YFDY---- -- | WGQGTLVTVSS | 193 |
| XPA-15-022_VH | Ab024 | EVQLLESGGGLVQ GFTFSD- PGGSLRLSCAAS YY | MSWIRRAPGKGLEWVSR | ISWNSGSI | GYADSLKGRFTISRDNSKNTLYLQMNSLRAEDTAVYYC | ----ARER- -G------- -YGYDY--- -- | WGQGTLVTVSS | 192 |
| XPA-15-023_VH | Ab025 | EVQLLESGGGLVQ GFTFSSNY- PGGSLRLSCAAS | MSWVRQAPGKGLEWVSG | ISGSGGST | YYADSVKGRFTISRDNSKNTLYLQMNSLRAEDTAVYYC | ----ARVG- SSGWYY--- -FDY----- -- | WGQGTLVTVSS | 171 |
| XPA-15-026_VH | Ab026 | EVQLLESGGGLVQ GFTFSN- PGGSLRLSCAAS YV | ISWVRQAPGKGLEWVSA | ISGSGGST | FYPDSVKGRFTISRDNSKNTLYLQMNSLRAEDTAMYYC | ----ARVG- LSGWYY--- -FDY----- -- | WGQGTLVTVSS | 194 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA-15-033_VH |  | EVQLLESGGGLVQ PGGSLRLSCAAS | GFTFSD-YY | MSWVRQAPGKGLEWVAV | ISYDGSNK | YYADSVKGRFTISRDNSKNTLYLQMNSLRAEDTAVYYC | ------AR--GS-----SSFDY---- | WGQGTLVTVSS | 217 |
| XPA-15-036_VH | Ab030 | EVQLLESGGGLVQ PGGSLRLSCAAS | GFTFSS-YS | MNWVRQAPGKGLEWVSA | ISGSGGST | YYADSVKGRFTISRDNSKNTLYLQMNSLRAEDTAVYYC | ----ARD---SWELLGYDAFDI---- | WGQGTLVTVSS | 220 |
| XPA-15-037_VH | Ab031 | EVQLLESGGGLVQ PGGSLRLSCAAS | GFTFSSNY- | MSWVRQAPGKGLEWVSS | I--SGGST | YYADSRKGRFTISRDNSKNTLYLQMNSLRAEDTAVYYC | ----ARL---DWS---SGAFDI---- | WGQGTLVTVSS | 218 |
| XPA-15-042_VH | Ab027 | EVQLLESGGGLVQ PGGSLGLSCAAS | GFTFNN-YW | MSWVRQAPGKGLEWVSY | ISGSGRTI | YYADSVKGRFTISRDNSKNTLYLQMNSLRAEDTAVYYC | ----ARVG-SSGWYY---FDY---- | WGQGTLVTVSS | 219 |
| XPA-15-047_VH | Ab036 | EVQLLESGGGLVQ PGGSLRLSCAAS | GFTFSN-YA | MGWVRQAPGKGLEWVSS | ISGSGGTT | YYADSVKGRFTISRDNSKNTLYLQMNSLRAEDTAVYYC | ----AR---HKGLQ--PLDY---- | WGQGTLVTVSS | 180 |
| XPA-15-048_VH | Ab037 | EVQLLESGGGLVQ PGGSLRLSCAAS | GFTFSS-YE | MNWVRQAPGKGLEWVSS | ISSSSRYA | DVANSVVGRFTISRDNSKNTLYLQMNSLRAEDTAVYYC | ----AR---GEWLD--HEDY---- | WGQGTLVTVSS | 195 |
| XPA-15-059_VH | Ab028 | EVQLLESGGGLVQ PGGSLRLSCAAS | GFTFRN-YW | MTWVRQAPGKGLEWVAN | IKQDSEK | YYVDSVKGRSTISRDNSKNTLYLQMNSLRAEDTAVYYC | ----ARQV--G----GGPFDI---- | WGQGTLVTVSS | 191 |
| XPA-15-064_VH |  | EVQLLESGGGLVQ PGGSLRLSCAAS | GFTFSD-YY | MNWVRQAPGKGLEWVAL | ISYDGSNK | YYADSVKGRFTISRDNSKNTLYLQMNSLRAEDTALYYC | ----AS---QSTAFDI---- | WGQGTLVTVSS | 196 |
| XPA-15-065_VH | Ab038 | EVQLLESGGGLVQ PGGSLRLSCAAS | GFTFSN-YA | MTWVRQAPGKGLEWVSY | IHAGGGT- | HYANSVKGRFTISRDNSKNTLYLQMNSLRAEDTAVYYC | ----ARDL---HWEG----WGLGFDY-- | WGQGTLVTVSS | 183 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA-15-066_VH_ | Ab004 | EVQLLESGGGLVQPGGSLRLSCAAS | GFTFRNFA | MMWVRQAPGKGLEWVSG | ISWNSGSIGYADSVKGRFTISRDNSKNTLYLQMNSLRAEDTAVYYC | | ----ARPS----GAYPT----PFDN---- | WGQGTLVTVSS | 223 |
| XPA-15-068_VH_ | Ab013 | EVQLLESGGGLVQPGGSLRLSCAAS | GFTFSSNY | MSWVRQAPGKGLEWVSG | ISGSGGSTYYADSVKGRFTISRDNSKNTLYLQMNSLRAEDTAVYYC | | ----ARVG---SSGWYY----FDY--- | WGQGTLVTVSS | 172 |
| XPA-15-074_VH_ | Ab039 | EVQLLESGGGLVQPGGSLRLSCAAS | GFTFSSYW | MSWVRQAPGKGLEWVSG | ISGSGGYTSYADSVKGRFTISRDNSKNTLYLQMNSLRAEDTAVYYC | | ----AKDS----SDWY----INS--- | WGQGTLVTVSS | 222 |
| XPA-15-075_VH_ | Ab009 | EVQLLESGGGLVQPWGSLRLSCAAS | GFTFSNYA | MGWVRQAPGKGLEWVSS | ISGSGGTTYYADSVKGRFTISRDNSKNTPYLQMNSLRAEDTAVYYC | | ----AR----HKGLQ----PLDY--- | WGQGTLVTVSS | 181 |
| XPA-15-077_VH_ | Ab040 | EVQLLESGGGLVQPGGSLRLSCAAS | GFTFSSYW | MSWVRQAPGKGLEWVAV | ISKDGSSTDYAHSVKGRFTISRDNSKNTLYLQMNSLRAEDTAVYYC | | ----ARDR----DWIP----GDV--- | WGQGTLVTVSS | 197 |
| XPA-15-080_VH_ | Ab041 | EVQLLESGGGLVQPGGSLRLSCAAS | GFTFSSYS | MNWVRQAPGKGLEWVSA | ISGSGGRTYYADSVKGRFTISRDNSKNTLYLQMNSLRAEDTAVYYC | | ----ARDG----IWSA----MDV--- | WGQGTLVTVSS | 224 |
| XPA-15-081_VH_ | | EVQLLESGGGLVQPGGSLRLSCAAS | GFTFSSNY | MSWVRQAPGKGLEWVSG | ISGSGGSTYYADSVKGRFTISRDNSKNTLYLQMNSLRAEDTAVYYC | | ----ARVG---SSGWYY----FDY--- | WGQGTLVTVSS | 173 |
| XPA-15-082_VH_ | Ab041 | EVQLLESGGGLVQPGGSLRLSCAAS | GFTFSNYA | MTWVRQAPGKGLEWVSY | IHAGGGT-HYANSVKGRFTISRDNSKNTLYLQMNSLRAEDTAVYYC | | ----ARDL----HWEG---WGLGFDY-- | WGQGTLVTVSS | 186 |
| XPA-15-086_VH_ | Ab042 | EVQLLESGGGLVQPGGSLRLSCAAS | GFTFSNYA | MTWVRQAPGKGLEWVSY | IHAGGGT-HYANSVKGRFTISRDNSKNTLYLQMNSLRAEDTAVYYC | | ----ARDL----HWEG---WGLGFDY-- | WGQGTLVTVSS | 184 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA-15-088_VH_ | | EVQLLESGGGLVQPGGSLRLSCAAS | GFTFSN-YN | MQWVRQAPGKGLEWVSG | VSWNGSRT HYADSVKGRFTISRDNSKNTLYLQMNSLRAEDTAVYYC | ----ARER--GSWDTT-GYYNYYYGMDV | WGQGTLVTVSS | 187 |
| XPA-15-093_VH_ | Ab032 | EVQLLESGGGLVQPGGSLRLSCAAS | GFTFSN-YA | MGWVRQAPGKGLEWVSS | ISGSGGTT YYADSVKGRFTISRDNSKNTLYLQMNSLRAEDTAVYYC | ----AR---HKGLQ---PLDY---- | WGQGTLVTVSS | 177 |
| XPA-15-094_VH_ | Ab043 | EVQLLESGGGLVQPGGSLRLSCAAS | GFTFSN-YA | MGWVRQAPGKGLEWVSS | ISGSGGTT YYADSVKGRFTISRDNSKNTLYLQMNSLRAEDTAVYYC | ----AR---HKGLQ---PLDY---- | WGQGTLVTVSS | 178 |
| XPA-15-096_VH_ | | EVQLLESGGGLVQPGGSLRLSCAAS | GFTFSS-YS | MNWVRQAPGKGLEWVAN | IKQDGRET YYVDSVTGRFTISRDNSKNTLYLQMNSLRAEDTAMYYC | ----TTDL-GRYYDILTGYYAPNY--- | WGQGTLVTVSS | 198 |
| XPA-15-100_VH_ | | EVQLLESGGGLVQPGGSLRLSCAAS | GFTFSN-YN | MQWVRQAPGKGLEWVSG | VSWNGSRT HYADSVKGRFTISRDNSKNTLYLQMNSLRAEDTAVYYC | ----ARER--GSWDTT-GYYNYYYGMDV | WGQGTLVTVSS | 188 |
| XPA-15-102_VH_ | Ab044 | EVQLLESGGGLVQPGGSLRLSCAASNY- | GFTFSSNY- | MSWVRQAPGKGLEWVSG | ISGSGGST YYADSVKGRFTISRDNSKNTLYLQMNSLRAEDTAVYYC | ----ARVG-SSGWYY---FDY---- | WGQGTLVTVSS | 176 |
| XPA-15-105_VH_ | | EVQLLESGGGLVQPGGSLRLSCAAS | GFTFSN-YA | MGWVRQAPGKGLEWVSS | ISGSGGTT YYADSVKGRFTISRDNSKNTLYLQMNSLRAEDTAVYYC | ----ARDH-SSSW---AFDY---- | WGQGTLVTVSS | 199 |
| XPA-15-106_VH_ | | EVQLLESGGGLVQPGGSLRLSCAAS | GFTFSN-YA | MTWVRQAPGKGLEWVSY | IHAGGGT - HYANSVKGRFTISRDNSKNTLYLQMNSLRAEDTAVYYC | ----ARDL--HWEG---WGLGFDY- | WGQGTLVTVSS | 185 |
| XPA-15-110_VH_ | | EVQLLESGGGLVQPGGSLRLSCAAS | GFTFSS-YT | MDWVRQAPGKGLEWVSG | INWNGGST GYADSVKGRFTISRDNSKNTLYLQMNSLRAEDTAVYYC | ----ARVK--GYCSST-SCYFDYYYGMDV | WGQGTLVTVSS | 200 |
| XPA-15-111_VH_ | Ab045 | EVQLLESGGGLVQPGGSLRLSCAAS | GFTFSS-YW | MSWVRQAPGKGLEWVSG | ISGSGGST DYADSVKGRFTISRDNSKNTLYLQMNSLRAEDTAVYYC | ----AREL--PAFWS---AFDY---- | WGQGTLVTVSF | 225 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA-15-115_VH | Ab046 | EVQLLESGGGLVQ PGGSLRLSCAAS | GFTFSN-YA | MGWVRQAPGKGLEWVSS | ISGSGGTT | YYADSVKGRFTISRDNSKNTLYLQMNSLRAEDTAVYYC | ----AR---HKGLQ---PLDY---- | WGQGTLVTVSS | 182 |
| XPA-15-120_VH | | EVQLLESGGGLVQ PGGSLRLSCAAS | GFTFSS-YW | MSWVRQAPGKGLEWVAN | IKQDGSEK | YYVDSVKGRFTISRDNSKNTLYLQMNSLRAEDTAVYYC | -G-----ARQV----GGPFDI--- | WGQGTLVTVSS | 190 |
| XPA-15-121_VH | Ab047 | EVQLLESGGGLVQ PGGSLRLSCAAS | GFTFSS-YA | MSWVRQAPGKGLEWVSS | I--SGGST | YYADSRKGRFTISRDNSKNTLYLQMNSLRAEDTAVYYC | ----ARH--ADQWP--GSWFDP--- | WGQGTLVTVSS | 202 |
| XPA-15-122_VH | | EVQLLESGGGLVQ PGGSLRLSCAAS | GFTFRN-YA | MSWVRQAPGKGLEWVSS | I--SGGST | YYADSRKGRFTISRDNSKNTLYLQMNSLRAEDTAVYYC | ----AR----GGV---GDWFDP--- | WGQGTLVTVSS | 203 |
| XPA-15-124_VH | | EVQLLESGGGLVQ PGGSLRLSCAAS | GFTFST-YV | MTWVRQAPGKGLEWVSV | IY-SGGST | YYADSVKGRFTISRDNSKNTLYLQMNSLRAEDTAVYYC | ----ARI---NWND--GGNEDY--- | WGQGTLVTVSS | 201 |
| XPA-15-125_VH | | EVQLLESGGGLVQ PGGSLRLSCAAS | GFTFSD-YY | MSWIRQAPGKGLEWVSA | ISGSGGST | YYADSVKGRFTISRDNSKNTLYLQMNSLRAEDTAVYYC | ---ARG---PVGI--SGNYDY--- | WGQGTLVTVSS | 205 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA-15-127_VH_ | | EVQLLESGGGLVQPGGSLRLSCAAS | GFTFNK-FA | VHWVRQAPGKGLEWVSA | ISGSGGST | YYADSVKGRFTISRDNSKNTLYLQMNSLRAEDTAVYYC | ----ASDV-E-----GGYFHNSGPDH- | WGQGTLVTVSS | 204 |
| XPA-15-133_VH_ | | EVQLLESGGGLVQPGGSLRLSCAAS | GFTFSS-YE | MNWVRQAPGKGLEWVAL | ISYDGSNKDYADSVKGRFTISRDNSKNTLYLQMNSLRAEDTALYYC | | --AADLGI--GS-----GYFDY--- | WGQGTLVTVSS | 206 |
| XPA-15-135_VH_ | | EVQLLESGGGLVQPGGSLRLSCAAS | GFTFSN-AW | MSWVRQAPGKGLEWVSA | ISGSGGST | YYADSVKGRFTISRDNSKNTLYLQMNSLRAEDTAVYYC | ----ARD-----PGGI---YDYFDY--- | WGQGTLVTVSS | 207 |
| XPA-15-138_VH_ | Ab001 | EVQLLESGGGLVQPGGSLRLSCAAS | GFTFSS-YE | MNWVRQAPGKGLEWVSS | ISSSSSYI | YYADSVKGRFTISRDNSKNTLYLQMNSLRAEDTAVYYC | ----ARV----RWYK-DSDAFDI--- | WGQGTLVTVSS | 209 |
| XPA-15-139_VH_ | Ab018 | EVQLLESGGGLVQPGGSLRLSCAAS | GFTFSS-YW | MSWVRQAPGKGLEWVSG | ISGSGGYI | HYADSVKGRFTISRDDSKNTLYLQMNSLRAEDTAVYYC | --AREG----SGWL-----VDQ--- | WGQGTLVTVSS | 208 |
| XPA-15-140_VH_ | | EVQLLESGGGLVQPGGSLRLSCAAS | GFTFSS-YT | MDWVRQAPGKGLEWVSS | ISSSSSYI | YYADSVKGRFTISRDNSKNTLYLQMNSLRAEDTAVYYC | VREAWREN---NDWYE----LDY--- | WGQGTLVTVSS | 212 |
| XPA-15-143_VH_ | | EVQLLESGGGLVQPGGSLRLSCAAS | GFTFSN-YA | MNWVRQAPGKGLEWVAH | INQDSEK | YYVESVKGRFTISRDNSKNTLYLQMNSLRAEDTAVYYC | ----GKLR---GG-----AYNDY--- | WGQGTLVTVSS | 210 |
| XPA-15-145_VH_ | | EVQLLESGGGLVQPGGSLRLSCAAS | GFTFSN-YA | MTWVRQSPGKGLEWVSV | ISGSGGTT | YYADSVKGRFTISRDNSKNTLYLQMNSLRAEDTAVYYC | ----AKAK----GS-----QVFDY--- | WGQGTLVTVSS | 211 |
| XPA-15-159VH_ | Ab015 | EVQLLESGGGLVQPGGSLRLSCAAS | GFTFSSNY- | MSWVRQAPGKGLEWVSG | ISGSGGST | YYADSVKGRFTISRDNSKNTLYLQMNSLRAEDTAVYYC | ----ARVG---SSGWYY----FDY--- | WGQGTLVTVSS | 174 |

TABLE 2-continued

Heavy Chain Sequences

| Name | Ab # | H-FR1 | H-CDR1 | H-FR2 | H-CDR2 | H-FR3 | H-CDR3 | H-FR4 | SEQ ID NO: |
|---|---|---|---|---|---|---|---|---|---|
| XPA-15-163_VH_ | | EVQLLESGGGLVQPGGSLRLSCAAS | GFTFTN-YN | MIWVRQAPGKGLEWVSG | VSWNGSRT | HYADSVKGRFTISRDNSKNTLYLQMNSLRAEDTAVYYC | ----ARER--GSWDTT-GYYNYYYGMDV | WGQGTLVTVSS | 189 |
| XPA-15-167_VH_ | | EVQLLESGGGLVQPGGSLRLSCAAS | GFTFDD-YG | MSWVRQAPGKGLEWVSF | ISGSGGST | NYADSVKGRFTISRDNSKNTLYLQMNSLRAEDTAVYYC | ----ARVG---SSGWYY----FDY----- | WGQGTLVTVSS | 213 |
| XPA-15-169_VH_ | Ab034 | EVQLLESGGGLVQPGGSLRLSCAAS | GFTFSS-YW | MSWVRQAPGKGLEWVSS | I--SGGST | YYADSRKGRFTISRDNSKNTLYLQMNSLRAEDTAVYYC | ----AREV---EYSS--SWGAFDI-- | WGQGTLVTVSS | 214 |
| XPA-15-171_VH_ | Ab016 | EVQLLESGGGLVQPGGSLRLSCAAS | GFTFSD-YY | MSWIRQAPGKGLEWVSA | ISGSGGGT | YYADSVKGRFTISRDNSKNTLYLQMNSLRAEDTAVYYC | ----ARVG---SSGWYY----FDY----- | WGQGTLVTVSS | 175 |
| XPA.15.196 | Ab053 | QVQLVQSGAEVKKPGASVKVSCKAS | GYTFTGHY | MHWVRQAPGQGLEWMGW | INPNSGGT | NYAQKFQGRVTMTRDTSISTAYMELSRLRSDDTAVYYC | ARGSSSSWPVYFYYMDV | WGKGSTVTVSS | 303 |

TABLE 3

| Clone No. | Antibody No. | Light Chain SEQ ID NO: | Heavy Chain SEQ ID NO: |
|---|---|---|---|
| XPA.015.172 |  | 20 | 151 |
| XPA.015.173 | Ab087 | 18 | 169 |
| XPA.015.174 |  | 19 | 170 |
| XPA.015.175 | Ab019 | 1 | 160 |
| XPA.015.176 | Ab088 | 2 | 153 |
| XPA.015.177 |  | 3 | 159 |
| XPA.015.178 | Ab089 | 4 | 154 |
| XPA.015.179 |  | 5 | 161 |
| XPA.015.181 | Ab010* | 6 | 163 |
| XPA.015.182 |  | 7 | 164 |
| XPA.015.183 | Ab020 | 8 | 155 |
| XPA.015.184 |  | 9 | 162 |
| XPA.015.185 | Ab003 | 10 | 157 |
| XPA.015.186 |  | 11 | 165 |
| XPA.015.187 |  | 12 | 166 |
| XPA.015.188 | Ab008 | 13 | 156 |
| XPA.015.189 |  | 14 | 152 |
| XPA.015.190 | Ab002 | 15 | 167 |
| XPA.015.191 |  | 16 | 168 |
| XPA.015.192 |  | 17 | 158 |
| XPA.015.006 | Ab021 | 74 | 288 |
| XPA.015.007 | Ab029 | 52 | 221 |
| XPA.015.009 | Ab022 | 46 | 289 |
| XPA.015.013 | Ab006 | 43 | 179 |
| XPA.015.017 | Ab017 | 45 | 216 |
| XPA.015.019 |  | 72 | 290 |
| XPA.015.020 |  | 44 | 215 |
| XPA.015.021 | Ab023 | 73 | 193 |
| XPA.015.022 | Ab024 | 71 | 192 |
| XPA.015.023 | Ab025 | 70 | 171 |
| XPA.015.026 | Ab026 | 75 | 194 |
| XPA.015.033 |  | 47 | 217 |
| XPA.015.036 | Ab030 | 50 | 220 |
| XPA.015.037 | Ab031 | 48 | 218 |
| XPA.015.042 | Ab027 | 49 | 219 |
| XPA.015.043 |  | 76 | 291 |
| XPA.015.047 | Ab036 | 51 | 180 |
| XPA.015.048 | Ab037 | 77 | 195 |
| XPA.015.059 | Ab028 | 79 | 191 |
| XPA.015.062 |  | 78 | 292 |
| XPA.015.064 |  | 80 | 196 |
| XPA.015.065 | Ab038 | 83 | 183 |
| XPA.015.066 | Ab004 | 57 | 223 |
| XPA.015.068 | Ab013 | 81 | 172 |
| XPA.015.074 | Ab039 | 53 | 222 |
| XPA.015.075 | Ab009 | 55 | 181 |
| XPA.015.077 | Ab040 | 84 | 197 |
| XPA.015.080 |  | 58 | 224 |
| XPA.015.081 |  | 82 | 173 |
| XPA.015.082 | Ab041 | 56 | 186 |
| XPA.015.085 | Ab011 | 54 | 293 |
| XPA.015.086 | Ab042 | 85 | 184 |
| XPA.015.088 |  | 86 | 187 |
| XPA.015.093 | Ab032 | 21 | 177 |
| XPA.015.094 | Ab043 | 23 | 178 |
| XPA.015.096 |  | 22 | 198 |
| XPA.015.099 |  | 59 | 294 |
| XPA.015.100 |  | 26 | 188 |
| XPA.015.102 | Ab044 | 60 | 176 |
| XPA.015.105 |  | 97 | 199 |
| XPA.015.106 |  | 24 | 185 |
| XPA.015.110 |  | 148 | 200 |
| XPA.015.111 | Ab045 | 62 | 225 |
| XPA.015.115 | Ab046 | 61 | 182 |
| XPA.015.120 |  | 149 | 190 |
| XPA.015.121 | Ab047 | 28 | 202 |
| XPA.015.122 |  | 29 | 203 |
| XPA.015.124 |  | 27 | 201 |
| XPA.015.125 |  | 31 | 205 |
| XPA.015.127 |  | 30 | 204 |
| XPA.015.133 |  | 32 | 206 |
| XPA.015.135 |  | 33 | 207 |
| XPA.015.138 | Ab001 | 35 | 209 |
| XPA.015.139 | Ab018 | 34 | 208 |
| XPA.015.140 |  | 39 | 212 |
| XPA.015.141 |  | 37 | 295 |
| XPA.015.142 |  | 63 | 296 |
| XPA.015.143 |  | 36 | 210 |
| XPA.015.144 | Ab033 | 65 | 297 |
| XPA.015.145 |  | 38 | 211 |
| XPA.015.146 |  | 64 | 298 |
| XPA.015.154 |  | 66 | 299 |
| XPA.015.155 |  | 68 | 300 |
| XPA.015.158 | Ab014 | 67 | 301 |
| XPA.015.159 | Ab015 | 40 | 174 |
| XPA.015.163 |  | 150 | 189 |
| XPA.015.165 | Ab049 | 69 | 302 |
| XPA.015.167 |  | 41 | 213 |
| XPA.015.169 | Ab034 | 42 | 214 |
| XPA.015.171 | Ab016 | 151 | 175 |
| XPA.015.193 | Ab050 | 87 | 226 |
| XPA.015.194 | Ab051 | 88 | 227 |
| XPA.015.195 | Ab052 | 89 | 228 |
| XPA.015.196 | Ab053 | 90 | 229 (303) |
| XPA.015.197 | Ab054 | 91 | 230 |
| XPA.015.198 | Ab055 | 92 | 231 |
| XPA.015.199 | Ab056 | 93 | 232 |
| XPA.015.200 | Ab057 | 94 | 233 |
| XPA.015.201 |  | 95 | — |
| XPA.015.202 | Ab058 | 96 | 234 |
| XPA.015.203 |  | 97 | 235 |
| XPA.015.204 | Ab059 | 98 | 236 |
| XPA.015.205 |  | 99 | 237 |
| XPA.015.206 |  | 100 | 238 |
| XPA.015.207 | Ab060 | 101 | 239 |
| XPA.015.208 |  | 102 | 240 |
| XPA.015.209 | Ab061 | 103 | 241 |
| XPA.015.210 |  | — | 242 |
| XPA.015.211 | Ab062 | 104 | 243 |
| XPA.015.212 | Ab063 | 105 | 244 |
| XPA.015.213 | Ab064 | 106 | 245 |
| XPA.015.214 | Ab065 | 107 | 246 |
| XPA.015.215 | Ab066 | 108 | 247 |
| XPA.015.216 | Ab067 | 109 | 248 |
| XPA.015.217 | Ab068 | 110 | 249 |
| XPA.015.218 |  | 111 | 250 |
| XPA.015.219 | Ab086 | 112 | 251 |
| XPA.015.220 |  | 113 | 252 |
| XPA.015.221 |  | 114 | 253 |
| XPA.015.222 | Ab069 | 115 | 254 |
| XPA.015.223 |  | 116 | 255 |
| XPA.015.224 |  | 117 | 256 |
| XPA.015.225 |  | 118 | 257 |
| XPA.015.226 | Ab070 | 119 | 258 |
| XPA.015.227 | Ab071 | 120 | 259 |
| XPA.015.228 | Ab072 | 121 | 260 |
| XPA.015.229 | Ab073 | 122 | 261 |
| XPA.015.230 | Ab074 | 123 | 262 |
| XPA.015.231 |  | 124 | 263 |
| XPA.015.232 | Ab075 | 125 | 264 |
| XPA.015.233 |  | 126 | 265 |
| XPA.015.234 |  | 127 | 266 |
| XPA.015.235 |  | 128 | 267 |
| XPA.015.236 |  | 129 | 268 |
| XPA.015.237 |  | 130 | 269 |
| XPA.015.238 |  | 131 | 270 |
| XPA.015.239 |  | 132 | 271 |
| XPA.015.240 |  | — | 272 |
| XPA.015.241 | Ab076 | 133 | 273 |
| XPA.015.242 |  | 134 | 274 |
| XPA.015.243 | Ab077 | 135 | 275 |
| XPA.015.244 | Ab078 | 136 | 276 |
| XPA.015.245 | Ab079 | 137 | 277 |
| XPA.015.246 | Ab080 | 138 | 278 |
| XPA.015.247 | Ab081 | 139 | 279 |
| XPA.015.248 | Ab082 | 140 | 280 |
| XPA.015.249 | Ab083 | 141 | 281 |
| XPA.015.250 | Ab084 | 142 | 282 |
| XPA.015.272 |  | 143 | 283 |
| XPA.015.275 | Ab085 | 144 | 284 |
| XPA.015.282 |  | 145 | 285 |
| XPA.015.284 |  | 146 | 286 |
| XPA.015.293 |  | 147 | 287 |

We claim:

1. An IgG antibody that binds insulin receptor with an affinity of $10^{-7}$ M or less, and that comprises
   (a) a first heavy chain CDR, a second heavy chain CDR, and a third heavy chain CDR set out in SEQ ID NO: 195, and
   (b) a first light chain CDR, a second light chain CDR, and a third light chain CDR set out in SEQ ID NO: 77.

2. An IgG antibody that binds insulin receptor and that comprises a heavy chain variable region of SEQ ID NO: 195 and a light chain variable region of SEQ ID NO: 77.

3. The antibody of claim 1 or 2, wherein the antibody binds to insulin receptor with an affinity of $10^{-8}$ M or less.

4. The antibody of claim 1 or 2, wherein the IgG is a human IgG1 or IgG3 heavy chain constant region.

5. The antibody of claim 1 or 2, wherein the IgG is a human IgG2 or IgG4 heavy chain constant region.

6. The antibody of claim 1 or 2, further comprising a human light chain constant region.

7. The antibody of claim 1 or 2, wherein the antibody reduces fasting blood glucose levels in a subject having elevated blood glucose toward normal glucose levels.

8. The antibody of claim 1 or 2, wherein said antibody is a human antibody.

9. A method of treating hyperglycemia, comprising administering an antibody of claim 1 or 2 in an amount effective to treat hyperglycemia.

10. A method for reducing blood glucose levels in a subject comprising administering an antibody of claim 1 or 2 in an amount effective to reduce blood glucose levels.

11. A method of preparing a sterile pharmaceutical composition, comprising adding a sterile pharmaceutically acceptable diluent to an antibody of claim 1 or 2.

12. A sterile composition comprising the antibody of claim 1 or 2 and a sterile pharmaceutically acceptable diluent.

13. A method of treating diabetes, comprising administering an antibody of claim 1 or 2 in an amount effective to treat diabetes.

14. The method of claim 13, wherein the diabetes is Type 1 diabetes or Type 2 diabetes mellitus.

15. The method of claim 14, wherein the treatment reduces blood glucose levels.

16. The method of claim 14, wherein the treatment results in a decrease in HbA1c levels compared to an untreated subject.

17. The method of claim 13, wherein the treatment results in an improved glucose tolerance test, or reduced 2-hour glucose level during a glucose tolerance test.

18. The method of claim 13, wherein the treatment results in an improvement in a symptom associated with diabetes selected from the group consisting of dyslipidemia, plasma triglycerides, HOMA-IR, plasma unesterified cholesterol, plasma total cholesterol, plasma insulin, non-HDL/HDL cholesterol ratio, total/HDL cholesterol ratio, beta cell function and plasma leptin levels.

19. The method of claim 13, wherein the disorder is Type 1 diabetes.

20. The method of claim 13, wherein the disorder is Type 2 diabetes mellitus.

* * * * *

UNITED STATES PATENT AND TRADEMARK OFFICE
CERTIFICATE OF CORRECTION

| | | |
|---|---|---|
| PATENT NO. | : 9,725,510 B2 | Page 1 of 1 |
| APPLICATION NO. | : 14/555243 | |
| DATED | : August 8, 2017 | |
| INVENTOR(S) | : John Corbin et al. | |

It is certified that error appears in the above-identified patent and that said Letters Patent is hereby corrected as shown below:

On the Title Page

In Item (72), under "Inventors", in Column 1, Line 3, "Susan R. Watson," should be -- Susan R. Watson, Deceased, --, therefor.

In the Claims

At Column 530, Line 25, "claim 14," should be -- claim 13, --.

At Column 530, Line 27, "claim 14," should be -- claim 13, --.

Signed and Sealed this
Twenty-seventh Day of March, 2018

Andrei Iancu
*Director of the United States Patent and Trademark Office*

SEQUENCE LISTING

<160> NUMBER OF SEQ ID NOS: 303

<210> SEQ ID NO 1
<211> LENGTH: 111
<212> TYPE: PRT
<213> ORGANISM: Mus musculus
<220> FEATURE:
<221> NAME/KEY: MISC_FEATURE
<223> OTHER INFORMATION: Clone XPA.015.175 light chain
<220> FEATURE:
<221> NAME/KEY: MISC_FEATURE
<222> LOCATION: (27)..(36)
<223> OTHER INFORMATION: L-CDR1
<220> FEATURE:
<221> NAME/KEY: MISC_FEATURE
<222> LOCATION: (54)..(56)
<223> OTHER INFORMATION: L-CDR2
<220> FEATURE:
<221> NAME/KEY: MISC_FEATURE
<222> LOCATION: (93)..(98)
<223> OTHER INFORMATION: L-CDR3

<400> SEQUENCE: 1

Asp Leu Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Asn Arg
                85                  90                  95

Glu Pro Arg Thr Phe Gly Gly Gly Thr Asn Leu Glu Ile Lys Arg
            100                 105                 110

<210> SEQ ID NO 2
<211> LENGTH: 111
<212> TYPE: PRT
<213> ORGANISM: Mus musculus
<220> FEATURE:
<221> NAME/KEY: MISC_FEATURE
<223> OTHER INFORMATION: Clone XPA.015.176 light chain
<220> FEATURE:
<221> NAME/KEY: MISC_FEATURE
<222> LOCATION: (27)..(36)
<223> OTHER INFORMATION: L-CDR1
<220> FEATURE:
<221> NAME/KEY: MISC_FEATURE
<222> LOCATION: (54)..(56)
<223> OTHER INFORMATION: L-CDR2
<220> FEATURE:
<221> NAME/KEY: MISC_FEATURE
<222> LOCATION: (93)..(98)
<223> OTHER INFORMATION: L-CDR3

<400> SEQUENCE: 2

Asp Leu Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Thr Thr Ser
            20                  25                  30

Gly Tyr Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Ala Pro Ala

```
                    50                  55                  60

Arg Phe Ser Gly Ser Gly Ser Gly Thr Asp Phe Thr Leu Asn Ile His
 65                  70                  75                  80

Pro Val Glu Glu Glu Asp Ala Gly Asn Tyr Tyr Cys Gln His Asn Arg
                 85                  90                  95

Glu Pro Arg Thr Phe Gly Gly Gly Thr Lys Leu Glu Ile Lys Arg
            100                 105                 110

<210> SEQ ID NO 3
<211> LENGTH: 111
<212> TYPE: PRT
<213> ORGANISM: Mus musculus
<220> FEATURE:
<221> NAME/KEY: MISC_FEATURE
<223> OTHER INFORMATION: Clone XPA.015.177 light chain
<220> FEATURE:
<221> NAME/KEY: MISC_FEATURE
<222> LOCATION: (27)..(36)
<223> OTHER INFORMATION: L-CDR1
<220> FEATURE:
<221> NAME/KEY: MISC_FEATURE
<222> LOCATION: (54)..(56)
<223> OTHER INFORMATION: L-CDR2
<220> FEATURE:
<221> NAME/KEY: MISC_FEATURE
<222> LOCATION: (93)..(98)
<223> OTHER INFORMATION: L-CDR3

<400> SEQUENCE: 3

Asp Ile Val Met Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
             20                  25                  30

Gly Tyr Ser Tyr Ile His Trp Tyr Gln Gln Lys Pro Gly Gln Pro Pro
         35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Asn Arg
                 85                  90                  95

Glu Pro Arg Thr Phe Gly Gly Gly Thr Asn Leu Glu Ile Lys Arg
            100                 105                 110

<210> SEQ ID NO 4
<211> LENGTH: 111
<212> TYPE: PRT
<213> ORGANISM: Mus musculus
<220> FEATURE:
<221> NAME/KEY: MISC_FEATURE
<223> OTHER INFORMATION: Clone XPA.015.178 light chain
<220> FEATURE:
<221> NAME/KEY: MISC_FEATURE
<222> LOCATION: (27)..(36)
<223> OTHER INFORMATION: L-CDR1
<220> FEATURE:
<221> NAME/KEY: MISC_FEATURE
<222> LOCATION: (54)..(56)
<223> OTHER INFORMATION: L-CDR2
<220> FEATURE:
<221> NAME/KEY: MISC_FEATURE
<222> LOCATION: (93)..(98)
<223> OTHER INFORMATION: L-CDR3

<400> SEQUENCE: 4

Asp Leu Val Leu Thr Gln Ser Pro Ala Ser Leu Ala Val Ser Leu Gly
```

```
                1               5                  10                 15
            Gln Arg Ala Thr Ile Ser Cys Arg Ala Ser Lys Ser Val Ser Thr Ser
                            20                  25                  30

Gly Tyr Ser Tyr Ile His Trp Tyr Gln Gln Lys Pro Gly Gln Pro Pro
                        35                  40                  45

Lys Leu Leu Ile Tyr Leu Ala Ser Asn Leu Glu Ser Gly Val Pro Ala
                    50                  55                  60

Arg Phe Ser Gly Ser Gly Ser Gly Thr Asp Phe Thr Leu Asn Ile His
            65                  70                  75                  80

Pro Val Glu Glu Glu Asp Ala Ala Thr Tyr Tyr Cys Gln His Asn Arg
                                85                  90                  95

Glu Leu Arg Thr Phe Gly Gly Gly Thr Lys Leu Glu Ile Lys Arg
                            100                 105                 110
```

<210> SEQ ID NO 5
<211> LENGTH: 111
<212> TYPE: PRT
<213> ORGANISM: Mus musculus
<220> FEATURE:
<221> NAME/KEY: MISC_FEATURE
<223> OTHER INFORMATION: Clone XPA.015.179 light chain
<220> FEATURE:
<221> NAME/KEY: MISC_FEATURE
<222> LOCATION: (27)..(36)
<223> OTHER INFORMATION: L-CDR1
<220> FEATURE:
<221> NAME/KEY: MISC_FEATURE
<222> LOCATION: (54)..(56)
<223> OTHER INFORMATION: L-CDR2
<220> FEATURE:
<221> NAME/KEY: MISC_FEATURE
<222> LOCATION: (93)..(98)
<223> OTHER INFORMATION: L-CDR3

<400> SEQUENCE: 5

```
            Asp Leu Val Leu Thr Gln Ser Pro Ala Ser Val Ala Val Ser Leu Gly
            1               5                   10                  15

Gln Arg Ala Thr Ile Ser Cys Arg Ala Ser Lys Ser Val Ser Thr Ser
                            20                  25                  30

Gly Tyr Ser Tyr Met His Trp Tyr Gln Gln Lys Pro Gly Gln Pro Pro
                        35                  40                  45

Lys Leu Leu Ile Tyr Leu Ala Ser Asn Leu Glu Ser Gly Val Pro Ala
                    50                  55                  60

Arg Phe Ser Gly Ser Gly Ser Gly Thr Asp Phe Thr Leu Asn Ile His
            65                  70                  75                  80

Pro Val Glu Glu Glu Asp Val Ala Thr Tyr Tyr Cys Gln His Asn Arg
                                85                  90                  95

Asp Pro Arg Thr Phe Gly Gly Gly Thr Lys Leu Glu Ile Lys Arg
                            100                 105                 110
```

<210> SEQ ID NO 6
<211> LENGTH: 108
<212> TYPE: PRT
<213> ORGANISM: Mus musculus
<220> FEATURE:
<221> NAME/KEY: MISC_FEATURE
<223> OTHER INFORMATION: Clone XPA.015.181 light chain
<220> FEATURE:
<221> NAME/KEY: MISC_FEATURE
<222> LOCATION: (27)..(32)
<223> OTHER INFORMATION: L-CDR1
<220> FEATURE:
<221> NAME/KEY: MISC_FEATURE
<222> LOCATION: (50)..(52)

<223> OTHER INFORMATION: L-CDR2
<220> FEATURE:
<221> NAME/KEY: MISC_FEATURE
<222> LOCATION: (89)..(95)
<223> OTHER INFORMATION: L-CDR3

<400> SEQUENCE: 6

Asp Val Gln Ile Ile Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Ala Gly Thr Lys Leu Glu Leu Lys Arg
            100                 105

<210> SEQ ID NO 7
<211> LENGTH: 108
<212> TYPE: PRT
<213> ORGANISM: Mus musculus
<220> FEATURE:
<221> NAME/KEY: MISC_FEATURE
<223> OTHER INFORMATION: Clone XPA.015.182 light chain
<220> FEATURE:
<221> NAME/KEY: MISC_FEATURE
<222> LOCATION: (27)..(32)
<223> OTHER INFORMATION: L-CDR1
<220> FEATURE:
<221> NAME/KEY: MISC_FEATURE
<222> LOCATION: (50)..(52)
<223> OTHER INFORMATION: L-CDR2
<220> FEATURE:
<221> NAME/KEY: MISC_FEATURE
<222> LOCATION: (89)..(95)
<223> OTHER INFORMATION: L-CDR3

<400> SEQUENCE: 7

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Ala Gly Thr Lys Leu Glu Leu Lys Arg
            100                 105

<210> SEQ ID NO 8
<211> LENGTH: 111
<212> TYPE: PRT
<213> ORGANISM: Mus musculus
<220> FEATURE:

<221> NAME/KEY: MISC_FEATURE
<223> OTHER INFORMATION: Clone XPA.015.183 light chain
<220> FEATURE:
<221> NAME/KEY: MISC_FEATURE
<222> LOCATION: (27)..(36)
<223> OTHER INFORMATION: L-CDR1
<220> FEATURE:
<221> NAME/KEY: MISC_FEATURE
<222> LOCATION: (54)..(56)
<223> OTHER INFORMATION: L-CDR2
<220> FEATURE:
<221> NAME/KEY: MISC_FEATURE
<222> LOCATION: (93)..(98)
<223> OTHER INFORMATION: L-CDR3

<400> SEQUENCE: 8

Asp Leu Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Asn Arg
                85                  90                  95

Glu Leu Arg Thr Phe Gly Gly Gly Thr Lys Leu Glu Ile Lys Arg
            100                 105                 110

<210> SEQ ID NO 9
<211> LENGTH: 111
<212> TYPE: PRT
<213> ORGANISM: Mus musculus
<220> FEATURE:
<221> NAME/KEY: MISC_FEATURE
<223> OTHER INFORMATION: Clone XPA.015.184 light chain
<220> FEATURE:
<221> NAME/KEY: MISC_FEATURE
<222> LOCATION: (27)..(36)
<223> OTHER INFORMATION: L-CDR1
<220> FEATURE:
<221> NAME/KEY: MISC_FEATURE
<222> LOCATION: (54)..(56)
<223> OTHER INFORMATION: L-CDR2
<220> FEATURE:
<221> NAME/KEY: MISC_FEATURE
<222> LOCATION: (93)..(98)
<223> OTHER INFORMATION: L-CDR3

<400> SEQUENCE: 9

Asp Ile Val Met Thr Gln Ser Pro Thr Ser Leu Ala Val Ser Leu Gly
1               5                   10                  15

Gln Arg Ala Thr Ile Ser Cys Arg Ala Ser Glu Ser Val Ser Ile Ser
            20                  25                  30

Gly Tyr Ser Tyr Ile His Trp Tyr Gln Gln Arg Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Val Ala Thr Tyr Tyr Cys Gln His Asn Arg
                85                  90                  95

Asp Pro Arg Thr Phe Gly Gly Gly Thr Lys Leu Glu Ile Lys Arg
            100                 105                 110

<210> SEQ ID NO 10
<211> LENGTH: 108
<212> TYPE: PRT
<213> ORGANISM: Mus musculus
<220> FEATURE:
<221> NAME/KEY: MISC_FEATURE
<223> OTHER INFORMATION: Clone XPA.015.185 light chain
<220> FEATURE:
<221> NAME/KEY: MISC_FEATURE
<222> LOCATION: (27)..(32)
<223> OTHER INFORMATION: L-CDR1
<220> FEATURE:
<221> NAME/KEY: MISC_FEATURE
<222> LOCATION: (50)..(52)
<223> OTHER INFORMATION: L-CDR2
<220> FEATURE:
<221> NAME/KEY: MISC_FEATURE
<222> LOCATION: (89)..(95)
<223> OTHER INFORMATION: L-CDR3

<400> SEQUENCE: 10

Asp Ile Gln Met Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Ala Gly Thr Lys Leu Glu Leu Lys Arg
            100                 105

<210> SEQ ID NO 11
<211> LENGTH: 108
<212> TYPE: PRT
<213> ORGANISM: Mus musculus
<220> FEATURE:
<221> NAME/KEY: MISC_FEATURE
<223> OTHER INFORMATION: Clone XPA.015.186 light chain
<220> FEATURE:
<221> NAME/KEY: MISC_FEATURE
<222> LOCATION: (27)..(32)
<223> OTHER INFORMATION: L-CDR1
<220> FEATURE:
<221> NAME/KEY: MISC_FEATURE
<222> LOCATION: (50)..(52)
<223> OTHER INFORMATION: L-CDR2
<220> FEATURE:
<221> NAME/KEY: MISC_FEATURE
<222> LOCATION: (89)..(95)
<223> OTHER INFORMATION: L-CDR3

<400> SEQUENCE: 11

Asp Ile Gln Met Thr Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Thr Trp Tyr Gln Gln Lys Pro Gly Asn Ile Pro Lys Leu Leu Ile
        35                  40                  45

-continued

```
Ser Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys Arg
                100                 105
```

<210> SEQ ID NO 12
<211> LENGTH: 111
<212> TYPE: PRT
<213> ORGANISM: Mus musculus
<220> FEATURE:
<221> NAME/KEY: MISC_FEATURE
<223> OTHER INFORMATION: Clone XPA.015.187 light chain
<220> FEATURE:
<221> NAME/KEY: MISC_FEATURE
<222> LOCATION: (27)..(36)
<223> OTHER INFORMATION: L-CDR1
<220> FEATURE:
<221> NAME/KEY: MISC_FEATURE
<222> LOCATION: (54)..(56)
<223> OTHER INFORMATION: L-CDR2
<220> FEATURE:
<221> NAME/KEY: MISC_FEATURE
<222> LOCATION: (93)..(98)
<223> OTHER INFORMATION: L-CDR3

<400> SEQUENCE: 12

```
Asp Leu Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Ser Tyr Ile His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Gly Asn Tyr Tyr Cys Gln His Asn Arg
                85                  90                  95

Glu Pro Arg Thr Phe Gly Gly Gly Thr Lys Leu Glu Ile Lys Arg
                100                 105                 110
```

<210> SEQ ID NO 13
<211> LENGTH: 108
<212> TYPE: PRT
<213> ORGANISM: Mus musculus
<220> FEATURE:
<221> NAME/KEY: MISC_FEATURE
<223> OTHER INFORMATION: Clone XPA.015.188 light chain
<220> FEATURE:
<221> NAME/KEY: MISC_FEATURE
<222> LOCATION: (27)..(32)
<223> OTHER INFORMATION: L-CDR1
<220> FEATURE:
<221> NAME/KEY: MISC_FEATURE
<222> LOCATION: (50)..(52)
<223> OTHER INFORMATION: L-CDR2
<220> FEATURE:
<221> NAME/KEY: MISC_FEATURE
<222> LOCATION: (89)..(95)
<223> OTHER INFORMATION: L-CDR3

<400> SEQUENCE: 13

```
Asp Val Gln Ile Thr Gln Ser Pro Ser Tyr Leu Thr Ala Ser Pro Gly
1               5                   10                  15

Glu Thr Ile Thr Ile Asn Cys Arg Ala Ser Lys Ser Ile Ser Asn Tyr
            20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Phe Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Ala Gly Thr Lys Leu Glu Leu Lys Arg
            100                 105
```

<210> SEQ ID NO 14
<211> LENGTH: 111
<212> TYPE: PRT
<213> ORGANISM: Mus musculus
<220> FEATURE:
<221> NAME/KEY: MISC_FEATURE
<223> OTHER INFORMATION: Clone XPA.015.189 light chain
<220> FEATURE:
<221> NAME/KEY: MISC_FEATURE
<222> LOCATION: (27)..(36)
<223> OTHER INFORMATION: L-CDR1
<220> FEATURE:
<221> NAME/KEY: MISC_FEATURE
<222> LOCATION: (54)..(56)
<223> OTHER INFORMATION: L-CDR2
<220> FEATURE:
<221> NAME/KEY: MISC_FEATURE
<222> LOCATION: (93)..(98)
<223> OTHER INFORMATION: L-CDR3

<400> SEQUENCE: 14

```
Asp Ile Val Met Thr Gln Ser Pro Ala Ser Leu Ala Val Ser Leu Gly
1               5                   10                  15

Gln Arg Ala Thr Ile Ser Cys Arg Ala Ser Lys Ser Val Ser Ile Ser
            20                  25                  30

Gly Tyr Ser Tyr Ile His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Gly Asn Tyr Tyr Cys Gln His Asn Arg
                85                  90                  95

Glu Pro Arg Thr Phe Gly Gly Gly Thr Lys Leu Glu Ile Lys Arg
            100                 105                 110
```

<210> SEQ ID NO 15
<211> LENGTH: 108
<212> TYPE: PRT
<213> ORGANISM: Mus musculus
<220> FEATURE:
<221> NAME/KEY: MISC_FEATURE
<223> OTHER INFORMATION: Clone XPA.015.190 light chain
<220> FEATURE:
<221> NAME/KEY: MISC_FEATURE
<222> LOCATION: (27)..(32)
<223> OTHER INFORMATION: L-CDR1
<220> FEATURE:
<221> NAME/KEY: MISC_FEATURE

```
<222> LOCATION: (54)..(56)
<223> OTHER INFORMATION: L-CDR2
<220> FEATURE:
<221> NAME/KEY: MISC_FEATURE
<222> LOCATION: (93)..(98)
<223> OTHER INFORMATION: L-CDR3

<400> SEQUENCE: 15
```

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Phe Tyr Cys Gln Gln Tyr Ser Asp Leu Pro Tyr
                85                  90                  95

Thr Phe Gly Gly Gly Thr Lys Leu Glu Ile Lys Arg
            100                 105

```
<210> SEQ ID NO 16
<211> LENGTH: 108
<212> TYPE: PRT
<213> ORGANISM: Mus musculus
<220> FEATURE:
<221> NAME/KEY: MISC_FEATURE
<223> OTHER INFORMATION: Clone XPA.015.191 light chain
<220> FEATURE:
<221> NAME/KEY: MISC_FEATURE
<222> LOCATION: (27)..(32)
<223> OTHER INFORMATION: L-CDR1
<220> FEATURE:
<221> NAME/KEY: MISC_FEATURE
<222> LOCATION: (50)..(52)
<223> OTHER INFORMATION: L-CDR2
<220> FEATURE:
<221> NAME/KEY: MISC_FEATURE
<222> LOCATION: (89)..(95)
<223> OTHER INFORMATION: L-CDR3

<400> SEQUENCE: 16
```

Asp Val Gln Ile Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Ser Ala Thr Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Pro
65                  70                  75                  80

Glu Asp Phe Val Asp Tyr Tyr Cys Leu Gln Tyr Ala Ser Tyr Pro Phe
                85                  90                  95

Thr Phe Gly Ser Gly Thr Lys Val Glu Ile Lys Arg
            100                 105

```
<210> SEQ ID NO 17
<211> LENGTH: 108
<212> TYPE: PRT
<213> ORGANISM: Mus musculus
```

```
<220> FEATURE:
<221> NAME/KEY: MISC_FEATURE
<223> OTHER INFORMATION: Clone XPA.015.192 light chain
<220> FEATURE:
<221> NAME/KEY: MISC_FEATURE
<222> LOCATION: (27)..(32)
<223> OTHER INFORMATION: L-CDR1
<220> FEATURE:
<221> NAME/KEY: MISC_FEATURE
<222> LOCATION: (50)..(52)
<223> OTHER INFORMATION: L-CDR2
<220> FEATURE:
<221> NAME/KEY: MISC_FEATURE
<222> LOCATION: (89)..(95)
<223> OTHER INFORMATION: L-CDR3

<400> SEQUENCE: 17

Asp Ile Gln Met Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Ala Gly Thr Lys Leu Glu Leu Lys Arg
            100                 105

<210> SEQ ID NO 18
<211> LENGTH: 107
<212> TYPE: PRT
<213> ORGANISM: Mus musculus
<220> FEATURE:
<221> NAME/KEY: MISC_FEATURE
<223> OTHER INFORMATION: Clone XPA.015.173 light chain
<220> FEATURE:
<221> NAME/KEY: MISC_FEATURE
<222> LOCATION: (27)..(32)
<223> OTHER INFORMATION: L-CDR1
<220> FEATURE:
<221> NAME/KEY: MISC_FEATURE
<222> LOCATION: (50)..(52)
<223> OTHER INFORMATION: L-CDR2
<220> FEATURE:
<221> NAME/KEY: MISC_FEATURE
<222> LOCATION: (89)..(94)
<223> OTHER INFORMATION: L-CDR3

<400> SEQUENCE: 18

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln His Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Tyr Thr
                85                  90                  95
```

Phe Gly Gly Gly Thr Lys Leu Glu Ile Lys Arg
            100                 105

<210> SEQ ID NO 19
<211> LENGTH: 108
<212> TYPE: PRT
<213> ORGANISM: Mus musculus
<220> FEATURE:
<221> NAME/KEY: MISC_FEATURE
<223> OTHER INFORMATION: Clone XPA.015.174 light chain
<220> FEATURE:
<221> NAME/KEY: MISC_FEATURE
<222> LOCATION: (27)..(32)
<223> OTHER INFORMATION: L-CDR1
<220> FEATURE:
<221> NAME/KEY: MISC_FEATURE
<222> LOCATION: (50)..(52)
<223> OTHER INFORMATION: L-CDR2
<220> FEATURE:
<221> NAME/KEY: MISC_FEATURE
<222> LOCATION: (89)..(95)
<223> OTHER INFORMATION: L-CDR3

<400> SEQUENCE: 19

Asp Ile Val Met Thr Gln Ser Pro Ser Leu Phe Ala Ser Leu Gly
1               5                   10                  15

Glu Arg Val Ser Leu Thr Cys Arg Ala Ser Gln Asp Ile Gly Asp Arg
            20                  25                  30

Leu Tyr Trp Leu Gln Gln Glu Pro Asp Gly Ala Ile Lys Arg Leu Ile
        35                  40                  45

Phe Ala Thr Ser Ser Leu Asp Ser Gly Val Pro Lys Arg Phe Ser Gly
50                  55                  60

Ser Arg Ser Gly Ser Glu Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Trp
            85                  90                  95

Thr Phe Gly Gly Gly Thr Lys Leu Glu Ile Lys Arg
            100                 105

<210> SEQ ID NO 20
<211> LENGTH: 111
<212> TYPE: PRT
<213> ORGANISM: Mus musculus
<220> FEATURE:
<221> NAME/KEY: MISC_FEATURE
<223> OTHER INFORMATION: Clone XPA.015.172 light chain
<220> FEATURE:
<221> NAME/KEY: MISC_FEATURE
<222> LOCATION: (27)..(36)
<223> OTHER INFORMATION: L-CDR1
<220> FEATURE:
<221> NAME/KEY: MISC_FEATURE
<222> LOCATION: (54)..(56)
<223> OTHER INFORMATION: L-CDR2
<220> FEATURE:
<221> NAME/KEY: MISC_FEATURE
<222> LOCATION: (93)..(98)
<223> OTHER INFORMATION: L-CDR3

<400> SEQUENCE: 20

Asp Ile Val Met Thr Gln Ser Pro Thr Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Ile His Trp Tyr Gln Gln Lys Pro Gly Gln Pro Pro
        35                  40                  45

```
Lys Leu Leu Ile Tyr Leu Ala Ser Asn Leu Glu Ser Gly Val Pro Ala
     50                  55                  60

Arg Phe Ser Gly Ser Gly Ser Gly Thr Asp Phe Ile Leu Asn Ile His
65                  70                  75                  80

Pro Val Glu Glu Asp Ala Ala Thr Tyr Tyr Cys Gln His Asn Arg
                85                  90                  95

Asp Pro Arg Thr Phe Gly Gly Gly Thr Lys Leu Glu Leu Lys Arg
            100                 105                 110

<210> SEQ ID NO 21
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.093 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 21

Gln Ser Val Leu Thr Gln Pro Pro Ser Ala Ser Gly Thr Pro Gly Gln
1               5                   10                  15

Arg Val Thr Ile Ser Cys Ser Gly Ser Ile Ser Asn Ile Gly Ser Asn
                20                  25                  30

Tyr Val Ser Trp Tyr Gln Gln Leu Pro Gly Thr Ala Pro Lys Leu Leu
                35                  40                  45

Ile Tyr Gly Asn Ser Asn Arg Pro Ser Gly Val Pro Asp Arg Phe Ser
     50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Pro His Val Val Phe Gly Gly Gly Thr Lys Leu Thr Val Leu Gly
                100                 105                 110

<210> SEQ ID NO 22
<211> LENGTH: 99
<212> TYPE: PRT
<213> ORGANISM: Homo sapiens
<220> FEATURE:
<221> NAME/KEY: MISC_FEATURE
<223> OTHER INFORMATION: XPA.15.096 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 22
```

Gln Ser Val Leu Thr Gln Pro Pro Ser Ala Ser Gly Thr Pro Gly Gln
1               5                   10                  15

Arg Val Thr Ile Ser Cys Ser Gly Ser Phe Ser Asn Ile Gly Ser Asn
                20                  25                  30

Tyr Val Tyr Trp Tyr Gln Gln Leu Pro Gly Thr Ala Arg Lys Leu Leu
            35                  40                  45

Ile Tyr Ala Asp Thr Phe Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Val

<210> SEQ ID NO 23
<211> LENGTH: 100
<212> TYPE: PRT
<213> ORGANISM: Homo sapiens
<220> FEATURE:
<221> NAME/KEY: MISC_FEATURE
<223> OTHER INFORMATION: Clone XPA.15.094 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 23

Gln Ser Val Leu Thr Gln Pro Pro Ser Ala Ser Gly Thr Pro Gly Gln
1               5                   10                  15

Arg Val Thr Ile Ser Cys Ser Gly Ser Ile Ser Asn Ile Gly Ser Asn
                20                  25                  30

Tyr Val Ser Trp Tyr Gln Gln Leu Pro Gly Thr Ala Pro Lys Leu Leu
            35                  40                  45

Ile Tyr Gly Asn Ser Asn Arg Pro Ser Gly Val Pro Gly Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Pro His Val
            100

<210> SEQ ID NO 24
<211> LENGTH: 99
<212> TYPE: PRT
<213> ORGANISM: Homo sapiens
<220> FEATURE:
<221> NAME/KEY: MISC_FEATURE
<223> OTHER INFORMATION: Clone XPA.15.106 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE

```
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 24

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Thr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Gly Trp

<210> SEQ ID NO 25
<211> LENGTH: 97
<212> TYPE: PRT
<213> ORGANISM: Homo sapiens
<220> FEATURE:
<221> NAME/KEY: MISC_FEATURE
<223> OTHER INFORMATION: Clone XPA.15.105 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(97)
<223> OTHER INFORMATION: L-CDR3

<400> SEQUENCE: 25

Gln Ser Val Leu Thr Gln Pro Pro Ser Ala Ser Gly Thr Pro Gly Gln
1               5                   10                  15

Arg Val Thr Ile Ser Cys Ser Gly Gly Pro Ser Asn Ile Gly Ser Asn
            20                  25                  30

Ile Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Glu Thr Trp Asp Ser Asn Thr
                85                  90                  95

Gln

<210> SEQ ID NO 26
<211> LENGTH: 112
<212> TYPE: PRT
<213> ORGANISM: Homo sapiens
<220> FEATURE:
<221> NAME/KEY: MISC_FEATURE
```

-continued

```
<223> OTHER INFORMATION: Clone XPA.15.100 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 26

Gln Ser Val Leu Thr Gln Pro Pro Ser Ala Ser Gly Thr Pro Gly Gln
1               5                   10                  15

Arg Val Thr Ile Ser Cys Ser Gly Ser Ala Ser Asn Leu Gly Met His
            20                  25                  30

Phe Val Ser Trp Tyr Gln Gln Leu Pro Gly Thr Ala Pro Lys Leu Leu
        35                  40                  45

Ile Tyr Asp Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Pro Val Leu Phe Gly Gly Gly Thr Lys Leu Thr Val Leu Gly
            100                 105                 110

<210> SEQ ID NO 27
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.124 light chain
<220> FEATURE:
<221> NAME/KEY: MISC_FEATURE
<222> LOCATION: (26)..(34)
<223> OTHER INFORMATION: L-CDR1
<220> FEATURE:
<221> NAME/KEY: MISC_FEATURE
<222> LOCATION: (52)..(54)
<223> OTHER INFORMATION: L-CDR2
<220> FEATURE:
<221> NAME/KEY: MISC_FEATURE
<222> LOCATION: (91)..(100)
<223> OTHER INFORMATION: L-CDR3

<400> SEQUENCE: 27

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Pro Val Phe Gly Gly Gly Thr Lys Leu Thr Val Leu Gly
```

<210> SEQ ID NO 28
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.121 light chain
<220> FEATURE:
<221> NAME/KEY: MISC_FEATURE
<222> LOCATION: (23)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 28

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Trp Glu Val Phe Gly Gly Gly Thr Lys Leu Thr Val Leu Gly
            100                 105                 110

<210> SEQ ID NO 29
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.122 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 29

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser

```
                    50                  55                  60
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                     85                  90                  95

Asn Gly Gln Val Phe Gly Gly Gly Thr Lys Leu Thr Val Leu Gly
                100                 105                 110
```

<210> SEQ ID NO 30
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.127 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 30

```
Gln Ser Val Leu Thr Gln Pro Pro Ser Ala Ser Gly Thr Pro Gly Gln
  1               5                  10                  15

Arg Val Thr Ile Ser Cys Ser Gly Asn Ser Ser Asn Ile Gly Asn Asn
                 20                  25                  30

Tyr Val Ala Trp Tyr Gln Gln Leu Pro Gly Thr Ala Pro Lys Leu Leu
             35                  40                  45

Ile Tyr Ser Asp His Gln Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                     85                  90                  95

Ser Gly His Val Ile Phe Gly Gly Gly Thr Lys Leu Thr Val Leu Gly
                100                 105                 110
```

<210> SEQ ID NO 31
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.125 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 31

Gln Ser Val Leu Thr Gln Pro Pro Ser Ala Ser Gly Thr Pro Gly Gln

-continued

```
                1               5                   10                  15
            Arg Val Thr Ile Ser Cys Ser Gly Ser Asn Ser Asn Ile Gly Ser Arg
                            20                  25                  30

Thr Val Asn Trp Tyr Gln Gln Leu Pro Gly Thr Ala Pro Lys Leu Leu
                        35                  40                  45

Ile Tyr Glu Asn Asn Lys Arg Pro Ser Gly Val Pro Asp Arg Phe Ser
                50                  55                  60

Gly Ser Lys Ser Gly Thr Ser Ala Ser Leu Ala Ile Ser Gly Leu Arg
            65                  70                  75                  80

Ser Glu Asp Glu Ala Asp Tyr Tyr Cys Ser Tyr Ala Gly Ser Asn
                            85                  90                  95

Asn Leu Gly Val Phe Gly Gly Gly Thr Lys Leu Thr Val Leu Gly
                        100                 105                 110
```

<210> SEQ ID NO 32
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.133 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 32

```
            Gln Ser Val Leu Thr Gln Pro Pro Ser Ala Ser Gly Thr Pro Gly Gln
            1               5                   10                  15

Arg Val Thr Ile Ser Cys Ser Gly Ser Phe Ser Asn Ile Gly Gly Asn
                            20                  25                  30

Thr Val Asn Trp Tyr Gln Gln Leu Pro Gly Thr Ala Pro Lys Leu Leu
                        35                  40                  45

Ile Tyr Ser Tyr Asp Gln Arg Pro Ser Gly Val Pro Asp Arg Phe Ser
                50                  55                  60

Gly Ser Lys Ser Gly Thr Ser Ala Ser Leu Ala Ile Ser Gly Leu Arg
            65                  70                  75                  80

Ser Glu Asp Glu Ala Asp Tyr Tyr Cys Ala Ser Trp Asp Val Ser Leu
                            85                  90                  95

Ser Gly Val Val Phe Gly Gly Gly Thr Lys Leu Thr Val Leu Gly
                        100                 105                 110
```

<210> SEQ ID NO 33
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.135 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)

```
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 33

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
            35                  40                  45

Ile Tyr Thr Asp Ser Arg Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Val Ser Arg Asp Asp Ser Leu
                85                  90                  95

Asn Gly Trp Val Phe Gly Gly Gly Thr Lys Leu Thr Val Leu Gly
            100                 105                 110

<210> SEQ ID NO 34
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.139 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 34

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Asn Gly Pro Ile Phe Gly Gly Gly Thr Lys Leu Thr Val Leu Gly
            100                 105                 110

<210> SEQ ID NO 35
<211> LENGTH: 112
<212> TYPE: PRT
<213> ORGANISM: Homo sapiens
<220> FEATURE:
```

```
<221> NAME/KEY: MISC_FEATURE
<223> OTHER INFORMATION: Clone XPA.15.138 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 35

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Phe Val Val Phe Gly Gly Thr Lys Leu Thr Val Leu Gly
            100                 105                 110

<210> SEQ ID NO 36
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.143 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 36

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Gly Asn Thr Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95
```

```
Ser Gly Val Val Phe Gly Gly Gly Thr Lys Leu Thr Val Leu Gly
            100                 105                 110

<210> SEQ ID NO 37
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.141 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 37

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Phe Trp Tyr Gln Gln Leu Pro Gly Thr Ala Pro Lys Leu Leu
        35                  40                  45

Ile Tyr Arg Asn Tyr Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Thr Gly Trp Val Phe Gly Gly Gly Thr Lys Leu Thr Val Leu Gly
            100                 105                 110

<210> SEQ ID NO 38
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.145 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 38

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ala Asn
            20                  25                  30

Thr Val Asn Trp Tyr Gln Gln Leu Pro Gly Thr Ala Pro Lys Leu Leu
        35                  40                  45
```

```
Ile Tyr Gly Val Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly
                100                 105                 110
```

<210> SEQ ID NO 39
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.140 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 39

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Gly Ala Thr Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ser Trp Asp Asp Ser Leu
                85                  90                  95

Ser Gly Pro Val Phe Gly Gly Gly Thr Lys Leu Thr Val Leu Gly
                100                 105                 110
```

<210> SEQ ID NO 40
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.159 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 40

```
Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ala Trp Asp Asp Thr Leu
                85                  90                  95

Asn Gly Pro Val Phe Gly Gly Gly Thr Lys Leu Thr Val Leu Gly
            100                 105                 110
```

<210> SEQ ID NO 41
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.167 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 41

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asp Ile Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Asn Gly Pro Val Phe Gly Gly Gly Thr Lys Leu Thr Val Leu Gly
            100                 105                 110
```

<210> SEQ ID NO 42
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.169 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE

```
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 42
```

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Tyr Trp Tyr Gln Gln Leu Pro Gly Thr Ala Pro Lys Leu Leu
        35                  40                  45

Ile Tyr Asp Asn Asn Lys Arg Pro Ala Gly Val Pro Asp Arg Phe Ser
    50                  55                  60

Gly Ser Lys Ser Gly Thr Ser Ala Ser Leu Ala Ile Ser Gly Leu Arg
65              70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
            100                 105                 110

```
<210> SEQ ID NO 43
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.013 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 43
```

Gln Ser Val Leu Thr Gln Pro Pro Ser Ala Ser Gly Thr Pro Gly Gln
1               5                   10                  15

Arg Val Thr Ile Ser Cys Ser Gly Ser Ile Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65              70                  75                  80

Ser Glu Asp Glu Ala Asp Tyr Tyr Cys Ala Ala Trp Asp Asp Ser Leu
                85                  90                  95

Ser Pro His Val Val Phe Gly Gly Gly Thr Lys Leu Thr Val Leu Gly
            100                 105                 110

```
<210> SEQ ID NO 44
<211> LENGTH: 111
<212> TYPE: PRT
<213> ORGANISM: Homo sapiens
```

```
<220> FEATURE:
<221> NAME/KEY: MISC_FEATURE
<223> OTHER INFORMATION: Clone XPA.15.020 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 44

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Leu Val Phe Gly Gly Gly Thr Lys Leu Thr Val Leu Gly
            100                 105                 110

<210> SEQ ID NO 45
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.017 light chain
<220> FEATURE:
<221> NAME/KEY: MISC_FEATURE
<222> LOCATION: (26)..(34)
<223> OTHER INFORMATION: L-CDR1
<220> FEATURE:
<221> NAME/KEY: MISC_FEATURE
<222> LOCATION: (52)..(54)
<223> OTHER INFORMATION: L-CDR2
<220> FEATURE:
<221> NAME/KEY: MISC_FEATURE
<222> LOCATION: (91)..(100)
<223> OTHER INFORMATION: L-CDR3

<400> SEQUENCE: 45

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95
```

Leu Ser Gly Trp Val Phe Gly Gly Gly Thr Lys Leu Thr Val Leu Gly
            100                 105                 110

<210> SEQ ID NO 46
<211> LENGTH: 113
<212> TYPE: PRT
<213> ORGANISM: Homo sapiens
<220> FEATURE:
<221> NAME/KEY: MISC_FEATURE
<223> OTHER INFORMATION: Clone XPA.15.009 light chain
<220> FEATURE:
<221> NAME/KEY: MISC_FEATURE
<222> LOCATION: (26)..(34)
<223> OTHER INFORMATION: L-CDR1
<220> FEATURE:
<221> NAME/KEY: MISC_FEATURE
<222> LOCATION: (52)..(54)
<223> OTHER INFORMATION: L-CDR2
<220> FEATURE:
<221> NAME/KEY: MISC_FEATURE
<222> LOCATION: (91)..(101)
<223> OTHER INFORMATION: L-CDR3

<400> SEQUENCE: 46

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Arg Asn Asp Gln Arg Pro Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp His Ser
                85                  90                  95

Leu Ser Ala His Val Val Phe Gly Gly Gly Thr Lys Leu Thr Val Leu
            100                 105                 110

Gly

<210> SEQ ID NO 47
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.033 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 47

Gln Ser Val Leu Thr Gln Pro Pro Ser Ala Ser Gly Thr Pro Gly Gln
1               5                   10                  15

Arg Val Thr Ile Ser Cys Ser Gly Thr Ser Ser Asn Phe Gly Arg Arg
            20                  25                  30

```
Thr Val Asn Trp Tyr Gln Gln Leu Pro Gly Thr Ala Pro Lys Leu Leu
             35                  40                  45

Ile Tyr Ser Asn Asn Leu Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Gly Thr Lys Leu Thr Val Leu Gly
                100                 105                 110

<210> SEQ ID NO 48
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.037 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 48

Gln Ser Val Leu Thr Gln Pro Pro Ser Ala Ser Gly Thr Pro Gly Gln
 1               5                  10                  15

Arg Val Thr Ile Ser Cys Ser Gly Arg Ser Ser Asn Ile Gly Tyr Asn
                 20                  25                  30

Tyr Val Ser Trp Tyr Gln Gln Leu Pro Gly Thr Ala Pro Lys Leu Leu
             35                  40                  45

Ile Tyr Gly Asn Ser Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Pro Val Phe Gly Gly Gly Thr Lys Leu Thr Val Leu Gly
                100                 105                 110

<210> SEQ ID NO 49
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.042 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3
```

<400> SEQUENCE: 49

Gln Ser Val Leu Thr Gln Pro Pro Ser Ala Ser Gly Thr Pro Gly Gln
1               5                   10                  15

Arg Val Thr Ile Ser Cys Ser Gly Arg Ser Ser Asn Ile Glu Asn Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly
            100                 105                 110

<210> SEQ ID NO 50
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.036 light chain
<220> FEATURE:
<221> NAME/KEY: MISC_FEATURE
<222> LOCATION: (26)..(34)
<223> OTHER INFORMATION: L-CDR1
<220> FEATURE:
<221> NAME/KEY: MISC_FEATURE
<222> LOCATION: (52)..(54)
<223> OTHER INFORMATION: L-CDR2
<220> FEATURE:
<221> NAME/KEY: MISC_FEATURE
<222> LOCATION: (91)..(100)
<223> OTHER INFORMATION: L-CDR3

<400> SEQUENCE: 50

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ser Trp Asp Asp Ser
                85                  90                  95

His Leu His Val Leu Phe Gly Gly Gly Thr Lys Leu Thr Val Leu Gly
            100                 105                 110

<210> SEQ ID NO 51
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.047 light chain
<220> FEATURE:
<221> NAME/KEY: MISC_FEATURE
<222> LOCATION: (26)..(33)

<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 51

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Gly Asn
            20                  25                  30

Ser Val His Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Pro His Val Val Phe Gly Gly Gly Thr Lys Leu Thr Val Leu Gly
            100                 105                 110

<210> SEQ ID NO 52
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.007 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 52

Gln Ser Val Leu Thr Gln Pro Pro Ser Ala Ser Gly Thr Pro Gly Gln
1               5                   10                  15

Arg Val Thr Ile Ser Cys Ser Gly Asn Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Ser Asn Asp Ile Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Val Phe Gly Gly Gly Thr Lys Leu Thr Val Leu Gly
            100                 105                 110

<210> SEQ ID NO 53

<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.074 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 53

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Val Phe Gly Gly Gly Thr Lys Leu Thr Val Leu Gly
            100                 105                 110

<210> SEQ ID NO 54
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.085 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 54

Gln Ser Val Leu Thr Gln Pro Pro Ser Ala Ser Gly Thr Pro Gly Gln
1               5                   10                  15

Arg Val Thr Ile Ser Cys Ser Gly Ser Ile Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

-continued

Ser Glu Asp Glu Ala Asp Tyr Tyr Cys Ala Ala Trp Asp Asp Ser Leu
                85                  90                  95

Ser Pro His Val Val Phe Gly Gly Gly Thr Lys Leu Thr Val Leu Gly
            100                 105                 110

<210> SEQ ID NO 55
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.075 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 55

Gln Ser Val Leu Thr Gln Pro Pro Ser Ala Ser Gly Thr Pro Gly Gln
1               5                   10                  15

Arg Val Thr Ile Ser Cys Ser Gly Ser Ile Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Pro His Val Val Phe Gly Gly Gly Thr Lys Leu Thr Val Leu Gly
            100                 105                 110

<210> SEQ ID NO 56
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.082 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

```
Thr Val Thr Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Gly Trp Val Phe Gly Gly Gly Thr Lys Leu Thr Val Leu Gly
                100                 105                 110
```

<210> SEQ ID NO 57
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.066 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 57

```
Gln Ser Val Leu Thr Gln Pro Pro Ser Ala Ser Gly Thr Pro Gly Gln
1               5                   10                  15

Arg Val Thr Ile Ser Cys Ser Gly Gly Asn Ser Asn Ile Gly Ser Asn
            20                  25                  30

Tyr Val Ser Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Arg Val Phe Gly Gly Gly Thr Lys Leu Thr Val Leu Gly
                100                 105                 110
```

<210> SEQ ID NO 58
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.080 light chain
<220> FEATURE:
<221> NAME/KEY: MISC_FEATURE
<222> LOCATION: (26)..(34)
<223> OTHER INFORMATION: L-CDR1
<220> FEATURE:
<221> NAME/KEY: MISC_FEATURE
<222> LOCATION: (52)..(54)
<223> OTHER INFORMATION: L-CDR2
<220> FEATURE:
<221> NAME/KEY: MISC_FEATURE
<222> LOCATION: (91)..(100)

<223> OTHER INFORMATION: L-CDR3

<400> SEQUENCE: 58

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Thr Asn Asp Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Arg Ser
                85                  90                  95

Leu Ser Gly Ser Val Phe Gly Gly Gly Thr Lys Leu Thr Val Leu Gly
            100                 105                 110

<210> SEQ ID NO 59
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.099 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 59

Gln Ser Val Leu Thr Gln Pro Pro Ser Ala Ser Gly Thr Pro Gly Gln
1               5                   10                  15

Arg Val Thr Ile Ser Cys Ser Gly Ser Ile Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Pro His Val Val Phe Gly Gly Gly Thr Lys Leu Thr Val Leu Gly
            100                 105                 110

<210> SEQ ID NO 60
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.102 light chain
<220> FEATURE:
<221> NAME/KEY: MISC_FEATURE

```
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 60

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ala Trp Asp Asp Thr Leu
                85                  90                  95

Asn Gly Pro Val Phe Gly Gly Gly Thr Lys Leu Thr Val Leu Gly
            100                 105                 110

<210> SEQ ID NO 61
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.115 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 61

Gln Ser Val Leu Thr Gln Pro Pro Ser Ala Ser Gly Thr Pro Gly Gln
1               5                   10                  15

Arg Val Thr Ile Ser Cys Ser Gly Ser Ile Ser Asn Ile Gly Ser Asn
            20                  25                  30

Tyr Val Ser Trp Tyr Gln Xaa Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95
```

-continued

Ser Pro His Val Val Phe Gly Gly Gly Thr Lys Leu Thr Val Leu Gly
            100                 105                 110

<210> SEQ ID NO 62
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.111 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 62

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Gly Asn Ser Asn Arg Ser Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Asn Gly Pro Val Phe Gly Gly Gly Thr Lys Leu Thr Val Leu Gly
            100                 105                 110

<210> SEQ ID NO 63
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.142 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 63

Gln Ser Val Leu Thr Gln Pro Pro Ser Ala Ser Gly Thr Pro Gly Gln
1               5                   10                  15

Arg Val Thr Ile Ser Cys Ser Gly Arg Asn Ser Asn Ile Gly Ser Asn
            20                  25                  30

Tyr Val Ser Trp Tyr Gln Gln Leu Pro Gly Thr Ala Pro Lys Leu Leu
            35                  40                  45

```
Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Val Ala Asp Tyr Tyr Cys Ser Ser Tyr Ala Gly Ser Asn
                85                  90                  95

Asn Phe Val Val Phe Gly Gly Gly Thr Lys Leu Thr Val Leu Gly
                100                 105                 110
```

<210> SEQ ID NO 64
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.146 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 64

```
Gln Ser Val Leu Thr Gln Pro Pro Ser Ala Ser Gly Thr Pro Gly Gln
1               5                   10                  15

Arg Val Thr Ile Ser Cys Ser Gly Thr Asp Ser Asn Phe Gly Ser Asn
                20                  25                  30

Ser Val Asn Trp Tyr Gln Gln Leu Pro Gly Thr Ala Pro Lys Leu Leu
                35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly
                100                 105                 110
```

<210> SEQ ID NO 65
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.144 light chain
<220> FEATURE:
<221> NAME/KEY: MISC_FEATURE
<222> LOCATION: (26)..(34)
<223> OTHER INFORMATION: L-CDR1
<220> FEATURE:
<221> NAME/KEY: MISC_FEATURE
<222> LOCATION: (52)..(54)
<223> OTHER INFORMATION: L-CDR2
<220> FEATURE:
<221> NAME/KEY: MISC_FEATURE
<222> LOCATION: (91)..(100)
<223> OTHER INFORMATION: L-CDR3

<400> SEQUENCE: 65

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Pro
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Thr Ser Tyr Thr Gly Asn
                85                  90                  95

Asn Gln Phe Val Ile Phe Gly Gly Gly Thr Lys Leu Thr Val Leu Gly
                100                 105                 110
```

<210> SEQ ID NO 66
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.154 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 66

```
Gln Ser Val Leu Thr Gln Pro Pro Ser Ala Ser Gly Thr Pro Gly Gln
1               5                   10                  15

Arg Val Thr Ile Ser Cys Ser Gly Ile Ser Ser Asn Ile Gly Asn Asn
                20                  25                  30

Phe Val Ser Trp Tyr Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Arg Gly Pro Val Phe Gly Gly Gly Thr Lys Leu Thr Val Leu Gly
                100                 105                 110
```

<210> SEQ ID NO 67
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.158 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE

```
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 67

Gln Ser Val Leu Thr Gln Pro Pro Ser Ala Ser Gly Thr Pro Gly Gln
 1               5                  10                  15

Arg Val Thr Ile Ser Cys Ser Gly Cys Ser Ser Asn Ile Gly Asn Asn
             20                  25                  30

Ala Val Asn Trp Tyr Gln Gln Leu Pro Gly Thr Ala Pro Lys Leu Leu
         35                  40                  45

Ile Tyr Arg Ser Asp Gln Arg Leu Ala Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ser Tyr Asp Ser Ser Leu
                 85                  90                  95

Ile Gly His Trp Val Phe Gly Gly Gly Thr Lys Leu Thr Val Leu Gly
            100                 105                 110

<210> SEQ ID NO 68
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.155 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 68

Gln Ser Val Leu Thr Gln Pro Pro Ser Ala Ser Gly Thr Pro Gly Gln
 1               5                  10                  15

Arg Val Thr Ile Ser Cys Ser Gly Ile Ser Ser Asn Ile Gly Asn Asn
             20                  25                  30

Phe Val Ser Trp Tyr Gln Gln Leu Pro Gly Thr Ala Pro Lys Leu Leu
         35                  40                  45

Ile Tyr Gly Asn Ser Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Pro
                 85                  90                  95

Arg Gly Pro Val Phe Gly Gly Gly Thr Lys Leu Thr Val Leu Gly
            100                 105                 110

<210> SEQ ID NO 69
<211> LENGTH: 111
<212> TYPE: PRT
<213> ORGANISM: Homo sapiens
```

```
<220> FEATURE:
<221> NAME/KEY: MISC_FEATURE
<223> OTHER INFORMATION: Clone XPA.15.165 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 69

Gln Ser Val Leu Thr Gln Pro Pro Ser Ala Ser Gly Thr Pro Gly Gln
1               5                   10                  15

Arg Val Thr Ile Ser Cys Ser Gly Arg Ser Ser Asn Ile Gly Tyr Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Val Phe Gly Gly Gly Thr Lys Leu Thr Val Leu Gly
            100                 105                 110

<210> SEQ ID NO 70
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.023 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 70

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ala Trp Asp Asp Thr Leu
                85                  90                  95
```

Asn Gly Pro Val Phe Gly Gly Gly Thr Lys Leu Thr Val Leu Gly
            100                 105                 110

<210> SEQ ID NO 71
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.022 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 71

Gln Ser Val Leu Thr Gln Pro Pro Ser Ala Ser Gly Thr Pro Gly Gln
1               5                   10                  15

Arg Val Thr Ile Ser Cys Ser Gly Thr Ser Ser Asn Leu Gly Ser His
            20                  25                  30

Thr Val Ser Trp Tyr Gln Gln Leu Pro Gly Thr Ala Pro Lys Leu Leu
        35                  40                  45

Ile Tyr Asp Asn Asn Glu Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Trp Val Phe Gly Gly Gly Thr Lys Leu Thr Val Leu Gly
            100                 105                 110

<210> SEQ ID NO 72
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.019 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 72

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Thr Ala Pro Lys Leu Leu
        35                  40                  45

```
Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Asp Ser Leu
                 85                  90                  95

Ser Val Trp Val Phe Gly Gly Gly Thr Lys Leu Thr Val Leu Gly
                100                 105                 110
```

<210> SEQ ID NO 73
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.021 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 73

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                 20                  25                  30

Pro Val Asn Trp Tyr Gln Gln Leu Pro Gly Thr Ala Pro Lys Leu Leu
                 35                  40                  45

Ile Tyr Asp Asn Ser Lys Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Asp Ser Leu
                 85                  90                  95

Ser Val Trp Val Phe Gly Gly Gly Thr Lys Leu Thr Val Leu Gly
                100                 105                 110
```

<210> SEQ ID NO 74
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.006 light chain
<220> FEATURE:
<221> NAME/KEY: MISC_FEATURE
<222> LOCATION: (26)..(34)
<223> OTHER INFORMATION: L-CDR1
<220> FEATURE:
<221> NAME/KEY: MISC_FEATURE
<222> LOCATION: (52)..(54)
<223> OTHER INFORMATION: L-CDR2
<220> FEATURE:
<221> NAME/KEY: MISC_FEATURE
<222> LOCATION: (91)..(100)
<223> OTHER INFORMATION: L-CDR3

<400> SEQUENCE: 74

```
Gln Ser Val Leu Thr Gln Pro Pro Ser Ala Ser Gly Thr Pro Gly Gln
1               5                   10                  15

Arg Val Thr Ile Ser Cys Thr Gly Thr Ser Ser Asn Ile Gly Ala Gly
                20                  25                  30

Phe Asp Val His Trp Tyr Gln Gln Leu Pro Gly Thr Ala Pro Lys Leu
            35                  40                  45

Leu Ile Tyr Ser Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Leu Val Phe Gly Gly Gly Thr Lys Leu Thr Val Leu Gly
                100                 105                 110

<210> SEQ ID NO 75
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.026 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 75

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
                100                 105                 110

<210> SEQ ID NO 76
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.043 light chain
<220> FEATURE:
<221> NAME/KEY: MISC_FEATURE
<222> LOCATION: (26)..(34)
<223> OTHER INFORMATION: L-CDR1
<220> FEATURE:
```

```
<221> NAME/KEY: MISC_FEATURE
<222> LOCATION: (52)..(54)
<223> OTHER INFORMATION: L-CDR2
<220> FEATURE:
<221> NAME/KEY: MISC_FEATURE
<222> LOCATION: (91)..(99)
<223> OTHER INFORMATION: L-CDR3

<400> SEQUENCE: 76

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Lys Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Gly Gly Val Phe Gly Gly Gly Thr Lys Leu Thr Val Leu Gly
            100                 105                 110

<210> SEQ ID NO 77
<211> LENGTH: 109
<212> TYPE: PRT
<213> ORGANISM: Homo sapiens
<220> FEATURE:
<221> NAME/KEY: MISC_FEATURE
<223> OTHER INFORMATION: Clone XPA.15.048 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(97)
<223> OTHER INFORMATION: L-CDR3

<400> SEQUENCE: 77

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Ser
            20                  25                  30

Ala Val Asn Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Val Trp Asp Ser Gly Thr
                85                  90                  95

Ala Val Phe Gly Gly Gly Thr Lys Leu Thr Val Leu Gly
            100                 105

<210> SEQ ID NO 78
<211> LENGTH: 111
<212> TYPE: PRT
```

```
<213> ORGANISM: Homo sapiens
<220> FEATURE:
<221> NAME/KEY: MISC_FEATURE
<223> OTHER INFORMATION: Clone XPA.15.062 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 78

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
            100                 105                 110

<210> SEQ ID NO 79
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.059 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 79

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
```

```
                    85                  90                  95

Asn Gly Leu Val Phe Gly Gly Gly Thr Lys Leu Thr Val Leu Gly
            100                 105                 110

<210> SEQ ID NO 80
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.064 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 80

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Arg
            20                  25                  30

Thr Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Asn Gly Trp Val Phe Gly Gly Gly Thr Lys Leu Thr Val Leu Gly
            100                 105                 110

<210> SEQ ID NO 81
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.068 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 81

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Asn Asn
            20                  25                  30

Tyr Val Ser Trp Tyr Gln Gln Leu Pro Gly Thr Ala Pro Lys Leu Leu
```

```
                35                  40                  45
Ile Tyr Gly Asn Ser Asn Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ser Ala Trp Asp Asp Thr Leu
                 85                  90                  95

Asn Gly Pro Val Phe Gly Gly Gly Thr Lys Leu Thr Val Leu Gly
            100                 105                 110
```

<210> SEQ ID NO 82
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clona XPA.15.081 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 82

```
Gln Ser Val Leu Thr Gln Pro Pro Ser Ala Ser Gly Thr Pro Gly Gln
 1               5                  10                  15

Arg Val Thr Ile Ser Cys Ser Gly Ser Thr Ser Asn Ile Gly Asn Asn
             20                  25                  30

Tyr Val Ser Trp Tyr Gln Gln Leu Pro Gly Thr Ala Pro Lys Leu Leu
             35                  40                  45

Ile Tyr Gly Asn Ser Asn Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ser Ala Trp Asp Asp Thr Leu
                 85                  90                  95

Asn Gly Pro Val Phe Gly Gly Gly Thr Lys Leu Thr Val Leu Gly
            100                 105                 110
```

<210> SEQ ID NO 83
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.065 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 83

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Thr Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Gly Trp Val Phe Gly Gly Gly Thr Lys Leu Thr Val Leu Gly
            100                 105                 110

<210> SEQ ID NO 84
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.077 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 84

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ser Val Asn Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Val Phe Gly Gly Gly Thr Lys Leu Thr Val Leu Gly
            100                 105                 110

<210> SEQ ID NO 85
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.086 light chain
<220> FEATURE:
<221> NAME/KEY: MISC_FEATURE
<222> LOCATION: (26)..(33)
<223> OTHER INFORMATION: L-CDR1

```
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(99)
<223> OTHER INFORMATION: L-CDR3

<400> SEQUENCE: 85
```

| Gln | Ser | Val | Leu | Thr | Gln | Pro | Pro | Ser | Ala | Ser | Gly | Thr | Pro | Gly | Gln |
|---|---|---|---|---|---|---|---|---|---|---|---|---|---|---|---|
| 1 | | | | 5 | | | | | 10 | | | | | 15 | |
| Arg | Val | Thr | Ile | Ser | Cys | Ser | Gly | Ser | Ser | Ser | Asn | Ile | Gly | Ser | Asn |
| | | | 20 | | | | | 25 | | | | | 30 | | |
| Thr | Val | Thr | Trp | Tyr | Gln | Gln | Leu | Pro | Gly | Thr | Ala | Pro | Lys | Pro | Leu |
| | | 35 | | | | | 40 | | | | | 45 | | | |
| Ile | Tyr | Ser | Asn | Asn | Gln | Arg | Pro | Ser | Gly | Val | Pro | Asp | Arg | Phe | Ser |
| 50 | | | | | 55 | | | | | 60 | | | | | |
| Gly | Ser | Lys | Ser | Gly | Thr | Ser | Ala | Ser | Leu | Ala | Ile | Ser | Gly | Leu | Arg |
| 65 | | | | | 70 | | | | | 75 | | | | | 80 |
| Ser | Glu | Asp | Glu | Ala | Asp | Tyr | Tyr | Cys | Ala | Thr | Trp | Asp | Asp | Ser | Leu |
| | | | | 85 | | | | | 90 | | | | | 95 | |
| Ser | Gly | Trp | Val | Phe | Gly | Gly | Gly | Thr | Lys | Leu | Thr | Val | Leu | Gly | |
| | | | 100 | | | | | 105 | | | | | 110 | | |

```
<210> SEQ ID NO 86
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.088 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (90)..(100)
<223> OTHER INFORMATION: L-CDR3

<400> SEQUENCE: 86
```

| Gln | Ser | Val | Leu | Thr | Gln | Pro | Pro | Ser | Ala | Ser | Gly | Thr | Pro | Gly | Gln |
|---|---|---|---|---|---|---|---|---|---|---|---|---|---|---|---|
| 1 | | | | 5 | | | | | 10 | | | | | 15 | |
| Arg | Val | Thr | Ile | Ser | Cys | Ser | Gly | Ser | Ala | Ser | Asn | Leu | Gly | Met | His |
| | | | 20 | | | | | 25 | | | | | 30 | | |
| Phe | Val | Ser | Trp | Tyr | Gln | Gln | Leu | Pro | Gly | Thr | Ala | Pro | Lys | Leu | Leu |
| | | 35 | | | | | 40 | | | | | 45 | | | |
| Ile | Tyr | Asp | Asn | Asp | Gln | Arg | Pro | Ser | Gly | Val | Pro | Asp | Arg | Phe | Ser |
| 50 | | | | | 55 | | | | | 60 | | | | | |
| Gly | Ser | Lys | Ser | Gly | Thr | Ser | Ala | Ser | Leu | Ala | Ile | Ser | Gly | Leu | Arg |
| 65 | | | | | 70 | | | | | 75 | | | | | 80 |
| Ser | Glu | Asp | Glu | Ala | Asp | Tyr | Tyr | Cys | Gln | Ser | Tyr | Asp | Ser | Ser | Leu |
| | | | | 85 | | | | | 90 | | | | | 95 | |
| Ser | Gly | Pro | Val | Leu | Phe | Gly | Gly | Gly | Thr | Lys | Leu | Thr | Val | Leu | Gly |
| | | | 100 | | | | | 105 | | | | | 110 | | |

```
<210> SEQ ID NO 87
<211> LENGTH: 110
```

```
<212> TYPE: PRT
<213> ORGANISM: Homo sapiens
<220> FEATURE:
<221> NAME/KEY: MISC_FEATURE
<223> OTHER INFORMATION: Clone XPA.15.193 light chain
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (92)..(99)
<223> OTHER INFORMATION: LCDR3

<400> SEQUENCE: 87

Asn Phe Met Leu Thr Gln Pro His Ser Val Ser Glu Ser Pro Gly Lys
1               5                   10                  15

Thr Val Ser Ile Ser Cys Thr Gly Ser Ser Gly Ser Ile Gly Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Tyr Asn
                85                  90                  95

Ser Asn Val Val Phe Gly Gly Gly Thr Lys Leu Thr Val Leu
            100                 105                 110

<210> SEQ ID NO 88
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.194 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 88

Ser Ser Glu Leu Thr Gln Asp Pro Ala Val Ser Val Ala Leu Gly Gln
1               5                   10                  15

Thr Val Arg Ile Thr Cys Gln Gly Asn Ser Leu Arg Ser Phe Tyr Ala
            20                  25                  30

Thr Trp Tyr Gln Gln Lys Pro Gly Gln Ala Pro Val Leu Val Ile Tyr
        35                  40                  45

Gly Lys Asn Ile Arg Pro Ser Gly Ile Pro Asp Arg Phe Ser Gly Ser
    50                  55                  60

Asn Ser Gly Asp Thr Ala Ser Leu Thr Ile Thr Gly Thr Gln Ala Glu
65                  70                  75                  80
```

```
Asp Glu Ala Asp Tyr Tyr Cys Asn Ser Arg Asp Asn Asn Arg Asn His
                85                  90                  95

Leu Leu Phe Ala Gly Gly Thr Lys Val Thr Val Leu
            100                 105

<210> SEQ ID NO 89
<211> LENGTH: 115
<212> TYPE: PRT
<213> ORGANISM: Homo sapiens
<220> FEATURE:
<221> NAME/KEY: MISC_FEATURE
<223> OTHER INFORMATION: Clone XPA.15.195 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(58)
<223> OTHER INFORMATION: LCDR2
<220> FEATURE:
<221> NAME/KEY: MISC_FEATURE
<222> LOCATION: (97)..(104)
<223> OTHER INFORMATION: LCDR3

<400> SEQUENCE: 89

Gln Ala Met Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Val Ala
            20                  25                  30

Tyr Asn Ile Tyr Trp Tyr Arg Gln Lys Ser Gly Ser Pro Pro Gln Ser
        35                  40                  45

Val Leu Arg Tyr Lys Ser Asp Ser Asp Ser Glu Arg Asp Ser Gly Val
    50                  55                  60

Pro Ser Arg Phe Ser Gly Ser Lys Asp Val Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Leu Ile Trp His Asn Ser Ala Trp Val Phe Gly Gly Gly Thr Gln Leu
            100                 105                 110

Thr Val Leu
        115

<210> SEQ ID NO 90
<211> LENGTH: 110
<212> TYPE: PRT
<213> ORGANISM: Homo sapiens
<220> FEATURE:
<221> NAME/KEY: MISC_FEATURE
<223> OTHER INFORMATION: Clone XPA.15.196 light chain
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (92)..(99)
<223> OTHER INFORMATION: LCDR3

<400> SEQUENCE: 90

Gln Ser Ala Leu Thr Gln Pro Arg Ser Val Ser Glu Ser Pro Gly Lys
1               5                   10                  15
```

```
Thr Val Thr Ile Ser Cys Thr Gly Ser Gly Ser Ile Gly Ser Asn
            20                  25                  30

Tyr Val Gln Trp Tyr Gln Gln Arg Pro Gly Ser Ala Pro Thr Thr Val
        35                  40                  45

Ile Phe Glu Asp Asn Arg Arg Pro Ser Gly Val Pro Asp Arg Phe Ser
    50                  55                  60

Gly Ser Ile His Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Val Gly
                85                  90                  95

Thr Ile Val Val Phe Gly Gly Gly Thr Lys Val Thr Val Leu
            100                 105                 110
```

<210> SEQ ID NO 91
<211> LENGTH: 110
<212> TYPE: PRT
<213> ORGANISM: Homo sapiens
<220> FEATURE:
<221> NAME/KEY: MISC_FEATURE
<223> OTHER INFORMATION: Clone XPA.15.197 light chain
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (92)..(99)
<223> OTHER INFORMATION: LCDR3

<400> SEQUENCE: 91

```
Gln Ser Ala Leu Thr Gln Pro Arg Ser Val Ser Glu Ser Pro Gly Lys
1               5                   10                  15

Thr Val Thr Ile Ser Cys Thr Gly Ser Gly Ser Ile Gly Ser Asn
            20                  25                  30

Tyr Val Gln Trp Tyr Gln Gln Arg Pro Gly Ser Ala Pro Thr Thr Val
        35                  40                  45

Ile Phe Glu Asp Asn Arg Arg Pro Ser Gly Val Pro Asp Arg Phe Ser
    50                  55                  60

Gly Ser Ile His Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Val Gly
                85                  90                  95

Thr Ile Val Val Phe Gly Gly Gly Thr Lys Val Thr Val Leu
            100                 105                 110
```

<210> SEQ ID NO 92
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.198 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:

<221> NAME/KEY: MISC_FEATURE
<222> LOCATION: (88)..(97)
<223> OTHER INFORMATION: LCDR2

<400> SEQUENCE: 92

Ser Tyr Glu Leu Thr Gln Leu Pro Ser Val Ser Val Ser Pro Gly Gln
1               5                   10                  15

Thr Ala Arg Ile Thr Cys Ser Gly Asp Ala Leu Pro Asn Lys Tyr Ala
            20                  25                  30

Tyr Trp Tyr Gln Gln Lys Ser Gly Gln Ala Pro Val Leu Val Ile Tyr
        35                  40                  45

Glu Asp Thr Arg Arg Pro Ser Glu Ile Pro Glu Arg Phe Ser Ala Ser
    50                  55                  60

Ser Ser Gly Thr Met Ala Thr Leu Thr Ile Ser Gly Ala Gln Val Glu
65                  70                  75                  80

Asp Glu Ala Glu Tyr Tyr Cys Tyr Ser Thr Asp Ser Ser Gly Asn Glu
                85                  90                  95

Arg Val Phe Gly Gly Gly Thr Lys Leu Thr Val Leu
            100                 105

<210> SEQ ID NO 93
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.199 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(54)
<223> OTHER INFORMATION: LCDR2
<220> FEATURE:
<221> NAME/KEY: MISC_FEATURE
<222> LOCATION: (91)..(100)
<223> OTHER INFORMATION: LCDR3

<400> SEQUENCE: 93

Gln Ser Ala Leu Thr Gln Pro Ala Ser Val Ser Glu Ser Pro Gly Gln
1               5                   10                  15

Ser Ile Thr Ile Ser Cys Thr Gly Thr Gly Ser Asp Ile Gly Thr Tyr
            20                  25                  30

Asn Leu Val Ser Trp Tyr Gln Gln His Pro Gly Lys Ala Pro Lys Leu
        35                  40                  45

Met Ile Tyr Glu Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Thr Gly Thr Lys Leu Thr Val Leu
            100                 105                 110

<210> SEQ ID NO 94
<211> LENGTH: 110
<212> TYPE: PRT
<213> ORGANISM: Homo sapiens
<220> FEATURE:
<221> NAME/KEY: MISC_FEATURE
<223> OTHER INFORMATION: Clone XPA.15.200 light chain

```
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(54)
<223> OTHER INFORMATION: LCDR2
<220> FEATURE:
<221> NAME/KEY: MISC_FEATURE
<222> LOCATION: (91)..(99)
<223> OTHER INFORMATION: LCDR3

<400> SEQUENCE: 94
```

Gln Thr Val Val Thr Gln Glu Pro Ser Phe Ser Val Ser Pro Gly Gly
1               5                   10                  15

Thr Val Thr Leu Thr Cys Gly Leu Thr Ser Gly Ser Val Ser Thr Ser
            20                  25                  30

Tyr Tyr Pro Ser Trp Tyr Gln Gln Thr Pro Gly Gln Ala Pro Arg Met
        35                  40                  45

Leu Val His Ser Thr Ser Thr Arg Tyr Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Tyr Met Gly Gly
                85                  90                  95

Gly Ile Tyr Val Phe Gly Gly Gly Thr Gln Leu Thr Val Leu
            100                 105                 110

```
<210> SEQ ID NO 95
<211> LENGTH: 116
<212> TYPE: PRT
<213> ORGANISM: Homo sapiens
<220> FEATURE:
<221> NAME/KEY: MISC_FEATURE
<223> OTHER INFORMATION: Clone XPA.15.201 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(58)
<223> OTHER INFORMATION: LCDR2
<220> FEATURE:
<221> NAME/KEY: MISC_FEATURE
<222> LOCATION: (97)..(105)
<223> OTHER INFORMATION: LCDR2

<400> SEQUENCE: 95
```

Gln Ala Val Leu Thr Gln Pro Ser Ser Ser Ala Ser Pro Gly Glu
1               5                   10                  15

Ser Ala Arg Leu Thr Cys Thr Leu Pro Ser Asp Ile Asn Val Arg Tyr
            20                  25                  30

His Asn Ile Tyr Trp Tyr Gln Glu Lys Pro Gly Ser Pro Pro Arg Tyr
        35                  40                  45

Leu Leu Tyr Tyr Tyr Ser Asp Ser Ser Lys Gly Gln Gly Ser Gly Val
    50                  55                  60

Pro Ser Arg Phe Ser Gly Ser Lys Asp Val Ser Thr Asn Thr Gly Ile
65                  70                  75                  80

Leu Val Ile Ser Gly Leu Gln Ser Glu Asp Glu Ala Glu Tyr Tyr Cys
                85                  90                  95

Met Thr Trp Ser Ser Asn Gly Ser Gly Val Phe Gly Gly Gly Thr Gln
            100                 105                 110

Leu Thr Val Leu
        115

<210> SEQ ID NO 96
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.202 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(54)
<223> OTHER INFORMATION: LCDR2
<220> FEATURE:
<221> NAME/KEY: MISC_FEATURE
<222> LOCATION: (91)..(100)
<223> OTHER INFORMATION: LCDR3

<400> SEQUENCE: 96

Gln Ser Val Leu Thr Gln Pro Pro Ser Val Ser Gly Ala Pro Gly Gln
1               5                   10                  15

Arg Val Thr Ile Ser Cys Thr Gly Ser Arg Ser Asn Ile Gly Ala Asp
            20                  25                  30

His Asp Val His Trp Tyr Gln Gln Ile Pro Gly Arg Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Gly Ser Val Phe Gly Gly Gly Thr Lys Leu Thr Val Leu
            100                 105                 110

<210> SEQ ID NO 97
<211> LENGTH: 110
<212> TYPE: PRT
<213> ORGANISM: Homo sapiens
<220> FEATURE:
<221> NAME/KEY: MISC_FEATURE
<223> OTHER INFORMATION: Clone XPA.15.203 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(54)
<223> OTHER INFORMATION: LCDR2
<220> FEATURE:
<221> NAME/KEY: MISC_FEATURE
<222> LOCATION: (91)..(99)
<223> OTHER INFORMATION: LCDR3

<400> SEQUENCE: 97

Gln Thr Val Val Thr Gln Glu Pro Ser Phe Ser Val Ser Pro Gly Gly
1               5                   10                  15

Thr Val Thr Leu Thr Cys Gly Leu Asn Ser Ala Ser Val Ser Thr Tyr
            20                  25                  30

Ser Tyr Pro Ser Trp Tyr Gln Gln Thr Pro Gly Gln Ala Pro Arg Met
        35                  40                  45

```
Leu Ile Tyr Ser Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
 65              70                  75                  80

Gln Ala Asp Asp Glu Ser Asp Tyr Tyr Cys Ala Leu Tyr Met Gly Ser
                85                  90                  95

Gly Ile Trp Val Phe Gly Gly Gly Thr Lys Leu Thr Val Leu
                100                 105                 110

<210> SEQ ID NO 98
<211> LENGTH: 115
<212> TYPE: PRT
<213> ORGANISM: Homo sapiens
<220> FEATURE:
<221> NAME/KEY: MISC_FEATURE
<223> OTHER INFORMATION: Clone XPA.15.204 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(58)
<223> OTHER INFORMATION: LCDR2
<220> FEATURE:
<221> NAME/KEY: MISC_FEATURE
<222> LOCATION: (97)..(104)
<223> OTHER INFORMATION: LCDR3

<400> SEQUENCE: 98

Gln Ala Val Leu Thr Gln Pro Ala Ser Leu Ser Ala Ser Pro Gly Ala
 1               5                  10                  15

Ser Ala Ser Leu Thr Cys Thr Leu Arg Ser Asp Ile Ser Val Gly Val
                20                  25                  30

Tyr Arg Ile Ser Trp Tyr Gln Gln Lys Pro Gly Ser Pro Pro Gln Tyr
                35                  40                  45

Leu Leu Ser Tyr Asn Ser Asp Ser Asn Asn His Gln Gly Ser Gly Val
        50                  55                  60

Pro Ser Arg Phe Ser Gly Ser Lys Asp Ala Ser Ala Asn Ala Gly Ile
 65              70                  75                  80

Leu Leu Ile Ser Gly Leu Gln Ser Glu Asp Glu Ala Asp Tyr Tyr Cys
                85                  90                  95

Met Ile Trp His Ile Asn Ala Trp Val Phe Gly Gly Gly Thr Lys Val
                100                 105                 110

Thr Val Leu
        115

<210> SEQ ID NO 99
<211> LENGTH: 110
<212> TYPE: PRT
<213> ORGANISM: Homo sapiens
<220> FEATURE:
<221> NAME/KEY: MISC_FEATURE
<223> OTHER INFORMATION: Clone XPA.15.205 light chain
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (90)..(99)
```

<223> OTHER INFORMATION: LCDR3

<400> SEQUENCE: 99

Gln Ser Val Leu Thr Gln Pro Pro Ser Val Ser Gly Ala Pro Gly Gln
1               5                   10                  15

Arg Val Thr Ile Ser Cys Ile Gly Ser Arg Ser Asp Ile Gly Tyr Tyr
            20                  25                  30

Ala Val His Trp Tyr Arg Gln Leu Pro Gly Thr Ala Pro Lys Leu Val
        35                  40                  45

Ile Tyr Ala Asn Asp Asn Arg Pro Ser Gly Val Pro Asp Arg Phe Ser
    50                  55                  60

Gly Ser Lys Ser Gly Thr Ser Ala Phe Leu Ala Ile Ser Gly Leu Gln
65                  70                  75                  80

Ala Asp Asp Glu Ala Asp Tyr Tyr Cys Gln Ser Tyr Asp Thr Val Thr
                85                  90                  95

Gly Lys Gly Val Phe Gly Gly Gly Thr Lys Val Thr Val Leu
            100                 105                 110

<210> SEQ ID NO 100
<211> LENGTH: 113
<212> TYPE: PRT
<213> ORGANISM: Homo sapiens
<220> FEATURE:
<221> NAME/KEY: MISC_FEATURE
<223> OTHER INFORMATION: Clone XPA.15.206 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(54)
<223> OTHER INFORMATION: LCDR2
<220> FEATURE:
<221> NAME/KEY: MISC_FEATURE
<222> LOCATION: (91)..(102)
<223> OTHER INFORMATION: LCDR3

<400> SEQUENCE: 100

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Tyr Ala His Trp Tyr Gln Gln Leu Pro Gly Thr Ala Pro Arg Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Pro Asn Tyr Val Phe Gly Thr Gly Thr Lys Val Thr Val
            100                 105                 110

Leu

<210> SEQ ID NO 101
<211> LENGTH: 116
<212> TYPE: PRT
<213> ORGANISM: Homo sapiens
<220> FEATURE:
<221> NAME/KEY: MISC_FEATURE
<223> OTHER INFORMATION: Clone XPA.15.207 light chain

```
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(58)
<223> OTHER INFORMATION: LCDR2
<220> FEATURE:
<221> NAME/KEY: MISC_FEATURE
<222> LOCATION: (97)..(105)
<223> OTHER INFORMATION: LCDR3

<400> SEQUENCE: 101
```

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Asn Lys Asp Gln Gly Ser Gly Val
    50                  55                  60

Pro Ser Arg Phe Ser Gly Ser Lys Asp Val Ser Thr Asn Thr Gly Ile
65                  70                  75                  80

Leu Val Ile Ser Gly Leu Gln Ser Glu Asp Glu Ala Glu Tyr Tyr Cys
                85                  90                  95

Met Thr Trp Ser Ser Asn Gly Ser Gly Val Phe Gly Gly Gly Thr Gln
            100                 105                 110

Leu Thr Val Leu
        115

```
<210> SEQ ID NO 102
<211> LENGTH: 116
<212> TYPE: PRT
<213> ORGANISM: Homo sapiens
<220> FEATURE:
<221> NAME/KEY: MISC_FEATURE
<223> OTHER INFORMATION: Clone XPA.15.208 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (26)..(58)
<223> OTHER INFORMATION: LCDR2
<220> FEATURE:
<221> NAME/KEY: MISC_FEATURE
<222> LOCATION: (97)..(105)
<223> OTHER INFORMATION: LCDR3

<400> SEQUENCE: 102
```

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

His Asn Ile Tyr Trp Tyr Gln Glu Lys Pro Gly Ser Pro Pro Arg Tyr
        35                  40                  45

Leu Leu Tyr Tyr Tyr Ser Asp Ser Ser Lys Gly Gln Gly Ser Gly Val
    50                  55                  60

Pro Ser Arg Phe Ser Gly Ser Lys Asp Val Ser Thr Asn Thr Gly Ile
65                  70                  75                  80

Leu Val Ile Ser Gly Leu Gln Ser Glu Asp Glu Ala Glu Tyr Tyr Cys
                85                  90                  95

-continued

```
Met Thr Trp Ser Ser Asn Gly Ser Gly Val Phe Gly Gly Thr Lys
            100                 105                 110

Leu Thr Val Leu
        115

<210> SEQ ID NO 103
<211> LENGTH: 110
<212> TYPE: PRT
<213> ORGANISM: Homo sapiens
<220> FEATURE:
<221> NAME/KEY: MISC_FEATURE
<223> OTHER INFORMATION: Clone XPA.15.209 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(54)
<223> OTHER INFORMATION: LCDR2
<220> FEATURE:
<221> NAME/KEY: MISC_FEATURE
<222> LOCATION: (91)..(99)
<223> OTHER INFORMATION: LCDR3

<400> SEQUENCE: 103

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Gly
            20                  25                  30

Tyr Ser Pro Gly Trp Tyr Gln Gln Thr Pro Gly Gln Ala Pro Arg Thr
        35                  40                  45

Leu Val Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Tyr Met Gly Ser
                85                  90                  95

Gly Thr Tyr Val Phe Gly Gly Gly Thr Lys Leu Thr Val Leu
            100                 105                 110

<210> SEQ ID NO 104
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.211 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(54)
<223> OTHER INFORMATION: LCDR2
<220> FEATURE:
<221> NAME/KEY: MISC_FEATURE
<222> LOCATION: (91)..(101)
<223> OTHER INFORMATION: LCDR3

<400> SEQUENCE: 104

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

```
Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Gly Val Phe Gly Gly Gly Thr Lys Val Thr Val Leu
                100                 105                 110

<210> SEQ ID NO 105
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.212 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 105

Ser Ser Glu Leu Thr Gln Pro Pro Ser Val Ser Val Ala Pro Gly Lys
 1               5                  10                  15

Thr Ala Thr Ile Thr Cys Gly Gly Asp Asn Ile Ala Ser Lys Ser Val
                 20                  25                  30

His Trp Tyr Gln Gln Lys Pro Gly Gln Ala Pro Val Leu Val Leu Tyr
                 35                  40                  45

Asp Asp Ser Val Arg Pro Ser Asp Ile Pro Glu Arg Phe Ser Gly Ser
 50                  55                  60

Asn Ser Ala Asn Thr Ala Thr Leu Thr Leu Thr Arg Val Glu Ala Gly
 65                  70                  75                  80

Asp Glu Gly Glu Tyr Tyr Cys Gln Val Trp Asp Val Arg Ser Asp His
                 85                  90                  95

Pro Phe Phe Gly Pro Gly Thr Lys Val Thr Val Leu
                100                 105

<210> SEQ ID NO 106
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.213 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(54)
<223> OTHER INFORMATION: LCDR2
<220> FEATURE:
<221> NAME/KEY: MISC_FEATURE
<222> LOCATION: (91)..(100)
```

<223> OTHER INFORMATION: LCDR3

<400> SEQUENCE: 106

Gln Ala Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Tyr Pro Asn Trp Phe Gln Gln Lys Pro Gly Gln Ala Pro Arg Ala
        35                  40                  45

Leu Ile Tyr Ser Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Gln Pro Trp Val Phe Gly Gly Gly Thr Gln Leu Thr Val Leu
            100                 105                 110

<210> SEQ ID NO 107
<211> LENGTH: 110
<212> TYPE: PRT
<213> ORGANISM: Homo sapiens
<220> FEATURE:
<221> NAME/KEY: MISC_FEATURE
<223> OTHER INFORMATION: Clone XPA.15.214 light chain
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (90)..(99)
<223> OTHER INFORMATION: LCDR3

<400> SEQUENCE: 107

Gln Ala Gly Leu Thr Gln Pro Pro Ser Val Ser Lys Gly Leu Arg Gln
1               5                   10                  15

Thr Ala Thr Leu Thr Cys Thr Gly Asp Asn Asn Ile Val Gly Asp Gln
            20                  25                  30

Gly Ala Ala Trp Leu Gln Gln His Gln Gly His Pro Pro Lys Leu Leu
        35                  40                  45

Ser Phe Arg Asn Asn Ser Arg Pro Ser Gly Ile Ser Glu Arg Phe Ser
    50                  55                  60

Ala Ser Arg Ser Arg Asn Thr Ala Ser Leu Thr Ile Thr Arg Leu Gln
65                  70                  75                  80

Pro Glu Asp Ala Ala Asp Tyr Tyr Cys Ser Ala Trp Asp Ser Phe Leu
                85                  90                  95

Ser Ala Trp Val Phe Gly Gly Gly Thr Lys Leu Thr Val Leu
            100                 105                 110

<210> SEQ ID NO 108
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.215 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 108

Ser Ser Glu Leu Thr Gln Asp Pro Ala Val Ser Val Ala Val Gly Gln
1               5                   10                  15

Ser Val Arg Ile Thr Cys Gln Gly Asp Ser Leu Lys Asn Phe Tyr Ala
            20                  25                  30

Thr Trp Tyr Gln Gln Arg Pro Gly Gln Ala Pro Leu Leu Val Ile Phe
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Val Thr Gly Ala Gln Ala Asp
65                  70                  75                  80

Asp Glu Ala Asp Tyr Tyr Cys Asn Ser Pro Asp Ser Ser Asn Lys Leu
                85                  90                  95

Val Val Phe Gly Gly Gly Thr Lys Leu Thr Val Leu
            100                 105

<210> SEQ ID NO 109
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.216 light chain
<220> FEATURE:
<221> NAME/KEY: MISC_FEATURE
<222> LOCATION: (27)..(33)
<223> OTHER INFORMATION: LCDR1
<220> FEATURE:
<221> NAME/KEY: MISC_FEATURE
<222> LOCATION: (51)..(54)
<223> OTHER INFORMATION: LCDR2
<220> FEATURE:
<221> NAME/KEY: MISC_FEATURE
<222> LOCATION: (91)..(97)
<223> OTHER INFORMATION: LCDR3

<400> SEQUENCE: 109

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Gly Thr Phe Gly Gln Gly Thr Lys Leu Glu Ile Lys
            100                 105

```
<210> SEQ ID NO 110
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.217 light chain
<220> FEATURE:
<221> NAME/KEY: MISC_FEATURE
<222> LOCATION: (27)..(37)
<223> OTHER INFORMATION: LCDR1
<220> FEATURE:
<221> NAME/KEY: MISC_FEATURE
<222> LOCATION: (55)..(57)
<223> OTHER INFORMATION: LCDR2
<220> FEATURE:
<221> NAME/KEY: MISC_FEATURE
<222> LOCATION: (94)..(100)
<223> OTHER INFORMATION: LCDR3

<400> SEQUENCE: 110

Asp Val Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Leu Tyr Thr
            20                  25                  30

Asn Gly Asp Thr Tyr Val Ser Trp Tyr Val Gln Lys Pro Gly Gln Ala
        35                  40                  45

Pro Gln Leu Leu Phe Ser Asp Val Ser Ser Arg Phe Phe Gly Val Pro
    50                  55                  60

Asp Arg Phe Ser Ala Ser Gly Ser Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Met Tyr Leu Pro Leu Val Phe Gly Gln Gly Thr Lys Val Glu Ile Lys
            100                 105                 110

<210> SEQ ID NO 111
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.218 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 111

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
```

```
                65                  70                  75                  80
Asp Glu Ala Asp Tyr Tyr Cys Asn Ser Arg Asp Ser Ser Gly Asn His
                    85                  90                  95
Leu Met Phe Gly Gly Gly Thr Gln Leu Thr Val Leu
                100                 105
```

<210> SEQ ID NO 112
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.219 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(54)
<223> OTHER INFORMATION: LCDR2
<220> FEATURE:
<221> NAME/KEY: MISC_FEATURE
<222> LOCATION: (91)..(100)
<223> OTHER INFORMATION: LCDR3

<400> SEQUENCE: 112

```
Gln Ser Ala Leu Thr Gln Pro Ala Ser Val Ser Gly Ser Leu Gly Gln
1               5                   10                  15

Ser Ile Thr Ile Ser Cys Thr Gly Thr Ser Ser Asp Ile Gly Leu Tyr
                20                  25                  30

Lys Phe Val Ser Trp Tyr Gln Gln His Pro Gly Lys Ala Pro Lys Leu
            35                  40                  45

Met Ile Tyr Asp Val Ser Tyr Arg Pro Ser Gly Val Ser Asn Arg Phe
        50                  55                  60

Ser Gly Ser Ser Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Ser
                85                  90                  95

Ser Thr Leu Val Val Phe Gly Gly Gly Thr Lys Leu Thr Val Leu
                100                 105                 110
```

<210> SEQ ID NO 113
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.220 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 113

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Tyr Ala
```

```
                    20                  25                  30

Ser Trp Tyr Gln Gln Lys Pro Gly Gln Ala Pro Leu Leu Val Met Tyr
            35                  40                  45

Asp Arg Asn Ser Arg Pro Ser Gly Ile Pro Asp Arg Phe Ser Gly Ser
    50                  55                  60

Arg Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Ala Val Phe Gly Gly Gly Thr Gln Leu Thr Val Leu
            100                 105

<210> SEQ ID NO 114
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.221 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 114

Ser Tyr Glu Leu Met Gln Pro Pro Ser Val Ser Val Ala Pro Gly Gln
1               5                   10                  15

Thr Ala Thr Ile Thr Cys Gly Gly Asn Asn Ile Gly Thr Lys Ser Val
            20                  25                  30

His Trp Tyr Gln Gln Lys Thr Gly Gln Ala Pro Val Leu Val Val Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Leu Glu Ala Gly
65                  70                  75                  80

Asp Glu Ala Asp Tyr Tyr Cys Gln Val Trp Asp Arg Ser Ser Glu His
                85                  90                  95

His Val Phe Gly Gly Gly Thr Gln Leu Thr Val Leu
            100                 105

<210> SEQ ID NO 115
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.222 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
```

<222> LOCATION: (88)..(97)
<223> OTHER INFORMATION: LCDR3

<400> SEQUENCE: 115

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Arg Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Val Thr Val Leu
            100                 105
```

<210> SEQ ID NO 116
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.223 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 116

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Ser Val
            20                  25                  30

Ala Trp Tyr Gln Gln Lys Pro Gly Gln Ala Pro Leu Leu Val Ile Tyr
        35                  40                  45

Gly Asn Thr Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Ala Ser Ser Gly Phe Ser
                85                  90                  95

Trp Val Phe Gly Gly Gly Thr Lys Val Thr Val Leu
            100                 105
```

<210> SEQ ID NO 117
<211> LENGTH: 109
<212> TYPE: PRT
<213> ORGANISM: Homo sapiens
<220> FEATURE:
<221> NAME/KEY: MISC_FEATURE
<223> OTHER INFORMATION: Clone XPA.15.224 light chain
<220> FEATURE:

```
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 117

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Ala Val Phe Gly Gly Gly Thr Gln Leu Thr Val Leu Gly
            100                 105

<210> SEQ ID NO 118
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.225 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 118

Ser Tyr Glu Leu Met Gln Pro Pro Ser Val Ser Val Ala Pro Gly Gln
1               5                   10                  15

Thr Ala Thr Ile Thr Cys Gly Gly Asn Asn Ile Gly Thr Lys Ser Val
            20                  25                  30

His Trp Tyr Gln Gln Lys Thr Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Leu Glu Ala Gly
65                  70                  75                  80

Asp Glu Ala Asp Tyr Tyr Cys Gln Val Trp Asp Arg Ser Ser Glu His
                85                  90                  95

His Val Phe Gly Gly Gly Thr Gln Leu Thr Val Leu
            100                 105
```

```
<210> SEQ ID NO 119
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.226 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 119

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Thr
            20                  25                  30

Ser Trp Tyr Gln Gln Lys Pro Gly Gln Ala Pro Val Leu Val Ile Phe
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Tyr
                85                  90                  95

Ala Val Phe Gly Gly Gly Thr Gln Leu Thr Val Leu
            100                 105

<210> SEQ ID NO 120
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.227 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 120

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Phe Tyr
        35                  40                  45

Gly Lys Asn Asn Arg Pro Ser Gly Ile Pro Gly Arg Phe Ser Gly Ser
    50                  55                  60
```

```
Lys Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Trp Val Phe Gly Gly Gly Thr Lys Leu Thr Val Leu
            100                 105
```

<210> SEQ ID NO 121
<211> LENGTH: 110
<212> TYPE: PRT
<213> ORGANISM: Homo sapiens
<220> FEATURE:
<221> NAME/KEY: MISC_FEATURE
<223> OTHER INFORMATION: Clone XPA.15.228 light chain
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (90)..(99)
<223> OTHER INFORMATION: LCDR3

<400> SEQUENCE: 121

```
Ser Tyr Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
                20                  25                  30

Phe Val Thr Trp Tyr Gln Gln Leu Pro Gly Ala Ala Pro Lys Leu Leu
            35                  40                  45

Ile Tyr Thr Asn Ser Gln Arg Pro Ser Gly Val Pro Asp Arg Phe Ser
        50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Phe Cys Ala Ala Trp Asp Asp Ser Leu
                85                  90                  95

Asn Gly Pro Val Phe Gly Gly Gly Thr Gln Leu Thr Val Leu
            100                 105                 110
```

<210> SEQ ID NO 122
<211> LENGTH: 109
<212> TYPE: PRT
<213> ORGANISM: Homo sapiens
<220> FEATURE:
<221> NAME/KEY: MISC_FEATURE
<223> OTHER INFORMATION: Clone XPA.15.229 light chain
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (90)..(98)
<223> OTHER INFORMATION: LCDR3

<400> SEQUENCE: 122

```
Gln Ser Val Leu Thr Gln Pro Pro Ser Val Ser Ala Ala Ala Gly Gln
1               5                   10                  15
```

```
Lys Val Thr Ile Ser Cys Ser Gly Ser Ser Asn Ile Gly Asn Asn
            20                  25                  30

Tyr Val Thr Trp Tyr Gln His Val Pro Gly Thr Ala Pro Lys Leu Leu
            35                  40                  45

Ile Phe Asp Asn Asp Lys Arg Pro Ser Gly Ile Pro Asp Arg Phe Ser
            50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Ser Ser Leu
                85                  90                  95

Asn Pro Leu Phe Gly Gly Ser Thr Gln Leu Thr Val Leu
            100                 105

<210> SEQ ID NO 123
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.230 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
<221> NAME/KEY: MISC_FEATURE
<222> LOCATION: (88)..(97)
<223> OTHER INFORMATION: LCDR3

<400> SEQUENCE: 123

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asp Gln
                85                  90                  95

Trp Val Phe Gly Gly Gly Thr Lys Leu Thr Val Leu
            100                 105

<210> SEQ ID NO 124
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.231 light chain
<220> FEATURE:
<221> NAME/KEY: MISC_FEATURE
<222> LOCATION: (26)..(31)
<223> OTHER INFORMATION: LCDR1
<220> FEATURE:
<221> NAME/KEY: MISC_FEATURE
<222> LOCATION: (49)..(51)
<223> OTHER INFORMATION: LCDR2
<220> FEATURE:
```

```
<221> NAME/KEY: MISC_FEATURE
<222> LOCATION: (88)..(97)
<223> OTHER INFORMATION: LCDR3

<400> SEQUENCE: 124

Ser Ser Glu Leu Thr Gln Asn Pro Ala Val Ser Val Ala Leu Gly Gln
1               5                   10                  15

Thr Val Arg Ile Thr Cys Gln Gly Asp Ser Leu Arg Asn Tyr Tyr Ala
            20                  25                  30

Ser Trp Tyr Gln Gln Lys Pro Gly Gln Ala Pro Leu Leu Val Met Tyr
        35                  40                  45

Asp Arg Asn Ser Arg Pro Ser Gly Ile Pro Asp Arg Phe Ser Gly Ser
    50                  55                  60

Arg Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Ala Val Phe Gly Gly Gly Thr Gln Leu Thr Val Leu
            100                 105

<210> SEQ ID NO 125
<211> LENGTH: 109
<212> TYPE: PRT
<213> ORGANISM: Homo sapiens
<220> FEATURE:
<221> NAME/KEY: MISC_FEATURE
<223> OTHER INFORMATION: Clone XPA.15.232 light chain
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (88)..(96)
<223> OTHER INFORMATION: LCDR3

<400> SEQUENCE: 125

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Thr Trp Tyr Gln His Val Pro Gly Thr Ala Pro Lys Leu Leu
        35                  40                  45

Ile Phe Asp Asn Asp Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Ser Ser Leu
                85                  90                  95

Asn Pro Leu Phe Gly Gly Gly Thr Gln Leu Thr Val Leu
            100                 105

<210> SEQ ID NO 126
<211> LENGTH: 109
<212> TYPE: PRT
<213> ORGANISM: Homo sapiens
<220> FEATURE:
<221> NAME/KEY: MISC_FEATURE
<223> OTHER INFORMATION: Clone XPA.15.233 light chain
```

```
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (88)..(96)
<223> OTHER INFORMATION: LCDR3

<400> SEQUENCE: 126

Gln Ser Val Leu Thr Gln Pro Pro Ser Val Ser Ala Ala Ala Gly Gln
1               5                   10                  15

Lys Val Thr Ile Ser Cys Ser Gly Ser Ser Asn Ile Gly Asn Asn
            20                  25                  30

Tyr Val Thr Trp Tyr Gln His Val Pro Gly Thr Ala Pro Lys Leu Leu
        35                  40                  45

Ile Phe Asp Asn Asp Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Ser Ser Leu
                85                  90                  95

Asn Pro Leu Phe Gly Gly Gly Thr Gln Leu Thr Val Leu
            100                 105

<210> SEQ ID NO 127
<211> LENGTH: 109
<212> TYPE: PRT
<213> ORGANISM: Homo sapiens
<220> FEATURE:
<221> NAME/KEY: MISC_FEATURE
<223> OTHER INFORMATION: Clone XPA.15.234 light chain
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (88)..(96)
<223> OTHER INFORMATION: LCDR3

<400> SEQUENCE: 127

Gln Ser Val Leu Thr Gln Pro Pro Ser Val Ser Ala Ala Ala Gly Gln
1               5                   10                  15

Lys Val Thr Ile Ser Cys Ser Gly Ser Ser Asn Ile Gly Asn Asn
            20                  25                  30

Tyr Val Thr Trp Tyr Gln His Val Pro Gly Thr Ala Pro Lys Leu Leu
        35                  40                  45

Ile Phe Asp Asn Asp Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Ser Ser Leu
                85                  90                  95

Asn Pro Leu Phe Gly Gly Gly Thr Gln Leu Thr Val Leu
            100                 105
```

<210> SEQ ID NO 128
<211> LENGTH: 110
<212> TYPE: PRT
<213> ORGANISM: Homo sapiens
<220> FEATURE:
<221> NAME/KEY: MISC_FEATURE
<223> OTHER INFORMATION: Clone XPA.15.235 light chain
<220> FEATURE:
<221> NAME/KEY: MISC_FEATURE
<222> LOCATION: (27)..(37)
<223> OTHER INFORMATION: LCDR1
<220> FEATURE:
<221> NAME/KEY: MISC_FEATURE
<222> LOCATION: (55)..(57)
<223> OTHER INFORMATION: LCDR2
<220> FEATURE:
<221> NAME/KEY: MISC_FEATURE
<222> LOCATION: (94)..(98)
<223> OTHER INFORMATION: LCDR3

<400> SEQUENCE: 128

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Ser Phe Gly Gln Gly Thr Arg Leu Glu Ile Lys
            100                 105                 110

<210> SEQ ID NO 129
<211> LENGTH: 107
<212> TYPE: PRT
<213> ORGANISM: Homo sapiens
<220> FEATURE:
<221> NAME/KEY: MISC_FEATURE
<223> OTHER INFORMATION: Clone XPA.15.236 light chain
<220> FEATURE:
<221> NAME/KEY: MISC_FEATURE
<222> LOCATION: (27)..(32)
<223> OTHER INFORMATION: LCDR1
<220> FEATURE:
<221> NAME/KEY: MISC_FEATURE
<222> LOCATION: (50)..(52)
<223> OTHER INFORMATION: LCDR2
<220> FEATURE:
<221> NAME/KEY: MISC_FEATURE
<222> LOCATION: (99)..(105)
<223> OTHER INFORMATION: LCDR3

<400> SEQUENCE: 129

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Ile Ser Gly Val Pro Ser Arg Phe Ser Gly
    50                  55                  60

```
Ser Gly Ser Gly Thr Asp Phe Thr Leu Thr Asn Ser Leu Glu Ala
 65                  70                  75                  80

Glu Asp Ala Ala Thr Tyr Tyr Cys His Gln Ser Ser Leu Pro Trp
                 85                  90                  95

Thr Phe Gly Gln Gly Thr Lys Val Glu Ile Lys
            100                 105

<210> SEQ ID NO 130
<211> LENGTH: 107
<212> TYPE: PRT
<213> ORGANISM: Homo sapiens
<220> FEATURE:
<221> NAME/KEY: MISC_FEATURE
<223> OTHER INFORMATION: Clone XPA.15.237 light chain
<220> FEATURE:
<221> NAME/KEY: MISC_FEATURE
<222> LOCATION: (27)..(32)
<223> OTHER INFORMATION: LCDR1
<220> FEATURE:
<221> NAME/KEY: MISC_FEATURE
<222> LOCATION: (50)..(52)
<223> OTHER INFORMATION: LCDR2
<220> FEATURE:
<221> NAME/KEY: MISC_FEATURE
<222> LOCATION: (99)..(105)
<223> OTHER INFORMATION: LCDR3

<400> SEQUENCE: 130

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Ser
                 20                  25                  30

Leu Ala Trp Tyr Gln Gln Lys Pro Gly Lys Ala Pro Lys Leu Leu Leu
            35                  40                  45

Tyr Ala Ala Ser Arg Leu Glu Ser Gly Val Pro Ser Arg Phe Ser Gly
        50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Tyr Ser Thr Leu Leu
                 85                  90                  95

Thr Phe Gly Gly Gly Thr Lys Val Asp Ile Lys
            100                 105

<210> SEQ ID NO 131
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.226 light chain
<220> FEATURE:
<221> NAME/KEY: MISC_FEATURE
<223> OTHER INFORMATION: Clone XPA.15.238 light chain
<220> FEATURE:
<221> NAME/KEY: MISC_FEATURE
<222> LOCATION: (27)..(32)
<223> OTHER INFORMATION: LCDR1
<220> FEATURE:
<221> NAME/KEY: MISC_FEATURE
<222> LOCATION: (50)..(52)
<223> OTHER INFORMATION: LCDR2
<220> FEATURE:
<221> NAME/KEY: MISC_FEATURE
<222> LOCATION: (99)..(105)
<223> OTHER INFORMATION: LCDR3

<400> SEQUENCE: 131
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Arg Lys Pro Gly Arg Ala Pro Arg Leu Leu
        35                  40                  45

Ile Tyr Gly Ala Ser Ser Arg Ala Thr Gly Ile Pro Asn Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Thr Phe Gly Gln Gly Thr Lys Leu Glu Ile Lys
            100                 105

<210> SEQ ID NO 132
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.239 light chain
<220> FEATURE:
<221> NAME/KEY: MISC_FEATURE
<222> LOCATION: (27)..(37)
<223> OTHER INFORMATION: LCDR1
<220> FEATURE:
<221> NAME/KEY: MISC_FEATURE
<222> LOCATION: (55)..(57)
<223> OTHER INFORMATION: LCDR2
<220> FEATURE:
<221> NAME/KEY: MISC_FEATURE
<222> LOCATION: (94)..(100)
<223> OTHER INFORMATION: LCDR3

<400> SEQUENCE: 132

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro His Thr Phe Gly Gln Gly Thr Lys Leu Glu Ile Lys
            100                 105                 110

<210> SEQ ID NO 133
<211> LENGTH: 106
<212> TYPE: PRT
<213> ORGANISM: Homo sapiens
<220> FEATURE:
<221> NAME/KEY: MISC_FEATURE
<223> OTHER INFORMATION: Clone XPA.15.241 light chain
<220> FEATURE:
<221> NAME/KEY: MISC_FEATURE
<222> LOCATION: (27)..(32)
<223> OTHER INFORMATION: LCDR1
<220> FEATURE:

```
<221> NAME/KEY: MISC_FEATURE
<222> LOCATION: (50)..(52)
<223> OTHER INFORMATION: LCDR2
<220> FEATURE:
<221> NAME/KEY: MISC_FEATURE
<222> LOCATION: (99)..(104)
<223> OTHER INFORMATION: LCDR3

<400> SEQUENCE: 133

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Thr Asn
            20                  25                  30

Leu Ala Trp Tyr Gln Gln Lys Pro Gly Gln Thr Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Ser Glu Ile Ser
                85                  90                  95

Phe Gly Gln Gly Thr Arg Leu Glu Ile Lys
            100                 105

<210> SEQ ID NO 134
<211> LENGTH: 106
<212> TYPE: PRT
<213> ORGANISM: Homo sapiens
<220> FEATURE:
<221> NAME/KEY: MISC_FEATURE
<223> OTHER INFORMATION: Clone XPA.15.242 light chain
<220> FEATURE:
<221> NAME/KEY: MISC_FEATURE
<222> LOCATION: (27)..(32)
<223> OTHER INFORMATION: LCDR1
<220> FEATURE:
<221> NAME/KEY: MISC_FEATURE
<222> LOCATION: (50)..(52)
<223> OTHER INFORMATION: LCDR2
<220> FEATURE:
<221> NAME/KEY: MISC_FEATURE
<222> LOCATION: (99)..(104)
<223> OTHER INFORMATION: LCDR3

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Thr Ser Arg Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Ser Tyr Tyr Cys Gln Gln Phe Tyr Ser Asn Pro Ser
                85                  90                  95

Phe Gly Gln Gly Thr Lys Val Glu Ile Lys
            100                 105

<210> SEQ ID NO 135
<211> LENGTH: 107
<212> TYPE: PRT
```

```
<213> ORGANISM: Homo sapiens
<220> FEATURE:
<221> NAME/KEY: MISC_FEATURE
<223> OTHER INFORMATION: Clone XPA.15.243 light chain
<220> FEATURE:
<221> NAME/KEY: MISC_FEATURE
<222> LOCATION: (27)..(32)
<223> OTHER INFORMATION: LCDR1
<220> FEATURE:
<221> NAME/KEY: MISC_FEATURE
<222> LOCATION: (50)..(52)
<223> OTHER INFORMATION: LCDR2
<220> FEATURE:
<221> NAME/KEY: MISC_FEATURE
<222> LOCATION: (99)..(105)
<223> OTHER INFORMATION: LCDR3

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 136
<211> LENGTH: 107
<212> TYPE: PRT
<213> ORGANISM: Homo sapiens
<220> FEATURE:
<221> NAME/KEY: MISC_FEATURE
<223> OTHER INFORMATION: Clone XPA.15.244 light chain
<220> FEATURE:
<221> NAME/KEY: MISC_FEATURE
<222> LOCATION: (27)..(32)
<223> OTHER INFORMATION: LCDR1
<220> FEATURE:
<221> NAME/KEY: MISC_FEATURE
<222> LOCATION: (50)..(52)
<223> OTHER INFORMATION: LCDR2
<220> FEATURE:
<221> NAME/KEY: MISC_FEATURE
<222> LOCATION: (99)..(105)
<223> OTHER INFORMATION: LCDR3

<400> SEQUENCE: 136

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Val Leu Ile
        35                  40                  45

Tyr Asp Ala Ser Ser Leu Glu Arg Gly Val Pro Ser Arg Phe Ser Gly
    50                  55                  60

Ser Gly Thr Gly Thr Asp Phe Thr Leu Thr Ile Ser Ser Leu Gln Pro
65                  70                  75                  80

Glu Asp Phe Ala Ser Tyr Tyr Cys His Gln Phe Asn Ser Tyr Pro Asp
```

```
                85                  90                  95
Thr Phe Gly Gln Gly Thr Arg Leu Glu Ile Lys
            100                 105

<210> SEQ ID NO 137
<211> LENGTH: 107
<212> TYPE: PRT
<213> ORGANISM: Homo sapiens
<220> FEATURE:
<221> NAME/KEY: MISC_FEATURE
<223> OTHER INFORMATION: Clone XPA.15.245 light chain
<220> FEATURE:
<221> NAME/KEY: MISC_FEATURE
<222> LOCATION: (27)..(32)
<223> OTHER INFORMATION: LCDR1
<220> FEATURE:
<221> NAME/KEY: MISC_FEATURE
<222> LOCATION: (50)..(52)
<223> OTHER INFORMATION: LCDR2
<220> FEATURE:
<221> NAME/KEY: MISC_FEATURE
<222> LOCATION: (99)..(105)
<223> OTHER INFORMATION: LCDR3

<400> SEQUENCE: 137

Ala Ile Arg Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Thr Thr Ser Thr Leu Glu Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 138
<211> LENGTH: 108
<212> TYPE: PRT
<213> ORGANISM: Homo sapiens
<220> FEATURE:
<221> NAME/KEY: MISC_FEATURE
<223> OTHER INFORMATION: Clone XPA.15.246 light chain
<220> FEATURE:
<221> NAME/KEY: MISC_FEATURE
<222> LOCATION: (27)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (100)..(106)
<223> OTHER INFORMATION: LCDR3

<400> SEQUENCE: 138

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Ser Ser Ser
            20                  25                  30

Phe Leu Ala Trp Tyr Gln Gln Lys Pro Gly Gln Ala Pro Arg Leu Leu
```

```
                35                  40                  45

Ile Tyr Gly Ala Gly Ser Arg Ala Thr Gly Val Pro Asp Arg Phe Ser
 50                  55                  60

Gly Ser Gly Tyr Gly Thr Asp Phe Ser Leu Thr Ile Ser Arg Leu Glu
 65                  70                  75                  80

Leu Glu Asp Phe Ala Val Tyr Tyr Cys Gln Gln Tyr Asp Arg Ser Gln
                     85                  90                  95

Ile Thr Phe Gly Gln Gly Thr Arg Leu Glu Ile Lys
                100                 105
```

<210> SEQ ID NO 139
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.247 light chain
<220> FEATURE:
<221> NAME/KEY: MISC_FEATURE
<222> LOCATION: (27)..(37)
<223> OTHER INFORMATION: LCDR1
<220> FEATURE:
<221> NAME/KEY: MISC_FEATURE
<222> LOCATION: (55)..(57)
<223> OTHER INFORMATION: LCDR2
<220> FEATURE:
<221> NAME/KEY: MISC_FEATURE
<222> LOCATION: (94)..(100)
<223> OTHER INFORMATION: LCDR3

<400> SEQUENCE: 139

```
Asp Val Val Met Thr Gln Ser Pro Leu Ser Leu Ser Val Thr Leu Gly
 1               5                  10                  15

Gln Pro Ala Ser Ile Ser Cys Arg Ser Ser Leu Ser Leu Val Tyr Gly
                 20                  25                  30

Asp Glu Asn Thr Tyr Leu Asn Trp Phe Gln Gln Arg Pro Gly Gln Ser
             35                  40                  45

Pro Arg Arg Leu Leu Tyr Lys Val Ser Asp Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Asp Asp Val Gly Val Tyr Tyr Cys Met Gln Gly
                 85                  90                  95

Thr His Trp Pro Tyr Thr Phe Gly Gln Gly Thr Lys Leu Glu Ile Lys
                100                 105                 110
```

<210> SEQ ID NO 140
<211> LENGTH: 107
<212> TYPE: PRT
<213> ORGANISM: Homo sapiens
<220> FEATURE:
<221> NAME/KEY: MISC_FEATURE
<223> OTHER INFORMATION: Clone XPA.15.248 light chain
<220> FEATURE:
<221> NAME/KEY: MISC_FEATURE
<222> LOCATION: (27)..(32)
<223> OTHER INFORMATION: LCDR1
<220> FEATURE:
<221> NAME/KEY: MISC_FEATURE
<222> LOCATION: (50)..(52)
<223> OTHER INFORMATION: LCDR2
<220> FEATURE:
<221> NAME/KEY: MISC_FEATURE
<222> LOCATION: (99)..(105)
<223> OTHER INFORMATION: LCDR3

-continued

<400> SEQUENCE: 140

Glu Ile Val Leu Thr Gln Ser Pro Asp Phe Gln Ser Val Thr Pro Lys
1               5                   10                  15

Glu Thr Val Thr Ile Ser Cys Arg Ala Ser Gln Asn Ile Gly Val Ser
            20                  25                  30

Leu His Trp Tyr Gln Gln Lys Pro Asp Gln Ser Pro Lys Val Leu Ile
        35                  40                  45

Lys Tyr Ala Ser Gln Ser Leu Ser Gly Val Pro Ser Arg Phe Ser Gly
    50                  55                  60

Thr Gly Ser Gly Thr Asp Phe Thr Leu Thr Ile Lys Ser Leu Glu Ala
65                  70                  75                  80

Glu Asp Ala Ala Thr Tyr Tyr Cys Leu Gln Thr Ser Ser Leu Pro Trp
                85                  90                  95

Thr Phe Gly Gln Gly Thr Lys Val Glu Ile Lys
            100                 105

<210> SEQ ID NO 141
<211> LENGTH: 107
<212> TYPE: PRT
<213> ORGANISM: Homo sapiens
<220> FEATURE:
<221> NAME/KEY: MISC_FEATURE
<223> OTHER INFORMATION: Clone XPA.15.249 light chain
<220> FEATURE:
<221> NAME/KEY: MISC_FEATURE
<222> LOCATION: (27)..(32)
<223> OTHER INFORMATION: LCDR1
<220> FEATURE:
<221> NAME/KEY: MISC_FEATURE
<222> LOCATION: (50)..(52)
<223> OTHER INFORMATION: LCDR2
<220> FEATURE:
<221> NAME/KEY: MISC_FEATURE
<222> LOCATION: (99)..(105)
<223> OTHER INFORMATION: LCDR3

<400> SEQUENCE: 141

Ala Ile Gln Leu Thr Gln Ser Pro Ser Ser Leu Ser Ala Ser Val Gly
1               5                   10                  15

Asp Arg Val Thr Ile Ser Cys Arg Ala Ser Gln Ser Ile Thr Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ala Gly Leu Gln Pro
65                  70                  75                  80

Glu Asp Phe Ala Thr Tyr Tyr Cys Gln Gln Phe Asp Ser Tyr Pro Phe
                85                  90                  95

Thr Phe Gly Gly Gly Thr Lys Leu Glu Ile Lys
            100                 105

<210> SEQ ID NO 142
<211> LENGTH: 107
<212> TYPE: PRT
<213> ORGANISM: Homo sapiens
<220> FEATURE:
<221> NAME/KEY: MISC_FEATURE
<223> OTHER INFORMATION: Clone XPA.15.250 light chain
<220> FEATURE:
<221> NAME/KEY: MISC_FEATURE
<222> LOCATION: (27)..(32)
<223> OTHER INFORMATION: LCDR1

```
<220> FEATURE:
<221> NAME/KEY: MISC_FEATURE
<222> LOCATION: (50)..(52)
<223> OTHER INFORMATION: LCDR2
<220> FEATURE:
<221> NAME/KEY: MISC_FEATURE
<222> LOCATION: (99)..(105)
<223> OTHER INFORMATION: LCDR3

<400> SEQUENCE: 142
```

Ala Ile Arg Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Thr Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gly Gly Thr Lys Val Glu Ile Lys
            100                 105

```
<210> SEQ ID NO 143
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.272 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(54)
<223> OTHER INFORMATION: LCDR2
<220> FEATURE:
<221> NAME/KEY: MISC_FEATURE
<222> LOCATION: (91)..(100)
<223> OTHER INFORMATION: LCDR3

<400> SEQUENCE: 143
```

Gln Ser Ala Leu Thr Gln Pro Ala Ser Val Ser Gly Ser Pro Gly Gln
1               5                   10                  15

Ser Ile Thr Ile Ser Cys Leu Gly Thr Ile Asn Asp Val Gly Leu Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Val Tyr Tyr Cys Asn Ser Tyr Thr Ser Ser
                85                  90                  95

Ser Asn Phe Trp Val Phe Gly Gly Thr Gln Leu Thr Val Leu Gly
            100                 105                 110

```
<210> SEQ ID NO 144
<211> LENGTH: 111
```

```
<212> TYPE: PRT
<213> ORGANISM: Homo sapiens
<220> FEATURE:
<221> NAME/KEY: MISC_FEATURE
<223> OTHER INFORMATION: Clone XPA.15.275 light chain
<220> FEATURE:
<221> NAME/KEY: MISC_FEATURE
<222> LOCATION: (26)..(34)
<223> OTHER INFORMATION: LCDR1
<220> FEATURE:
<221> NAME/KEY: MISC_FEATURE
<222> LOCATION: (52)..(54)
<223> OTHER INFORMATION: LCDR2
<220> FEATURE:
<221> NAME/KEY: MISC_FEATURE
<222> LOCATION: (91)..(99)
<223> OTHER INFORMATION: LCDR3

<400> SEQUENCE: 144

Gln Thr Val Val Thr Gln Glu Pro Ser Phe Ser Val Ser Pro Gly Gly
1               5                   10                  15

Thr Val Thr Leu Thr Cys Gly Leu Thr Ser Gly Ser Val Ser Thr Arg
            20                  25                  30

Asn Phe Pro Gly Trp Tyr Gln Gln Thr Pro Gly Gln Thr Leu Arg Thr
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Thr Gly
                85                  90                  95

Asp Ile Trp Val Phe Gly Gly Gly Thr Lys Val Thr Val Leu Gly
            100                 105                 110

<210> SEQ ID NO 145
<211> LENGTH: 110
<212> TYPE: PRT
<213> ORGANISM: Homo sapiens
<220> FEATURE:
<221> NAME/KEY: MISC_FEATURE
<223> OTHER INFORMATION: Clone XPA.15.282 light chain
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (90)..(98)
<223> OTHER INFORMATION: LCDR3

<400> SEQUENCE: 145

Gln Ser Val Leu Thr Gln Pro Pro Ser Val Ser Ala Ala Gly Gln
1               5                   10                  15

Lys Val Thr Ile Ser Cys Ser Gly Ser Ser Asn Ile Gly Asn Asn
            20                  25                  30

Tyr Val Thr Trp Tyr Gln His Val Pro Gly Thr Ala Pro Lys Leu Leu
        35                  40                  45

Ile Phe Asp Asn Asp Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80
```

```
Thr Gly Asp Glu Ala Asp Tyr Tyr Cys Gly Thr Trp Asp Ser Ser Leu
            85                  90                  95

Asn Pro Leu Phe Gly Gly Gly Thr Gln Leu Thr Val Leu Gly
            100                 105                 110

<210> SEQ ID NO 146
<211> LENGTH: 110
<212> TYPE: PRT
<213> ORGANISM: Homo sapiens
<220> FEATURE:
<221> NAME/KEY: MISC_FEATURE
<223> OTHER INFORMATION: Clone XPA.15.284 light chain
<220> FEATURE:
<221> NAME/KEY: MISC_FEATURE
<222> LOCATION: (26)..(33)
<223> OTHER INFORMATION: LCDR1
<220> FEATURE:
<221> NAME/KEY: MISC_FEATURE
<222> LOCATION: (51)..(53)
<223> OTHER INFORMATION: LCDR2
<220> FEATURE:
<221> NAME/KEY: MISC_FEATURE
<222> LOCATION: (90)..(98)
<223> OTHER INFORMATION: LCDR3

<400> SEQUENCE: 146

Gln Ser Val Leu Thr Gln Pro Pro Ser Val Ser Ala Ala Gly Gln
1               5                   10                  15

Lys Val Thr Ile Ser Cys Ser Gly Ser Ser Ser Asn Ile Gly Asn Asn
            20                  25                  30

Tyr Val Thr Trp Tyr Gln His Val Pro Gly Thr Ala Pro Lys Leu Leu
            35                  40                  45

Ile Phe Asp Asn Asp Lys Arg Pro Ser Gly Ile Pro Asp Arg Phe Ser
50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Ser Ser Leu
            85                  90                  95

Asn Pro Leu Phe Gly Gly Gly Thr Gln Leu Thr Val Leu Gly
            100                 105                 110

<210> SEQ ID NO 147
<211> LENGTH: 114
<212> TYPE: PRT
<213> ORGANISM: Homo sapiens
<220> FEATURE:
<221> NAME/KEY: MISC_FEATURE
<223> OTHER INFORMATION: Clone XPA.15.293 light chain
<220> FEATURE:
<221> NAME/KEY: MISC_FEATURE
<222> LOCATION: (27)..(38)
<223> OTHER INFORMATION: LCDR1
<220> FEATURE:
<221> NAME/KEY: MISC_FEATURE
<222> LOCATION: (56)..(58)
<223> OTHER INFORMATION: LCDR2
<220> FEATURE:
<221> NAME/KEY: MISC_FEATURE
<222> LOCATION: (95)..(101)
<223> OTHER INFORMATION: LCDR3

<400> SEQUENCE: 147

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30
```

```
Asp Asp Gly Asn Thr Tyr Leu Asp Trp Tyr Val Gln Lys Pro Gly Gln
            35                  40                  45

Ser Pro Gln Leu Leu Met Tyr Ser Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Ile Glu Phe Pro Tyr Thr Phe Gly Gln Gly Thr Lys Leu Glu Ile
                100                 105                 110

Lys Arg

<210> SEQ ID NO 148
<211> LENGTH: 113
<212> TYPE: PRT
<213> ORGANISM: Homo sapiens
<220> FEATURE:
<221> NAME/KEY: MISC_FEATURE
<223> OTHER INFORMATION: Clone XPA.15.110 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
<220> FEATURE:
<221> NAME/KEY: MISC_FEATURE
<222> LOCATION: (97)..(101)
<223> OTHER INFORMATION: L-CDR3

<400> SEQUENCE: 148

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Arg Asn
                 20                  25                  30

Pro Ile Ser Trp Tyr Gln Gln Leu Pro Gly Thr Ala Pro Lys Leu Leu
                 35                  40                  45

Ile Tyr Asn Asn Asp Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Pro Val Trp Val Phe Gly Gly Gly Thr Lys Leu Thr Val Leu
                100                 105                 110

Gly

<210> SEQ ID NO 149
<211> LENGTH: 111
<212> TYPE: PRT
<213> ORGANISM: Homo sapiens
<220> FEATURE:
<221> NAME/KEY: MISC_FEATURE
<223> OTHER INFORMATION: Clone XPA.15.120 light chain
<220> FEATURE:
<221> NAME/KEY: MISC_FEATURE
<222> LOCATION: (26)..(33)
<223> OTHER INFORMATION: L-CDR1
<220> FEATURE:
<221> NAME/KEY: MISC_FEATURE
<222> LOCATION: (51)..(53)
<223> OTHER INFORMATION: L-CDR2
```

-continued

```
<220> FEATURE:
<221> NAME/KEY: MISC_FEATURE
<222> LOCATION: (90)..(99)
<223> OTHER INFORMATION: L-CDR3

<400> SEQUENCE: 149

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Val Val Phe Gly Gly Gly Thr Lys Leu Thr Val Leu Gly
                100                 105                 110

<210> SEQ ID NO 150
<211> LENGTH: 112
<212> TYPE: PRT
<213> ORGANISM: Homo sapiens
<220> FEATURE:
<221> NAME/KEY: MISC_FEATURE
<223> OTHER INFORMATION: Clone XPA.15.163 light chain
<220> FEATURE:
<221> NAME/KEY: MISC_FEATURE
<222> LOCATION: (26)..(34)
<223> OTHER INFORMATION: L-CDR1
<220> FEATURE:
<221> NAME/KEY: MISC_FEATURE
<222> LOCATION: (52)..(54)
<223> OTHER INFORMATION: L-CDR2
<220> FEATURE:
<221> NAME/KEY: MISC_FEATURE
<222> LOCATION: (91)..(100)
<223> OTHER INFORMATION: L-CDR3

<400> SEQUENCE: 150

Gln Ser Val Leu Thr Gln Pro Pro Ser Ala Ser Gly Thr Pro Gly Leu
1               5                   10                  15

Arg Val Ile Ile Ser Cys Ala Gly Ser Ser Asn Ile Gly Ala Gly
            20                  25                  30

Tyr Asp Val His Trp Tyr His Gln Leu Pro Gly Thr Ala Pro Lys Leu
            35                  40                  45

Leu Ile Tyr Gly Asn Ser Asn Gln Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Thr Ser Tyr Thr Gly Asn
                85                  90                  95

Asn Gln Phe Val Ile Phe Gly Gly Gly Thr Lys Leu Thr Val Leu Gly
                100                 105                 110

<210> SEQ ID NO 151
<211> LENGTH: 119
<212> TYPE: PRT
<213> ORGANISM: Mus musculus
<220> FEATURE:
<221> NAME/KEY: MISC_FEATURE
```

```
<223> OTHER INFORMATION: Clone XPA.015.172 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(108)
<223> OTHER INFORMATION: H-CDR3

<400> SEQUENCE: 151

Gln Val Gln Leu Gln Gln Ser Glu Ala Glu Leu Val Lys Pro Gly Ala
1               5                   10                  15

Ser Val Lys Ile Ser Cys Lys Ala Ser Gly Tyr Thr Phe Ser Ser Tyr
            20                  25                  30

Trp Met Ser Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Gly Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Ser Gly Tyr Gly Ala Met Asp Tyr Trp Gly Gln Gly
            100                 105                 110

Thr Ser Val Thr Val Ser Ser
        115

<210> SEQ ID NO 152
<211> LENGTH: 119
<212> TYPE: PRT
<213> ORGANISM: Mus musculus
<220> FEATURE:
<221> NAME/KEY: MISC_FEATURE
<223> OTHER INFORMATION: Clone XPA.015.189 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(108)
<223> OTHER INFORMATION: H-CDR3

<400> SEQUENCE: 152

Glu Val Gln Leu Gln Gln Ser Val Ala Glu Leu Val Lys Pro Gly Ala
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Gly Thr Ala Tyr
65                  70                  75                  80

Met Gln Leu Ser Ser Leu Thr Ser Glu Asp Ser Ala Val Tyr Phe Cys
```

```
                    85                  90                  95

Ala Arg Gly Val Ser Gly Tyr Gly Ala Met Asp Tyr Trp Gly Gln Gly
                100                 105                 110

Thr Ser Val Thr Val Ser Ser
        115

<210> SEQ ID NO 153
<211> LENGTH: 119
<212> TYPE: PRT
<213> ORGANISM: Mus musculus
<220> FEATURE:
<221> NAME/KEY: MISC_FEATURE
<223> OTHER INFORMATION: Clone XPA.015.176 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(108)
<223> OTHER INFORMATION: H-CDR3

<400> SEQUENCE: 153

Gln Val Gln Leu Gln Gln Ser Glu Ala Glu Leu Val Lys Pro Gly Ala
1               5                   10                  15

Ser Val Lys Ile Ser Cys Lys Ala Ser Gly Tyr Thr Phe Ser Ser Tyr
                20                  25                  30

Trp Met Ser Trp Val Lys Gln Arg Pro Gly Lys Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Lys Ala Thr Leu Thr Ala Asp Lys Ser Ser Gly Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Ser Gly Tyr Gly Ala Met Asp Tyr Trp Gly Gln Gly
                100                 105                 110

Thr Ser Val Thr Val Ser Ser
        115

<210> SEQ ID NO 154
<211> LENGTH: 119
<212> TYPE: PRT
<213> ORGANISM: Mus musculus
<220> FEATURE:
<221> NAME/KEY: MISC_FEATURE
<223> OTHER INFORMATION: Clone XPA.015.178 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(108)
<223> OTHER INFORMATION: H-CDR3

<400> SEQUENCE: 154

Gln Val Gln Leu Gln Gln Ser Glu Ala Glu Leu Val Lys Pro Gly Ala
```

-continued

```
                 1               5                  10                 15
              Ser Val Lys Ile Ser Cys Lys Ala Ser Gly Tyr Thr Phe Ser Ser Tyr
                             20                  25                 30

Trp Met Asn Trp Val Lys Gln Arg Pro Gly Lys Gly Leu Glu Trp Ile
                         35                  40                 45

Gly Gln Ile Tyr Pro Gly Asp Gly Asp Thr Asn Tyr Asn Val Lys Phe
                     50                  55                 60

Lys Gly Lys Ala Thr Leu Thr Ala Asp Lys Ser Ser Gly Thr Ala Tyr
               65                  70                  75                 80

Met Gln Leu Ser Ser Leu Thr Ser Glu Asp Ser Ala Val Tyr Phe Cys
                                 85                  90                 95

Ala Arg Gly Val Ser Gly Tyr Gly Ala Met Asp Tyr Trp Gly Gln Gly
                             100                 105                110

Thr Ser Val Thr Val Ser Ser
                         115

<210> SEQ ID NO 155
<211> LENGTH: 119
<212> TYPE: PRT
<213> ORGANISM: Mus musculus
<220> FEATURE:
<221> NAME/KEY: MISC_FEATURE
<223> OTHER INFORMATION: Clone XPA.015.183 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(108)
<223> OTHER INFORMATION: H-CDR3

<400> SEQUENCE: 155

Gln Val Gln Leu Gln Gln Ser Glu Ala Glu Leu Val Lys Pro Gly Ala
 1               5                  10                 15

Ser Val Lys Ile Ser Cys Lys Ala Ser Gly Tyr Thr Phe Ser Ser Tyr
             20                  25                 30

Trp Met Asn Trp Val Lys Gln Arg Pro Gly Lys Gly Leu Glu Trp Ile
         35                  40                 45

Gly Gln Ile Tyr Pro Gly Asp Gly Asp Thr Asn Tyr Asn Val Lys Phe
     50                  55                 60

Lys Gly Lys Ala Thr Leu Thr Ala Asp Lys Ser Ser Gly Thr Ala Tyr
 65                  70                  75                 80

Met Gln Leu Ser Ser Leu Thr Ser Glu Asp Ser Ala Val Tyr Phe Cys
                 85                  90                 95

Ala Arg Gly Val Ser Gly Tyr Gly Ala Met Asp Tyr Trp Gly Gln Gly
             100                 105                110

Thr Ser Val Thr Val Ser Ser
         115

<210> SEQ ID NO 156
<211> LENGTH: 116
<212> TYPE: PRT
<213> ORGANISM: Mus musculus
<220> FEATURE:
<221> NAME/KEY: MISC_FEATURE
<223> OTHER INFORMATION: Clone XPA.015.188 heavy chain
<220> FEATURE:
```

<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(105)
<223> OTHER INFORMATION: H-CDR3

<400> SEQUENCE: 156

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Ser
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Asn Tyr Asn Gln Lys Phe
    50                  55                  60

Lys Asp Lys Ala Thr Leu Thr Val Asp Lys Ser Ser Ser Ala Phe
65                  70                  75                  80

Met Glu Leu Arg Ser Leu Thr Ser Glu Asp Ser Ala Val Tyr Tyr Cys
                85                  90                  95

Ala Arg Arg Gly Ala Met Asp Tyr Trp Gly Gln Gly Thr Ser Val
            100                 105                 110

Thr Val Ser Ser
        115

<210> SEQ ID NO 157
<211> LENGTH: 116
<212> TYPE: PRT
<213> ORGANISM: Mus musculus
<220> FEATURE:
<221> NAME/KEY: MISC_FEATURE
<223> OTHER INFORMATION: Clone XPA.015.185 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(105)
<223> OTHER INFORMATION: H-CDR3

<400> SEQUENCE: 157

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Ser
            20                  25                  30

Tyr Met Asn Trp Val Lys Gln Ser His Gly Lys Ser Leu Lys Trp Ile
        35                  40                  45

Gly Asp Ile Asn Pro Asn Asn Gly Gly Ser Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Arg Gly Ala Met Asp Tyr Trp Gly Gln Gly Thr Ser Val
            100                 105                 110

Thr Val Ser Ser
        115

<210> SEQ ID NO 158
<211> LENGTH: 116
<212> TYPE: PRT
<213> ORGANISM: Mus musculus
<220> FEATURE:
<221> NAME/KEY: MISC_FEATURE
<223> OTHER INFORMATION: Clone XPA.015.192 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(105)
<223> OTHER INFORMATION: H-CDR3

<400> SEQUENCE: 158

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Ser
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Asp Thr Asn Tyr Asn Gln Lys Phe
    50                  55                  60

Lys Asp Lys Ala Thr Leu Thr Val Asp Lys Ser Ser Ser Ser Ala Phe
65                  70                  75                  80

Met Glu Leu Arg Ser Leu Thr Ser Glu Asp Ser Ala Val Tyr Tyr Cys
                85                  90                  95

Ala Arg Arg Arg Gly Ala Met Asp Tyr Trp Gly Gln Gly Thr Ser Val
            100                 105                 110

Thr Val Ser Ser
        115

<210> SEQ ID NO 159
<211> LENGTH: 119
<212> TYPE: PRT
<213> ORGANISM: Mus musculus
<220> FEATURE:
<221> NAME/KEY: MISC_FEATURE
<223> OTHER INFORMATION: Clone XPA.015.177 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(108)
<223> OTHER INFORMATION: H-CDR3

<400> SEQUENCE: 159

Gln Val Gln Leu Gln Gln Ser Glu Ala Glu Leu Val Lys Pro Gly Ala
1               5                   10                  15

```
Ser Val Lys Ile Ser Cys Lys Ala Ser Gly Tyr Thr Phe Ser Asn Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Glu Ala Thr Leu Ile Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Ser Gly Tyr Gly Ala Met Asp Tyr Trp Gly Gln Gly
                100                 105                 110

Thr Ser Val Thr Val Ser Ser
            115

<210> SEQ ID NO 160
<211> LENGTH: 119
<212> TYPE: PRT
<213> ORGANISM: Mus musculus
<220> FEATURE:
<221> NAME/KEY: MISC_FEATURE
<223> OTHER INFORMATION: Clone XPA.015.175 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(108)
<223> OTHER INFORMATION: H-CDR3

<400> SEQUENCE: 160

Gln Val Gln Leu Gln Gln Ser Glu Ala Glu Leu Val Lys Pro Gly Ala
1               5                   10                  15

Ser Val Lys Ile Ser Cys Lys Ala Ser Gly Tyr Thr Phe Ser Asn Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Ile Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Ser Gly Tyr Gly Ala Met Asp Tyr Trp Gly Gln Gly
                100                 105                 110

Thr Ser Val Thr Val Ser Ser
            115

<210> SEQ ID NO 161
<211> LENGTH: 119
<212> TYPE: PRT
<213> ORGANISM: Mus musculus
<220> FEATURE:
<223> OTHER INFORMATION: Clone XPA.015.179 heavy chain
<220> FEATURE:
<221> NAME/KEY: MISC_FEATURE
<222> LOCATION: (26)..(33)
```

```
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(108)
<223> OTHER INFORMATION: H-CDR3

<400> SEQUENCE: 161

Glu Val Gln Leu Gln Gln Ser Val Ala Glu Leu Val Lys Pro Gly Ala
1               5                   10                  15

Ser Val Lys Ile Ser Cys Lys Ala Ser Gly Tyr Thr Phe Ser Asn Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Arg Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Ser Gly Tyr Gly Ala Met Asp Tyr Trp Gly Gln Gly
            100                 105                 110

Thr Ser Val Thr Val Ser Ser
        115

<210> SEQ ID NO 162
<211> LENGTH: 119
<212> TYPE: PRT
<213> ORGANISM: Mus musculus
<220> FEATURE:
<221> NAME/KEY: MISC_FEATURE
<223> OTHER INFORMATION: Clone XPA.015.184 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(108)
<223> OTHER INFORMATION: H-CDR3

<400> SEQUENCE: 162

Glu Val Gln Leu Gln Gln Ser Val Ala Glu Leu Val Lys Pro Gly Ala
1               5                   10                  15

Ser Val Lys Ile Ser Cys Lys Ala Ser Gly Tyr Thr Phe Ser Asn Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Arg Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Ser Gly Tyr Gly Ala Met Asp Tyr Trp Gly Gln Gly
            100                 105                 110
```

Thr Ser Val Thr Val Ser Ser
        115

<210> SEQ ID NO 163
<211> LENGTH: 116
<212> TYPE: PRT
<213> ORGANISM: Mus musculus
<220> FEATURE:
<221> NAME/KEY: MISC_FEATURE
<223> OTHER INFORMATION: Clone XPA.015.181 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(105)
<223> OTHER INFORMATION: H-CDR3

<400> SEQUENCE: 163

Glu Val Gln Leu Gln Gln Ser Gly Pro Val Leu Val Lys Pro Gly Ala
1               5                   10                  15

Ser Val Lys Met Ser Cys Lys Ala Ala Gly Tyr Thr Phe Thr Asp Ser
            20                  25                  30

Tyr Met Asn Trp Val Lys Gln Ser His Gly Lys Ser Leu Glu Trp Ile
        35                  40                  45

Gly Asp Ile Asn Pro Tyr Asn Gly Gly Thr Ser Tyr Asn Gln His Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Arg Arg Gly Ala Met Asp Tyr Trp Gly Gln Gly Thr Ser Val
            100                 105                 110

Thr Val Ser Ser
        115

<210> SEQ ID NO 164
<211> LENGTH: 116
<212> TYPE: PRT
<213> ORGANISM: Mus musculus
<220> FEATURE:
<221> NAME/KEY: MISC_FEATURE
<223> OTHER INFORMATION: Clone XPA.015.182 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(105)
<223> OTHER INFORMATION: H-CDR3

<400> SEQUENCE: 164

Glu Ile Gln Leu Gln Gln Ser Gly Pro Val Leu Val Lys Pro Gly Ala
1               5                   10                  15

Ser Val Lys Met Ser Cys Lys Ala Ala Gly Tyr Thr Phe Thr Asp Ser
            20                  25                  30

```
Tyr Met Asn Trp Val Lys Gln Ser His Gly Lys Ser Leu Glu Trp Ile
            35                  40                  45

Gly Asp Ile Asn Pro Tyr Asn Gly Gly Thr Ser Tyr Asn Gln His Phe
        50                  55                  60

Lys Gly Lys Ala Thr Leu Thr Val Asp Lys Ser Ser Thr Ala Tyr
 65                  70                  75                  80

Met Glu Leu Asn Ser Leu Thr Ser Glu Asp Ser Ala Val Tyr Tyr Cys
                85                  90                  95

Ala Arg Arg Arg Gly Ala Met Asp Tyr Trp Gly Gln Gly Thr Ser Val
            100                 105                 110

Thr Val Ser Ser
        115

<210> SEQ ID NO 165
<211> LENGTH: 120
<212> TYPE: PRT
<213> ORGANISM: Mus musculus
<220> FEATURE:
<221> NAME/KEY: MISC_FEATURE
<223> OTHER INFORMATION: Clone XPA.015.186 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 165

Gln Val Gln Leu Gln Gln Ser Arg Ala Glu Leu Val Lys Pro Gly Ala
 1               5                  10                  15

Ser Val Lys Leu Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
            35                  40                  45

Gly Met Ile His Pro Asn Ser Gly Thr Asn Tyr Asn Glu Lys Phe
        50                  55                  60

Arg Ser Lys Ala Thr Leu Thr Gly Asp Lys Ser Ser Ser Thr Ala Tyr
 65                  70                  75                  80

Met Gln Leu Asn Ser Leu Thr Ser Asp Asp Ser Ala Val Tyr Tyr Cys
                85                  90                  95

Ala Arg Trp Asp Tyr Gly Ser Ala Ser Tyr Phe Asp Phe Trp Gly Gln
            100                 105                 110

Gly Thr Thr Leu Ile Val Ser Ser
        115                 120

<210> SEQ ID NO 166
<211> LENGTH: 119
<212> TYPE: PRT
<213> ORGANISM: Mus musculus
<220> FEATURE:
<221> NAME/KEY: MISC_FEATURE
<223> OTHER INFORMATION: Clone XPA.015.187 heavy chain
<220> FEATURE:
<221> NAME/KEY: MISC_FEATURE
<222> LOCATION: (26)..(33)
<223> OTHER INFORMATION: H-CDR1
<220> FEATURE:
```

```
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(108)
<223> OTHER INFORMATION: H-CDR3

<400> SEQUENCE: 166

Glu Val Gln Leu Gln Gln Ser Gly Ala Glu Leu Val Lys Pro Gly Ala
1               5                   10                  15

Ser Val Lys Ile Ser Cys Lys Ala Ser Gly Tyr Thr Phe Ser Asn Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Gly Thr Ala Tyr
65                  70                  75                  80

Met Gln Leu Ser Ser Leu Thr Ser Glu Asp Ser Ala Asp Tyr Phe Cys
                85                  90                  95

Ala Arg Gly Val Ser Gly Tyr Gly Ala Val Asp His Trp Gly Gln Gly
            100                 105                 110

Thr Ser Val Thr Val Ser Ser
        115

<210> SEQ ID NO 167
<211> LENGTH: 115
<212> TYPE: PRT
<213> ORGANISM: Mus musculus
<220> FEATURE:
<221> NAME/KEY: MISC_FEATURE
<223> OTHER INFORMATION: Clone XPA.015.190 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(104)
<223> OTHER INFORMATION: H-CDR3

<400> SEQUENCE: 167

Glu Val Lys Leu Val Glu Ser Glu Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Asp Gly Gly His Tyr Thr Tyr Tyr Ser Asp Thr Ile
    50                  55                  60

Lys Gly Arg Phe Thr Ile Ser Arg Asp Asn Ala Lys Asn Asn Leu Phe
65                  70                  75                  80

Leu Gln Leu Ser His Leu Lys Ser Glu Asp Thr Ala Ile Tyr Tyr Cys
                85                  90                  95

Ala Arg Gly Thr Val Phe Asp Tyr Trp Gly Gln Gly Thr Thr Leu Thr
            100                 105                 110

Val Ser Ser
```

115

<210> SEQ ID NO 168
<211> LENGTH: 120
<212> TYPE: PRT
<213> ORGANISM: Mus musculus
<220> FEATURE:
<221> NAME/KEY: MISC_FEATURE
<223> OTHER INFORMATION: Clone XPA.015.191 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 168

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ile Phe Thr Asn Tyr
            20                  25                  30

Trp Met His Gly Val Lys Gln Arg Pro Gly Gln Gly Leu Glu Trp Ile
        35                  40                  45

Gly Met Ile His Pro Asn Ser Gly Ser Thr Tyr Asn Glu Lys Phe
    50                  55                  60

Lys Thr Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Tyr Gly Ser Thr Tyr Trp Tyr Phe Asp Val Trp Gly Thr
            100                 105                 110

Gly Thr Thr Val Thr Val Ser Ser
        115                 120

<210> SEQ ID NO 169
<211> LENGTH: 115
<212> TYPE: PRT
<213> ORGANISM: Mus musculus
<220> FEATURE:
<221> NAME/KEY: MISC_FEATURE
<223> OTHER INFORMATION: Clone XPA.015.173 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(104)
<223> OTHER INFORMATION: H-CDR3

<400> SEQUENCE: 169

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val

```
                35                  40                  45
Ala Thr Ile Ser Asp Gly Gly His Tyr Ile Asp Tyr Pro Asp Asn Val
        50                  55                  60

Lys Gly Arg Phe Thr Ile Ser Arg Asp Asn Ala Lys Asn Asn Leu Tyr
 65                  70                  75                  80

Leu Gln Met Ser His Leu Arg Ser Glu Asp Ser Ala Met Tyr Tyr Cys
                85                  90                  95

Ala Arg Ala Thr Asn Phe Ala Tyr Trp Gly Gln Gly Thr Leu Val Thr
            100                 105                 110

Val Ser Ala
        115

<210> SEQ ID NO 170
<211> LENGTH: 113
<212> TYPE: PRT
<213> ORGANISM: Mus musculus
<220> FEATURE:
<221> NAME/KEY: MISC_FEATURE
<223> OTHER INFORMATION: Clone XPA.015.174 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(102)
<223> OTHER INFORMATION: H-CDR3

<400> SEQUENCE: 170

Gln Val Gln Leu Gln Gln Ser Gly Pro Glu Leu Val Lys Pro Gly Ala
 1               5                  10                  15

Ser Val Lys Leu Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Arg Asp Gly Ser Thr Lys Ser Asn Glu Lys Phe
    50                  55                  60

Lys Gly Lys Ala Thr Leu Thr Val Asp Thr Ser Ser Ser Thr Ala Tyr
 65                  70                  75                  80

Met Glu Leu His Ser Leu Thr Ser Glu Asp Ser Ala Val Tyr Phe Cys
                85                  90                  95

Ala Arg Glu Phe Asp Tyr Trp Gly Gln Gly Thr Leu Val Thr Val Ser
            100                 105                 110

Ala

<210> SEQ ID NO 171
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.023 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
```

```
<220> FEATURE:
<221> NAME/KEY: MISC_FEATURE
<222> LOCATION: (97)..(109)
<223> OTHER INFORMATION: H-CDR3

<400> SEQUENCE: 171

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ser Ser Gly Trp Tyr Tyr Phe Asp Tyr Trp Gly Gln
            100                 105                 110

Gly Thr Leu Val Thr Val Ser Ser
            115                 120

<210> SEQ ID NO 172
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.068 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ser Ser Gly Trp Tyr Tyr Phe Asp Tyr Trp Gly Gln
            100                 105                 110

Gly Thr Leu Val Thr Val Ser Ser
            115                 120
```

```
<210> SEQ ID NO 173
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.081 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 173
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ser Ser Gly Trp Tyr Tyr Phe Asp Tyr Trp Gly Gln
            100                 105                 110

Gly Thr Leu Val Thr Val Ser Ser
        115                 120

```
<210> SEQ ID NO 174
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA015.159 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 174
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Val Gly Ser Ser Gly Trp Tyr Tyr Phe Asp Tyr Trp Gly Gln
                100                 105                 110

Gly Thr Leu Val Thr Val Ser Ser
            115                 120

<210> SEQ ID NO 175
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.171 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 175

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
                 20                  25                  30

Tyr Met Ser Trp Ile Arg Gln Ala Pro Gly Lys Gly Leu Glu Trp Val
             35                  40                  45

Ser Ala Ile Ser Gly Ser Gly Gly Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Val Gly Ser Ser Gly Trp Tyr Tyr Phe Asp Tyr Trp Gly Gln
                100                 105                 110

Gly Thr Leu Val Thr Val Ser Ser
            115                 120

<210> SEQ ID NO 176
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.102 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
```

<222> LOCATION: (97)..(109)
<223> OTHER INFORMATION: H-CDR3

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ser Ser Gly Trp Tyr Tyr Phe Asp Tyr Trp Gly Gln
            100                 105                 110

Gly Thr Leu Val Thr Val Ser Ser
        115                 120

<210> SEQ ID NO 177
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.093 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ser Ile Ser Gly Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Lys Gly Leu Gln Pro Leu Asp Tyr Trp Gly Gln Gly Thr
            100                 105                 110

Leu Val Thr Val Ser Ser
        115

<210> SEQ ID NO 178
<211> LENGTH: 118

```
<212> TYPE: PRT
<213> ORGANISM: Homo sapiens
<220> FEATURE:
<221> NAME/KEY: MISC_FEATURE
<223> OTHER INFORMATION: Clone XPA.15.094 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 178

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ser Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Lys Gly Leu Gln Pro Leu Asp Tyr Trp Gly Gln Gly Thr
            100                 105                 110

Leu Val Thr Val Ser Ser
        115

<210> SEQ ID NO 179
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.013  heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 179

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ser Ile Ser Gly Ser Gly Gly Thr Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Lys Gly Leu Gln Pro Leu Asp Tyr Trp Gly Gln Gly Thr
            100                 105                 110

Leu Val Thr Val Ser Ser
        115
```

```
<210> SEQ ID NO 180
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.047 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 180
```

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Ala Met Gly Trp Val Arg Gln Ala Pro Gly Lys Gly Leu Glu Trp Val
            35                  40                  45

Ser Ser Ile Ser Gly Ser Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Lys Gly Leu Gln Pro Leu Asp Tyr Trp Gly Gln Gly Thr
            100                 105                 110

Leu Val Thr Val Ser Ser
        115
```

```
<210> SEQ ID NO 181
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.075 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3
```

<400> SEQUENCE: 181

```
Glu Val Gln Leu Leu Glu Ser Gly Gly Gly Leu Val Gln Pro Trp Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ser Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Pro Tyr
65                  70                  75                  80

Leu Gln Met Asn Ser Leu Arg Ala Glu Asp Thr Ala Val Tyr Tyr Cys
                85                  90                  95

Ala Arg His Lys Gly Leu Gln Pro Leu Asp Tyr Trp Gly Gln Gly Thr
            100                 105                 110

Leu Val Thr Val Ser Ser
            115
```

<210> SEQ ID NO 182
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.115 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 182

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ser Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Lys Gly Leu Gln Pro Leu Asp Tyr Trp Gly Gln Gly Thr
            100                 105                 110

Leu Val Thr Val Ser Ser
            115
```

<210> SEQ ID NO 183
<211> LENGTH: 121
<212> TYPE: PRT
<213> ORGANISM: Homo sapiens

```
<220> FEATURE:
<221> NAME/KEY: MISC_FEATURE
<223> OTHER INFORMATION: Clone XPA.15.065 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(57)
<223> OTHER INFORMATION: H-CDR2
<220> FEATURE:
<221> NAME/KEY: MISC_FEATURE
<222> LOCATION: (96)..(110)
<223> OTHER INFORMATION: H-CDR3

<400> SEQUENCE: 183

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Tyr Ile His Ala Gly Gly Thr His Tyr Ala Asn Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Leu His Trp Glu Gly Trp Gly Leu Gly Phe Asp Tyr Trp Gly
            100                 105                 110

Gln Gly Thr Leu Val Thr Val Ser Ser
        115                 120

<210> SEQ ID NO 184
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.086 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(57)
<223> OTHER INFORMATION: H-CDR2
<220> FEATURE:
<221> NAME/KEY: MISC_FEATURE
<222> LOCATION: (96)..(110)
<223> OTHER INFORMATION: H-CDR3

<400> SEQUENCE: 184

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Tyr Ile His Ala Gly Gly Gly Thr His Tyr Ala Asn Ser Val Lys
50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
                85                  90                  95

Arg Asp Leu His Trp Glu Gly Trp Gly Leu Gly Phe Asp Tyr Trp Gly
            100                 105                 110

Gln Gly Thr Leu Val Thr Val Ser Ser
        115                 120

<210> SEQ ID NO 185
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.106 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(57)
<223> OTHER INFORMATION: H-CDR2
<220> FEATURE:
<221> NAME/KEY: MISC_FEATURE
<222> LOCATION: (96)..(110)
<223> OTHER INFORMATION: H-CDR3

<400> SEQUENCE: 185

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Tyr Ile His Ala Gly Gly Thr His Tyr Ala Asn Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Leu His Trp Glu Gly Trp Gly Leu Gly Phe Asp Tyr Trp Gly
            100                 105                 110

Gln Gly Thr Leu Val Thr Val Ser Ser
        115                 120

<210> SEQ ID NO 186
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.082 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(57)
<223> OTHER INFORMATION: H-CDR2
<220> FEATURE:
<221> NAME/KEY: MISC_FEATURE
<222> LOCATION: (96)..(110)
<223> OTHER INFORMATION: H-CDR3

<400> SEQUENCE: 186
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Tyr Ile His Ala Gly Gly Thr His Tyr Ala Asn Ser Val Lys
50                      55                  60

Gly Arg Phe Thr Ile Ser Arg Asp Asn Ser Lys Asn Thr Leu Tyr Leu
65                      70                  75                  80

Gln Met Asn Ser Leu Arg Ala Glu Asp Thr Ala Val Tyr Tyr Cys Ala
                85                  90                  95

Arg Asp Leu His Trp Glu Gly Trp Gly Leu Gly Phe Asp Tyr Trp Gly
            100                 105                 110

Gln Gly Thr Leu Val Thr Val Ser Ser
            115                 120
```

<210> SEQ ID NO 187
<211> LENGTH: 129
<212> TYPE: PRT
<213> ORGANISM: Homo sapiens
<220> FEATURE:
<221> NAME/KEY: MISC_FEATURE
<223> OTHER INFORMATION: Clone XPA.15.088 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(118)
<223> OTHER INFORMATION: H-CDR3

<400> SEQUENCE: 187

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asn Met Gln Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Ser Trp Asp Thr Thr Gly Tyr Tyr Asn Tyr Tyr
            100                 105                 110

Tyr Tyr Gly Met Asp Val Trp Gly Gln Gly Thr Leu Val Thr Val Ser
        115                 120                 125

Ser
```

<210> SEQ ID NO 188
<211> LENGTH: 129
<212> TYPE: PRT
<213> ORGANISM: Homo sapiens

```
<220> FEATURE:
<221> NAME/KEY: MISC_FEATURE
<223> OTHER INFORMATION: Clone XPA.15.100 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(118)
<223> OTHER INFORMATION: H-CDR3

<400> SEQUENCE: 188
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asn Met Gln Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Ser Trp Asp Thr Thr Gly Tyr Tyr Asn Tyr Tyr
            100                 105                 110

Tyr Tyr Gly Met Asp Val Trp Gly Gln Gly Thr Leu Val Thr Val Ser
        115                 120                 125

Ser

```
<210> SEQ ID NO 189
<211> LENGTH: 129
<212> TYPE: PRT
<213> ORGANISM: Homo sapiens
<220> FEATURE:
<221> NAME/KEY: MISC_FEATURE
<223> OTHER INFORMATION: Clone XPA.15.163 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(118)
<223> OTHER INFORMATION: H-CDR3

<400> SEQUENCE: 189
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Asn Met Ile Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Gly Ser Trp Asp Thr Thr Gly Tyr Tyr Asn Tyr Tyr
            100                 105                 110

Tyr Tyr Gly Met Asp Val Trp Gly Gln Gly Thr Leu Val Thr Val Ser
            115                 120                 125

Ser

<210> SEQ ID NO 190
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.120 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 190

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Val Gly Gly Pro Phe Asp Ile Trp Gly Gln Gly Thr
            100                 105                 110

Leu Val Thr Val Ser Ser
            115

<210> SEQ ID NO 191
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.059 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
```

```
<222> LOCATION: (97)..(107)
<223> OTHER INFORMATION: H-CDR3

<400> SEQUENCE: 191
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Arg | Asn | Tyr |
| | | | 20 | | | | | 25 | | | | | 30 | | |

| Trp | Met | Thr | Trp | Val | Arg | Gln | Ala | Pro | Gly | Lys | Gly | Leu | Glu | Trp | Val |
| | | 35 | | | | | 40 | | | | | 45 | | | |

| Ala | Asn | Ile | Lys | Gln | Asp | Gly | Ser | Glu | Lys | Tyr | Tyr | Val | Asp | Ser | Val |
| | 50 | | | | | 55 | | | | | 60 | | | | |

| Lys | Gly | Arg | Ser | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ala | Arg | Gln | Val | Gly | Gly | Pro | Phe | Asp | Ile | Trp | Gly | Gln | Gly | Thr |
| | | | | 100 | | | | | 105 | | | | | 110 |

| Leu | Val | Thr | Val | Ser | Ser |
| | | | | 115 | |

```
<210> SEQ ID NO 192
<211> LENGTH: 117
<212> TYPE: PRT
<213> ORGANISM: Homo sapiens
<220> FEATURE:
<221> NAME/KEY: MISC_FEATURE
<223> OTHER INFORMATION: Clone XPA.15.022 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(106)
<223> OTHER INFORMATION: H-CDR3

<400> SEQUENCE: 192
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asp | Tyr |
| | | | 20 | | | | | 25 | | | | | 30 | | |

| Tyr | Met | Ser | Trp | Ile | Arg | Arg | Ala | Pro | Gly | Lys | Gly | Leu | Glu | Trp | Val |
| | | 35 | | | | | 40 | | | | | 45 | | | |

| Ser | Arg | Ile | Ser | Trp | Asn | Ser | Gly | Ser | Ile | Gly | Tyr | Ala | Asp | Ser | Leu |
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ala | Arg | Glu | Arg | Gly | Tyr | Gly | Tyr | Asp | Tyr | Trp | Gly | Gln | Gly | Thr | Leu |
| | | | | 100 | | | | | 105 | | | | | 110 | |

| Val | Thr | Val | Ser | Ser |
| | | | 115 | |

```
<210> SEQ ID NO 193
<211> LENGTH: 117
```

```
<212> TYPE: PRT
<213> ORGANISM: Homo sapiens
<220> FEATURE:
<221> NAME/KEY: MISC_FEATURE
<223> OTHER INFORMATION: Clone XPA.15.021 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(57)
<223> OTHER INFORMATION: H-CDR2
<220> FEATURE:
<221> NAME/KEY: MISC_FEATURE
<222> LOCATION: (96)..(106)
<223> OTHER INFORMATION: H-CDR3

<400> SEQUENCE: 193

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Arg Trp Leu Pro Tyr Phe Asp Tyr Trp Gly Gln Gly Thr Leu
            100                 105                 110

Val Thr Val Ser Ser
            115

<210> SEQ ID NO 194
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.026 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 194

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Val Ile Ser Trp Val Arg Gln Ala Pro Gly Lys Gly Leu Glu Trp Val
        35                  40                  45

Ser Ala Ile Ser Gly Ser Gly Gly Ser Thr Phe Tyr Pro Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Met Tyr Tyr Cys
                 85                  90                  95

Ala Arg Val Gly Leu Ser Gly Trp Tyr Tyr Phe Asp Tyr Trp Gly Gln
            100                 105                 110

Gly Thr Leu Val Thr Val Ser Ser
        115                 120

<210> SEQ ID NO 195
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.048 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 195

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Ser Ile Ser Ser Ser Ser Arg Tyr Ala Asp Val Ala Asn Ser Val
    50                  55                  60

Val Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Glu Trp Leu Asp His Phe Asp Tyr Trp Gly Gln Gly Thr
            100                 105                 110

Leu Val Thr Val Ser Ser
        115

<210> SEQ ID NO 196
<211> LENGTH: 116
<212> TYPE: PRT
<213> ORGANISM: Homo sapiens
<220> FEATURE:
<221> NAME/KEY: MISC_FEATURE
<223> OTHER INFORMATION: Clone XPA.15.064 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(105)
<223> OTHER INFORMATION: H-CDR3
```

<400> SEQUENCE: 196

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Val Arg Gln Ala Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Ser Gln Ser Thr Ala Phe Asp Ile Trp Gly Gln Gly Thr Leu Val
            100                 105                 110

Thr Val Ser Ser
            115
```

<210> SEQ ID NO 197
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.077 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 197

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Val Ile Ser Lys Asp Gly Ser Ser Thr Asp Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Trp Ile Pro Gly Asp Val Trp Gly Gln Gly Thr
            100                 105                 110

Leu Val Thr Val Ser Ser
            115
```

<210> SEQ ID NO 198
<211> LENGTH: 126
<212> TYPE: PRT
<213> ORGANISM: Homo sapiens

```
<220> FEATURE:
<221> NAME/KEY: MISC_FEATURE
<223> OTHER INFORMATION: Clone XPA.15.096 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(115)
<223> OTHER INFORMATION: H-CDR3

<400> SEQUENCE: 198

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Asn Ile Lys Gln Asp Gly Arg Glu Thr Tyr Tyr Val Asp Ser Val
    50                  55                  60

Thr Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Thr Thr Asp Leu Gly Arg Tyr Tyr Asp Ile Leu Thr Gly Tyr Tyr Ala
            100                 105                 110

Pro Asn Tyr Trp Gly Gln Gly Thr Leu Val Thr Val Ser Ser
        115                 120                 125

<210> SEQ ID NO 199
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.105 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(108)
<223> OTHER INFORMATION: H-CDR3

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ser Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp His Ser Ser Ser Trp Ala Phe Asp Tyr Trp Gly Gln Gly
            100                 105                 110

Thr Leu Val Thr Val Ser Ser
        115

<210> SEQ ID NO 200
<211> LENGTH: 129
<212> TYPE: PRT
<213> ORGANISM: Homo sapiens
<220> FEATURE:
<221> NAME/KEY: MISC_FEATURE
<223> OTHER INFORMATION: Clone XPA.15.110 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(118)
<223> OTHER INFORMATION: H-CDR3

<400> SEQUENCE: 200

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Asp Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Lys Gly Tyr Cys Ser Ser Thr Ser Cys Tyr Phe Asp Tyr
            100                 105                 110

Tyr Tyr Gly Met Asp Val Trp Gly Gln Gly Thr Leu Val Thr Val Ser
        115                 120                 125

Ser

<210> SEQ ID NO 201
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.124 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(57)
<223> OTHER INFORMATION: H-CDR2
<220> FEATURE:
<221> NAME/KEY: MISC_FEATURE
<222> LOCATION: (96)..(108)
<223> OTHER INFORMATION: H-CDR3
```

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Val Met Thr Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ile Asn Trp Asn Asp Gly Gly Asn Phe Asp Tyr Trp Gly Gln Gly
            100                 105                 110

Thr Leu Val Thr Val Ser Ser
        115

<210> SEQ ID NO 202
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.121 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(56)
<223> OTHER INFORMATION: H-CDR2
<220> FEATURE:
<221> NAME/KEY: MISC_FEATURE
<222> LOCATION: (95)..(108)
<223> OTHER INFORMATION: H-CDR3

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

His Ala Asp Gln Trp Pro Gly Ser Trp Phe Asp Pro Trp Gly Gln Gly
            100                 105                 110

Thr Leu Val Thr Val Ser Ser
        115

<210> SEQ ID NO 203
<211> LENGTH: 116
<212> TYPE: PRT
<213> ORGANISM: Homo sapiens

```
<220> FEATURE:
<221> NAME/KEY: MISC_FEATURE
<223> OTHER INFORMATION: Clone XPA.15.122 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(56)
<223> OTHER INFORMATION: H-CDR2
<220> FEATURE:
<221> NAME/KEY: MISC_FEATURE
<222> LOCATION: (95)..(105)
<223> OTHER INFORMATION: H-CDR3

<400> SEQUENCE: 203

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Gly Val Gly Asp Trp Phe Asp Pro Trp Gly Gln Gly Thr Leu Val
            100                 105                 110

Thr Val Ser Ser
            115

<210> SEQ ID NO 204
<211> LENGTH: 123
<212> TYPE: PRT
<213> ORGANISM: Homo sapiens
<220> FEATURE:
<221> NAME/KEY: MISC_FEATURE
<223> OTHER INFORMATION: Clone XPA.15.127 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(112)
<223> OTHER INFORMATION: H-CDR3

<400> SEQUENCE: 204

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Lys Phe
            20                  25                  30

Ala Val His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Ala Ser Asp Val Glu Gly Gly Tyr Phe His Asn Ser Gly Pro Asp His
            100                 105                 110

Trp Gly Gln Gly Thr Leu Val Thr Val Ser Ser
        115                 120

<210> SEQ ID NO 205
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.015.125 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 205

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Val Gly Ile Ser Gly Asn Tyr Asp Tyr Trp Gly Gln
            100                 105                 110

Gly Thr Leu Val Thr Val Ser Ser
        115                 120

<210> SEQ ID NO 206
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.133 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 206
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
            35                  40                  45

Ala Leu Ile Ser Tyr Asp Gly Ser Asn Lys Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Ala Asp Leu Gly Ile Gly Ser Gly Tyr Phe Asp Tyr Trp Gly Gln
            100                 105                 110

Gly Thr Leu Val Thr Val Ser Ser
        115                 120

<210> SEQ ID NO 207
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.135 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 207

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Gly Ile Tyr Asp Tyr Phe Asp Tyr Trp Gly Gln
            100                 105                 110

Gly Thr Leu Val Thr Val Ser Ser
        115                 120

<210> SEQ ID NO 208
<211> LENGTH: 118
<212> TYPE: PRT
<213> ORGANISM: Homo sapiens
<220> FEATURE:
<221> NAME/KEY: MISC_FEATURE

```
<223> OTHER INFORMATION: Clone XPA.15.139 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 208

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Gly Ile Ser Gly Ser Gly Gly Tyr Ile His Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Gly Trp Leu Val Asp Gln Trp Gly Gln Gly Thr
            100                 105                 110

Leu Val Thr Val Ser Ser
        115

<210> SEQ ID NO 209
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.138 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(110)
<223> OTHER INFORMATION: H-CDR3

<400> SEQUENCE: 209

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                85                  90                  95

Ala Arg Val Arg Trp Tyr Lys Asp Ser Asp Ala Phe Asp Ile Trp Gly
            100                 105                 110

Gln Gly Thr Leu Val Thr Val Ser Ser
        115                 120
```

<210> SEQ ID NO 210
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.143 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 210

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ala His Ile Asn Gln Asp Gly Ser Glu Lys Tyr Tyr Val Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Lys Leu Arg Gly Gly Ala Tyr Asn Asp Tyr Trp Gly Gln Gly Thr
            100                 105                 110

Leu Val Thr Val Ser Ser
        115
```

<210> SEQ ID NO 211
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.145 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 211

```
Glu Val Gln Leu Leu Glu Ser Gly Gly Gly Leu Val Gln Pro Gly Gly
```

```
                1               5                   10                  15
            Ser Leu Arg Leu Ser Cys Ala Ala Ser Gly Phe Thr Phe Ser Asn Tyr
                        20                  25                  30

Ala Met Thr Trp Val Arg Gln Ser Pro Gly Lys Gly Leu Glu Trp Val
                        35                  40                  45

Ser Val Ile Ser Gly Ser Gly Gly Thr Thr Tyr Tyr Ala Asp Ser Val
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Ala Lys Ala Lys Gly Ser Gln Val Phe Asp Tyr Trp Gly Gln Gly Thr
                        100                 105                 110

Leu Val Thr Val Ser Ser
                        115

<210> SEQ ID NO 212
<211> LENGTH: 123
<212> TYPE: PRT
<213> ORGANISM: Homo sapiens
<220> FEATURE:
<221> NAME/KEY: MISC_FEATURE
<223> OTHER INFORMATION: Clone XPA.15.140 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(112)
<223> OTHER INFORMATION: H-CDR3

<400> SEQUENCE: 212

Glu Val Gln Leu Leu Glu Ser Gly Gly Gly Leu Val Gln Pro Gly Gly
             1               5                   10                  15

Ser Leu Arg Leu Ser Cys Ala Ala Ser Gly Phe Thr Phe Ser Ser Tyr
                        20                  25                  30

Thr Met Asp Trp Val Arg Gln Ala Pro Gly Lys Gly Leu Glu Trp Val
                        35                  40                  45

Ser Ser Ile Ser Ser Ser Ser Ser Tyr Ile Tyr Tyr Ala Asp Ser Val
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Val Arg Glu Ala Trp Arg Glu Asn Asn Asp Trp Tyr Glu Leu Asp Tyr
                        100                 105                 110

Trp Gly Gln Gly Thr Leu Val Thr Val Ser Ser
                        115                 120

<210> SEQ ID NO 213
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.167 heavy chain
<220> FEATURE:
```

```
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 213
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Phe Ile Ser Gly Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ser Ser Gly Trp Tyr Tyr Phe Asp Tyr Trp Gly Gln
            100                 105                 110

Gly Thr Leu Val Thr Val Ser Ser
        115                 120

```
<210> SEQ ID NO 214
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.169 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(56)
<223> OTHER INFORMATION: H-CDR2
<220> FEATURE:
<221> NAME/KEY: MISC_FEATURE
<222> LOCATION: (95)..(109)
<223> OTHER INFORMATION: H-CDR3

<400> SEQUENCE: 214
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

```
Glu Val Glu Tyr Ser Ser Ser Trp Gly Ala Phe Asp Ile Trp Gly Gln
                100                 105                 110

Gly Thr Leu Val Thr Val Ser Ser
        115                 120

<210> SEQ ID NO 215
<211> LENGTH: 123
<212> TYPE: PRT
<213> ORGANISM: Homo sapiens
<220> FEATURE:
<221> NAME/KEY: MISC_FEATURE
<223> OTHER INFORMATION: Clone XPA.15.020 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(57)
<223> OTHER INFORMATION: H-CDR2
<220> FEATURE:
<221> NAME/KEY: MISC_FEATURE
<222> LOCATION: (96)..(112)
<223> OTHER INFORMATION: H-CDR3

<400> SEQUENCE: 215

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Leu Ile Tyr Arg Asp Gly Ser Thr Thr Tyr Ala Asp Ser Val Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Ser Thr Arg Leu Arg Gly Ser Tyr Tyr Tyr Gly Met Asp Val
            100                 105                 110

Trp Gly Gln Gly Thr Leu Val Thr Val Ser Ser
        115                 120

<210> SEQ ID NO 216
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.017 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(57)
<223> OTHER INFORMATION: H-CDR2
<220> FEATURE:
<221> NAME/KEY: MISC_FEATURE
<222> LOCATION: (96)..(110)
<223> OTHER INFORMATION: H-CDR3

<400> SEQUENCE: 216

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Val Ile Tyr Ser Gly Asp Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Gln Val Arg Asp Gly Asp Tyr Gly Asp Trp Phe Asp Pro Trp Gly
            100                 105                 110

Gln Gly Thr Leu Val Thr Val Ser Ser
            115                 120

<210> SEQ ID NO 217
<211> LENGTH: 116
<212> TYPE: PRT
<213> ORGANISM: Homo sapiens
<220> FEATURE:
<221> NAME/KEY: MISC_FEATURE
<223> OTHER INFORMATION: Clone XPA.15.033 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(105)
<223> OTHER INFORMATION: H-CDR3

<400> SEQUENCE: 217

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Ser Ser Phe Asp Tyr Trp Gly Gln Gly Thr Leu Val
            100                 105                 110

Thr Val Ser Ser
        115

<210> SEQ ID NO 218
<211> LENGTH: 117
<212> TYPE: PRT
<213> ORGANISM: Homo sapiens
<220> FEATURE:
<221> NAME/KEY: MISC_FEATURE
<223> OTHER INFORMATION: Clone XPA.15.037 heavy chain
<220> FEATURE:
<221> NAME/KEY: MISC_FEATURE
<222> LOCATION: (26)..(33)
```

```
<223> OTHER INFORMATION: H-CDR1
<220> FEATURE:
<221> NAME/KEY: MISC_FEATURE
<222> LOCATION: (51)..(56)
<223> OTHER INFORMATION: H-CDR2
<220> FEATURE:
<221> NAME/KEY: MISC_FEATURE
<222> LOCATION: (95)..(106)
<223> OTHER INFORMATION: H-CDR3

<400> SEQUENCE: 218

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Thr Leu Tyr Leu Gln
65                  70                  75                  80

Met Asn Ser Leu Arg Ala Glu Asp Thr Ala Val Tyr Tyr Cys Ala Arg
                85                  90                  95

Leu Asp Trp Ser Ser Gly Ala Phe Asp Ile Trp Gly Gln Gly Thr Leu
            100                 105                 110

Val Thr Val Ser Ser
            115

<210> SEQ ID NO 219
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.042 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 219

Glu Val Gln Leu Leu Glu Ser Gly Gly Gly Leu Val Gln Pro Gly Gly
1               5                   10                  15

Ser Leu Gly Leu Ser Cys Ala Ala Ser Gly Phe Thr Phe Asn Asn Tyr
            20                  25                  30

Trp Met Ser Trp Val Arg Gln Ala Pro Gly Lys Gly Leu Glu Trp Val
        35                  40                  45

Ser Tyr Ile Ser Gly Ser Gly Arg Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ser Ser Gly Trp Tyr Tyr Phe Asp Tyr Trp Gly Gln
            100                 105                 110
```

```
Gly Thr Leu Val Thr Val Ser Ser
        115                 120

<210> SEQ ID NO 220
<211> LENGTH: 122
<212> TYPE: PRT
<213> ORGANISM: Homo sapiens
<220> FEATURE:
<221> NAME/KEY: MISC_FEATURE
<223> OTHER INFORMATION: Clone XPA.15.036 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(111)
<223> OTHER INFORMATION: H-CDR3

<400> SEQUENCE: 220

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Trp Glu Leu Leu Gly Tyr Asp Ala Phe Asp Ile Trp
            100                 105                 110

Gly Gln Gly Thr Leu Val Thr Val Ser Ser
        115                 120

<210> SEQ ID NO 221
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.007 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(110)
<223> OTHER INFORMATION: H-CDR3

<400> SEQUENCE: 221

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Tyr Ser Ser Gly Trp Tyr Trp Ser Asp Tyr Trp Gly
                100                 105                 110

Gln Gly Thr Leu Val Thr Val Ser Ser
        115                 120

<210> SEQ ID NO 222
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.074 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 222

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Met Ser Trp Val Arg Gln Ala Pro Gly Lys Gly Leu Glu Trp Val
        35                  40                  45

Ser Gly Ile Ser Gly Ser Gly Gly Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Ser Asp Trp Tyr Ile Asn Ser Trp Gly Gln Gly Thr
                100                 105                 110

Leu Val Thr Val Ser Ser
        115

<210> SEQ ID NO 223
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.066 heavy chain
<220> FEATURE:
<221> NAME/KEY: MISC_FEATURE
<222> LOCATION: (26)..(33)
<223> OTHER INFORMATION: H-CDR1
<220> FEATURE:
```

```
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 223
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 |
| Ser | Leu | Arg | Leu | Ser | Cys | Ala | Ala | Ser | Gly | Phe | Thr | Phe | Arg | Asn | Phe |
| | | | 20 | | | | | 25 | | | | | 30 | |
| Ala | Met | Met | Trp | Val | Arg | Gln | Ala | Pro | Gly | Lys | Gly | Leu | Glu | Trp | Val |
| | | 35 | | | | | 40 | | | | | 45 | | |
| Ser | Gly | Ile | Ser | Trp | Asn | Ser | Gly | Ser | Ile | Gly | Tyr | Ala | Asp | Ser | Val |
| | 50 | | | | | 55 | | | | | 60 | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Pro | Ser | Gly | Ala | Tyr | Pro | Thr | Pro | Phe | Asp | Asn | Trp | Gly | Gln |
| | | | 100 | | | | | 105 | | | | | 110 | |
| Gly | Thr | Leu | Val | Thr | Val | Ser | Ser | | | | | | | | |
| | | | 115 | | | | | 120 | | | | | | | |

```
<210> SEQ ID NO 224
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.080 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(107)
<223> OTHER INFORMATION: H-CDR3

<400> SEQUENCE: 224
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | |
| Ser | Met | Asn | Trp | Val | Arg | Gln | Ala | Pro | Gly | Lys | Gly | Leu | Glu | Trp | Val |
| | | 35 | | | | | 40 | | | | | 45 | | |
| Ser | Ala | Ile | Ser | Gly | Ser | Gly | Gly | Arg | Thr | Tyr | Tyr | Ala | Asp | Ser | Val |
| | 50 | | | | | 55 | | | | | 60 | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Asp | Gly | Ile | Trp | Ser | Ala | Met | Asp | Val | Trp | Gly | Gln | Gly | Thr |
| | | | 100 | | | | | 105 | | | | | 110 | |
| Leu | Val | Thr | Val | Ser | Ser | | | | | | | | | | |

```
                115

<210> SEQ ID NO 225
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.111 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(109)
<223> OTHER INFORMATION: H-CDR3

<400> SEQUENCE: 225

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Gly Ile Ser Gly Ser Gly Gly Ser Thr Asp Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Pro Ala Phe Trp Ser Ala Phe Asp Tyr Trp Gly Gln
            100                 105                 110

Gly Thr Leu Val Thr Val Ser Phe
            115                 120

<210> SEQ ID NO 226
<211> LENGTH: 124
<212> TYPE: PRT
<213> ORGANISM: Homo sapiens
<220> FEATURE:
<221> NAME/KEY: MISC_FEATURE
<223> OTHER INFORMATION: Clone XPA.15.193 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(113)
<223> OTHER INFORMATION: HCDR3

<400> SEQUENCE: 226

Gln Val Gln Leu Val Gln Ser Gly Ala Glu Leu Lys Lys Pro Gly Ala
1               5                   10                  15

Thr Val Lys Ile Ser Cys Lys Val Ser Gly Tyr Thr Phe Gly Asp Tyr
            20                  25                  30

His Met His Trp Val Lys Gln Ala Pro Gly Lys Gly Leu Glu Trp Met
```

-continued

```
              35                  40                  45
Gly Leu Val Asp Pro Glu Asn Gly Glu Thr Glu Tyr Gly Glu Lys Phe
        50                  55                  60
Gln Asp Arg Ile Thr Met Ala Ala Asp Thr Ser Thr Asp Thr Ala Tyr
 65                  70                  75                  80
Met Glu Leu Ser Ser Leu Arg Ser Glu Asp Thr Ala Val Tyr Tyr Cys
                85                  90                  95
Ala Arg Ser Pro Ser Ser Gly Tyr Phe Arg Val Ala Gly Phe Asp
                100                 105                 110
Ile Trp Gly Gln Gly Thr Met Val Thr Val Ser Ser
            115                 120

<210> SEQ ID NO 227
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.194 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(110)
<223> OTHER INFORMATION: HCDR3

<400> SEQUENCE: 227

Gln Val Gln Leu Val Gln Ser Gly Ala Glu Val Lys Lys Pro Gly Ser
 1               5                  10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
            35                  40                  45
Gly Gly Ile Ile Pro Ile Phe Gly Thr Ala Asn Tyr Ala Gln Lys Phe
        50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Gly Lys Leu Tyr Ser Arg Asp Tyr Trp Tyr Phe Asp Leu Trp Gly
                100                 105                 110
Arg Gly Thr Leu Val Thr Val Ser Ser
            115                 120

<210> SEQ ID NO 228
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.195 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
```

<223> OTHER INFORMATION: HCDR2
<220> FEATURE:
<221> NAME/KEY: MISC_FEATURE
<222> LOCATION: (97)..(108)
<223> OTHER INFORMATION: HCDR3

<400> SEQUENCE: 228

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
                20                  25                  30

Trp Ile Gly Trp Val Arg Gln Met Pro Gly Arg Gly Leu Glu Trp Met
            35                  40                  45

Gly Ile Ile Tyr Pro Gly Asp Ser Asp Thr Arg Tyr Ser Pro Ser Phe
50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Thr His His Ala Ser Gly Arg Gly Leu Asp Pro Trp Gly Gln Gly
            100                 105                 110

Thr Leu Val Thr Val Ser Ser
            115

<210> SEQ ID NO 229
<211> LENGTH: 124
<212> TYPE: PRT
<213> ORGANISM: Homo sapiens
<220> FEATURE:
<221> NAME/KEY: MISC_FEATURE
<223> OTHER INFORMATION: Clone XPA.15.196 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (99)..(113)
<223> OTHER INFORMATION: HCDR3

<400> SEQUENCE: 229

Gln Val Gln Val Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ser Ser Ser Trp Pro Val Tyr Phe Tyr Tyr Met Asp
            100                 105                 110

Val Trp Gly Lys Gly Ser Thr Val Thr Val Ser Ser
            115                 120

```
<210> SEQ ID NO 230
<211> LENGTH: 124
<212> TYPE: PRT
<213> ORGANISM: Homo sapiens
<220> FEATURE:
<221> NAME/KEY: MISC_FEATURE
<223> OTHER INFORMATION: Clone XPA.15.197 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(113)
<223> OTHER INFORMATION: HCDR3

<400> SEQUENCE: 230

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ser Ser Ser Ser Trp Pro Val Tyr Phe Tyr Tyr Met Asp
            100                 105                 110

Val Trp Gly Lys Gly Thr Thr Val Thr Val Ser Ser
        115                 120

<210> SEQ ID NO 231
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.198 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(110)
<223> OTHER INFORMATION: HCDR3

<400> SEQUENCE: 231

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

```
Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Gly Trp Leu Arg Phe Tyr Gly Met Asp Val Trp Gly
                100                 105                 110

Gln Gly Thr Thr Val Thr Val Ser Ser
        115                 120
```

```
<210> SEQ ID NO 232
<211> LENGTH: 117
<212> TYPE: PRT
<213> ORGANISM: Homo sapiens
<220> FEATURE:
<221> NAME/KEY: MISC_FEATURE
<223> OTHER INFORMATION: Clone XPA.15.199 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(57)
<223> OTHER INFORMATION: HCDR2
<220> FEATURE:
<221> NAME/KEY: MISC_FEATURE
<222> LOCATION: (96)..(106)
<223> OTHER INFORMATION: HCDR3

<400> SEQUENCE: 232

Gln Val Gln Leu Val Gln Ser Gly Ser Glu Val Lys Lys Pro Gly Ala
1               5                   10                  15

Ser Val Lys Val Ser Cys Lys Ala Ser Gly Tyr Thr Phe Thr Asn Ser
                20                  25                  30

Tyr Met His Trp Val Arg Gln Ala Pro Gly Gln Gly Leu Glu Trp Met
            35                  40                  45

Gly Ile Ile Asn Pro Ser Ala Gly Thr Ser Tyr Ala Gln Lys Phe Gln
        50                  55                  60

Gly Arg Val Thr Met Thr Arg Asp Thr Ser Thr Ser Thr Val Tyr Met
65                  70                  75                  80

Glu Leu Ser Ser Leu Lys Ser Glu Asp Thr Ala Val Tyr Tyr Cys Ala
                85                  90                  95

Arg Asp Val Gly Trp Leu Pro Gly Asp Tyr Trp Gly Gln Gly Thr Leu
                100                 105                 110

Val Thr Val Ser Ser
        115
```

```
<210> SEQ ID NO 233
<211> LENGTH: 122
<212> TYPE: PRT
<213> ORGANISM: Homo sapiens
<220> FEATURE:
<221> NAME/KEY: MISC_FEATURE
<223> OTHER INFORMATION: Clone XPA.15.200 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
```

```
<221> NAME/KEY: MISC_FEATURE
<222> LOCATION: (97)..(111)
<223> OTHER INFORMATION: HCDR3

<400> SEQUENCE: 233

Gln Met Gln Leu Val Gln Ser Gly Ala Glu Val Lys Lys Pro Gly Glu
1               5                   10                  15

Ser Leu Lys Ile Ser Cys Lys Gly Tyr Gly Tyr Arg Phe Ser Asp Asn
            20                  25                  30

Trp Ile Gly Trp Val Arg Gln Met Pro Gly Arg Gly Leu Glu Trp Met
        35                  40                  45

Gly Ile Ile Tyr Pro Gly Asp Ser Glu Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Ala Pro Leu Ala Val Ala Gly Met Ala Leu Gly Asp Trp
            100                 105                 110

Gly Gln Gly Thr Leu Val Thr Val Ser Ser
        115                 120

<210> SEQ ID NO 234
<211> LENGTH: 122
<212> TYPE: PRT
<213> ORGANISM: Homo sapiens
<220> FEATURE:
<221> NAME/KEY: MISC_FEATURE
<223> OTHER INFORMATION: Clone XPA.15.202 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(57)
<223> OTHER INFORMATION: HCDR2
<220> FEATURE:
<221> NAME/KEY: MISC_FEATURE
<222> LOCATION: (96)..(111)
<223> OTHER INFORMATION: HCDR3

<400> SEQUENCE: 234

Gln Leu Gln Leu Gln Gln Trp Gly Ala Gly Leu Leu Lys Pro Ser Glu
1               5                   10                  15

Thr Leu Ser Leu Thr Cys Ala Val Tyr Ser Gly Ser Phe Ser Gly Tyr
            20                  25                  30

Tyr Tyr Ser Trp Ile Arg Gln Ser Pro Gly Arg Gly Leu Glu Trp Ile
        35                  40                  45

Gly Asp Ile Ser His Thr Gly Ser Thr Asp Tyr Asn Pro Ser Leu Lys
50                  55                  60

Thr Arg Val Thr Ile Ser Val Asp Thr Ser Lys Asn Gln Phe Ser Leu
65                  70                  75                  80

Asn Leu Asn Ser Val Thr Ala Ala Asp Thr Ala Val Tyr Tyr Cys Ala
                85                  90                  95

Arg Asp Ala Pro Lys Gly Gly Ser Gly Leu Tyr Leu Phe Asp Tyr Trp
            100                 105                 110

Gly Gln Gly Thr Leu Val Thr Val Ser Ser
        115                 120

<210> SEQ ID NO 235
```

```
<211> LENGTH: 126
<212> TYPE: PRT
<213> ORGANISM: Homo sapiens
<220> FEATURE:
<221> NAME/KEY: MISC_FEATURE
<223> OTHER INFORMATION: Clone XPA.15.203 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(115)
<223> OTHER INFORMATION: HCDR3

<400> SEQUENCE: 235

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Tyr Ser Ser Gly Trp Tyr Ser His Gly Pro Glu Tyr
            100                 105                 110

Phe Gln His Trp Gly Gln Gly Thr Leu Val Thr Val Ser Ser
        115                 120                 125

<210> SEQ ID NO 236
<211> LENGTH: 122
<212> TYPE: PRT
<213> ORGANISM: Homo sapiens
<220> FEATURE:
<221> NAME/KEY: MISC_FEATURE
<223> OTHER INFORMATION: Clone XPA.15.204 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(111)
<223> OTHER INFORMATION: HCDR3

<400> SEQUENCE: 236

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Ile Ala Asn Tyr Ala Gln Lys Phe
    50                  55                  60
```

```
Gln Gly Arg Val Thr Ile Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Pro Asp Tyr Asp Phe Trp Asn Ala Phe Asp Ile Trp
            100                 105                 110

Gly Gln Gly Thr Met Val Thr Val Ser Ser
        115                 120
```

<210> SEQ ID NO 237
<211> LENGTH: 126
<212> TYPE: PRT
<213> ORGANISM: Homo sapiens
<220> FEATURE:
<221> NAME/KEY: MISC_FEATURE
<223> OTHER INFORMATION: Clone XPA.15.205 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(115)
<223> OTHER INFORMATION: HCDR3

<400> SEQUENCE: 237

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser His Tyr Tyr Asp Phe Trp Ser Gly Tyr Gln Tyr Tyr Tyr Gly
            100                 105                 110

Met Asp Val Trp Gly Gln Gly Thr Thr Val Thr Val Ser Ser
        115                 120                 125
```

<210> SEQ ID NO 238
<211> LENGTH: 117
<212> TYPE: PRT
<213> ORGANISM: Homo sapiens
<220> FEATURE:
<221> NAME/KEY: MISC_FEATURE
<223> OTHER INFORMATION: Clone XPA.15.206 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(106)

<223> OTHER INFORMATION: HCDR3

<400> SEQUENCE: 238

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Arg Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Thr Ser Gly Ser Phe Asp Tyr Trp Gly Gln Gly Thr Leu
            100                 105                 110

Val Thr Val Ser Ser
        115

<210> SEQ ID NO 239
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.207 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(105)
<223> OTHER INFORMATION: HCDR3

<400> SEQUENCE: 239

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Arg Ser Thr Ser Thr Val Tyr
65                  70                  75                  80

Met Glu Leu Ser Ser Leu Thr Ser Glu Asp Thr Ala Val Tyr Tyr Cys
                85                  90                  95

Val Arg Asp Asn His Gly Trp Ser Phe Asp Tyr Trp Gly Gln Gly Thr
            100                 105                 110

Leu Val Thr Val Ser Ser
        115

<210> SEQ ID NO 240
<211> LENGTH: 127
<212> TYPE: PRT

<213> ORGANISM: Homo sapiens
<220> FEATURE:
<221> NAME/KEY: MISC_FEATURE
<223> OTHER INFORMATION: Clone XPA.15.208 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(116)
<223> OTHER INFORMATION: HCDR3

<400> SEQUENCE: 240

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Lys Gly Ser Asp Phe Trp Ser Gly Tyr Tyr Tyr Tyr Tyr Tyr
            100                 105                 110

Tyr Met Asp Val Trp Gly Lys Gly Thr Thr Val Thr Val Ser Ser
        115                 120                 125

<210> SEQ ID NO 241
<211> LENGTH: 122
<212> TYPE: PRT
<213> ORGANISM: Homo sapiens
<220> FEATURE:
<221> NAME/KEY: MISC_FEATURE
<223> OTHER INFORMATION: Clone XPA.15.209 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(111)
<223> OTHER INFORMATION: HCDR3

<400> SEQUENCE: 241

Gln Met Gln Leu Val Gln Ser Gly Ala Glu Val Lys Lys Thr Gly Glu
1               5                   10                  15

Ser Leu Lys Ile Ser Cys Gln Gly Tyr Gly Tyr Arg Phe Thr Asp Asn
            20                  25                  30

Trp Ile Gly Trp Val Arg Gln Met Pro Gly Arg Gly Leu Glu Trp Met
        35                  40                  45

Gly Ile Ile Tyr Pro Gly Asp Ser Glu Thr Arg Tyr Ser Pro Ser Phe
    50                  55                  60

Gln Gly Gln Val Thr Ile Ser Ala Asp Lys Ser Ile Ser Thr Ala Tyr

```
                65                  70                  75                  80
Leu Glu Trp Ser Ser Leu Lys Ala Ser Asp Thr Ala Met Tyr Tyr Cys
                    85                  90                  95

Ala Arg His Ala Pro Leu Ala Val Ala Gly Met Ala Leu Gly Asp Trp
                100                 105                 110

Gly Gln Gly Thr Leu Val Thr Val Ser Ser
                115                 120

<210> SEQ ID NO 242
<211> LENGTH: 133
<212> TYPE: PRT
<213> ORGANISM: Homo sapiens
<220> FEATURE:
<221> NAME/KEY: MISC_FEATURE
<223> OTHER INFORMATION: Clone XPA.15.210 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(122)
<223> OTHER INFORMATION: HCDR3

<400> SEQUENCE: 242

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Pro Pro Lys Pro Tyr Tyr Asp Phe Trp Ser Gly Tyr
                100                 105                 110

Trp Gly Tyr Tyr Tyr Tyr Gly Met Asp Val Trp Gly Gln Gly Thr Thr
            115                 120                 125

Val Thr Val Ser Ser
        130

<210> SEQ ID NO 243
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.211 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(57)
<223> OTHER INFORMATION: HCDR2
<220> FEATURE:
<221> NAME/KEY: MISC_FEATURE
```

-continued

```
<222> LOCATION: (96)..(109)
<223> OTHER INFORMATION: HCDR3

<400> SEQUENCE: 243
```

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Pro Ser Gly Trp Tyr Ile Arg Glu Phe Asp Tyr Trp Gly Gln
            100                 105                 110

Gly Thr Leu Val Thr Val Ser Ser
        115                 120

```
<210> SEQ ID NO 244
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.212 heavy chain
<220> FEATURE:
<221> NAME/KEY: MISC_FEATURE
<222> LOCATION: (26)..(35)
<223> OTHER INFORMATION: HCDR1
<220> FEATURE:
<221> NAME/KEY: MISC_FEATURE
<222> LOCATION: (53)..(61)
<223> OTHER INFORMATION: HCDR2
<220> FEATURE:
<221> NAME/KEY: MISC_FEATURE
<222> LOCATION: (100)..(110)
<223> OTHER INFORMATION: HCDR3

<400> SEQUENCE: 244
```

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Thr Asp Tyr Ala
    50                  55                  60

Leu Ser Val Lys Ser Arg Ile Thr Ile Asn Pro Asp Thr Ser Lys Asn
65                  70                  75                  80

Gln Phe Ser Leu His Leu Asn Ser Val Thr Pro Glu Asp Thr Ala Val
                85                  90                  95

Tyr Tyr Cys Ala Arg Glu Gly Trp Leu Gly Tyr Phe Asp Phe Trp Gly
            100                 105                 110

Gln Gly Thr Leu Val Thr Val Ser Ser
        115                 120

```
<210> SEQ ID NO 245
<211> LENGTH: 117
```

```
<212> TYPE: PRT
<213> ORGANISM: Homo sapiens
<220> FEATURE:
<221> NAME/KEY: MISC_FEATURE
<223> OTHER INFORMATION: Clone XPA.15.213 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(106)
<223> OTHER INFORMATION: HCDR3

<400> SEQUENCE: 245

Gln Val Gln Leu Val Gln Ser Gly Ala Glu Val Lys Lys Pro Gly Glu
1               5                   10                  15

Ser Leu Lys Ile Ser Cys Lys Gly Ser Gly Phe Ser Phe Pro Ser Tyr
            20                  25                  30

Trp Ile Gly Trp Val Arg Gln Met Pro Gly Lys Gly Leu Glu Leu Val
        35                  40                  45

Gly Ile Ile Tyr Pro Gly Asp Ser Asp Ile Arg Tyr Ser Pro Ser Phe
    50                  55                  60

Gln Gly Gln Val Thr Ile Ser Ala Asp Thr Ser Ile Ser Thr Val Tyr
65                  70                  75                  80

Leu Gln Trp Ser Ser Leu Gln Thr Thr Asp Thr Ala Thr Tyr Tyr Cys
                85                  90                  95

Ala Arg Gly Gly Phe Asn Trp Phe Asp Pro Trp Gly Gln Gly Thr Leu
            100                 105                 110

Val Thr Val Ser Ser
            115

<210> SEQ ID NO 246
<211> LENGTH: 116
<212> TYPE: PRT
<213> ORGANISM: Homo sapiens
<220> FEATURE:
<221> NAME/KEY: MISC_FEATURE
<223> OTHER INFORMATION: Clone XPA.15.214 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(105)
<223> OTHER INFORMATION: HCDR3

<400> SEQUENCE: 246

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60
```

-continued

```
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Glu Leu Gly Ile Asp Tyr Trp Gly Gln Gly Thr Leu Val
            100                 105                 110

Thr Val Ser Ser
        115

<210> SEQ ID NO 247
<211> LENGTH: 122
<212> TYPE: PRT
<213> ORGANISM: Homo sapiens
<220> FEATURE:
<221> NAME/KEY: MISC_FEATURE
<223> OTHER INFORMATION: Clone XPA.15.215 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(111)
<223> OTHER INFORMATION: HCDR3

<400> SEQUENCE: 247

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Ala Ser Tyr Gly Asn Ser Glu Gly Phe Asp Tyr Trp
            100                 105                 110

Gly Gln Gly Thr Leu Val Thr Val Ser Ser
        115                 120

<210> SEQ ID NO 248
<211> LENGTH: 128
<212> TYPE: PRT
<213> ORGANISM: Homo sapiens
<220> FEATURE:
<221> NAME/KEY: MISC_FEATURE
<223> OTHER INFORMATION: Clone XPA.15.216 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(117)
<223> OTHER INFORMATION: HCDR3
```

<400> SEQUENCE: 248

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Gly Asp Tyr Asp Phe Trp Ser Gly Tyr Tyr Gly Ala
            100                 105                 110

Glu Tyr Phe Gln His Trp Gly Gln Gly Thr Leu Val Thr Val Ser Ser
        115                 120                 125

<210> SEQ ID NO 249
<211> LENGTH: 131
<212> TYPE: PRT
<213> ORGANISM: Homo sapiens
<220> FEATURE:
<221> NAME/KEY: MISC_FEATURE
<223> OTHER INFORMATION: Clone XPA.15.217 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(62)
<223> OTHER INFORMATION: HCDR2
<220> FEATURE:
<221> NAME/KEY: MISC_FEATURE
<222> LOCATION: (101)..(120)
<223> OTHER INFORMATION: HCDR3

<400> SEQUENCE: 249

Glu Val Gln Leu Val Gln Ser Gly Ala Glu Val Lys Gln Pro Gly Ser
1               5                   10                  15

Ser Val Lys Val Ser Cys Lys Ala Ser Gly Gly Ser Phe Asn Ser Tyr
            20                  25                  30

Thr Phe Ser Trp Val Arg Gln Ala Pro Gly Gln Gly Leu Glu Trp Met
        35                  40                  45

Gly Trp Ile Ser Ala Tyr Asn Gly Gly Thr Asn Tyr Phe Ala Asn Tyr
50                  55                  60

Ala Leu Lys Phe Gln Gly Arg Val Thr Met Thr Thr Asp Thr Ser Thr
65                  70                  75                  80

Gly Thr Ala Tyr Met Glu Leu Arg Ser Leu Arg Ser Asp Asp Thr Ala
                85                  90                  95

Val Tyr Tyr Cys Ala Arg Val Arg Asp Ser Trp Ser His Glu Asp Tyr
            100                 105                 110

Ser Tyr Tyr Tyr Met Asp Val Trp Gly Lys Gly Thr Thr Val Thr
        115                 120                 125

Val Ser Ser
    130

<210> SEQ ID NO 250

```
<211> LENGTH: 129
<212> TYPE: PRT
<213> ORGANISM: Homo sapiens
<220> FEATURE:
<221> NAME/KEY: MISC_FEATURE
<223> OTHER INFORMATION: Clone XPA.15.218 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(118)
<223> OTHER INFORMATION: HCDR3

<400> SEQUENCE: 250

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Val Phe Pro Asp Tyr Tyr Asp Ser Ile Ala Ser Asn
            100                 105                 110

Tyr Pro Leu Asp Asp Ile Trp Gly Gln Gly Thr Met Val Thr Val Ser
        115                 120                 125

Ser

<210> SEQ ID NO 251
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.219 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(107)
<223> OTHER INFORMATION: HCDR3

<400> SEQUENCE: 251

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Gly Asp Tyr
            20                  25                  30

Gly Met Ser Trp Val Arg Gln Ala Pro Gly Lys Gly Leu Glu Trp Val
        35                  40                  45
```

-continued

```
Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Leu Gly Val Glu Phe Asp Tyr Trp Gly Gln Gly Thr
            100                 105                 110

Leu Val Thr Val Ser Ser
        115

<210> SEQ ID NO 252
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.220 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(108)
<223> OTHER INFORMATION: HCDR3

<400> SEQUENCE: 252

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ser Gly Ser Tyr Ser Phe Asp Tyr Trp Gly Gln Gly
            100                 105                 110

Thr Leu Val Thr Val Ser Ser
        115

<210> SEQ ID NO 253
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.221 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
```

```
<221> NAME/KEY: MISC_FEATURE
<222> LOCATION: (97)..(110)
<223> OTHER INFORMATION: HCDR3

<400> SEQUENCE: 253
```

Glu Val Gln Leu Val Glu Ser Gly Gly Val Val Gln Pro Gly Met
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ser Ile Ser Trp Asn Ser Ala Asn Ile Val Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Asp Asp Met Ala Leu Tyr Tyr Cys
                85                  90                  95

Val Lys Gly Asp Thr Thr Met Ile Tyr Tyr Ala Met Ala Val Trp Gly
            100                 105                 110

Gln Gly Thr Thr Val Thr Val Ser Ser
        115                 120

```
<210> SEQ ID NO 254
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.222 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(55)
<223> OTHER INFORMATION: HCDR2
<220> FEATURE:
<221> NAME/KEY: MISC_FEATURE
<222> LOCATION: (97)..(108)
<223> OTHER INFORMATION: HCDR3

<400> SEQUENCE: 254
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Ile Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Arg Gly Tyr Tyr Gly Met Asp Val Trp Gly Gln Gly
            100                 105                 110

Thr Thr Val Thr Val Ser Ser
        115

```
<210> SEQ ID NO 255
```

-continued

```
<211> LENGTH: 117
<212> TYPE: PRT
<213> ORGANISM: Homo sapiens
<220> FEATURE:
<221> NAME/KEY: MISC_FEATURE
<223> OTHER INFORMATION: Clone XPA.15.223 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(106)
<223> OTHER INFORMATION: HCDR3

<400> SEQUENCE: 255

Gln Met Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Pro Asp Ala Phe Asp Ile Trp Gly Gln Gly Thr Met
            100                 105                 110

Val Thr Val Ser Ser
        115

<210> SEQ ID NO 256
<211> LENGTH: 128
<212> TYPE: PRT
<213> ORGANISM: Homo sapiens
<220> FEATURE:
<221> NAME/KEY: MISC_FEATURE
<223> OTHER INFORMATION: Clone XPA.15.224 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(117)
<223> OTHER INFORMATION: HCDR3

<400> SEQUENCE: 256

Glu Val Gln Leu Val Glu Ser Gly Gly Ser Val Val Gln Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60
```

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asp Tyr Asp Phe Trp Ser Gly Tyr Tyr Asp Pro Tyr Tyr
            100                 105                 110

Tyr Gly Met Asp Val Trp Gly Gln Gly Thr Thr Val Thr Val Ser Ser
        115                 120                 125

<210> SEQ ID NO 257
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.225 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(110)
<223> OTHER INFORMATION: HCDR3

<400> SEQUENCE: 257

Glu Val Gln Leu Leu Glu Ser Gly Gly Gly Leu Val Gln Pro Gly Met
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ser Ile Ser Trp Asn Ser Ala Asn Ile Val Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Asp Asp Met Ala Leu Tyr Tyr Cys
                85                  90                  95

Val Lys Gly Asp Thr Thr Met Ile Tyr Tyr Ala Met Ala Val Trp Gly
            100                 105                 110

Gln Gly Thr Thr Val Thr Val Ser Ser
        115                 120

<210> SEQ ID NO 258
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.226 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(108)

-continued

<223> OTHER INFORMATION: HCDR3

<400> SEQUENCE: 258

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ser Tyr
65                  70                  75                  80

Leu Gln Trp Ser Ser Leu Arg Ala Ser Asp Thr Ala Met Tyr Tyr Cys
                85                  90                  95

Ala Arg Leu Gly Ser Gly Trp Tyr Gly Asn Asp Tyr Trp Gly Gln Gly
            100                 105                 110

Thr Leu Val Thr Val Ser Ser
        115

<210> SEQ ID NO 259
<211> LENGTH: 116
<212> TYPE: PRT
<213> ORGANISM: Homo sapiens
<220> FEATURE:
<221> NAME/KEY: MISC_FEATURE
<223> OTHER INFORMATION: Clone XPA.15.227 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(105)
<223> OTHER INFORMATION: HCDR3

<400> SEQUENCE: 259

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Asp Ala Gly Tyr Ser Pro Trp Gly Gln Gly Thr Leu Val
            100                 105                 110

Thr Val Ser Ser
        115

<210> SEQ ID NO 260
<211> LENGTH: 118
<212> TYPE: PRT

```
<213> ORGANISM: Homo sapiens
<220> FEATURE:
<221> NAME/KEY: MISC_FEATURE
<223> OTHER INFORMATION: Clone XPA.15.228 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(107)
<223> OTHER INFORMATION: HCDR3

<400> SEQUENCE: 260

Gln Met Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Gly Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Val Ser Asp Thr Ala Met Tyr Tyr Cys
                85                  90                  95

Gly Arg Ile Ser Thr Pro Tyr Ala Phe Asp Ile Trp Gly Gln Gly Thr
            100                 105                 110

Met Val Thr Val Ser Ser
        115

<210> SEQ ID NO 261
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.229 heavy chain
<220> FEATURE:
<221> NAME/KEY: MISC_FEATURE
<222> LOCATION: (26)..(34)
<223> OTHER INFORMATION: HCDR1
<220> FEATURE:
<221> NAME/KEY: MISC_FEATURE
<222> LOCATION: (52)..(58)
<223> OTHER INFORMATION: HCDR2
<220> FEATURE:
<221> NAME/KEY: MISC_FEATURE
<222> LOCATION: (97)..(108)
<223> OTHER INFORMATION: HCDR3

<400> SEQUENCE: 261

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
```

```
                65                  70                  75                  80
Leu Lys Leu Ser Ser Val Thr Ala Ala Asp Thr Ala Val Tyr Tyr Cys
                    85                  90                  95
Ala Arg Val Gly Ala Ala Ala Trp Phe Asp Pro Trp Gly Gln Gly
                100                 105                 110
Thr Leu Val Thr Val Ser Ser
            115

<210> SEQ ID NO 262
<211> LENGTH: 116
<212> TYPE: PRT
<213> ORGANISM: Homo sapiens
<220> FEATURE:
<221> NAME/KEY: MISC_FEATURE
<223> OTHER INFORMATION: Clone XPA.15.230 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(105)
<223> OTHER INFORMATION: HCDR3

<400> SEQUENCE: 262

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Asp Ala Gly Tyr Ser Pro Trp Gly Gln Gly Thr Leu Val
                100                 105                 110

Thr Val Ser Ser
        115

<210> SEQ ID NO 263
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.231 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(108)
<223> OTHER INFORMATION: HCDR3
```

-continued

<400> SEQUENCE: 263

Gln Met Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Ser
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Arg Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Gly Ala Ser Gly Trp Thr Phe Asp Tyr Trp Gly Gln Gly
            100                 105                 110

Thr Leu Val Thr Val Ser Ser
        115

<210> SEQ ID NO 264
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.232 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(107)
<223> OTHER INFORMATION: HCDR3

<400> SEQUENCE: 264

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Asp Met Tyr Trp Val Arg Gln Ala Pro Gly Lys Gly Leu Glu Trp Val
        35                  40                  45

Ala Val Ile Ser Tyr Asp Gly Asn Asp Lys Gln Tyr Ala Asp Ser Val
    50                  55                  60

Lys Gly Arg Phe Thr Ile Ser Arg Asp Asn Ser Lys Arg Thr Leu Tyr
65                  70                  75                  80

Leu Gln Met Asp Ser Leu Arg Thr Glu Asp Thr Ala Thr Tyr Tyr Cys
                85                  90                  95

Thr Arg Glu Gly Asn Gly Arg Glu Ile Asp Tyr Trp Gly Pro Gly Thr
            100                 105                 110

Leu Val Thr Val Ser Ser
        115

<210> SEQ ID NO 265
<211> LENGTH: 120
<212> TYPE: PRT
<213> ORGANISM: Homo sapiens
<220> FEATURE:

```
<221> NAME/KEY: MISC_FEATURE
<223> OTHER INFORMATION: Clone XPA.15.233 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(109)
<223> OTHER INFORMATION: HCDR3

<400> SEQUENCE: 265

Gln Val Gln Leu Val Gln Ser Gly Ala Glu Val Arg Arg Pro Gly Ala
1               5                   10                  15

Ser Val Lys Val Ser Cys Glu Ala Ser Gly Tyr Thr Phe His Ser Tyr
            20                  25                  30

Asp Ile Asn Trp Val Arg Gln Ala Thr Gly Gln Gly Leu Glu Trp Val
        35                  40                  45

Gly Trp Met Asn Pro Asn Ser Gly Asn Thr Asp Phe Ala Gln Lys Phe
50                  55                  60

Gln Gly Arg Val Thr Met Thr Arg Asn Thr Ser Ile Asn Thr Ala Tyr
65                  70                  75                  80

Met Glu Leu Ser Ser Leu Arg Ser Asp Asp Thr Ala Val Tyr Tyr Cys
                85                  90                  95

Ala Arg Val Asn Trp Asn Tyr Gly Gly Thr Ser Asp Ser Trp Gly Gln
            100                 105                 110

Gly Thr Leu Val Thr Val Ser Ser
        115                 120

<210> SEQ ID NO 266
<211> LENGTH: 117
<212> TYPE: PRT
<213> ORGANISM: Homo sapiens
<220> FEATURE:
<221> NAME/KEY: MISC_FEATURE
<223> OTHER INFORMATION: Clone XPA.15.234 heavy chain
<220> FEATURE:
<221> NAME/KEY: MISC_FEATURE
<222> LOCATION: (26)..(34)
<223> OTHER INFORMATION: HCDR1
<220> FEATURE:
<221> NAME/KEY: MISC_FEATURE
<222> LOCATION: (52)..(58)
<223> OTHER INFORMATION: HCDR2
<220> FEATURE:
<221> NAME/KEY: MISC_FEATURE
<222> LOCATION: (97)..(106)
<223> OTHER INFORMATION: HCDR3

<400> SEQUENCE: 266

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80
```

```
Leu Lys Leu Ser Ser Val Thr Ala Ala Asp Thr Ala Val Tyr Tyr Cys
            85                  90                  95

Ala Arg Val Gly Val Ala Ala Phe Asp Tyr Trp Gly Gln Gly Thr Leu
            100                 105                 110

Val Thr Val Ser Ser
            115

<210> SEQ ID NO 267
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.235 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(108)
<223> OTHER INFORMATION: HCDR3

<400> SEQUENCE: 267

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Cys
65                  70                  75                  80

Leu Gln Met Asn Ser Leu Arg Ala Glu Asp Thr Ala Val Tyr Tyr Cys
            85                  90                  95

Ala Arg Glu Glu Ala Tyr Gly Asp Ala Phe Asp Ile Trp Gly Gln Gly
            100                 105                 110

Thr Met Val Thr Val Ser Ser
            115

<210> SEQ ID NO 268
<211> LENGTH: 117
<212> TYPE: PRT
<213> ORGANISM: Homo sapiens
<220> FEATURE:
<221> NAME/KEY: MISC_FEATURE
<223> OTHER INFORMATION: Clone XPA.15.236 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(106)
<223> OTHER INFORMATION: HCDR3

<400> SEQUENCE: 268
```

-continued

Gln Met Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Pro Asp Ala Phe Asp Ile Trp Gly Gln Gly Thr Met
            100                 105                 110

Val Thr Val Ser Ser
            115

<210> SEQ ID NO 269
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.237 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(110)
<223> OTHER INFORMATION: HCDR3

<400> SEQUENCE: 269

Glu Val Gln Leu Val Glu Thr Gly Gly Gly Val Val Arg Pro Gly Arg
1               5                   10                  15

Ser Leu Arg Leu Ser Cys Ala Ala Ser Gly Phe Thr Phe Glu Asp Tyr
                20                  25                  30

Ala Met His Trp Val Arg Gln Gly Pro Gly Lys Gly Leu Glu Trp Val
            35                  40                  45

Ser Ser Ile Ser Trp Asn Gly Gly Phe Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Ser Ala Glu Asp Thr Ala Leu Tyr Tyr Cys
                85                  90                  95

Ala Lys Gly Ala Ser Tyr Asp Ser Tyr Ala Ala Met Asp Val Trp Gly
            100                 105                 110

Gln Gly Thr Thr Val Thr Val Ser Ser
            115                 120

<210> SEQ ID NO 270
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.238 heavy chain

```
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(108)
<223> OTHER INFORMATION: HCDR3

<400> SEQUENCE: 270
```

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Val Val His Arg Phe Asp Ile Trp Gly Gln Gly
            100                 105                 110

Thr Met Val Thr Val Ser Ser
        115

```
<210> SEQ ID NO 271
<211> LENGTH: 125
<212> TYPE: PRT
<213> ORGANISM: Homo sapiens
<220> FEATURE:
<221> NAME/KEY: MISC_FEATURE
<223> OTHER INFORMATION: Clone XPA.15.239 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(57)
<223> OTHER INFORMATION: HCDR2
<220> FEATURE:
<221> NAME/KEY: MISC_FEATURE
<222> LOCATION: (96)..(114)
<223> OTHER INFORMATION: HCDR3

<400> SEQUENCE: 271
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Thr Tyr
            20                  25                  30

Tyr Trp Ser Trp Val Arg Gln Ala Pro Gly Lys Gly Leu Glu Trp Ile
        35                  40                  45

Gly Asn Ile Tyr Tyr Ser Gly Lys Thr Asn Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Thr Ala Asp Thr Ala Val Tyr Tyr Cys Ala
                85                  90                  95

Arg Asp Ser Phe Tyr Phe Glu Ser Ser Arg Ser Trp Asn Asp Leu Phe
            100                 105                 110

Asp Ile Trp Gly Gln Gly Thr Met Val Thr Val Ser Ser
            115                 120                 125

<210> SEQ ID NO 272
<211> LENGTH: 125
<212> TYPE: PRT
<213> ORGANISM: Homo sapiens
<220> FEATURE:
<221> NAME/KEY: MISC_FEATURE
<223> OTHER INFORMATION: Clone XPA.15.240 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(57)
<223> OTHER INFORMATION: HCDR2
<220> FEATURE:
<221> NAME/KEY: MISC_FEATURE
<222> LOCATION: (96)..(114)
<223> OTHER INFORMATION: HCDR3

<400> SEQUENCE: 272

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Thr Tyr
            20                  25                  30

Tyr Trp Ser Trp Val Arg Gln Ala Pro Gly Lys Gly Leu Glu Trp Ile
        35                  40                  45

Gly Asn Ile Tyr Tyr Ser Gly Lys Thr Asn Tyr Asn Pro Ser Leu Gly
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Ser Phe Tyr Phe Glu Ser Ser Arg Ser Trp Asn Asp Leu Phe
            100                 105                 110

Asp Ile Trp Gly Gln Gly Thr Met Val Thr Val Ser Ser
            115                 120                 125

<210> SEQ ID NO 273
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.241 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(107)
<223> OTHER INFORMATION: HCDR3

<400> SEQUENCE: 273

Glu Val Gln Leu Val Glu Ser Gly Gly Gly Val Val Gln Pro Gly Gly
1               5                   10                  15

```
Ser Leu Arg Leu Ser Cys Ala Ala Ser Gly Phe Thr Phe Asp Asp Tyr
        20                  25                  30

Ala Met His Trp Val Arg Gln Ala Pro Gly Lys Gly Leu Glu Trp Val
            35                  40                  45

Ser Leu Ile Ser Trp Asp Gly Gly Ser Thr Tyr Tyr Ala Asp Ser Val
 50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Lys Ala Arg Gly Val Val Ile Ile Asp Tyr Trp Gly Gln Gly Thr
            100                 105                 110

Leu Val Thr Val Ser Ser
        115
```

```
<210> SEQ ID NO 274
<211> LENGTH: 125
<212> TYPE: PRT
<213> ORGANISM: Homo sapiens
<220> FEATURE:
<221> NAME/KEY: MISC_FEATURE
<223> OTHER INFORMATION: Clone XPA.15.242 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(57)
<223> OTHER INFORMATION: HCDR2
<220> FEATURE:
<221> NAME/KEY: MISC_FEATURE
<222> LOCATION: (96)..(114)
<223> OTHER INFORMATION: HCDR3

<400> SEQUENCE: 274
```

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Phe Ser Thr Tyr
            20                  25                  30

Tyr Trp Ser Trp Ile Arg Gln Ala Pro Gly Lys Gly Leu Glu Trp Ile
            35                  40                  45

Gly Asn Ile Tyr Tyr Ser Gly Lys Thr Asn Tyr Asn Pro Ser Leu Glu
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Asp Ser Phe Tyr Phe Glu Ser Ser Arg Ser Trp Asn Asp Leu Phe
            100                 105                 110

Asp Ile Trp Gly Gln Gly Thr Met Val Thr Val Ser Ser
            115                 120                 125
```

```
<210> SEQ ID NO 275
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.243 heavy chain
<220> FEATURE:
<221> NAME/KEY: MISC_FEATURE
```

```
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(107)
<223> OTHER INFORMATION: HCDR3

<400> SEQUENCE: 275
```

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Asn Gln Asp Gly Ser Glu Lys His Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
                85                  90                  95

Ala Arg Gly Arg Gly Ala Trp Ala Phe Asp Tyr Trp Gly Gln Gly Thr
            100                 105                 110

Leu Val Thr Val Ser Ser
        115

```
<210> SEQ ID NO 276
<211> LENGTH: 124
<212> TYPE: PRT
<213> ORGANISM: Homo sapiens
<220> FEATURE:
<221> NAME/KEY: MISC_FEATURE
<223> OTHER INFORMATION: Clone XPA.15.244 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(113)
<223> OTHER INFORMATION: HCDR3

<400> SEQUENCE: 276
```

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Gly Glu Leu Leu Gly Phe Thr Gly Tyr Phe Asp

```
                100             105             110
Tyr Trp Gly Gln Gly Thr Leu Val Thr Val Ser Ser
        115                 120

<210> SEQ ID NO 277
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.245 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(107)
<223> OTHER INFORMATION: HCDR3

<400> SEQUENCE: 277

Gln Met Gln Leu Val Gln Ser Gly Ala Glu Met Lys Lys Pro Gly Ala
1               5                   10                  15

Ser Val Lys Val Ser Cys Lys Ala Ser Gly Tyr Ser Phe Ser Asp Tyr
            20                  25                  30

Gly Ile Thr Trp Val Arg Gln Ala Pro Gly Gln Gly Pro Glu Trp Met
        35                  40                  45

Gly Trp Ile Ser Gly Tyr Asn Gly Asn Thr Asn Tyr Ala Gln Lys Phe
    50                  55                  60

Gln Asp Arg Val Thr Met Thr Thr Asp Thr Ser Thr Ser Thr Ala Tyr
65                  70                  75                  80

Met Glu Leu Arg Ser Leu Lys Ser Asp Asp Thr Ala Val Tyr Phe Cys
                85                  90                  95

Ala Arg Ala Arg Gly Val Trp Met Phe Asp Asn Trp Gly Gln Gly Thr
            100                 105                 110

Leu Val Thr Val Ser Ser
        115

<210> SEQ ID NO 278
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.246 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(107)
<223> OTHER INFORMATION: HCDR3

<400> SEQUENCE: 278

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
```

```
                  20                  25                  30

Ala Met His Trp Val Arg Gln Ala Pro Gly Lys Gly Leu Glu Trp Val
            35                  40                  45

Ser Leu Ile Ser Trp Asp Gly Ser Thr Tyr Tyr Ala Asp Ser Val
 50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Lys Ala Arg Gly Val Val Ile Ile Asp Tyr Trp Gly Gln Gly Thr
            100                 105                 110

Leu Val Thr Val Ser Ser
        115

<210> SEQ ID NO 279
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.247 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(107)
<223> OTHER INFORMATION: HCDR3

<400> SEQUENCE: 279

Glu Val Gln Leu Val Glu Thr Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Met Asp Val Trp Gly Gln Gly Thr
            100                 105                 110

Thr Val Thr Val Ser Ser
        115

<210> SEQ ID NO 280
<211> LENGTH: 117
<212> TYPE: PRT
<213> ORGANISM: Homo sapiens
<220> FEATURE:
<221> NAME/KEY: MISC_FEATURE
<223> OTHER INFORMATION: Clone XPA.15.248 heavy chain
<220> FEATURE:
<221> NAME/KEY: MISC_FEATURE
<222> LOCATION: (26)..(33)
<223> OTHER INFORMATION: HCDR1
```

```
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(106)
<223> OTHER INFORMATION: HCDR3

<400> SEQUENCE: 280
```

Gln Met Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Pro Asp Ala Phe Asp Ile Trp Gly Gln Gly Thr Met
            100                 105                 110

Val Thr Val Ser Ser
            115

```
<210> SEQ ID NO 281
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.249 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(110)
<223> OTHER INFORMATION: HCDR3

<400> SEQUENCE: 281
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Val Gly Ala Ala Asn Gly Trp Phe Asp Pro Trp Gly
            100                 105                 110

Gln Gly Thr Leu Val Thr Val Ser Ser
            115                 120

<210> SEQ ID NO 282
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.250 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(109)
<223> OTHER INFORMATION: HCDR3

<400> SEQUENCE: 282

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Asn Tyr
            20                  25                  30

Trp Met Thr Trp Val Arg Gln Ala Pro Gly Lys Gly Leu Glu Trp Val
        35                  40                  45

Ala Asp Ile Lys Gly Asp Gly Ser Arg Gln His Tyr Ala Asp Ser Val
    50                  55                  60

Lys Gly Arg Phe Thr Ile Ser Arg Asp Asn Ala Arg Asn Ser Leu Phe
65                  70                  75                  80

Leu Gln Met Asn Ser Leu Arg Val Glu Asp Thr Ala Leu Tyr Tyr Cys
                85                  90                  95

Ala Thr Asp Pro Pro Trp Asp Arg Asp Ala Phe Asp Leu Trp Gly Gln
            100                 105                 110

Gly Thr Met Val Thr Val Ser Ser
            115                 120

<210> SEQ ID NO 283
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.272 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(107)
<223> OTHER INFORMATION: HCDR3

<400> SEQUENCE: 283

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Gly Tyr
            20                  25                  30

```
Trp Met Ser Trp Val Arg Gln Ala Pro Gly Lys Gly Leu Glu Trp Val
            35                  40                  45

Ser Asn Ile Lys Gln Asp Gly Ser Glu Gln Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Ile Tyr Tyr Cys
                 85                  90                  95

Ala Arg Asp Arg Met Asp Tyr Ile Phe Asp Ile Trp Gly Arg Gly Thr
            100                 105                 110

Leu Val Thr Val Ser Ser
            115

<210> SEQ ID NO 284
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.275 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(109)
<223> OTHER INFORMATION: HCDR3

<400> SEQUENCE: 284

Glu Val Gln Leu Val Glu Ser Gly Gly Val Val Gln Pro Gly Arg
 1               5                  10                  15

Ser Leu Arg Leu Ser Cys Ala Ala Ser Gly Phe Ile Phe Ser Ser Tyr
            20                   25                  30

Gly Met His Trp Val Arg Gln Val Pro Asp Lys Gly Leu Glu Trp Val
             35                  40                  45

Ala Gly Ile Ser Leu Arg Gly Ser Asp Asn Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Asn Leu Arg Pro Asp Asp Thr Ala Val Tyr Tyr Cys
                 85                  90                  95

Ala Arg Gly Phe Arg Trp Pro Val Thr Pro Phe Asp His Trp Gly Gln
            100                 105                 110

Gly Thr Leu Val Thr Val Ser Ser
            115                 120

<210> SEQ ID NO 285
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.282 heavy chain
<220> FEATURE:
<221> NAME/KEY: MISC_FEATURE
<222> LOCATION: (26)..(34)
<223> OTHER INFORMATION: HCDR1
<220> FEATURE:
<221> NAME/KEY: MISC_FEATURE
```

```
<222> LOCATION: (52)..(58)
<223> OTHER INFORMATION: HCDR2
<220> FEATURE:
<221> NAME/KEY: MISC_FEATURE
<222> LOCATION: (97)..(110)
<223> OTHER INFORMATION: HCDR3

<400> SEQUENCE: 285
```

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Pro Asp Tyr Ser Asn Tyr Gly Gly Ala Phe Asp Tyr Trp Gly
            100                 105                 110

Gln Gly Thr Leu Val Thr Val Ser Ser
        115                 120

```
<210> SEQ ID NO 286
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.284 heavy chain
<220> FEATURE:
<221> NAME/KEY: MISC_FEATURE
<222> LOCATION: (26)..(34)
<223> OTHER INFORMATION: HCDR1
<220> FEATURE:
<221> NAME/KEY: MISC_FEATURE
<222> LOCATION: (52)..(58)
<223> OTHER INFORMATION: HCDR2
<220> FEATURE:
<221> NAME/KEY: MISC_FEATURE
<222> LOCATION: (97)..(108)
<223> OTHER INFORMATION: HCDR3

<400> SEQUENCE: 286
```

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Gly Ala Ala Ala Ala Trp Phe Asp Pro Trp Gly Gln Gly
            100                 105                 110

Thr Leu Val Thr Val Ser Ser
        115

```
<210> SEQ ID NO 287
<211> LENGTH: 125
<212> TYPE: PRT
<213> ORGANISM: Homo sapiens
<220> FEATURE:
<221> NAME/KEY: MISC_FEATURE
<223> OTHER INFORMATION: Clone XPA.15.293 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (52)..(58)
<223> OTHER INFORMATION: HCDR2
<220> FEATURE:
<221> NAME/KEY: MISC_FEATURE
<222> LOCATION: (97)..(115)
<223> OTHER INFORMATION: HCDR3

<400> SEQUENCE: 287

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Thr Tyr
            20                  25                  30

Tyr Trp Ser Trp Val Arg Gln Ala Pro Gly Lys Gly Leu Glu Trp Ile
        35                  40                  45

Gly Asn Ile Tyr Tyr Ser Gly Lys Thr Asn Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Ser Phe Tyr Phe Glu Ser Ser Arg Ser Trp Asn Asp Leu Phe
            100                 105                 110

Asp Ile Trp Gly Gln Gly Thr Met Val Thr Val Ser Ser
        115                 120                 125

<210> SEQ ID NO 288
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.006 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(109)
<223> OTHER INFORMATION: HCDR3

<400> SEQUENCE: 288

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Thr Gly Ile Gly Gly Tyr His Phe Asp Tyr Trp Gly Gln
            100                 105                 110

Gly Thr Leu Val Thr Val Ser Gln
        115                 120

<210> SEQ ID NO 289
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.009 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(109)
<223> OTHER INFORMATION: HCDR3

<400> SEQUENCE: 289

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Met His Trp Val Arg Gln Ala Pro Gly Lys Gly Leu Glu Trp Val
         35                  40                  45

Ser Gly Ile Asn Asn Ser Gly Gly Thr Thr Tyr Tyr Ala Asp Ala Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Arg Phe Leu Glu Trp Thr Phe Asp Tyr Trp Gly Gln
            100                 105                 110

Gly Thr Leu Val Thr Val Ser Gln
        115                 120

<210> SEQ ID NO 290
<211> LENGTH: 117
<212> TYPE: PRT
<213> ORGANISM: Homo sapiens
<220> FEATURE:
<221> NAME/KEY: MISC_FEATURE
<223> OTHER INFORMATION: Clone XPA.15.019 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(57)
<223> OTHER INFORMATION: HCDR2
```

```
<220> FEATURE:
<221> NAME/KEY: MISC_FEATURE
<222> LOCATION: (96)..(106)
<223> OTHER INFORMATION: HCDR3

<400> SEQUENCE: 290

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Tyr Cys Ala
            85                  90                  95

Lys Ser Arg Trp Leu Pro Tyr Phe Asp Tyr Trp Gly Gln Gly Thr Leu
            100                 105                 110

Val Thr Val Ser Gln
        115

<210> SEQ ID NO 291
<211> LENGTH: 123
<212> TYPE: PRT
<213> ORGANISM: Homo sapiens
<220> FEATURE:
<221> NAME/KEY: MISC_FEATURE
<223> OTHER INFORMATION: Clone XPA.15.043 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(112)
<223> OTHER INFORMATION: HCDR3

<400> SEQUENCE: 291

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
            85                  90                  95

Ala Lys Glu Ile Pro Gly Arg Trp Leu Gln Leu Gly Phe Asp Tyr
            100                 105                 110

Trp Gly Gln Gly Thr Leu Val Thr Val Arg Leu
        115                 120
```

```
<210> SEQ ID NO 292
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.062 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(109)
<223> OTHER INFORMATION: HCDR3

<400> SEQUENCE: 292
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Val Ile Ser Trp Val Arg Gln Ala Pro Gly Lys Gly Leu Glu Trp Val
        35                  40                  45

Ser Ala Ile Ser Gly Ser Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Val Gly Leu Ser Gly Trp Tyr Tyr Phe Asp Tyr Trp Gly Gln
            100                 105                 110

Gly Thr Leu Val Thr Val Ser Ser
        115                 120

```
<210> SEQ ID NO 293
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.085 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(107)
<223> OTHER INFORMATION: HCDR3

<400> SEQUENCE: 293
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ser Ile Ser Gly Ser Gly Gly Thr Thr Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Lys Gly Leu Gln Pro Leu Asp Tyr Trp Gly Gln Gly Thr
            100                 105                 110

Leu Val Thr Val Ser Phe
            115

<210> SEQ ID NO 294
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.099 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(107)
<223> OTHER INFORMATION: HCDR3

<400> SEQUENCE: 294

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                 20                  25                  30

Ala Met Gly Trp Val Arg Gln Ala Pro Gly Lys Gly Leu Glu Trp Val
             35                  40                  45

Ser Ser Ile Ser Gly Ser Gly Gly Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Lys Gly Leu Gln Pro Leu Asp Tyr Trp Gly Gln Gly Thr
            100                 105                 110

Leu Val Thr Val Ser Gln
            115

<210> SEQ ID NO 295
<211> LENGTH: 119
<212> TYPE: PRT
<213> ORGANISM: Homo sapiens
<220> FEATURE:
<221> NAME/KEY: MISC_FEATURE
<223> OTHER INFORMATION: Clone XPA.15.141 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
```

```
<222> LOCATION: (97)..(106)
<223> OTHER INFORMATION: HCDR3

<400> SEQUENCE: 295

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Ser Trp Asn Gly Ser Arg Thr His Tyr Ala Tyr Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Pro Leu Lys Asp Gly Phe Asp Ile Trp Gly Leu Gly
            100                 105                 110

Thr Leu Val Thr Val Thr Gln
        115

<210> SEQ ID NO 296
<211> LENGTH: 123
<212> TYPE: PRT
<213> ORGANISM: Homo sapiens
<220> FEATURE:
<221> NAME/KEY: MISC_FEATURE
<223> OTHER INFORMATION: Clone XPA.15.142 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(112)
<223> OTHER INFORMATION: HCDR3

<400> SEQUENCE: 296

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Lys Phe
            20                  25                  30

Ala Val His Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Val Glu Gly Gly Tyr Phe His Asn Ser Gly Pro Asp Tyr
            100                 105                 110

Trp Gly Gln Gly Thr Leu Val Thr Val Ser Ser
        115                 120

<210> SEQ ID NO 297
<211> LENGTH: 129
```

-continued

```
<212> TYPE: PRT
<213> ORGANISM: Homo sapiens
<220> FEATURE:
<221> NAME/KEY: MISC_FEATURE
<223> OTHER INFORMATION: Clone XPA.15.144 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(118)
<223> OTHER INFORMATION: HCDR3

<400> SEQUENCE: 297
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Asn Met Ile Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Ser Trp Asp Thr Thr Gly Tyr Tyr Asn Tyr Tyr
            100                 105                 110

Tyr Tyr Gly Met Asp Val Trp Gly Gln Gly Thr Leu Val Thr Val Ser
            115                 120                 125

Ser

```
<210> SEQ ID NO 298
<211> LENGTH: 118
<212> TYPE: PRT
<213> ORGANISM: Homo sapiens
<220> FEATURE:
<221> NAME/KEY: MISC_FEATURE
<223> OTHER INFORMATION: Clone XPA.15.146 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(57)
<223> OTHER INFORMATION: HCDR2
<220> FEATURE:
<221> NAME/KEY: MISC_FEATURE
<222> LOCATION: (97)..(107)
<223> OTHER INFORMATION: HCDR2

<400> SEQUENCE: 298
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ser Thr Val Ser Ala Thr Gly Pro His Thr Tyr Tyr Ala Asp Ser Ala

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Val Gly Gly Gly Pro Phe Asp Ile Trp Gly Gln Gly Thr
            100                 105                 110

Leu Val Thr Val Ser Ser
        115
```

<210> SEQ ID NO 299
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.154 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(109)
<223> OTHER INFORMATION: HCDR3

<400> SEQUENCE: 299

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Asn
             20                  25                  30

Tyr Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Gly Ser Ser Gly Trp Tyr Tyr Phe Asp Tyr Trp Gly Gln
            100                 105                 110

Gly Thr Leu Val Thr Val Ser Ser
        115                 120
```

<210> SEQ ID NO 300
<211> LENGTH: 120
<212> TYPE: PRT
<213> ORGANISM: Homo sapiens
<220> FEATURE:
<221> NAME/KEY: MISC_FEATURE
<223> OTHER INFORMATION: Clone XPA.15.155 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE

```
<222> LOCATION: (97)..(109)
<223> OTHER INFORMATION: HCDR3

<400> SEQUENCE: 300
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Asn |
|---|---|---|---|---|---|---|---|---|---|---|---|---|---|---|---|
| | | | 20 | | | | | 25 | | | | | 30 | | |

| Tyr | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ala | Ile | Ser | Gly | Ser | Gly | Gly | Ser | Thr | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Val | Gly | Ser | Ser | Gly | Trp | Tyr | Tyr | Phe | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser |
|---|---|---|---|---|---|---|---|
| | | | 115 | | | | 120 |

```
<210> SEQ ID NO 301
<211> LENGTH: 121
<212> TYPE: PRT
<213> ORGANISM: Homo sapiens
<220> FEATURE:
<221> NAME/KEY: MISC_FEATURE
<223> OTHER INFORMATION: Clone XPA.15.158 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (97)..(110)
<223> OTHER INFORMATION: HCDR3

<400> SEQUENCE: 301
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asn | Ala |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ala | Ile | Ser | Gly | Ser | Gly | Gly | Ser | Thr | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Ala | Pro | Thr | Val | Pro | Tyr | Tyr | Tyr | Tyr | Gly | Met | Asp | Val | Trp | Gly |
|---|---|---|---|---|---|---|---|---|---|---|---|---|---|---|---|
| | | | 100 | | | | | 105 | | | | | 110 | | |

| Gln | Gly | Thr | Leu | Val | Thr | Val | Ser | Ser |
|---|---|---|---|---|---|---|---|---|
| | | | 115 | | | | | 120 |

```
<210> SEQ ID NO 302
<211> LENGTH: 117
```

```
<212> TYPE: PRT
<213> ORGANISM: Homo sapiens
<220> FEATURE:
<221> NAME/KEY: MISC_FEATURE
<223> OTHER INFORMATION: Clone XPA.15.165 heavy chain
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(56)
<223> OTHER INFORMATION: HCDR2
<220> FEATURE:
<221> NAME/KEY: MISC_FEATURE
<222> LOCATION: (96)..(107)
<223> OTHER INFORMATION: HCDR3

<400> SEQUENCE: 302

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Leu Asp Trp Ser Ser Gly Ala Phe Asp Ile Trp Gly Gln Gly Thr Leu
            100                 105                 110

Val Thr Val Ser Ser
            115

<210> SEQ ID NO 303
<211> LENGTH: 124
<212> TYPE: PRT
<213> ORGANISM: Homo sapiens
<220> FEATURE:
<221> NAME/KEY: MISC_FEATURE
<223> OTHER INFORMATION: Clone XPA.15.196 heavy chain revised
<220> FEATURE:
<221> NAME/KEY: MISC_FEATURE
<222> LOCATION: (26)..(33)
<223> OTHER INFORMATION: HCDR1
<220> FEATURE:
<221> NAME/KEY: MISC_FEATURE
<222> LOCATION: (51)..(58)
<223> OTHER INFORMATION: HCDR2
<220> FEATURE:
<221> NAME/KEY: MISC_FEATURE
<222> LOCATION: (99)..(113)
<223> OTHER INFORMATION: HCDR3

<400> SEQUENCE: 303

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60
```

-continued

```
Gln Gly Arg Val Thr Met Thr Arg Asp Thr Ser Ile Ser Thr Ala Tyr
 65              70                  75                  80

Met Glu Leu Ser Arg Leu Arg Ser Asp Asp Thr Ala Val Tyr Tyr Cys
                 85                  90                  95

Ala Arg Gly Ser Ser Ser Ser Trp Pro Val Tyr Phe Tyr Tyr Met Asp
                100             105                 110

Val Trp Gly Lys Gly Ser Thr Val Thr Val Ser Ser
            115             120
```